US010752588B2

(12) United States Patent
Holson et al.

(10) Patent No.: US 10,752,588 B2
(45) Date of Patent: *Aug. 25, 2020

(54) DOPAMINE D2 RECEPTOR LIGANDS

(71) Applicants: The Broad Institute, Inc., Cambridge, MA (US); Massachusetts Institute of Technology, Cambridge, MA (US)

(72) Inventors: Edward Holson, Newton, MA (US); Florence Fevrier, Ashland, MA (US); Michel Weiwer, Cambridge, MA (US); Edward Scolnick, Wayland, MA (US); Michelle Palmer, Harvard, MA (US); Michael C. Lewis, Dedham, MA (US); Jennifer Q. Pan, Acton, MA (US); Yan-Ling Zhang, Lexington, MA (US); Qihong Xu, Newton, MA (US)

(73) Assignees: The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/537,738

(22) PCT Filed: Dec. 18, 2015

(86) PCT No.: PCT/US2015/066689
§ 371 (c)(1),
(2) Date: Jun. 19, 2017

(87) PCT Pub. No.: WO2016/100823
PCT Pub. Date: Jun. 23, 2016

(65) Prior Publication Data
US 2019/0023656 A1   Jan. 24, 2019
US 2019/0345105 A9   Nov. 14, 2019

Related U.S. Application Data

(60) Provisional application No. 62/094,510, filed on Dec. 19, 2014.

(51) Int. Cl.
| C07D 211/26 | (2006.01) |
| C07D 401/14 | (2006.01) |
| C07D 405/14 | (2006.01) |
| C07D 401/12 | (2006.01) |
| C07D 413/12 | (2006.01) |
| C07D 471/04 | (2006.01) |
| C07D 471/10 | (2006.01) |
| C07D 211/62 | (2006.01) |
| A61P 25/00  | (2006.01) |

(52) U.S. Cl.
CPC ............ *C07D 211/26* (2013.01); *A61P 25/00* (2018.01); *C07D 211/62* (2013.01); *C07D 401/12* (2013.01); *C07D 401/14* (2013.01); *C07D 405/14* (2013.01); *C07D 413/12* (2013.01); *C07D 471/04* (2013.01); *C07D 471/10* (2013.01)

(58) Field of Classification Search
None
See application file for complete search history.

(56) References Cited

U.S. PATENT DOCUMENTS

| 3,041,344 | A |   | 6/1962  | Janssen |
| 3,097,209 | A | * | 7/1963  | Janssen ............... A61K 31/445 |
|           |   |   |         |                             546/208 |
| 3,161,644 | A |   | 12/1964 | Janssen |
| 3,238,216 | A |   | 3/1966  | Janssen |
| 3,344,145 | A |   | 9/1967  | Grogan et al. |
| 3,679,666 | A |   | 7/1972  | Malatestinic et al. |
| 3,998,834 | A |   | 12/1976 | Janssen et al. |
| 4,104,396 | A |   | 8/1978  | Huebner |
| 4,179,569 | A |   | 12/1979 | Janssen et al. |
| 4,244,961 | A |   | 1/1981  | Kluge et al. |
| 4,255,432 | A |   | 3/1981  | Kluge et al. |
| 4,366,162 | A |   | 12/1982 | Björk et al. |
| 4,427,680 | A | * | 1/1984  | Friebe ................. C07D 401/12 |
|           |   |   |         |                             514/314 |
| 5,594,024 | A |   | 1/1997  | Svensson et al. |
| 5,741,789 | A |   | 4/1998  | Hibschman et al. |
| 5,808,064 | A | * | 9/1998  | Chen .................... C07D 209/12 |
|           |   |   |         |                             544/132 |
| 5,889,026 | A |   | 3/1999  | Alanine et al. |
| 5,891,889 | A |   | 4/1999  | Anthony et al. |
| 6,133,291 | A | * | 10/2000 | Wolin ................. C07D 401/06 |
|           |   |   |         |                            514/217.09 |

(Continued)

FOREIGN PATENT DOCUMENTS

| CA | 2608807 A1   | 4/2001 |
| DE | 22 41 027 A1 | 3/1973 |

(Continued)

OTHER PUBLICATIONS

CAPLUS 2004:453186.*
Invitation to Pay Additional Fees dated Feb. 4, 2016 for Application No. PCT/US2015/066928.
Extended European Search Report for European Application No. 15871169.7 dated Jun. 21, 2018.
Extended European Search Report for European Application No. 15871250.5 dated Jul. 6, 2018.
[No Author Listed], Chemical Abstracts STN Database Record for RN 136647-02-4, STN Entry Date Oct. 11, 1991.
[No Author Listed], Chemical Abstracts STN Database Record for RN 370086-17-2, STN Entry Date Nov. 15, 2001.
[No Author Listed], Chemical Abstracts STN Database Record for RN 1027427-24-2, STN Entry Date Jun. 11, 2008.
[No Author Listed], Chemical Abstracts STN Database Record for RN 1222869-57-9, STN Entry Date May 13, 2010.

(Continued)

*Primary Examiner* — Heidi Reese
(74) *Attorney, Agent, or Firm* — Wolf, Greenfield & Sacks, P.C.

(57) ABSTRACT

The present invention relates to novel dopamine D2 receptor ligands. The invention further relates to functionally-biased dopamine D2 receptor ligands and the use of these compounds for treating or preventing central nervous system and systemic disorders associated with dysregulation of dopaminergic activity.

28 Claims, 6 Drawing Sheets

(56) References Cited

U.S. PATENT DOCUMENTS

| | | | |
|---|---|---|---|
| 6,172,085 B1 * | 1/2001 | Ohkawa | C07D 307/81 514/320 |
| 6,297,259 B1 | 10/2001 | Maynard et al. | |
| 6,528,529 B1 | 3/2003 | Brann et al. | |
| 6,593,322 B1 | 7/2003 | Bhagwat et al. | |
| 8,618,133 B2 | 12/2013 | Li et al. | |
| 8,716,280 B2 * | 5/2014 | Gaucher | C07D 405/12 514/224.2 |
| 2004/0000250 A1 | 1/2004 | Stratum | |
| 2005/0054850 A1 | 3/2005 | Wu et al. | |
| 2006/0205719 A1 | 9/2006 | Hubschwerlen et al. | |
| 2007/0213359 A1 | 9/2007 | Burnstein et al. | |
| 2008/0004286 A1 | 1/2008 | Wang et al. | |
| 2008/0027039 A1 | 1/2008 | Arakawa et al. | |
| 2008/0194630 A1 | 8/2008 | Barchuk et al. | |
| 2008/0247964 A1 | 10/2008 | Xu et al. | |
| 2009/0029958 A1 | 1/2009 | Alcaraz et al. | |
| 2009/0325905 A1 | 12/2009 | Peterson et al. | |
| 2009/0325934 A1 | 12/2009 | Navratil et al. | |
| 2009/0325959 A1 | 12/2009 | Vittitow et al. | |
| 2009/0325960 A1 | 12/2009 | Fulcher et al. | |
| 2010/0168080 A1 | 7/2010 | Khamrai et al. | |
| 2010/0331294 A1 | 12/2010 | Black et al. | |
| 2011/0160176 A1 | 6/2011 | Drescher et al. | |
| 2013/0137679 A1 | 5/2013 | Jin et al. | |
| 2018/0155283 A1 | 6/2018 | Holson et al. | |

FOREIGN PATENT DOCUMENTS

| | | | |
|---|---|---|---|
| DE | 26 10 228 A1 | 9/1976 | |
| DE | 28 47 624 A1 | 5/1979 | |
| DE | 196 13 329 A1 | 10/1997 | |
| DE | 103 16 081 A1 | 10/2004 | |
| DE | 10 2004 000 026 A1 | 2/2006 | |
| EP | 0 100 046 A1 | 2/1984 | |
| EP | 0 297 661 A1 | 1/1989 | |
| EP | 0 325 755 A1 | 8/1989 | |
| EP | 0 393 738 A1 | 10/1990 | |
| EP | 0 396 282 A2 | 11/1990 | |
| EP | 0 474 561 A1 | 3/1992 | |
| EP | 0 824 098 A1 | 2/1998 | |
| EP | 1 254 661 A1 | 11/2002 | |
| EP | 1 829 869 A1 | 9/2007 | |
| FR | 2 738 245 A1 | 3/1997 | |
| JP | 47038970 B | 12/1972 | |
| WO | WO 92/01687 A1 | 2/1992 | |
| WO | WO-9206958 A1 * | 4/1992 | C07D 211/46 |
| WO | WO 94/02462 A1 | 2/1994 | |
| WO | WO 95/06037 A1 | 3/1995 | |
| WO | WO 97/18201 A1 | 5/1997 | |
| WO | WO 97/23202 A1 | 7/1997 | |
| WO | WO 97/23216 A1 | 7/1997 | |
| WO | WO 98/08842 A1 | 3/1998 | |
| WO | WO 98/35959 A1 | 8/1998 | |
| WO | WO 99/01423 A1 | 1/1999 | |
| WO | WO 99/04794 A1 | 2/1999 | |
| WO | WO 99/21539 A1 | 5/1999 | |
| WO | WO 00/00197 A1 | 1/2000 | |
| WO | WO 00/12074 A2 | 3/2000 | |
| WO | WO 00/29406 A2 | 5/2000 | |
| WO | WO 00/55137 A1 | 9/2000 | |
| WO | WO 00/66551 A1 | 11/2000 | |
| WO | WO 01/05763 A2 | 1/2001 | |
| WO | WO 01/25200 A1 | 4/2001 | |
| WO | WO 01/29000 A2 | 4/2001 | |
| WO | WO 01/40184 A2 | 6/2001 | |
| WO | WO 01/60796 A1 | 8/2001 | |
| WO | WO 01/81309 A2 | 11/2001 | |
| WO | WO 01/83472 A1 | 11/2001 | |
| WO | WO 2001/87839 A1 | 11/2001 | |
| WO | WO 01/98266 A2 | 12/2001 | |
| WO | WO 02/055496 A1 | 7/2002 | |
| WO | WO 03/020029 A1 | 3/2003 | |
| WO | WO 2003/049736 A1 | 6/2003 | |
| WO | WO 03/068760 A2 | 8/2003 | |
| WO | WO 03/068772 A1 | 8/2003 | |
| WO | WO 03/087086 A2 | 10/2003 | |
| WO | WO 2004/005295 A1 | 1/2004 | |
| WO | WO 2004/011438 A1 | 2/2004 | |
| WO | WO 2004/078114 A2 | 9/2004 | |
| WO | WO 2004/101518 A1 | 11/2004 | |
| WO | WO 2005/012296 A1 | 2/2005 | |
| WO | WO 2005/012297 A1 | 2/2005 | |
| WO | WO 2005/023794 A2 | 3/2005 | |
| WO | WO 2005/030722 A1 | 4/2005 | |
| WO | WO 2005/033073 A2 | 4/2005 | |
| WO | WO 2005/036961 A2 | 4/2005 | |
| WO | WO 2005/061499 A1 | 7/2005 | |
| WO | WO 2006/001752 A1 | 1/2006 | |
| WO | WO 2006/003147 A1 | 1/2006 | |
| WO | WO 2006/101245 A1 | 9/2006 | |
| WO | WO 2006/137465 A1 | 12/2006 | |
| WO | WO 2007/009462 A2 | 1/2007 | |
| WO | WO 2007/011833 A2 | 1/2007 | |
| WO | WO 2007/038669 A2 | 4/2007 | |
| WO | WO 2007/042325 A1 | 4/2007 | |
| WO | WO 2008/027932 A2 | 3/2008 | |
| WO | WO 2008/033299 A2 | 3/2008 | |
| WO | WO 2008/103126 A1 | 8/2008 | |
| WO | WO 2008/144268 A1 | 11/2008 | |
| WO | WO 2008/150848 A1 | 12/2008 | |
| WO | WO 2009/032885 A2 | 3/2009 | |
| WO | WO 2009/076212 A1 | 6/2009 | |
| WO | WO 2009/094428 A2 | 7/2009 | |
| WO | WO 2009/136350 A1 | 11/2009 | |
| WO | WO 2009/137843 A2 | 11/2009 | |
| WO | WO 2009/158587 A1 | 12/2009 | |
| WO | WO 2010/027567 A2 | 3/2010 | |
| WO | WO 2010/028862 A1 | 3/2010 | |
| WO | WO 2010/058333 A1 | 5/2010 | |
| WO | WO 2010/065782 A1 | 6/2010 | |
| WO | WO 2011/125006 A2 | 10/2011 | |
| WO | WO 2011/160084 A1 | 12/2011 | |
| WO | WO 2012/012366 A1 | 1/2012 | |
| WO | WO 2013/039802 A1 | 3/2013 | |
| WO | WO 2013/149704 A1 | 10/2013 | |
| WO | WO 2013/170072 A2 | 11/2013 | |
| WO | WO 2016/100823 A1 | 6/2016 | |
| WO | WO 2016/100940 A1 | 6/2016 | |

OTHER PUBLICATIONS

[No Author Listed], Chemical Abstracts STN Database Record for RN 1348075-95-5, STN Entry Date Dec. 4, 2011.

[No Author Listed], Chemical Abstracts STN Database Record for RN 1381735-89-2, STN Entry Date Jul. 5, 2012.

[No Author Listed], Chemical Abstracts STN Database Record for RN 1381650-39-0, STN Entry Date Jul. 5, 2012.

[No Author Listed], RN-1528719-86-9: -4-Piperidinol, 1-[(2,3-dihydro-1,4-benzodioxin-2-yl)methyl]-4-methyl- In: Chemical catalog, Jan. 23, 2014, Aurora Fine Chemicals, XP055487301. 1 page.

[No Author Listed], RN-1514639-84-9: -4-Piperidinol, 1-[(2-(2-fluorophenoxy)ethyl]-4-methyl- In: Chemical catalog, Jan. 8, 2014, Aurora Fine Chemicals, XP055487303. 1 page.

[No Author Listed], RN-1506817-27-1: -4-Piperidinol, 4-methyl-1-(2-phenoxyethyl)- In: Chemical catalog, Dec. 30, 2013, Aurora Fine Chemicals, XP055487304. 1 page.

[No Author Listed], Schizophrenia Working Group of the Psychiatric Genomics Consortium. Biological insights from 108 schizophrenia-associated genetic loci. Nature. Jul. 24, 2014;511(7510):421-7. doi: 10.1038/nature13595. Epub Jul. 22, 2014.

Allen et al., Discovery of β-arrestin-biased dopamine D2 ligands for probing signal transduction pathways essential for antipsychotic efficacy. Proc Natl Acad Sci U S A. Nov. 8, 2011;108(45):18488-93. doi: 10.1073/pnas.1104807108. Epub Oct. 24, 2011.

Bagley et al., New 1-(heterocyclylalkyl)-4-(propionanilido)-4-piperidinyl methyl ester and methylene methyl ether analgesics. J Med Chem. Feb. 1991;34(2):827-41.

Beaulieu et al., An Akt/beta-arrestin 2/PP2A signaling complex mediates dopaminergic neurotransmission and behavior. Cell. Jul. 29, 2005;122(2):261-73.

(56) References Cited

OTHER PUBLICATIONS

Burgess et al., The SAR of UK-78,282: A novel blocker of human T cell Kv1.3 potassium channels. Bioorganic & Medicinal Chemistry Letters (1997), 7(8), 1047-1052.
Chen et al., Structure-functional selectivity relationship studies of β-arrestin-biased dopamine $D_2$ receptor agonists. J Med Chem. Aug. 23, 2012;55(16):7141-53. doi: 10.1021/jm300603y. Epub Aug. 13, 2012.
Choi et al., Novel (bisarylmethoxy)butylpiperidine analogues as neurotransmitter transporter inhibitors with activity at dopamine receptor sites. Bioorg Med Chem. Dec. 2002;10(12):4091-102.
Conceição et al., Effects of microgram doses of haloperidol on open-field behavior in mice. Pharmacol Biochem Behav. Apr. 1996;53(4):833-8.
Dutta et al., Structure-activity relationship studies of novel 4-[2-[bis(4-fluorophenyl)methoxy]ethyl]-1-(3-phenylpropyl)piperidine analogs: synthesis and biological evaluation at the dopamine and serotonin transporter sites. J Med Chem. Feb. 2, 1996;39(3):749-56.
Gastambide et al., The mGlu$_5$ positive allosteric modulator LSN2463359 differentially modulates motor, instrumental and cognitive effects of NMDA receptor antagonists in the rat. Neuropharmacology. Jan. 2013;64:240-7. doi: 10.1016/j.neuropharm.2012.07.039. Epub Aug. 1, 2012.
Gilligan et al., Novel piperidine sigma receptor ligands as potential antipsychotic drugs. J Med Chem. Nov. 13, 1992;35(23):4344-61.
Grogan et al., Spiranes. VII. Neuroleptics Derived From Azaspiranes. J Med Chem. Jan. 1, 1965;8:62-73.
Henegar et al., Process Development and Scale-up of a β-Secretase Inhibitor via a Stereospecific Jocic Reaction. Org. Process Res. Dev., 2013, 17 (7), pp. 985-990.
Hoffman et al., Catalepsy as a rodent model for detecting antipsychotic drugs with extrapyramidal side effect liability. Psychopharmacology (Berl). Jul. 1995;120(2):128-33.
Kane et al., Clozapine for the treatment-resistant schizophrenic. A double-blind comparison with chlorpromazine. Arch Gen Psychiatry. Sep. 1988;45(9):789-96.
Lee et al., Stereoselective synthesis of spiropiperidines as BACE-1 aspartyl protease inhibitors via late stage N-arylation of a 1,8-diazaspiro[4.5]dec-3-en-2-one pharmacophore. J Org Chem. Mar. 15, 2013;78(6):2661-9. doi: 10.1021/jo400016m. Epub Mar. 4, 2013.
Leucht et al., Comparative efficacy and tolerability of 15 antipsychotic drugs in schizophrenia: a multiple-treatments meta-analysis. Lancet. Sep. 14, 2013;382(9896):951-62. doi: 10.1016/S0140-6736(13)60733-3. Epub Jun. 27, 2013. Review. Erratum in: Lancet. Sep. 14, 2013;382(9896):940.
Liang et al., Synthesis of UK-78282. The State Key Lab. of Applied Organic Chemistry and Institute of Organic Chemistry, Lanzhou University, Lanzhou, Gansu Province, 318000, Peop. Rep. China. Zhongguo Yiyao Gongye Zazhi (2005), 36(4), 193-195. Abstract.
Lowes et al., Optimization of propafenone analogues as antimalarial leads. J Med Chem. Nov. 10, 2011;54(21):7477-85. doi: 10.1021/jm2005546. Epub Oct. 10, 2011.
Maillard et al., Composes cycloalcane—spiro heterocycliques [Heterocyclic cycloalkane-spiro compounds]. European Journal of Medicinal Chemistry—Chimica Therapeutica, Edifor, FR, vol. 6(4); Jan. 1, 1971. pp. 257-261. XP008152319, ISSN: 0009-4374.
Masri et al., Antagonism of dopamine D2 receptor/beta-arrestin 2 interaction is a common property of clinically effective antipsychotics. Proc Natl Acad Sci U S A. Sep. 9, 2008;105(36):13656-61. doi: 10.1073/pnas.0803522105. Epub Sep. 3, 2008.
McCalmont et al., Design, synthesis, and biological evaluation of novel T-Type calcium channel antagonists. Bioorg Med Chem Lett. Jul. 16, 2004;14(14):3691-5.
Natesan et al., Amisulpride the 'atypical' atypical antipsychotic—comparison to haloperidol, risperidone and clozapine. Schizophr Res. Oct. 2008;105(1-3):224-35. doi: 10.1016/j.schres.2008.07.005. Epub Aug. 16, 2008.
Nguyen et al., Structure-activity relationship exploration of Kv1.3 blockers based on diphenoxylate. Bioorg Med Chem Lett. Dec. 1, 2012;22(23):7106-9. doi: 10.1016/j.bmcl.2012.09.080. Epub Sep. 29, 2012.
Schaefer et al., Drug interactions on spontaneous locomotor activity in rats. Neuroleptics and amphetamine-induced hyperactivity. Neuropharmacology. Aug. 1984;23(8):909-14.
Sharma et al., Eccentric Connectivity Index: A Novel Highly Discriminating Topological Descriptor for Structure—Property and Structure—Activity Studies. J. Chem. Inf. Comput. Sci., 1997, 37 (2), pp. 273-282.
Shonberg et al., A structure-activity analysis of biased agonism at the dopamine D2 receptor. J Med Chem. Nov. 27, 2013;56(22):9199-221. doi: 10.1021/jm401318w. Epub Nov. 8, 2013.
Su et al., A dopamine D2 receptor-DISC1 protein complex may contribute to antipsychotic-like effects. Neuron. Dec. 17, 2014;84(6):1302-16. doi: 10.1016/j.neuron.2014.11.007. Epub Nov. 26, 2014.
Watanuki et al., Synthesis and pharmacological evaluation of 1-alkyl-N-[(1R)-1-(4-fluorophenyl)-2-methylpropyl]piperidine-4-carboxamide derivatives as novel antihypertensive agents. Chem Pharm Bull (Tokyo). 2011;59(11):1376-85.
Wise et al., Examination of a series of 8-[3-[bis(4-fluorophenyl)amino]propyl]-1-aryl-1,3,8-triazaspiro[4.5]decan-4-ones as potential antipsychotic agents. J Med Chem. Dec. 1985;28(12):1811-7.
Yang et al., Anesthetic activity of some 4-substituted fentanyl derivatives in mice. Nanjing General Hospital, Nanjing Command, Nanjing, 210002, Peop. Rep. China. 1998, 13(2), 80-82. Abstract.
Yang et al., Synthesis and analgesic activity of analogs of 4-methoxymethyl fentanyl. Yao Xue Xue Bao. 1991;26(7):493-8. Chinese. Abstarct.
Zhou et al., 4-Hydroxy-1-[2-(4-hydroxyphenoxy)ethyl]-4-(4-methylbenzyl)piperidine: a novel, potent, and selective NR1/2B NMDA receptor antagonist. J Med Chem. Jul. 29, 1999;42(15):2993-3000.
International Search Report and Written Opinion dated Mar. 4, 2016 for Application No. PCT/US2015/066689.
International Preliminary Report on Patentability dated Jun. 29, 2017 for Application No. PCT/US2015/066689.
International Search Report and Written Opinion dated Apr. 29, 2016 for Application No. PCT/US2015/066928.
[No Author Listed], Pubchem, Substance record for SID 148597868, Create Date: Oct. 22, 2012. Retrieved on Jan. 30, 2016 from the Internet <https://pubchem.ncbi.nlm.nih.gov/substance/148597868/version/1#section=Top>.
[No Author Listed] CAPLUS. 2006; 1356865 pub. 2006.
Catafau et al., Characterization of the SPECT 5-HT2A receptor ligand 123I-R91150 in healthy volunteers: part 2—ketanserin displacement. J Nucl Med. Jun. 2006;47(6):929-37.
Hamprecht et al., 5-HT2C antagonists based on fused heterotricyclic templates: design, synthesis and biological evaluation. Bioorg Med Chem Lett. Jan. 15, 2007;17(2):424-7. Epub Oct. 17, 2006.

* cited by examiner

DOPAMINE D2 RECEPTOR LIGANDS

RELATED APPLICATIONS

The present application is a national stage filing under 35 U.S.C. § 371 of international PCT application, PCT/US2015/066689, filed Dec. 18, 2015, which claims priority under 35 U.S.C. § 119(e) to U.S. provisional patent application Ser. No. 62/094,510, filed Dec. 19, 2014, each of which is incorporated herein by reference.

FIELD OF THE INVENTION

The present invention relates to novel ligands of dopamine D2 receptors, in particular, functionally selective ligands of dopamine D2 receptors. The invention also relates to the use of these compounds in treating or preventing central nervous system disorders as well as systemic disorders associated with dopamine D2 receptors.

BACKGROUND OF THE INVENTION

G-protein-coupled receptors (GPCRs), also known as 7-transmembrane receptors, are the single largest class of drug targets, with more than 800 members in the human genome (Lefkowitz, Trends in Pharmacological Sciences (2004), 413). Dopamine receptors represent prototypic examples of GPCRs that mediate neurotransmission (Missale et al., Physiological Reviews (1998), 189). Dopamine is a monoamine neurotransmitter that exerts its action on neuronal circuitry via dopamine receptors. As dopaminergic innervations are most prominent in the brain, dopaminergic dysfunction can critically affect vital central nervous system (CNS) functions, ranging from voluntary movement, feeding, reward, affection, sleep, attention, working memory and learning (Carlsson, Science (2001), 1021, Beaulieu et al., Pharmacological Reviews (2011), 182). Apart from CNS functions, dopamine is also involved in important physiological roles such as the regulation of olfaction, cardiovascular functions, sympathetic regulation, hormonal regulation, retinal processes, immune system and renal function. Dysregulation of dopaminergic neurotransmission has been associated with multiple neurological and psychiatric conditions such as Parkinson's disease, Huntington's disease, attention deficit hyperactivity disorder (ADHD), mood disorders and schizophrenia (Carlsson, Science (2001), 1021), as well as various somatic disorders such as hypertension and kidney dysfunction (Missale et al., Physiological Reviews (1998), 189, Beaulieu et al., Pharmacological Reviews (2011), 182).

With the complex array of critical cellular functions mediated by dopamine receptors, and the multilevel interactions that are known to occur between dopamine and other extracellular messengers in the signaling pathways, there remains a need to better manage dopamine-related pathologic conditions by precise targeting of post-receptor intracellular signaling modalities, either directly or through ligand-biased signaling pharmacology.

As drug targets, GPCRs known to mediate dopamine functions can be broadly classified into D1 and D2 class receptors. D1 class receptors (D1R and D5R) are mostly coupled to Gαs and positively regulate the production of second messenger cAMP and the activity of protein kinase A (PKA) (Missale et al., Physiological Reviews (1998), 189). D2 class receptors (D2R, D3R and D4R) couple to Gαi/o, downregulating cAMP production and PKA activity (Missale et al., Physiological Reviews (1998), 189). Additionally, D2 class dopamine receptors also modulate intracellular $Ca^{2+}$ levels, resulting in changes in activity of $Ca^{2+}$ regulated signaling proteins such as protein phosphatase calcineurin (Nishi et al., J. Neurosci. (1997), 17, 8147).

D2 class dopamine (D2R) receptors are presently the best-established targets for antipsychotic drugs. Recent studies suggest that Varrestin 2 deficiency in mice results in reduction of dopamine-dependent behaviours (Beaulieu et al., Cell (2005), 261). The connection between β-arrestin 2 and dopamine-associated behaviours suggests that β-arrestin 2 could be a positive mediator of dopaminergic synaptic transmission and a potential pharmacological target for dopamine-related psychiatric disorders (Beaulieu et al., Cell (2005), 261).

Currently, all clinically marketed antipsychotics modulate dopamine by targeting D2R either as antagonists/inverse agonists (first- and second-generation antipsychotics, for example, chlorpromazine, clozapine) or partial agonists (third-generation antipsychotics, with aripiprazole as the sole example of this ligand class in the clinic). Antagonism of dopamine D2 receptor/β-arrestin 2 interaction has been found to be a common property of clinically-effective antipsychotics (Masri et al., Proceedings of the National Academy of Sciences of the United States of America (2008), 13656).

Structure-functional selectivity relationship studies of β-arrestin-biased dopamine D2 receptor agonists, based on the aripiprazole scaffold, have been conducted (Chen et al., Journal of Medicinal Chemistry (2012), 7141, Roth et al., US 2013/0137679, Shonberg et al., Journal of Medicinal Chemistry (2013), 9199). Known antipsychotics, even those that share a common mechanistic pathway such as haloperidol, clozapine, and risperidone, show highly diverse effects on D2R/G protein signaling and are not selective across GPCR receptors. There remains a lack of clinical drug candidates that offer highly functionalized targeting of dopamine D2 receptors that improve the clinical efficacy of antipsychotics, while at the same time limiting the undesirable side effects associated with D2-dopaminergic activity.

Selectively antagonizing the β-arrestin pathway at the D2 receptor could be sufficient to produce an antipsychotic effect, while at the same time, reduce potential side effects that could arise from antagonizing the cAMP pathway. Modulation of the β-arrestin-2 dependent pathway could lead to modulation of AKT and GSK3β target genes (Beaulieu et al., Frontiers in molecular neuroscience (2011), 38.). Development of compounds with cAMP biased agonist or antagonist or β-arrestin biased agonist or antagonist activity could offer a functionally selective means to modulate or treat dopamine-associated disorders, including Parkinson's disease, Huntington's disease, mood disorders, schizophrenia, attention deficit hyperactivity disorder (ADHD), restless legs syndrome (RLS), pituitary disorders such as pituitary adenoma or pituitary tumor (prolactinoma) or endocrine disorders, e.g., galactorrhea. Further, development of ligands that exhibit functional selectivity as agonists, antagonists, and partial agonists, as well as selectivity against other GPCRs, allows modulation of activity at the dopamine D2 receptors to be more finely-tuned to increase selectivity and hence clinical efficacy and safety in treatment. By increasing selectivity at dopamine D2 receptors while minimising undesirable side-effects, drugs in this category would also offer greater success potential with patient acceptance and compliance.

SUMMARY OF THE INVENTION

The present invention relates to novel compounds that modulate dopamine D2 receptors. In particular, compounds of the present invention show functional selectivity at the dopamine D2 receptors and exhibit selectivity downstream of the D2 receptors, on the β-arrestin pathway and/or on the cAMP pathway. Compounds of the present invention exhibit different activity profiles either as agonist, antagonist, inverse agonist, or partial agonist. As these compounds are functionally selective downstream of the D2 receptors, they offer more selectivity and functionality in treatment of diseases or disorders in which dopamine plays a role, such as central nervous system disorders associated with D2 receptors, while minimizing potential associated side effects. Use of β-arrestin biased D2 receptor antagonists which selectively antagonize the β-arrestin pathway may offer a means to treat psychotic disorders while also minimizing potential undesirable side-effects associated with D2 receptor activity. Similarly, biased D2 receptor agonists which selectively activate either the β-arrestin pathway or the cAMP pathway may also be advantageous in treatment of disorders associated with dopamine receptors, such as Parkinson's disease, ADHD and restless leg syndrome or an endocrine disorder, e.g., galactorrhea, with fewer side-effects.

The present invention provides a compound having Formula I:

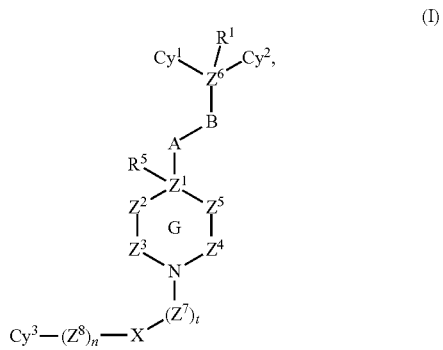

or a stereoisomer, racemate, tautomer, polymorph, hydrate, or solvate thereof, or a pharmaceutically acceptable salt thereof, wherein each of the variables is defined and illustrated in detail herein.

The present invention also provides a pharmaceutical composition comprising a compound of the invention or a pharmaceutically acceptable salt, stereoisomer, racemate, tautomer, polymorph, hydrate, or solvate thereof, and one or more pharmaceutically acceptable excipients or carriers.

The present invention also provides a method of modulating D2 receptor activity by administering a selective β-arrestin antagonist or a pharmaceutically acceptable salt, stereoisomer, racemate, tautomer, polymorph, hydrate, or solvate thereof.

The present invention also provides a method of modulating D2 receptor activity by administering a compound which is a β-arrestin antagonist and a cAMP agonist, or a pharmaceutically acceptable salt, stereoisomer, racemate, tautomer, polymorph, hydrate, or solvate thereof.

The present invention also provides a method of modulating D2 receptor activity by administering a compound of the invention or a pharmaceutically acceptable salt, stereoisomer, racemate, tautomer, polymorph, hydrate, or solvate thereof.

The present invention also provides use of a compound of the invention or a pharmaceutically acceptable salt, stereoisomer, racemate, tautomer, polymorph, hydrate, or solvate thereof, as a β-arrestin biased D2 receptor agonist or antagonist. The present invention also provides use of a compound of the invention or a pharmaceutically acceptable salt, stereoisomer, racemate, tautomer, polymorph, hydrate, or solvate thereof, as a cAMP biased agonist or antagonist. The present invention also provides use of a compound of the invention or a pharmaceutically acceptable salt, stereoisomer, racemate, tautomer, polymorph, hydrate, or solvate thereof, as a β-arrestin biased antagonist and cAMP biased agonist.

The present invention also provides a method of treating or preventing a disease or disorder in which modulation of D2 receptors (e.g., β-arrestin or Gi/cAMP) plays a role by administering to a subject in need thereof, a therapeutically effective amount of a selective β-arrestin antagonist, or a pharmaceutically acceptable salt, stereoisomer, racemate, tautomer, polymorph, hydrate, or solvate thereof, in combination with a pharmaceutically acceptable excipient or carrier, such that the disease or disorder is treated or prevented.

The present invention also provides a method of treating or preventing a disease or disorder in which modulation of D2 receptors (e.g., β-arrestin or Gi/cAMP) plays a role by administering to a subject in need thereof, a therapeutically effective amount of a compound which is a β-arrestin antagonist and a cAMP agonist, or a pharmaceutically acceptable salt, stereoisomer, racemate, tautomer, polymorph, hydrate, or solvate thereof, in combination with a pharmaceutically acceptable excipient or carrier, such that the disease or disorder is treated or prevented.

The present invention also provides a method of treating or preventing a disease or disorder in which modulation of D2 receptors (e.g., β-arrestin or Gi/cAMP) plays a role by administering to a subject in need thereof, a therapeutically effective amount of a compound of the invention, or a pharmaceutically acceptable salt, stereoisomer, racemate, tautomer, polymorph, hydrate, or solvate thereof, in combination with a pharmaceutically acceptable excipient or carrier, such that the disease or disorder is treated or prevented.

The present invention also provides a method of treating or preventing a disease or disorder in which modulation of D2 receptors (e.g., β-arrestin or Gi/cAMP) plays a role by administering to a subject in need thereof, a therapeutically effective amount of a pharmaceutical composition of the invention, such that the disease or disorder is treated or prevented.

The present invention also provides use of a selective β-arrestin antagonist, or a pharmaceutically acceptable salt, stereoisomer, racemate, tautomer, polymorph, hydrate, or solvate thereof, for treating or preventing a disease or disorder in which modulation of D2 receptors (e.g., β-arrestin or Gi/cAMP) plays a role in a subject in need thereof.

The present invention also provides use of a compound which is a β-arrestin antagonist and a cAMP agonist, or a pharmaceutically acceptable salt, stereoisomer, racemate, tautomer, polymorph, hydrate, or solvate thereof, for treating or preventing a disease or disorder in which modulation of D2 receptors (e.g., β-arrestin or Gi/cAMP) plays a role in a subject in need thereof.

The present invention also provides use of a compound of the invention, or a pharmaceutically acceptable salt, stereoisomer, racemate, tautomer, polymorph, hydrate, or solvate thereof, or use of a pharmaceutical composition of the invention, for treating or preventing a disease or disorder in which modulation of D2 receptors (e.g., β-arrestin or Gi/cAMP) plays a role in a subject in need thereof.

The present invention also provides use of a selective β-arrestin antagonist, or a pharmaceutically acceptable salt, stereoisomer, racemate, tautomer, polymorph, hydrate, or solvate thereof, in the manufacture of a medicament for the treatment or prevention of a disease or disorder in which modulation of D2 receptors (e.g., β-arrestin or Gi/cAMP) plays a role in a subject in need thereof.

The present invention also provides use of a compound which is a β-arrestin antagonist and a cAMP agonist, or a pharmaceutically acceptable salt, stereoisomer, racemate, tautomer, polymorph, hydrate, or solvate thereof, in the manufacture of a medicament for the treatment or prevention of a disease or disorder in which modulation of D2 receptors (e.g., β-arrestin or Gi/cAMP) plays a role in a subject in need thereof.

The present invention also provides use of a compound of the invention, or a pharmaceutically acceptable salt, stereoisomer, racemate, tautomer, polymorph, hydrate, or solvate thereof, or use of a pharmaceutical composition of the invention, in the manufacture of a medicament for the treatment or prevention of a disease or disorder in which modulation of D2 receptors (e.g., β-arrestin or Gi/cAMP) plays a role in a subject in need thereof.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the present invention. In the case of conflict, the present specification, including definitions, will control. In addition, the materials, methods and examples are illustrative only and are not intended to be limiting.

Other features and advantages of the invention will be apparent from the following detailed description and claims.

BRIEF DESCRIPTION OF THE DRAWINGS

The following detailed description, given by way of example, but not intended to limit the invention solely to the specific embodiments described, may be understood in conjunction with the accompanying drawings, in which.

DETAILED DESCRIPTION OF THE INVENTION

Compounds of the Invention

Figure 1:
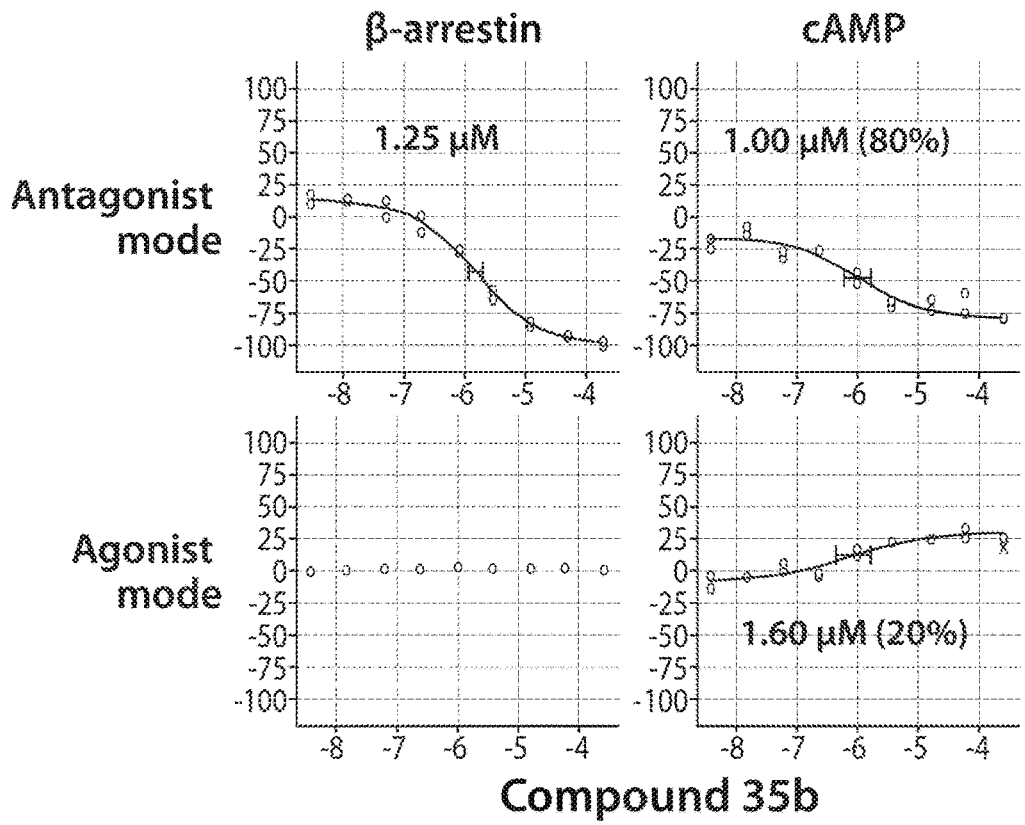
FIG. 1 shows representative curves for Compounds 35b, 63, 79, 16a, 52 and control compounds Clozapine and Aripiprazole across the β-arrestin and cAMP cell based assays in agonist and antagonist modes (see also Table 3).
Figure 1:
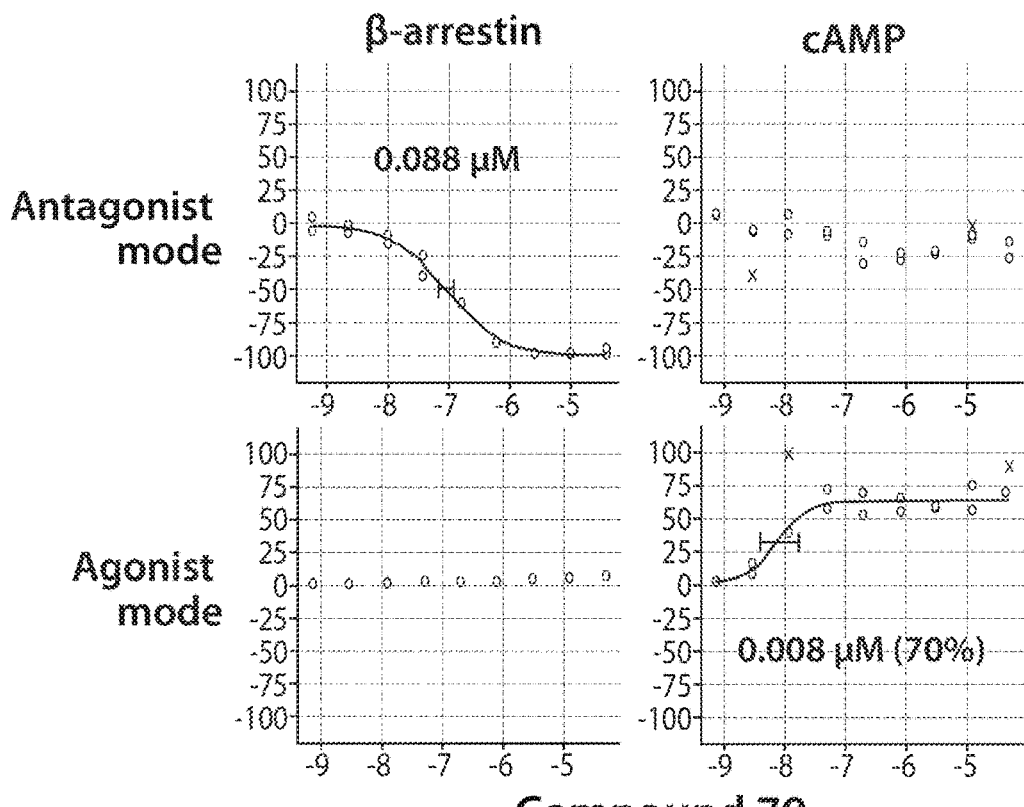

The present invention relates to novel ligands of dopamine D2 receptors. In particular, the invention relates to a compound having Formula I:

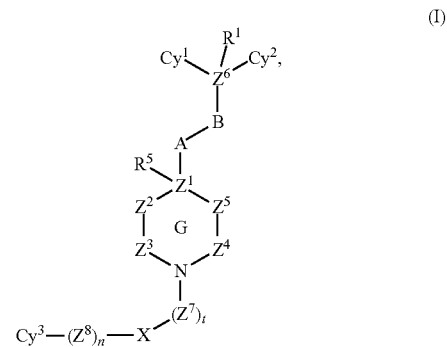

or a stereoisomer, racemate, tautomer, polymorph, hydrate, or solvate thereof, or a pharmaceutically acceptable salt thereof, wherein:

A-B is C(O)—NR$^{13}$, C(O)—CR$^{11}$R$^{12}$, C(O)—O, CR$^{11}$R$^{12}$—NR$^{13}$, CR$^{11}$R$^{12}$—NR$^{13}$, CR$^{11}$R$^{12}$—O, CR$^{11}$R$^{12}$—C(O), NR$^{13}$—C(O), NR$^{13}$—CR$^{11}$R$^{12}$, O—CR$^{11}$R$^{12}$, or O—C(O), wherein CR$^{11}$R$^{12}$—NR$^{13}$ or NR$^{13}$—CR$^{11}$R$^{12}$ can form a 3- to 6-membered ring, or A-Z$^1$—R$^5$ form a 3- to 6-membered ring, and B is C(O), CR$^{11}$R$^{12}$, O, or NR$^{13}$, or A-Z$^1$, together with any one or two of Z$^2$ and Z$^3$, or any one or two of Z$^4$ and Z$^5$, form a 3- to 6-membered ring, wherein the ring and ring G form a fused or bridged ring structure, and B is C(O), CR$^{11}$R$^{12}$, O, or NR$^{13}$, or B—Z$^6$-Cy$^1$ or B—Z$^6$-Cy$^2$ form a 3- to 6-membered ring, and A is C(O), CR$^{11}$R$^{12}$, O, or NR$^{13}$, or B—Z$^6$—R$^1$ form a 3- to 6-membered ring, and A is C(O), CR$^{11}$R$^{12}$, O, or NR$^{13}$, or A-B—Z$^6$-Cy$^1$ or A-B—Z$^6$-Cy$^2$ form a 5- to 8-membered ring, or A-B—Z$^6$ form a 3- to 6-membered ring, or B-A-Z$^1$ form a 3- to 6-membered ring, or B-A-Z$^1$, together with any one or two of Z$^2$ and Z$^3$, or any one or two of Z$^4$ and Z$^5$, form a 4- to 6-membered ring, wherein the ring and ring G form a fused or bridged ring structure;

R$^{11}$ and R$^{12}$ are each independently H, halogen, or C$_1$-C$_6$ alkyl, or R$^{11}$ and R$^{12}$, together with the carbon atom to which R$^{11}$ and R$^{12}$ are bonded, form a 3- to 6-membered ring, provided that when CR$^{11}$R$^{12}$—NR$^{13}$ or NR$^{13}$—CR$^{11}$R$^{12}$ forms a 3- to 6-membered ring, one of R$^{11}$ and R$^{12}$ is absent;

R$^{13}$ is H, C$_1$-C$_6$ alkyl, C$_1$-C$_6$ haloalkyl, C$_3$-C$_6$ cycloalkyl, C$_3$-C$_6$ heterocycle, C$_6$-C$_{10}$ aryl, heteroaryl comprising one or two 5- or 6-membered rings and one to four heteroatoms selected from N, O, and S, C(O)—C$_1$-C$_6$ alkyl, C(O)- phenyl, C(O)O—$C_1$-$C_6$ alkyl, C(O)NR$^{17}$R$^{18}$, S(O)$_2$—$C_1$-$C_6$ alkyl, or S(O)$_2$NR$^{17}$R$^{18}$, provided that when CR$^{11}$R$^{12}$—NR$^{13}$ or NR$^{13}$—CR$^{11}$R$^{12}$ forms a 3- to 6-membered ring, R$^{13}$ is absent;

R$^{17}$ and R$^{18}$ are each independently H, $C_1$-$C_6$ alkyl, or $C_6$-$C_{10}$ aryl;

$Z^1$ is a carbon atom;

R$^5$ is H, halogen, OH, $C_1$-$C_6$ alkyl, O—$C_1$-$C_6$ alkyl, OCF$_3$, OCHF$_2$, OCH$_2$F, NR$^{17}$R$^{18}$, NR$^{17}$C(O)—$C_1$-$C_6$ alkyl, C(O)NR$^{17}$R$^{18}$, S—$C_1$-$C_6$ alkyl, S(O)—$C_1$-$C_6$ alkyl, S(O)$_2$—$C_1$-$C_6$ alkyl, S(O)$_2$NR$^{17}$R$^{18}$, NR$^{17}$S(O)$_2$—$C_1$-$C_6$ alkyl, $C_6$-$C_{10}$ aryl, phenyl, benzyl, heteroaryl comprising one 5- or 6-membered ring and one to four heteroatoms selected from N, O, and S, $C_3$-$C_6$ cycloalkyl, or heterocyclyl comprising one 4- to 6-membered ring and one to four heteroatoms selected from N, O, and S, or when B-A-$Z^1$ form a 3- to 6-membered ring, absent, or A-$Z^1$—R$^5$ form a 3- to 6-membered ring, or $Z^1$—R$^5$, together with R$^2$ and the carbon atom to which the R$^2$ is bonded, form a 4- to 6-membered ring, wherein the ring and ring G form a fused or bridged ring structure, provided that when A-B is NR$^{13}$—C(O), NR$^{13}$—CR$^{11}$R$^{12}$, O—CR$^{11}$R$^{12}$, or O—C(O), then R$^5$ is not OH, O—$C_1$-$C_6$ alkyl, S—$C_1$-$C_6$ alkyl, NR$^{17}$R$^{18}$, NR$^{17}$C(O)—$C_1$-$C_6$ alkyl, or NR$^{17}$S(O)$_2$—$C_1$-$C_6$ alkyl;

$Z^2$ is C(R$^2$)$_p$ or C(O);

$Z^3$ is C(R$^2$)$_p$; or any one or two of $Z^2$ and $Z^3$, together with A-$Z^1$ or B-A-$Z^1$, form a 3- to 6-membered ring, wherein the ring and ring G form a fused or bridged ring structure, or when X is CR$^{14}$R$^{15}$ or NR$^{16}$, $Z^3$—N—(Z$^7$)$_t$—X form a 4- to 6-membered ring;

$Z^4$ is C(R$^2$)$_p$;

$Z^5$ is C(R$^2$)$_p$ or C(O); or any one or two of $Z^4$ and $Z^5$, together with A-$Z^1$ or B-A-$Z^1$, form a 3- to 6-membered ring, wherein the ring and ring G form a fused or bridged ring structure, or when X is CR$^{14}$R$^{15}$ or NR$^{16}$, $Z^4$—N—(Z$^7$)$_t$—X form a 4- to 6-membered ring;

p is 1 or 2;

each R$^2$ is independently H, halogen, OH, $C_1$-$C_6$ alkyl, CF$_3$, O—$C_1$-$C_6$ alkyl, OCF$_3$, OCHF$_2$, OCH$_2$F, $C_3$-$C_8$ cycloalkyl, $C_3$-$C_8$ heterocycle, $C_6$-$C_{10}$ aryl, O—$C_6$-$C_{10}$ aryl, C(O)—$C_1$-$C_6$ alkyl, C(O)NR$^{17}$R$^{18}$, NR$^{17}$R$^{18}$, NR$^{17}$C(O)—$C_1$-$C_6$ alkyl, S(O)$_2$NR$^{17}$R$^{18}$, or NR$^{17}$S(O)$_2$—$C_1$-$C_6$ alkyl, or any two R$^2$ bonded to different carbon atoms, together with the carbon atoms to which the two R$^2$ are bonded, form a 4- to 7-membered ring, or any two R$^2$ bonded to the same carbon atom, together with the carbon atom to which the two R$^2$ are bonded, form a 3- to 6-membered ring, or R$^2$, together with the carbon atom to which the R$^2$ is bonded, and $Z^1$—R$^5$, form a 4- to 6-membered ring, wherein the ring and ring G form a fused or bridged ring structure, provided that when R$^2$ is bonded to a carbon atom adjacent to the nitrogen atom in ring G, then R$^2$ is H, halogen, $C_1$-$C_6$ alkyl, CF$_3$, $C_3$-$C_8$ cycloalkyl, $C_3$-$C_8$ heterocycloalkyl, $C_6$-$C_{10}$ aryl, C(O)—$C_1$-$C_6$ alkyl, C(O)NR$^{17}$R$^{18}$, or S(O)$_2$NR$^{17}$R$^{18}$;

$Z^6$ is a carbon atom;

R$^1$ is H or $C_1$-$C_6$ alkyl, or when A-B—$Z^6$ form a 3- to 6-membered ring, absent, or B—$Z^6$—R$^1$ form a 3- to 6-membered ring;

Cy$^1$ and Cy$^2$ are each independently H, $C_1$-$C_6$ alkyl, $C_6$-$C_{10}$ aryl, heteroaryl comprising one or two 5- or 6-membered rings and one to four heteroatoms selected from N, O, and S, $C_3$-$C_{10}$ cycloalkyl, $C_5$-$C_{13}$ bicyclic group, or heterocyclyl comprising one or two 3- to 6-membered rings and one to four heteroatoms selected from N, O, and S, wherein the aryl, heteroaryl, cycloalkyl, bicyclic group, and heterocycyl are each independently optionally substituted with one or more substituents independently selected from:

halogen, CH$_2$F, CHF$_2$, CF$_3$, $C_1$-$C_6$ alkyl, $C_3$-$C_8$ cycloalkyl, OH, O—$C_1$-$C_6$ alkyl, OCF$_3$, OCHF$_2$, OCH$_2$F, $C_6$-$C_{10}$ aryl, heteroaryl comprising one 5- or 6-membered ring and one to four heteroatoms selected from N, O, and S, and NR$^{17}$R$^{18}$, or A-B—$Z^6$-Cy$^1$ or A-B—$Z^6$-Cy$^2$ form a 4- to 8-membered ring, or B—$Z^6$-Cy$^1$ or B—$Z^6$-Cy$^2$ form a 3- to 6-membered ring;

$Z^7$ is C(R$^3$)$_w$, or when X is CR$^{14}$R$^{15}$ or NR$^{16}$, $Z^3$—N—(Z$^7$)$_t$—X or $Z^4$—N—(Z$^7$)$_t$—X form a 4- to 6-membered ring, or when X is CR$^{14}$R$^{15}$, $Z^7$—X, together with R$^{14}$ or R$^{15}$, form a 3- to 6-membered ring, or when X is NR$^{16}$, $Z^7$—X, together with R$^{16}$, form a 3- to 6-membered ring, or $Z^7$—X—$Z^8$ form a 3- to 6-membered ring, or $Z^7$—X—$Z^8$-Cy$^3$ form a 4- to 6-membered ring;

each w is independently 1 or 2;

t is 1, 2, 3, or 4, provided that when X is O, S, S(O), S(O)$_2$, or NR$^{16}$, then t is not 1;

each R$^3$ is independently H, halogen, $C_1$-$C_6$ alkyl, $C_3$-$C_8$ cycloalkyl, $C_3$-$C_8$ heterocycle, OH, O—$C_1$-$C_6$ alkyl, S—$C_1$-$C_6$ alkyl, NR$^{17}$R$^{18}$, C(O)NR$^{17}$R$^{18}$, NR$^{17}$C(O)—$C_1$-$C_6$ alkyl, NR$^{17}$S(O)$_2$—$C_1$-$C_6$ alkyl, or S(O)$_2$NR$^{17}$R$^{18}$, or any two R$^3$ bonded to the same carbon atom, together with the carbon atom to which the two R$^3$ are bonded, form C═O, provided that the C═O is not directly bonded to the nitrogen atom in ring G, or any two R$^3$ bonded to the same carbon atom or different carbon atoms, together with the one or two carbon atoms to which the two R$^3$ are bonded, form a 3- to 6-membered ring, provided that when X is O, S, or NR$^{16}$, then the R$^3$ in the C(R$^3$)$_w$ directly bonded to X is not OH, O—$C_1$-$C_6$ alkyl, S—$C_1$-$C_6$ alkyl, NR$^{17}$R$^{18}$, NR$^{17}$C(O)—$C_1$-$C_6$ alkyl, NR$^{17}$S(O)$_2$—$C_1$-$C_6$ alkyl, or S(O)$_2$NR$^{17}$R$^{18}$;

X is a bond, O, CR$^{14}$R$^{15}$, S, S(O), S(O)$_2$, C═O, or NR$^{16}$, or when X is CR$^{14}$R$^{15}$ or NR$^{16}$, $Z^3$—N—$Z^7$—X or $Z^4$—N—$Z^7$—X form a 4- to 6-membered ring, or when X is CR$^{14}$R$^{15}$, $Z^7$—X or $Z^8$—X, together with R$^{14}$ or R$^{15}$, form a 3- to 6-membered ring, or when X is NR$^{16}$, $Z^7$—X or $Z^8$—X, together with R$^{16}$, form a 3- to 6-membered ring, or $Z^7$—X—$Z^8$ form a 3- to 6-membered ring, or $Z^7$—X—$Z^8$-Cy$^3$ form a 4- to 6-membered ring, or X—$Z^8$-Cy$^3$ form a 3- to 6-membered ring;

provided that when X is O, S, S(O), S(O)$_2$, or NR$^{16}$, then t is 2, 3, or 4;

R$^{14}$ and R$^{15}$ are each independently, H, halogen, $C_1$-$C_6$ alkyl, $C_3$-$C_6$ cycloalkyl, phenyl, or heteroaryl comprising one 5- or 6-membered ring and one to four heteroatoms selected from N, O, and S, or R$^{14}$ and R$^{15}$, together with the carbon atom to which R$^{14}$ and R$^{15}$ are bonded, form $C_3$-$C_6$ cycloalkyl, $C_5$-$C_{13}$ bicyclic group, or heterocyclyl comprising one or two 3- to 6-membered rings and one to four heteroatoms selected from N, O, and S, or when $Z^3$—N—$Z^7$—X or $Z^4$—N—$Z^7$—X form a 4- to 6-membered ring, absent, or $R^{14}$ or $R^{15}$, together with $Z^7$—X or $Z^8$—X, form a 3- to 6-membered ring;

$R^{16}$ is, H, $C_1$-$C_6$ alkyl, phenyl, heteroaryl comprising one 5- or 6-membered ring and one to four heteroatoms selected from N, O, and S, C(O)—$C_1$-$C_6$ alkyl, C(O)-phenyl, C(O)O—$C_1$-$C_6$ alkyl, C(O)$NR^{17}R^{18}$, S(O)$_2$—$C_1$-$C_6$ alkyl, or S(O)$_2NR^{17}R^{18}$, or when $Z^3$—N—$Z^7$—X or $Z^4$—N—$Z^7$—X form a 4- to 6-membered ring, absent, or $R^{16}$, together with $Z^7$—X or $Z^8$—X, form a 3- to 6-membered ring;

$Z^8$ is $C(R^4)_n$, or when X is $CR^{14}R^{15}$, $Z^8$—X, together with $R^{14}$ or $R^{15}$, form a 3- to 6-membered ring, or when X is $NR^{16}$, $Z^8$—X, together with $R^{16}$, form a 3- to 6-membered ring, or $Z^7$—X—$Z^8$ form a 3- to 6-membered ring, or $Z^7$—X—$Z^8$-$Cy^3$ form a 4- to 6-membered ring, or X—$Z^8$-$Cy^3$ form a 3- to 6-membered ring, or $Z^8$, together with $R^4$ and $Cy^3$, form a 3- to 6-membered ring;

each u is independently 1 or 2;

n is 0, 1, or 2;

each $R^4$ is independently H, halogen, $C_1$-$C_6$ alkyl, $C_3$-$C_8$ cycloalkyl, $C_3$-$C_8$ heterocycle, OH, O—$C_1$-$C_6$ alkyl, S—$C_1$-$C_6$ alkyl, $NR^{17}R^{18}$, C(O)$NR^{17}R^{18}$, $NR^{17}$C(O)—$C_1$-$C_6$ alkyl, $NR^{17}$S(O)$_2$—$C_1$-$C_6$ alkyl, or S(O)$_2NR^{17}R^{18}$, or any two $R^4$ bonded to the same carbon atom, together with the carbon atom to which the two $R^4$ are bonded, form C=O, or any two $R^4$ bonded to the same carbon atom or on different carbon atoms, together with the one or two carbon atoms to which the two $R^4$ are bonded, form a 3- to 6-membered ring, or $R^4$, together with $Z^8$-$Cy^3$, form a 3- to 6-membered ring, provided that when X is O, S, or $NR^{16}$, then the $R^4$ in the $C(R^4)_n$ directly bonded to X is not OH, O—$C_1$-$C_6$ alkyl, S—$C_1$-$C_6$ alkyl, or $NR^{17}R^{18}$; and $Cy^3$ is H, $C_1$-$C_6$ alkyl, $C_6$-$C_{10}$ aryl, heteroaryl comprising one or two 5- or 6-membered rings and one to four heteroatoms selected from N, O, and S, $C_3$-$C_{10}$ cycloalkyl, $C_5$-$C_{13}$ bicyclic group, or heterocyclyl comprising one or two 3- to 6-membered rings and one to four heteroatoms selected from N, O, and S, wherein the aryl, heteroaryl, cycloalkyl, bicyclic group, and heterocycyl are each independently optionally substituted with one or more substituents independently selected from:

halogen, $CH_2F$, $CHF_2$, $CF_3$, $C_1$-$C_6$ alkyl, $C_3$-$C_8$ cycloalkyl, OH, O—$C_1$-$C_6$ alkyl, $OCF_3$, $OCHF_2$, $OCH_2F$, $C_6$-$C_{10}$ aryl, heteroaryl comprising one 5- or 6-membered ring and one to four heteroatoms selected from N, O, and S, and $NR^{17}R^{18}$, or $Z^7$—X—$Z^8$-$Cy^3$ form a 4- to 6-membered ring, or X—$Z^8$-$Cy^3$ form a 3- to 6-membered ring, or $Z^8$-$Cy^3$, together with $R^4$, form a 3- to 6-membered ring, provided that when $Z^7$—X—$Z^8$ is $(CH_2)_{1-6}$, then $Cy^3$ is not phenyl, which is optionally substituted, methylenedioxyphenyl, isoindoline-1,3,-dione, or dihydrobenzofuranyl.

In certain embodiments, a compound of the invention is of Formula I, or a stereoisomer, racemate, tautomer, polymorph, hydrate, or solvate thereof, or a pharmaceutically acceptable salt thereof, wherein:

A-B is C(O)—$NR^{13}$, C(O)—$CR^{11}R^{12}$, C(O)—O. $CR^{11}R^{12}$—$NR^{13}$, $CR^{11}R^{12}$—O, $CR^{11}R^{12}$, C(O), $NR^{13}$—C(O), $NR^{13}$—$CR^{11}R^{12}$, O—$CR^{11}R^{12}$, or O—C(O), wherein $CR^{11}R^{12}$—$NR^{13}$ or $NR^{13}$, $CR^{11}R^{12}$ can form a 3- to 6-membered ring, or A-$Z^1$—$R^5$ form a 3- to 6-membered ring, and B is C(O), $CR^{11}R^{12}$, O, or $NR^{13}$, or A—$Z^1$, together with any one or two of $Z^2$ and $Z^3$, or any one or two of $Z^4$ and $Z^5$, form a 3- to 6-membered ring, wherein the ring and ring G form a fused or bridged ring structure, and B is C(O), $CR^{11}R^{12}$, O, or $NR^{13}$, or B—$Z^6$-$Cy^1$ or B—$Z^6$-$Cy^2$ form a 3- to 6-membered ring, and A is C(O), $CR^{11}R^{12}$, O, or $NR^{13}$, or B—$Z^6$—$R^1$ form a 3- to 6-membered ring, and A is C(O), $CR^{11}R^{12}$, O, or $NR^{13}$, or A-B—$Z^6$-$Cy^1$ or A-B—$Z^6$-$Cy^2$ form a 5- to 8-membered ring, or A-B—$Z^6$ form a 3- to 6-membered ring, or B-A-$Z^1$ form a 3- to 6-membered ring, or B-A-$Z^1$, together with any one or two of $Z^2$ and $Z^3$, or any one or two of $Z^4$ and $Z^5$, form a 4- to 6-membered ring, wherein the ring and ring G form a fused or bridged ring structure;

$R^{11}$ and $R^{12}$ are each independently H, halogen, or $C_1$-$C_6$ alkyl, or $R^{11}$ and $R^{12}$, together with the carbon atom to which $R^{11}$ and $R^{12}$ are bonded, form a 3- to 6-membered ring, provided that when $CR^{11}R^{12}$—$NR^{13}$ or $NR^{13}$—$CR^{11}R^{12}$ forms a 3- to 6-membered ring, one of $R^{11}$ and $R^{12}$ is absent;

$R^{13}$ is H, $C_1$-$C_6$ alkyl, $C_3$-$C_6$ cycloalkyl, $C_3$-$C_6$ heterocycle, $C_6$-$C_{10}$ aryl, heteroaryl comprising one or two 5- or 6-membered rings and one to four heteroatoms selected from N, O, and S, C(O)—$C_1$-$C_6$ alkyl, C(O)-phenyl, C(O)O—$C_1$-$C_6$ alkyl, C(O)$NR^{17}R^{18}$, S(O)$_2$—$C_1$-$C_6$ alkyl, or S(O)$_2NR^{17}R^{18}$, provided that when $CR^{11}R^{12}$—$NR^{13}$ or $NR^{13}$—$CR^{11}R^{12}$ forms a 3- to 6-membered ring, $R^{13}$ is absent;

$R^{17}$ and $R^{18}$ are each independently H, $C_1$-$C_6$ alkyl, or $C_6$-$C_{10}$ aryl;

$Z^1$ is a carbon atom;

$R^5$ is H, halogen, OH, $C_1$-$C_6$ alkyl, O—$C_1$-$C_6$ alkyl, $OCF_3$, $OCHF_2$, $OCH_2F$, $NR^{17}R^{18}$, $NR^{17}$C(O)—$C_1$-$C_6$ alkyl, C(O)$NR^{17}R^{18}$, S—$C_1$-$C_6$ alkyl, S(O)—$C_1$-$C_6$ alkyl, S(O)$_2$—$C_1$-$C_6$ alkyl, S(O)$_2NR^{17}R^{18}$, $NR^{17}$S(O)$_2$—$C_1$-$C_6$ alkyl, $C_6$-$C_{10}$ aryl, phenyl, benzyl, heteroaryl comprising one 5- or 6-membered ring and one to four heteroatoms selected from N, O, and S, $C_3$-$C_6$ cycloalkyl, or heterocyclyl comprising one 4- to 6-membered ring and one to four heteroatoms selected from N, O, and S, or when B-A-$Z^1$ form a 3- to 6-membered ring, absent, or A-$Z^1$—$R^5$ form a 3- to 6-membered ring, or $Z^1$—$R^5$, together with $R^2$ and the carbon atom to which the $R^2$ is bonded, form a 4- to 6-membered ring, wherein the ring and ring G form a fused or bridged ring structure, provided that when A-B is $NR^{13}$—C(O), $NR^{13}$—$CR^{11}R^{12}$, O—$CR^{11}R^{12}$, or O—C(O), then $R^5$ is not OH, O—$C_1$-$C_6$ alkyl, S—$C_1$-$C_6$ alkyl, $NR^{17}R^{18}$, $NR^{17}$C(O)—$C_1$-$C_6$ alkyl, or $NR^{17}$S(O)$_2$—$C_1$-$C_6$ alkyl;

$Z^2$ is $C(R^2)_p$ or C(O);

$Z^3$ is $C(R^2)_p$; or any one or two of $Z^2$ and $Z^3$, together with A-$Z^1$ or B-A-$Z^1$, form a 3- to 6-membered ring, wherein the ring and ring G form a fused or bridged ring structure, or when X is $CR^{14}R^{15}$ or $NR^{16}$, $Z^3$—N—$(Z^7)_t$—X form a 4- to 6-membered ring;

$Z^4$ is $C(R^2)_p$;

$Z^5$ is $C(R^2)_p$ or C(O); or any one or two of $Z^4$ and $Z^5$, together with A-$Z^1$ or B-A-$Z^1$, form a 3- to 6-membered ring, wherein the ring and ring G form a fused or bridged ring structure, or when X is $CR^{14}R^{15}$ or $NR^{16}$, $Z^4$—N—$(Z^7)_t$—X form a 4- to 6-membered ring;

p is 1 or 2;

each $R^2$ is independently H, halogen, OH, $C_1$-$C_6$ alkyl, $CF_3$, O—$C_1$-$C_6$ alkyl, $OCF_3$, $OCHF_2$, $OCH_2F$, $C_3$-$C_8$ cycloalkyl, $C_3$-$C_8$ heterocycle, $C_6$-$C_{10}$ aryl, O—$C_6$-$C_{10}$ aryl, C(O)—$C_1$-$C_6$ alkyl, C(O)$NR^{17}R^{18}$, $NR^{17}R^{18}$, $NR^{17}C(O)$—$C_1$-$C_6$ alkyl, $S(O)_2NR^{17}R^{18}$, or $NR^{17}S(O)_2$—$C_1$-$C_6$ alkyl, or any two $R^2$ bonded to different carbon atoms, together with the carbon atoms to which the two $R^2$ are bonded, form a 4- to 7-membered ring, or any two $R^2$ bonded to the same carbon atom, together with the carbon atom to which the two $R^2$ are bonded, form a 3- to 6-membered ring, or $R^2$, together with the carbon atom to which the $R^2$ is bonded, and $Z^1$—$R^5$, form a 4- to 6-membered ring, wherein the ring and ring G form a fused or bridged ring structure, provided that when $R^2$ is bonded to a carbon atom adjacent to the nitrogen atom in ring G, then $R^2$ is H, halogen, $C_1$-$C_6$ alkyl, $CF_3$, $C_3$-$C_8$ cycloalkyl, $C_3$-$C_8$ heterocycloalkyl, $C_6$-$C_{10}$ aryl, C(O)—$C_1$-$C_6$ alkyl, C(O)$NR^{17}R^{18}$, or $S(O)_2NR^{17}R^{18}$;

$Z^6$ is a carbon atom;

$R^1$ is H or $C_1$-$C_6$ alkyl, or when A-B—$Z^6$ form a 3- to 6-membered ring, absent, or B—$Z^6$—$R^1$ form a 3- to 6-membered ring;

$Cy^1$ and $Cy^2$ are each independently H, $C_1$-$C_6$ alkyl, $C_6$-$C_{10}$ aryl, heteroaryl comprising one or two 5- or 6-membered rings and one to four heteroatoms selected from N, O, and S, $C_3$-$C_{10}$ cycloalkyl, $C_5$-$C_{13}$ bicyclic group, or heterocyclyl comprising one or two 3- to 6-membered rings and one to four heteroatoms selected from N, O, and S, wherein the aryl, heteroaryl, cycloalkyl, bicyclic group, and heterocycyl are each independently optionally substituted with one or more substituents independently selected from:

halogen, $CH_2F$, $CHF_2$, $CF_3$, $C_1$-$C_6$ alkyl, $C_3$-$C_8$ cycloalkyl, OH, O—$C_1$-$C_6$ alkyl, $OCF_3$, $OCHF_2$, $OCH_2F$, $C_6$-$C_{10}$ aryl, heteroaryl comprising one 5- or 6-membered ring and one to four heteroatoms selected from N, O, and S, and $NR^{17}R^{18}$, or A-B—$Z^6$-$Cy^1$ or A-B—$Z^6$-$Cy^2$ form a 4- to 8-membered ring, or B—$Z^6$-$Cy^1$ or B—$Z^6$-$Cy^2$ form a 3- to 6-membered ring;

$Z^7$ is $C(R^3)_w$, or when X is $CR^{14}R^{15}$ or $NR^{16}$, $Z^3$—N—$(Z^7)_t$—X or $Z^4$—N—$(Z^7)_t$—X form a 4- to 6-membered ring, or when X is $CR^{14}R^{15}$, $Z^7$—X, together with $R^{14}$ or $R^{15}$, form a 3- to 6-membered ring, or when X is $NR^{16}$, $Z^7$—X, together with $R^{16}$, form a 3- to 6-membered ring, or $Z^7$—X—$Z^8$ form a 3- to 6-membered ring, or $Z^7$—X—$Z^8$-$Cy^3$ form a 4- to 6-membered ring;

each w is independently 1 or 2;

t is 1, 2, 3, or 4, provided that when X is O, S, S(O), $S(O)_2$, or $NR^{16}$, then t is not 1;

each $R^3$ is independently H, halogen, $C_1$-$C_6$ alkyl, $C_3$-$C_8$ cycloalkyl, $C_3$-$C_8$ heterocycle, OH, O—$C_1$-$C_6$ alkyl, S—$C_1$-$C_6$ alkyl, $NR^{17}R^{18}$, C(O)$NR^{17}R^{18}$, $NR^{17}C(O)$—$C_1$-$C_6$ alkyl, $NR^{17}S(O)_2$—$C_1$-$C_6$ alkyl, or $S(O)_2NR^{17}R^{18}$, or any two $R^3$ bonded to the same carbon atom, together with the carbon atom to which the two $R^3$ are bonded, form C=O, provided that the C=O is not directly bonded to the nitrogen atom in ring G, or any two $R^3$ bonded to the same carbon atom or different carbon atoms, together with the one or two carbon atoms to which the two $R^3$ are bonded, form a 3- to 6-membered ring, provided that when X is O, S, or $NR^{16}$, then the $R^3$ in the $C(R^3)_w$ directly bonded to X is not OH, O—$C_1$-$C_6$ alkyl, S—$C_1$-$C_6$ alkyl, $NR^{17}R^{18}$, $NR^{17}C(O)$—$C_1$-$C_6$ alkyl, $NR^{17}S(O)_2$—$C_1$-$C_6$ alkyl, or $S(O)_2NR^{17}R^{18}$;

X is a bond, O, $CR^{14}R^{15}$, S, S(O), $S(O)_2$, C=O, or $NR^{16}$, or when X is $CR^{14}R^{15}$ or $NR^{16}$, $Z^3$—N—$Z^7$—X or $Z^4$—N—$Z^7$—X form a 4- to 6-membered ring, or when X is $CR^{14}R^{15}$, $Z^7$—X or $Z^8$—X, together with $R^{14}$ or $R^{15}$, form a 3- to 6-membered ring, or when X is $NR^{16}$, $Z^7$—X or $Z^8$—X, together with $R^{16}$, form a 3- to 6-membered ring, or $Z^7$—X—$Z^8$ form a 3- to 6-membered ring, or $Z^7$—X—$Z^8$-$Cy^3$ form a 4- to 6-membered ring, or X—$Z^8$-$Cy^3$ form a 3- to 6-membered ring;

provided that when X is O, S, S(O), $S(O)_2$, or $NR^{16}$, then t is 2, 3, or 4;

$R^{14}$ and $R^{15}$ are each independently, H, halogen, $C_1$-$C_6$ alkyl, $C_3$-$C_6$ cycloalkyl, phenyl, or heteroaryl comprising one 5- or 6-membered ring and one to four heteroatoms selected from N, O, and S, or $R^{14}$ and $R^{15}$, together with the carbon atom to which $R^{14}$ and $R^{15}$ are bonded, form $C_3$-$C_6$ cycloalkyl, $C_5$-$C_{13}$ bicyclic group, or heterocyclyl comprising one or two 3- to 6-membered rings and one to four heteroatoms selected from N, O, and S, or when $Z^3$—N—$Z^7$—X or $Z^4$—N—$Z^7$—X form a 4- to 6-membered ring, absent, or $R^{14}$ or $R^{15}$, together with $Z^7$—X or $Z^8$—X, form a 3- to 6-membered ring;

$R^{16}$ is, H, $C_1$-$C_6$ alkyl, phenyl, heteroaryl comprising one 5- or 6-membered ring and one to four heteroatoms selected from N, O, and S, C(O)—$C_1$-$C_6$ alkyl, C(O)-phenyl, C(O)O—$C_1$-$C_6$ alkyl, C(O)$NR^{17}R^{18}$, $S(O)_2$—$C_1$-$C_6$ alkyl, or $S(O)_2NR^{17}R^{18}$, or when $Z^3$—N—$Z^7$—X or $Z^4$—N—$Z^7$—X form a 4- to 6-membered ring, absent, or $R^{16}$, together with $Z^7$—X or $Z^8$—X, form a 3- to 6-membered ring;

$Z^8$ is $C(R^4)_n$, or when X is $CR^{14}R^{15}$, $Z^8$—X, together with $R^{14}$ or $R^{15}$, form a 3- to 6-membered ring, or when X is $NR^{16}$, $Z^8$—X, together with $R^{16}$, form a 3- to 6-membered ring, or $Z^7$—X—$Z^8$ form a 3- to 6-membered ring, or $Z^7$—X—$Z^8$-$Cy^3$ form a 4- to 6-membered ring, or X—$Z^8$-$Cy^3$ form a 3- to 6-membered ring, or $Z^8$, together with $R^4$ and $Cy^3$, form a 3- to 6-membered ring;

each u is independently 1 or 2;

n is 0, 1, or 2;

each $R^4$ is independently H, halogen, $C_1$-$C_6$ alkyl, $C_3$-$C_8$ cycloalkyl, $C_3$-$C_8$ heterocycle, OH, O—$C_1$-$C_6$ alkyl, S—$C_1$-$C_6$ alkyl, $NR^{17}R^{18}$, C(O)$NR^{17}R^{18}$, $NR^{17}C(O)$—$C_1$-$C_6$ alkyl, $NR^{17}S(O)_2$—$C_1$-$C_6$ alkyl, or $S(O)_2NR^{17}R^{18}$, or any two $R^4$ bonded to the same carbon atom, together with the carbon atom to which the two $R^4$ are bonded, form C=O, or any two $R^4$ bonded to the same carbon atom or on different carbon atoms, together with the one or two carbon atoms to which the two $R^4$ are bonded, form a 3- to 6-membered ring, or $R^4$, together with $Z^8$-$Cy^3$, form a 3- to 6-membered ring, provided that when X is O, S, or $NR^{16}$, then the $R^4$ in the $C(R^4)_n$ directly bonded to X is not OH, O—$C_1$-$C_6$ alkyl, S—$C_1$-$C_6$ alkyl, or $NR^{17}R^{18}$; and $Cy^3$ is H, $C_1$-$C_6$ alkyl, $C_6$-$C_{10}$ aryl, heteroaryl comprising one or two 5- or 6-membered rings and one to four heteroatoms selected from N, O, and S, $C_3$-$C_{10}$ cycloalkyl, $C_5$-$C_{13}$ bicyclic group, or heterocyclyl comprising one or two 3- to 6-membered rings and one to four heteroatoms selected from N, O, and S, wherein the aryl, heteroaryl, cycloalkyl, bicyclic group, and heterocyclyl are each independently optionally substituted with one or more substituents independently selected from:

halogen, $CH_2F$, $CHF_2$, $CF_3$, $C_1$-$C_6$ alkyl, $C_3$-$C_8$ cycloalkyl, OH, O—$C_1$-$C_6$ alkyl, $OCF_3$, $OCHF_2$, $OCH_2F$, $C_6$-$C_{10}$ aryl, heteroaryl comprising one 5- or 6-membered ring and one to four heteroatoms selected from N, O, and S, and $NR^{17}R^{18}$, or $Z^7$—X—$Z^8$-$Cy^3$ form a 4- to 6-membered ring, or X—$Z^8$-$Cy^3$ form a 3- to 6-membered ring, or $Z^8$-$Cy^3$, together with $R^4$, form a 3- to 6-membered ring, provided that when $Z^7$—X—$Z^8$ is $(CH_2)_{1-6}$, then $Cy^3$ is not phenyl, which is optionally substituted, methylenedioxyphenyl, isoindoline-1,3,-dione, or dihydrobenzofuranyl.

The language "$A^1$-$A^2$ forms a ring," wherein each of $A^1$ and $A^2$ is a moiety described herein, refers to taken together $A^1$ and $A^2$ forming a ring. The language "$A^1$-$A^2$-$A^3$ forms a ring," wherein each of $A^1$, $A^2$, and $A^3$ is a moiety described herein, refers to taken together, with the intervening $A^2$, $A^1$ and $A^3$ forming a ring. The language "$A^1$-$A^2$-$A^3$-$A^4$ forms a ring," wherein each of $A^1$, $A^2$, $A^3$, and $A^4$ is a moiety described herein, refers to taken together, with the intervening $A^2$ and $A^3$, $A^1$ and $A^4$ forming a ring.

In some embodiments, $Cy^1$, $Cy^2$ and $Cy^3$ are each different. In further embodiments, $Cy^1$ and $Cy^2$ are different.

In certain embodiments, none of $Cy^1$ and $Cy^2$ is H. In certain embodiments, $Cy^3$ is not H. In certain embodiments, each of $Cy^1$, $Cy^2$, and $Cy^3$ is not H. In certain embodiments, each of $Cy^1$ and $Cy^2$ is not H or $C_1$-$C_6$ alkyl. In certain embodiments, $Cy^3$ is not H or $C_1$-$C_6$ alkyl. In certain embodiments, each of $Cy^1$, $Cy^2$, and $Cy^3$ is not H or $C_1$-$C_6$ alkyl.

In some embodiments, $Cy^1$, $Cy^2$ or $Cy^3$ is independently $C_6$-$C_{10}$ aryl, heteroaryl comprising one or two 5- or 6-membered rings and one to four heteroatoms selected from N, O, and S, $C_3$-$C_{10}$ cycloalkyl, or $C_5$-$C_{13}$ bicyclic group, wherein the aryl, heteroaryl, cycloalkyl, and bicyclic group are each independently optionally substituted with one or more substituents independently selected from halogen, $CH_2F$, $CHF_2$, $CF_3$, $C_1$-$C_6$ alkyl, OH, O—$C_1$-$C_6$ alkyl, $OCF_3$, $OCHF_2$, $OCH_2F$, and $NR^{17}R^{18}$. In further embodiments, $Cy^1$, $Cy^2$ or $Cy^3$ is independently phenyl, dihydroindenyl, pyridyl, pyridinonyl, quinolinyl, benzodihydrodioxinyl, quinolinonyl, benzofuranyl, benzoxazolyl, benzothiazolyl, or methylenedioxyphenyl, each of which is independently optionally substituted with one or more substituents independently selected from Cl, F, $CF_3$, methyl, OH, $OCH_3$, and $OCF_3$.

In other embodiments, $Cy^1$, $Cy^2$ or $Cy^3$ is independently $C_3$-$C_{10}$ cycloalkyl (e.g., cyclohexyl) or $C_5$-$C_{13}$ bicyclic group, wherein the cycloalkyl and bicyclic group are each independently optionally substituted with one or more substituents independently selected from halogen, $CH_2F$, $CHF_2$, $CF_3$, $C_1$-$C_6$ alkyl, OH, O—$C_1$-$C_6$ alkyl, $OCF_3$, $OCHF_2$, $OCH_2F$, and $NR^{17}R^{18}$.

In other embodiments, $Cy^1$, $Cy^2$ or $Cy^3$ is independently heterocyclyl comprising one or two 3- to 6-membered rings and one to four heteroatoms selected from N, O, and S, wherein the heterocyyl is optionally substituted with one or more substituents independently selected from halogen, $CH_2F$, $CHF_2$, $CF_3$, $C_1$-$C_6$-alkyl, OH, O—$C_1$-$C_6$-alkyl, $OCF_3$, $OCHF_2$, $OCH_2F$, and $NR^{17}R^{18}$.

In other embodiments, $Cy^1$, $Cy^2$ or $Cy^3$ is independently $C_5$-$C_{13}$ bicyclic group, wherein the bicyclic group includes spirocyclic rings or fused rings, and the bicyclic group includes aromatic, partially saturated, and/or saturated rings. In further embodiments, $Cy^1$, $Cy^2$ or $Cy^3$ is independently

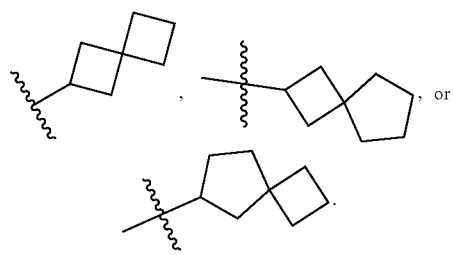

In certain embodiments, each of $Cy^1$ and $Cy^2$ is phenyl, wherein the phenyl groups are independently optionally substituted with one or more substituents as described herein.

In certain embodiments, $Cy^1$ is phenyl, and $Cy^2$ is heteroaryl comprising one 5- or 6-membered ring and one to four heteroatoms selected from N, O, and S, wherein the phenyl and the heteroaryl are independently optionally substituted with one or more substituents as described herein. In certain embodiments, $Cy^1$ is phenyl, and $Cy^2$ is pyridyl, wherein the phenyl and the pyridyl are independently optionally substituted with one or more substituents as described herein. In certain embodiments, $Cy^1$ is phenyl, and $Cy^2$ is 2-pyridyl, wherein the phenyl and the 2-pyridyl are independently optionally substituted with one or more substituents as described herein. In certain embodiments, $Cy^1$ is phenyl, and $Cy^2$ is 3-pyridyl or 4-pyridyl, wherein the phenyl, the 3-pyridyl, and the 4-pyridyl are independently optionally substituted with one or more substituents as described herein.

In certain embodiments, $Cy^1$ is phenyl, and $Cy^2$ is oxazolyl (e.g., 4-oxazolyl), wherein the phenyl and the oxazolyl (e.g., 4-oxazolyl) are independently optionally substituted with one or more substituents as described herein.

In certain embodiments, $Cy^1$ is phenyl, and $Cy^2$ is heteroaryl comprising one 5- or 6-membered rings that are fused to each other and one to four heteroatoms selected from N, O, and S, wherein the phenyl and the heteroaryl are independently optionally substituted with one or more substituents as described herein. In certain embodiments, $Cy^1$ is phenyl, and $Cy^2$ is quinolinyl (e.g., 2-quinolinyl), wherein the phenyl and the quinolinyl (e.g., 2-quinolinyl) are independently optionally substituted with one or more substituents as described herein.

In certain embodiments, each of $Cy^1$ and $Cy^2$ is heteroaryl comprising one 5- or 6-membered ring and one to four heteroatoms selected from N, O, and S, wherein the phenyl and the heteroaryl are independently optionally substituted with one or more substituents as described herein. In certain embodiments, each of $Cy^1$ and $Cy^2$ is pyridyl, wherein the pyridyl groups are independently optionally substituted with one or more substituents as described herein. In certain embodiments, $Cy^1$ is pyridyl, and $Cy^2$ is 2-pyridyl, wherein the pyridyl and the 2-pyridyl are independently optionally substituted with one or more substituents as described herein. In certain embodiments, $Cy^1$ is pyridyl, and $Cy^2$ is 3-pyridyl or 4-pyridyl, wherein the pyridyl, the 3-pyridyl, and the 4-pyridyl are independently optionally substituted with one or more substituents as described herein.

In certain embodiments, $Cy^1$ is a $C_5$-$C_{13}$ bicyclic group (e.g., phenyl fused with monocylic, 5- to 6-membered heterocyclyl, wherein 1 or 2 atoms in the heterocyclyl ring system are independently N, O, or S), and $Cy^2$ is heteroaryl comprising one 5- or 6-membered ring and one to four heteroatoms selected from N, O, and S, wherein the $C_5$-$C_{13}$ bicyclic group and the heteroaryl are independently optionally substituted with one or more substituents as described herein. In certain embodiments, $Cy^1$ is a $C_5$-$C_{13}$ bicyclic group (e.g., phenyl fused with monocylic, 5- to 6-membered heterocyclyl, wherein 1 or 2 atoms in the heterocyclyl ring system are independently N, O, or S), and $Cy^2$ is pyridyl (e.g., 2-pyridyl), wherein the $C_5$-$C_{13}$ bicyclic group and the pyridyl (e.g., 2-pyridyl) are independently optionally substituted with one or more substituents as described herein.

In certain embodiments, $Cy^1$ is $C_3$-$C_{10}$ cycloalkyl (e.g., cyclohexyl), and $Cy^2$ is heteroaryl comprising one 5- or 6-membered ring and one to four heteroatoms selected from N, O, and S, wherein the $C_3$-$C_{10}$ cycloalkyl (e.g., cyclohexyl) and the heteroaryl are independently optionally substituted with one or more substituents as described herein. In certain embodiments, $Cy^1$ is $C_3$-$C_{10}$ cycloalkyl (e.g., cyclohexyl), and $Cy^2$ is pyridyl (e.g., 2-pyridyl), wherein the $C_3$-$C_{10}$ cycloalkyl (e.g., cyclohexyl) and the pyridyl (e.g., 2-pyridyl) are independently optionally substituted with one or more substituents as described herein.

In certain embodiments, $Cy^3$ is $C_1$-$C_6$ alkyl (e.g., Me).

In certain embodiments, $Cy^3$ is unsubstituted phenyl.

In certain embodiments, $Cy^3$ is phenyl substituted with one or more substituents as described herein.

In certain embodiments, $Cy^3$ is heterocyclyl comprising one 3- to 6-membered ring and one to four heteroatoms selected from N, O, and S, wherein the heterocyyl is optionally substituted with one or more substituents as described herein. In certain embodiments, $Cy^3$ is heterocyclyl comprising one 6-membered ring and one to four heteroatoms selected from N, O, and S, wherein the heterocycyl is optionally substituted with one or more substituents as described herein. In certain embodiments, $Cy^3$ is heterocyclyl comprising one 3- to 6-membered ring and one heteroatom selected from N, wherein the heterocycyl is optionally substituted with one or more substituents as described herein.

In certain embodiments, $Cy^3$ is heteroaryl comprising one 5- or 6-membered ring and one to four heteroatoms selected from N, O, and S, wherein the heteroaryl is optionally substituted with one or more substituents as described herein. In certain embodiments, $Cy^3$ is pyridyl (e.g., 2-pyridyl, 3-pyridyl, or 4-pyridyl), wherein the pyridyl (e.g., 2-pyridyl, 3-pyridyl, or 4-pyridyl) is optionally substituted with one or more substituents as described herein.

In certain embodiments, $Cy^3$ is heteroaryl comprising two 6-membered rings that are fused to each other and one to four heteroatoms selected from N, O, and S, wherein the heteroaryl is optionally substituted with one or more substituents as described herein. In certain embodiments, $Cy^3$ is quinolinyl (e.g., 7-quinolinyl), wherein the quinolinyl (e.g., 7-quinolinyl) is optionally substituted with one or more substituents as described herein.

In certain embodiments, $Cy^3$ is heteroaryl comprising one 5-membered ring and one 6-membered ring and one to four heteroatoms selected from N, O, and S, wherein the 5-membered ring and the 6-membered ring are fused to each other, and wherein the heteroaryl is optionally substituted with one or more substituents as described herein. In certain embodiments, $Cy^3$ is benzothiazolyl (e.g., 6-benzothiazolyl), wherein the benzothiazolyl (e.g., 6-benzothiazolyl) is optionally substituted with one or more substituents as described herein. In certain embodiments, $Cy^3$ is benzofuranyl (e.g., 2-benzofuranyl), wherein the benzofuranyl (e.g., 2-benzofuranyl) is optionally substituted with one or more substituents as described herein. In certain embodiments, $Cy^3$ is benzoxazolyl (e.g., 2-benzoxazolyl), wherein the benzoxazolyl (e.g., 2-benzoxazolyl) is optionally substituted with one or more substituents as described herein.

In certain embodiments, $Cy^3$ is $C_3$-$C_{10}$ cycloalkyl (e.g., cyclohexyl), wherein the $C_3$-$C_{10}$ cycloalkyl (e.g., cyclohexyl) is optionally substituted with one or more substituents as described herein.

In certain embodiments, $Cy^3$ is a $C_5$-$C_{13}$ bicyclic group (e.g., phenyl fused with $C_3$-$C_7$ carbocycle), wherein the $C_5$-$C_{13}$ bicyclic group is optionally substituted with one or more substituents as described herein.

In some embodiments, $R^1$ is H. In other embodiments, $R^1$ is $C_1$-$C_6$ alkyl.

In some embodiments, A-B is C(O)—$NR^{13}$, $CR^{11}R^{12}$—$NR^{13}$, $NR^{13}$—C(O), C(O), or $CR^{11}R^{12}$—O. In further embodiments, A-B is C(O)—$NR^{13}$ or $CR^{11}R^{12}$—$NR^{13}$.

In some embodiments, A-B is C(O)—$NR^{13}$. In further embodiments, A-B is C(O)—NH. In other embodiments, A-B is C(O)—N—$C_1$-$C_6$ alkyl. In further embodiments, A-B is C(O)—$NCH_3$.

In other embodiments, A-B is $CR^{11}R^{12}$—$NR^{13}$. In further embodiments, A-B is $CH_2$—NH. In other embodiments, A-B is $CH_2$—N—$C_1$-$C_6$ alkyl. In further embodiments, A-B is $CH_2$—$NCH_3$. In other embodiments, A-B is $CHCH_3$—$NCH_3$.

In other embodiments, A-B is $NR^{13}$—C(O). In further embodiments, A-B is NH—C(O).

In other embodiments, A-B is or $CR^{11}R^{12}$—O. In further embodiments, A-B is $CH_2$—O.

In other embodiments, A-B is C(O)—$CR^{11}R^{12}$ or C(O)—O.

In other embodiments, A-B is $CR^{11}R^{12}$—C(O), $NR^{13}$—$CR^{11}R^{12}$, O—$CR^{11}R^{12}$, or O—C(O).

In some embodiments, $R^{11}$ and $R^{12}$ are each independently H, halogen, or $C_1$-$C_6$ alkyl. In further embodiments, $R^{11}$ and $R^{12}$ are each independently H or methyl. In further embodiments, $R^{11}$ and $R^{12}$ are each H. In other embodiments, one of $R^{11}$ and $R^{12}$ is H, and the other is methyl.

In other embodiments, $R^{11}$ and $R^{12}$, together with the carbon atom to which $R^{11}$ and $R^{12}$ are attached, form a 3- to 6-membered ring optionally comprising one to three heteroatoms selected from N, O, and S.

In certain embodiments, $R^{13}$ is H, $C_1$-$C_6$ alkyl, $C_3$-$C_6$ cycloalkyl, $C_3$-$C_6$ heterocycle, $C_6$-$C_{10}$ aryl, heteroaryl comprising one or two 5- or 6-membered rings and one to four heteroatoms selected from N, O, and S, C(O)—$C_1$-$C_6$ alkyl, C(O)-phenyl, C(O)O—$C_1$-$C_6$ alkyl, C(O)$NR^{17}R^{18}$, $S(O)_2$—$C_1$-$C_6$ alkyl, or $S(O)_2NR^{17}R^{19}$, provided that when $CR^{11}R^{12}$—$N^{13}$ or $NR^{13}$—$CR^{11}R^{12}$ forms a 3- to 6-membered ring, $R^{13}$ is absent.

In some embodiments, $R^{13}$ is H or straight-chain $C_1$-$C_6$ or branched $C_3$-$C_6$ alkyl. In further embodiments, $R^{13}$ is H, methyl, ethyl, $CH_2CF_3$, or i-propyl. In further embodiments, $R^{13}$ is H. In other embodiments, $R^{13}$ is methyl. In certain embodiments, $R^{13}$ is $C_1$-$C_6$ haloalkyl (e.g., $C_1$-$C_6$ fluoroalkyl). In certain embodiments, $R^{13}$ is —$CH_2CF_3$.

In other embodiments, $R^{13}$ is C(O)—$C_1$-$C_6$ alkyl. In further embodiments, $R^{13}$ is C(O)$CH_3$.

In some embodiments, A-Z$^1$—R$^5$ form a 3- to 6-membered ring optionally comprising one to three heteroatoms selected from N, O, and S.

In some embodiments, B-A-Z$^1$ form a 3- to 6-membered ring optionally comprising one to three heteroatoms selected from N, O, and S. In further embodiments, B-A-Z$^1$ form a 4- to 6-membered ring optionally comprising one to three heteroatoms selected from N, O, and S. In further embodiments, B-A-Z$^1$ form a 4- to 6-membered ring optionally comprising one N. In further embodiments, the N is bonded to Z$^6$.

In some embodiments, A-Z$^1$ or B-A-Z$^1$, together with any one or two of Z$^2$ and Z$^3$, or any one or two of Z$^4$ and Z$^5$, form a 4- to 6-membered ring optionally comprising one to three heteroatoms selected from N, O, and S, wherein the ring and ring G form a bridged or fused ring structure. In further embodiments, B-A-Z$^1$, together with Z$^2$ or Z$^5$, form a 4- to 6-membered ring optionally comprising one to three heteroatoms selected from N, O, and S, wherein the ring and ring G form a fused ring structure. In further embodiments, B-A-Z$^1$, together with Z$^2$ or Z$^5$, form a 5- to 6-membered ring optionally comprising one to three heteroatoms selected from N, O, and S, wherein the ring and ring G form a fused ring structure. In further embodiments, B-A-Z$^1$, together with Z$^2$ or Z$^5$, form a 5- to 6-membered ring optionally comprising one N, wherein the ring and ring G form a fused ring structure. In further embodiments, the N is bonded to Z$^6$.

In some embodiments, R$^5$ is H, methyl, benzyl or F. In further embodiments, R$^5$ is H or methyl. In further embodiments, R$^5$ is H. In further embodiments, R$^5$ is methyl.

In some embodiments, each R$^2$ is independently H, F, CH$_3$, or CF$_3$. In further embodiments, each R$^2$ is H.

In some embodiments, any two R$^2$ bonded to different carbon atoms, together with the carbon atoms to which the two R$^2$ are bonded, form a 4- to 7-membered ring, which can be saturated, partially saturated, unsaturated, or aromatic, and can comprise 0-4 heteroatoms selected from N, O, and S. In further embodiments, any two R$^2$ bonded to different carbon atoms, together with the carbon atoms to which the two R$^2$ are bonded, form a phenyl ring.

In some embodiments, X is O. In other embodiments, X is a bond. In other embodiments, X is S, S(O), or S(O)$_2$. In yet other embodiments, X is NR$^{16}$.

In some embodiments, R$^3$ and R$^4$ are each independently H or C$_1$-C$_6$ alkyl. In further embodiments, R$^3$ and R$^4$ are each independently H or methyl. In further embodiments, R$^3$ and R$^4$ are each H. In some embodiments, at least one of R$^3$ and R$^4$ is not H.

In some embodiments, R$^{14}$ and R$^{15}$ are each independently H, halogen, C$_1$-C$_6$ alkyl, phenyl, or heteroaryl comprising one 5- or 6-membered ring and one to four heteroatoms selected from N, O, and S. In further embodiments, R$^{14}$ and R$^{15}$ are each independently H, halogen, or phenyl. In further embodiments, R$^{14}$ and R$^{15}$ are each H.

In some embodiments, R$^{16}$ is H, C$_1$-C$_6$ alkyl, or C(O)—C$_1$-C$_6$ alkyl. In further embodiments, R$^{16}$ is H. In other embodiments, R$^{16}$ is phenyl or heteroaryl comprising one 5- or 6-membered ring and one to four heteroatoms selected from N, O, and S. In further embodiments, R$^{16}$ is phenyl or pyridyl.

In some embodiments, R$^{17}$ and R$^{18}$ are each independently H, methyl, or ethyl.

In some embodiments, n is 0 or 1. In further embodiments, n is 0. In other embodiments, n is 1 or 2.

In some embodiments, t is 1, 2, or 3. In further embodiments, t is 2 or 3. In some embodiments, t is 1. In other embodiments, t is 2. In other embodiments, t is 3. In other embodiments, t is 4.

Any of the embodiments described above or herein below can be combined with one another.

In some embodiments, n is 0 and X is O. In other embodiments, n is 0 and X is a bond.

In some embodiments, t is 2 or 3 and X is O. In further embodiments, t is 2 and X is O. In other embodiments, t is 1 or 2 and X is a bond.

In certain embodiments, —(Z$^8$)$_n$—X—(Z$^7$)$_t$— is —O—(C(R$^3$)$_2$)$_t$—. In certain embodiments, —(Z$^8$)$_n$—X—(Z$^7$)$_t$— is —O—(CH$_2$)$_t$—. In certain embodiments, —(Z$^8$)$_n$—X—(Z$^7$)$_t$— is —O—(CH$_2$)$_2$—. In certain embodiments, —(Z$^8$)$_n$—X—(Z$^7$)$_t$— is —O—(CH$_2$)$_3$— or —O—(CH$_2$)$_4$—. In certain embodiments, —(Z$^8$)$_n$—X—(Z$^7$)$_t$— is —O—(C(R$^3$)$_2$)$_2$— (e.g., —O—CH$_2$—CHMe- or —O—CH$_2$—C(Me)$_2$-).

In certain embodiments, —(Z$^8$)$_n$—X—(Z$^7$)$_t$— is —(C(R$^3$)$_2$)$_t$—. In certain embodiments, —(Z$^8$)$_n$—X—(Z$^7$)$_t$— is —(CH$_2$)$_t$— (e.g., —CH$_2$—, —(CH$_2$)$_2$—, —(CH$_2$)$_3$—, or —(CH$_2$)$_4$—).

In some embodiments, A-B is C(O)—NR$^{13}$ or CH$_2$—NR$^{13}$, each R$^3$ is independently H or C$_1$-C$_6$ alkyl, and t is 2 or 3. In further embodiments, each R$^3$ is H. In further embodiments, A-B is C(O)—NH or CH$_2$—NH, and t is 2 or 3. In further embodiments, t is 2. In further embodiments, n is 0. In further embodiments, R$^5$ is H or methyl.

In some embodiments, A-B is C(O)—NR$^{13}$, and X is O. In further embodiments, A-B is C(O)—NH, X is O, and each R$^3$ is H. In further embodiments, A-B is C(O)—NH, X is O, each R$^3$ is H, and n is 0. In further embodiments, A-B is C(O)—NH, X is O, each R$^3$ is H, n is 0, and t is 2.

In some embodiments, A-B is C(O)—NR$^{13}$, X is O, and Cy$^1$, Cy$^2$ or Cy$^3$ is independently phenyl, pyridyl, or methylenedioxyphenyl, each of which is optionally substituted. In further embodiments, Cy$^1$, Cy$^2$ or Cy$^3$ is independently phenyl, pyridyl, or methylenedioxyphenyl, each of which is optionally substituted with one or more substituents independently selected from Cl, F, CF$_3$, methyl, OH, OCH$_3$, and OCF$_3$. In further embodiments, A-B is C(O)—NH, X is O, each R$^3$ is H, Cy$^1$, Cy$^2$ or Cy$^3$ is independently phenyl, pyridyl, or methylenedioxyphenyl, each of which is optionally substituted, and n is 0. In further embodiments, A-B is C(O)—NH, X is O, each R$^3$ is H, Cy$^1$, Cy$^2$ or Cy$^3$ is independently phenyl, pyridyl, or methylenedioxyphenyl, each of which is optionally substituted, n is 0, and t is 2.

In other embodiments, A-B is CH$_2$—NR$^{13}$, and X is O. In further embodiments, A-B is CH$_2$—NH, X is O, and each R$^3$ is H. In further embodiments, A-B is CH$_2$—NH, X is O, each R$^3$ is H, and n is 0. In further embodiments, A-B is CH$_2$—NH, X is O, each R$^3$ is H, n is 0, and t is 2.

In some embodiments, A-B is CH$_2$—NH, X is O, and Cy$^1$, Cy$^2$ or Cy$^3$ is independently phenyl, pyridyl, or methylenedioxyphenyl, each of which is optionally substituted. In further embodiments, Cy$^1$, Cy$^2$ or Cy$^3$ is independently phenyl, pyridyl, or methylenedioxyphenyl, each of which is optionally substituted with one or more substituents independently selected from Cl, F, CF$_3$, methyl, OH, OCH$_3$, and OCF$_3$. In further embodiments, A-B is CH$_2$—NH, X is O, each R$^3$ is H, Cy$^1$, Cy$^2$ or Cy$^3$ is independently phenyl, pyridyl, or methylenedioxyphenyl, each of which is optionally substituted, and n is 0. In further embodiments, A-B is CH$_2$—NH, X is O, each R$^3$ is H, Cy$^1$, Cy$^2$ or Cy$^3$ is independently phenyl, pyridyl, or methylenedioxyphenyl, each of which is optionally substituted, n is 0, and t is 2.

In certain embodiments, a phenyl group described herein is substituted at the 2-position with one substituent as described herein. In certain embodiments, a phenyl group described herein is substituted at the 3-position with one substituent as described herein. In certain embodiments, a phenyl group described herein is substituted at the 4-position with one substituent as described herein. In certain embodiments, a phenyl group described herein is substituted at the 2- and 3-positions, or at the 2- and 4-positions, or at the 2- and 5-positions, or at the 2- and 6-positions, or at the 3- and 4-positions, or at the 3- and 5-positions, with two substituents as described herein.

In certain embodiments, each of $Z^2$, $Z^3$, $Z^4$, and $Z^5$ is $C(R^2)_2$. In certain embodiments, each of $Z^2$, $Z^3$, $Z^4$, and $Z^5$ is $CH_2$.

In certain embodiments, $Z^6$ is of the R configuration. In certain embodiments, $Z^6$ is of the S configuration.

In one embodiment, the present invention provides a compound having Formula II:

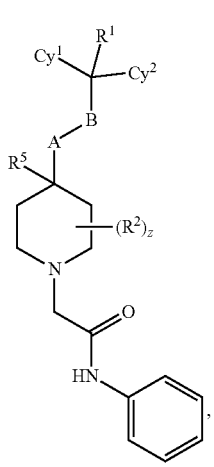

(II)

wherein z is 1, 2, 3, 4, 5, 6, 7, or 8, and each of the other variables are as defined for Formula I, and can be any substituent as illustrated herein.

In one embodiment, the present invention provides a compound having Formula IV:

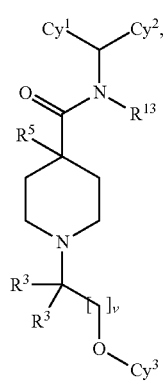

(IV)

or a stereoisomer, racemate, tautomer, polymorph, hydrate, or solvate thereof, or a pharmaceutically acceptable salt thereof, wherein:

$Cy^1$, $Cy^2$, and $Cy^3$ are each independently H, $C_1$-$C_3$ alkyl, phenyl, heteroaryl comprising one or two 5- or 6-membered rings and one to four heteroatoms selected from N, O, and S, $C_5$-$C_6$ cycloalkyl, $C_5$-$C_{13}$ bicyclic group, or heterocyclyl comprising one or two 3- to 6-membered rings and one to four heteroatoms selected from N, O, and S, wherein $Cy^1$, $Cy^2$, and $Cy^3$ are each independently optionally substituted with one or more substituents independently selected from halogen, $CH_2F$, $CHF_2$, $CF_3$, $C_1$-$C_6$ alkyl, OH, O—$C_1$-$C_6$ alkyl, $OCF_3$, $OCHF_2$, $OCH_2F$, and $NR^{17}R^{18}$;

each $R^3$ is the same and is selected from H and $C_1$-$C_3$ alkyl;

$R^5$ is H or $C_1$-$C_3$ alkyl;

$R^{13}$ is H or $C_1$-$C_3$ alkyl;

$R^{17}$ and $R^{18}$ are each independently H or $C_1$-$C_3$ alkyl; and v is 1, 2, or 3.

In certain embodiments, a compound of Formula IV is of the formula:

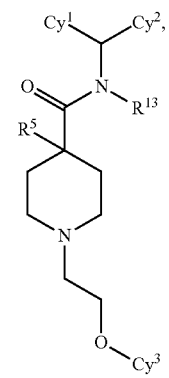

or a stereoisomer, racemate, tautomer, polymorph, hydrate, or solvate thereof, or a pharmaceutically acceptable salt thereof.

In certain embodiments, a compound of Formula IV is of the formula:

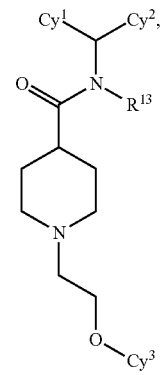

or a stereoisomer, racemate, tautomer, polymorph, hydrate, or solvate thereof, or a pharmaceutically acceptable salt thereof.

In certain embodiments, a compound of Formula IV is of the formula:

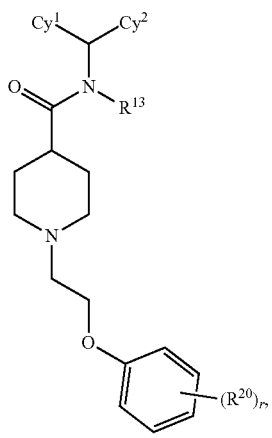

or a stereoisomer, racemate, tautomer, polymorph, hydrate, or solvate thereof, or a pharmaceutically acceptable salt thereof, wherein:

each instance of $R^{20}$ is independently selected from halogen, $CH_2F$, $CHF_2$, $CF_3$, $C_1$-$C_6$ alkyl, OH, O—$C_1$-$C_6$ alkyl, $OCF_3$, $OCHF_2$, $OCH_2F$, and $NR^{17}R^{18}$; and r is 0, 1, 2, 3, 4, or 5.

In certain embodiments, a compound of Formula IV is of the formula:

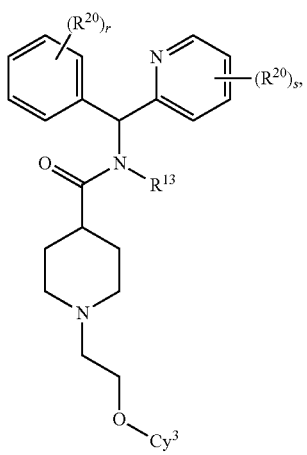

or a stereoisomer, racemate, tautomer, polymorph, hydrate, or solvate thereof, or a pharmaceutically acceptable salt thereof, wherein:

each instance of $R^{20}$ is independently selected from halogen, $CH_2F$, $CHF_2$, $CF_3$, $C_1$-$C_6$ alkyl, OH, O—$C_1$-$C_6$ alkyl, $OCF_3$, $OCHF_2$, $OCH_2F$, and $NR^{17}R^{18}$;

s is 0, 1, 2, 3, or 4; and r is 0, 1, 2, 3, 4, or 5.

In certain embodiments, a compound of Formula IV is of the formula:

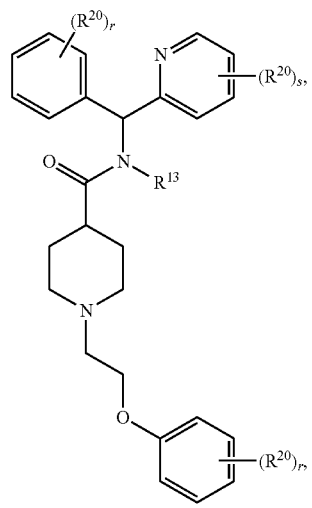

or a stereoisomer, racemate, tautomer, polymorph, hydrate, or solvate thereof, or a pharmaceutically acceptable salt thereof, wherein:

each instance of $R^{20}$ is independently selected from halogen, $CH_2F$, $CHF_2$, $CF_3$, $C_1$-$C_6$ alkyl, OH, O—$C_1$-$C_6$ alkyl, $OCF_3$, $OCHF_2$, $OCH_2F$, and $NR^{17}R^{18}$;

s is 0, 1, 2, 3, or 4; and each instance of r is independently 0, 1, 2, 3, 4, or 5.

In certain embodiments, a compound of Formula IV is of the formula:

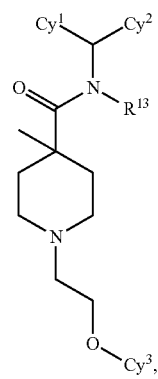

or a stereoisomer, racemate, tautomer, polymorph, hydrate, or solvate thereof, or a pharmaceutically acceptable salt thereof.

In certain embodiments, a compound of Formula IV is of the formula:

23

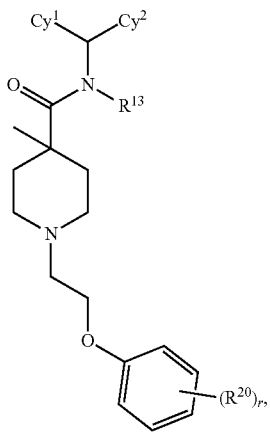

or a stereoisomer, racemate, tautomer, polymorph, hydrate, or solvate thereof, or a pharmaceutically acceptable salt thereof, wherein:

each instance of $R^{20}$ is independently selected from halogen, $CH_2F$, $CHF_2$, $CF_3$, $C_1$-$C_6$ alkyl, OH, O—$C_1$-$C_6$ alkyl, $OCF_3$, $OCHF_2$, $OCH_2F$, and $NR^{17}R^{18}$; and r is 0, 1, 2, 3, 4, or 5.

In certain embodiments, a compound of Formula IV is of the formula:

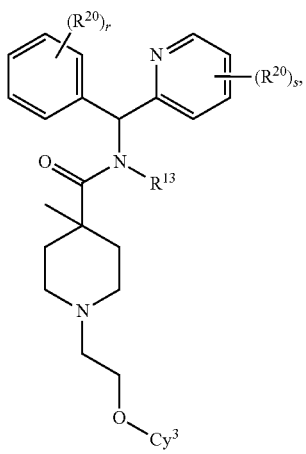

or a stereoisomer, racemate, tautomer, polymorph, hydrate, or solvate thereof, or a pharmaceutically acceptable salt thereof, wherein:

each instance of $R^{20}$ is independently selected from halogen, $CH_2F$, $CHF_2$, $CF_3$, $C_1$-$C_6$ alkyl, OH, O—$C_1$-$C_6$ alkyl, $OCF_3$, $OCHF_2$, $OCH_2F$, and $NR^{17}R^{18}$;

s is 0, 1, 2, 3, or 4; and r is 0, 1, 2, 3, 4, or 5.

In certain embodiments, a compound of Formula IV is of the formula:

24

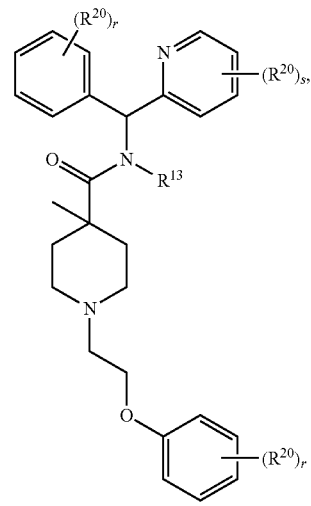

or a stereoisomer, racemate, tautomer, polymorph, hydrate, or solvate thereof, or a pharmaceutically acceptable salt thereof, wherein:

each instance of $R^{20}$ is independently selected from halogen, $CH_2F$, $CHF_2$, $CF_3$, $C_1$-$C_6$ alkyl, OH, O—$C_1$-$C_6$ alkyl, $OCF_3$, $OCHF_2$, $OCH_2F$, and $NR^{17}R^{18}$;

s is 0, 1, 2, 3, or 4; and each instance of r is independently 0, 1, 2, 3, 4, or 5.

In some embodiments, $Cy^1$, $Cy^2$, or $Cy^3$ is independently phenyl, heteroaryl comprising one or two 5- or 6-membered rings and one to four heteroatoms selected from N, O, and S, $C_5$-$C_6$ cycloalkyl, or $C_5$-$C_{13}$ bicyclic group, each independently optionally substituted with one or more substituents independently selected from halogen, $CH_2F$, $CHF_2$, $CF_3$, $C_1$-$C_6$ alkyl, OH, O—$C_1$-$C_6$ alkyl, $OCF_3$, $OCHF_2$, $OCH_2F$, and $NR^{17}R^{18}$. In further embodiments, $Cy^1$, $Cy^2$, or $Cy^3$ is independently phenyl, methylenedioxyphenyl, dihydroindenyl, pyridyl, pyridinonyl, quinolinyl, benzodihydrodioxinyl, quinolinonyl, benzofuranyl, benzoxazolyl, or benzothiazolyl, each independently optionally substituted with one or more substituents independently selected from halogen, $CH_2F$, $CHF_2$, $CF_3$, $C_1$-$C_6$ alkyl, OH, O—$C_1$-$C_6$ alkyl, $OCF_3$, $OCHF_2$, $OCH_2F$, and $NR^{17}R^{18}$. In further embodiments, $Cy^1$, $Cy^2$, or $Cy^3$ is independently phenyl, methylenedioxyphenyl, dihydroindenyl, pyridyl, pyridinonyl, quinolinyl, benzodihydrodioxinyl, quinolinonyl, benzofuranyl, benzoxazolyl, or benzothiazolyl, each independently optionally substituted with one or more substituents independently selected from halogen, $CH_2F$, $CHF_2$, $CF_3$, O—$C_1$-$C_6$ alkyl, $OCF_3$, $OCHF_2$, and $OCH_2F$, preferably from Cl, F, $CH_3$, $CF_3$, $OCH_3$, and $OCF_3$.

In further embodiments, one of $Cy^1$ and $Cy^2$ is phenyl or methylenedioxyphenyl, the other is heteroaryl comprising one or two 5- or 6-membered rings and one to four heteroatoms selected from N, O, and S, preferably pyridyl or quinolinyl, more preferably pyridyl, and $Cy^3$ is $C_1$-$C_3$ alkyl, phenyl, heteroaryl comprising one or two 5- or 6-membered rings and one to four heteroatoms selected from N, O, and S, $C_5$-$C_6$ cycloalkyl, or $C_5$-$C_{13}$ bicyclic group, preferably phenyl or heteroaryl comprising one or two 5- or 6-membered rings and one to four heteroatoms selected from N, O, and S, more preferably phenyl, dihydroindenyl, pyridyl, pyridinonyl, quinolinyl, benzodihydrodioxinyl, quinolinonyl, benzofuranyl, benzoxazolyl, or benzothiazolyl, more preferably phenyl or pyridyl, wherein $Cy^1$, $Cy^2$ and $Cy^3$ are each independently optionally substituted with one or more substituents independently selected from Cl, F, $CH_3$, $CF_3$, $OCH_3$, and $OCF_3$.

In other embodiments, $Cy^1$ and $Cy^2$ are each heteroaryl comprising one or two 5- or 6-membered rings and one to four heteroatoms selected from N, O, and S, preferably pyridyl, and $Cy^3$ is phenyl, wherein $Cy^1$, $Cy^2$ and $Cy^3$ are each independently optionally substituted with one or more substituents independently selected from Cl, F, $CH_3$, $CF_3$, $OCH_3$, and $OCF_3$.

In other embodiments, $Cy^1$, $Cy^2$ and $Cy^3$ are each phenyl, optionally substituted with one or more substituents independently selected from Cl, F, $CH_3$, $CF_3$, $OCH_3$, and $OCF_3$.

In some embodiments, $Cy^3$ is phenyl, one of $Cy^1$ and $Cy^2$ is heteroaryl comprising one or two 5- or 6-membered rings and one to four heteroatoms selected from N, O, and S, preferably pyridyl or quinolinyl, more preferably pyridyl, and the other is H, straight-chain $C_1$-$C_6$ or branched $C_3$-$C_6$ alkyl, or $C_5$-$C_6$ cycloalkyl, wherein the phenyl and heteroaryl are each independently optionally substituted with one or more substituents independently selected from halogen, $CH_2F$, $CHF_2$, $CF_3$, $C_1$-$C_6$ alkyl, OH, O—$C_1$-$C_6$ alkyl, $OCF_3$, $OCHF_2$, $OCH_2F$, and $NR^{17}R^{18}$, preferably halogen, $CH_2F$, $CHF_2$, $CF_3$, O—$C_1$-$C_6$ alkyl, $OCHF_2$, $OCH_2F$, and $OCF_3$, more preferably Cl, F, $CH_3$, $CF_3$, $OCH_3$, and $OCF_3$.

In some embodiments, each $R^3$ is H or methyl. In further embodiments, each $R^3$ is H.

In some embodiments, $R^5$ is H. In other embodiments, $R^5$ is $CH_3$.

In some embodiments, $R^{13}$ is H or methyl. In further embodiments, $R^{13}$ is H.

In some embodiments, $R^{17}$ and $R^{18}$ are each independently H. In some embodiments, $R^{17}$ and $R^{18}$ are each independently methyl. In some embodiments, one of $R^{17}$ and $R^{18}$ is H, and the other is methyl.

In some embodiments, v is 1.

Any of the embodiments described above or herein below can be combined with one another.

In one embodiment, the present invention provides a compound having Formula V:

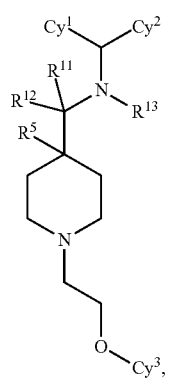

(V)

or a stereoisomer, racemate, tautomer, polymorph, hydrate, or solvate thereof, or a pharmaceutically acceptable salt thereof, wherein:

$Cy^1$, $Cy^2$ and $Cy^3$ are each independently phenyl, heteroaryl comprising one or two 5- or 6-membered rings and one to four heteroatoms selected from N, O, and S, or $C_5$-$C_{13}$ bicyclic group, wherein $Cy^1$, $Cy^2$, and $Cy^3$ are each independently optionally substituted with one or more substituents independently selected from halogen, $CH_2F$, $CHF_2$, $CF_3$, $C_1$-$C_6$ alkyl, OH, O—$C_1$-$C_6$ alkyl, $OCF_3$, $OCHF_2$, $OCH_2F$, and $NR^{17}R^{18}$;

$R^5$ is H or $C_1$-$C_3$ alkyl;

$R^{11}$ and $R^{12}$ are each independently H or $C_1$-$C_3$ alkyl;

$R^{13}$ is H, $C_1$-$C_3$ alkyl, $C_1$-$C_3$ haloalkyl, or C(O)—$C_1$-$C_3$ alkyl; and $R^{17}$ and $R^{18}$ are each independently H or $C_1$-$C_3$ alkyl. In certain embodiments, a compound of the invention is of Formula V, or a stereoisomer, racemate, tautomer, polymorph, hydrate, or solvate thereof, or a pharmaceutically acceptable salt thereof, wherein:

$Cy^1$, $Cy^2$ and $Cy^3$ are each independently phenyl, heteroaryl comprising one or two 5- or 6-membered rings and one to four heteroatoms selected from N, O, and S, or $C_5$-$C_{13}$ bicyclic group, wherein $Cy^1$, $Cy^2$, and $Cy^3$ are each independently optionally substituted with one or more substituents independently selected from halogen, $CH_2F$, $CHF_2$, $CF_3$, $C_1$-$C_6$ alkyl, OH, O—$C_1$-$C_6$ alkyl, $OCF_3$, $OCHF_2$, $OCH_2F$, and $NR^{17}R^{18}$;

$R^5$ is H or $C_1$-$C_3$ alkyl;

$R^{11}$ and $R^{12}$ are each independently H or $C_1$-$C_3$ alkyl;

$R^{13}$ is H, $C_1$-$C_3$ alkyl, $CH_2CF_3$, or C(O)—$C_1$-$C_3$ alkyl; and $R^{17}$ and $R^{18}$ are each independently H or $C_1$-$C_3$ alkyl.

In certain embodiments, a compound of Formula V is of the formula:

or a stereoisomer, racemate, tautomer, polymorph, hydrate, or solvate thereof, or a pharmaceutically acceptable salt thereof, wherein:

each instance of $R^{20}$ is independently selected from halogen, $CH_2F$, $CHF_2$, $CF_3$, $C_1$-$C_6$ alkyl, OH, O—$C_1$-$C_6$ alkyl, $OCF_3$, $OCHF_2$, $OCH_2F$, and $NR^{17}R^{18}$; and r is 0, 1, 2, 3, 4, or 5.

In certain embodiments, a compound of Formula V is of the formula:

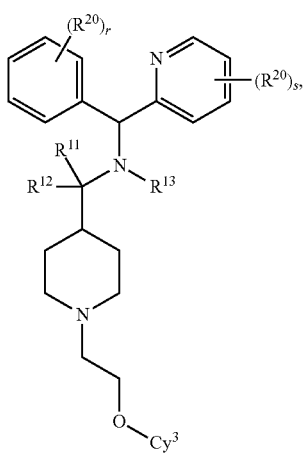

or a stereoisomer, racemate, tautomer, polymorph, hydrate, or solvate thereof, or a pharmaceutically acceptable salt thereof, wherein:

each instance of $R^{20}$ is independently selected from halogen, $CH_2F$, $CHF_2$, $CF_3$, $C_1$-$C_6$ alkyl, OH, O—$C_1$-$C_6$ alkyl, $OCF_3$, $OCHF_2$, $OCH_2F$, and $NR^{17}R^{18}$;

s is 0, 1, 2, 3, or 4; and r is 0, 1, 2, 3, 4, or 5.

In certain embodiments, a compound of Formula V is of the formula:

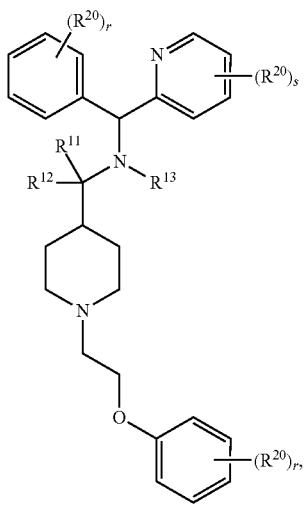

or a stereoisomer, racemate, tautomer, polymorph, hydrate, or solvate thereof, or a pharmaceutically acceptable salt thereof, wherein:

each instance of $R^{20}$ is independently selected from halogen, $CH_2F$, $CHF_2$, $CF_3$, $C_1$-$C_6$ alkyl, OH, O—$C_1$-$C_6$ alkyl, $OCF_3$, $OCHF_2$, $OCH_2F$, and $NR^{17}R^{18}$;

s is 0, 1, 2, 3, or 4; and each instance of r is independently 0, 1, 2, 3, 4, or 5.

In some embodiments, $Cy^1$, $Cy^2$, or $Cy^3$ is independently phenyl or heteroaryl comprising one or two 5- or 6-membered rings and one to four heteroatoms selected from N, O, and S, each independently optionally substituted with one or more substituents independently selected from halogen, $CH_2F$, $CHF_2$, $CF_3$, $C_1$-$C_6$ alkyl, OH, O—$C_1$-$C_6$ alkyl, $OCF_3$, $OCHF_2$, and $NR^{17}R^{18}$. In further embodiments, $Cy^1$, $Cy^2$, or $Cy^3$ is independently phenyl or pyridyl, each independently optionally substituted with one or more substituents independently selected from halogen, $CH_2F$, $CHF_2$, $CF_3$, $C_1$-$C_6$ alkyl, OH, O—$C_1$-$C_6$ alkyl, $OCF_3$, $OCHF_2$, $OCH_2F$, and $NR^{17}R^{18}$. In further embodiments, $Cy^1$, $Cy^2$, or $Cy^3$ is independently phenyl or pyridyl, each independently optionally substituted with one or more substituents independently selected from halogen, $CH_2F$, $CHF_2$, $CF_3$, O—$C_1$-$C_6$ alkyl, $OCF_3$, $OCHF_2$, and $OCH_2F$, preferably from Cl, F, $CH_3$, $CF_3$, $OCH_3$, and $OCF_3$.

In further embodiments, one of $Cy^1$ and $Cy^2$ is phenyl, the other is heteroaryl comprising one or two 5- or 6-membered rings and one to four heteroatoms selected from N, O, and S, preferably pyridyl, and $Cy^3$ is phenyl, wherein $Cy^1$, $Cy^2$ and $Cy^3$ are each independently optionally substituted with one or more substituents independently selected from Cl, F, $CH_3$, $CF_3$, $OCH_3$, and $OCF_3$.

In other embodiments, $Cy^1$, $Cy^2$ and $Cy^3$ are each phenyl, optionally substituted with one or more substituents independently selected from Cl, F, $CH_3$, $CF_3$, $OCH_3$, and $OCF_3$.

In other embodiments, one of $Cy^1$ and $Cy^2$ is $C_5$-$C_{13}$ bicyclic group, the other is heteroaryl comprising one or two 5- or 6-membered rings and one to four heteroatoms selected from N, O, and S, and $Cy^3$ is phenyl, wherein $Cy^1$, $Cy^2$ and $Cy^3$ are each independently optionally substituted with one or more substituents independently selected from Cl, F, $CH_3$, $CF_3$, $OCH_3$, and $OCF_3$.

In some embodiments, $R^5$ is H or methyl. In further embodiments, $R^5$ is H.

In some embodiments, $R^{11}$ and $R^{12}$ are each independently H or methyl. In further embodiments, $R^{11}$ and $R^{12}$ are each H. In other embodiments, one of $R^{11}$ and $R^{12}$ is H, and the other is methyl.

In certain embodiments, $R^{13}$ is H, $C_1$-$C_3$ alkyl, or C(O)—$C_1$-$C_3$ alkyl. In some embodiments, $R^{13}$ is H, methyl, isopropyl, $CH_2CF_3$, or $C(O)CH_3$. In further embodiments, $R^{13}$ is H or methyl. In some embodiments, $R^{13}$ is H. In some embodiments, $R^{13}$ is methyl or isopropyl. In certain embodiments, $R^{13}$ is $C_1$-$C_3$ haloalkyl (e.g., $C_1$-$C_3$ fluoroalkyl). In certain embodiments, $R^{13}$ is —$CH_2CF_3$.

In some embodiments, $R^{17}$ and $R^{18}$ are each independently H. In some embodiments, $R^{17}$ and $R^{18}$ are each independently methyl. In some embodiments, one of $R^{17}$ and $R^{18}$ is H, and the other is methyl.

In one embodiment, the present invention provides a compound having Formula VI:

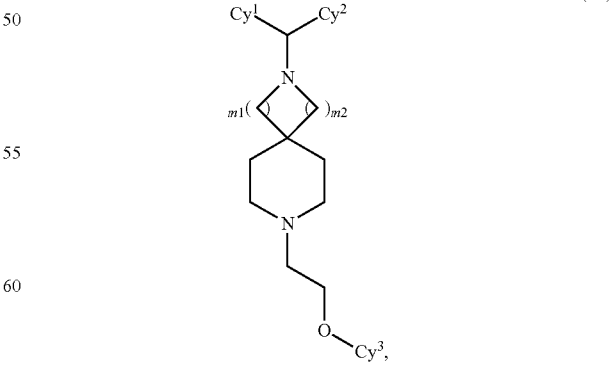

(VI)

or a stereoisomer, racemate, tautomer, polymorph, hydrate, or solvate thereof, or a pharmaceutically acceptable salt thereof, wherein:

Cy$^1$, Cy$^2$ and Cy$^3$ are each independently phenyl or heteroaryl comprising one or two 5- or 6-membered rings and one to four heteroatoms selected from N, O, and S, wherein Cy$^1$, Cy$^2$, and Cy$^3$ are each independently optionally substituted with one or more substituents independently selected from halogen, CH$_2$F, CHF$_2$, CF$_3$, C$_1$-C$_6$ alkyl, OH, O—C$_1$-C$_6$ alkyl, OCF$_3$, OCHF$_2$, OCH$_2$F, and NR$^{17}$R$^{18}$;

m1 and m2 are each independently is 0, 1, or 2, provided that m1 and m2 are not both 0; and R$^{17}$ and R$^{18}$ are each independently H or C$_1$-C$_3$ alkyl.

In some embodiments, Cy$^1$, Cy$^2$, or Cy$^3$ is independently phenyl or heteroaryl comprising one or two 5- or 6-membered rings and one to four heteroatoms selected from N, O, and S, each independently optionally substituted with one or more substituents independently selected from Cl, F, CH$_3$, CF$_3$, OCH$_3$, and OCF$_3$.

In further embodiments, Cy$^1$, Cy$^2$, or Cy$^3$ is independently phenyl or pyridyl, each independently optionally substituted with one or more substituents independently selected from Cl, F, CH$_3$, CF$_3$, OCH$_3$, and OCF$_3$.

In further embodiments, one of Cy$^1$ and Cy$^2$ is phenyl, the other is heteroaryl comprising one or two 5- or 6-membered rings and one to four heteroatoms selected from N, O, and S, preferably pyridyl, and Cy$^3$ is phenyl, wherein Cy$^1$, Cy$^2$ and Cy$^3$ are each independently optionally substituted with one or more substituents independently selected from Cl, F, CH$_3$, CF$_3$, OCH$_3$, and OCF$_3$, preferably Cl or CF$_3$.

In some embodiments, m1 is 1. In some embodiments, m2 is 1. In some embodiments, one of m1 and m2 is 1, and the other of m1 and m2 is 2.

In some embodiments, R$^{17}$ and R$^{18}$ are each independently H. In some embodiments, R$^{17}$ and R$^{18}$ are each independently methyl. In some embodiments, one of R$^{17}$ and R$^{18}$ is H, and the other is methyl.

In one embodiment, the present invention provides a compound having Formula VII:

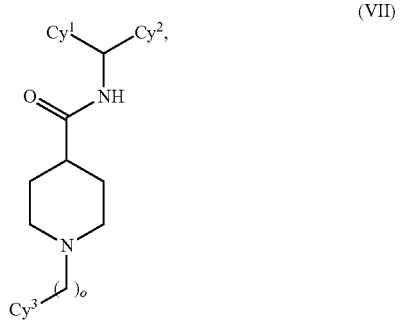

(VII)

or a stereoisomer, racemate, tautomer, polymorph, hydrate, or solvate thereof, or a pharmaceutically acceptable salt thereof, wherein:

Cy$^1$, Cy$^2$ and Cy$^3$ are each independently phenyl, heteroaryl comprising one or two 5- or 6-membered rings and one to four heteroatoms selected from N, O, and S, or C$_5$-C$_{13}$ bicyclic group, wherein Cy$^1$, Cy$^2$, and Cy$^3$ are each independently optionally substituted with one or more substituents independently selected from halogen, CH$_2$F, CHF$_2$, CF$_3$, C$_1$-C$_6$ alkyl, OH, O—C$_1$-C$_6$ alkyl, OCF$_3$, OCHF$_2$, OCH$_2$F, and NR$^{17}$R$^{18}$;

R$^{17}$ and R$^{18}$ are each independently H or C$_1$-C$_3$ alkyl; and o is 1, 2, or 3.

In certain embodiments, a compound of Formula VII is of the formula:

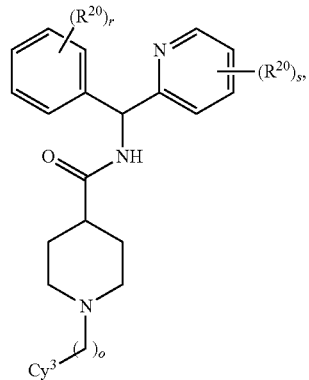

or a stereoisomer, racemate, tautomer, polymorph, hydrate, or solvate thereof, or a pharmaceutically acceptable salt thereof, wherein:

each instance of R$^{20}$ is independently selected from halogen, CH$_2$F, CHF$_2$, CF$_3$, C$_1$-C$_6$ alkyl, OH, O—C$_1$-C$_6$ alkyl, OCF$_3$, OCHF$_2$, OCH$_2$F, and NR$^{17}$R$^{18}$;

s is 0, 1, 2, 3, or 4; and r is 0, 1, 2, 3, 4, or 5.

In some embodiments, Cy$^1$, Cy$^2$, or Cy$^3$ is independently phenyl, pyridyl, pyridinonyl, benzofuranyl, benzoxazolyl, dihydroindenyl, or benzodihydrodioxinyl, each independently optionally substituted with one or more substituents independently selected from halogen, CH$_2$F, CHF$_2$, CF$_3$, C$_1$-C$_6$ alkyl, OH, O—C$_1$-C$_6$ alkyl, OCF$_3$, OCHF$_2$, OCH$_2$F, or NR$^{17}$R$^{18}$, preferably halogen, more preferably F.

In further embodiments, one of Cy$^1$ and Cy$^2$ is phenyl, the other is heteroaryl comprising one or two 5- or 6-membered rings and one to four heteroatoms selected from N, O, and S, preferably pyridyl, and Cy$^3$ is heteroaryl comprising one or two 5- or 6-membered rings and one to four heteroatoms selected from N, O, and S or bicyclic group, preferably pyridinonyl, benzofuranyl, benzoxazolyl, dihydroindenyl, or benzodihydrodioxinyl, wherein Cy$^1$, Cy$^2$, and Cy$^3$ are each independently optionally substituted with one or more substituents independently selected from halogen, CH$_2$F, CHF$_2$, CF$_3$, C$_1$-C$_6$ alkyl, OH, O—C$_1$-C$_6$ alkyl, OCF$_3$, OCHF$_2$, OCH$_2$F, and NR$^{17}$R$^{18}$, preferably halogen, more preferably F.

In some embodiments, R$^{17}$ and R$^{18}$ are each independently H. In some embodiments, R$^{17}$ and R$^{18}$ are each independently methyl. In some embodiments, one of R$^{17}$ and R$^{18}$ is H, and the other is methyl.

In some embodiments, o is 1. In some embodiments, o is 2. In some embodiments, o is 3.

In certain embodiments, a compound of the invention is not of the formula:

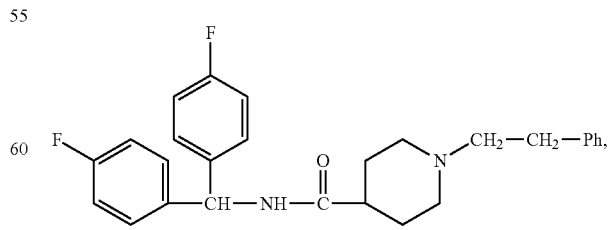

or a salt thereof.

In certain embodiments, at least one of Cy$^1$, Cy$^2$, and Cy$^3$ is not substituted or unsubstituted phenyl.

In yet another embodiment, the present invention provides a compound having Formula VIII:

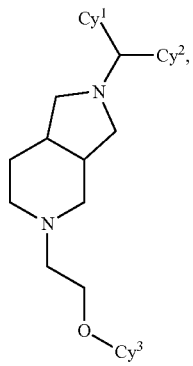

(VIII)

or a stereoisomer, racemate, tautomer, polymorph, hydrate, or solvate thereof, or a pharmaceutically acceptable salt thereof, wherein:

$Cy^1$, $Cy^2$ and $Cy^3$ are each independently phenyl or heteroaryl comprising one or two 5- or 6-membered rings and one to four heteroatoms selected from N, O, and S, wherein $Cy^1$, $Cy^2$, and $Cy^3$ are each independently optionally substituted with one or more substituents independently selected from halogen, $CH_2F$, $CHF_2$, $CF_3$, $C_1$-$C_6$ alkyl, OH, O—$C_1$-$C_6$ alkyl, $OCF_3$, $OCHF_2$, $OCH_2F$, and $NR^{17}R^{18}$; and $R^{17}$ and $R^{18}$ are each independently H or $C_1$-$C_3$ alkyl.

In some embodiments, $Cy^1$, $Cy^2$, or $Cy^3$ is independently phenyl or heteroaryl comprising one or two 5- or 6-membered rings and one to four heteroatoms selected from N, O, and S, each independently optionally substituted with one or more substituents independently selected from Cl, F, $CH_3$, $CF_3$, $OCH_3$, and $OCF_3$.

In further embodiments, $Cy^1$, $Cy^2$, or $Cy^3$ is independently phenyl or pyridyl, each independently optionally substituted with one or more substituents independently selected from Cl, F, $CH_3$, $CF_3$, $OCH_3$, and $OCF_3$.

In further embodiments, one of $Cy^1$ and $Cy^2$ is phenyl, the other is heteroaryl comprising one or two 5- or 6-membered rings and one to four heteroatoms selected from N, O, and S, preferably pyridyl, and $Cy^3$ is phenyl, wherein $Cy^1$, $Cy^2$ and $Cy^3$ are each independently optionally substituted with one or more substituents independently selected from Cl, F, $CH_3$, $CF_3$, $OCH_3$, and $OCF_3$, preferably Cl or $CF_3$.

In some embodiments, $R^{17}$ and $R^{18}$ are each independently H. In some embodiments, $R^{17}$ and $R^{18}$ are each independently methyl. In some embodiments, one of $R^{17}$ and $R^{18}$ is H, and the other is methyl.

In certain embodiments, at least one instance of $R^{20}$ is halogen. In certain embodiments, at least one instance of $R^{20}$ is F. In certain embodiments, at least one instance of $R^{20}$ is Cl. In certain embodiments, at least one instance of $R^{20}$ is Br or I. In certain embodiments, at least one instance of $R^{20}$ is $C_1$-$C_6$ alkyl (e.g., Me). In certain embodiments, at least one instance of $R^{20}$ is O—$C_1$-$C_6$ alkyl. In certain embodiments, at least one instance of $R^{20}$ is —OMe. In certain embodiments, all instances of $R^{20}$ are the same.

In certain embodiments, at least one instance of r is 0. In certain embodiments, each instance of r is 0. In certain embodiments, at least one instance of r is 1. In certain embodiments, at least one instance of r is 2, 3, or 4. In certain embodiments, at least one instance of r is 5. In certain embodiments, two instances of r are the same.

In certain embodiments, s is 0. In certain embodiments, s is 1. In certain embodiments, s is 2 or 3. In certain embodiments, s is 4.

In certain embodiments, a compound of the invention is a compound shown in Table 1, or a stereoisomer, racemate, tautomer, polymorph, hydrate, or solvate thereof, or a pharmaceutically acceptable salt thereof.

TABLE 1

| Compound # | Compound Name |
|---|---|
| 1 | (R)-1-(2-(3-chlorophenoxy)ethyl)-N-((4-chlorophenyl)(pyridin-2-yl)methyl)piperidine-4-carboxamide |
|  | (S)-1-(2-(3-chlorophenoxy)ethyl)-N-((4-chlorophenyl)(pyridin-2-yl)methyl)piperidine-4-carboxamide |
| 2 | (R)-1-(2-(4-chlorophenoxy)ethyl)-N-((4-chlorophenyl)(pyridine-2-yl)methyl) piperidine-4-carboxamide |
|  | (S)-1-(2-(4-chlorophenoxy)ethyl)-N-((4-chlorophenyl)(pyridine-2-yl)methyl) piperidine-4-carboxamide |
| 3 | (R)-N-((4-chlorophenyl)(pyridin-2-yl)methyl)-1-(2-(2-fluorophenoxy)ethyl)piperidine-4-carboxamide |
|  | (S)-N-((4-chlorophenyl)(pyridin-2-yl)methyl)-1-(2-(2-fluorophenoxy)ethyl)piperidine-4-carboxamide |
| 4 | (R)-N-((4-chlorophenyl)(pyridin-2-yl)methyl)-1-(2-(3-fluorophenoxy)ethyl)piperidine-4-carboxamide |
|  | (S)-N-((4-chlorophenyl)(pyridin-2-yl)methyl)-1-(2-(3-fluorophenoxy)ethyl)piperidine-4-carboxamide |
| 5 | (R)-N-((4-chlorophenyl)(pyridin-2-yl)methyl)-1-(2-(4-fluorophenoxy)ethyl)piperidine-4-carboxamide |
|  | (S)-N-((4-chlorophenyl)(pyridin-2-yl)methyl)-1-(2-(4-fluorophenoxy)ethyl)piperidine-4-carboxamide |
| 6 | (R)-N-((4-chlorophenyl)(pyridin-2-yl)methyl)-1-(2-(2-(trifluoromethyl)phenoxy)ethyl) piperidine-4-carboxamide |
|  | (S)-N-((4-chlorophenyl)(pyridin-2-yl)methyl)-1-(2-(2-(trifluoromethyl)phenoxy)ethyl) piperidine-4-carboxamide |
| 7 | (R)-N-((4-chlorophenyl)(pyridin-2-yl)methyl)-1-(2-(3-(trifluoromethyl)phenoxy)ethyl) piperidine-4-carboxamide |
|  | (S)-N-((4-chlorophenyl)(pyridin-2-yl)methyl)-1-(2-(3-(trifluoromethyl)phenoxy)ethyl) piperidine-4-carboxamide |

TABLE 1-continued

| Compound # | Compound Name |
|---|---|
| 8 | (R)-N-((4-chlorophenyl)(pyridin-2-yl)methyl)-1-(2-(4-(trifluoromethyl)phenoxy)ethyl) piperidine-4-carboxamide<br>(S)-N-((4-chlorophenyl)(pyridin-2-yl)methyl)-1-(2-(4-(trifluoromethyl)phenoxy)ethyl) piperidine-4-carboxamide |
| 9 | (R)-N-((4-chlorophenyl)(pyridin-2-yl)methyl)-1-(2-(2-oxopyridin-1(2H)-yl)ethyl) piperidine-4-carboxamide<br>(S)-N-((4-chlorophenyl)(pyridin-2-yl)methyl)-1-(2-(2-oxopyridin-1(2H)-yl)ethyl) piperidine-4-carboxamide |
| 10 | (R)-N-((4-chlorophenyl)(pyridin-2-yl)methyl)-1-(2-(pyridin-3-yloxy)ethyl)piperidine-4-carboxamide<br>(S)-N-((4-chlorophenyl)(pyridin-2-yl)methyl)-1-(2-(pyridin-3-yloxy)ethyl)piperidine-4-carboxamide |
| 11 | (R)-N-((4-chlorophenyl)(pyridin-2-yl)methyl)-1-(2-(4-oxopyridin-1(4H)-yl)ethyl) piperidine-4-carboxamide<br>(S)-N-((4-chlorophenyl)(pyridin-2-yl)methyl)-1-(2-(4-oxopyridin-1(4H)-yl)ethyl) piperidine-4-carboxamide |
| 12 | (R)-N-((4-chlorophenyl) (pyridin-2-yl) methyl)-1-(2-(3-methoxyphenoxy) ethyl) piperidine-4-carboxamide<br>(S)-N-((4-chlorophenyl) (pyridin-2-yl) methyl)-1-(2-(3-methoxyphenoxy) ethyl) piperidine-4-carboxamide |
| 13 | (R)-N-((4-chlorophenyl)(pyridin-2-yl)methyl)-1-(2-(4-methoxyphenoxy)ethyl) piperidine-4-carboxamide<br>(S)-N-((4-chlorophenyl)(pyridin-2-yl)methyl)-1-(2-(4-methoxyphenoxy)ethyl) piperidine-4-carboxamide |
| 14 | (R)-N-((4-chlorophenyl)(pyridin-2-yl)methyl)-1-(2-(2,5-difluorophenoxy)ethyl) piperidine-4-carboxamide<br>(S)-N-((4-chlorophenyl)(pyridin-2-yl)methyl)-1-(2-(2,5-difluorophenoxy)ethyl) piperidine-4-carboxamide |
| 15 | (R)-N-((4-chlorophenyl)(pyridin-2-yl)methyl)-1-(2-((2-oxo-1,2,3,4-tetrahydroquinolin-7-yl)oxy)ethyl)piperidine-4-carboxamide<br>(S)-N-((4-chlorophenyl)(pyridin-2-yl)methyl)-1-(2-((2-oxo-1,2,3,4-tetrahydroquinolin-7-yl)oxy)ethyl)piperidine-4-carboxamide |
| 16 | (R)-N-((4-chlorophenyl)(pyridin-2-yl)methyl)-1-(2-(quinolin-7-yloxy)ethyl) piperidine-4-carboxamide<br>(S)-N-((4-chlorophenyl)(pyridin-2-yl)methyl)-1-(2-(quinolin-7-yloxy)ethyl) piperidine-4-carboxamide |
| 17 | (R)-N-((4-chlorophenyl) (pyridin-2-yl) methyl)-1-(2-(cyclohexyloxy) ethyl) piperidine-4-carboxamide<br>(S)-N-((4-chlorophenyl) (pyridin-2-yl) methyl)-1-(2-(cyclohexyloxy) ethyl) piperidine-4-carboxamide |
| 18 | (R)-N-((4-chlorophenyl)(pyridin-2-yl)methyl)-1-(3-phenylpropyl)piperidine-4-carboxamide<br>(S)-N-((4-chlorophenyl)(pyridin-2-yl)methyl)-1-(3-phenylpropyl)piperidine-4-carboxamide |
| 19 | (R)-1-(2-(Benzo[d] thiazol-6-yloxy) ethyl)-N-((4-chlorophenyl)(pyridin-2-yl) methyl) piperidine-4-carboxamide<br>(S)-1-(2-(Benzo[d] thiazol-6-yloxy) ethyl)-N-((4-chlorophenyl)(pyridin-2-yl) methyl) piperidine-4-carboxamide |
| 20 | (R)-N-((3-methoxyphenyl)(pyridin-2-yl)methyl)-1-(2-(2-(trifluoromethyl)phenoxy) ethyl) piperidine-4-carboxamide<br>(S)-N-((3-methoxyphenyl)(pyridin-2-yl)methyl)-1-(2-(2-(trifluoromethyl)phenoxy) ethyl) piperidine-4-carboxamide |
| 21 | (R)-1-(2-(2-chlorophenoxy)ethyl)-N-((3-methoxyphenyl)(pyridin-2-yl)methyl) piperidine-4-carboxamide<br>(S)-1-(2-(2-chlorophenoxy)ethyl)-N-((3-methoxyphenyl)(pyridin-2-yl)methyl) piperidine-4-carboxamide |
| 22 | (R)-1-(2-(2-fluorophenoxy)ethyl)-N-((3-methoxyphenyl)(pyridin-2-yl)methyl) piperidine-4-carboxamide<br>(S)-1-(2-(2-fluorophenoxy)ethyl)-N-((3-methoxyphenyl)(pyridin-2-yl)methyl) piperidine-4-carboxamide |
| 23 | (R)-N-((3-chlorophenyl)(pyridin-2-yl)methyl)-1-(2-phenoxyethyl)piperidine-4-carboxamide<br>(S)-N-((3-chlorophenyl)(pyridin-2-yl)methyl)-1-(2-phenoxyethyl)piperidine-4-carboxamide |
| 24 | (R)-N-((2-chlorophenyl)(pyridin-2-yl)methyl)-1-(2-phenoxyethyl)piperidine-4-carboxamide<br>(S)-N-((2-chlorophenyl)(pyridin-2-yl)methyl)-1-(2-phenoxyethyl)piperidine-4-carboxamide |
| 25 | (R)-N-((4-fluorophenyl)(pyridin-2-yl)methyl)-1-(2-phenoxyethyl)piperidine-4-carboxamide<br>(S)-N-((4-fluorophenyl)(pyridin-2-yl)methyl)-1-(2-phenoxyethyl)piperidine-4-carboxamide |
| 26 | (R)-N-((3-fluorophenyl)(pyridin-2-yl)methyl)-1-(2-phenoxyethyl)piperidine-4-carboxamide<br>(S)-N-((3-fluorophenyl)(pyridin-2-yl)methyl)-1-(2-phenoxyethyl)piperidine-4-carboxamide |
| 27 | (R)-N-((3-fluorophenyl)(pyridin-2-yl)methyl)-1-(2-phenoxyethyl)piperidine-4-carboxamide |

TABLE 1-continued

| Compound # | Compound Name |
|---|---|
| | (S)-N-((3-fluorophenyl)(pyridin-2-yl)methyl)-1-(2-phenoxyethyl)piperidine-4-carboxamide |
| 28 | (R)-N-((2-fluorophenyl)(pyridin-2-yl)methyl)-1-(2-phenoxyethyl)piperidine-4-carboxamide |
| | (S)-N-((2-fluorophenyl)(pyridin-2-yl)methyl)-1-(2-phenoxyethyl)piperidine-4-carboxamide |
| 29 | (R)-1-(2-phenoxyethyl)-N-(pyridin-2-yl(pyridin-3-yl)methyl)piperidine-4-carboxamide |
| | (S)-1-(2-phenoxyethyl)-N-(pyridin-2-yl(pyridin-3-yl)methyl)piperidine-4-carboxamide |
| 30 | N-(di(pyridin-2-yl)methyl)-1-(2-phenoxyethyl)piperidine-4-carboxamide |
| 31 | (R)-1-(2-phenoxyethyl)-N-(pyridin-2-yl(4-(trifluoromethyl)phenyl)methyl)piperidine-4-carboxamide |
| | (S)-1-(2-phenoxyethyl)-N-(pyridin-2-yl(4-(trifluoromethyl)phenyl)methyl)piperidine-4-carboxamide |
| 32 | (R)-1-(2-phenoxyethyl)-N-(pyridin-2-yl(3-(trifluoromethyl)phenyl)methyl)piperidine-4-carboxamide |
| | (S)-1-(2-phenoxyethyl)-N-(pyridin-2-yl(3-(trifluoromethyl)phenyl)methyl)piperidine-4-carboxamide |
| 33 | (R)-1-(2-phenoxyethyl)-N-(pyridin-2-yl(2-(trifluoromethyl)phenyl)methyl)piperidine-4-carboxamide |
| | (S)-1-(2-phenoxyethyl)-N-(pyridin-2-yl(2-(trifluoromethyl)phenyl)methyl)piperidine-4-carboxamide |
| 34 | (R)-N-((4-methoxyphenyl)(pyridin-2-yl)methyl)-1-(2-phenoxyethyl)piperidine-4-carboxamide |
| | (S)-N-((4-methoxyphenyl)(pyridin-2-yl)methyl)-1-(2-phenoxyethyl)piperidine-4-carboxamide |
| 35 | (R)-N-((3-methoxyphenyl)(pyridin-2-yl)methyl)-1-(2-phenoxyethyl)piperidine-4-carboxamide |
| | (S)-N-((3-methoxyphenyl)(pyridin-2-yl)methyl)-1-(2-phenoxyethyl)piperidine-4-carboxamide |
| 36 | (R)-N-((2-methoxyphenyl)(pyridin-2-yl)methyl)-1-(2-phenoxyethyl)piperidine-4-carboxamide |
| | (S)-N-((2-methoxyphenyl)(pyridin-2-yl)methyl)-1-(2-phenoxyethyl)piperidine-4-carboxamide |
| 37 | (R)-N-(cyclohexyl(pyridin-2-yl)methyl)-1-(2-phenoxyethyl)piperidine-4-carboxamide |
| | (S)-N-(cyclohexyl(pyridin-2-yl)methyl)-1-(2-phenoxyethyl)piperidine-4-carboxamide |
| 38 | (R)-N-(2-methyl-1-(pyridin-2-yl)propyl)-1-(2-phenoxyethyl)piperidine-4-carboxamide |
| | (S)-N-(2-methyl-1-(pyridin-2-yl)propyl)-1-(2-phenoxyethyl)piperidine-4-carboxamide |
| 39 | (R)-N-((4-chlorophenyl)(phenyl)methyl)-1-(2-phenoxyethyl)piperidine-4-carboxamide |
| | (S)-N-((4-chlorophenyl)(phenyl)methyl)-1-(2-phenoxyethyl)piperidine-4-carboxamide |
| 40 | (R)-N-((4-chlorophenyl)(2-fluorophenyl)methyl)-1-(2-phenoxyethyl)piperidine-4-carboxamide |
| | (S)-N-((4-chlorophenyl)(2-fluorophenyl)methyl)-1-(2-phenoxyethyl)piperidine-4-carboxamide |
| 41 | (R)-N-((4-chlorophenyl)(3-fluorophenyl)methyl)-1-(2-phenoxyethyl)piperidine-4-carboxamide |
| | (S)-N-((4-chlorophenyl)(3-fluorophenyl)methyl)-1-(2-phenoxyethyl)piperidine-4-carboxamide |
| 42 | (R)-N-((4-chlorophenyl)(4-fluorophenyl)methyl)-1-(2-phenoxyethyl)piperidine-4-carboxamide |
| | (S)-N-((4-chlorophenyl)(4-fluorophenyl)methyl)-1-(2-phenoxyethyl)piperidine-4-carboxamide |
| 43 | (R)-N-((4-chlorophenyl)(2-methoxyphenyl)methyl)-1-(2-phenoxyethyl)piperidine-4-carboxamide |
| | (S)-N-((4-chlorophenyl)(2-methoxyphenyl)methyl)-1-(2-phenoxyethyl)piperidine-4-carboxamide |
| 44 | (R)-N-((4-chlorophenyl)(4-methoxyphenyl)methyl)-1-(2-phenoxyethyl)piperidine-4-carboxamide |
| | (S)-N-((4-chlorophenyl)(4-methoxyphenyl)methyl)-1-(2-phenoxyethyl)piperidine-4-carboxamide |
| 45 | (R)-N-((4-fluorophenyl)(phenyl)methyl)-1-(2-phenoxyethyl)piperidine-4-carboxamide |
| | (S)-N-((4-fluorophenyl)(phenyl)methyl)-1-(2-phenoxyethyl)piperidine-4-carboxamide |
| 46 | (R)-N-((3-methoxyphenyl)(phenyl)methyl)-1-(2-phenoxyethyl)piperidine-4-carboxamide |
| | (S)-N-((3-methoxyphenyl)(phenyl)methyl)-1-(2-phenoxyethyl)piperidine-4-carboxamide |
| 47 | N-(bis(4-fluorophenyl)methyl)-1-(2-phenoxyethyl)piperidine-4-carboxamide |
| 48 | N-(bis(2-fluorophenyl)methyl)-1-(2-phenoxyethyl)piperidine-4-carboxamide |

TABLE 1-continued

| Compound # | Compound Name |
|---|---|
| 49 | (R)-N-((2-fluorophenyl)(4-fluorophenyl)methyl)-1-(2-phenoxyethyl)piperidine-4-carboxamide<br>(S)-N-((2-fluorophenyl)(4-fluorophenyl)methyl)-1-(2-phenoxyethyl)piperidine-4-carboxamide |
| 50 | (R)-N-((2-fluorophenyl)(3-methoxyphenyl)methyl)-1-(2-phenoxyethyl)piperidine-4-carboxamide<br>(S)-N-((2-fluorophenyl)(3-methoxyphenyl)methyl)-1-(2-phenoxyethyl)piperidine-4-carboxamide |
| 51 | (R)-N-((4-chlorophenyl)(pyridin-2-yl)methyl)-N-methyl-1-(2-phenoxyethyl) piperidine-4-carboxamide<br>(S)-N-((4-chlorophenyl)(pyridin-2-yl)methyl)-N-methyl-1-(2-phenoxyethyl) piperidine-4-carboxamide |
| 52 | (R)-N-((4-fluorophenyl)(pyridin-2-yl)methyl)-1-(2-(2-(trifluoromethyl)phenoxy)ethyl) piperidine-4-carboxamide<br>(S)-N-((4-fluorophenyl)(pyridin-2-yl)methyl)-1-(2-(2-(trifluoromethyl)phenoxy)ethyl) piperidine-4-carboxamide |
| 53 | (R)-1-(2-(2-chlorophenoxy)ethyl)-N-((4-fluorophenyl)(pyridin-2-yl)methyl) piperidine-4-carboxamide<br>(S)-1-(2-(2-chlorophenoxy)ethyl)-N-((4-fluorophenyl)(pyridin-2-yl)methyl) piperidine-4-carboxamide |
| 54 | (R)-1-(2-(2-fluorophenoxy)ethyl)-N-((4-fluorophenyl)(pyridin-2-yl)methyl) piperidine-4-carboxamide<br>(S)-1-(2-(2-fluorophenoxy)ethyl)-N-((4-fluorophenyl)(pyridin-2-yl)methyl) piperidine-4-carboxamide |
| 55 | (R)-1-(2-(benzo[d]thiazol-6-yloxy)ethyl)-N-((4-fluorophenyl)(pyridin-2-yl)methyl)piperidine-4-carboxamide<br>(S)-1-(2-(benzo[d]thiazol-6-yloxy)ethyl)-N-((4-fluorophenyl)(pyridin-2-yl)methyl)piperidine-4-carboxamide |
| 56 | (R)-1-(2-(2,6-difluorophenoxy)ethyl)-N-((4-fluorophenyl)(pyridin-2-yl)methyl) piperidine-4-carboxamide<br>(S)-1-(2-(2,6-difluorophenoxy)ethyl)-N-((4-fluorophenyl)(pyridin-2-yl)methyl) piperidine-4-carboxamide |
| 57 | (R)-1-(2-(2,5-difluorophenoxy)ethyl)-N-((4-fluorophenyl)(pyridin-2-yl)methyl) piperidine-4-carboxamide<br>(S)-1-(2-(2,5-difluorophenoxy)ethyl)-N-((4-fluorophenyl)(pyridin-2-yl)methyl) piperidine-4-carboxamide |
| 58 | (R)-N-((4-fluorophenyl)(pyridin-2-yl)methyl)-1-(2-methyl-1-phenoxypropan-2-yl)piperidine-4-carboxamide<br>(S)-N-((4-fluorophenyl)(pyridin-2-yl)methyl)-1-(2-methyl-1-phenoxypropan-2-yl)piperidine-4-carboxamide |
| 59 | (R)-1-(benzofuran-2-ylmethyl)-N-((4-fluorophenyl)(pyridin-2-yl)methyl)piperidine-4-carboxamide<br>(S)-1-(benzofuran-2-ylmethyl)-N-((4-fluorophenyl)(pyridin-2-yl)methyl)piperidine-4-carboxamide |
| 60 | (R)-1-(benzo[d]oxazol-2-ylmethyl)-N-((4-fluorophenyl)(pyridin-2-yl)methyl)piperidine-4-carboxamide<br>(S)-1-(benzo[d]oxazol-2-ylmethyl)-N-((4-fluorophenyl)(pyridin-2-yl)methyl)piperidine-4-carboxamide |
| 61 | (R)-1-((2,3-dihydro-1H-inden-2-yl)methyl)-N-((4-fluorophenyl)(pyridin-2-yl)methyl) piperidine-4-carboxamide<br>(S)-1-((2,3-dihydro-1H-inden-2-yl)methyl)-N-((4-fluorophenyl)(pyridin-2-yl)methyl) piperidine-4-carboxamide |
| 62 | (R)-N-((4-chlorophenyl)(pyridin-2-yl)methyl)-1-(3-phenoxypropyl)piperidine-4-carboxamide<br>(S)-N-((4-chlorophenyl)(pyridin-2-yl)methyl)-1-(3-phenoxypropyl)piperidine-4-carboxamide |
| 63 | (R)-N-((4-chlorophenyl)(pyridin-2-yl)methyl)-1-(2-phenoxyethyl)piperidine-4-carboxamide<br>(S)-N-((4-chlorophenyl)(pyridin-2-yl)methyl)-1-(2-phenoxyethyl)piperidine-4-carboxamide |
| 64 | (R)-N-((4-chlorophenyl)(pyridin-2-yl)methyl)-1-methylpiperidine-4-carboxamide<br>(S)-N-((4-chlorophenyl)(pyridin-2-yl)methyl)-1-methylpiperidine-4-carboxamide |
| 65 | (R)-N-((4-chlorophenyl)(pyridin-2-yl)methyl)-1-(2-methoxyethyl)piperidine-4-carboxamide<br>(S)-N-((4-chlorophenyl)(pyridin-2-yl)methyl)-1-(2-methoxyethyl)piperidine-4-carboxamide |
| 66 | (R)-1-(2-(2-chlorophenoxy)ethyl)-N-((4-chlorophenyl)(pyridin-2-yl)methyl) piperidine-4-carboxamide<br>(S)-1-(2-(2-chlorophenoxy)ethyl)-N-((4-chlorophenyl)(pyridin-2-yl)methyl) piperidine-4-carboxamide |
| 67 | (R)-N-((4-chlorophenyl)(pyridin-2-yl)methyl)-1-(2-(2,6-difluorophenoxy)ethyl) piperidine-4-carboxamide<br>(S)-N-((4-chlorophenyl)(pyridin-2-yl)methyl)-1-(2-(2,6-difluorophenoxy)ethyl) piperidine-4-carboxamide |
| 68 | (R)-N-((4-chlorophenyl)(pyridin-2-yl)methyl)-1-(2-(2-(trifluoromethoxy)phenoxy) ethyl) piperidine-4-carboxamide |

TABLE 1-continued

| Compound # | Compound Name |
|---|---|
| | (S)-N-((4-chlorophenyl)(pyridin-2-yl)methyl)-1-(2-(2-(trifluoromethoxy)phenoxy) ethyl) piperidine-4-carboxamide |
| 69 | (R)-N-((4-fluorophenyl)(pyridin-2-yl)methyl)-4-methyl-1-(2-phenoxyethyl)piperidine-4-carboxamide |
| | (S)-N-((4-fluorophenyl)(pyridin-2-yl)methyl)-4-methyl-1-(2-phenoxyethyl)piperidine-4-carboxamide |
| 70 | (R)-N-((4-fluorophenyl)(pyridin-2-yl)methyl)-4-methyl-1-(2-(2-(trifluoromethyl) phenoxy)ethyl) piperidine-4-carboxamide |
| | (S)-N-((4-fluorophenyl)(pyridin-2-yl)methyl)-4-methyl-1-(2-(2-(trifluoromethyl) phenoxy)ethyl) piperidine-4-carboxamide |
| 71 | (R)-1-(2-(2-fluorophenoxy)ethyl)-N-((4-fluorophenyl)(pyridin-2-yl)methyl)-4-methylpiperidine-4-carboxamide |
| | (S)-1-(2-(2-fluorophenoxy)ethyl)-N-((4-fluorophenyl)(pyridin-2-yl)methyl)-4-methylpiperidine-4-carboxamide |
| 72 | (R)-1-(4-chlorophenyl)-N-((1-(2-(2-fluorophenoxy)ethyl)piperidin-4-yl)methyl)-N-methyl-1-(pyridin-2-yl)methanamine |
| | (S)-1-(4-chlorophenyl)-N-((1-(2-(2-fluorophenoxy)ethyl)piperidin-4-yl)methyl)-N-methyl-1-(pyridin-2-yl)methanamine |
| 73 | (R)-1-(4-chlorophenyl)-N-methyl-1-(pyridin-2-yl)-N-((1-(2-(2-(trifluoromethyl) phenoxy)ethyl)piperidin-4-yl)methyl)methanamine |
| | (S)-1-(4-chlorophenyl)-N-methyl-1-(pyridin-2-yl)-N-((1-(2-(2-(trifluoromethyl) phenoxy)ethyl)piperidin-4-yl)methyl)methanamine |
| 74 | (R)-1-(4-fluorophenyl)-N-methyl-N-((1-(2-phenoxyethyl)piperidin-4-yl)methyl)-1-(pyridin-2-yl)methanamine |
| | (S)-1-(4-fluorophenyl)-N-methyl-N-((1-(2-phenoxyethyl)piperidin-4-yl)methyl)-1-(pyridin-2-yl)methanamine |
| 75 | (R)-N-((1-(2-(2-fluorophenoxy)ethyl)piperidin-4-yl)methyl)-1-(4-fluorophenyl)-N-methyl-1-(pyridin-2-yl)methanamine |
| | (S)-N-((1-(2-(2-fluorophenoxy)ethyl)piperidin-4-yl)methyl)-1-(4-fluorophenyl)-N-methyl-1-(pyridin-2-yl)methanamine |
| 76 | (R)-1-(3-methoxyphenyl)-N-methyl-N-((1-(2-phenoxyethyl)piperidin-4-yl)methyl)-1-(pyridin-2-yl)methanamine |
| | (S)-1-(3-methoxyphenyl)-N-methyl-N-((1-(2-phenoxyethyl)piperidin-4-yl)methyl)-1-(pyridin-2-yl)methanamine |
| 77 | (R)-N-((1-(2-(2-fluorophenoxy)ethyl)piperidin-4-yl)methyl)-1-(3-methoxyphenyl)-N-methyl-1-(pyridin-2-yl)methanamine |
| | (S)-N-((1-(2-(2-fluorophenoxy)ethyl)piperidin-4-yl)methyl)-1-(3-methoxyphenyl)-N-methyl-1-(pyridin-2-yl)methanamine |
| 78 | (R)-1-(4-fluorophenyl)-N-((1-(2-phenoxyethyl)piperidin-4-yl)methyl)-1-(pyridin-2-yl) methanamine |
| | (S)-1-(4-fluorophenyl)-N-((1-(2-phenoxyethyl)piperidin-4-yl)methyl)-1-(pyridin-2-yl) methanamine |
| 79 | (R)-1-(4-chlorophenyl)-N-methyl-N-((1-(2-phenoxyethyl)piperidin-4-yl)methyl)-1-(pyridin-2-yl)methanamine |
| | (S)-1-(4-chlorophenyl)-N-methyl-N-((1-(2-phenoxyethyl)piperidin-4-yl)methyl)-1-(pyridin-2-yl)methanamine |
| 80 | (R)-1-(3-methoxyphenyl)-N-((1-(2-phenoxyethyl)piperidin-4-yl)methyl)-1-(pyridin-2-yl)methanamine |
| | (S)-1-(3-methoxyphenyl)-N-((1-(2-phenoxyethyl)piperidin-4-yl)methyl)-1-(pyridin-2-yl)methanamine |
| 81 | (R)-1-(4-chlorophenyl)-1-(2-fluorophenyl)-N-((1-(2-phenoxyethyl)piperidine-4-yl) methyl)methanamine |
| | (S)-1-(4-chlorophenyl)-1-(2-fluorophenyl)-N-((1-(2-phenoxyethyl)piperidine-4-yl) methyl)methanamine |
| 82 | (R)-1-(2-(benzo[d]thiazol-6-yloxy)ethyl)-N-((3-methoxyphenyl)(pyridin-2-yl)methyl) piperidine-4-carboxamide |
| | (S)-1-(2-(benzo[d]thiazol-6-yloxy)ethyl)-N-((3-methoxyphenyl)(pyridin-2-yl)methyl) piperidine-4-carboxamide |
| 83 | N-(bis(4-fluorophenyl)methyl)-1-(2-(2-chlorophenoxy)ethyl)piperidine-4-carboxamide |
| 84 | N-(bis(2-fluorophenyl)methyl)-1-(2-(2-chlorophenoxy)ethyl)piperidine-4-carboxamide |
| 85 | (R)-1-(2-(2-chlorophenoxy)ethyl)-N-((2-fluorophenyl)(4-fluorophenyl)methyl) piperidine-4-carboxamide |
| | (S)-1-(2-(2-chlorophenoxy)ethyl)-N-((2-fluorophenyl)(4-fluorophenyl)methyl) piperidine-4-carboxamide |
| 86 | (R)-1-(2-(2-chlorophenoxy)ethyl)-N-((2-fluorophenyl)(3-methoxyphenyl) methyl) piperidine-4-carboxamide |
| | (S)-1-(2-(2-chlorophenoxy)ethyl)-N-((2-fluorophenyl)(3-methoxyphenyl) methyl) piperidine-4-carboxamide |
| 87 | (R)-1-(4-chlorophenyl)-N-((1-(2-(2-fluorophenoxy)ethyl)piperidin-4-yl)methyl)-1-(2-fluorophenyl)methanamine |
| | (S)-1-(4-chlorophenyl)-N-((1-(2-(2-fluorophenoxy)ethyl)piperidin-4-yl)methyl)-1-(2-fluorophenyl)methanamine |
| 88 | (R)-N-((1-(2-(2-fluorophenoxy)ethyl)piperidin-4-yl)methyl)-1-(3-methoxyphenyl)-1-(pyridin-2-yl)methanamine |
| | (S)-N-((1-(2-(2-fluorophenoxy)ethyl)piperidin-4-yl)methyl)-1-(3-methoxyphenyl)-1-(pyridin-2-yl)methanamine |

TABLE 1-continued

| Compound # | Compound Name |
|---|---|
| 89 | (R)-1-(4-chlorophenyl)-N-((1-(2-(2,5-difluorophenoxy)ethyl)piperidin-4-yl)methyl)-1-(pyridin-2-yl)methanamine<br>(S)-1-(4-chlorophenyl)-N-((1-(2-(2,5-difluorophenoxy)ethyl)piperidin-4-yl)methyl)-1-(pyridin-2-yl)methanamine |
| 90 | (R)-1-(2-(2,5-difluorophenoxy)ethyl)-N-((3-methoxyphenyl)(pyridin-2-yl)methyl) piperidine-4-carboxamide<br>(S)-1-(2-(2,5-difluorophenoxy)ethyl)-N-((3-methoxyphenyl)(pyridin-2-yl)methyl) piperidine-4-carboxamide |
| 91 | (R)-N-((4-chlorophenyl)(3-fluoropyridin-4-yl)methyl)-1-(2-(2-fluorophenoxy)ethyl) piperidine-4-carboxamide<br>(S)-N-((4-chlorophenyl)(3-fluoropyridin-4-yl)methyl)-1-(2-(2-fluorophenoxy)ethyl) piperidine-4-carboxamide |
| 92 | (R)-N-((4-chlorophenyl)(5-fluoropyridin-2-yl)methyl)-1-(2-(2-fluorophenoxy)ethyl) piperidine-4-carboxamide<br>(S)-N-((4-chlorophenyl)(5-fluoropyridin-2-yl)methyl)-1-(2-(2-fluorophenoxy)ethyl) piperidine-4-carboxamide |
| 93 | (R)-1-(2-(2-fluorophenoxy)ethyl)-N-(pyridin-2-yl(3-(trifluoromethoxy)phenyl)methyl)piperidine-4-carboxamide<br>(S)-1-(2-(2-fluorophenoxy)ethyl)-N-(pyridin-2-yl(3-(trifluoromethoxy)phenyl)methyl)piperidine-4-carboxamide |
| 94 | (R)-N-((2,2-difluorobenzo[d][1,3]dioxol-5-yl)(pyridin-2-yl)methyl)-1-(2-(2-fluoro phenoxy)ethyl)piperidine-4-carboxamide<br>(S)-N-((2,2-difluorobenzo[d][1,3]dioxol-5-yl)(pyridin-2-yl)methyl)-1-(2-(2-fluoro phenoxy)ethyl)piperidine-4-carboxamide |
| 95 | (R)-N-(benzo[d][1,3]dioxol-5-yl(pyridin-2-yl)methyl)-1-(2-(2-fluorophenoxy) ethyl) piperidine-4-carboxamide<br>(R)-N-(benzo[d][1,3]dioxol-5-yl(pyridin-2-yl)methyl)-1-(2-(2-fluorophenoxy) ethyl) piperidine-4-carboxamide |
| 96 | (R)-N-((4-chlorophenyl)(2-fluorophenyl)methyl)-1-(2-(2-fluorophenoxy)ethyl) piperidine-4-carboxamide<br>(S)-N-((4-chlorophenyl)(2-fluorophenyl)methyl)-1-(2-(2-fluorophenoxy)ethyl) piperidine-4-carboxamide |
| 97 | N-((4-chlorophenyl)(pyridin-2-yl)methyl)-N-methyl-1-(1-(2-phenoxy ethyl) piperidin-4-yl)ethan-1-amine |
| 98 | 2-((4-chlorophenyl)(pyridin-2-yl)methyl)-5-(2-phenoxyethyl)octahydro-1H-pyrrolo[3,4-c]pyridine |
| 99 | (R)-2-((4-chlorophenyl)((1-(2-phenoxyethyl)piperidin-4-yl)methoxy) methyl) pyridine<br>(S)-2-((4-chlorophenyl)((1-(2-phenoxyethyl)piperidin-4-yl)methoxy) methyl) pyridine |
| 100 | (R)-2-((4-chlorophenyl)(pyridin-2-yl)methyl)-5-(2-(2-(trifluoromethyl)phenoxy) ethyl)octahydro-1H-pyrrolo[3,4-c]pyridine<br>(S)-2-((4-chlorophenyl)(pyridin-2-yl)methyl)-5-(2-(2-(trifluoromethyl)phenoxy) ethyl)octahydro-1H-pyrrolo[3,4-c]pyridine |
| 101 | (R)-1-(4-fluorophenyl)-N-((4-methyl-1-(2-(2-(trifluoromethyl)phenoxy)ethyl) piperidin-4-yl)methyl)-1-(pyridin-2-yl)methanamine<br>(S)-1-(4-fluorophenyl)-N-((4-methyl-1-(2-(2-(trifluoromethyl)phenoxy)ethyl) piperidin-4-yl)methyl)-1-(pyridin-2-yl)methanamine |
| 102 | (R)-1-(benzo[d][1,3]dioxol-5-yl)-N-((1-(2-phenoxyethyl)piperidin-4-yl)methyl)-1-(pyridin-2-yl)methanamine<br>(S)-1-(benzo[d][1,3]dioxol-5-yl)-N-((1-(2-phenoxyethyl)piperidin-4-yl)methyl)-1-(pyridin-2-yl)methanamine |
| 103 | (R)-N-((4-chlorophenyl)(pyridin-2-yl)methyl)-N-((1-(2-phenoxyethyl)piperidin-4-yl) methyl) propan-2-amine<br>(S)-N-((4-chlorophenyl)(pyridin-2-yl)methyl)-N-((1-(2-phenoxyethyl)piperidin-4-yl) methyl) propan-2-amine |
| 104 | (R)-2-((4-chlorophenyl)(pyridin-2-yl)methyl)-7-(2-phenoxyethyl)-2,7-diaza spiro[3.5]nonane<br>(S)-2-((4-chlorophenyl)(pyridin-2-yl)methyl)-7-(2-phenoxyethyl)-2,7-diaza spiro[3.5]nonane |
| 105 | (R)-2-((4-chlorophenyl)(pyridin-2-yl)methyl)-8-(2-phenoxyethyl)-2,8-diazaspiro[4.5] decane<br>(S)-2-((4-chlorophenyl)(pyridin-2-yl)methyl)-8-(2-phenoxyethyl)-2,8-diazaspiro[4.5] decane |
| 106 | (R)-2-((4-chlorophenyl)(pyridin-2-yl)methyl)-8-(2-(2-(trifluoromethyl)phenoxy) ethyl)-2,8-diazaspiro[4.5]decane<br>(S)-2-((4-chlorophenyl)(pyridin-2-yl)methyl)-8-(2-(2-(trifluoromethyl)phenoxy) ethyl)-2,8-diazaspiro[4.5]decane |
| 107 | (R)-N-((4-chlorophenyl)(pyridin-2-yl)methyl)-N-((1-(2-phenoxyethyl)piperidin-4-yl) methyl) acetamide<br>(S)-N-((4-chlorophenyl)(pyridin-2-yl)methyl)-N-((1-(2-phenoxyethyl)piperidin-4-yl) methyl) acetamide |
| 108 | N-(isoquinolin-1-ylmethyl)-1-(2-(2-methoxyphenoxy)ethyl)piperidine-4-carboxamide |
| 109 | (R)-N-((4-chlorophenyl)(pyridin-2-yl)methyl)-1-(2-(2-methoxyphenoxy) ethyl)piperidine-4-carboxamide<br>(S)-N-((4-chlorophenyl)(pyridin-2-yl)methyl)-1-(2-(2-methoxyphenoxy) ethyl)piperidine-4-carboxamide |

TABLE 1-continued

| Compound # | Compound Name |
|---|---|
| 110 | (R)-N-((4-chlorophenyl)(pyridin-2-yl)methyl)-1-(4-henoxybutyl)piperidine-4-carboxamide |
| | (S)-N-((4-chlorophenyl)(pyridin-2-yl)methyl)-1-(4-henoxybutyl)piperidine-4-carboxamide |
| 111 | (R)-N-((4-chlorophenyl)(pyridin-3-yl)methyl)-1-(2-phenoxyethyl) piperidine-4-carboxamide |
| | (S)-N-((4-chlorophenyl)(pyridin-3-yl)methyl)-1-(2-phenoxyethyl) piperidine-4-carboxamide |
| 112 | (R)-N-((4-chlorophenyl)(pyridin-4-yl)methyl)-1-(2-phenoxyethyl) piperidine-4-carboxamide |
| | (S)-N-((4-chlorophenyl)(pyridin-4-yl)methyl)-1-(2-phenoxyethyl) piperidine-4-carboxamide |
| 113 | (R)-1-(2-phenoxyethyl)-N-(phenyl(pyridin-2-yl)methyl)piperidine-4-carboxamide |
| | (S)-1-(2-phenoxyethyl)-N-(phenyl(pyridin-2-yl)methyl)piperidine-4-carboxamide |
| 114 | (R)-1-(4-chlorophenyl)-N-((1-(2-phenoxyethyl)piperidin-4-yl)methyl)-1-(pyridin-2-yl)methanamine |
| | (S)-1-(4-chlorophenyl)-N-((1-(2-phenoxyethyl)piperidin-4-yl)methyl)-1-(pyridin-2-yl)methanamine |
| 115 | (R)-N-((4-chlorophenyl)(pyridin-2-yl)methyl)-1-(2-(2,4-difluorophenoxy)ethyl)piperidine-4-carboxamide |
| | (S)-N-((4-chlorophenyl)(pyridin-2-yl)methyl)-1-(2-(2,4-difluorophenoxy)ethyl)piperidine-4-carboxamide |
| 116 | (R)-N-((4-chlorophenyl)(5-fluoropyridin-2-yl)methyl)-1-(2-phenoxyethyl)piperidine-4-carboxamide |
| | (S)-N-((4-chlorophenyl)(5-fluoropyridin-2-yl)methyl)-1-(2-phenoxyethyl)piperidine-4-carboxamide |
| 117 | (R)-N-((4-chlorophenyl)(3-fluoropyridin-4-yl)methyl)-1-(2-phenoxyethyl)piperidine-4-carboxamide |
| | (S)-N-((4-chlorophenyl)(3-fluoropyridin-4-yl)methyl)-1-(2-phenoxyethyl)piperidine-4-carboxamide |
| 118 | (R)-1-(2-phenoxyethyl)-N-(pyridin-2-yl(3-(trifluoromethoxy)phenyl)methyl)piperidine-4-carboxamide |
| | (S)-1-(2-phenoxyethyl)-N-(pyridin-2-yl(3-(trifluoromethoxy)phenyl)methyl)piperidine-4-carboxamide |
| 119 | (R)-N-((2,2-difluorobenzo[d][1,3]dioxol-5-yl)(pyridin-2-yl)methyl)-1-(2-phenoxyethyl)piperidine-4-carboxamide |
| | (S)-N-((2,2-difluorobenzo[d][1,3]dioxol-5-yl)(pyridin-2-yl)methyl)-1-(2-phenoxyethyl)piperidine-4-carboxamide |
| 120 | (R)-1-(4-chlorophenyl)-1-(pyridin-2-yl)-N-((1-(2-(2-(trifluoromethyl)phenoxy)ethyl)piperidin-4-yl)methyl)methanamine |
| | (S)-1-(4-chlorophenyl)-1-(pyridin-2-yl)-N-((1-(2-(2-(trifluoromethyl)phenoxy)ethyl)piperidin-4-yl)methyl)methanamine |
| 121 | (R)-1-(4-chlorophenyl)-N-((1-(2-(2-fluorophenoxy) ethyl) piperidin-4-yl) methyl)-1-(pyridin-2-yl) methanamine |
| | (S)-1-(4-chlorophenyl)-N-((1-(2-(2-fluorophenoxy) ethyl) piperidin-4-yl) methyl)-1-(pyridin-2-yl) methanamine |
| 122 | (R)-N-((1-(2-(2-fluorophenoxy) ethyl) piperidin-4-yl) methyl)-1-(4-fluorophenyl)-1-(pyridin-2-yl) methanamine |
| | (S)-N-((1-(2-(2-fluorophenoxy) ethyl) piperidin-4-yl) methyl)-1-(4-fluorophenyl)-1-(pyridin-2-yl) methanamine |
| 123 | (R)-N-((4-chlorophenyl)(2-fluorophenyl)methyl)-1-(2-(2,5-difluorophenoxy) ethyl) piperidine-4-carboxamide |
| | (S)-N-((4-chlorophenyl)(2-fluorophenyl)methyl)-1-(2-(2,5-difluorophenoxy) ethyl) piperidine-4-carboxamide |
| 125 | (R)-N-((4-chlorophenyl)(pyridin-2-yl)methyl)-2,2,2-trifluoro-N-((1-(2-phenoxyethyl)piperidin-4-yl)methyl)ethanamine |
| | (S)-N-((4-chlorophenyl)(pyridin-2-yl)methyl)-2,2,2-trifluoro-N-((1-(2-phenoxyethyl)piperidin-4-yl)methyl)ethanamine |
| 126 | (R)-2-(4-chlorophenyl)-N-(1-(2-phenoxyethyl)piperidin-4-yl)-2-(pyridin-2-yl)acetamide |
| | (S)-2-(4-chlorophenyl)-N-(1-(2-phenoxyethyl)piperidin-4-yl)-2-(pyridin-2-yl)acetamide |
| 127 | (R)-2-((4-chlorophenyl)((1-(2-(2-(trifluoromethyl)phenoxy)ethyl)piperidin-4-yl)methoxy)methyl)pyridine |
| | (S)-2-((4-chlorophenyl)((1-(2-(2-(trifluoromethyl)phenoxy)ethyl)piperidin-4-yl)methoxy)methyl)pyridine |
| 129 | (R)-N-((3-methoxyphenyl)(oxazol-4-yl)methyl)-1-(2-phenoxyethyl)piperidine-4-carboxamide |
| | (S)-N-((3-methoxyphenyl)(oxazol-4-yl)methyl)-1-(2-phenoxyethyl)piperidine-4-carboxamide |
| 130 | (R)-N-((2,2-difluorobenzo[d][1,3]dioxol-5-yl)(pyridin-2-yl)methyl)-1-(2-(2,4-difluorophenoxy)ethyl)piperidine-4-carboxamide |
| | (S)-N-((2,2-difluorobenzo[d][1,3]dioxol-5-yl)(pyridin-2-yl)methyl)-1-(2-(2,4-difluorophenoxy)ethyl)piperidine-4-carboxamide |
| 131 | (R)-1-(4-chlorophenyl)-N-methyl-N-((4-methyl-1-(2-phenoxyethyl)piperidin-4-yl)methyl)-1-(pyridin-2-yl)methanamine |

TABLE 1-continued

| Compound # | Compound Name |
|---|---|
| | (S)-1-(4-chlorophenyl)-N-methyl-N-((4-methyl-1-(2-phenoxyethyl)piperidin-4-yl)methyl)-1-(pyridin-2-yl)methanamine |
| 132 | (R)-1-(4-chlorophenyl)-N-((1-(2-(4-fluorophenoxy)ethyl)piperidin-4-yl)methyl)-1-(pyridin-2-yl)methanamine |
| | (S)-1-(4-chlorophenyl)-N-((1-(2-(4-fluorophenoxy)ethyl)piperidin-4-yl)methyl)-1-(pyridin-2-yl)methanamine |
| 133 | (R)-N-((4-chlorophenyl)(pyridin-2-yl)methyl)-N-((1-(2-(2-fluorophenoxy)ethyl)piperidin-4-yl)methyl)propan-2-amine |
| | (S)-N-((4-chlorophenyl)(pyridin-2-yl)methyl)-N-((1-(2-(2-fluorophenoxy)ethyl)piperidin-4-yl)methyl)propan-2-amine |
| 134 | (R)-N-((1-(2-(2-fluorophenoxy)ethyl)piperidin-4-yl)methyl)-N-((3-methoxyphenyl)(pyridin-2-yl)methyl)propan-2-amine |
| | (S)-N-((1-(2-(2-fluorophenoxy)ethyl)piperidin-4-yl)methyl)-N-((3-methoxyphenyl)(pyridin-2-yl)methyl)propan-2-amine |
| 135 | (R)-N-((4-chlorophenyl)(pyridin-2-yl)methyl)-N-((1-(2-(4-fluorophenoxy)ethyl)piperidin-4-yl)methyl)propan-2-amine |
| | (S)-N-((4-chlorophenyl)(pyridin-2-yl)methyl)-N-((1-(2-(4-fluorophenoxy)ethyl)piperidin-4-yl)methyl)propan-2-amine |
| 136 | (R)-N-((4-chlorophenyl)(pyridin-2-yl)methyl)-2,2,2-trifluoro-N-((1-(2-(2-fluorophenoxy)ethyl)piperidin-4-yl)methyl)ethan-1-amine |
| | (S)-N-((4-chlorophenyl)(pyridin-2-yl)methyl)-2,2,2-trifluoro-N-((1-(2-(2-fluorophenoxy)ethyl)piperidin-4-yl)methyl)ethan-1-amine |
| 137 | (R)-1-(4-chlorophenyl)-N-methyl-1-(pyridin-2-yl)-N-((1-(2-(4-(trifluoromethyl)phenoxy)ethyl)piperidin-4-yl)methyl)methanamine |
| | (S)-1-(4-chlorophenyl)-N-methyl-1-(pyridin-2-yl)-N-((1-(2-(4-(trifluoromethyl)phenoxy)ethyl)piperidin-4-yl)methyl)methanamine |
| 138 | (R)-1-(benzo[d][1,3]dioxol-5-yl)-N-((1-(2-(2-fluorophenoxy)ethyl)piperidin-4-yl)methyl)-N-methyl-1-(pyridin-2-yl)methanamine |
| | (S)-1-(benzo[d][1,3]dioxol-5-yl)-N-((1-(2-(2-fluorophenoxy)ethyl)piperidin-4-yl)methyl)-N-methyl-1-(pyridin-2-yl)methanamine |
| 139 | (R)-1-(benzo[d][1,3]dioxol-5-yl)-N-((1-(2-(2-fluorophenoxy)ethyl)piperidin-4-yl)methyl)-1-(pyridin-2-yl)methanamine |
| | (S)-1-(benzo[d][1,3]dioxol-5-yl)-N-((1-(2-(2-fluorophenoxy)ethyl)piperidin-4-yl)methyl)-1-(pyridin-2-yl)methanamine |
| 140 | N-((4-chlorophenyl)(pyridin-2-yl)methyl)-1-((2,3-dihydrobenzo[b][1,4]dioxin-2-yl)methyl)piperidine-4-carboxamide |
| 141 | (R)-N-((4-chlorophenyl)(pyridin-2-yl)methyl)-1-(2-(pyridin-2-yloxy)ethyl)piperidine-4-carboxamide |
| | (S)-N-((4-chlorophenyl)(pyridin-2-yl)methyl)-1-(2-(pyridin-2-yloxy)ethyl)piperidine-4-carboxamide |
| 142 | (R)-N-((4-chlorophenyl)(pyridin-2-yl)methyl)-1-(2-(pyridin-4-yloxy)ethyl)piperidine-4-carboxamide |
| | (S)-N-((4-chlorophenyl)(pyridin-2-yl)methyl)-1-(2-(pyridin-4-yloxy)ethyl)piperidine-4-carboxamide |
| 143 | (R)-N-((3-methoxyphenyl)(pyridin-2-yl)methyl)-4-methyl-1-(2-phenoxyethyl)piperidine-4-carboxamide |
| | (S)-N-((3-methoxyphenyl)(pyridin-2-yl)methyl)-4-methyl-1-(2-phenoxyethyl)piperidine-4-carboxamide |
| 144 | (R)-N-((4-chlorophenyl)(pyridin-2-yl)methyl)-4-methyl-1-(2-phenoxyethyl)piperidine-4-carboxamide |
| | (S)-N-((4-chlorophenyl)(pyridin-2-yl)methyl)-4-methyl-1-(2-phenoxyethyl)piperidine-4-carboxamide |
| 145 | (R)-1-(2-(2,4-difluorophenoxy)ethyl)-N-((3-methoxyphenyl)(pyridin-2-yl)methyl)piperidine-4-carboxamide |
| | (S)-1-(2-(2,4-difluorophenoxy)ethyl)-N-((3-methoxyphenyl)(pyridin-2-yl)methyl)piperidine-4-carboxamide |
| 146 | (R)-N-((3-methoxyphenyl)(phenyl)methyl)-1-(2-phenoxyethyl)piperidine-4-carboxamide |
| | (S)-N-((3-methoxyphenyl)(phenyl)methyl)-1-(2-phenoxyethyl)piperidine-4-carboxamide |

In certain embodiments, a compound of the present invention is a compound shown in Table 1, or a stereoisomer, racemate, or tautomer thereof, or a pharmaceutically acceptable salt thereof. In certain embodiments, a compound of the present invention is a compound shown in Table 1, or a pharmaceutically acceptable salt thereof.

The present invention relates to novel compounds that modulate dopamine D2 receptors. For example, compounds of the present invention have an $EC_{50}$<0.1 µM in the assay for β-arrestin antagonist activity. For example, compounds of the present invention have an $EC_{50}$ of 0.1-1.0 µM in the assay for β-arrestin antagonist activity. For example, compounds of the present invention have an $EC_{50}$ of 1.0-10.0 µM in the assay for β-arrestin antagonist activity. For example, compounds of the present invention have an $EC_{50}$ of 10.0-30.0 µM in the assay for β-arrestin antagonist activity. Accordingly, compounds of the present invention are useful in treating or preventing a disease or disorder in which modulation of D2 receptors plays a role.

For example, compounds of the present invention are selective antagonists of D2 receptors. For example, compounds of the present invention are selective β-arrestin antagonists, but not cAMP antagonists. For example, compounds of the present invention display at least 1.5-fold, 2-fold, 3-fold, 4-fold, 5-fold, 6-fold, 7-fold, 8-fold, 9-fold, 10-fold, 15-fold, 20-fold, 30-fold, 40-fold, 50-fold, or 100- fold stronger β-arrestin antagonist activity than cAMP antagonist activity. For example, compounds of the present invention display at least 1.5-fold, 2-fold, 3-fold, 4-fold, 5-fold, 6-fold, 7-fold, 8-fold, 9-fold, 10-fold, 15-fold, 20-fold, 30-fold, 40-fold, 50-fold, or 100-fold decrease in $EC_{50}$ for β-arrestin antagonist activity than cAMP antagonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention have an $EC_{50}<0.1$ μM in the assay for β-arrestin antagonist activity and an $EC_{50}≥0.1$ μM in the assay for cAMP antagonist activity. For example, compounds of the present invention have an $EC_{50}<0.1$ μM in the assay for β-arrestin antagonist activity and an $EC_{50}$ of 0.1-1.0 μM in the assay for cAMP antagonist activity. For example, compounds of the present invention have an $EC_{50}<0.1$ μM in the assay for β-arrestin antagonist activity and an $EC_{50}$ of 1.0-10.0 μM in the assay for cAMP antagonist activity. For example, compounds of the present invention have an $EC_{50}<0.1$ μM in the assay for β-arrestin antagonist activity and an $EC_{50}$ of 10.0-30.0 μM in the assay for cAMP antagonist activity. For example, compounds of the present invention have an $EC_{50}<0.1$ μM in the assay for β-arrestin antagonist activity and an $EC_{50}≥30.0$ μM in the assay for cAMP antagonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention have an $EC_{50}$ of 0.1-1.0 μM in the assay for β-arrestin antagonist activity and an $EC_{50}>1.0$ μM in the assay for cAMP antagonist activity. For example, compounds of the present invention have an $EC_{50}$ of 0.1-1.0 μM in the assay for β-arrestin antagonist activity and an $EC_{50}$ of 1.0-10.0 μM in the assay for cAMP antagonist activity. For example, compounds of the present invention have an $EC_{50}$ of 0.1-1.0 μM in the assay for β-arrestin antagonist activity and an $EC_{50}$ of 10.0-30.0 μM in the assay for cAMP antagonist activity. For example, compounds of the present invention have an $EC_{50}$ of 0.1-1.0 μM in the assay for β-arrestin antagonist activity and an $EC_{50}≥30.0$ μM in the assay for cAMP antagonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention have an $EC_{50}$ of 1.0-10.0 μM in the assay for β-arrestin antagonist activity and an $EC_{50}>10.0$ μM in the assay for cAMP antagonist activity. For example, compounds of the present invention have an $EC_{50}$ of 1.0-10.0 μM in the assay for β-arrestin antagonist activity and an $EC_{50}$ of 10.0-30.0 μM in the assay for cAMP antagonist activity. For example, compounds of the present invention have an $EC_{50}$ of of 1.0-10.0 μM in the assay for β-arrestin antagonist activity and an $EC_{50}≥30.0$ μM in the assay for cAMP antagonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention have an $EC_{50}$ of 10.0-30.0 μM in the assay for β-arrestin antagonist activity and an $EC_{50}>30.0$ μM in the assay for cAMP antagonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention are selective β-arrestin antagonists and cAMP agonists. For example, compounds of the present invention have an $EC_{50}<0.1$ μM in the assay for β-arrestin antagonist activity and an $EC_{50}<0.1$ μM in the assay for cAMP agonist activity. For example, compounds of the present invention have an $EC_{50}<0.1$ μM in the assay for β-arrestin antagonist activity and an $EC_{50}$ of 0.1-1.0 μM in the assay for cAMP agonist activity. For example, compounds of the present invention have an $EC_{50}<0.1$ μM in the assay for β-arrestin antagonist activity and an $EC_{50}$ of 1.0-10.0 μM in the assay for cAMP agonist activity. For example, compounds of the present invention have an $EC_{50}<0.1$ μM in the assay for β-arrestin antagonist activity and an $EC_{50}$ of 10.0-30.0 μM in the assay for cAMP agonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention have an $EC_{50}$ of 0.1-1.0 μM in the assay for β-arrestin antagonist activity and an $EC_{50}<0.1$ μM in the assay for cAMP agonist activity. For example, compounds of the present invention have an $EC_{50}$ of 0.1-1.0 μM in the assay for β-arrestin antagonist activity and an $EC_{50}$ of 0.1-1.0 μM in the assay for cAMP agonist activity. For example, compounds of the present invention have an $EC_{50}$ of 0.1-1.0 μM in the assay for β-arrestin antagonist activity and an $EC_{50}$ of 1.0-10.0 μM in the assay for cAMP agonist activity. For example, compounds of the present invention have an $EC_{50}$ of 0.1-1.0 μM in the assay for β-arrestin antagonist activity and an $EC_{50}$ of 10.0-30.0 μM in the assay for cAMP agonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention have an $EC_{50}$ of 1.0-10.0 μM in the assay for β-arrestin antagonist activity and an $EC_{50}<0.1$ μM in the assay for cAMP agonist activity. For example, compounds of the present invention have an $EC_{50}$ of 1.0-10.0 μM in the assay for β-arrestin antagonist activity and an $EC_{50}$ of 0.1-1.0 μM in the assay for cAMP agonist activity. For example, compounds of the present invention have an $EC_{50}$ of 1.0-10.0 μM in the assay for β-arrestin antagonist activity and an $EC_{50}$ of 1.0-10.0 μM in the assay for cAMP agonist activity. For example, compounds of the present invention have an $EC_{50}$ of 1.0-10.0 μM in the assay for β-arrestin antagonist activity and an $EC_{50}$ of 10.0-30.0 μM in the assay for cAMP agonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention have an $EC_{50}$ of 10.0-30.0 µM in the assay for β-arrestin antagonist activity and an $EC_{50}$<0.1 µM in the assay for cAMP agonist activity. For example, compounds of the present invention have an $EC_{50}$ of 10.0-30.0 µM in the assay for β-arrestin antagonist activity and an $EC_{50}$ of 0.1-1.0 µM in the assay for cAMP agonist activity. For example, compounds of the present invention have an $EC_{50}$ of 10.0-30.0 µM in the assay for β-arrestin antagonist activity and an $EC_{50}$ of 1.0-10.0 µM in the assay for cAMP agonist activity. For example, compounds of the present invention have an $EC_{50}$ of 10.0-30.0 µM in the assay for β-arrestin antagonist activity and an $EC_{50}$ of 10.0-30.0 µM in the assay for cAMP agonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention are selective β-arrestin antagonists and agonists of cAMP and β-arrestin. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention are β-arrestin antagonists and cAMP antagonists. For example, compounds of the present invention have an $EC_{50}$<0.1 µM in the assay for β-arrestin antagonist activity and an $EC_{50}$<0.1 µM in the assay for cAMP antagonist activity. For example, compounds of the present invention have an $EC_{50}$<0.1 µM in the assay for β-arrestin antagonist activity and an $EC_{50}$ of 0.1-1.0 µM in the assay for cAMP antagonist activity. For example, compounds of the present invention have an $EC_{50}$ of 0.1-1.0 µM in the assay for β-arrestin antagonist activity and an $EC_{50}$ of 0.1-1.0 µM in the assay for cAMP antagonist activity. For example, compounds of the present invention have an $EC_{50}$ of 0.1-1.0 µM in the assay for β-arrestin antagonist activity and an $EC_{50}$ of 1.0-10.0 µM in the assay for cAMP antagonist activity. For example, compounds of the present invention have an $EC_{50}$ of 1.0-10.0 µM in the assay for β-arrestin antagonist activity and an $EC_{50}$ of 1.0-10.0 µM in the assay for cAMP antagonist activity. For example, compounds of the present invention have an $EC_{50}$ of of 1.0-10.0 µM in the assay for β-arrestin antagonist activity and an $EC_{50}$ of 10.0-30.0 µM in the assay for cAMP antagonist activity. For example, compounds of the present invention have an $EC_{50}$ of 10.0-30.0 µM in the assay for β-arrestin antagonist activity and an $EC_{50}$ of 10.0-30.0 µM in the assay for cAMP antagonist activity. Accordingly, compounds of the present invention are useful in treating or preventing a disease or disorder in which modulation of D2 receptors plays a role.

The present invention relates to novel compounds that modulate dopamine D2 receptors. For example, compounds of the present invention have an $EC_{50}$<0.1 µM in the assay for β-arrestin agonist activity. For example, compounds of the present invention have an $EC_{50}$ of 0.1-1.0 µM in the assay for β-arrestin agonist activity. For example, compounds of the present invention have an $EC_{50}$ of 1.0-10.0 µM in the assay for β-arrestin agonist activity. For example, compounds of the present invention have an $EC_{50}$ of 10.0-30.0 µM in the assay for β-arrestin agonist activity. Accordingly, compounds of the present invention are useful in treating or preventing a disease or disorder in which modulation of D2 receptors plays a role.

For example, compounds of the present invention are selective agonists of D2 receptors. For example, compounds of the present invention are selective β-arrestin agonists, but not cAMP agonists. For example, compounds of the present invention display at least 1.5-fold, 2-fold, 3-fold, 4-fold, 5-fold, 6-fold, 7-fold, 8-fold, 9-fold, 10-fold, 15-fold, 20-fold, 30-fold, 40-fold, 50-fold, or 100-fold stronger β-arrestin agonist activity than cAMP agonist activity. For example, compounds of the present invention display at least 1.5-fold, 2-fold, 3-fold, 4-fold, 5-fold, 6-fold, 7-fold, 8-fold, 9-fold, 10-fold, 15-fold, 20-fold, 30-fold, 40-fold, 50-fold, or 100-fold decrease in $EC_{50}$ for β-arrestin agonist activity than cAMP agonist activity. Accordingly, compounds of the present invention are useful in treating or preventing a disease or disorder in which modulation of D2 receptors plays a role.

For example, compounds of the present invention have an $EC_{50}$<0.1 µM in the assay for β-arrestin agonist activity and an $EC_{50}$≥0.1 µM in the assay for cAMP agonist activity. For example, compounds of the present invention have an $EC_{50}$<0.1 µM in the assay for β-arrestin agonist activity and an $EC_{50}$ of 0.1-1.0 µM in the assay for cAMP agonist activity. For example, compounds of the present invention have an $EC_{50}$<0.1 µM in the assay for β-arrestin agonist activity and an $EC_{50}$ of 1.0-10.0 µM in the assay for cAMP agonist activity. For example, compounds of the present invention have an $EC_{50}$<0.1 µM in the assay for β-arrestin agonist activity and an $EC_{50}$ of 10.0-30.0 µM in the assay for cAMP agonist activity. For example, compounds of the present invention have an $EC_{50}$<0.1 µM in the assay for β-arrestin agonist activity and an $EC_{50}$≥30.0 µM in the assay for cAMP agonist activity. Accordingly, compounds of the present invention are useful in treating or preventing a disease or disorder in which modulation of D2 receptors plays a role.

For example, compounds of the present invention have an $EC_{50}$ of 0.1-1.0 µM in the assay for β-arrestin agonist activity and an $EC_{50}$>1.0 µM in the assay for cAMP agonist activity. For example, compounds of the present invention have an $EC_{50}$ of 0.1-1.0 µM in the assay for β-arrestin agonist activity and an $EC_{50}$ of 1.0-10.0 µM in the assay for cAMP agonist activity. For example, compounds of the present invention have an $EC_{50}$ of 0.1-1.0 µM in the assay for β-arrestin agonist activity and an $EC_{50}$ of 10.0-30.0 µM in the assay for cAMP agonist activity. For example, compounds of the present invention have an $EC_{50}$ of 0.1-1.0 µM in the assay for β-arrestin agonist activity and an $EC_{50}$≥30.0 µM in the assay for cAMP agonist activity. Accordingly, compounds of the present invention are useful in treating or preventing a disease or disorder in which modulation of D2 receptors plays a role.

For example, compounds of the present invention have an $EC_{50}$ of 1.0-10.0 µM in the assay for β-arrestin agonist activity and an $EC_{50}$>10.0 µM in the assay for cAMP agonist activity. For example, compounds of the present invention have an $EC_{50}$ of of 1.0-10.0 µM in the assay for β-arrestin agonist activity and an $EC_{50}$ of 10.0-30.0 µM in the assay for cAMP agonist activity. For example, compounds of the present invention have an $EC_{50}$ of of 1.0-10.0 µM in the assay for β-arrestin agonist activity and an $EC_{50}$≥30.0 µM in the assay for cAMP agonist activity. Accordingly, compounds of the present invention are useful in treating or preventing a disease or disorder in which modulation of D2 receptors plays a role.

For example, compounds of the present invention have an $EC_{50}$ of of 10.0-30.0 µM in the assay for β-arrestin agonist activity and an $EC_{50}$>30.0 µM in the assay for cAMP agonist activity. Accordingly, compounds of the present invention are useful in treating or preventing a disease or disorder in which modulation of D2 receptors plays a role.

For example, compounds of the present invention are selective β-arrestin agonists and cAMP antagonists. For example, compounds of the present invention have an $EC_{50}$<0.1 µM in the assay for β-arrestin agonist activity and an $EC_{50}$<0.1 µM in the assay for cAMP antagonist activity. For example, compounds of the present invention have an $EC_{50}$<0.1 µM in the assay for β-arrestin agonist activity and an $EC_{50}$ of 0.1-1.0 µM in the assay for cAMP antagonist activity. For example, compounds of the present invention have an $EC_{50}$<0.1 µM in the assay for β-arrestin agonist activity and an $EC_{50}$ of 1.0-10.0 µM in the assay for cAMP antagonist activity. For example, compounds of the present invention have an $EC_{50}$<0.1 µM in the assay for β-arrestin agonist activity and an $EC_{50}$ of 10.0-30.0 µM in the assay for cAMP antagonist activity. Accordingly, compounds of the present invention are useful in treating or preventing a disease or disorder in which modulation of D2 receptors plays a role.

For example, compounds of the present invention have an $EC_{50}$ of 0.1-1.0 µM in the assay for β-arrestin agonist activity and an $EC_{50}$<0.1 µM in the assay for cAMP antagonist activity. For example, compounds of the present invention have an $EC_{50}$ of 0.1-1.0 µM in the assay for β-arrestin agonist activity and an $EC_{50}$ of 0.1-1.0 µM in the assay for cAMP antagonist activity. For example, compounds of the present invention have an $EC_{50}$ of 0.1-1.0 µM in the assay for β-arrestin agonist activity and an $EC_{50}$ of 1.0-10.0 µM in the assay for cAMP antagonist activity. For example, compounds of the present invention have an $EC_{50}$ of 0.1-1.0 µM in the assay for β-arrestin agonist activity and an $EC_{50}$ of 10.0-30.0 µM in the assay for cAMP antagonist activity. Accordingly, compounds of the present invention are useful in treating or preventing a disease or disorder in which modulation of D2 receptors plays a role.

For example, compounds of the present invention have an $EC_{50}$ of 1.0-10.0 µM in the assay for β-arrestin agonist activity and an $EC_{50}$<0.1 µM in the assay for cAMP antagonist activity. For example, compounds of the present invention have an $EC_{50}$ of 1.0-10.0 µM in the assay for β-arrestin agonist activity and an $EC_{50}$ of 0.1-1.0 µM in the assay for cAMP antagonist activity. For example, compounds of the present invention have an $EC_{50}$ of 1.0-10.0 µM in the assay for β-arrestin agonist activity and an $EC_{50}$ of 1.0-10.0 µM in the assay for cAMP antagonist activity. For example, compounds of the present invention have an $EC_{50}$ of 1.0-10.0 µM in the assay for β-arrestin agonist activity and an $EC_{50}$ of 10.0-30.0 µM in the assay for cAMP antagonist activity. Accordingly, compounds of the present invention are useful in treating or preventing a disease or disorder in which modulation of D2 receptors plays a role.

For example, compounds of the present invention have an $EC_{50}$ of 10.0-30.0 µM in the assay for β-arrestin agonist activity and an $EC_{50}$<0.1 µM in the assay for cAMP antagonist activity. For example, compounds of the present invention have an $EC_{50}$ of 10.0-30.0 µM in the assay for β-arrestin agonist activity and an $EC_{50}$ of 0.1-1.0 µM in the assay for cAMP antagonist activity. For example, compounds of the present invention have an $EC_{50}$ of 10.0-30.0 µM in the assay for β-arrestin agonist activity and an $EC_{50}$ of 1.0-10.0 µM in the assay for cAMP antagonist activity. For example, compounds of the present invention have an $EC_{50}$ of 10.0-30.0 µM in the assay for β-arrestin agonist activity and an $EC_{50}$ of 10.0-30.0 µM in the assay for cAMP antagonist activity. Accordingly, compounds of the present invention are useful in treating or preventing a disease or disorder in which modulation of D2 receptors plays a role.

For example, compounds of the present invention are selective β-arrestin agonists and antagonists of cAMP and β-arrestin. Accordingly, compounds of the present invention are useful in treating or preventing a disease or disorder in which modulation of D2 receptors plays a role.

For example, compounds of the present invention are β-arrestin agonists and cAMP agonists. For example, compounds of the present invention have an $EC_{50}$<0.1 µM in the assay for β-arrestin agonist activity and an $EC_{50}$<0.1 µM in the assay for cAMP agonist activity. For example, compounds of the present invention have an $EC_{50}$<0.1 µM in the assay for β-arrestin agonist activity and an $EC_{50}$ of 0.1-1.0 µM in the assay for cAMP agonist activity. For example, compounds of the present invention have an $EC_{50}$ of 0.1-1.0 µM in the assay for β-arrestin agonist activity and an $EC_{50}$ of 0.1-1.0 µM in the assay for cAMP agonist activity. For example, compounds of the present invention have an $EC_{50}$ of 0.1-1.0 µM in the assay for β-arrestin agonist activity and an $EC_{50}$ of 1.0-10.0 µM in the assay for cAMP agonist activity. For example, compounds of the present invention have an $EC_{50}$ of 1.0-10.0 µM in the assay for β-arrestin agonist activity and an $EC_{50}$ of 1.0-10.0 µM in the assay for cAMP agonist activity. For example, compounds of the present invention have an $EC_{50}$ of of 1.0-10.0 µM in the assay for β-arrestin agonist activity and an $EC_{50}$ of 10.0-30.0 µM in the assay for cAMP agonist activity. For example, compounds of the present invention have an $EC_{50}$ of 10.0-30.0 µM in the assay for β-arrestin agonist activity and an $EC_{50}$ of 10.0-30.0 µM in the assay for cAMP agonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway). The present invention relates to novel compounds that modulate dopamine D2 receptors. For example, compounds of the present invention have an $EC_{50}$<0.1 µM in the assay for cAMP antagonist activity. For example, compounds of the present invention have an $EC_{50}$ of 0.1-1.0 µM in the assay for cAMP antagonist activity. For example, compounds of the present invention have an $EC_{50}$ of 1.0-10.0 µM in the assay for cAMP antagonist activity. For example, compounds of the present invention have an $EC_{50}$ of 10.0-30.0 µM in the assay for cAMP antagonist activity. Accordingly, compounds of the present invention are useful in treating or preventing a disease or disorder in which modulation of D2 receptors plays a role.

For example, compounds of the present invention are selective antagonists of D2 receptors. For example, compounds of the present invention are selective cAMP antagonists, but not β-arrestin antagonists. For example, compounds of the present invention display at least 1.5-fold, 2-fold, 3-fold, 4-fold, 5-fold, 6-fold, 7-fold, 8-fold, 9-fold, 10-fold, 15-fold, 20-fold, 30-fold, 40-fold, 50-fold, or 100-fold stronger cAMP antagonist activity than β-arrestin antagonist activity. For example, compounds of the present invention display at least 1.5-fold, 2-fold, 3-fold, 4-fold, 5-fold, 6-fold, 7-fold, 8-fold, 9-fold, 10-fold, 15-fold, 20-fold, 30-fold, 40-fold, 50-fold, or 100-fold decrease in $EC_{50}$ for cAMP antagonist activity than β-arrestin antagonist activity. Accordingly, compounds of the present invention are useful in treating or preventing a disease or disorder in which modulation of D2 receptors plays a role.

For example, compounds of the present invention have an $EC_{50}$<0.1 μM in the assay for cAMP antagonist activity and an $EC_{50}$≥0.1 μM in the assay for β-arrestin antagonist activity. For example, compounds of the present invention have an $EC_{50}$<0.1 μM in the assay for cAMP antagonist activity and an $EC_{50}$ of 0.1-1.0 μM in the assay for β-arrestin antagonist activity. For example, compounds of the present invention have an $EC_{50}$<0.1 μM in the assay for cAMP antagonist activity and an $EC_{50}$ of 1.0-10.0 μM in the assay for β-arrestin antagonist activity. For example, compounds of the present invention have an $EC_{50}$<0.1 μM in the assay for cAMP antagonist activity and an $EC_{50}$ of 10.0-30.0 μM in the assay for β-arrestin antagonist activity. For example, compounds of the present invention have an $EC_{50}$<0.1 μM in the assay for cAMP antagonist activity and an $EC_{50}$≥30.0 μM in the assay for β-arrestin antagonist activity. Accordingly, compounds of the present invention are useful in treating or preventing a disease or disorder in which modulation of D2 receptors plays a role.

For example, compounds of the present invention have an $EC_{50}$ of 0.1-1.0 μM in the assay for cAMP antagonist activity and an $EC_{50}$>1.0 μM in the assay for β-arrestin antagonist activity. For example, compounds of the present invention have an $EC_{50}$ of 0.1-1.0 μM in the assay for cAMP antagonist activity and an $EC_{50}$ of 1.0-10.0 μM in the assay for β-arrestin antagonist activity. For example, compounds of the present invention have an $EC_{50}$ of 0.1-1.0 μM in the assay for cAMP antagonist activity and an $EC_{50}$ of 10.0-30.0 μM in the assay for β-arrestin antagonist activity. For example, compounds of the present invention have an $EC_{50}$ of 0.1-1.0 μM in the assay for cAMP antagonist activity and an $EC_{50}$≥30.0 μM in the assay for β-arrestin antagonist activity. Accordingly, compounds of the present invention are useful in treating or preventing a disease or disorder in which modulation of D2 receptors plays a role.

For example, compounds of the present invention have an $EC_{50}$ of 1.0-10.0 μM in the assay for cAMP antagonist activity and an $EC_{50}$>10.0 μM in the assay for β-arrestin antagonist activity. For example, compounds of the present invention have an $EC_{50}$ of of 1.0-10.0 μM in the assay for cAMP antagonist activity and an $EC_{50}$ of 10.0-30.0 μM in the assay for β-arrestin antagonist activity. For example, compounds of the present invention have an $EC_{50}$ of of 1.0-10.0 μM in the assay for cAMP antagonist activity and an $EC_{50}$≥30.0 μM in the assay for β-arrestin antagonist activity. Accordingly, compounds of the present invention are useful in treating or preventing a disease or disorder in which modulation of D2 receptors plays a role.

For example, compounds of the present invention have an $EC_{50}$ of of 10.0-30.0 μM in the assay for cAMP antagonist activity and an $EC_{50}$>30.0 μM in the assay for β-arrestin antagonist activity. Accordingly, compounds of the present invention are useful in treating or preventing a disease or disorder in which modulation of D2 receptors plays a role.

For example, compounds of the present invention are selective cAMP antagonists and β-arrestin agonists. For example, compounds of the present invention have an $EC_{50}$<0.1 μM in the assay for cAMP antagonist activity and an $EC_{50}$<0.1 μM in the assay for β-arrestin agonist activity. For example, compounds of the present invention have an $EC_{50}$<0.1 μM in the assay for cAMP antagonist activity and an $EC_{50}$ of 0.1-1.0 μM in the assay for β-arrestin agonist activity. For example, compounds of the present invention have an $EC_{50}$<0.1 μM in the assay for cAMP antagonist activity and an $EC_{50}$ of 1.0-10.0 μM in the assay for β-arrestin agonist activity. For example, compounds of the present invention have an $EC_{50}$<0.1 μM in the assay for cAMP antagonist activity and an $EC_{50}$ of 10.0-30.0 μM in the assay for β-arrestin agonist activity. Accordingly, compounds of the present invention are useful in treating or preventing a disease or disorder in which modulation of D2 receptors plays a role.

For example, compounds of the present invention have an $EC_{50}$ of 0.1-1.0 μM in the assay for cAMP antagonist activity and an $EC_{50}$<0.1 μM in the assay for β-arrestin agonist activity. For example, compounds of the present invention have an $EC_{50}$ of 0.1-1.0 μM in the assay for cAMP antagonist activity and an $EC_{50}$ of 0.1-1.0 μM in the assay for β-arrestin agonist activity. For example, compounds of the present invention have an $EC_{50}$ of 0.1-1.0 μM in the assay for cAMP antagonist activity and an $EC_{50}$ of 1.0-10.0 μM in the assay for β-arrestin agonist activity. For example, compounds of the present invention have an $EC_{50}$ of 0.1-1.0 μM in the assay for cAMP antagonist activity and an $EC_{50}$ of 10.0-30.0 μM in the assay for β-arrestin agonist activity. Accordingly, compounds of the present invention are useful in treating or preventing a disease or disorder in which modulation of D2 receptors plays a role.

For example, compounds of the present invention have an $EC_{50}$ of 1.0-10.0 μM in the assay for cAMP antagonist activity and an $EC_{50}$<0.1 μM in the assay for β-arrestin agonist activity. For example, compounds of the present invention have an $EC_{50}$ of 1.0-10.0 μM in the assay for cAMP antagonist activity and an $EC_{50}$ of 0.1-1.0 μM in the assay for β-arrestin agonist activity. For example, compounds of the present invention have an $EC_{50}$ of 1.0-10.0 μM in the assay for cAMP antagonist activity and an $EC_{50}$ of 1.0-10.0 μM in the assay for β-arrestin agonist activity. For example, compounds of the present invention have an $EC_{50}$ of 1.0-10.0 μM in the assay for cAMP antagonist activity and an $EC_{50}$ of 10.0-30.0 μM in the assay for β-arrestin agonist activity. Accordingly, compounds of the present invention are useful in treating or preventing a disease or disorder in which modulation of D2 receptors plays a role.

For example, compounds of the present invention have an $EC_{50}$ of 10.0-30.0 μM in the assay for cAMP antagonist activity and an $EC_{50}$<0.1 μM in the assay for β-arrestin agonist activity. For example, compounds of the present invention have an $EC_{50}$ of 10.0-30.0 μM in the assay for cAMP antagonist activity and an $EC_{50}$ of 0.1-1.0 μM in the assay for β-arrestin agonist activity. For example, compounds of the present invention have an $EC_{50}$ of 10.0-30.0 μM in the assay for cAMP antagonist activity and an $EC_{50}$ of 1.0-10.0 μM in the assay for β-arrestin agonist activity. For example, compounds of the present invention have an $EC_{50}$ of 10.0-30.0 μM in the assay for cAMP antagonist activity and an $EC_{50}$ of 10.0-30.0 μM in the assay for β-arrestin agonist activity. Accordingly, compounds of the present invention are useful in treating or preventing a disease or disorder in which modulation of D2 receptors plays a role.

For example, compounds of the present invention are selective cAMP antagonists and agonists of cAMP and β-arrestin. Accordingly, compounds of the present invention are useful in treating or preventing a disease or disorder in which modulation of D2 receptors plays a role.

For example, compounds of the present invention are cAMP antagonists and β-arrestin antagonists. For example, compounds of the present invention have an $EC_{50}$<0.1 μM in the assay for cAMP antagonist activity and an $EC_{50}<0.1$ µM in the assay for β-arrestin antagonist activity. For example, compounds of the present invention have an $EC_{50}<0.1$ µM in the assay for cAMP antagonist activity and an $EC_{50}$ of 0.1-1.0 µM in the assay for β-arrestin antagonist activity. For example, compounds of the present invention have an $EC_{50}$ of 0.1-1.0 µM in the assay for cAMP antagonist activity and an $EC_{50}$ of 0.1-1.0 µM in the assay for β-arrestin antagonist activity. For example, compounds of the present invention have an $EC_{50}$ of 0.1-1.0 µM in the assay for cAMP antagonist activity and an $EC_{50}$ of 1.0-10.0 µM in the assay for β-arrestin antagonist activity. For example, compounds of the present invention have an $EC_{50}$ of 1.0-10.0 µM in the assay for cAMP antagonist activity and an $EC_{50}$ of 1.0-10.0 µM in the assay for β-arrestin antagonist activity. For example, compounds of the present invention have an $EC_{50}$ of of 1.0-10.0 µM in the assay for cAMP antagonist activity and an $EC_{50}$ of 10.0-30.0 µM in the assay for β-arrestin antagonist activity. For example, compounds of the present invention have an $EC_{50}$ of 10.0-30.0 µM in the assay for cAMP antagonist activity and an $EC_{50}$ of 10.0-30.0 µM in the assay for β-arrestin antagonist activity. Accordingly, compounds of the present invention are useful in treating or preventing a disease or disorder in which modulation of D2 receptors plays a role.

The present invention relates to novel compounds that modulate dopamine D2 receptors. For example, compounds of the present invention have an $EC_{50}<0.1$ µM in the assay for cAMP agonist activity. For example, compounds of the present invention have an $EC_{50}$ of 0.1-1.0 µM in the assay for cAMP agonist activity. For example, compounds of the present invention have an $EC_{50}$ of 1.0-10.0 µM in the assay for cAMP agonist activity. For example, compounds of the present invention have an $EC_{50}$ of 10.0-30.0 µM in the assay for cAMP agonist activity. Accordingly, compounds of the present invention are useful in treating or preventing a disease or disorder in which modulation of D2 receptors plays a role.

For example, compounds of the present invention are selective agonists of D2 receptors. For example, compounds of the present invention are selective cAMP agonists, but not β-arrestin agonists. For example, compounds of the present invention display at least 1.5-fold, 2-fold, 3-fold, 4-fold, 5-fold, 6-fold, 7-fold, 8-fold, 9-fold, 10-fold, 15-fold, 20-fold, 30-fold, 40-fold, 50-fold, or 100-fold stronger cAMP agonist activity than β-arrestin agonist activity. For example, compounds of the present invention display at least 1.5-fold, 2-fold, 3-fold, 4-fold, 5-fold, 6-fold, 7-fold, 8-fold, 9-fold, 10-fold, 15-fold, 20-fold, 30-fold, 40-fold, 50-fold, or 100-fold decrease in $EC_{50}$ for cAMP agonist activity than β-arrestin agonist activity.

For example, compounds of the present invention have an $EC_{50}<0.1$ µM in the assay for cAMP agonist activity and an $EC_{50}\geq0.1$ µM in the assay for β-arrestin agonist activity. For example, compounds of the present invention have an $EC_{50}<0.1$ µM in the assay for cAMP agonist activity and an $EC_{50}$ of 0.1-1.0 µM in the assay for β-arrestin agonist activity. For example, compounds of the present invention have an $EC_{50}<0.1$ µM in the assay for cAMP agonist activity and an $EC_{50}$ of 1.0-10.0 µM in the assay for β-arrestin agonist activity. For example, compounds of the present invention have an $EC_{50}<0.1$ µM in the assay for cAMP agonist activity and an $EC_{50}$ of 10.0-30.0 µM in the assay for β-arrestin agonist activity. For example, compounds of the present invention have an $EC_{50}<0.1$ µM in the assay for cAMP agonist activity and an $EC_{50}\geq30.0$ µM in the assay for β-arrestin agonist activity. Accordingly, compounds of the present invention are useful in treating or preventing a disease or disorder in which modulation of D2 receptors plays a role.

For example, compounds of the present invention have an $EC_{50}$ of 0.1-1.0 µM in the assay for cAMP agonist activity and an $EC_{50}>1.0$ µM in the assay for β-arrestin agonist activity. For example, compounds of the present invention have an $EC_{50}$ of 0.1-1.0 µM in the assay for cAMP agonist activity and an $EC_{50}$ of 1.0-10.0 µM in the assay for β-arrestin agonist activity. For example, compounds of the present invention have an $EC_{50}$ of 0.1-1.0 µM in the assay for cAMP agonist activity and an $EC_{50}$ of 10.0-30.0 µM in the assay for β-arrestin agonist activity. For example, compounds of the present invention have an $EC_{50}$ of 0.1-1.0 µM in the assay for cAMP agonist activity and an $EC_{50}\geq30.0$ µM in the assay for β-arrestin agonist activity. Accordingly, compounds of the present invention are useful in treating or preventing a disease or disorder in which modulation of D2 receptors plays a role.

For example, compounds of the present invention have an $EC_{50}$ of 1.0-10.0 µM in the assay for cAMP agonist activity and an $EC_{50}>10.0$ µM in the assay for β-arrestin agonist activity. For example, compounds of the present invention have an $EC_{50}$ of of 1.0-10.0 µM in the assay for cAMP agonist activity and an $EC_{50}$ of 10.0-30.0 µM in the assay for β-arrestin agonist activity. For example, compounds of the present invention have an $EC_{50}$ of of 1.0-10.0 µM in the assay for cAMP agonist activity and an $EC_{50}\geq30.0$ µM in the assay for β-arrestin agonist activity. Accordingly, compounds of the present invention are useful in treating or preventing a disease or disorder in which modulation of D2 receptors plays a role.

For example, compounds of the present invention have an $EC_{50}$ of of 10.0-30.0 µM in the assay for cAMP agonist activity and an $EC_{50}>30.0$ µM in the assay for β-arrestin agonist activity. Accordingly, compounds of the present invention are useful in treating or preventing a disease or disorder in which modulation of D2 receptors plays a role.

For example, compounds of the present invention are selective cAMP agonists and β-arrestin antagonists. For example, compounds of the present invention have an $EC_{50}<0.1$ µM in the assay for cAMP agonist activity and an $EC_{50}<0.1$ µM in the assay for β-arrestin antagonist activity. For example, compounds of the present invention have an $EC_{50}<0.1$ µM in the assay for cAMP agonist activity and an $EC_{50}$ of 0.1-1.0 µM in the assay for β-arrestin antagonist activity. For example, compounds of the present invention have an $EC_{50}<0.1$ µM in the assay for cAMP agonist activity and an $EC_{50}$ of 1.0-10.0 µM in the assay for β-arrestin antagonist activity. For example, compounds of the present invention have an $EC_{50}<0.1$ µM in the assay for cAMP agonist activity and an $EC_{50}$ of 10.0-30.0 µM in the assay for β-arrestin antagonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention have an $EC_{50}$ of 0.1-1.0 µM in the assay for cAMP agonist activity and an $EC_{50}<0.1$ µM in the assay for β-arrestin antagonist activity. For example, compounds of the present invention have an $EC_{50}$ of 0.1-1.0 µM in the assay for cAMP agonist activity and an $EC_{50}$ of 0.1-1.0 µM in the assay for β-arrestin antagonist activity. For example, compounds of the present invention have an $EC_{50}$ of 0.1-1.0 µM in the assay for cAMP agonist activity and an $EC_{50}$ of 1.0-10.0 µM in the assay for β-arrestin antagonist activity. For example, compounds of the present invention have an $EC_{50}$ of 0.1-1.0 μM in the assay for cAMP agonist activity and an $EC_{50}$ of 10.0-30.0 μM in the assay for β-arrestin antagonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention have an $EC_{50}$ of 1.0-10.0 μM in the assay for cAMP agonist activity and an $EC_{50}$<0.1 μM in the assay for β-arrestin antagonist activity. For example, compounds of the present invention have an $EC_{50}$ of 1.0-10.0 μM in the assay for cAMP agonist activity and an $EC_{50}$ of 0.1-1.0 μM in the assay for β-arrestin antagonist activity. For example, compounds of the present invention have an $EC_{50}$ of 1.0-10.0 μM in the assay for cAMP agonist activity and an $EC_{50}$ of 1.0-10.0 μM in the assay for β-arrestin antagonist activity. For example, compounds of the present invention have an $EC_{50}$ of 1.0-10.0 μM in the assay for cAMP agonist activity and an $EC_{50}$ of 10.0-30.0 μM in the assay for β-arrestin antagonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention have an $EC_{50}$ of 10.0-30.0 μM in the assay for cAMP agonist activity and an $EC_{50}$<0.1 μM in the assay for β-arrestin antagonist activity. For example, compounds of the present invention have an $EC_{50}$ of 10.0-30.0 μM in the assay for cAMP agonist activity and an $EC_{50}$ of 0.1-1.0 μM in the assay for β-arrestin antagonist activity. For example, compounds of the present invention have an $EC_{50}$ of 10.0-30.0 μM in the assay for cAMP agonist activity and an $EC_{50}$ of 1.0-10.0 μM in the assay for β-arrestin antagonist activity. For example, compounds of the present invention have an $EC_{50}$ of 10.0-30.0 μM in the assay for cAMP agonist activity and an $EC_{50}$ of 10.0-30.0 μM in the assay for β-arrestin antagonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention are selective cAMP agonists and antagonists of cAMP and β-arrestin. Accordingly, compounds of the present invention are useful in treating or preventing a disease or disorder in which modulation of D2 receptors plays a role.

For example, compounds of the present invention are cAMP agonists and β-arrestin agonists. For example, compounds of the present invention have an $EC_{50}$<0.1 μM in the assay for cAMP agonist activity and an $EC_{50}$<0.1 μM in the assay for β-arrestin agonist activity. For example, compounds of the present invention have an $EC_{50}$<0.1 μM in the assay for cAMP agonist activity and an $EC_{50}$ of 0.1-1.0 μM in the assay for β-arrestin agonist activity. For example, compounds of the present invention have an $EC_{50}$ of 0.1-1.0 μM in the assay for cAMP agonist activity and an $EC_{50}$ of 0.1-1.0 μM in the assay for β-arrestin agonist activity. For example, compounds of the present invention have an $EC_{50}$ of 0.1-1.0 μM in the assay for cAMP agonist activity and an $EC_{50}$ of 1.0-10.0 μM in the assay for β-arrestin agonist activity. For example, compounds of the present invention have an $EC_{50}$ of 1.0-10.0 μM in the assay for cAMP agonist activity and an $EC_{50}$ of 1.0-10.0 μM in the assay for β-arrestin agonist activity. For example, compounds of the present invention have an $EC_{50}$ of of 1.0-10.0 μM in the assay for cAMP agonist activity and an $EC_{50}$ of 10.0-30.0 μM in the assay for β-arrestin agonist activity. For example, compounds of the present invention have an $EC_{50}$ of 10.0-30.0 μM in the assay for cAMP agonist activity and an $EC_{50}$ of 10.0-30.0 μM in the assay for β-arrestin agonist activity. Accordingly, compounds of the present invention are useful in treating or preventing a disease or disorder in which modulation of D2 receptors plays a role.

TABLE 2

| Abbreviations | |
|---|---|
| TFA: | trifluoroacetic acid |
| HATU: | 1-[Bis(dimethylamino)methylene]-1H-1,2,3-triazolo[4,5-h]pyridinium 3-oxid hexafluorophosphate, N-[(Dimethylamino)-1H-1,2,3-triazolo-[4,5-b]pyridin-1-ylmethylene]-N-methylmethanaminium hexafluorophosphate N-oxide |
| LAH: | lithium aluminium hydride |
| DMP: | Dess Martin periodinane |
| [O]: | oxidation using suitable oxidants such as Dess Martin periodinane, pyridinium chlorochromate, pyridinium dichromate, or oxidation reagents used in Swern oxidation, Parikh-Doering oxidation, Corey-Kim oxidation or Pfitzner-Moffatt oxidation |
| Boc: | tert-butyloxycarbonyl |
| Fmoc: | 9-fluorenylmethoxycarbonyl |

The terms "compounds of the invention", "compound of the invention", "compounds of the present invention" and "compounds of the present invention", and the like, unless the context indicates otherwise, refer collectively to the novel compounds of any formulae or specific compounds described herein, and their salts, solvates, stereoisomers, tautomers, racemates, polymorphs and hydrates.

When a range of values is listed, it is intended to encompass each value and sub-range within the range. For example "C1-6 alkyl" is intended to encompass, C1, C2, C3, C4, C5, C6, C1-6, C1-5, C1-4, C1-3, C1-2, C2-6, C2-5, C2-4, C2-3, C3-6, C3-5, C3-4, C4-6, C4-5, and C5-6 alkyl. For example "1-6" is intended to encompass, 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6.

As used herein, the term "halogen" refers to fluorine, chlorine, bromine or iodine.

As used herein, the term "alkyl" refers to a radical of a straight-chain or branched saturated hydrocarbon group having from 1 to 20 carbon atoms ("C1-20 alkyl"). In some embodiments, an alkyl group has 1 to 10 carbon atoms ("C1-10 alkyl"). In some embodiments, an alkyl group has 1 to 9 carbon atoms ("C1-9 alkyl"). In some embodiments, an alkyl group has 1 to 8 carbon atoms ("C1-8 alkyl"). In some embodiments, an alkyl group has 1 to 7 carbon atoms ("C1-7 alkyl"). In some embodiments, an alkyl group has 1 to 6 carbon atoms ("C1-6 alkyl"). In some embodiments, an alkyl group has 1 to 5 carbon atoms ("C1-5 alkyl"). In some embodiments, an alkyl group has 1 to 4 carbon atoms ("C1-4 alkyl"). In some embodiments, an alkyl group has 1 to 3 carbon atoms ("C1-3 alkyl"). In some embodiments, an alkyl group has 1 to 2 carbon atoms ("C1-2 alkyl"). In some embodiments, an alkyl group has 1 carbon atom ("C1 alkyl"). In some embodiments, an alkyl group has 2 to 6 carbon atoms ("C2-6 alkyl"). Examples of C1-6 alkyl groups include methyl (C1), ethyl (C2), n-propyl (C3), isopropyl (C3), n-butyl (C4), tert-butyl (C4), sec-butyl (C4), iso-butyl (C4), n-pentyl (C5), 3-pentanyl (C5), amyl (C5), neopentyl (C5), 3-methyl-2-butanyl (C5), tertiary amyl (C5), and n-hexyl (C6). Additional examples of alkyl groups include n-heptyl (C7), n-octyl (C8) and the like. Unless otherwise specified, each instance of an alkyl group is independently optionally substituted, e.g., unsubstituted (an "unsubstituted alkyl") or substituted (a "substituted alkyl") with one or more substituents.

The term "substituted alkyl" refers to alkyl moieties having substituents replacing one or more hydrogen atoms on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_1$-$C_8$ haloalkyl"). In some embodiments, the haloalkyl moiety has 1 to 6 carbon atoms ("$C_1$-$C_6$ haloalkyl"). In some embodiments, the haloalkyl moiety has 1 to 4 carbon atoms ("$C_1$-$C_4$ haloalkyl"). In some embodiments, the haloalkyl moiety has 1 to 3 carbon atoms ("$C_1$-$C_3$ haloalkyl"). In some embodiments, the haloalkyl moiety has 1 to 2 carbon atoms ("$C_1$-$C_2$ haloalkyl"). Examples of haloalkyl groups include —$CH_2F$, —$CHF_2$, —$CF_3$, —$CH_2CF_3$, —$CF_2CF_3$, —$CF_2CF_2CF_3$, —$CCl_3$, —$CFCl_2$, —$CF_2Cl$, and the like.

As used herein, the term "cyclic ring" or "cyclic group" refers to a saturated or unsaturated carbocyclic ring, i.e., a ring composed exclusively of carbon atoms, or to a saturated or unsaturated heterocyclic ring, i.e., a carbocyclic ring wherein one or more ring atoms are replaced with an heteroatom independently selected from oxygen, nitrogen, and sulfur. Cyclic rings may involve 3-10 atoms that form the ring. In some embodiments, the cyclic rings involve 3-5 ring atoms, in other embodiments, the cyclic rings involve 4-6 ring atoms, in yet other embodiments, cyclic rings involve 5-7 ring atoms. The cyclic rings can be monocyclic rings or fused systems that may include bicyclic rings, for example, 5-5, 5-6, 6-5, 6-6 as well as spirocyclic systems such as 4-4, 4-5, 4-6, 5-6 and 6-6. The cyclic ring may be further substituted with substituents such as C1-C6 alkyl (linear, branched, cyclic or heterocyclic): In some embodiments, cyclic groups may include pseudo-cyclic groups comprising straight- or branched substituted or substituted alkyl groups, for example $C_3$-$C_{10}$ alkyl groups.

As used herein, the term "cycloalkyl" refers to a saturated or unsaturated cyclic monovalent hydrocarbon, containing one or two rings and comprising 3-10 ring atoms, preferably 4-8 ring atoms, and more preferably 5-6 ring carbon atoms. Examples of a cycloalkyl useful in the context of the present invention are cyclopropyl, cyclobutyl, cyclopentyl, cyclohexyl, cycloheptyl and cyclooctyl, preferably cyclopentyl and cyclohexyl, more preferably cyclohexyl. Cycloalkyl also includes hydrocarbon spirocyclique groups.

As used herein, the term "heterocyclyl" refers to a saturated or unsaturated cycloalkyl wherein one or more ring atoms are replaced with an heteroatom independently selected from oxygen, nitrogen, and sulfur. The term heterocyclyl also encompasses partially hydrogenated and oxo derivatives of heteroaryl compounds. Examples of a heterocyclyl useful in the context of the present invention are pyrrolidinyl, tetrahydrofuranyl, tetrahydrothiophenyl, piperidinyl, tetrahydropyranyl, tetrahydrothiopyranyl, imidazolidinyl, pyrazolidinyl, oxazolidinyl, isoxazolidinyl, thiazolidinyl, isothiazolidinyl, dioxolanyl, and dithiolanyl.

As used herein, the term "bicyclic group" refers to a group containing two cyclic groups, with 5-12 or 6-12 ring atoms, optionally containing 1-3 heteroatoms independently selected from nitrogen, oxygen or sulfur, said two cyclic groups being fused or bridged or forming a spirocycle. Preferably, the two cyclic groups are fused and one of the two cyclic groups is a phenyl while the other is a cycloalkyl or heterocycloalkyl, wherein the phenyl, cycloalkyl and heterocycloalkyl are optionally substituted. Examples of a bicyclic group useful in the context of the present invention are oxo-tetrahydroquinolinyl, benzodioxolyl, difluorobenzodioxolyl and dihydroindenyl. Each cycle in the bicyclic group can be independently aromatic, unsaturated, partially saturated, or saturated.

As used herein, the term "spirocycle" refers to a bicyclic compound wherein the two cyclic groups connect only through one atom.

Further examples of bicyclic groups include bridged ring systems such as bicycloalkanes and azabicycloalkanes although such bridged ring systems are generally less preferred. By "bridged ring systems" is meant ring systems in which two rings share more than two atoms, see for example Advanced Organic Chemistry, by Jerry March, 4th. Edition, Wiley Interscience, pages 131-133, 1992. Examples of bridged ring systems include bicyclo[2.2.1]heptane, aza-bicyclo[2.2.1]heptane, bicyclo[2.2.2]octane, aza-bicyclo[2.2.2]octane, bicyclo[3.2.1]octane and aza-bicyclo[3.2.1]octane. A particular example of a bridged ring system is the 1-aza-bicyclo[2.2.2]octan-3-yl group.

As used herein, the term "aryl" refers to a polyunsaturated aromatic carbocyclic group comprising one ring (i.e., phenyl) or several fused rings (for example naphthyl) or several rings linked via a covalent bond (for example biphenyl), which typically contain 5 to 12 and preferentially 6 to 10 carbon atoms, and wherein at least one ring is aromatic. An aryl group described herein may be monocyclic, bicyclic, or tricyclic. Examples of an aryl useful in the context of the present invention are phenyl, naphthyl and biphenyl, preferably phenyl.

As used herein, the term "heteroaryl" refers to an aryl containing 1-4 ring heteroatoms independently selected from nitrogen, oxygen, and sulphur. The nitrogen heteroatom may be substituted or unsubstituted with substituents, for example with an alkyl group and/or the nitrogen heteroatom may be derivatised to form a salt or amine oxide. A heteroaryl group described herein may be monocyclic, bicyclic, or tricyclic. Examples of a heteroaryl useful in the context of the present invention are furyl, thienyl, pyrrolyl, pyranyl, thiopyranyl, imidazolyl, pyrazolyl, oxazolyl, isoxazolyl, thiazolyl, isothiazolyl, pyridyl, quinolinyl, isoquinolinyl, indolyl, benzofuranyl, benzoxazolyl, benzisoxazolyl, benzothiazolyl, benzisothiazolyl, benzoimidazolyl and benzopyrazole, preferably pyridyl, quinolinyl, benzofuranyl, benzoxazolyl and benzothiazolyl.

The terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthridine, indole, benzofuran, purine, benzofuran, deazapurine, and indolizine. In the case of multicyclic aromatic rings, only one of the rings needs to be aromatic (e.g., 2,3-dihydroindole), although all of the rings may be aromatic (e.g., quinoline). The second ring can also be fused or bridged.

The aryl or heteroaryl aromatic ring can be substituted at one or more ring positions with such substituents as described above, for example, alkyl, alkenyl, akynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic, or tricyclic ring having the specified number of carbons, any of which may be saturated, unsaturated, or aromatic. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0] bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" includes any ring structure (saturated or partially unsaturated) which contains at least one ring heteroatom (e.g., N, O or S). A heterocycle group described herein may be monocyclic, bicyclic, or tricyclic. A heterocycle group described herein may comprise only carbon and nitrogen atoms in the heterocyclic ring system. A heterocycle group described herein may comprise only carbon and oxygen atoms in the heterocyclic ring system. Examples of heterocycles include, but are not limited to, morpholine, pyrrolidine, tetrahydrothiophene, piperidine, piperazine and tetrahydrofuran. Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "x- to y-membered ring" (wherein x is an integer selected from 3, 4, 5, 6, 7, and 8, preferably from 3, 4, and 5, and more preferably from 3 and 4; and y is an integer selected from 4, 5, 6, 7, 8, 9, 10, 11, and 12, preferably from 5, 6, 7, 8, and 9, and 10) includes cyclic ring, cyclic group, carbocycle, heterocycle, aryl, and heteroaryl, each having x- to y-number of ring atoms, as defined herein.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "substituted", as used herein, means that any one or more hydrogen atoms on the designated atom is replaced with a selection from the indicated groups, provided that the designated atom's normal valency is not exceeded, and that the substitution results in a stable compound. When a substituent is keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents and/or variables are permissible, but only if such combinations result in stable compounds.

Except as described herein, any of the above defined alkyl, cycloalkyl, aryl, heteroaryl, carbocycle, heterocycle, and alkoxy, may be unsubstituted or independently substituted with up to six, preferably one, two or three substituents, selected from the group consisting of: halo (such as F, Cl or Br); hydroxy; lower alkyl (such as $C_1$-$C_6$ alkyl, $C_1$-$C_3$ alkyl), wherein the lower alkyl may be substituted with any of the substituents defined herein; lower alkanoyl; lower alkoxy (such as methoxy); aryl (such as phenyl or naphthyl); substituted aryl (such as fluoro phenyl or methoxy phenyl); aryl lower alkyl such as benzyl; amino; mono or di-lower alkyl amino (such as dimethylamino); lower alkanoyl amino acetylamino; amino lower alkoxy (such as ethoxyamine); nitro; cyano; cyano lower alkyl; carboxy; lower carbalkoxy (such as methoxy carbonyl; n-propoxy carbonyl or isopropoxy carbonyl); lower aryloyl, such as benzoyl; carbamoyl; N-mono- or N,N di-lower alkyl carbamoyl; lower alkyl carbamic acid ester; amidino; guanidine; ureido; mercapto; sulfo; lower alkylthio; sulfoamino; sulfonamide; benzosulfonamide; sulfonate; sulfanyl lower alkyl (such as methyl sulfanyl); sulfoamino; aryl sulfonamide; halogen substituted or unsubstituted aryl sulfonate (such as chloro-phenyl sulfonate); lower alkylsulfinyl; arylsulfinyl; aryl-lower alkylsulfinyl; lower alkylarylsulfinyl; lower alkanesulfonyl; arylsulfonyl; aryl-lower alkylsulfonyl; lower aryl alkyl; lower alkylarylsulfonyl; halogen-lower alkylmercapto; halogen-lower alkylsulfonyl; such as trifluoromethane sulfonyl; phosphono(—P(=O)(OH)$_2$); hydroxy-lower alkoxy phosphoryl or di-lower alkoxyphosphoryl; urea and substituted urea; and alkyl carbamic acid ester or carbamates (such as ethyl-N-phenyl-carbamate).

The compounds of the present invention are capable of further forming salts. All of these forms are also contemplated within the scope of the claimed invention.

As used herein, a salt of the compound of the invention refers to derivatives of the compounds of the present invention wherein the parent compound is modified by making acid or base salts thereof. Examples of salts include, but are not limited to, mineral or organic acid salts of basic residues such as amines, alkali or organic salts of acidic residues such as carboxylic acids, and the like. The salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of salts of the compounds of the invention include salts with the following acid: hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The free base of the compounds of the present invention can be protonated at the N atom(s) of an amine and/or N containing heterocycle moiety to form a salt. The term "free base" refers to the amine compounds in non-salt form. The free form of the specific salt compounds described may be isolated using techniques known in the art. For example, the free form may be regenerated by treating the salt with a suitable dilute aqueous base solution such as dilute aqueous sodium hydroxide, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The salts can be synthesized from the compounds of the invention which contain basic moieties by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents.

The salts of the instant invention can be prepared from compounds of the invention by reacting with an inorganic, organic acid or polymeric acid. For example, conventional non-toxic salts include those derived from acids such as hydrochloric acid, toluenesulfonic acid, sulfuric acid, benzenesulfonic acid, fumaric acid or succinic acid, especially toluenesulfonic acid, pamoic acid (see for example, WO2005/016261; U.S. Pat. No. 6,987,111; US 20050032836; US 20060040922).

Compounds of the present invention that contain nitrogens can be converted to N-oxides by treatment with an oxidizing agent (e.g., 3-chloroperoxybenzoic acid (m-CPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present invention. Furthermore, so-called metabolite which is produced by degradation of the present compound in vivo is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four nonidentical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this invention include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine.

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The compounds of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p1-92, Elesevier, New York-Oxford (1985).

As used herein, the term "combination", as applied to two or more compounds and/or agents (also referred to herein as the components), is intended to define material in which the two or more compounds/agents are associated. The terms "combined" and "combining" in this context are to be interpreted accordingly.

As used herein, the term "in combination" may refer to compounds/agents that are administered as part of the same overall treatment regimen. As such, the posology of each of the two or more compounds/agents may differ: each may be administered at the same time or at different times. It will therefore be appreciated that the compounds/agents of the combination may be administered sequentially (e.g., before or after) or simultaneously, either in the same pharmaceutical formulation (i.e., together), or in different pharmaceutical formulations (i.e., separately). Simultaneously in the same formulation is as a unitary formulation whereas simultaneously in different pharmaceutical formulations is non-unitary. The posologies of each of the two or more compounds/agents in a combination therapy may also differ with respect to the route of administration.

The term "drug" or "active substance" as used herein includes the free base, or pharmaceutically acceptable salts, solvates, stereoisomers, racemates, tautomers, polymorphs and hydrates thereof, or mixtures thereof.

As used herein, the term "selective" when used to describe β-arrestin antagonist, β-arrestin agonist, cAMP antagonist, or cAMP agonist means "biased" β-arrestin antagonist, β-arrestin agonist, cAMP antagonist, or cAMP agonist, unless the specific circumstances dictate otherwise (i.e., "selective" and "biased" are used interchangeably). The term "selective" or "biased" means that a compound preferentially binds to or otherwise interacts with one of β-arrestin and cAMP over the other. For example, the compound binds to or otherwise interacts with one of β-arrestin and cAMP with an $EC_{50}$ that is lower that the $EC_{50}$ for the other, such as described herein.

Synthesis of the Compounds of the Invention

The present invention provides methods for the synthesis of the compounds of each of the formulae described herein. The present invention also provides detailed methods for the synthesis of various disclosed compounds of the present invention according to the following schemes and examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester or prodrug thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5th edition, John Wiley & Sons: New York, 2001; and Greene, T. W., Wuts, P. G. M., *Protective Groups in Organic Synthesis*, 3rd edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present invention.

Compounds of the present invention can be conveniently prepared by a variety of methods familiar to those skilled in the art. The compounds each of the formulae described herein may be prepared according to the following procedures from commercially available starting materials or starting materials which can be prepared using literature procedures. These procedures show the preparation of representative compounds of the invention.

All the abbreviations used in this application are found in "Protective Groups in Organic Synthesis" by John Wiley & Sons, Inc, or the MERCK INDEX by MERCK & Co., Inc, or other chemistry books or chemicals catalogs by chemicals vendor such as Aldrich, or according to usage know in the art.

A general synthetic scheme is presented in Scheme 1 below.

Scheme 1

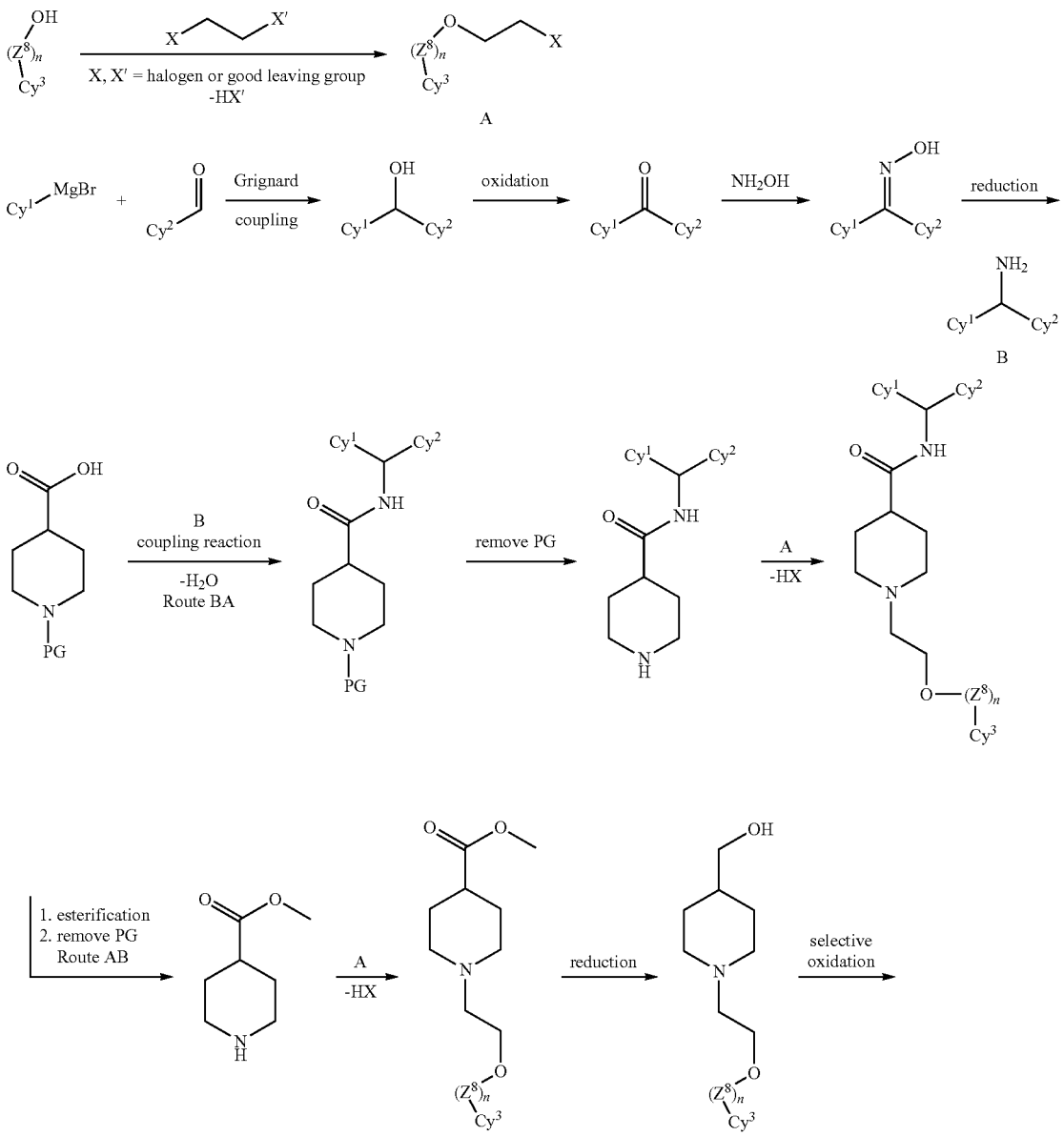

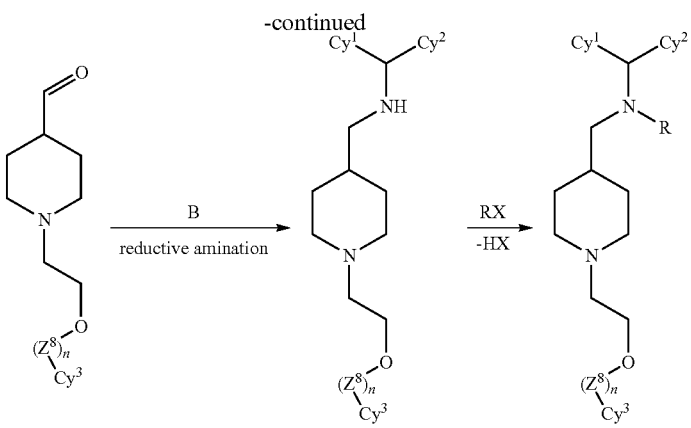

PG: protecting group.

Scheme 1 illustrates a general synthetic route, using piperidine-4-carboxylic acid as a starting material. The piperidine nitrogen is first protected with labile protecting groups known in the art, such as Boc or Fmoc (representative protecting groups and deprotecting reagents can be found, for example, in Greene and Wuts, Protective Groups in Organic Synthesis, 2nd ed., John Wiley & Sons, New York, 1991, Encyclopedia of Reagents for Organic Synthesis (Ed: L. Paquette) 2004, J. Wiley & Sons, New York). Compounds of the present invention may be synthesized by coupling of suitable amides at the 4-carboxylic acid moiety of the piperidine ring (referred to herein as the northern end of the piperidine ring), as well as extending the molecule by alkylation at the piperidine nitrogen (referred to herein as the southern end of the piperidine ring). The synthesis may involve coupling first at the northern end of the piperidine ring, followed by alkylation at the southern end of the piperdine ring (route BA), or alkylation at the southern end of the piperidine ring first, followed by coupling at the northern end of the piperidine ring (route AB), as depicted in Scheme 1.

Examples of suitable building blocks or synthons A and B, for use respectively, in alkylation at the southern end and coupling at the northern end of the piperidine ring are also depicted in Scheme 1. Depending on the specific substituents, one skilled in the art would know that the Grignard reagent used in the synthesis of synthon B may be prepared using either $Cy^1MgBr$ or $Cy^2MgBr$, to couple with the corresponding aldehyde or ketone, to form the corresponding alcohol that contains both $Cy^1$ and $Cy^2$. Methods of alkylation to form synthon A and Grignard coupling, followed by oxidative amination to form synthon B are well-known in the art of organic synthesis.

The amino compounds synthesized by route AB may be further derivatised at the amino group, for example, with alkylating agents to form the corresponding N-alkylated compound, as depicted in Scheme 1.

An exemplary synthetic route for the synthesis of compounds of the present invention is further illustrated in Scheme 1A.

Scheme 1A

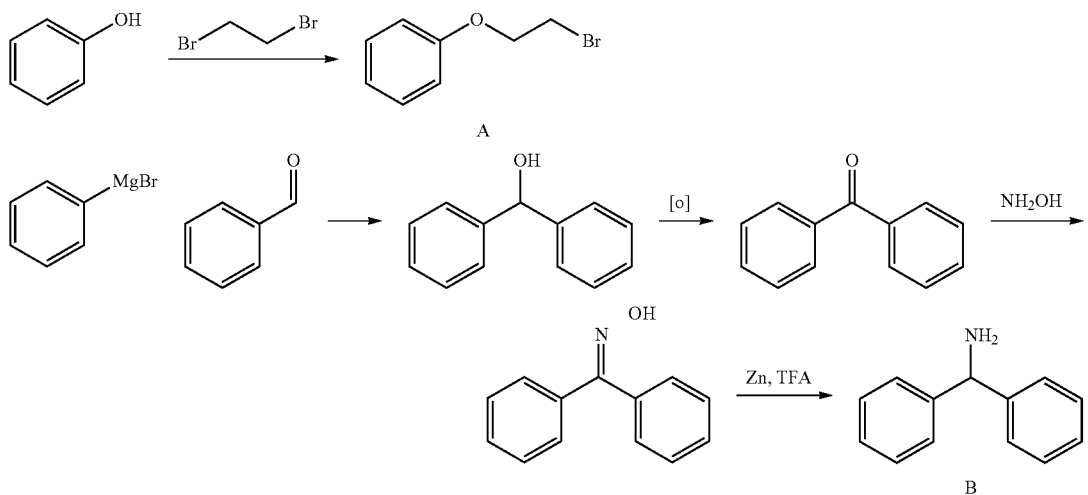

-continued

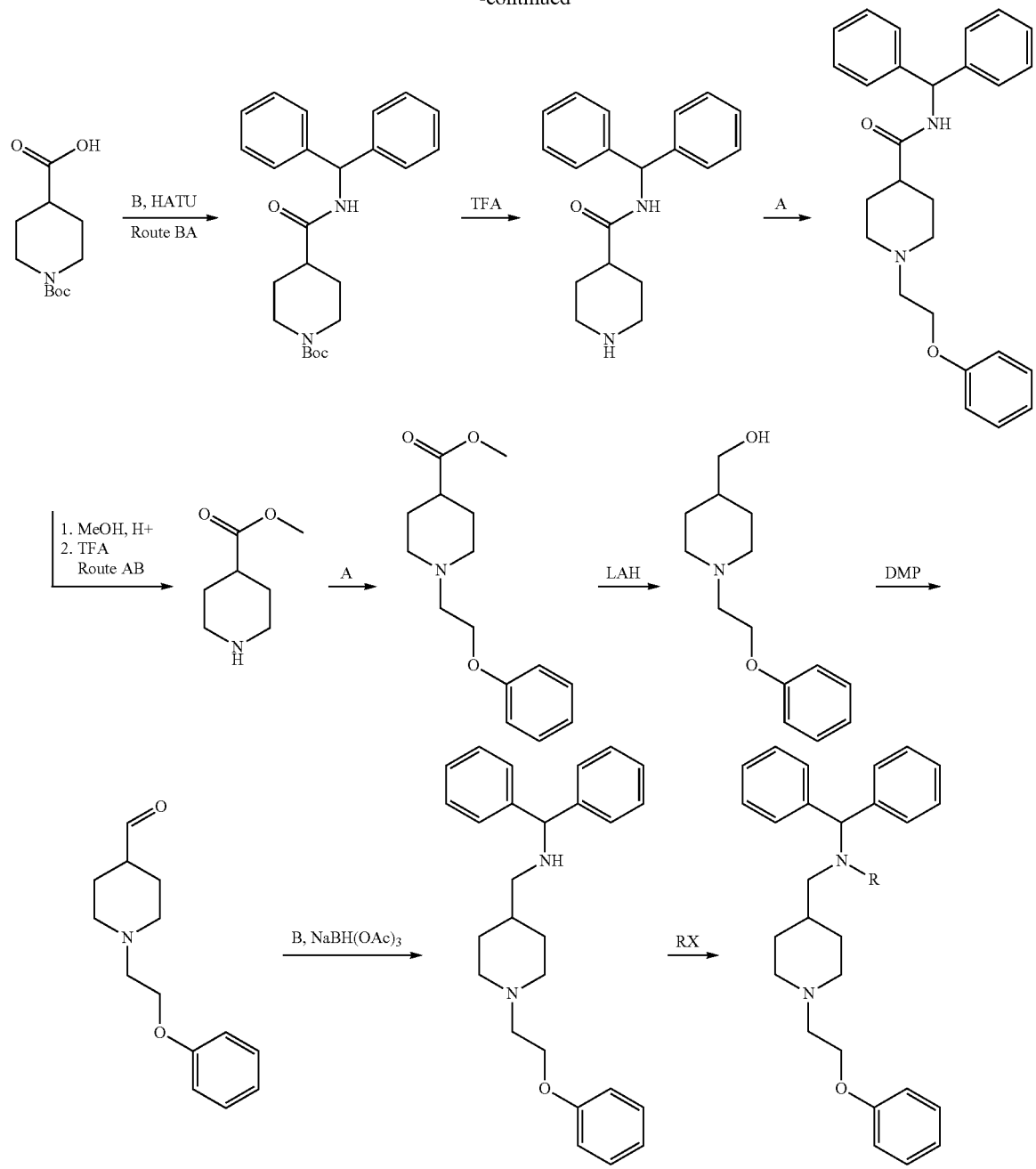

Assays for Activities of the Compounds of the Invention

The present invention provides methods for assessing the in vitro and in vivo biological activities (e.g., antagonistic or agonistic activities) of the compounds of the invention. Biological activities (e.g., antagonistic or agonistic activities) of the compounds of the present invention can be tested in a variety of ways using commercially available materials, reagents known in the literature or readily prepared, by employing routine methods and procedures either known to those skilled in the art, or which will be apparent to the skilled artisan in light of the teachings herein. Theses methods and procedures can be obtained from the relevant scientific literature or from standard textbooks in the field. The following descriptions of assays are designed to illustrate, but not to limit, general procedures for evaluating the activities of compounds of the present invention.

A general description of the assays is presented below.

Preparation of Cells for Biological Assays

Cells are prepared for assays by growing cultures for the requisite period of time (e.g., up to 2 weeks). Frozen cells are thawed, and then transferred into growth media. If necessary, the cells can be gently centrifuged and then resuspended in growth media. When the cells reached the necessary confluence (e.g., ~95%), the cells are passaged and used for various biological assays, such as those described herein below.

β-Arrestin Agonist Assay

The assays can be performed using proper detection reagents either prepared using routine methods known in the art or commercially available (e.g., PathHunter® β-Arrestin Detecting Kit (DiscoveR$_X$)). Cells are grown to the necessary confluence and then detached. The cells are then centrifuged, washed, resuspended, and seeded into a container (e.g., 384-well plate). The cells are incubated (e.g., at 37° C., 5% $CO_2$) for the appropriate period of time (e.g., 24 hours), before various compounds (e.g., a compound of the invention or a control compound) are added to the cells. After incubation of the cells with the compounds, detection reagents (e.g., a buffer containing Emerald II: Galactor-Star as provided DiscoveR$_X$) are added to the cells. The read-out (e.g., luminescence, or fluorescence) is detected using standard equipment.

β-Arrestin Antagonist Assay

The assays can be conducted in the same manner as the β-arrestin agonist assay, except that before addition of the detection reagents, a D2 receptor agonist (e.g., Quinpirole) is added to the cells. The detection reagents are then added, and the read-out is detected.

Gi/cAMP Agonist Assay

The assays can be performed using proper detection reagents either prepared using routine methods known in the art or commercially available (e.g., PE Lance Ultra cAMP kit (TRF0263)). Cells are grown to the necessary confluence and then detached. The cells are then centrifuged, washed, resuspended, and seeded into a container (e.g., 384-well plate). The cells are incubated (e.g., at 37° C., 5% $CO_2$) for the appropriate period of time (e.g., 24 hours), before various compounds (e.g., a compound of the invention or a control compound) are added to the cells. Afterwards, cAMP inducing agents (e.g., Forskolin) are added to and incubated with the cells before detection reagents (e.g., a cAMP antibody, such as ULight-anti-cAMP solution) are added to the cells. Read-out (e.g., luminescence, or fluorescence) is detected using standard equipment.

Gi/cAMP Antagonist Assay

The assays can be conducted in the same manner as the Gi/cAMP agonist assay, except that before addition of the detection reagents, a D2 receptor agonist (e.g., Quinpirole) is added to the cells. The detection reagents are then added, and the read-out is detected.

Pharmacokinetic Studies on Mice Brains

Test animals are administered (e.g., intraperitoneally, intravenously, orally) with a dose of test compounds (e.g., compounds of the invention). Blood samples are collected and plasma is harvested from the blood. Brain tissues are also isolated and homogenized. Concentrations of the test compounds administered in the plasma and brain samples are determined using routine analytic methods, such as LC-MS/MS.

Positron Emission Tomography Studies on Rodents

Non-radiolabeled test compounds (e.g., vehicle, compounds of the invention, control compounds) are administered to the test animal, followed by administration of a radiotracer (e.g., carbon 11-labeled raclopride ([$^{11}$C]RAC), which can be synthesized from the O-desmethyl RAC precursor and [11C] methyl iodide and subsequently purified by high-performance liquid chromatography as previously described (Farde L, et al. (1985) PNAS, USA 82(11):3863-3867)). Positron emission tomography (PET) and skeletal computed tomography (CT) data are collected using standard equipment, such as a GammaMedica Triumph trimodal PET/SPECT/CT scanner (Quebec, Canada) or a Concorde Microsystems R4 microPET scanner (Knoxville, Tenn., USA). Routine data processing is employed, including substraction of random coincidences collected in a delayed time window, and reconstruction of scatter-corrected sinograms using a known algorithm (e.g., 3-dimensional iterative maximum likelihood expectation maximization (3D-MLEM) algorithm). Regions of Interest (ROIs) are drawn on reconstructed images estimating peak [$^{11}$C]RAC uptake in striata (averaged between left and right hemispheres) and cerebellum as reference region for non-displaceable (ND) tracer uptake. ROI dimensions, placement and striatal D2/D3 binding potential ($BP_{ND}$) are evaluated by graphical analysis (e.g., using Logan distribution volume ratio (DVR) linearization as previously described ($BP_{ND}$=DVR-1; Alexoff D, et al. (2002) JNucMed 44(5): 815-822; Logan J, et al. (1996) JCerebral Blood Flow and Metabolism 16(5):843-840)).

Amphetamine Induced Hyperactivity Studies

Amphetamine-induced hyperactivity (AIH) can be examined using routine behavior methods, such as in open-field chambers. Activity is detected by various methods, such as infrared beam. Daily sessions are binned for statistical analysis. AIH can be run over various time frames, according to the need of the study, such as as follows:

Day 1: test animals are acclimated to the injection procedure by injecting prior to being placed in the chambers. Test animals are then placed into the open-field a certain time period (e.g., 20 min) and then removed for a saline injection. Test animals are placed back into the open-field for an additional period of time (e.g., 30 min), at which point the test animals are returned to their home cage.

Day 2: repeat Day 1, with the exception that the timing may be different (e.g., the second day may last for one hour (20 minutes injection 40 minutes)).

Day 3: test animals are challenged by amphetamine. Test animals are pre-treated with D2 antagonist compounds (e.g., compounds of the invention) prior to being placed in the open field. After a certain period of time, test animals are removed and challenged with amphetamine, following protocols known to one skilled in the art, for example Jones C. A, et. al. *Br J Pharmacol*. 2011, 164(4):1162-1194; Pan J Q, et. al. *Neuropsychopharmacology*. 2011, 36(7):1397-1411.

Rotarod Performance

In the test, test animals are placed on a horizontally oriented, rotating cylinder (rod) suspended above a cage floor. The test animals naturally try to stay on the rotating cylinder, or rotarod, and avoid falling to the ground. Test animals are administered with various compounds (e.g., compounds of the invention or control compounds). The length of time that a given animal stays on this rotating rod is a measure of the animal's balance, coordination, physical condition, and motor-planning. The speed of the rotarod is mechanically driven, and can be held constant.

Pharmaceutical Compositions

The present invention also provides a pharmaceutical composition comprising a compound of any formulae or selected from any compounds described herein, and at least one pharmaceutically acceptable excipient or carrier.

The term "pharmaceutical composition" is defined herein as comprising an effective amount of at least one active substance (e.g., compounds of the present invention), and at least one pharmaceutically acceptable carrier or excipient, in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, parenteral, topical, intranasal, ophthalmic, otic, rectal, transdermal, and transmucosal, and the like. Dosage forms for the topical or transdermal administration of a compound of the invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

The term "pharmaceutically acceptable" as used herein pertains to compounds, materials, compositions, and/or dosage forms which are, within the scope of sound medical judgment, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

The term "pharmaceutically acceptable carrier or excipient" refers to a carrier medium which does not interfere with the effectiveness of the biological activity of the active compound(s) and which is not excessively toxic to the host at the concentration at which it is administered. The term includes solvents, dispersion media, coatings, isotonic agents, adsorption delaying agents, and the like. The use of such media and agents for pharmaceutically active substances is well known in the art (see for example", E. W. Martin, 18$^{th}$ Ed., 1990, Mack Publishing Co. Easton, Pa., which is incorporated herein by reference in its entirety). In certain embodiments, the pharmaceutically acceptable carrier or excipient is a veterinary acceptable carrier or excipient.

The term "therapeutically effective amount" or "effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

For any compound, the therapeutically effective amount can be estimated initially either in cell culture assays, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The compounds may be in fine particulate form, freeze-dried as a powder formulation (see for example, CA 2837693; WO2009/017250; US 20100196486), in a low hygroscopic form (see for example, U.S. Pat. Nos. 7,910,589, 8,017,615, 8,399,469, 8,580,796, 8,642,760; US 20040058935), or liquid or gel formulations (see for example, US 20130209552; US 20130171237; WO2012/058091).

Any suitable pharmaceutically acceptable excipient can be added to the compositions of the invention. Excipients may be added for numerous reasons, for example to facilitate manufacture, enhance stability, control release, enhance product characteristics, enhance bioavailability, enhance patient acceptability and combinations thereof. Examples of pharmaceutically acceptable excipients include diluents, vehicles, binders, disintegrants, glidants, compression aids, colouring agents, organoleptic ingredients such as flavoring agents or sweeteners, suspending agents, dispersing agents, film formers, printing inks, lubricants, preservatives, fillers, buffers, stabilisers, or other materials well known to those skilled in the art. These excipients may be used in a conventional manner, and alone or in any combination.

Exemplary binders, which may be used to help to hold the dosage form together, include polyvinyl pyrrolidone, hydroxypropyl cellulose, hydroxypropyl methylcellulose, methylcellulose, hydroxyethyl cellulose, sugars, and combinations thereof. Disintegrants (such as croscarmellose sodium) expand when wet causing a tablet to break apart. Lubricants typically aid in the processing of powder materials. Exemplary lubricants include calcium stearate, glycerol behenate, magnesium stearate, mineral oil, polyethylene glycol, sodium stearylfumarate, stearic acid, talc, vegetable oil, zinc stearate, and combinations thereof An example of a glidant is silicon dioxide.

The formulations described herein may contain a filler, such as a water insoluble or water soluble filler, or combinations thereof. Typical water insoluble fillers include silicon dioxide, titanium dioxide, talc, aluinina, starch, kaolin, polacrilin potassiuin, powdered cellulose, microcrystalline cellulose, and combinations thereof. Typical water-soluble fillers include water soluble sugars and sugar alcohols, preferably lactose, glucose, fructose, sucrose, mannose, dextrose, galactose, the corresponding sugar alcohols and other sugar alcohols, such as mannitol, sorbitol, xylitol, and combinations thereof.

The present invention further provides pharmaceutical compositions, as defined above, and methods of making a pharmaceutical composition comprising admixing such as blending, filling, granulation and compressing, at least one active compound, as defined above, together with one or more pharmaceutically acceptable carriers or excipients, as described herein. The compositions of the invention can be prepared for example by Direct compression and wet granulation. These and other methods are described and/or exemplified in more detail herein.

The pharmaceutical compositions can be in any form suitable for administration via various routes, including but not limited to, oral, parenteral, topical, intranasal, ophthalmic, otic, rectal, transdermal, and transmucosal. Where the compositions are intended for parenteral administration, they can be formulated for intravenous, intramuscular, intraperitoneal, or subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump.

Pharmaceutical formulations adapted for parenteral administration include aqueous and non-aqueous sterile solutions which may contain a sterile diluent such as water, saline solution, fixed oils, polyethylene glycols, glycerine, propylene glycol or other synthetic solvents; anti-oxidants such as ascorbic acid or sodium bisulfite; buffers such as acetates, citrates or phosphates; bacteriostats such as benzyl alcohol or methyl parabens; co-solvents; organic solvent mixtures; chelating agents such as ethylenediaminetetraacetic acid; agents for the adjustment of tonicity such as sodium chloride or dextrose; cyclodextrin complexation agents; emulsifying agents (for forming and stabilizing emulsion formulations); liposome components for forming liposomes; gellable polymers for forming polymeric gels; lyophilisation protectants; and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230). Pharmaceutical formulations for parenteral administration may also be provided in finely divided sterile powder form for making up extemporaneously with sterile water for injection.

A drug molecule that is ionizable can be solubilized to the desired concentration by pH adjustment if the drug's $pK_a$ is sufficiently away from the formulation pH value. The acceptable range is pH 2-12 for intravenous and intramuscular administration, but subcutaneously the range is pH 2.7-9.0. The solution pH is controlled by either the salt form of the drug, strong acids/bases such as hydrochloric acid or sodium hydroxide, or by solutions of buffers which include but are not limited to buffering solutions formed from glycine, citrate, acetate, maleate, succinate, histidine, phosphate, tris(hydroxymethyl)-aminomethane (TRIS), or carbonate.

The combination of an aqueous solution and a water-soluble organic solvent/surfactant (i.e., a cosolvent) is often used in injectable formulations. The water-soluble organic solvents and surfactants used in injectable formulations include but are not limited to propylene glycol, ethanol, polyethylene glycol 300, polyethylene glycol 400, glycerin, dimethylacetamide (DMA), N-methyl-2-pyrrolidone (NMP; Pharmasolve), dimethylsulphoxide (DMSO), Solutol HS15, Cremophor EL, Cremophor RH 60, and polysorbate 80. Such formulations can usually be, but are not always, diluted prior to injection.

Propylene glycol, PEG 300, ethanol, Cremophor EL, Cremophor RH 60, and polysorbate 80 are the entirely organic water-miscible solvents and surfactants used in commercially available injectable formulations and can be used in combinations with each other. The resulting organic formulations are usually diluted at least 2-fold prior to IV bolus or IV infusion.

Alternatively increased water solubility can be achieved through molecular complexation with cyclodextrins.

Liposomes are closed spherical vesicles composed of outer lipid bilayer membranes and an inner aqueous core and with an overall diameter of <100 μm. Depending on the level of hydrophobicity, moderately hydrophobic drugs can be solubilized by liposomes if the drug becomes encapsulated or intercalated within the liposome. Hydrophobic drugs can also be solubilized by liposomes if the drug molecule becomes an integral part of the lipid bilayer membrane, and in this case, the hydrophobic drug is dissolved in the lipid portion of the lipid bilayer. A typical liposome formulation contains water with phospholipid at 5-20 mg/ml, an isotonicifier, a pH 5-8 buffer, and optionally cholesterol.

The formulations may be presented in unit-dose or multi-dose containers, for example sealed ampoules, vials and disposable syringes, and may be stored in a freeze-dried (lyophilised) condition requiring only the addition of the sterile liquid carrier, for example water for injections, immediately prior to use.

The pharmaceutical formulation can be prepared by lyophilising a compound of the invention or acid addition salt thereof. Lyophilisation refers to the procedure of freeze-drying a composition. Freeze-drying and lyophilisation are therefore used herein as synonyms. A typical process is to solubilise the compound and the resulting formulation is clarified, sterile filtered and aseptically transferred to containers appropriate for lyophilisation (e.g., vials). In the case of vials, they are partially stoppered with lyo-stoppers. The formulation can be cooled to freezing and subjected to lyophilisation under standard conditions and then hermetically capped forming a stable, dry lyophile formulation. The composition will typically have a low residual water content, e.g., less than 5%, e.g., less than 1% by weight based on weight of the lyophile.

The lyophilisation formulation may contain other excipients for example, thickening agents, dispersing agents, buffers, antioxidants, preservatives, and tonicity adjusters. Typical buffers include phosphate, acetate, citrate and glycine. Examples of antioxidants include ascorbic acid, sodium bisulphite, sodium metabisulphite, monothioglycerol, thiourea, butylated hydroxytoluene, butylated hydroxyl anisole, and ethylenediaminetetraacetic acid salts. Preservatives may include benzoic acid and its salts, sorbic acid and its salts, alkyl esters of para-hydroxybenzoic acid, phenol, chlorobutanol, benzyl alcohol, thimerosal, benzalkonium chloride and cetylpyridinium chloride. The buffers mentioned previously, as well as dextrose and sodium chloride, can be used for tonicity adjustment if necessary. Bulking agents are generally used in lyophilisation technology for facilitating the process and/or providing bulk and/or mechanical integrity to the lyophilized cake. Bulking agent means a freely water soluble, solid particulate diluent that when co-lyophilised with the compound or salt thereof, provides a physically stable lyophilized cake, a more optimal freeze-drying process and rapid and complete reconstitution. The bulking agent may also be utilised to make the solution isotonic.

The water-soluble bulking agent can be any of the pharmaceutically acceptable inert solid materials typically used for lyophilisation. Such bulking agents include, for example, sugars such as glucose, maltose, sucrose, and lactose; polyalcohols such as sorbitol or mannitol; amino acids such as glycine; polymers such as polyvinylpyrrolidine; and polysaccharides such as dextran.

The ratio of the weight of the bulking agent to the weight of active compound is typically within the range from about 1 to about 5, for example of about 1 to about 3, e.g., in the range of about 1 to 2.

Alternatively they can be provided in a solution form which may be concentrated and sealed in a suitable vial. Sterilisation of dosage forms may be via filtration or by autoclaving of the vials and their contents at appropriate stages of the formulation process. The supplied formulation may require further dilution or preparation before delivery for example dilution into suitable sterile infusion packs.

Extemporaneous injection solutions and suspensions may be prepared from sterile powders, granules and tablets.

In one preferred embodiment of the invention, the pharmaceutical composition is in a form suitable for intravenous administration, for example by injection or infusion. In another preferred embodiment, the pharmaceutical composition is in a form suitable for subcutaneous (s.c.) administration.

The compounds may be in the form of a solid or solution, or modified so as to be suitable for oral administration (see for example, U.S. Pat. Nos. 7,655,798, 8,093,387, 8,529,949; US 20020193438, WO2006/097344). Suitable formulated may include wet granulation pharmaceutical compositions (see for example, US 20070154544; WO2007/081366), inclusion complexes, for example with cyclodextrin (see for example, U.S. Pat. Nos. 7,115,587, 7,550,445; WO2004/017897), formulated with microspheres (see for example, US 20090043898; WO2009/00169) or formulated as a patch for transdermal delivery (see for example, US 20130171237; US 20130209552; WO2012/058091). Compounds of the present invention may also be formulated to have extended-release profiles, see for example, U.S. Pat. Nos. 8,338,427, 8,338,428; WO2005/016262, WO2013/133448).

Pharmaceutical compositions containing a compound of the invention can be formulated in accordance with known techniques, e.g., by means of conventional mixing, dissolving, granulating, dragee-making, levigating, emulsifying, encapsulating, entrapping, or lyophilizing processes, see for example, Remington's Pharmaceutical Sciences, Mack Publishing Company, Easton, Pa., USA. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Tablet compositions can contain a unit dosage of active compound together with an inert diluent or carrier such as a sugar or sugar alcohol, e.g., lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g., swellable crosslinked polymers such as crosslinked carboxymethylcellulose), lubricating agents (e.g., stearates), preservatives (e.g., parabens), antioxidants (e.g., BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (tablets, capsules etc.) can be coated or un-coated, but typically have a coating, for example a protective film coating (e.g., a wax or varnish) or a release controlling coating. The coating (e.g., a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum. Alternatively or additionally, the coating can be used as a taste masking agent to mask unpleasant tastes such as bitter tasting drugs. The coating may contain sugar or other agents that assist in masking unpleasant tastes.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g., a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

Compositions for topical use include ointments, creams, sprays, patches, gels, liquid drops and inserts (for example intraocular inserts). Such compositions can be formulated in accordance with known methods.

Further examples of topical compositions include dressings such as bandages and adhesive plasters impregnated with active ingredients and optionally one or more excipients or diluents. Carriers which may be used include e.g., polyhydric alcohols such as polyethylene glycols, propylene glycol or glycerol. Suitable excipients are those known in the art to be appropriate.

Examples of formulations for rectal or intra-vaginal administration include pessaries and suppositories which may be, for example, formed from a shaped mouldable or waxy material containing the active compound. Thus, unit-dose suppositories or pessaries may be prepared by admixture of the active ingredient with one or more conventional solid carriers, for example coca butter, and shaping the resulting mixture. Further examples of mouldable waxy materials include polymers such as high molecular weight polyalkylene glycols, e.g., high molecular weight polyethylene glycols. Alternatively, in the case of vaginal administration, the formulation may be presented as a tampon impregnated with the active ingredients and optionally one or more excipients or diluents. Other formulations suitable for rectal and vaginal administration include creams, gels, foams, pastes and sprays.

Compositions for administration by inhalation may take the form of inhalable powder compositions or liquid or powder sprays, and can be administered in standard form using powder inhaler devices or aerosol dispensing devices. Such devices are well known. For administration by inhalation, the powdered formulations typically comprise the active compound together with an inert solid powdered diluent such as lactose. The compounds are delivered in the form of an aerosol spray from pressured container or dispenser, which contains a suitable propellant, e.g., a gas such as carbon dioxide, or a nebulizer.

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

The pharmaceutical formulations can be included in a container, pack, or dispenser together with instructions for administration. The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

The invention also provides a pharmaceutical composition comprising one or more compounds of the present invention and a pharmaceutically acceptable carrier or excipient, in combination with another pharmaceutically active substance selected from a lithium compound selected from lithium carbonate, lithium citrate, lithium orotate, lithium bromide or lithium chloride; valproate; a serotonin reuptake inhibitor selected from fluoxetine, venlafaxine, citalopram, paroxetine, sertraline, indalpine, zimelidine, dapoxetine, fluvoxamine, tianeptine, duloxetine or escitalopram; chlorpromazine, droperidol, fluphenazine, haloperidol, loxapine, molindone, perphenazine, pimozide, prochlorperazine, thiothixene, thioridazine, trifluoperazine, levomepromazine, aripiprazole, asenapine, clozapine, iloperidone, lurasidone, olanzapine, paliperidone, quetiapine, risperidone, ziprasidone, amisulpride, blonanserin, clotiapine, mosapramine, perospirone, sertindole, sulpiride; caffeine, a caffeine derivative, nicotine, a nicotine derivative, phencyclidine, quinpirole, salvinorin a, apomorphine, bromocriptine, cabergoline, ciladopa, dihydrexidine, dinapsoline, doxanthrine, epicriptine, lisuride, pergolide, piribedil, pramipexole, propylnorapomorphine, quinagolide, ropinirole, rotigotine, roxindole, sumanirole; other compounds with interact with dopamine D2 receptor selected from amisulpride, nemomapride, nemoxipride, eticlopride, reclopride, talipexole, roxindole, bifeprunox, aplindore, mesoridazine, haloperidol, thixathene, flupenthixol, butyrophenone, perclamol [(−) 3-PPP], saritozan, olanzapine, dopanmine, quinpirole, bromocriptine; anti-depressants selected from agomelatine, amitriptyline, amoxapine, clomipramine, desipramine, dosulepine hydrochloride, doxepine, imipramine, maprotiline, a mixture of nortriptyline and fluphenazine, opipramol, quinupramine, trimipramine, a mixture of melitracene and flupentixol, pranipexole.

The invention also provides a kit comprising (i) one or more compounds of the present invention, (ii) an additional compound selected from a lithium compound selected from lithium carbonate, lithium citrate, lithium orotate, lithium bromide or lithium chloride; valproate; a serotonin reuptake inhibitor selected from fluoxetine, venlafaxine, citalopram, paroxetine, sertraline, indalpine, zimelidine, dapoxetine, fluvoxamine, tianeptine, duloxetine or escitalopram; Chlorpromazine, Droperidol, Fluphenazine, Haloperidol, Loxapine, Molindone, Perphenazine, Pimozide, Prochlorperazine, Thiothixene, Thioridazine, Trifluoperazine, Levomepromazine, Aripiprazole, Asenapine, Clozapine, Iloperidone, Lurasidone, Olanzapine, Paliperidone, Quetiapine, Risperidone, Ziprasidone, Amisulpride, Blonanserin, Clotiapine, Mosapramine, Perospirone, Sertindole, Sulpiride; caffeine, a caffeine derivative, nicotine, a nicotine derivative, Phencyclidine, Quinpirole, Salvinorin A, Apomorphine, Bromocriptine, Cabergoline, Ciladopa, Dihydrexidine, Dinapsoline, Doxanthrine, Epicriptine, Lisuride, Pergolide, Piribedil, Pramipexole, Propylnorapomorphine, Quinagolide, Ropinirole, Rotigotine, Roxindole, Sumanirole; other compounds with interact with dopamine D2 receptor selected from Amisulpride, nemomapride, nemoxipride, eticlopride, reclopride, talipexole, roxindole, bifeprunox, aplindore, mesoridazine, haloperidol, thixathene, flupenthixol, butyrophenone, perclamol [(−) 3-PPP], saritozan, olanzapine, dopanmine, quinpirole, bromocriptine; other anti-depressants selected from Agomelatine, amitriptyline, amoxapine, clomipramine, desipramine, dosulepine hydrochloride, doxepine, imipramine, maprotiline, a mixture of nortriptyline and fluphenazine, opipramol, quinupramine, trimipramine, a mixture of melitracene and flupentixol, pranipexole, and (iii) instructions for administration of (i) and (ii). The association of the two or more compounds/agents in a combination may be physical or non-physical. Examples of physically associated combined compounds/agents include: compositions (e.g., unitary formulations) comprising the two or more compounds/agents in a mixture (for example within the same unit dose); compositions comprising material in which the two or more compounds/agents are chemically/physicochemically linked (for example by crosslinking, molecular agglomeration or binding to a common vehicle moiety); compositions comprising material in which the two or more compounds/agents are chemically/physicochemically co-packaged (for example, disposed on or within lipid vesicles, particles (e.g., micro- or nanoparticles) or emulsion droplets); pharmaceutical kits, pharmaceutical packs or patient packs in which the two or more compounds/agents are co-packaged or co-presented (e.g., as part of an array of unit doses);

Examples of non-physically associated combined compounds/agents include: material (e.g., a non-unitary formulation) comprising at least one of the two or more compounds/agents together with instructions for the extemporaneous association of the at least one compound to form a physical association of the two or more compounds/agents; material (e.g., a non-unitary formulation) comprising at least one of the two or more compounds/agents together with instructions for combination therapy with the two or more compounds/agents; material comprising at least one of the two or more compounds/agents together with instructions for administration to a patient population in which the other(s) of the two or more compounds/agents have been (or are being) administered; material comprising at least one of the two or more compounds/agents in an amount or in a form which is specifically adapted for use in combination with the other(s) of the two or more compounds/agents.

As used herein, the term "pharmaceutical pack" defines an array of one or more unit doses of a pharmaceutical composition, optionally contained within common outer packaging. In pharmaceutical packs comprising a combination of two or more compounds/agents, the individual compounds/agents may be unitary or non-unitary formulations. The unit dose(s) may be contained within a blister pack. The pharmaceutical pack may optionally further comprise instructions for use.

As used herein, the term "pharmaceutical kit" or "kit" defines an array of one or more unit doses of a pharmaceutical composition together with dosing means (e.g., measuring device) and/or delivery means (e.g., inhaler or syringe), optionally all contained within common outer packaging. In pharmaceutical kits comprising a combination of two or more compounds/agents, the individual compounds/agents may be unitary or non-unitary formulations. The unit dose(s) may be contained within a blister pack. The pharmaceutical kit may optionally further comprise instructions for use.

As used herein, the term "patient pack" defines a package, prescribed to a patient, which contains pharmaceutical compositions for the whole course of treatment. Patient packs usually contain one or more blister pack(s). Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

The term "stable" as used herein, refers to dosage form which is physically, or polymorphically stable. The dosage form according to present invention may remain physically stable, that is there are no substantial changes with respect to physical attributes like colour etc. The dosage form according to present invention may remain polymorphically stable that is the polymorph (crystalline or amorphous) in the dosage form does not rearranges into another form upon storage.

Method of Use

The term "patient" refers to a warm-blood animal, preferably a human being, i.e., a subject of both genders and at any stage development (i.e., neonate, infant, juvenile, adolescent, adult). The invention is particularly directed to adolescents and adults. Some embodiments, in particular concerning regulation of galactorrhea, are specifically directed to female.

As used herein, "treating" or "treat" describes the management and care of a patient for the purpose of combating a disease, condition, or disorder and includes the administration of a compound of the present invention, or a pharmaceutically acceptable salt, prodrug, metabolite, polymorph or solvate thereof, to alleviate the symptoms or complications of a disease, condition or disorder, or to eliminate the disease, condition or disorder.

As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "modulation", as applied to the activity of the dopamine activity at D2 receptors, is intended to define a change in the level of biological activity of the dopaminergic activity. Thus, modulation encompasses physiological changes which effect an increase or decrease in the dopaminergic activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of dopaminergic activity. Thus, modulation may imply elevated/suppressed expression or over- or under-expression of dopaminergic activity, including gene amplification (i.e., multiple gene copies) and/or increased or decreased expression by a transcriptional effect, as well as hyper- (or hypo-) activity and (de)activation of dopaminergic activity (including (de)activation) by mutation(s). The terms "modulated", "modulating" and "modulate" are to be interpreted accordingly.

The present invention provides a method of modulating D2 receptor activity by administering one or more compounds of the present invention to a subject. The active compound will be administered to a subject in need thereof (for example a human or animal patient) in an amount sufficient to achieve the desired therapeutic effect.

The present invention also provides use of one or more compounds of the present invention as a β-arrestin biased D2 receptor agonist or antagonist. The present invention also provides use of one or more compounds of the present invention as a biased cAMP agonist or antagonist.

The present invention provides a method of treating or preventing a disease or disorder, comprising administering a compound of the invention, wherein modulation of the D2 receptors (e.g., β-arrestin or Gi/cAMP) plays a role in the disease or disorder (iniation, development, etc.). In one embodiment, the disease or disorder is a nervous system disease or disorder in which modulation of D2 receptors (e.g., β-arrestin or Gi/cAMP) plays a role. The nervous system disorder is selected from an anxiety disorder (e.g., phobias, generalized anxiety disorder, social anxiety disorder, panic disorder, agoraphobia, obsessive-compulsive disorder, and post-traumatic stress disorder), a dissociative disorder (e.g., dissociative amnesia, dissociative fugue, dissociative identity (multiple personality) disorder, and depersonalization disorder), a mood disorder (e.g., depression, dysthymia, bipolar disorder, mania, hypomania, and Cyclothymic Disorder), an eating disorder (e.g., anorexia nervosa, bulimia nervosa, exercise bulimia, and binge eating disorder), a sleep disorder (insomnia, hypersomnia, narcolepsy, nightmare disorder, sleep terror disorder, and sleepwalking), a developmental disorder (e.g., autism spectrum disorders, oppositional defiant disorder and conduct disorder, and attention deficit hyperactivity disorder), a somatoform disorder (e.g., body dysmorphic disorder, conversion disorder, hypochondriasis disorder, pain disorder, and somatization disorder), a personality disorder (e.g., antisocial personality disorder, borderline personality disorder, narcissistic personality disorder), a psychiatric syndrome (e.g., Capgras syndrome, De Clerambault syndrome, Othello syndrome, Ganser syndrome, Cotard delusion, and Ekbom syndrome, and additional disorders such as the Couvade syndrome and Geschwind syndrome), a psychotic disorder (e.g., brief psychotic disorder, delusional disorder, Schizoaffective disorder, Schizophrenia, Schizophreniform, shared psychotic disorder), substance abuse, Parkinson's disease, Huntington's disease, Alzheimer's disease, dementia, Niemann-Pick disorder, a pituitary disorder (e.g., pituitary adenoma, and a pituitary tumor such as prolactinoma)), Tourette's syndrome, Tourette-like disorders, and restless leg syndrome.

In one embodiment, the present invention provides a method of treating or preventing a disease or disorder in which modulation of D2 receptors (e.g., β-arrestin or Gi/cAMP) plays a role, selected from obsessive-compulsive disorder, post-traumatic stress disorder, depression, bipolar disorder, mania, hypomania, autism spectrum disorders, attention deficit hyperactivity disorder, delusional disorder, Schizoaffective disorder, Schizophrenia, Schizophreniform, substance abuse, Parkinson's disease, Huntington's disease, Alzheimer's disease, dementia, Niemann-Pick disorder, a pituitary disorder, Tourette's syndrome, Tourette-like disorders, and restless leg syndrome.

In another embodiment, the disease or disorder is a non-nervous system disease or disorder in which modulation of D2 receptors (e.g., β-arrestin or Gi/cAMP) plays a role, such as cardiovascular diseases or disorders (e.g., hypertension), renal diseases or disorders (e.g., a disease or disorder associated with diuresis and natriuresis), and endocrine diseases or disorders (e.g., galactorrhea), and immunological diseases or disorders.

The present invention also provides a method of treating or preventing a disease or disorder in which modulation of D2 receptors (e.g., β-arrestin or Gi/cAMP) plays a role (e.g., the diseases and disorders described above), comprising administering a compound of the invention and an additional therapeutic agent. In one embodiment, the additional therapeutic agent is lithium carbonate, lithium citrate, lithium orotate, lithium bromide or lithium chloride. In another embodiment, the additional therapeutic agent is valproate. In another embodiment, the additional therapeutic agent is caffeine (e.g., as to Parkinsons), a caffeine derivative (e.g., as to Parkinsons), nicotine (e.g., as to Parkinsons), a nicotine derivative (e.g., as to Parkinsons), Phencyclidine (a.k.a. PCP), Quinpirole, Salvinorin A (chief active constituent of the herb salvia divinorum), Apomorphine (Apokyn) (e.g., as to Parkinson's disease, restless leg syndrome), Bromocriptine (Parlodel) (e.g., as to Parkinson's disease, restless leg syndrome), Cabergoline (Dostinex) (e.g., as to Parkinson's disease, restless leg syndrome), Ciladopa (e.g., as to Parkinson's disease, restless leg syndrome), Dihydrexidine (e.g., as to Parkinson's disease, restless leg syndrome), Dinapsoline (e.g., as to Parkinson's disease, restless leg syndrome), Doxanthrine (e.g., as to Parkinson's disease, restless leg syndrome), Epicriptine (e.g., as to Parkinson's disease, restless leg syndrome), Lisuride (e.g., as to Parkinson's disease, restless leg syndrome), Pergolide (e.g., as to Parkinson's disease, restless leg syndrome), Piribedil (e.g., as to Parkinson's disease, restless leg syndrome), Pramipexole (e.g., as to Parkinson's disease, restless leg syndrome) (Mirapex and Sifrol), Propylnorapomorphine (e.g., as to Parkinson's disease, restless leg syndrome), Quinagolide (Norprolac) (e.g., as to Parkinson's disease, restless leg syndrome), Ropinirole (e.g., as to Parkinson's disease, restless leg syndrome) (Requip), Rotigotine (e.g., as to Parkinson's disease, restless leg syndrome) (Neupro), Roxindole (e.g., as to Parkinson's disease, restless leg syndrome), or Sumanirole (e.g., as to Parkinson's disease, restless leg syndrome).

The present invention also provides a method of treating or preventing a disease or disorder in which modulation of D2 receptors (e.g., β-arrestin or Gi/cAMP) plays a role (e.g., the diseases and disorders described above), comprising administering a compound of the invention and a serotonin reuptake inhibitor such as fluoxetine, venlafaxine, citalopram, paroxetine, sertraline, indalpine, zimelidine, dapoxetine, fluvoxamine, tianeptine, duloxetine or escitalopram (see for example, US20060154938).

The present invention also provides a method of treating or preventing a disease or disorder in which modulation of D2 receptors (e.g., β-arrestin or Gi/cAMP) plays a role (e.g., the diseases and disorders described above), comprising administering a compound of the invention alone or in combination with antipsychotics. Examples of typical (first generation) antipsychotics include Chlorpromazine, Droperidol, Fluphenazine, Haloperidol, Loxapine, Molindone, Perphenazine, Pimozide, Prochlorperazine, Thiothixene, Thioridazine, Trifluoperazine, Levomepromazine. Examples of atypical (second generation) antipsychotics include Aripiprazole, Asenapine, Clozapine, Iloperidone, Lurasidone, Olanzapine, Paliperidone, Quetiapine, Risperidone, Ziprasidone, Amisulpride, Blonanserin, Clotiapine, Mosapramine, Perospirone, Sertindole, Sulpiride. Other compounds which can be used in combination with the compounds of the invention are for example compounds that interact with dopamine D2 receptor selected from amisulpride, nemomapride, nemoxipride, eticlopride, reclopride, talipexole, roxindole, bifeprunox, aplindore, mesoridazine, haloperidol, thixathene, flupenthixol, butyrophenone, perclamol [(−)3-PPP], saritozan, olanzapine, dopanmine, quinpirole, bromocriptine; other anti-depressants selected from Agomelatine, amitriptyline, amoxapine, clomipramine, desipramine, dosulepine hydrochloride, doxepine, imipramine, maprotiline, a mixture of nortriptyline and fluphenazine, opipramol, quinupramine, trimipramine, a mixture of melitracene and flupentixol, pranipexole.

The compounds are generally administered to a subject in need of such administration, for example, a human or animal patient, preferably a human.

The compounds will typically be administered in amounts that are therapeutically or prophylactically useful and which generally are non-toxic. However, in certain situations (for example in the case of life threatening diseases), the benefits of administering a compound of the Formula I may outweigh the disadvantages of any toxic effects or side effects, in which case it may be considered desirable to administer compounds in amounts that are associated with a degree of toxicity. The quantity of compound administered and the type of composition used will be commensurate with the nature of the disease or physiological condition being treated and will be at the discretion of the physician.

The compounds may be administered over a prolonged term to maintain beneficial therapeutic effects or may be administered for a short period only. Alternatively they may be administered in a pulsatile or continuous manner.

The compounds as defined herein can be administered as the sole therapeutic agent or they can be administered in combination therapy with one of more other compounds for treatment of a particular disease state, for example, a nervous system disorder. The compounds of the invention may also be administered in conjunction with other treatments such as radiotherapy, photodynamic therapy, gene therapy, surgery and controlled diets.

Where the compound is administered in combination with other therapeutic agents, the compounds can be administered simultaneously or sequentially. When administered sequentially, they can be administered at closely spaced intervals (e.g., within minutes) or at longer intervals (e.g., hours apart, or longer), the precise dosage regimen being commensurate with the properties of the therapeutic agent(s).

For use in combination therapy with another therapeutic agent, the compound and other therapeutic agents can be, for example, formulated together in a dosage form. In an alternative, the individual therapeutic agents may be formulated separately and presented together in the form of a kit, optionally with instructions for their use.

Actual dosage levels of the active ingredients in the pharmaceutical compositions of the invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A person skilled in the art would know through his or her common general knowledge the use of suitable dosing regimes and combination therapies. The regimen of administration can affect what constitutes an effective amount. The compound of the invention can be administered to the subject either prior to or after the onset of a dopaminergic disorder. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

While it is possible for a compound of the present invention to be administered alone, it is preferable to administer the compound as a pharmaceutical composition.

The present invention also relates to use of a compound of the invention or a pharmaceutically acceptable salt, stereoisomer, racemate, tautomer, polymorph, hydrate, or solvate thereof, or use of a pharmaceutical composition of the invention, for treating treating or preventing a disease or disorder in which modulation of D2 receptors (e.g., β-arrestin or Gi/cAMP) plays a role (e.g., diseases and disorders described herein). In one embodiment, the disease or disorder is a nervous system disease or disorder selected from obsessive-compulsive disorder, post-traumatic stress disorder, depression, bipolar disorder, mania, hypomania, autism spectrum disorders, attention deficit hyperactivity disorder, delusional disorder, Schizoaffective disorder, Schizophrenia, Schizophreniform, substance abuse, Parkinson's disease, Huntington's disease, Alzheimer's disease, dementia, Niemann-Pick disorder, a pituitary disorder, Tourette's syndrome, Tourette-like disorders, and restless leg syndrome. In another embodiment, the disease or disorder is a non-nervous system disease or disorder in which modulation of D2 receptors (e.g., β-arrestin or Gi/cAMP) plays a role, such as cardiovascular diseases or disorders (e.g., hypertension), renal diseases or disorders (e.g., a disease or disorder associated with diuresis and natriuresis), and endocrine diseases or disorders (e.g., galactorrhea), and immunological diseases or disorders.

The present invention also relates to use of a compound of the invention, or a pharmaceutically acceptable salt, stereoisomer, racemate, tautomer, polymorph, hydrate, or solvate thereof, or use of a pharmaceutical composition of the invention, in the manufacture of a medicament for the treatment or prevention of a disease or disorder in which modulation of D2 receptors (e.g., β-arrestin or Gi/cAMP) plays a role (e.g., diseases and disorders described herein). In one embodiment, the disease or disorder is a nervous system disease or disorder selected from obsessive-compulsive disorder, post-traumatic stress disorder, depression, bipolar disorder, mania, hypomania, autism spectrum disorders, attention deficit hyperactivity disorder, delusional disorder, Schizoaffective disorder, Schizophrenia, Schizophreniform, substance abuse, Parkinson's disease, Huntington's disease, Alzheimer's disease, dementia, Niemann-Pick disorder, a pituitary disorder, Tourette's syndrome, Tourette-like disorders, and restless leg syndrome. In another embodiment, the disease or disorder is a non-nervous system disease or disorder associated with modulation of D2 receptors (e.g., β-arrestin or Gi/cAMP) plays a role, such as cardiovascular diseases or disorders (e.g., hypertension), renal diseases or disorders (e.g., a disease or disorder associated with diuresis and natriuresis), and endocrine diseases or disorders (e.g., galactorrhea), and immunological diseases or disorders.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

EXAMPLES

Synthesis of Intermediate I

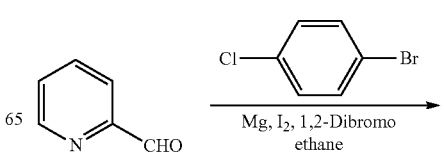

91

-continued

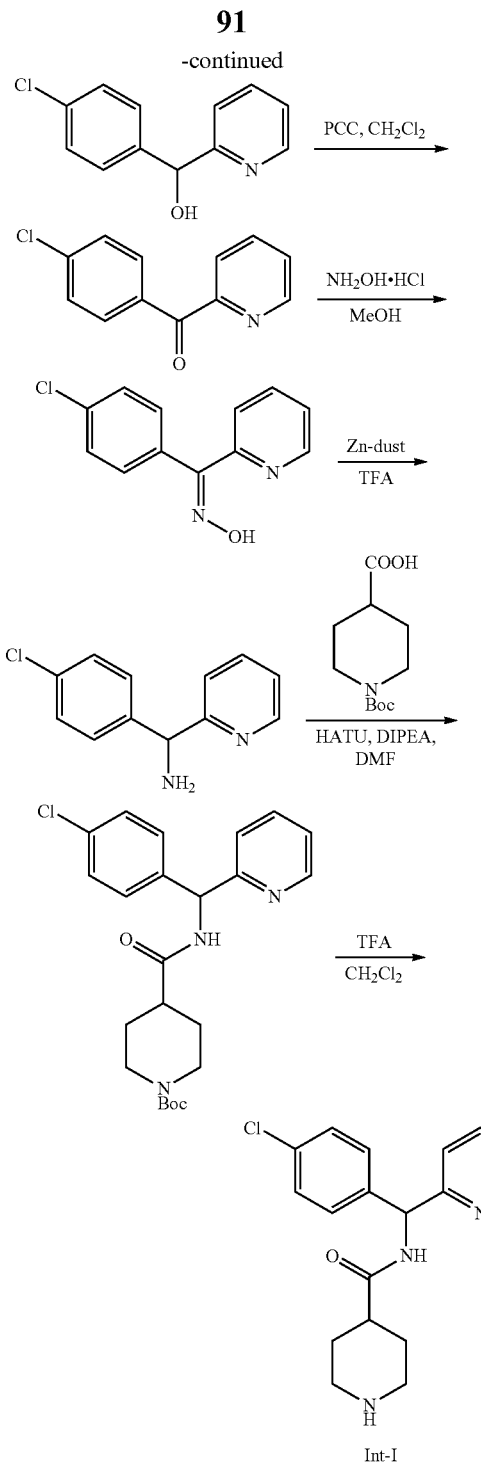

Step 1: (4-Chlorophenyl)(pyridin-2-yl)methanol

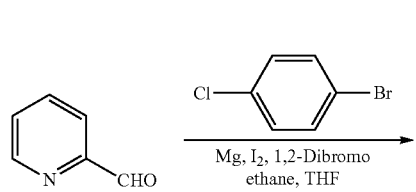

92

-continued

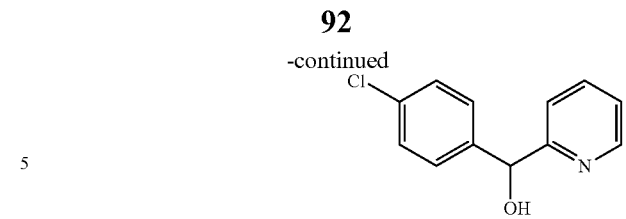

To a stirred suspension of magnesium (5.37 g, 223.75 mmol, 3 equiv) in dry THF (60 mL) under argon atmosphere was added iodine (2 crystals), 1,2-dibromo ethane (2 drops). 1-bromo-4-chlorobenzene (25.76 g, 134.39 mmol, 1.8 equiv) was then added dropwise for 1 h at room temperature. The reaction mixture was stirred at room temperature for 1 h. A solution of picolinaldehyde (8 g, 74.68 mmol) in dry THF (19 mL) was added drop wise at room temperature and stirred for 2 h. After completion of reaction, the reaction mixture was quenched with saturated ammonium chloride solution and extracted with EtOAc. The combined organic extract was washed with water, brine, dried over sodium sulfate, filtered and concentrated under reduced pressure. Purification using silica gel column chromatography (40% EtOAc/hexanes as eluent) afforded 12.26 g of (4-chlorophenyl) (pyridin-2-yl) methanol (yield=75%). ESI+MS: m/z 220 ([M+H]$^+$).

Step 2: (4-Chlorophenyl)(pyridin-2-yl)methanone

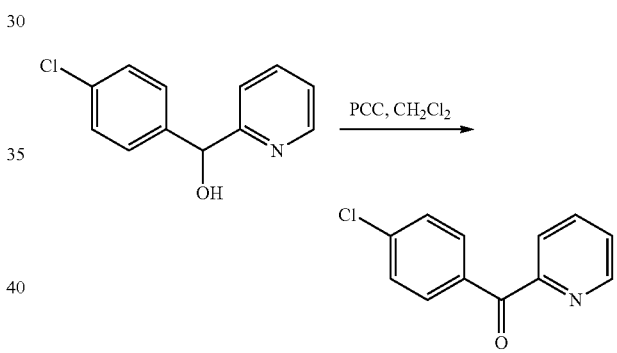

To a stirred solution of (4-chlorophenyl) (pyridin-2-yl) methanol (5 g, 22.83 mmol) in CH$_2$Cl$_2$ (85 mL) under argon atmosphere was added pyridinium chlorochromate (5.9 g, 27.37 mmol, 1.2 equiv) and celite (5 g) at 0° C. The reaction mixture was warmed to room temperature and stirred for 2 h. After completion of the reaction, the reaction mixture was filtered through celite, washed with CH$_2$Cl$_2$ and the filtrate was concentrated under reduced pressure. Purification using silica gel column chromatography (20% EtOAc/Hexanes as eluent) afforded 3.5 g of (4-chlorophenyl) (pyridin-2-yl) methanone (Yield=71%). ESI+MS: m/z 218 ([M+H]$^+$).

Step 3: (4-Chlorophenyl)(pyridin-2-yl)methanone oxime

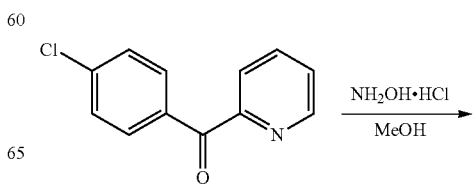

-continued

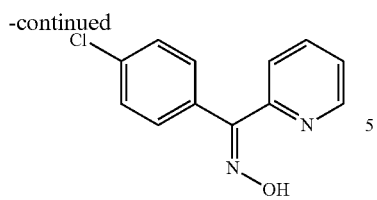

To a stirred solution of (4-chlorophenyl) (pyridin-2-yl) methanone (3.5 g, 16.12 mmol) in MeOH (35 mL) under argon atmosphere was added hydroxyl amine hydrochloride (3.36 g, 48.35 mmol, 3 equiv) at 0° C. The reaction mixture was warmed to room temperature and stirred for 12 h. After completion, the volatiles were removed under reduced pressure and ethyl acetate was added to the residue. The organic layer was washed with saturated NaHCO$_3$ solution, dried over sodium sulfate, filtered and the concentrate under reduced pressure. The crude was triturated with n-hexane to afford 3.1 g of (4-chlorophenyl) (pyridin-2-yl) methanone oxime (Yield=83%). ESI+MS: m/z 233 ([M+H]$^+$).

Step 4: (4-Chlorophenyl)(pyridin-2-yl)methanamine

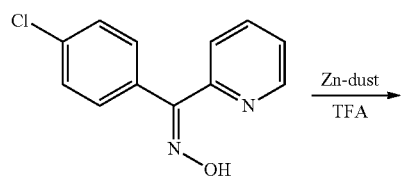

To a stirred solution of (4-chlorophenyl) (pyridin-2-yl) methanone oxime (3.1 g, 13.36 mmol) in trifluoro acetic acid (20 mL) under argon atmosphere was added Zn-dust (2.6 g, 40.00 mmol, 3 equiv) at 0° C. The reaction mixture was warmed to room temperature and stirred for 4 h. After completion, the volatiles were removed under reduced pressure, the pH was adjusted to ~8 with 10% NaHCO$_3$ solution and extracted with EtOAc. The combined organic extract was dried over sodium sulfate, filtered and concentrated under reduced pressure to afford 2.18 g of (4-chlorophenyl) (pyridin-2-yl) methanamine (Yield=75%). Ion trap: m/z 219.1 ([M+H]$^+$).

Step 5: tert-butyl 4-(((4-chlorophenyl)(pyridin-2-yl) methyl)carbamoyl)piperidine-1-carboxylate

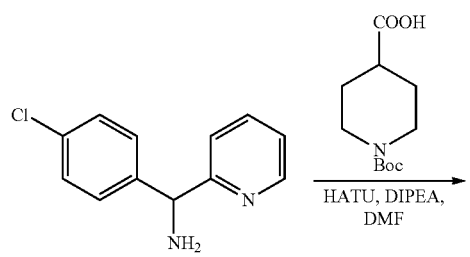

-continued

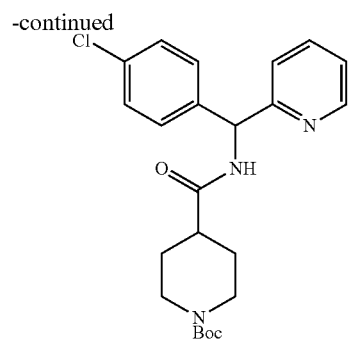

To a stirred solution of (4-chlorophenyl) (pyridin-2-yl) methanamine (2 g, 9.17 mmol) in DMF (10 mL) under argon atmosphere were added 1-(tert-butoxycarbonyl) piperidine-4-carboxylic acid (2.1 g, 9.16 mmol, 1 equiv), HATU (5.23 g, 13.75 mmol, 1.5 equiv) and diisopropyl ethyl amine (3.23 mL, 18.34 mmol, 2 equiv) at 0° C. The reaction mixture was warmed to room temperature and stirred for 4 h. After completion, the reaction mixture was quenched with ice cold water and extracted with EtOAc. The combined organic extract was dried over sodium sulfate, filtered and concentrated under reduced pressure. Purification using silica gel column chromatography (40% EtOAc/Hexanes as eluent) afforded 2.5 g of tert-butyl 4-(((4-chlorophenyl) (pyridin-2-yl) methyl) carbamoyl) piperidine-1-carboxylate (Yield=64%). ESI+MS: m/z 430 ([M+H]$^+$).

Step 6: N-((4-chlorophenyl)(pyridin-2-yl)methyl) piperidine-4-carboxamide (Intermediate-I)

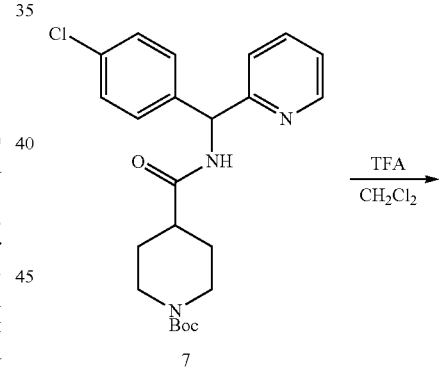

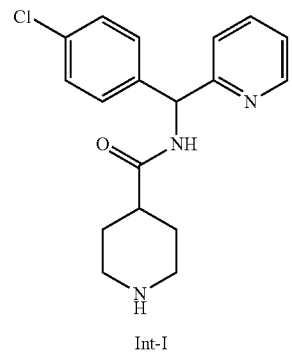

Int-I

To a stirred solution of tert-butyl 4-(((4-chlorophenyl) (pyridin-2-yl) methyl) carbamoyl) piperidine-1-carboxylate (2.5 g, 5.87 mmol) in CH$_2$Cl$_2$ (20 mL) under argon atmosphere was added trifluoro acetic acid (2.23 mL, 29.13 mmol, 5 equiv) at 0° C. The reaction mixture was warmed to room temperature and stirred for 3 h. After completion of the reaction, the volatiles were removed and the solvent was removed under reduced pressure. The pH was adjusted to ~7 with saturated NaHCO$_3$ solution and extracted with CH$_2$Cl$_2$. The combined organic extract was dried over sodium sulfate, filtered and concentrated under reduced pressure to afford 1.63 g of N-((4-chlorophenyl) (pyridin-2-yl) methyl) piperidine-4-carboxamide (Int-I) (Yield=85%). ESI+MS: m/z 330 ([M+H]$^+$).

Synthesis of Intermediate-1

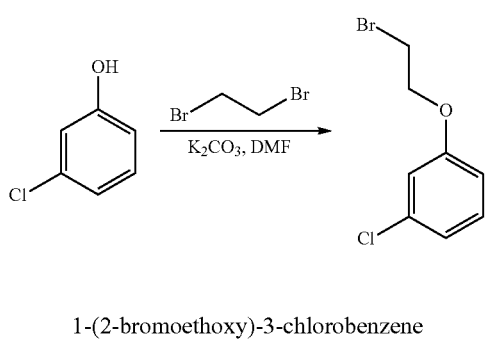

1-(2-bromoethoxy)-3-chlorobenzene

To a stirred solution of 3-chlorophenol (5 g, 39.06 mmol) in DMF (30 mL) under argon atmosphere were added 1,2-dibromo ethane (6.7 mL, 77.71 mmol, 2 equiv) and potassium carbonate (5.4 g, 39.13 mmol, 1 equiv) at room temperature. The reaction mixture was heated at 100° C. and stirred for 16 h. After completion, the reaction mixture was diluted with water and extracted with EtOAc. The combined organic extract was washed with brine, dried over sodium sulphate, filtered and concentrated under reduced pressure. Purification using silica gel column chromatography (2% EtOAc/Hexanes as eluent) afforded 3.1 g of 1-(2-bromoethoxy)-3-chlorobenzene (Yield=34%).

Synthesis of Intermediate-2

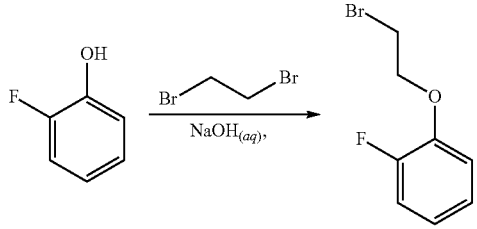

1-(2-Bromoethoxy)-2-fluorobenzene

To a stirred solution of 2-fluorophenol (0.5 g, 4.46 mmol) in aqueous sodium hydroxide solution (0.78 g, 4.46 mmol, 1 equiv, in 5 mL of water) was added 1,2-dibromo ethane (1.25 g, 6.69 mmol, 1.5 equiv) at room temperature. The reaction mixture was heated at 130° C. and stirred for 16 h. After completion, the reaction mixture was extracted with EtOAc. The combined organic extract was washed with brine, dried over sodium sulphate, filtered and concentrated under reduced pressure. Purification using silica gel column chromatography (2% EtOAc/Hexanes as eluent) afforded 0.340 g of 1-(2-bromoethoxy)-2-fluorobenzene (Yield=34.8%).

Synthesis of Intermediate-3

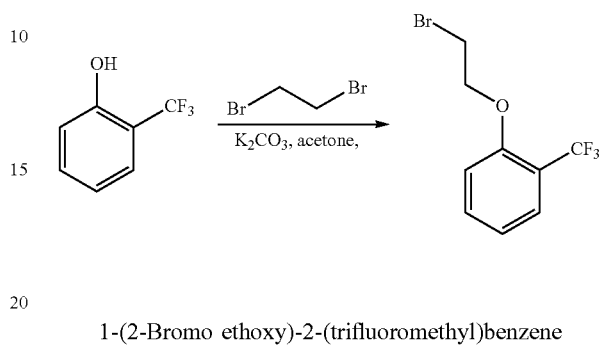

1-(2-Bromo ethoxy)-2-(trifluoromethyl)benzene

To a stirred solution of 2-(trifluoromethyl) phenol (1 g, 6.17 mmol) in acetone (20 mL) under argon atmosphere were added potassium carbonate (0.851 g, 6.15 mmol, 1 equiv) and 1,2-dibromo ethane (1.07 mL, 12.34 mmol, 2 equiv) at room temperature. The reaction mixture was heated at 60° C. and stirred for 16 h. After completion, the reaction mixture was diluted with water and extracted with EtOAc. The combined organic extract was dried over sodium sulfate, filtered and concentrated under reduced pressure. Purification using silica gel column chromatography (2% EtOAc/Hexanes as eluent) afforded 0.40 g of 1-(2-bromoethoxy)-2-(trifluoromethyl) benzene (Yield=24%).

Synthesis of Intermediate-4

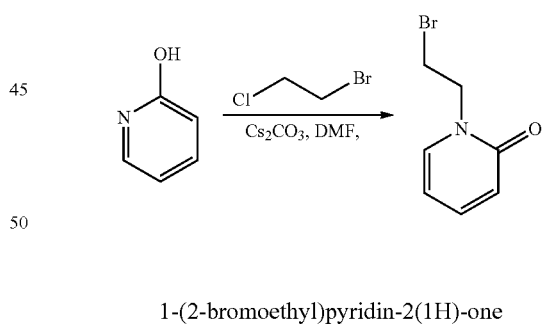

1-(2-bromoethyl)pyridin-2(1H)-one

To a stirred solution of pyridin-2-ol (5 g, 52.57 mmol) in DMF (50 mL) under argon atmosphere were added cesium carbonate (17.03 g, 52.56 mmol, 1.0 eqiuv) and 1-chloro-2-bromo ethane (15.06 g, 104.94 mmol, 2 equiv) at room temperature and stirred for 16 h. After completion, the reaction mixture was diluted with water and extracted with CH$_2$Cl$_2$. The combined organic extract was dried over sodium sulfate, filtered and concentrated under reduced pressure. Purification using silica gel column chromatography (1% MeOH/CH$_2$Cl$_2$ as eluent) afforded 1.0 g of 1-(2-bromoethyl)pyridin-2(1H)-one (Yield=12%). ESI+MS: m/z 158.1 ([M+H]$^+$).

Synthesis of Intermediate-5

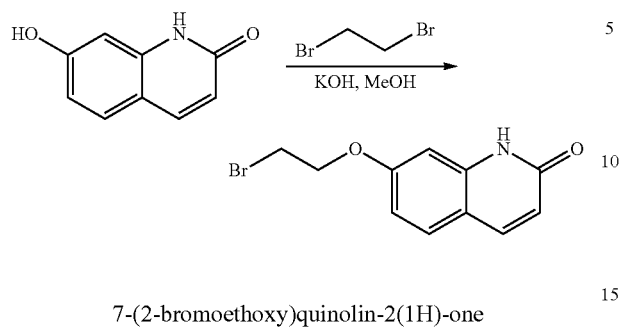

7-(2-bromoethoxy)quinolin-2(1H)-one

To a stirred solution of 7-hydroxyquinolin-2(1H)-one (1 g, 6.21 mmol) in MeOH (20 mL) under argon atmosphere were added 1,2-dibromo ethane (1.74 g, 9.31 mmol, 1.5 equiv) and potassium hydroxide (0.453 g, 8.07 mmol, 1.3 equiv) at room temperature. The reaction mixture was heated at 65° C. and stirred for 4 h. After completion, the volatiles were removed under reduced pressure. The residue was diluted with water and extracted with EtOAc. The combined organic extract was dried over sodium sulfate, filtered and concentrated under reduced pressure. Purification using silica gel column chromatography (1% MeOH/ $CH_2Cl_2$ as eluent) afforded 7-(2-bromoethoxy)quinolin-2(1H)-one 0.27 g (Yield=16.2%). ESI+MS: m/z 267.9 ([M+H]$^+$).

One skilled in the art will recognize that other compounds described below were prepared in a similar manner to the procedures described above.

One skilled in the art will recognize that other compounds described below were prepared in a similar manner to the procedures described above.

(2-Bromoethoxy)benzene

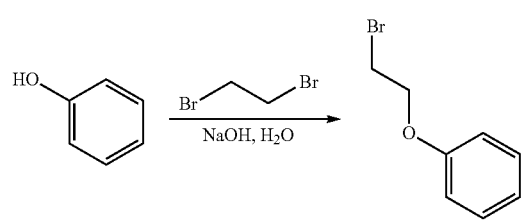

Title compound was prepared from phenol (20 g, 213 mmol) using the general methodology of Int-2 and afforded 26 g of (2-bromoethoxy)benzene (Yield=61%).

2-(2-bromoethoxy)-2-chlorobenzene

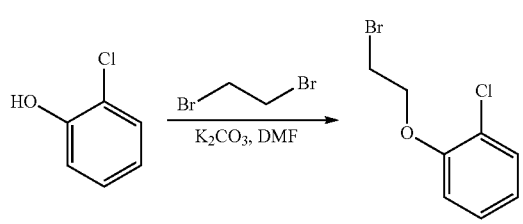

Title compound was prepared from 2-chlorophenol (1 g, 7.78 mmol) using general methodology of Intermediate-1 to obtain 0.348 g of 1-(2-bromoethoxy)-2-chlorobenzene (Yield=19%).

1-(2-Bromoethoxy)-4-chlorobenzene

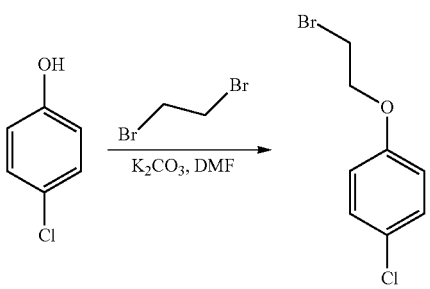

Title compound was prepared from 4-chlorophenol (5 g, 39.06 mmol) using the general methodology of Intermediate-1 and afforded 3 g of 1-(2-Bromoethoxy)-4-chlorobenzene (Yield=33%).

1-(2-Bromoethoxy)-3-fluorobenzene

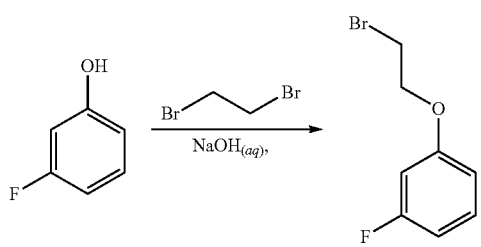

Title compound was prepared from 3-fluorophenol (4 g, 35.71 mmol) using the general methodology of Intermediate-2 and afforded 3 g of 1-(2-Bromoethoxy)-3-fluorobenzene (Yield=38%).

1-(2-bromoethoxy)-4-fluorobenzene

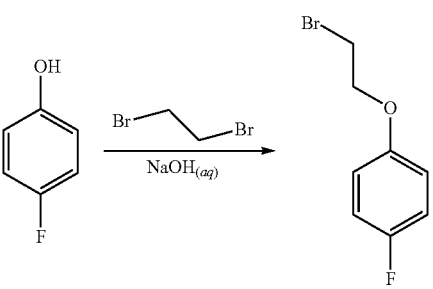

Title compound was prepared from 4-fluorophenol (4 g, 35.71-mmol) using the general methodology of Intermediate-2 and afforded 2.8 g of 1-(2-Bromoethoxy)-4-fluorobenzene (Yield=35%).

2-(2-Bromoethoxy)-1,4-difluorobenzene

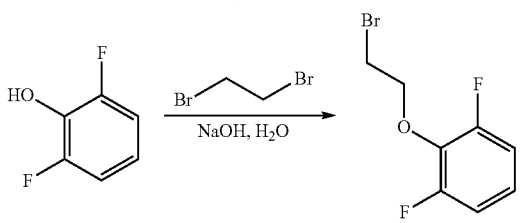

Title compound was prepared from 2,6-difluorophenol (1 g, 7.69 mmol) using the general methodology of Intermediate-2 and afforded 1.1 g of 2-(2-bromoethoxy)-1,4-difluorobenzene (Yield=60%).

2-(2-bromoethoxy)-1,4-difluorobenzene

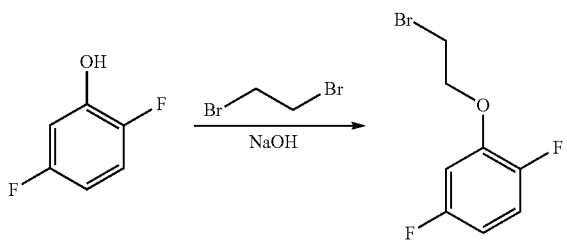

Title compound was prepared from 2,5-difluorophenol (5 g, 38.4 mmol) using the general methodology of Int-2 and afforded 3.5 g of 2-(2-bromoethoxy)-1,4-difluorobenzene (Yield=39%).

1-(2-bromoethoxy)-2-(trifluoromethyl)benzene

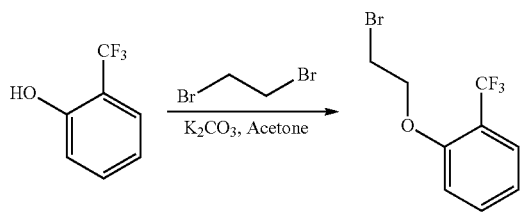

Title compound was prepared from 2-(trifluoromethyl)phenol (1 g, 6.17 mmol) using the general methodology of Intermediate-3 to obtain 0.398 g of 1-(2-bromoethoxy)-2-(trifluoromethyl)benzene (Yield=24%).

1-(2-bromoethoxy)-3-(trifluoromethyl)benzene

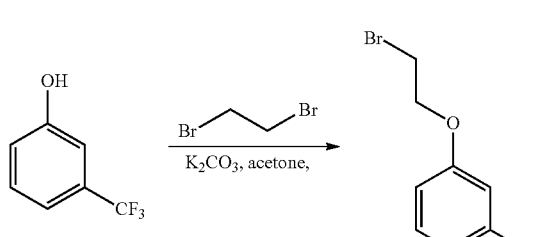

Title compound was prepared from 3-(trifluoromethyl)phenol (2 g, 12.34 mmol) using general methodology of Intermediate-3 and afforded 0.74 g of 1-(2-bromoethoxy)-3-(trifluoromethyl) benzene (Yield=22%).

1-(2-bromoethoxy)-4-(trifluoromethyl)benzene

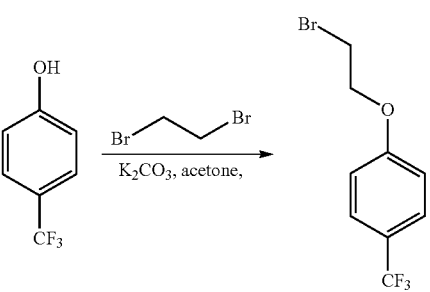

Title compound was prepared from 4-(trifluoromethyl)phenol (1 g, 6.17 mmol) using the general methodology of Intermediate-3 and afforded 0.3 g of 1-(2-bromoethoxy)-4-(trifluoromethyl) benzene (Yield=19%).

3-(2-Bromoethoxy) pyridine

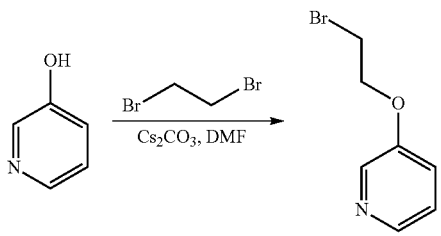

Title compound was prepared from pyridin-3-ol (5 g, 52.57 mmol) using the general methodology of Intermediate-4 and afforded 0.6 g of 3-(2-bromoethoxy) pyridine (Yield=6%).

1-(2-bromoethyl)pyridin-4(1H)-one

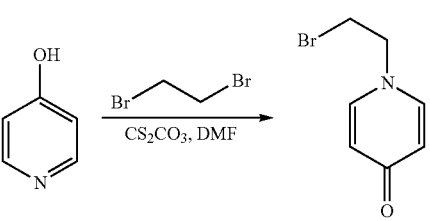

Title compound was prepared from pyridin-4-ol (5 g, 52.5 mmol) using the general methodology of Intermediate-4 and afforded 0.85 g of 1-(2-bromoethyl)pyridin-4(1H)-one (Yield=8%).

1-(2-bromoethoxy)-3-methoxybenzene

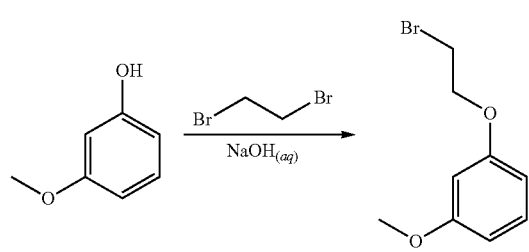

Title compound was prepared from 3-methoxyphenol (5 g, 40.27 mmol) using the general methodology of Intermediate-2 and afforded 3.6 g of 1-(2-bromoethoxy)-3-methoxybenzene (Yield=39%).

1-(2-bromoethoxy)-4-methoxybenzene

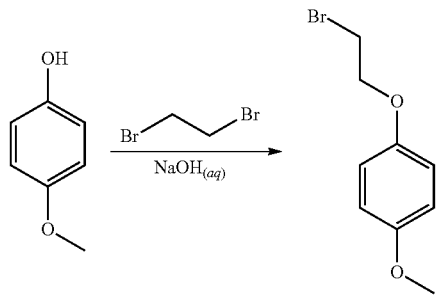

Title compound was prepared from 3-methoxyphenol (5 g, 40.27 mmol) using the general methodology of Int-2 and afforded 3.5 g of 1-(2-bromoethoxy)-4-methoxybenzene (Yield=38%).

7-(2-bromoethoxy) quinolone

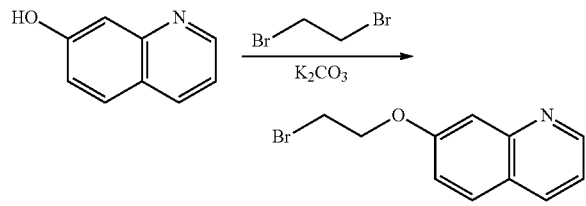

Title compound was prepared from quinolin-7-ol (1 g, 6.89 mmol) using the general methodology of Int-1 and afforded 0.21 g of 7-(2-bromoethoxy) quinolone (Yield=21%).

6-(2-Bromoethoxy) benzo[d]thiazole

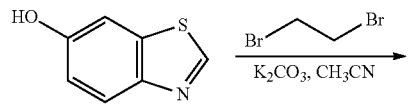

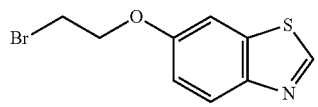

Title compound was prepared from benzo[d]thiazol-6-ol (1 g, 6.62 mmol) using the general methodology of Int-1 and afforded 0.39 g of 6-(2-bromoethoxy) benzo[d]thiazole (Yield=23%).

(3-bromopropoxy)benzene

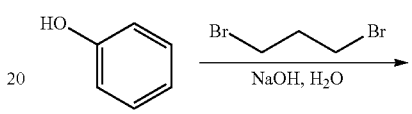

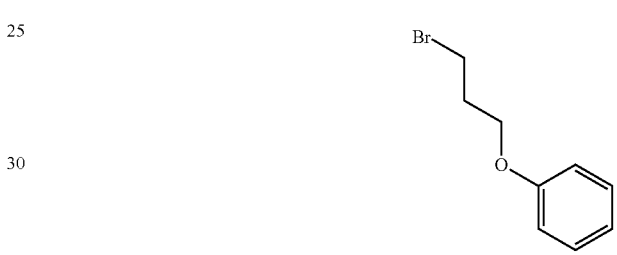

Title compound was prepared from phenol (5 g, 53.1 mmol) using the general methodology of Intermediate-2 and afforded 9 g of (3-bromopropoxy)benzene (Yield=79%).

Synthesis of Intermediate-6

(2-Chlorophenyl)(pyridin-2-yl)methanamine

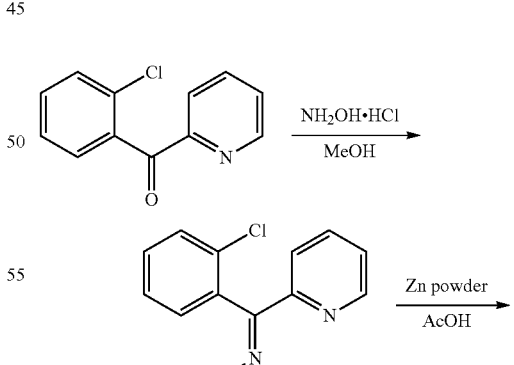

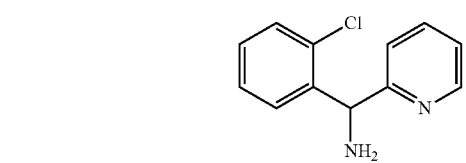

(2-Chlorophenyl)(pyridin-2-yl)methanone Oxime

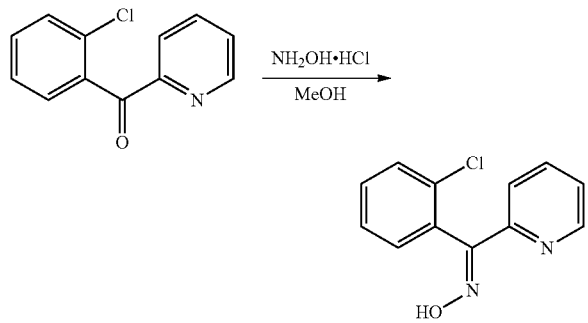

Title compound was prepared from (2-chlorophenyl)(pyridin-2-yl)methanone (0.250 g, 1.14 mmol) using the conditions of step 3 in the general methodology of key Intermediate-I to obtain 0.25 g of (E)-(2-chlorophenyl)(pyridin-2-yl)methanone oxime (Yield=94%).

(2-Chlorophenyl)(pyridin-2-yl)methanamine

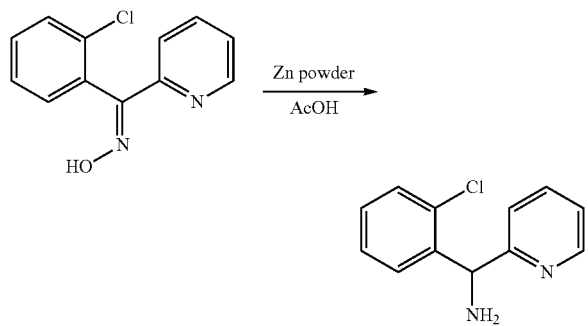

Title compound was prepared from (E)-(3-chlorophenyl)(pyridin-2-yl)methanone oxime (0.250 g, 1.07 mmol) using the conditions of step 4 in the general methodology of key Intermediate-I and afforded 0.180 g of (2-chlorophenyl)(pyridin-2-yl)methanamine (Yield=77%). ESI+MS: m/z: 219.2 ([M+H]$^+$).

One skilled in the art will recognize that other compounds described below were prepared in a similar manner to the procedures described above.

(4-fluorophenyl)(pyridin-2-yl)methanamine

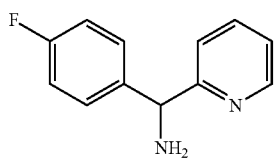

Title compound was prepared using the same chemistry as for intermediate-6 and replacing (2-chlorophenyl)(pyridin-2-yl)methanone with (4-fluorophenyl)(pyridin-2-yl)methanone and afforded 0.160 g of (4-fluorophenyl)(pyridin-2-yl)methanamine (Yield=71%); ESI+MS: m/z: 203.1 ([M+H]$^+$).

(3-fluorophenyl)(pyridin-2-yl)methanamine

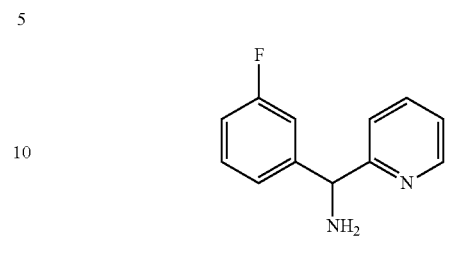

Title compound was prepared using the same chemistry as for intermediate-6 and replacing (2-chlorophenyl)(pyridin-2-yl)methanone with (3-fluorophenyl)(pyridin-2-yl)methanone and afforded 0.180 g of (3-fluorophenyl)(pyridin-2-yl)methanamine (Yield=96%); ESI+MS: m/z: 203.2 ([M+H]$^+$).

(2-fluorophenyl)(pyridin-2-yl)methanamine

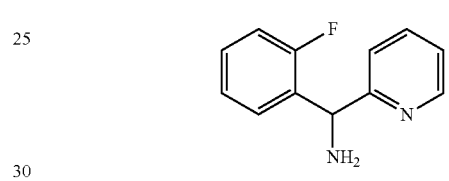

Title compound was prepared using the same chemistry as for intermediate-6 and replacing (2-chlorophenyl)(pyridin-2-yl)methanone with (2-fluorophenyl)(pyridin-2-yl)methanone and afforded 0.140 g of (2-fluorophenyl)(pyridin-2-yl)methanamine (Yield=68%); ESI+MS: m/z: 202.8 ([M+H]$^+$).

(4-methoxyphenyl)(pyridin-2-yl)methanamine

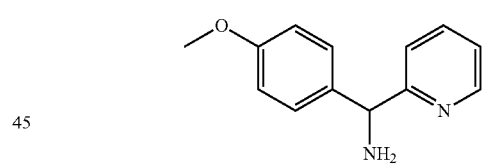

Title compound was prepared using the same chemistry as for intermediate-6 and replacing (2-chlorophenyl)(pyridin-2-yl)methanone with (4-methoxyphenyl)(pyridin-2-yl)methanone and afforded 0.180 g of (4-methoxyphenyl)(pyridin-2-yl)methanamine (Yield=96%).

(3-Methoxyphenyl)(pyridin-2-yl)methanamine

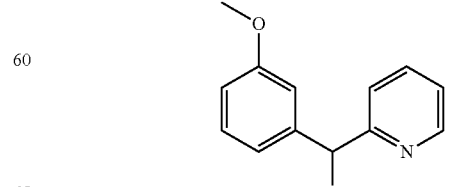

Title compound was prepared using the same chemistry as for intermediate-6 and replacing (2-chlorophenyl)(pyridin-2-yl)methanone with (3-methoxyphenyl)(pyridin-2-yl)methanone and afforded 0.140 g of (3-methoxyphenyl)(pyridin-2-yl)methanamine (Yield=60%).

(2-Methoxyphenyl)(pyridin-2-yl)methanamine

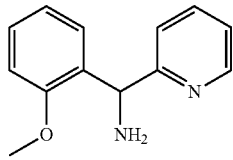 [SMILES: COc1ccccc1C(N)c1ccccn1]

Title compound was prepared using the same chemistry as for intermediate-6 and replacing (2-chlorophenyl)(pyridin-2-yl)methanone with (2-methoxyphenyl)(pyridin-2-yl)methanone and afforded 0.180 g of (2-methoxyphenyl)(pyridin-2-yl)methanamine (Yield=96%).

Cyclohexyl(pyridin-2-yl)methanamine

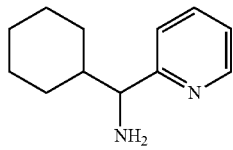 [SMILES: NC(c1ccccn1)C1CCCCC1]

Title compound was prepared using the same chemistry as for intermediate-6 and replacing (2-chlorophenyl)(pyridin-2-yl)methanone with cyclohexyl(pyridin-2-yl)methanone and afforded 0.180 g of cyclohexyl(pyridin-2-yl)methanamine (Yield=74%).

2-Methyl-1-(pyridin-2-yl)propan-1-amine

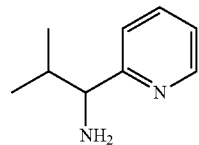

Title compound was prepared using the same chemistry as for intermediate-6 and replacing (2-chlorophenyl)(pyridin-2-yl)methanone with 2-methyl-1-(pyridin-2-yl)propan-1-one and afforded 0.1 g of 2-methyl-1-(pyridin-2-yl)propan-1-amine (Yield=44%).

(4-Chlorophenyl)(phenyl)methanamine

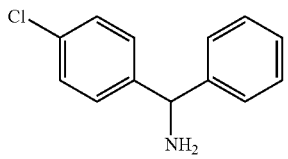 [SMILES: NC(c1ccccc1)c1ccc(Cl)cc1]

Title compound was prepared using the same chemistry as for intermediate-6 and replacing (2-chlorophenyl)(pyridin-2-yl)methanone with (4-chlorophenyl)(phenyl)methanone and afford 0.2 g of (4-chlorophenyl)(phenyl)methanamine (Yield=93%).

(4-chlorophenyl)(2-fluorophenyl)methanamine

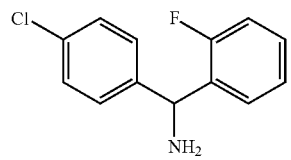 [SMILES: NC(c1ccc(Cl)cc1)c1ccccc1F]

Title compound was prepared using the same chemistry as for intermediate-6 and replacing (2-chlorophenyl)(pyridin-2-yl)methanone with (4-chlorophenyl)(2-fluorophenyl)methanone and afford 0.060 g of (4-chlorophenyl)(2-fluorophenyl)methanamine (Yield=32%).

(4-Chlorophenyl)(3-fluorophenyl)methanamine

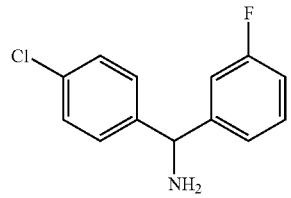 [SMILES: NC(c1ccc(Cl)cc1)c1cccc(F)c1]

Title compound was prepared using the same chemistry as for intermediate-6 and replacing (2-chlorophenyl)(pyridin-2-yl)methanone with (4-chlorophenyl)(3-fluorophenyl)methanone and afforded 0.140 g of (4-chlorophenyl)(3-fluorophenyl)methanamine (Yield=82%).

(4-Chlorophenyl)(4-fluorophenyl)methanamine

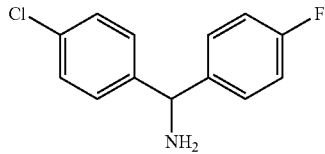 [SMILES: NC(c1ccc(F)cc1)c1ccc(Cl)cc1]

Title compound was prepared using the same chemistry as for intermediate-6 and replacing (2-chlorophenyl)(pyridin-2-yl)methanone with (4-chlorophenyl)(4-fluorophenyl)methanone and afforded 0.120 g of (4-chlorophenyl)(4-fluorophenyl)methanamine (Yield=69%).

107

(4-chlorophenyl)(2-methoxyphenyl)methanamine

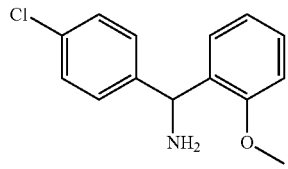 [SMILES: COc1ccccc1C(N)c1ccc(Cl)cc1]

Title compound was prepared using the same chemistry as for intermediate-6 and replacing (2-chlorophenyl)(pyridin-2-yl)methanone with (4-chlorophenyl)(2-methoxyphenyl) methanone and afforded 0.120 g of (4-chlorophenyl)(2-methoxyphenyl)methanamine (Yield=70%).

(4-Chlorophenyl)(4-methoxyphenyl)methanamine

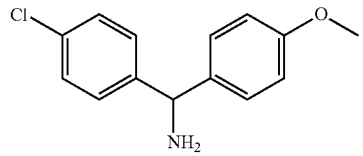 [SMILES: COc1ccc(C(N)c2ccc(Cl)cc2)cc1]

Title compound was prepared using the same chemistry as for intermediate-6 and replacing (2-chlorophenyl)(pyridin-2-yl)methanone with (4-chlorophenyl)(4-methoxyphenyl) methanone and afforded 0.1 g of (4-chlorophenyl)(4-methoxyphenyl)methanamine (Yield=59%).

(4-Fluorophenyl)(phenyl)methanamine

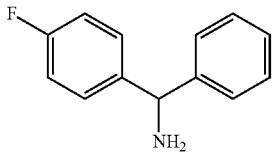 [SMILES: NC(c1ccccc1)c1ccc(F)cc1]

Title compound was prepared using the same chemistry as for intermediate-6 and replacing (2-chlorophenyl)(pyridin-2-yl)methanone with (4-fluorophenyl)(phenyl)methanone and afforded 0.150 g of (4-fluorophenyl)(phenyl)methanamine (Yield=64%).

(3-Methoxyphenyl)(phenyl)methanamine

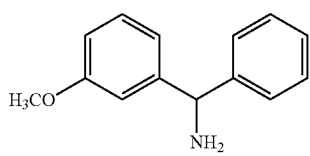 [SMILES: COc1cccc(C(N)c2ccccc2)c1]

Title compound was prepared using the same chemistry as for intermediate-6 and replacing (2-chlorophenyl)(pyridin-

108

2-yl)methanone with (3-methoxyphenyl)(phenyl)methanone and afforded 0.150 g of (3-methoxyphenyl)(phenyl)methanamine (Yield=80%).

Bis(4-fluorophenyl)methanamine

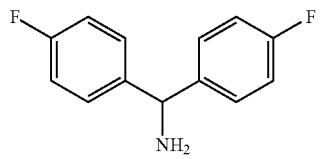 [SMILES: NC(c1ccc(F)cc1)c1ccc(F)cc1]

Title compound was prepared using the same chemistry as for intermediate-6 and replacing (2-chlorophenyl)(pyridin-2-yl)methanone with bis(4-fluorophenyl)methanone and afforded 0.650 g of bis(4-fluorophenyl)methanamine (Yield=86%).

(2-Fluorophenyl)(3-methoxyphenyl)methanamine

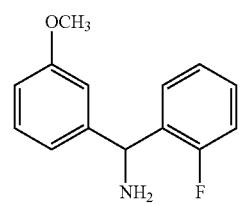 [SMILES: COc1cccc(C(N)c2ccccc2F)c1]

Title compound was prepared using the same chemistry as for intermediate-6 and replacing (2-chlorophenyl)(pyridin-2-yl)methanone with (2-fluorophenyl)(3-methoxyphenyl) methanone and afforded 0.4 g of (2-fluorophenyl)(3-methoxyphenyl)methanamine (Yield=80%).

(4-fluorophenyl)(pyridin-2-yl)methanamine

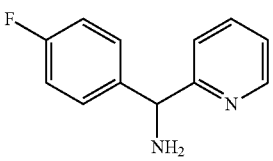 [SMILES: NC(c1ccc(F)cc1)c1ccccn1]

Title compound was prepared using the same chemistry as for intermediate-6 and replacing (2-chlorophenyl)(pyridin-2-yl)methanone with (4-fluorophenyl)(pyridin-2-yl)methanone and afforded 0.5 g of (4-fluorophenyl)(pyridin-2-yl) methanamine (Yield=89%).

Synthesis of Intermediate-7

Pyridin-2-yl(pyridin-4-yl)methanamine

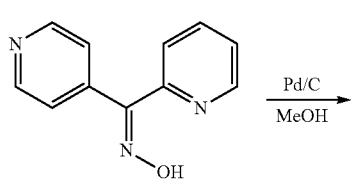

-continued

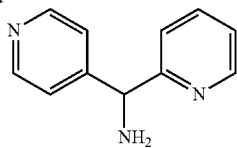

To a stirred solution of (Z)-pyridin-2-yl(pyridin-4-yl)methanone oxime (0.225 g, 1.12 mmol) in MeOH (3 mL) under argon was added 10% Pd/C (0.075 g) at room temperature. The reaction mixture was stirred for 4 h under $H_2$ balloon pressure. After completion of the reaction, the reaction mixture was filtered through celite, washed with methanol and the solvent was removed under reduced pressure to afford 0.180 g of pyridin-2-yl(pyridin-4-yl)methanamine (Yield=86%).

One skilled in the art will recognize that other compounds described below were prepared in a similar manner to the procedures described above.

Pyridin-2-yl(pyridin-3-yl)methanamine

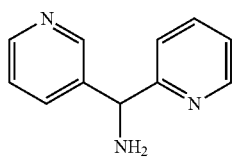 [SMILES: NC(c1cccnc1)c1ccccn1]

Title compound was prepared using the same chemistry as for intermediate-7 and replacing (Z)-pyridin-2-yl(pyridin-4-yl)methanone oxime with (Z)-pyridin-2-yl(pyridin-3-yl)methanone oxime and afforded 0.175 g of pyridin-2-yl(pyridin-3-yl)methanamine (Yield=84%); ESI+MS: m/z: 186.0 ([M+H]$^+$).

Di(pyridin-2-yl)methanamine

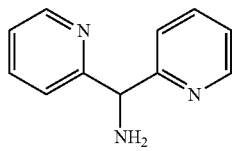 [SMILES: NC(c1ccccn1)c1ccccn1]

Title compound was prepared was prepared using the same chemistry as for intermediate-7 and replacing (Z)-pyridin-2-yl(pyridin-4-yl)methanone oxime with di(pyridin-2-yl)methanone oxime (0.150 g, 0.753 mmol) and afforded 0.1 g of di(pyridin-2-yl)methanamine (Yield=72%). ESI+MS: m/z: 186.0 ([M+H]$^+$).

Bis(2-fluorophenyl)methanamine

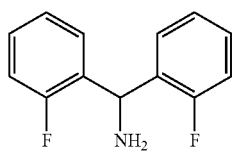 [SMILES: NC(c1ccccc1F)c1ccccc1F]

Title compound was prepared using the same chemistry as for intermediate-7 and replacing (Z)-pyridin-2-yl(pyridin-4-yl)methanone oxime with bis(2-fluorophenyl)methanone oxime and afforded 0.6 g of bis(2-fluorophenyl)methanamine (Yield=80%).

(2-fluorophenyl)(4-fluorophenyl)methanamine

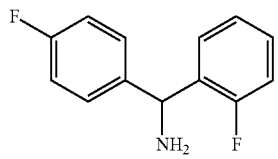 [SMILES: NC(c1ccc(F)cc1)c1ccccc1F]

Title compound was prepared using the same chemistry as for intermediate-7 and replacing (Z)-pyridin-2-yl(pyridin-4-yl)methanone oxime with 2-fluorophenyl)(4-fluorophenyl)methanone oxime and afforded 0.6 g of (2-fluorophenyl)(4-fluorophenyl)methanamine (Yield=80%).

(3-methoxyphenyl)(oxazol-4-yl)methanamine

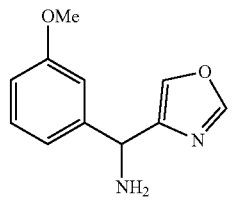 [SMILES: COc1cccc(C(N)c2cocn2)c1]

Title compound was prepared using the same chemistry as for intermediate-7 and replacing (Z)-pyridin-2-yl(pyridin-4-yl)methanone oxime with (Z)-(3-methoxyphenyl)(oxazol-4-yl)methanone oxime and afforded 0.19 g of (3-methoxyphenyl)(oxazol-4-yl)methanamine (Yield=quantitative).

Synthesis of Intermediate-8

Pyridin-2-yl(4-(trifluoromethyl)phenyl)methanamine

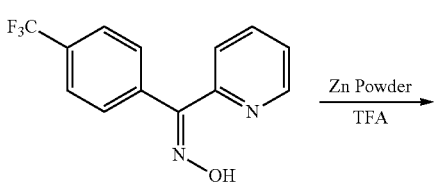

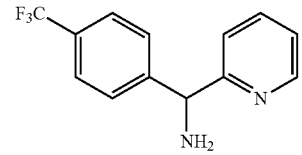

Title compound was prepared from (Z)-pyridin-2-yl(4-(trifluoromethyl)phenyl)methanone oxime (0.150 g, 0.753 mmol) using the conditions in step 4 in the general methodology of key Intermediate-I and afforded 0.140 g of pyridin-2-yl(4-(trifluoromethyl)phenyl)methanamine (Yield=74%). ESI+MS: m/z: 253.2 ([M+H]$^+$).

One skilled in the art will recognize that other compounds described below were prepared in a similar manner to the procedures described above.

Pyridin-2-yl(3-(trifluoromethyl)phenyl)methanamine

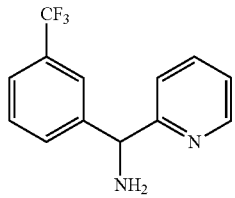 [SMILES: NC(c1cccc(C(F)(F)F)c1)c1ccccn1]

Title compound was prepared using the same chemistry as for intermediate-8 by replacing (Z)-pyridin-2-yl(4-(trifluoromethyl)phenyl)methanone oxime with (Z)-pyridin-2-yl(3-(trifluoromethyl)phenyl)methanone oxime and afforded 0.2 g of (Z)-pyridin-2-yl(3-(trifluoromethyl)phenyl)methanone oxime (Yield=75%). ESI+MS: m/z: 267.1 ([M+H]$^+$).

Pyridin-2-yl(2-(trifluoromethyl)phenyl)methanamine

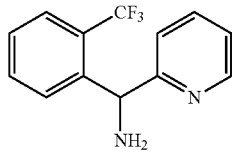 [SMILES: NC(c1ccccn1)c1ccccc1C(F)(F)F]

Title compound was prepared using the same chemistry as for intermediate-8 by replacing (Z)-pyridin-2-yl(4-(trifluoromethyl)phenyl)methanone oxime with (Z)-pyridin-2-yl(2-(trifluoromethyl)phenyl)methanone oxime and afforded 0.1 g of pyridin-2-yl(2-(trifluoromethyl)phenyl)methanamine (Yield=53%).

(4-chlorophenyl)(3-fluoropyridin-4-yl)methanamine

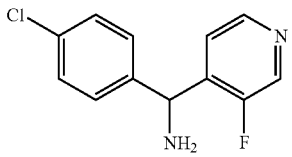 [SMILES: NC(c1ccc(Cl)cc1)c1ccncc1F]

Title compound was prepared in 4 steps using chemistry described for key intermediate-I and replacing picolinaldehyde with 3-fluoroisonicotinaldehyde and afforded 0.7 g of (4-chlorophenyl)(3-fluoropyridin-4-yl)methanamine (Yield=93%).

(4-chlorophenyl)(5-fluoropyridin-2-yl)methanamine

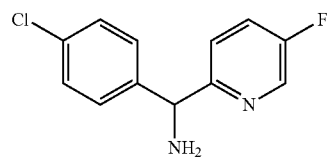 [SMILES: NC(c1ccc(Cl)cc1)c1ccc(F)cn1]

Title compound was prepared in 4 steps using chemistry described for key intermediate-I and replacing picolinaldehyde with 5-fluoropicolinaldehyde and afforded 0.4 g of (4-chlorophenyl)(5-fluoropyridin-2-yl)methanamine (Yield=94%).

Pyridin-2-yl(3-(trifluoromethoxy)phenyl)methanamine

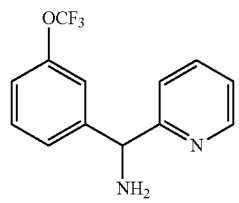 [SMILES: NC(c1cccc(OC(F)(F)F)c1)c1ccccn1]

Title compound was prepared in 4 steps using chemistry described for key intermediate-I and replacing 1-bromo-4-chlorobenzene with 1-bromo-3-(trifluoromethoxy)benzene and afforded 0.3 g of pyridin-2-yl(3-(trifluoromethoxy)phenyl)methanamine (Yield=79%). ESI+MS: m/z: 269.2 ([M+H]$^+$).

(2,2-difluorobenzo[d][1,3]dioxol-5-yl)(pyridin-2-yl)methanamine

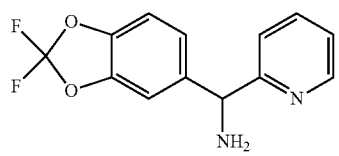 [SMILES: NC(c1ccc2c(c1)OC(F)(F)O2)c1ccccn1]

Title compound was prepared in 4 steps using chemistry described for key intermediate-I and replacing 1-bromo-4-chlorobenzene with 5-bromo-2,2-difluorobenzo[d][1,3]dioxole and afforded 0.45 g of (2,2-difluorobenzo[d][1,3]dioxol-5-yl)(pyridin-2-yl)methanamine (Yield=86%). ESI+MS: m/z: 265.2 ([M+H]$^+$).

Benzo[d][1,3]dioxol-5-yl(pyridin-2-yl)methanamine

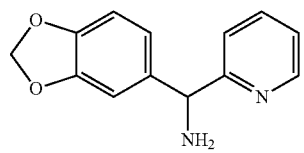

Title compound was prepared in 4 steps using chemistry described for key intermediate-I and replacing 1-bromo-4-chlorobenzene with 5-bromobenzo[d][1,3]dioxole and afforded 0.6 g of benzo[d][1,3]dioxol-5-yl(pyridin-2-yl)methanamine (Yield=71%). ESI+MS: m/z: 229.1 ([M+H]+).

(4-chlorophenyl)(pyridin-3-yl)methanamine

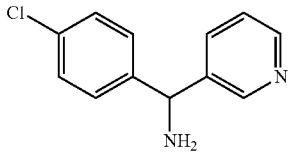 [SMILES: NC(c1ccc(Cl)cc1)c1cccnc1]

Title compound was prepared in 4 steps using chemistry described for key intermediate-I and replacing pyridine-2-carboxaldehyde with pyridine-3-carboxaldehyde and afforded 0.6 g of (4-chlorophenyl)(pyridin-3-yl)methanamine (Yield=64%). ESI+MS: m/z: 219.2 ([M+H]+).

(4-chlorophenyl)(pyridin-4-yl)methanamine

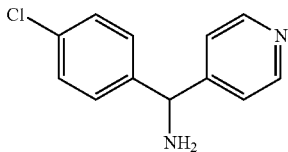 [SMILES: NC(c1ccncc1)c1ccc(Cl)cc1]

Title compound was prepared in 4 steps using chemistry described for key intermediate-I and replacing pyridine-2-carboxaldehyde with pyridine-4-carboxaldehyde and afforded 0.15 g of (4-chlorophenyl)(pyridin-4-yl)methanamine (Yield=80%). ESI+MS: m/z: 219.0 ([M+H]+).

Phenyl(pyridin-2-yl)methanamine

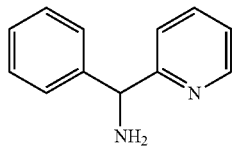

Title compound was prepared in 4 steps using chemistry described for key intermediate-I and replacing 1-bromo-4-chlorobenzene with bromobenzene and afforded 0.41 g of phenyl(pyridin-2-yl)methanamine (Yield=88%). ESI+MS: m/z: 185.2 ([M+H]+).

Example-1: 1-(2-(3-chlorophenoxy)ethyl)-N-((4-chlorophenyl)(pyridin-2-yl)methyl)piperidine-4-carboxamide (I)

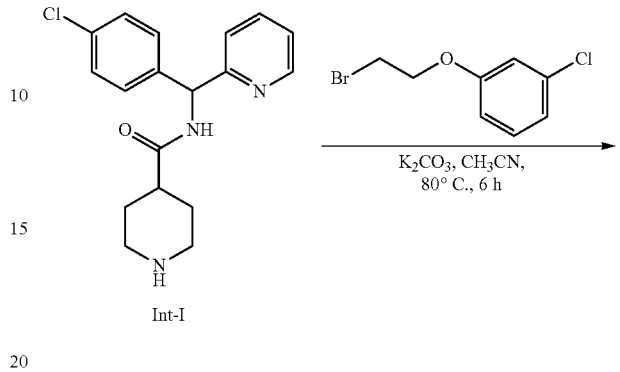

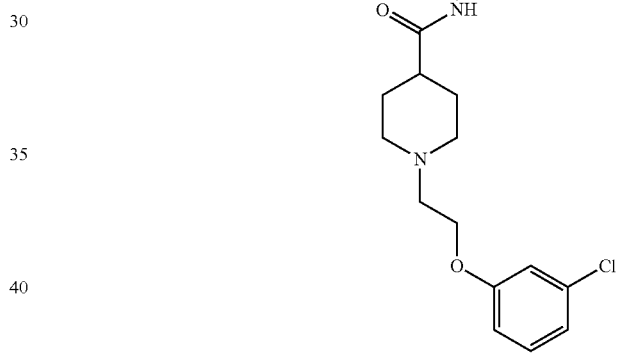

To a stirred solution of N-((4-chlorophenyl)(pyridin-2-yl)methyl)piperidine-4-carboxamide (Int-I) (0.20 g, 0.60 mmol) in $CH_3CN$ (5 mL) were added potassium carbonate (0.251 g, 1.81 mmol, 3 equiv) and 1-(2-bromoethoxy)-3-chlorobenzene (0.143 g, 0.60 mmol, 1 equiv) at room temperature. The reaction mixture was heated at 80° C. and stirred for 6 h. After completion, the reaction mixture was diluted with water and extracted with $CH_2Cl_2$. The combined organic extract was dried over sodium sulfate, filtered and concentrated under reduced pressure. Purification using silica gel column chromatography (3% MeOH/$CH_2Cl_2$ as eluent) afforded 0.05 g of 1-(2-(3-chlorophenoxy) ethyl)-N-((4-chlorophenyl) (pyridin-2-yl) methyl) piperidine-4-carboxamide (Yield=17%).

$^1$H NMR (400 MHz, DMSO-$d_6$): δ 8.71 (d, 1H, J=6.4 Hz), 8.51 (d, 1H, J=4.0 Hz), 7.78-7.76 (m, 1H), 7.44 (d, 1H, J=8.0 Hz), 7.37-7.25 (m, 6H), 7.21-7.09 (m, 3H), 6.13 (d, 1H, J=8.4 Hz), 4.20-4.10 (m, 2H), 2.90-2.80 (m, 2H), 2.70-2.65 (m, 2H), 2.33 (t, 1H, J=2.4 Hz), 2.01 (bs, 2H), 1.66-1.58 (m, 4H); ESI+MS: m/z:484.5 ([M+H]+). Enantiomers of 1 were separated using chiral HPLC (method D) and afforded pure enantiomers 1a and 1b.

Example-2: 1-(2-(4-chlorophenoxy)ethyl)-N-((4-chlorophenyl)(pyridine-2-yl)methyl) piperidine-4-carboxamide (2)

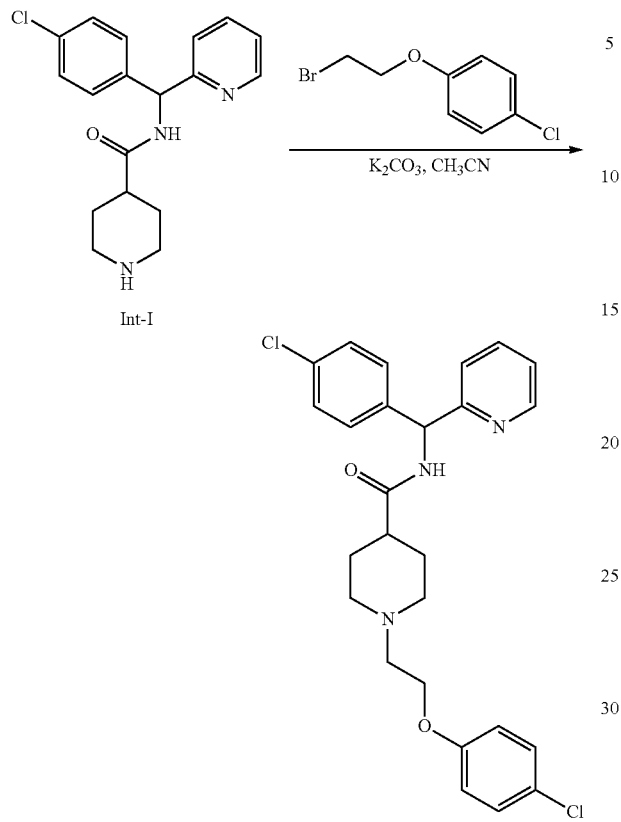

Title compound was prepared from N-((4-chlorophenyl) (pyridin-2-yl) methyl) piperidine-4-carboxamide (Int-I) (0.20 g, 0.60 mmol) using the general methodology of Example-1. The product was washed with n-pentane and ether and afforded 0.1 g of 1-(2-(4-chlorophenoxy) ethyl)-N-((4-chlorophenyl) (pyridine-2-yl) methyl) piperidine-4-carboxamide (Yield=34%).

$^1$H NMR (400 MHz, DMSO-$d_6$): δ 8.70 (d, 1H, J=8.0 Hz), 8.51 (d, 1H, J=4.0 Hz), 7.80-7.75 (m, 1H), 7.44 (d, 1H, J=8.0 Hz), 7.37-7.35 (m, 7H), 6.96 (d, 2H, J=8.8 Hz), 6.13 (d, 1H, J=8.4 Hz), 4.05 (bs, 2H), 2.92 (bs, 2H), 2.65 (bs, 2H), 2.33-2.32 (m, 1H), 2.01 (bs, 2H), 1.66-1.55 (m, 4H); ESI+MS: m/z: 484.5 ([M+H]$^+$).

Example-3: N-((4(4-chlorophenyl)(pyridin-2-yl) methyl)-1-(2-(2-fluorophenoxy)ethyl)piperidine-4-carboxamide (3)

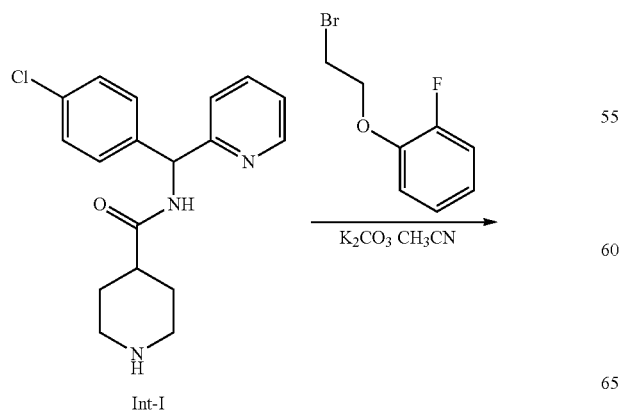

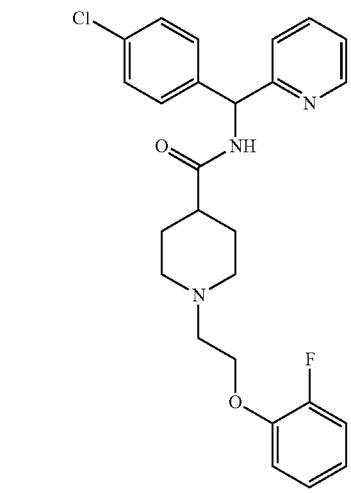

Title compound was prepared from N-((4-chlorophenyl) (pyridin-2-yl)methyl)piperidine-4-carboxamide (Int-I) (0.20 g, 0.60 mmol) using the general methodology of Example-1, and afforded 0.06 g of N((4-chlorophenyl)(pyridin-2-yl) methyl)-1-(2-(2-fluorophenoxy)ethyl) piperidine-4-carboxamide (Yield=21%).

$^1$H NMR (400 MHz, DMSO-$d_6$): δ 8.71 (d, 1H, J=6.4 Hz), 8.51 (d, 1H, J=4.0 Hz), 7.78-7.76 (m, 1H), 7.44 (d, 1H, J=8.0 Hz), 7.37-7.25 (m, 5H), 7.21-7.09 (m, 3H), 6.92 (d, 1H, J=5.2 Hz), 6.13 (d, 1H, J=8.4 Hz), 4.20-4.10 (m, 2H), 2.90-2.80 (m, 2H), 2.70-2.65 (m, 2H), 2.33 (t, 1H, J=2.4 Hz), 2.04 (s, 2H), 1.66-1.58 (m, 4H); ESI+MS: m/z: 468 ([M+H]$^+$). Enantiomers of 3 were separated using chiral HPLC (method D) and afforded pure enantiomers 3a and 3b.

Example-4: N-((4(4-chlorophenyl)(pyridin-2-yl) methyl)-1-(2-(3-fluorophenoxy)ethyl)piperidine-4-carboxamide (4)

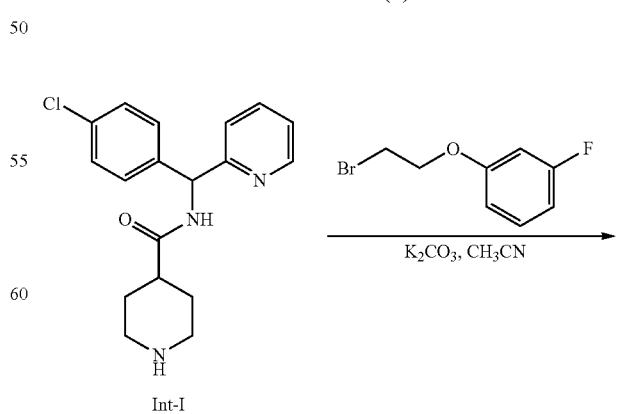

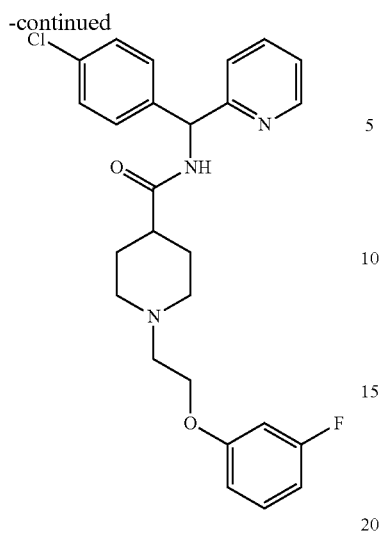

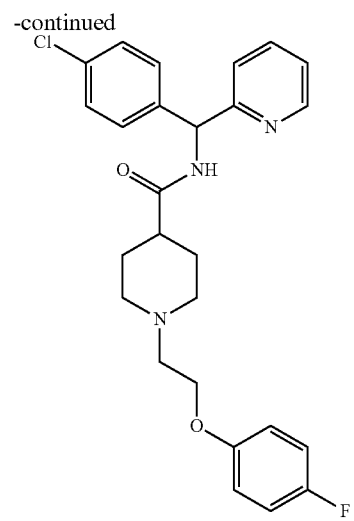

Title compound was prepared from N-((4-chlorophenyl) (pyridin-2-yl) methyl) piperidine-4-carboxamide (Int-I) (0.20 g, 0.60 mmol) using the general methodology of Example-1 and afforded 0.08 g of N-((4-chlorophenyl) (pyridin-2-yl) methyl)-1-(2-(3-fluorophenoxy) ethyl) piperidine-4-carboxamide (Yield=28%). $^1$H NMR (400 MHz, DMSO-d$_6$): δ 8.71 (d, 1H, J=7.6 Hz), 8.51 (d, 1H, J=3.6 Hz), 7.80-7.76 (m, 1H), 7.44 (d, 1H, J=7.6 Hz), 7.37-7.26 (m, 6H), 6.83-6.72 (m, 3H), 6.13 (d, 1H, J=8.4 Hz), 4.20-4.07 (m, 2H), 2.99-2.93 (m, 2H), 2.70-2.60 (m, 2H), 2.40-2.33 (m, 1H), 2.10-1.95 (m, 2H), 1.66-1.55 (m, 4H); ESI+MS: m/z: 468.5 ([M+H]$^+$). Enantiomers of 4 were separated using chiral HPLC (method E) and afforded pure enantiomers 4a and 4b.

Title compound was prepared from N-((4-chlorophenyl) (pyridin-2-yl)methyl)piperidine-4-carboxamide (Int-I) (0.20 g, 0.60 mmol) using the general methodology of Example-1 and afforded 0.1 g of N((4-chlorophenyl)(pyridin-2-yl) methyl)-1-(2-(4-fluoro phenoxy) ethyl) piperidine-4-carboxamide (Yield=35%). $^1$H NMR (500 MHz, DMSO-d$_6$): δ 8.70 (d, 1H, J=8.0 Hz), 8.50 (d, 1H, J=4.0 Hz), 7.79-7.75 (m, 1H), 7.44 (d, 1H, J=8.0 Hz), 7.36-7.25 (m, 5H), 7.10-7.07 (m, 2H), 6.94-6.92 (m, 2H), 6.12 (d, 1H, J=8.5 Hz), 4.05-3.95 (m, 2H), 2.95-2.90 (m, 2H), 2.65-2.60 (m, 2H), 2.36-2.30 (m, 1H), 2.05-1.96 (m, 2H), 1.65-1.54 (m, 4H); ESI+MS: m/z 468 ([M+H]$^+$).

Example-5: N-((4(4-chlorophenyl)(pyridin-2-yl) methyl)-1-(2-(4-fluorophenoxy)ethyl)piperidine-4-carboxamide (5)

Example-6: N-((4(4-chlorophenyl)(pyridin-2-yl) methyl)-1-(2-(2-(trifluoromethyl)phenoxy)ethyl) piperidine-4-carboxamide (6)

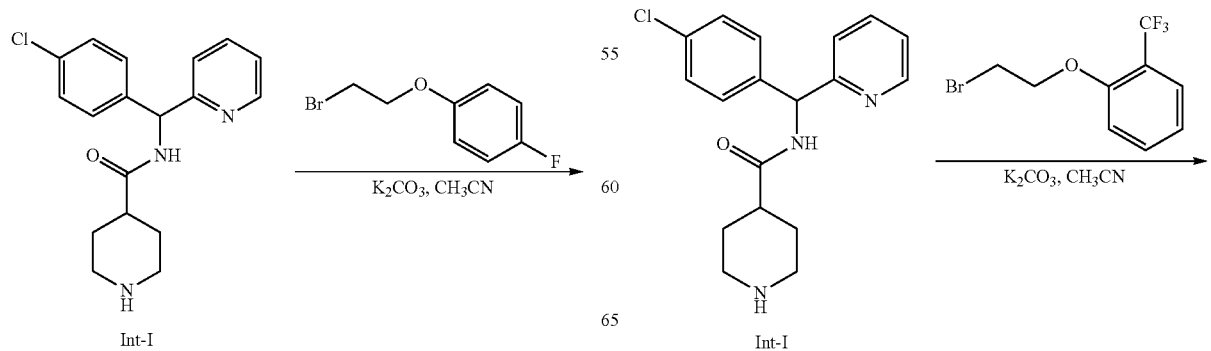

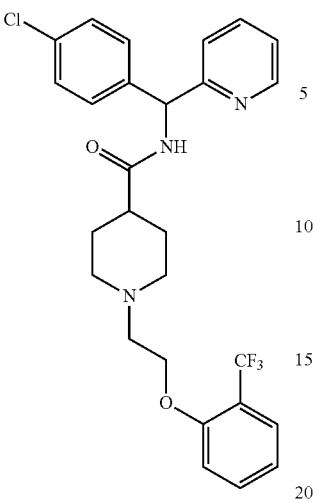

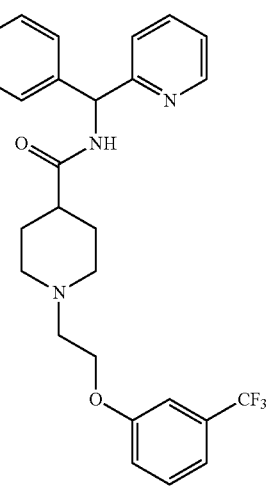

Title compound was prepared from N-((4-chlorophenyl)(pyridin-2-yl) methyl) piperidine-4-carboxamide (Int-I) (0.20 g, 0.60 mmol) using the general methodology of Example-1 and afforded 0.02 g of N-((4(4-chlorophenyl)(pyridin-2-yl)methyl)-1-(2-(2-(trifluoromethyl) phenoxy)ethyl) piperidine-4-carboxamide (Yield=6%). $^1$H NMR (500 MHz, DMSO-$d_6$): δ 8.71 (d, 1H, J=7.5 Hz), 8.51 (d, 1H, J=4.5 Hz), 7.78 (t, 1H, J=7.0 Hz), 7.62-7.59 (m, 2H), 7.44, (d, 1H, J=7.5 Hz), 7.37-7.26 (m, 6H), 7.08 (t, 1H, J=7.5 Hz), 6.13 (d, 1H, J=8.0 Hz), 4.22-4.18 (m, 2H), 2.97-2.90 (m, 2H), 2.75-2.68 (m, 2H), 2.38-2.30 (m, 1H), 2.10-2.00 (m, 2H), 1.68-1.52 (m, 4H); ESI+MS: m/z: 518 ([M+H]$^+$). Enantiomers of 6 were separated using chiral HPLC (method F) and afforded pure enantiomers 6a and 6b.

Example-7: N-((4-chlorophenyl)(pyridin-2-yl) methyl)-1-(2-(3-(trifluoromethyl)phenoxy)ethyl) piperidine-4-carboxamide (7)

Title compound was prepared from N-((4-chlorophenyl)(pyridin-2-yl) methyl) piperidine-4-carboxamide (Int-I) (0.20 g, 0.60 mmol) using the general methodology of Example-1 and afforded 0.09 g of N-((4-chlorophenyl)(pyridin-2-yl) methyl)-1-(2-(3-(trifluoromethyl) phenoxy) ethyl) piperidine-4-carboxamide (Yield=29%). $^1$H NMR (500 MHz, DMSO-$d_6$): δ 8.71 (d, 1H, J=8.0 Hz), 8.51 (d, 1H, J=4.5 Hz), 7.78 (t, 1H, J=7.0 Hz), 7.55-7.42 (m, 2H), 7.40-7.23 (m, 8H), 6.13 (d, 1H, J=8.5 Hz), 4.17-4.12 (m, 2H), 2.97-2.93 (m, 2H), 2.69-2.67 (m, 2H), 2.37-2.31 (m, 1H), 2.04-1.99 (m, 2H), 1.69-1.51 (m, 4H); ESI+MS: m/z: 517.6 ([M+H]$^+$).

Example-8: N-((4-chlorophenyl)(pyridin-2-yl) methyl)-1-(2-(4-(trifluoromethyl)phenoxy)ethyl) piperidine-4-carboxamide (8)

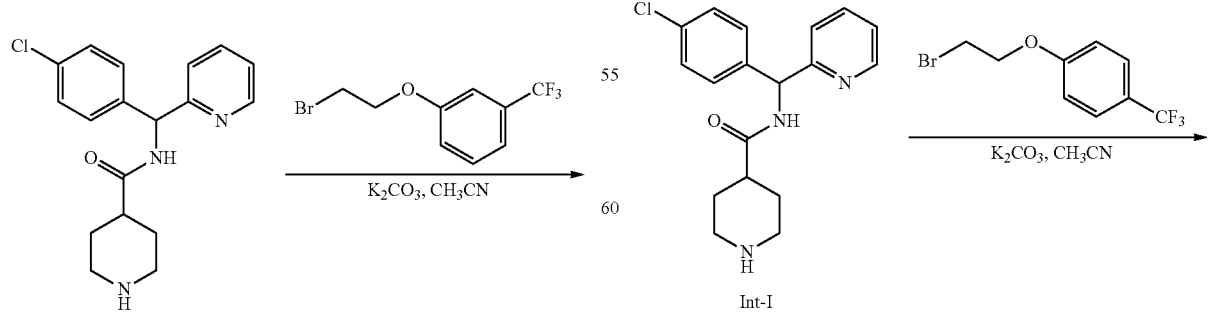

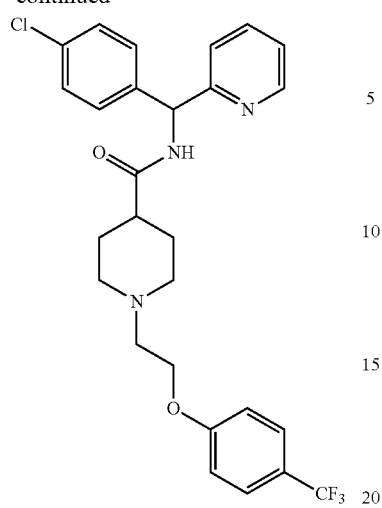

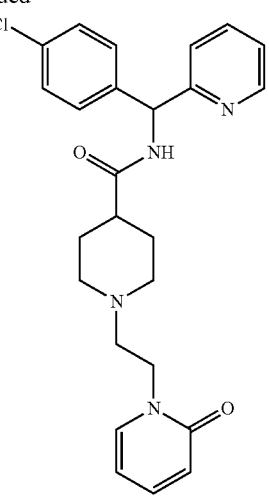

Title compound was prepared from N-((4-chlorophenyl)(pyridin-2-yl) methyl) piperidine-4-carboxamide (Int-I) (0.20 g, 0.61 mmol) using the general methodology of Example-1 and afforded 0.1 g of N-((4-chlorophenyl) (pyridin-2-yl) methyl)-1-(2-(4-(trifluoromethyl) phenoxy)ethyl) piperidine-4-carboxamide (Yield=32%). $^1$H NMR (400 MHz, DMSO-d$_6$): δ 8.71 (d, 1H, J=8.0 Hz), 8.51 (d, 1H, J=4.0 Hz), 7.80-7.76 (m, 1H), 7.63 (d, 2H, J=8.4 Hz), 7.45 (d, 1H, J=8.0 Hz), 7.37-7.27 (m, 4H), 7.27-7.26 (m, 1H), 7.12 (d, 2H, J=8.4 Hz), 6.13 (d, 1H, J=8.0 Hz), 4.20-4.15 (m, 2H), 2.99-2.95 (m, 2H), 2.71-2.63 (m, 2H), 2.40-2.30 (m, 1H), 2.10-1.95 (m, 2H), 1.74-1.55 (m, 4H); ESI+MS: m/z: 518.6 ([M+H]$^+$).

Example-9: N((4-chlorophenyl)(pyridin-2-yl)methyl)-1-(2-(2-oxopyridin-1(2H)-yl)ethyl) piperidine-4-carboxamide (9)

Title compound was prepared from N-((4-chlorophenyl)(pyridin-2-yl) methyl) piperidine-4-carboxamide (Int-I) (0.20 g, 0.60 mmol) using the general methodology of Example-1 and afforded 0.09 g of N-((4-chlorophenyl)(pyridin-2-yl)methyl)-1-(2-(2-oxopyridin-1(2H)-yl)ethyl)piperidine-4-carboxamide (Yield=33%). $^1$H NMR (500 MHz, CD$_3$OD): δ 8.51 (d, 1H, J=4.5 Hz), 7.80-7.77 (m, 1H), 7.60 (d, 1H, J=6.5 Hz), 7.51-7.48 (m, 1H), 7.38 (d, 1H, J=7.5 Hz), 7.31-7.24 (m, 5H), 6.51 (d, 1H, J=9.0 Hz), 6.35 (t, 1H, J=6.5 Hz), 6.14 (s, 1H), 4.10 (t, 2H, J=7.0 Hz), 3.00 (d, 2H, J=11.5 Hz), 2.67 (t, 2H, J=7.0 Hz), 2.41-2.35 (m, 1H), 2.18-2.13 (m, 2H), 1.80-1.69 (m, 4H); ESI+MS: m/z 451 ([M+H]$^+$).

Example-10: N-((4(4-chlorophenyl)(pyridin-2-yl)methyl)-1-(2-(pyridin-3-yloxy)ethyl)piperidine-4-carboxamide (10)

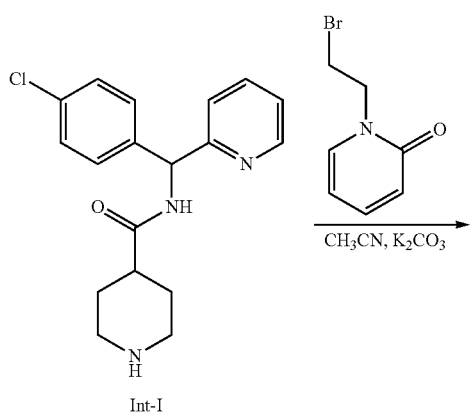

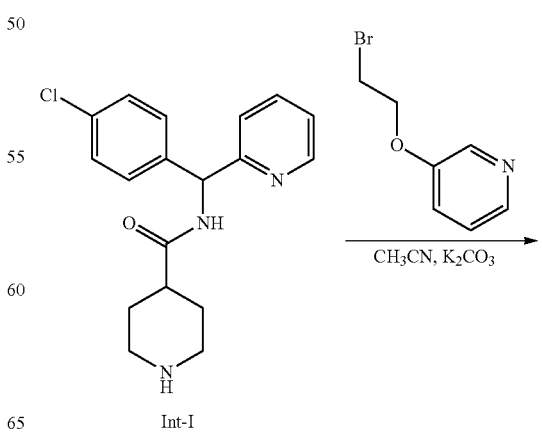

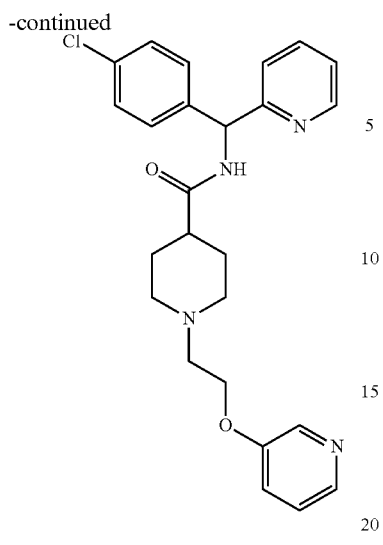
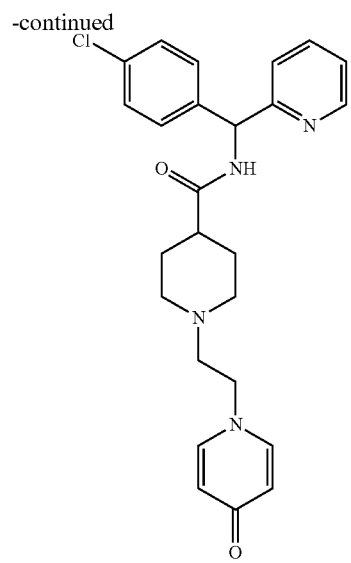

Title compound was prepared from N-((4-chlorophenyl) (pyridin-2-yl) methyl) piperidine-4-carboxamide (Int-I) (0.20 g, 0.60 mmol) using the general methodology of Example-1 and afforded 0.09 g of N-((4-chlorophenyl) (pyridin-2-yl) methyl)-1-(2-(pyridin-3-yloxy) ethyl) piperidine-4-carboxamide (Yield=33%). $^1$H NMR (500 MHz, DMSO-$d_6$): δ 8.70 (d, 1H, J=8.5 Hz), 8.51 (d, 1H, J=4.0 Hz), 8.28 (d, 1H, J=3.0 Hz), 8.15 (d, 1H, J=4.0 Hz), 7.78-7.76 (m, 1H), 7.44 (d, 1H, J=7.5 Hz), 7.40-7.26 (m, 7H), 6.13 (d, 1H, J=8.0 Hz), 4.13 (t, 2H, J=5.5 Hz), 2.94 (d, 2H, J=10.5 Hz), 2.69-2.63 (m, 2H), 2.36-2.32 (m, 1H), 2.02 (t, 2H, J=11.5 Hz), 1.66-1.52 (m, 4H); ESI+MS: m/z:451 ([M+H]$^+$).

Example-11: N-((4(4-chlorophenyl)(pyridin-2-yl) methyl)-1-(2-(4-oxopyridin-1(4H)-yl)ethyl) piperidine-4-carboxamide (11)

Title compound was prepared from N-((4-chlorophenyl) (pyridin-2-yl)methyl)piperidine-4-carboxamide (Int-I) (0.20 g, 0.60 mmol) using the general methodology of Example-1. The crude was purified using preparative HPLC to afford 0.02 g of N-((4-chlorophenyl)(pyridin-2-yl) methyl)-1-(2-(4-oxopyridin-1(4H)-yl)ethyl)piperidine-4-carboxamide (Yield=7.3%).

$^1$H NMR (400 MHz, DMSO-$d_6$): δ 8.72 (d, 1H, J=8.4 Hz), 8.51 (d, 1H, J=4.0 Hz), 7.80-7.75 (m, 1H), 7.62 (d, 2H, J=7.6 Hz), 7.44 (d, 1H J=8.0 Hz), 7.37-7.25 (m, 5H), 6.13-6.05 (m, 2H), 5.73 (d, 1H, J=11.6 Hz), 3.95-3.85 (m, 2H), 2.90-2.82 (m, 2H), 2.65-2.55 (m, 2H), 2.40-2.35 (m, 1H), 2.00-1.92 (m, 2H), 1.70-1.60 (m, 2H), 1.58-1.45 (m, 2H); ESI+MS: m/z: 451 ([M+H]$^+$). Enantiomers of 11 were separated using chiral HPLC (method G) and afforded pure enantiomers 11a and 11b.

Example-12: N-((4-chlorophenyl) (pyridin-2-yl) methyl)-1-(2-(3-methoxyphenoxy) ethyl) piperidine-4-carboxamide (12)

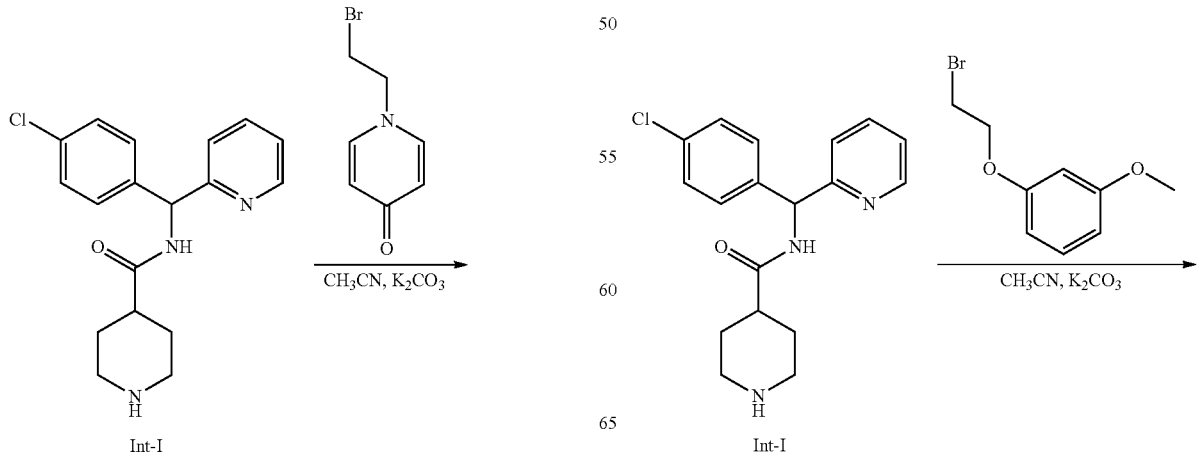

125

-continued

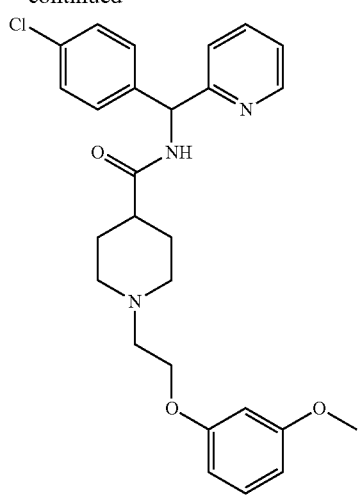

126

-continued

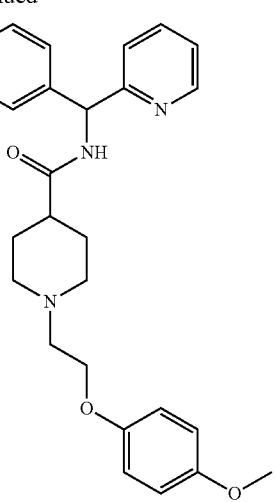

Title compound was prepared from N-((4-chlorophenyl)(pyridin-2-yl)methyl)piperidine-4-carboxamide (Int-I) (0.20 g, 0.60 mmol) using the general methodology of Example-1 and afforded 0.09 g of N-((4-chlorophenyl) (pyridin-2-yl)methyl)-1-(2-(3-methoxyphenoxy) ethyl) piperidine-4-carboxamide (Yield=30%). $^1$H NMR (400 MHz, DMSO-$d_6$): δ 8.72 (br s, 1H), 8.51 (d, 1H, J=4.0 Hz), 7.80-7.76 (m, 1H), 7.44 (d, 1H, J=8.0 Hz), 7.37-7.29 (m, 4H), 7.27-7.26 (m, 1H), 7.16 (t, 1H, J=8.0 Hz), 6.52-6.49 (m, 3H), 6.13 (d, 1H, J=8.4 Hz), 4.10-4.04 (m, 2H), 3.11 (s, 3H), 2.99-2.94 (m, 2H), 2.67-2.66 (m, 2H), 2.40-2.32 (m, 1H), 2.10-2.04 (m, 2H), 1.74-1.58 (m, 4H); ESI+MS: m/z: 480.5 ([M+H]$^+$).

Example-13: N-((4-chlorophenyl)(pyridin-2-yl)methyl)-1-(2-(4-methoxyphenoxy)ethyl) piperidine-4-carboxamide (13)

Title compound was prepared from N-((4-chlorophenyl)(pyridin-2-yl)methyl)piperidine-4-carboxamide (Int-I) (0.20 g, 0.60 mmol) using the general methodology of Example-1 and afforded 0.11 g of N-((4-chlorophenyl) (pyridin-2-yl)methyl)-1-(2-(4-methoxyphenoxy)ethyl) piperidine-4-carboxamide (Yield=37%). $^1$H NMR (400 MHz, DMSO-$d_6$): δ 8.71 (d, 1H, J=6.4 Hz), 8.51 (d, 1H, J=4.0 Hz), 7.80-7.76 (m, 1H), 7.44 (d, 1H, J=7.6 Hz), 7.37-7.29 (m, 4H), 7.27-7.26 (m, 1H), 6.88-6.82 (m, 4H), 6.37 (d, 1H, J=8.4 Hz), 4.01-3.98 (m, 2H), 3.68 (s, 3H), 2.99-2.93 (m, 2H), 2.66-2.64 (m, 2H), 2.35-2.34 (m, 1H), 2.10-2.01 (m, 2H), 1.74-1.58 (m, 4H); ESI+MS: m/z:480.5 ([M+H]$^+$).

Example-14: N-((4(4-chlorophenyl)(pyridin-2-yl)methyl)-1-(2-(2,5-difluorophenoxy)ethyl) piperidine-4-carboxamide (14)

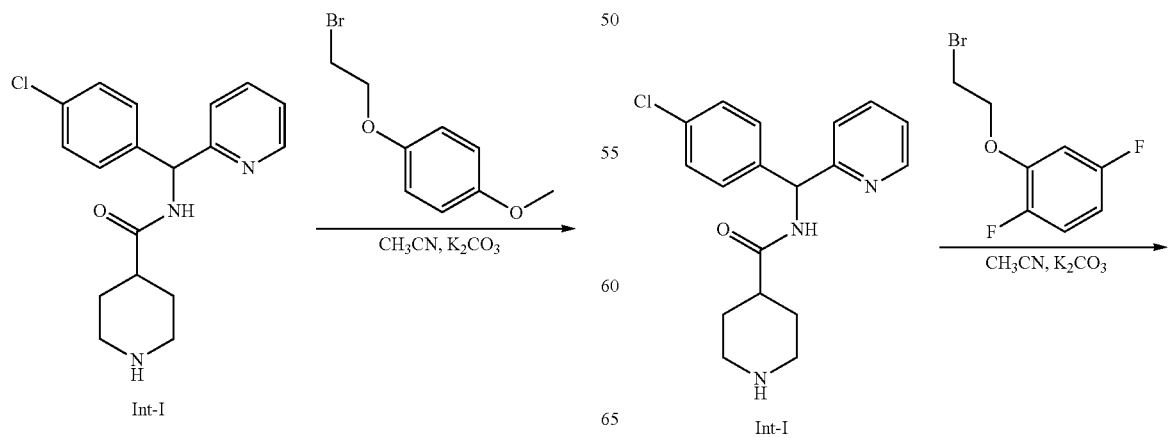

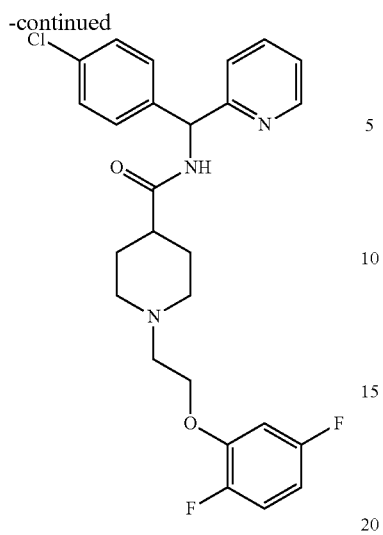
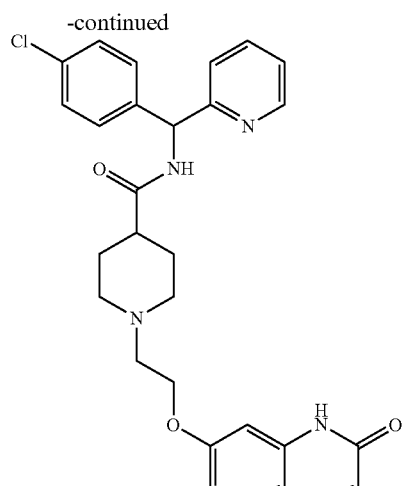

Title compound was prepared from N-((4-chlorophenyl)(pyridin-2-yl) methyl) piperidine-4-carboxamide (Int-I) (0.20 g, 0.60 mmol) using the general methodology of Example-1 and afforded 0.05 g of N-((4-chlorophenyl)(pyridin-2-yl) methyl)-1-(2-(2,5-difluorophenoxy) ethyl) piperidine-4-carboxamide (Yield=34%) as white solid. $^1$H NMR (400 MHz, DMSO-$d_6$): δ 8.711 (d, 1H, J=8.4 Hz), 8.51 (d, 1H, J=4.8 Hz), 7.80-7.76 (m, 1H), 7.45 (d, 1H, J=8.0 Hz), 7.37-7.33 (m, 4H), 7.31-7.19 (m, 2H), 7.16-7.11 (m, 1H), 6.76-6.72 (m, 1H), 6.13 (d, 1H, J=8.4 Hz), 4.14 (t, 2H, J=11.6 Hz), 2.94 (d, 2H, J=11.6 Hz), 2.69 (t, 2H, J=11.2 Hz), 2.36-2.31 (m, 1H), 2.02 (t, 2H, J=11.6 Hz), 1.65-1.51 (m, 4H); ESI+MS: m/z 486 ([M+H]$^+$). Enantiomers of 14 were separated using chiral HPLC (method G) and afforded pure enantiomers 14a and 14b.

Title compound was prepared from N-((4-chlorophenyl)(pyridin-2-yl)methyl)piperidine-4-carboxamide (Int-I) (0.154 g, 0.46 mmol) using the general methodology of Example-1 and afforded 0.03 g of N-((4(4-chlorophenyl)(pyridin-2-yl)methyl)-1-(2-((2-oxo-1,2-dihydroquinolin-7-yl)oxy)ethyl)piperidine-4-carboxamide (Yield=12%). $^1$H NMR (500 MHz, DMSO-$d_6$): δ 11.54 (s, 1H), 8.71 (d, 1H, J=7.0 Hz), 8.51 (d, 1H, J=4.0 Hz), 7.80-7.76 (m, 2H), 7.54 (d, 1H, J=4.5 Hz), 7.44 (d, 1H, J=8.0 Hz), 7.37-7.33 (m, 4H), 7.27 (t, 1H, J=7.0 Hz), 6.79 (s, 2H), 6.28 (d, 1H, J=8.0 Hz), 6.13 (d, 1H, J=8.5 Hz), 4.10-4.05 (m, 2H), 2.99-2.94 (m, 2H), 2.69-2.63 (m, 2H), 2.36-2.35 (m, 1H), 2.08-2.03 (m, 2H), 1.67-1.66 (m, 2H), 1.58-1.56 (m, 2H); ESI+MS: m/z: 517.3 ([M+H]$^+$).

Example-15: N-((4(4-chlorophenyl)(pyridin-2-yl)methyl)-1-(2-((2-oxo-1,2-dihydroquinolin-7-yl)oxy)ethyl)piperidine-4-carboxamide (15)

Example-16: N-((4(4-chlorophenyl)(pyridin-2-yl)methyl)-1-(2-(quinolin-7-yloxy)ethyl) piperidine-4-carboxamide (16)

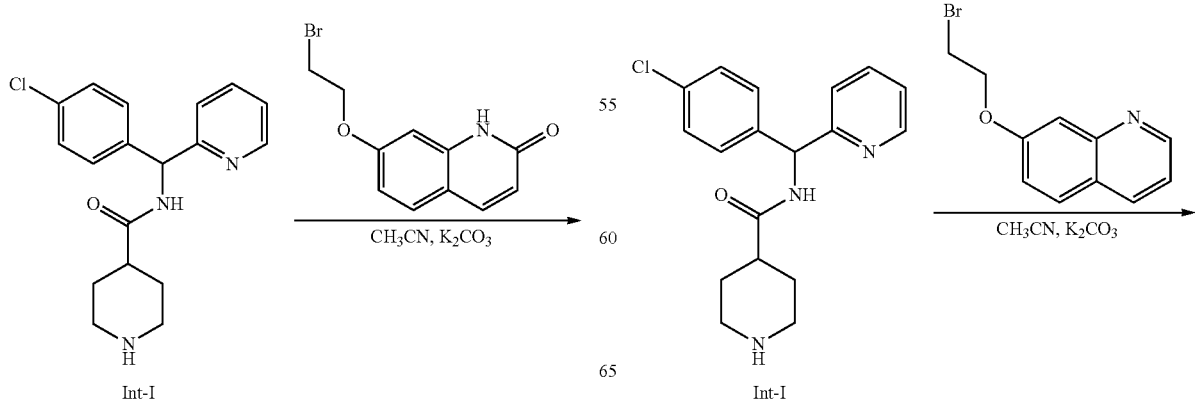

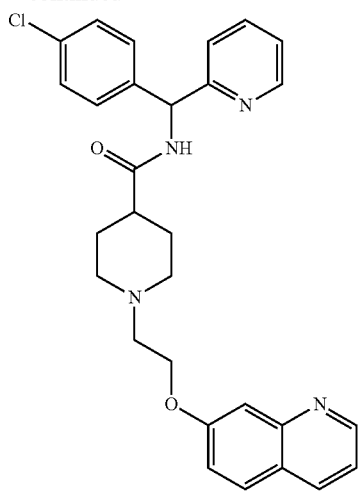

Title compound was prepared from N-((4-chlorophenyl)(pyridin-2-yl)methyl)piperidine-4-carboxamide (Int-1) (0.20 g, 0.60 mmol) using the general methodology of Example-1 and afforded 0.05 g of N-((4(4-chlorophenyl)(pyridin-2-yl)methyl)-1-(2-(quinolin-7-yloxy)ethyl) piperidine-4-carboxamide (Yield=17%). ¹H NMR (500 MHz, DMSO-$d_6$): δ 8.82-8.79 (m, 1H), 8.71 (br s, 1H), 8.50 (d, 1H, J=4.0 Hz), 8.25 (d, 1H, J=8.0 Hz), 7.86 (d, 1H, J=9.0 Hz), 7.77 (t, 1H, J=8.0 Hz), 7.44 (d, 1H, J=8.0 Hz), 7.40-7.31 (m, 6H), 7.32-7.22 (m, 2H), 6.13 (d, 1H, J=8.0 Hz), 4.25-4.20 (m, 2H), 3.00-2.90 (m, 2H), 2.78-2.70 (m, 2H), 2.30-2.28 (m, 1H), 2.10-2.02 (m, 2H), 1.70-1.55 (m, 4H); ESI+MS: m/z: 501 ([M+H]⁺). Enantiomers of 16 were separated using chiral HPLC (method H) and afforded pure enantiomers 16a and 16b.

Example-17: N-((4-chlorophenyl) (pyridin-2-yl)methyl)-1-(2-(cyclohexyloxy) ethyl) piperidine-4-carboxamide (17)

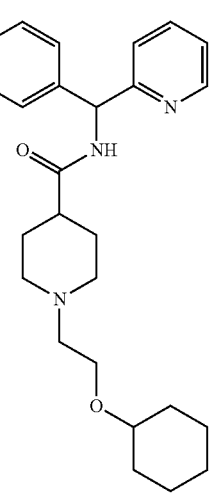

To a stirred solution of N-((4-chlorophenyl)(pyridin-2-yl)methyl)piperidine-4-carboxamide (Int-I) (0.20 g, 0.60 mmol) in CH₃CN (5 mL) was added (2-bromoethoxy)cyclohexane (0.15 g, 0.72 mmol, 1.2 equiv) and potassium carbonate (0.251 g, 1.81 mmol, 3 equiv) at room temperature. The reaction mixture was heated at 80° C. and stirred for 16 h in a sealed tube. After completion, the reaction mixture was diluted with water and extracted with CH₂Cl₂. The combined organic extract was dried over sodium sulfate, filtered and the solvent was removed under reduced pressure. Purification using silica gel column chromatography (5% MeOH/CH₂Cl₂ as eluent) afforded 0.04 g of N-((4 (4-chlorophenyl)(pyridin-2-yl)methyl)-1-(2-(cyclohexyloxy)ethyl) piperidine-4-carboxamide (Yield=14%). ¹H NMR (500 MHz, CD₃OD): δ 8.54 (d, 1H, J=5.0 Hz), 7.82-7.81 (m, 1H), 7.40 (d, 1H, J=8.0 Hz), 7.34-7.28 (m, 5H), 6.17 (s, 1H), 3.71-3.68 (m, 2H), 3.30-3.25 (m, 2H), 2.90-2.80 (m, 2H), 2.55 (d, 3H, J=10.5 Hz), 1.95-1.85 (m, 6H), 1.78-1.73 (m, 2H), 1.55-1.50 (m, 1H), 1.35-1.25 (m, 6H); ESI+MS: m/z 456 ([M+H]⁺).

Example-18: N-((4-chlorophenyl)(pyridin-2-yl)methyl)-1-(3-phenylpropyl)piperidine-4-carboxamide (18)

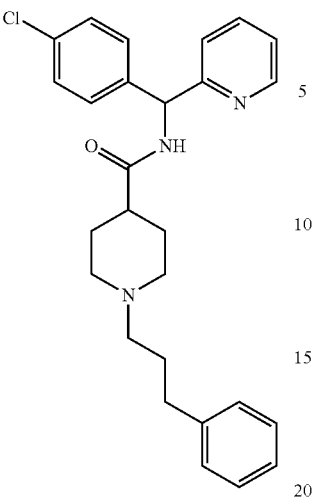

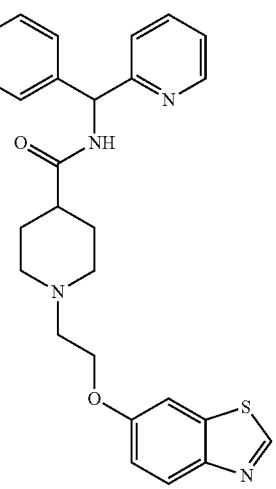

Title compound was prepared from N-((4-chlorophenyl)(pyridin-2-yl)methyl)piperidine-4-carboxamide (Int-1) (0.20 g, 0.60 mmol) using the general methodology of Example-1. The crude was purified using preparative HPLC purification to afford 0.08 g of N-((4-chlorophenyl)(pyridin-2-yl)methyl)-1-(3-phenylpropyl)piperidine-4-carboxamide (Yield=29%).

¹HNMR (400 MHz, DMSO-d$_6$): δ 8.70 (d, 1H, J=8.4 Hz), 8.50 (d, 1H, J=3.6 Hz), 7.80-7.75 (m, 1H), 7.44 (d, 1H, J=7.6 Hz), 7.37-7.31 (m, 4H), 7.28-7.24 (m, 3H), 7.19-7.13 (m, 3H), 6.13 (d, 1H, J=8.4 Hz), 2.90-2.85 (m, 2H), 2.56 (t, 2H, J=7.6 Hz), 2.33-2.30 (m, 1H), 2.24-2.23 (m, 2H), 1.90-1.83 (m, 2H), 1.72-1.54 (m, 6H); ESI+MS: m/z: 448.5 ([M+H]⁺).

Title compound was prepared from N-((4-chlorophenyl)(pyridin-2-yl)methyl)piperidine-4-carboxamide (Int-I) (0.15 g, 0.45 mmol) using the general methodology of Example-1 and afforded 0.09 g of 1-(2-(benzo[d]thiazol-6-yloxy)ethyl)-N((4-chlorophenyl (pyridin-2-yl) methyl)piperidine-4-carboxamide (Yield=39%). ¹H NMR (400 MHz, DMSO-d$_6$): δ 9.17 (s, 1H), 8.71 (d, 1H, J=8.0 Hz), 8.51 (d, 1H, J=4.0 Hz), 7.94 (d, 1H, J=9.2 Hz), 7.80-7.73 (m, 2H), 7.45 (d, 1H, J=8.0 Hz), 7.37-7.31 (m, 4H), 7.28-7.25 (m, 1H), 7.12 (dd, 1H, J$_{1,2}$=2.8 Hz, J$_{1,3}$=9.2 Hz), 6.13 (d, 1H, J=8.4 Hz), 4.14 (t, 2H, J=5.6 Hz), 2.98-2.94 (m, 2H), 2.72-2.69 (m, 2H), 2.37-2.32 (m, 1H), 2.06-2.01 (m, 2H), 1.66-1.53 (m, 4H); ESI+MS: m/z: 507 ([M+H]⁺).

Synthesis of Intermediate II

Example-19: 1-(2-(Benzo[d]thiazol-6-yloxy) ethyl)-N-((4-chlorophenyl)(pyridin-2-yl) methyl) piperidine-4-carboxamide (19)

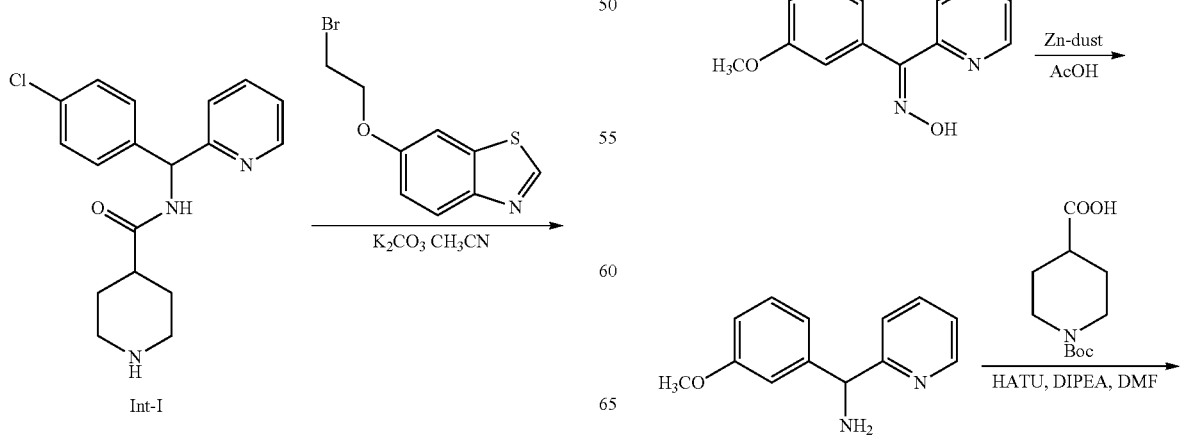

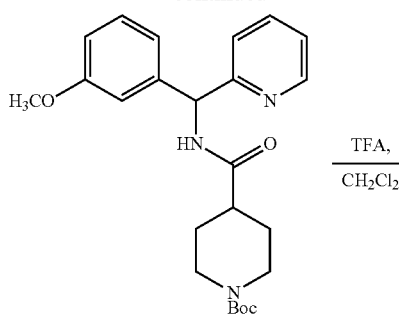

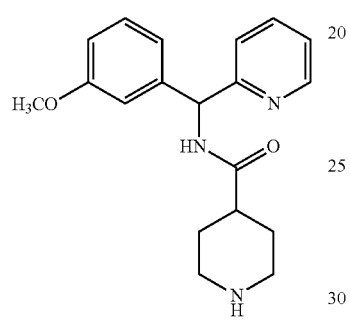

Key intermediate II was synthesized using a similar synthetic sequence as key intermediate I but (4-chlorophenyl) (pyridin-2-yl) methanone was replaced with (3-methoxyphenyl) (pyridin-2-yl) methanone in step 3.

Example-20: N-((3-methoxyphenyl)(pyridin-2-yl) methyl)-1-(2-(2-(trifluoromethyl)phenoxy) ethyl) piperidine-4-carboxamide (20)

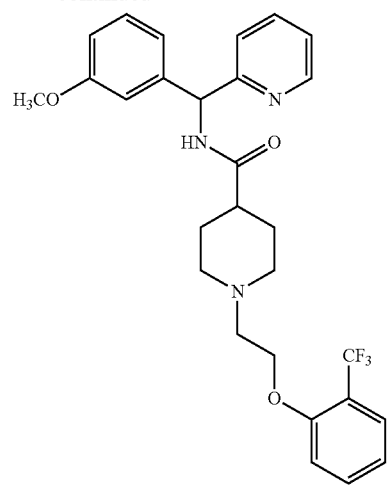

Title compound was prepared from N-((3-methoxyphenyl) (pyridin-2-yl) methyl) piperidine-4-carboxamide (Int-II) (0.13 g, 0.40 mmol) using the general methodology of Example-1 and afforded 0.05 g of N-((3-methoxyphenyl) (pyridin-2-yl) methyl)-1-(2-(2-(trifluoromethyl) phenoxy) ethyl) piperidine-4-carboxamide (Yield=24%). $^1$H NMR (400 MHz, CD$_3$OD): δ 8.51 (dd, 1H, J$_{1,2}$=0.8, J$_{1,3}$=1.6 Hz), 7.79 (dd, 1H, J$_{1,2}$=9.6, J$_{1,3}$=2.0 Hz), 7.57-7.53 (m, 2H), 7.39 (d, 1H, J=8.0 Hz), 7.31-7.28 (m, 1H), 7.23-7.16 (m, 2H), 7.05 (t, 1H, J=7.6 Hz), 6.84-6.80 (m, 3H), 6.13 (s, 1H), 4.24 (t, 2H, J=10.8 Hz), 3.75 (s, 3H), 3.13-3.09 (m, 2H), 2.86 (t, 2H, J=5.2 Hz), 2.45-2.38 (m, 1H), 2.31-2.24 (m, 2H), 1.90-1.75 (m, 4H); ESI+MS: m/z 514 ([M+H]$^+$).

Example-21: 1-(2-(2-chlorophenoxy)ethyl)-N-((3-methoxyphenyl)(pyridin-2-yl)methyl) piperidine-4-carboxamide (21)

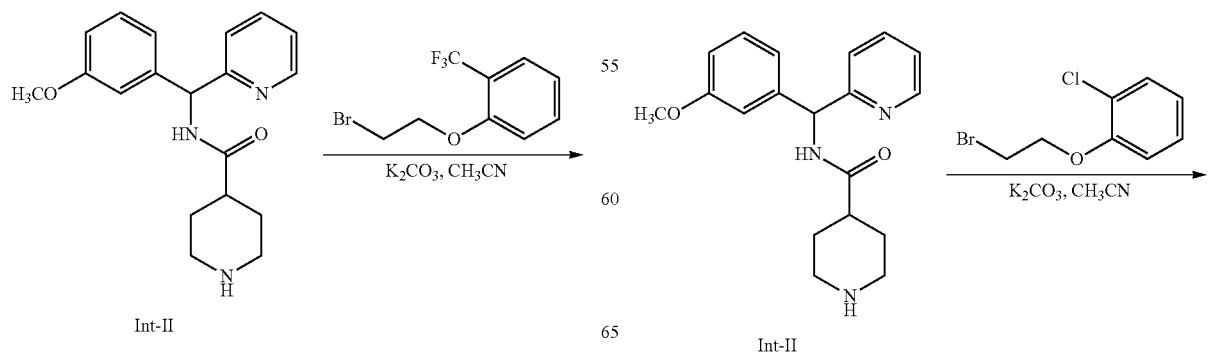

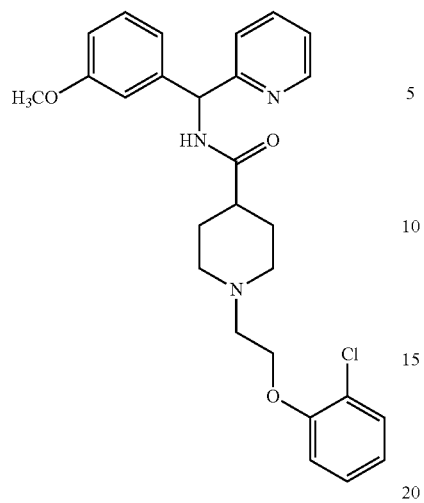
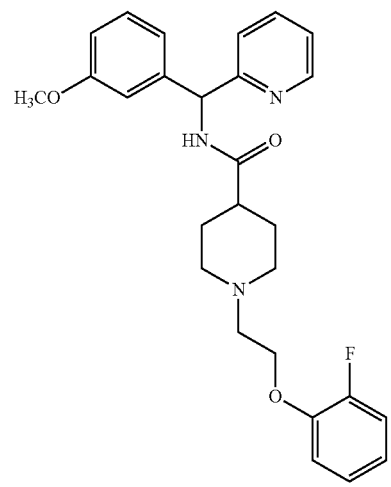

Title compound was prepared from N-((3-methoxyphenyl)(pyridin-2-yl)methyl)piperidine-4-carboxamide (Int-II) (0.12 g, 0.36 mmol) using the general methodology of Example-1. The crude was purified by preparative HPLC purification and afforded 0.035 g of 1-(2-(2-chlorophenoxy)ethyl)-N-((3-methoxyphenyl) (pyridin-2-yl) methyl) piperidine-4-carboxamide (Yield=20%). $^1$HNMR (400 MHz, $CD_3OD$): δ 8.51 (d, 1H, J=4.4 Hz), 7.78 (dt, 1H, $J_{1,2}$=1.6 Hz, $J_{1,4}$=9.2 Hz), 7.39 (d, 1H, J=7.6 Hz), 7.34 (dd, 1H, $J_{1,2}$=1.6 Hz, $J_{1,3}$=8.0 Hz), 7.31-7.19 (m, 3H) 7.07-7.05 (m, 1H), 6.91 (dt, 1H, $J_{1,2}$=1.2 Hz, $J_{1,4}$=8.8 Hz), 6.84-6.80 (m, 3H), 6.13 (s, 1H), 4.19 (t, 2H, J=5.6 Hz), 3.75 (s, 3H) 3.15 (d, 2H, J=11.6 Hz), 2.87 (t, 2H, J=5.6 Hz), 2.46-2.38 (m, 1H), 2.34-2.27 (m, 2H), 1.90-1.77 (m, 4H); ESI+MS: m/z 480 ([M+H]$^+$).

Example-22: 1-(2-(2-fluorophenoxy)ethyl)-N-((3-methoxyphenyl)(pyridin-2-yl)methyl) piperidine-4-carboxamide (22)

Title compound was prepared from N((3-methoxyphenyl) (pyridin-2-yl) methyl)piperidine-4-carboxamide (Int-II) (0.15 g, 0.46 mmol) using the general methodology of Example-1. The crude was purified by preparative HPLC and afforded 0.05 g of 1-(2-(2-fluorophenoxy)ethyl)-N-((4 (3-methoxyphenyl)(pyridin-2-yl)methyl)piperidine-4-carboxamide (Yield=23%). $^1$HNMR (400 MHz, $CD_3OD$): δ 8.51-8.50 (m, 1H), 7.78 (dt, 1H, $J_{1,2}$=1.6 Hz, $J_{1,4}$=9.2 Hz), 7.39 (d, 1H, J=8.0 Hz), 7.31-7.28 (m, 1H), 7.23-7.19 (m, 1H), 7.11-7.04 (m, 3H), 6.93-6.88 (m, 1H), 6.84-6.79 (m, 3H), 6.13 (s, 1H), 4.18 (t, 2H, J=5.6 Hz), 3.74 (s, 3H), 3.10 (d, 2H, J=11.6 Hz), 2.85-2.81 (m, 2H), 2.45-2.37 (m, 1H), 2.29-2.22 (m, 2H), 1.85-1.76 (m, 4H); ESI+MS: m/z 464 ([M+H]$^+$). Enantiomers of 22 were separated using chiral HPLC (method I) and afforded pure enantiomers 22a and 22b.

Synthesis of Key Intermediate III 1-(2-phenoxyethyl) piperidine-4-carboxylic acid (Int-III)

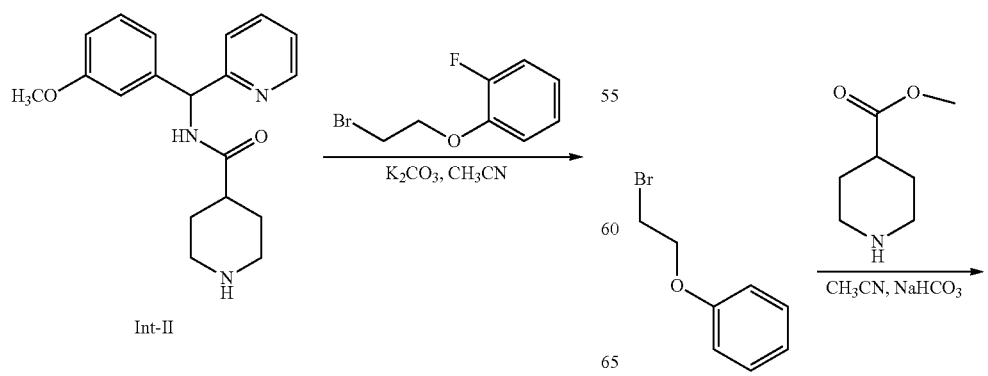

-continued

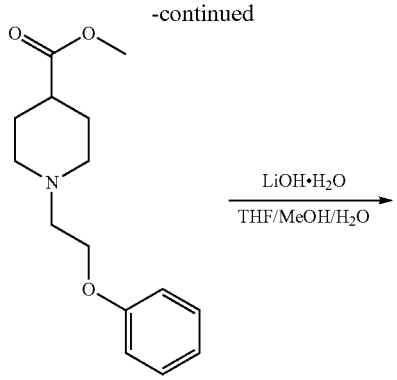

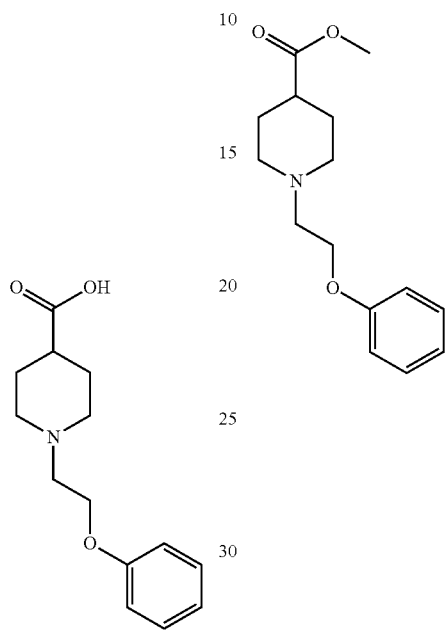

Int-III

Step 1: Methyl 1-(2-phenoxyethyl)piperidine-4-carboxylate

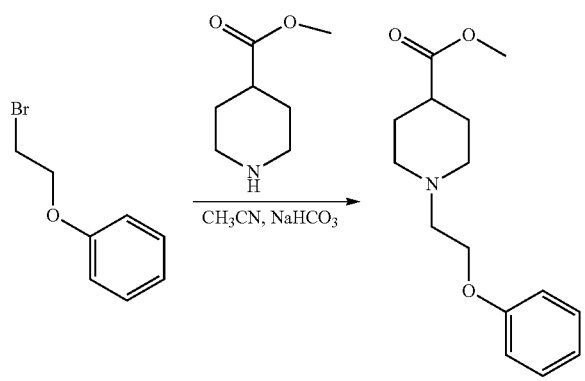

To a stirred solution of (2-bromoethoxy)benzene (1 g, 5 mmol) in CH₃CN (50 mL) were added methyl piperidine-4-carboxylate (0.715 g, 5 mmol, 1 equiv) and sodium bicarbonate (1.26 g, 15 mmol, 3 equiv) at room temperature. The reaction mixture was heated at 100° C. and stirred for 16 h. After completion, the reaction mixture was diluted with water and extracted with EtOAc. The combined organic extract was washed with brine, filtered and dried over sodium sulphate. The solvent was removed under reduced pressure. Purification using silica gel column chromatography (20% EtOAc/Hexanes as eluent) afforded 1 g of methyl 1-(2-phenoxyethyl) piperidine-4-carboxylate (Yield=76%). ESI+MS: m/z: 264.1 ([M+H]⁺).

Step 2: 1-(2-Phenoxyethyl) piperidine-4-carboxylic acid (Int-III)

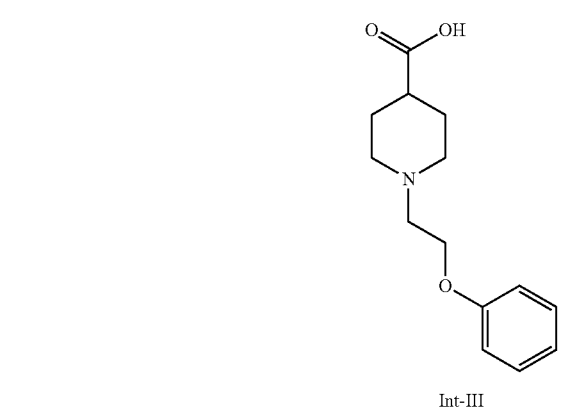

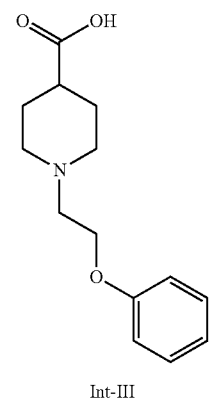

Int-III

To a stirred solution of methyl 1-(2-phenoxyethyl) piperidine-4-carboxylate (1 g, 3.80 mmol) in THF/H₂O/MeOH (15:5:15) was added lithium hydroxide (0.479 g, 11.4 mmol, 3 equiv) at 0° C. and the reaction was stirred at room temperature for 3 h. After completion, the reaction was diluted with water and methanol and THF were removed under reduced pressure. The pH was adjusted to 7 with 1N HCl (aq) and extracted with EtOAc. The combined organic extract was washed with brine, filtered and dried over sodium sulphate. The solvent was removed under reduced pressure to afforded 0.8 g of 1-(2-Phenoxyethyl) piperidine-4-carboxylic acid (Yield=84%). Ion trap: m/z: 250.2 ([M+H]⁺).

1-(2-(2-chlorophenoxy)ethyl)piperidine-4-carboxylic acid

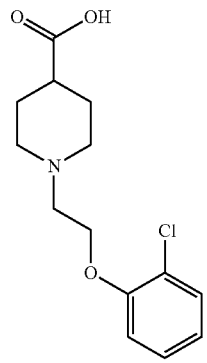 [SMILES: O=C(O)C1CCN(CCOc2ccccc2Cl)CC1]

Title compound was prepared in 2 steps using the same chemistry described for intermediate III by replacing (2-bromoethoxy)benzene with (2-bromoethoxy)-2-chlorobenzene and afforded 0.75 g of 1-(2-(2-chlorophenoxy)ethyl)piperidine-4-carboxylic acid (Yield=79%); Ion trap: m/z: 284.2 ([M+H]$^+$).

1-(2-(2-fluorophenoxy)ethyl)piperidine-4-carboxylic acid

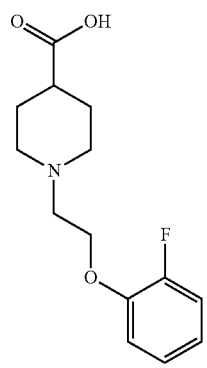 [SMILES: O=C(O)C1CCN(CCOc2ccccc2F)CC1]

Title compound was prepared in 2 steps using the same chemistry described for intermediate III by replacing (2-bromoethoxy)benzene with (2-bromoethoxy)-2-fluorobenzene and afforded 1.2 g of 1-(2-(2-fluorophenoxy)ethyl)piperidine-4-carboxylic acid (Yield=70%). ESI+MS: m/z: 268.2 ([M+H]$^+$).

1-(2-(2-methoxyphenoxy)ethyl)piperidine-4-carboxylic acid

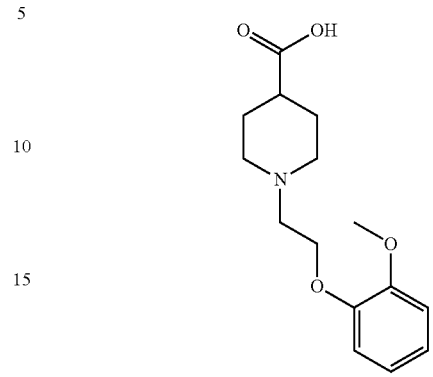

Title compound was prepared in 2 steps using the same chemistry described for intermediate III by replacing (2-bromoethoxy)benzene with (2-bromoethoxy)-2-methoxybenzene and afforded 0.62 g of 1-(2-(2-methoxyphenoxy)ethyl)piperidine-4-carboxylic acid (Yield=90%). ESI+MS: m/z: 280.6 ([M+H]$^+$).

Example-23: N-((4(3-chlorophenyl)(pyridin-2-yl)methyl)-1-(2-phenoxyethyl)piperidine-4-carboxamide (23)

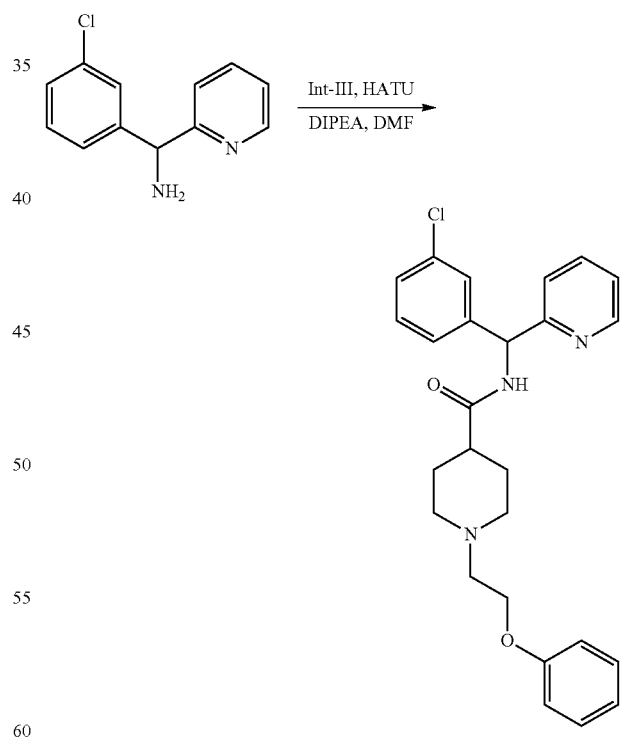

Title compound was prepared from coupling of (3-chlorophenyl) (pyridin-2-yl)methanamine (0.2 g, 0.915 mmol, 1 equiv) and 1-(2-phenoxyethyl) piperidine-4-carboxylic acid (Int-III) (0.274 g, 1.09 mmol, 2 equiv) using the amide bond coupling step conditions used in general methodology for key Intermediate-I and afforded 0.04 g of N-((3-chlorophenyl) (pyridin-2-yl) methyl)-1-(2-phenoxyethyl) piperidine-4-carboxamide (Yield=10%). $^1$H NMR (500 MHz, DMSO-d$_6$): δ 8.75 (d, 1H, J=8.0 Hz), 8.52 (d, 1H, J=4.0 Hz), 7.80-7.77 (m, 1H), 7.47 (d, 1H, J=8.0 Hz), 7.39 (s, 1H), 7.35-7.25 (m, 6H), 6.93-6.90 (m, 3H), 6.15 (d, 1H, J=8.0 Hz), 4.10-4.05 (m, 2H), 2.99-2.95 (m, 2H), 2.69-2.64 (m, 2H), 2.39-2.35 (m, 1H), 2.05-2.03 (m, 2H), 1.68-1.57 (m, 4H); ESI+MS: m/z: 470.5 ([M+H]$^+$).

Example-24: N-((4(2-chlorophenyl)(pyridin-2-yl)methyl)-1-(2-phenoxyethyl)piperidine-4-carboxamide (24)

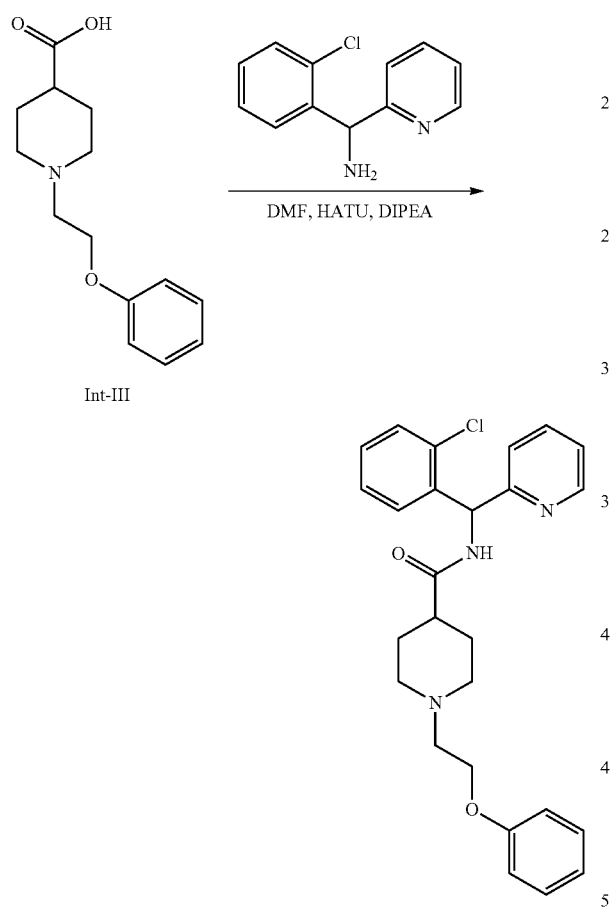

Title compound was prepared from coupling of 1-(2-phenoxyethyl)piperidine-4-carboxylic acid III (0.299 g, 1.2 mmol, 1.5 equiv) and (2-chlorophenyl)(pyridin-2-yl)methanamine (0.175 g, 0.8 mmol, 1 equiv) using the conditions in step 5 in the general methodology of key Intermediate-I. The crude compound was purified by washing with pentane to afforded 0.06 g of N-((2-chlorophenyl)(pyridin-2-yl)methyl)-1-(2-phenoxyethyl)piperidine-4-carboxamide (Yield=16%). $^1$H NMR (500 MHz, DMSO-d$_6$): δ 8.70 (d, 1H, J=8.0 Hz), 8.49 (d, 1H, J=4.5 Hz), 7.79-7.75 (m, 1H), 7.41 (d, 1H, J=7.5 Hz), 7.36-7.24 (m, 7H), 6.92-6.88 (m, 3H), 6.45 (d, 1H, J=8.0 Hz), 4.04 (t, 2H, J=6.5 Hz), 2.91 (d, 2H, J=10.5 Hz), 2.65 (t, 2H, J=6.0 Hz), 2.32-2.28 (m, 1H), 2.00 (t, 2H, J=10.5 Hz), 1.67-1.53 (m, 4H); ESI+MS: m/z: 450.2 ([M+H]$^+$).

Example-25: N-((4(4-fluorophenyl)(pyridin-2-yl)methyl)-1-(2-phenoxyethyl)piperidine-4-carboxamide (25)

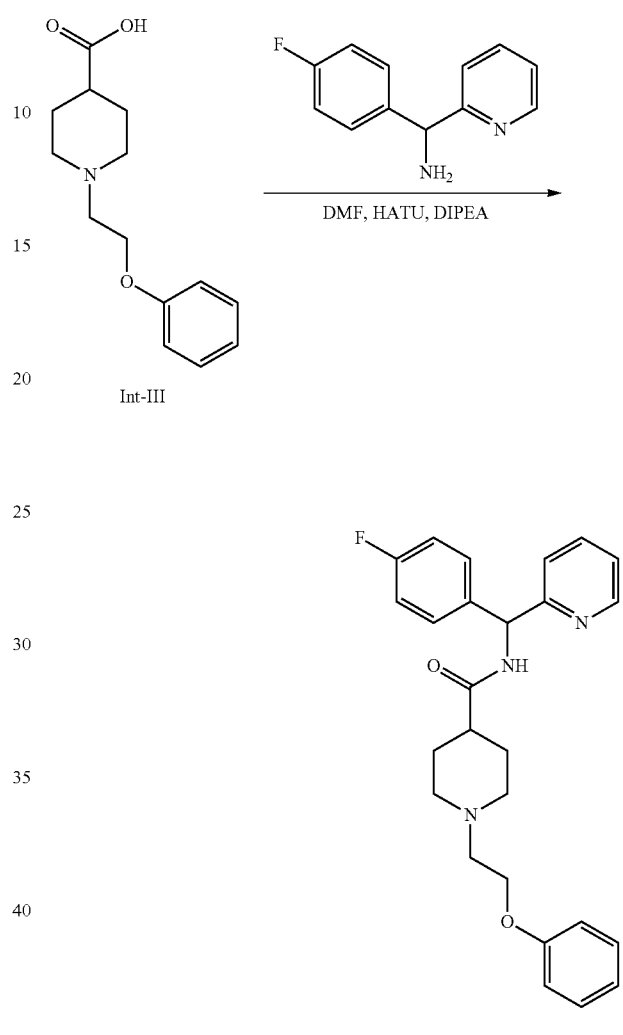

Title compound was prepared from coupling of 1-(2-phenoxyethyl)piperidine-4-carboxylic acid (Int-III) (0.296 g, 1.18 mmol, 1.5 equiv) and (4-fluorophenyl)(pyridin-2-yl)methanamine (0.160 g, 0.791 mmol, 1 equiv) using the conditions in step 5 in the general methodology of key Intermediate-I. The crude compound was purified by washings with pentane to afford 0.18 g of N-((4-fluorophenyl)(pyridin-2-yl)methyl)-1-(2-phenoxyethyl)piperidine-4-carboxamide (Yield=53%).

$^1$H NMR (500 MHz, DMSO-d$_6$): δ 8.67 (d, 1H, J=8.5 Hz), 8.49 (s, 1H), 7.76 (t, 1H, J=7.5 Hz), 7.43 (d, 1H, J=7.5 Hz,), 7.32 (t, 2H, J=6.5 Hz), 7.25 (d, 3H, J=7.0 Hz), 7.11 (t, 2H, J=8.5 Hz), 6.91 (d, 2H, J=8.5 Hz), 6.12 (d, 1H, J=8.5 Hz), 4.03 (t, 2H, J=6.5 Hz), 2.93 (d, 2H, J=10.0 Hz), 2.69-2.61 (m, 2H), 2.39-2.35 (m, 1H), 2.00 (t, 2H, J=10.5 Hz), 1.69-1.61 (s, 2H), 1.56 (t, 2H, J=11.5 Hz); Ion Trap: m/z: 434.5 ([M+H]$^+$).

Example-26: N-((4(3-fluorophenyl)(pyridin-2-yl)methyl)-1-(2-phenoxyethyl)piperidine-4-carboxamide (26)

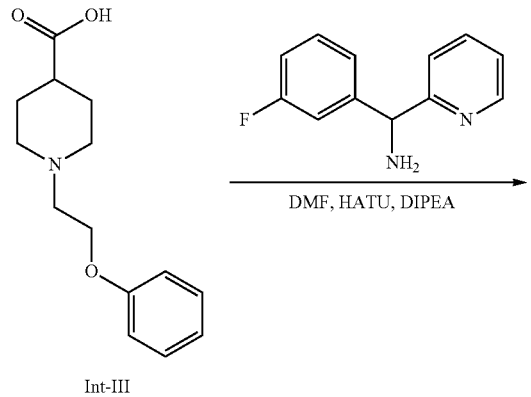

Example-27: N-((4(3-fluorophenyl)(pyridin-2-yl)methyl)-1-(2-phenoxyethyl)piperidine-4-carboxamide (27)

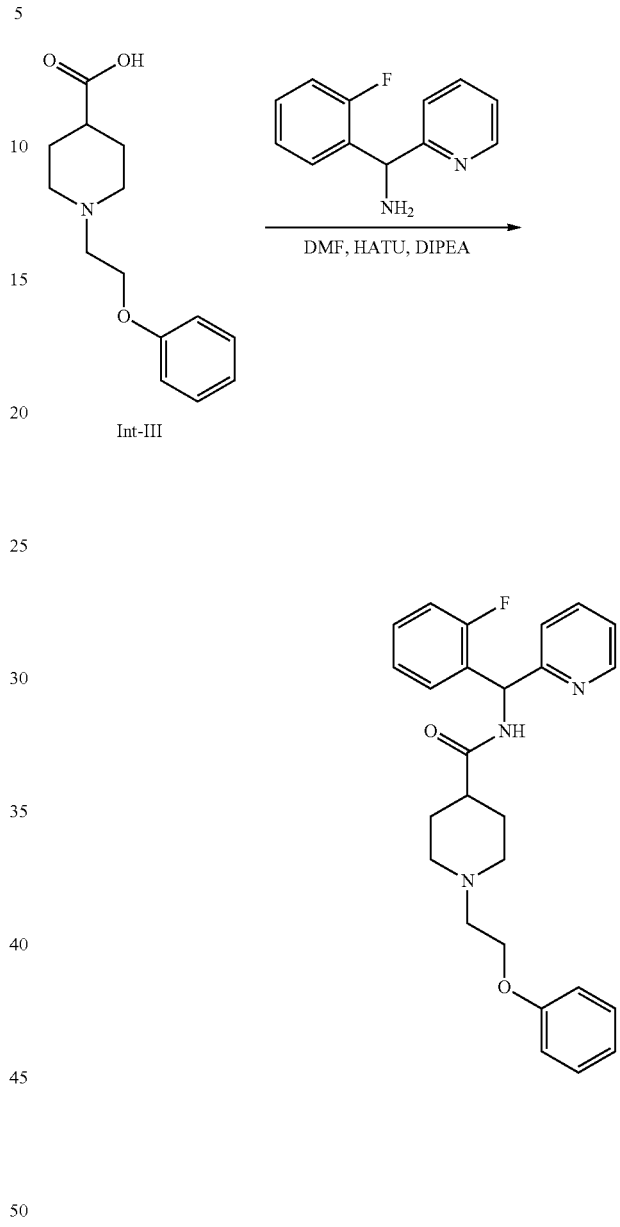

Title compound was prepared from coupling of 1-(2-phenoxyethyl)piperidine-4-carboxylic acid (Int-III) (0.266 g, 1.06 mmol, 1.2 equiv) and (3-fluorophenyl)(pyridin-2-yl)methanamine (0.180 g, 0.890 mmol, 1 equiv) using the conditions in step 5 in the general methodology of key Intermediate-I. The crude residue was purified by column chromatography eluting with 2% MeOH in DCM to afford 0.04 g of N-((3-dihydroindole), dihydroindole), 2-yl)methyl)-1-(2-phenoxyethyl)piperidine-4-carboxamide (Yield=10%). $^1$H NMR (500 MHz, DMSO-d$_6$): δ 8.73 (d, 1H, J=8.0 Hz), 8.51 (d, 1H, J=5.0 Hz), 7.78 (t, 1H, J=7.0 Hz), 7.47 (d, 1H, J=7.5 Hz), 7.36-7.22 (m, 4H), 7.17-7.14 (m, 2H), 7.07-7.03 (m, 1H), 6.94-6.90 (m, 3H), 6.16 (d, 1H, J=8.5 Hz), 4.14-4.07 (m, 2H), 2.98-2.95 (m, 2H), 2.69-2.64 (m, 2H), 2.38-2.35 (m, 1H), 2.07-2.03 (m, 2H), 1.70-1.58 (m, 4H). Ion Trap: m/z: 434.3 ([M+H]$^+$).

Title compound was prepared from coupling of 1-(2-phenoxyethyl)piperidine-4-carboxylic acid (Int-III) (0.259 g, 1.03 mmol, 1.5 equiv) and (2-fluorophenyl)(pyridin-2-yl)methanamine (0.140 g, 0.692 mmol, 1 equiv) using the conditions in step 5 in the general methodology of key Intermediate-I. The crude compound was purified by washing with pentane (4 times) to furnish 0.150 g of N-((3-fluorophenyl)(pyridin-2-yl)methyl)-1-(2-phenoxyethyl)piperidine-4-carboxamide (Yield=50%). $^1$H NMR (400 MHz, DMSO-d$_6$): δ 8.71 (d, 1H, J=8.5 Hz), 8.48 (d, 1H, J=4.0 Hz), 7.77 (t, 1H, J=8.0 Hz), 7.36-7.24 (m, 6H), 7.16-7.11 (m, 2H), 6.92-6.88 (m, 3H), 6.37 (d, 1H J=8.0 Hz), 4.03 (t, 2H, J=6.0 Hz), 2.94-2.93 (m, 2H), 2.65 (t, 2H, J=11.5 Hz), 2.34-2.30 (m, 1H), 2.00 (t, 2H, J=11.0 Hz), 1.66-1.60 (m, 2H), 1.58-1.54 (m, 2H). Ion Trap: m/z: 434.5 ([M+H]$^+$).

Example-28: N-((4(2-fluorophenyl)(pyridin-2-yl)methyl)-1-(2-phenoxyethyl)piperidine-4-carboxamide (28)

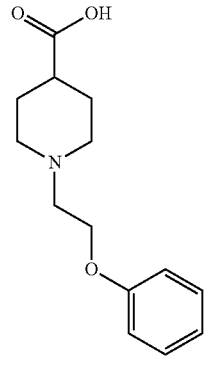 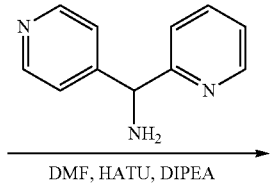

Int-III

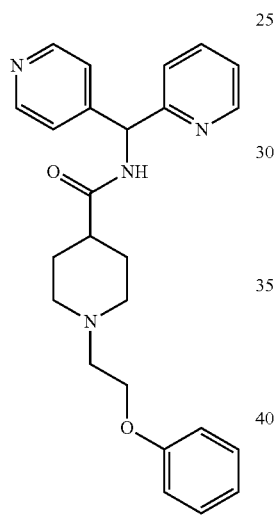

Title compound was prepared from coupling of 1-(2-phenoxyethyl)piperidine-4-carboxylic acid (Int-III) (0.202 g, 0.810 mmol, 1.5 equiv) and pyridin-2-yl(pyridin-4-yl)methanamine (0.100 g, 0.540 mmol, 1 equiv) using the conditions in step 5 in the general methodology of key Intermediate-I. The crude compound was purified by washing with pentane (4 times) to furnish 0.025 g of N-((2-fluorophenyl)(pyridin-2-yl)methyl)-1-(2-phenoxyethyl)piperidine-4-carboxamide as (Yield=11%). $^1$H NMR (500 MHz, DMSO-$d_6$): δ 8.78 (d, 1H, J=8.5 Hz), 8.52-8.47 (m, 3H), 7.80 (t, 1H, J=15.5 Hz), 7.49 (d, 1H, J=8.5 Hz), 7.31-7.25 (m, 5H), 6.93-6.89 (m, 3H), 6.15 (d, 1H, J=8.0 Hz), 4.04 (t, 2H, J=11.5 Hz), 2.94 (bs, 2H), 2.67-2.63 (m, 2H), 2.36 (bs, 1H), 2.02 (bs, 2H), 1.72-1.64 (m, 2H), 1.60-1.53 (m, 2H); ESI+MS: m/z: 417.4 ([M+H]$^+$).

Example-29: 1-(2-phenoxyethyl)-N-(pyridin-2-yl(pyridin-3-yl)methyl)piperidine-4-carboxamide (29)

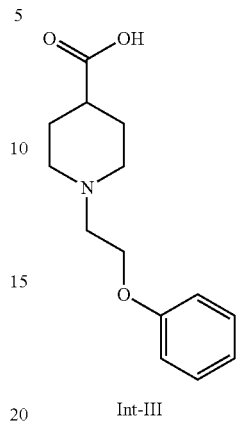 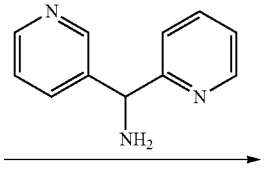

Int-III

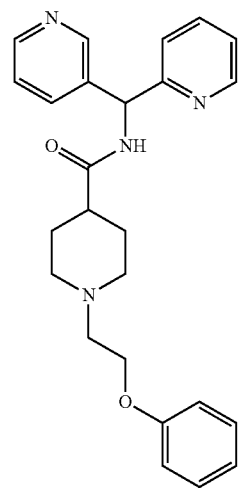

Title compound was prepared from coupling of 1-(2-phenoxyethyl)piperidine-4-carboxylic acid (Int-III) (0.202 g, 0.810 mmol, 1.5 equiv) and pyridin-2-yl(pyridin-3-yl)methanamine (0.100 g, 0.540 mmol, 1 equiv) using the conditions in step 5 in the general methodology of key Intermediate-I. The crude compound was purified by washing with pentane (4 times) to furnish 0.080 g of 1-(2-phenoxyethyl)-N-(pyridin-2-yl(pyridin-3-yl)methyl)piperidine-4-carboxamide (Yield=36%). $^1$H NMR (500 MHz, DMSO-$d_6$): δ 8.78 (d, 1H, J=8.0 Hz), 8.536-8.51 (m, 2H), 8.43-8.42 (m, 1H), 7.79 (t, 1H, J=15.0 Hz), 7.69 (d, 1H, J=8.0 Hz), 7.48 (d, 1H, J=8.0 Hz), 7.34-7.25 (m, 4H), 6.91 (t, 3H, J=16.5 Hz), 6.18 (d, 1H, J=8.0 Hz), 4.04 (t, 2H, J=11.5 Hz), 2.94 (d, 2H, J=11.5 Hz), 2.66-2.63 (m, 2H), 2.35-2.31 (m, 2H), 2.02 (t, 2H, J=12.0 Hz), 1.67 (d, 2H, J=12.5 Hz), 1.58-1.55 (m, 2H); ESI+MS: m/z: 417.4 ([M+H]$^+$).

147

Example-30: N-(di(pyridin-2-yl)methyl)-1-(2-phenoxyethyl)piperidine-4-carboxamide (30)

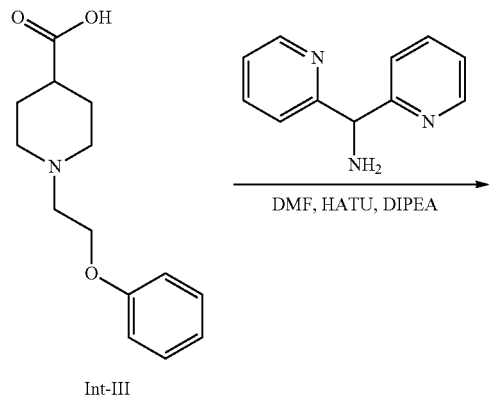

Int-III

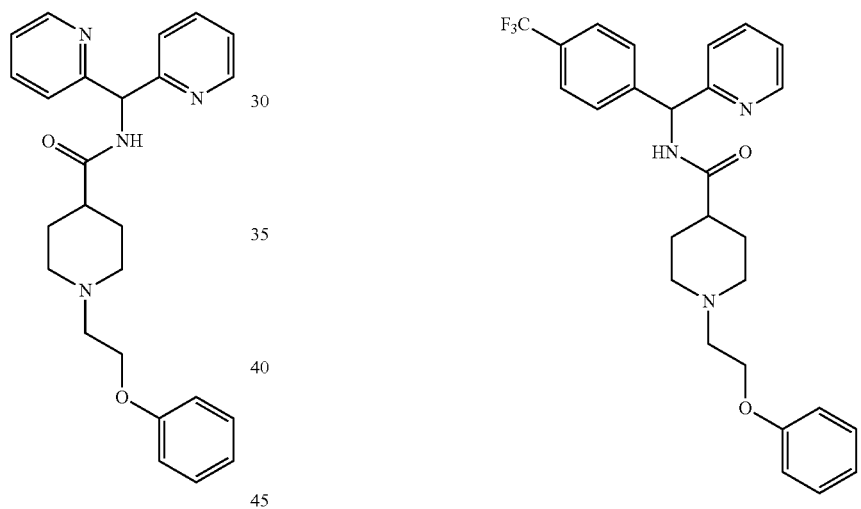

Title compound was prepared from coupling of 1-(2-phenoxyethyl)piperidine-4-carboxylic acid (Int-III) (0.202 g, 0.810 mmol, 1.5 equiv) and di(pyridin-2-yl)methanamine (0.100 g, 0.540 mmol, 1 equiv) using the conditions in step 5 in the general methodology of key Intermediate-I. The crude compound was purified by washing with pentane (4 times) to furnish 0.090 g of N-(di(pyridin-2-yl)methyl)-1-(2-phenoxyethyl)piperidine-4-carboxamide (Yield=40%). $^1$H NMR (500 MHz, DMSO-$d_6$): δ 8.69 (d, 1H, J=7.6 Hz), 8.47-8.46 (m, 2H), 7.77-7.73 (m, 2H), 7.45 (d, 2H, J=7.6 Hz), 7.29-7.23 (m, 4H), 6.92 (t, 3H, J=16.0 Hz), 6.17 (d, 1H, J=8.0 Hz), 4.06 (s, 2H), 2.95 (s, 2H), 2.73-2.67 (m, 2H), 2.41 (s, 1H), 2.03 (s, 2H), 1.69 (s, 2H), 1.580 (d, 2H, J=10.8 Hz); ESI+MS: m/z: 417.5 ([M+H]$^+$).

148

Example-31: 1-(2-phenoxyethyl)-N-(pyridin-2-yl(4-(trifluoromethyl)phenyl)methyl) piperidine-4-carboxamide (31)

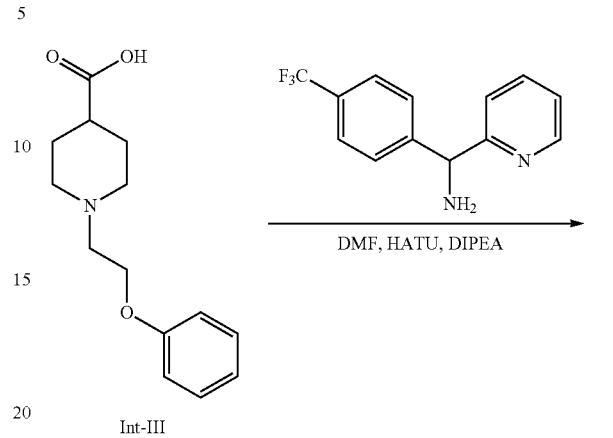

Int-III

Title compound was prepared from coupling of 1-(2-phenoxyethyl)piperidine-4-carboxylic acid III (0.166 g, 0.66 mmol, 1.2 equiv) and pyridin-2-yl(4-(trifluoromethyl) phenyl) methanamine (0.140 g, 0.55 mmol, 1 equiv) using the conditions in step 5 in the general methodology of key Intermediate-I. The crude compound was purified by HPLC to afford 0.030 g of 1-(2-phenoxyethyl)-N-(pyridin-2-yl(4-(trifluoromethyl)phenyl)methyl)piperidine-4-carboxamide (Yield=11%). $^1$H NMR (500 MHz, DMSO-$d_6$): δ 8.79 (d, 1H, J=8.0 Hz), 8.52 (d, 1H, J=4.0 Hz), 7.80 (t, 1H, J=7.5 Hz), 7.67 (d, 2H, J=8.0 Hz), 7.55-7.48 (m, 3H), 7.30-7.25 (m, 3H), 6.93-6.90 (m, 3H), 6.23 (d, 1H, J=7.5 Hz), 4.05 (t, 2H, J=6.0 Hz), 2.95 (d, 2H, J=10.0 Hz), 2.68-2.67 (m, 2H), 2.38-2.35 (m, 1H), 2.04-2.00 (m, 2H), 1.69-1.67 (m, 2H), 1.61-1.56 (m, 2H). ESI+MS: m/z: 484.3 ([M+H]$^+$).

Example-32: 1-(2-phenoxyethyl)-N-(pyridin-2-yl(3-(trifluoromethyl)phenyl)methyl) piperidine-4-carboxamide (32)

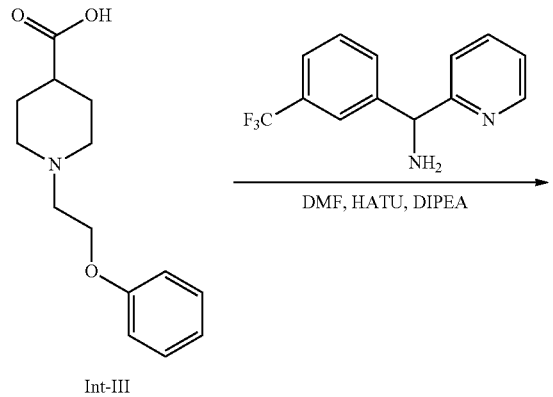

Example-33: 1-(2-phenoxyethyl)-N-(pyridin-2-yl(2-(trifluoromethyl)phenyl)methyl) piperidine-4-carboxamide (33)

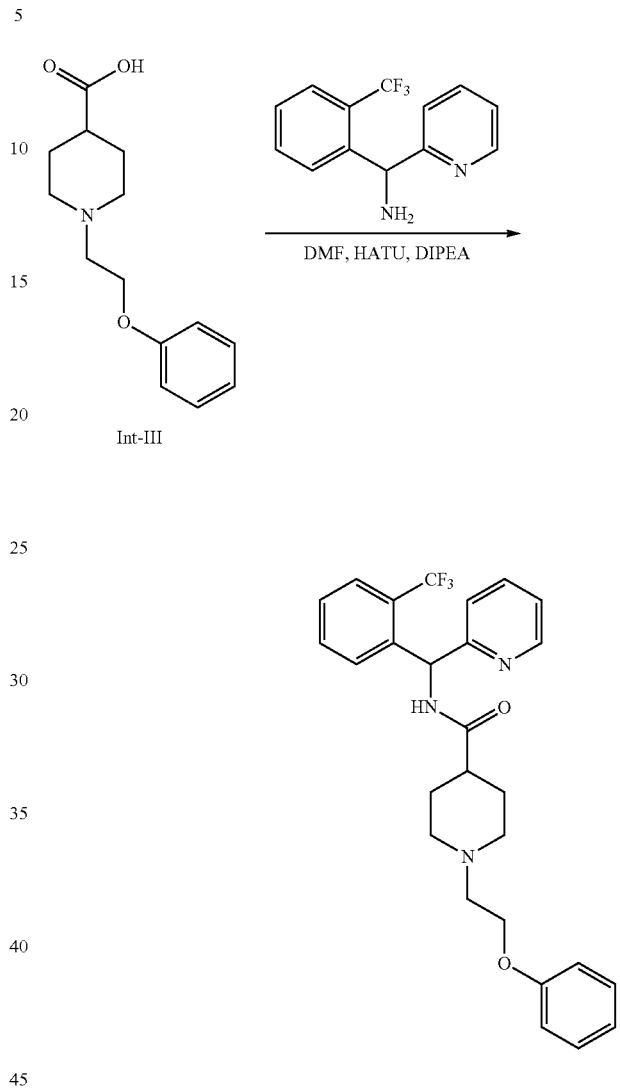

Title compound was prepared from coupling of 1-(2-phenoxyethyl)piperidine-4-carboxylic acid III (0.178 g, 0.714 mmol, 1.2 equiv) and pyridin-2-yl(3-(trifluoromethyl)phenyl) methanamine (0.150 g, 0.595 mmol, 1 equiv) using the conditions in step 5 in the general methodology of key Intermediate-I. The crude residue was purified by column chromatography (2% MeOH in DCM as eluent) to afford 0.040 g of 1-(2-phenoxyethyl)-N-(pyridin-2-yl(3-(trifluoromethyl)phenyl) methyl) piperidine-4-carboxamide (Yield=13%).

$^1$H NMR (500 MHz, DMSO-$d_6$): δ 8.81 (d, 1H, J=3.5 Hz), 8.52 (d, 1H, J=4.5 Hz), 7.81-7.79 (m, 1H), 7.69 (s, 1H), 7.65-7.50 (m, 4H), 7.30-7.25 (m, 3H), 6.93-6.90 (m, 3H), 6.25 (d, 1H, J=8.0 Hz), 4.05 (t, 2H, J=6.0 Hz), 2.95 (d, 2H, J=10.0 Hz), 2.68-2.63 (m, 2H), 2.38-2.34 (m, 1H), 2.02 (t, 2H, J=11.5 Hz), 1.67-1.64 (m, 2H), 1.58-1.56 (m, 2H). Ion Trap: m/z: 484.5 ([M+H]$^+$).

Title compound was prepared from coupling of 1-(2-phenoxyethyl)piperidine-4-carboxylic acid III (0.119 g, 0.476 mmol, 1.2 equiv) and pyridin-2-yl(2-(trifluoromethyl)phenyl) methanamine (0.100 g, 0.396 mmol, 1 equiv) using the conditions in step 5 in the general methodology of key Intermediate-I. The crude compound was purified by prep HPLC and afforded 0.025 g of 1-(2-phenoxyethyl)-N-(pyridin-2-yl(2-(trifluoromethyl)phenyl)methyl) piperidine-4-carboxamide (Yield=13%). $^1$H NMR (500 MHz, DMSO-$d_6$): δ 8.72 (d, 1H, J=5.0 Hz), 8.47 (d, 1H, J=4.5 Hz), 7.80-7.77 (m, 1H), 7.71 (d, 1H, J=7.5 Hz), 7.64 (t, 1H, J=7.5 Hz), 7.48 (d, 2H, J=6.5 Hz), 7.27 (t, 4H, J=8.5 Hz), 6.93-6.90 (m, 3H), 6.48 (d, 1H, J=7.5 Hz), 4.04 (t, 2H, J=6.0 Hz), 2.96-2.92 (m, 2H), 2.67-2.64 (m, 2H), 2.29-2.25 (m, 1H), 2.20-1.96 (m, 2H), 1.70-1.67 (m, 1H), 1.61-1.52 (m, 3H). ESI+MS: m/z: 484.3 ([M+H]$^+$).

Example-34: N-((4(4-methoxyphenyl)(pyridin-2-yl)methyl)-1-(2-phenoxyethyl)piperidine-4-carboxamide (34)

Example-35: N-((4(3-methoxyphenyl)(pyridin-2-yl)methyl)-1-(2-phenoxyethyl)piperidine-4-carboxamide (35)

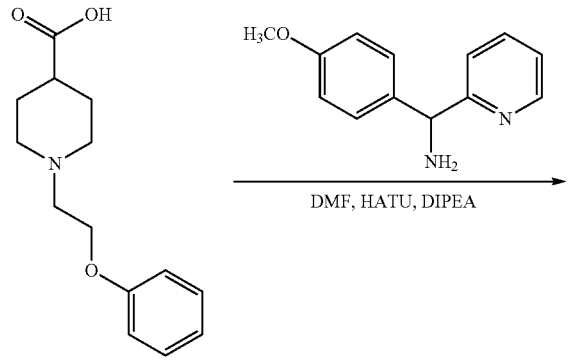

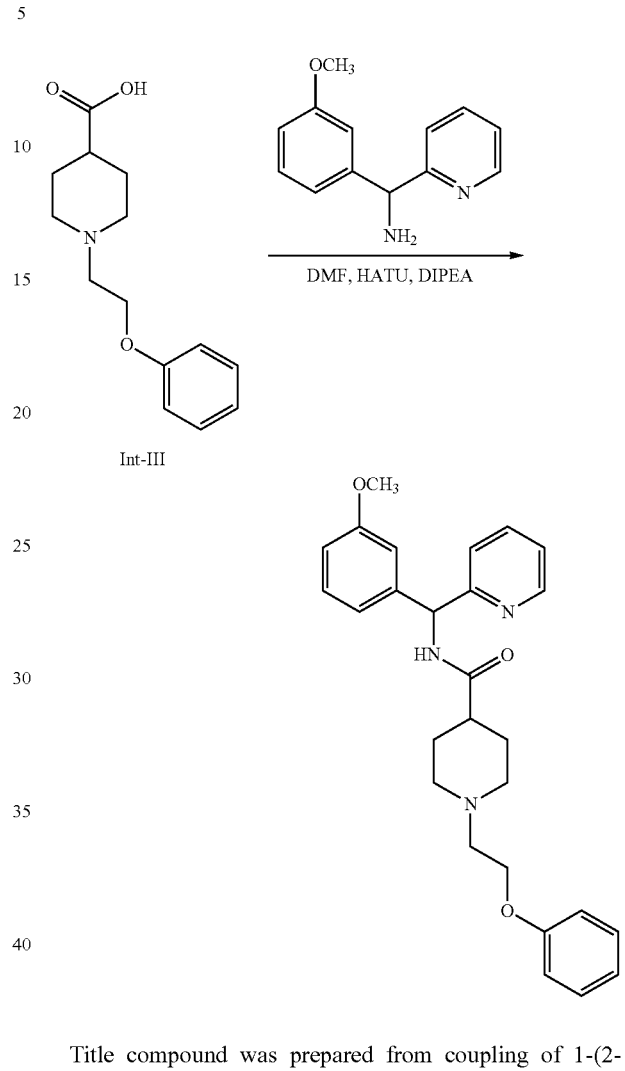

Title compound was prepared from coupling of 1-(2-phenoxyethyl)piperidine-4-carboxylic acid III (0.251 g, 1.008 mmol, 1.2 equiv) and (4-methoxyphenyl)(pyridin-2-yl)methanamine (0.180 g, 0.840 mmol, 1 equiv) using the conditions in step 5 in the general methodology of key Intermediate-I. The crude residue was purified by column chromatography (2% MeOH in DCM as elutant) to afford 0.050 g of N-((4(4-methoxyphenyl)(pyridin-2-yl)methyl)-1-(2-phenoxyethyl) piperidine-4-carboxamide (Yield=13%). $^1$H NMR (500 MHz, DMSO-d$_6$): δ 8.59 (d, 1H, J=8.5 Hz), 8.47 (d, 1H, J=3.5 Hz), 7.76-7.71 (m, 1H), 7.39 (d, 1H, J=8.0 Hz), 7.27-7.18 (m, 5H), 6.91 (d, 3H, J=8.0 Hz), 6.83 (d, 2H, J=8.0 Hz), 6.04 (d, 1H, J=8.5 Hz), 4.06-4.03 (m, 2H), 3.69 (s, 3H), 2.97-2.93 (m, 2H), 2.68-2.59 (m, 1H), 2.00-1.97 (m, 4H), 1.64-1.56 (m, 4H); ESI+MS: m/z: 446.6 ([M+H]$^+$).

Figure 7:
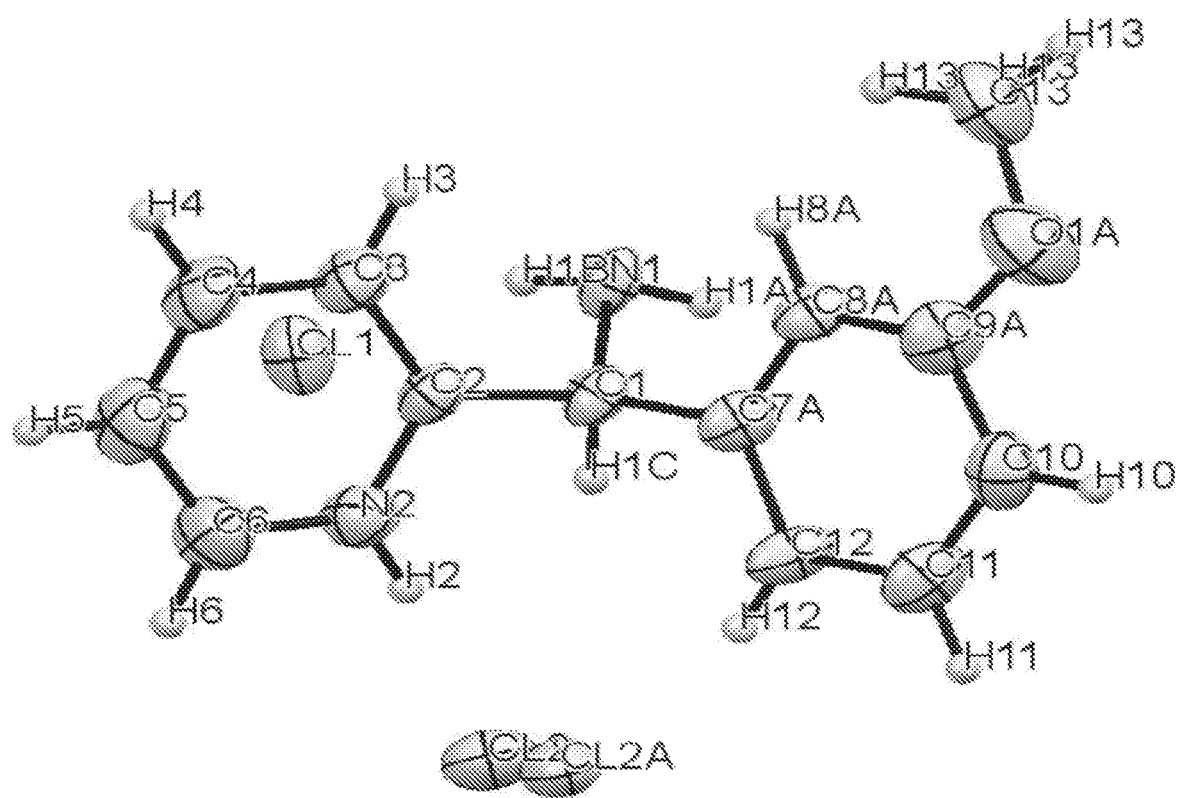
FIG. 7 is an ortep representation of an X-ray crystal structure of (S)-(3-methoxyphenyl)(pyridin-2-yl)methanamine hydrochloride.

Title compound was prepared from coupling of 1-(2-phenoxyethyl)piperidine-4-carboxylic acid III (0.227 g, 0.910 mmol, 1.5 equiv) and (3-methoxyphenyl)(pyridin-2-yl)methanamine (0.130 g, 0.607 mmol, 1 equiv) using the conditions in step 5 in the general methodology of key Intermediate-I. The crude residue was purified by washing with pentane to furnish 0.060 g of N-((3-methoxyphenyl)(pyridin-2-yl)methyl)-1-(2-phenoxyethyl)piperidine-4-carboxamide (Yield=22%). $^1$H NMR (500 MHz, DMSO-d$_6$): δ 8.64 (d, 1H, J=8.5 Hz), 8.49 (d, 1H, J=4.5 Hz), 7.75 (t, 1H, J=8.0 Hz), 7.43 (d, 1H, J=8.0 Hz), 7.27-7.17 (m, 4H), 6.91-6.85 (m, 5H), 6.77 (d, 1H, J=7.5 Hz), 6.08 (d, 1H, J=8.5 Hz), 4.04 (t, 2H, J=5.5 Hz), 3.69 (s, 3H), 2.94 (d, 2H, J=9.5 Hz), 2.65-2.62 (m, 2H), 2.34-2.31 (m, 1H), 2.02 (t, 2H, J=11 Hz), 1.68-1.59 (m, 2H), 1.59-1.54 (m, 2H); ESI+MS: m/z: 446.3 ([M+H]$^+$). Enantiomers of 35 were separated using chiral HPLC (method J) and afforded pure enantiomers 35a and 35b. The absolute configuration of 35b was confirmed to be (S) through crystallization of (S)-(3-methoxyphenyl)(pyridin-2-yl)methanamine hydrochloride (see ortep representation on FIG. 7).

153

Example-36: N((2-methoxyphenyl)(pyridin-2-yl)methyl)-1-(2-phenoxyethyl) piperidine-4-carboxamide (36)

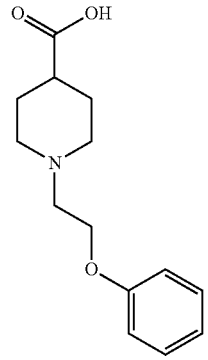 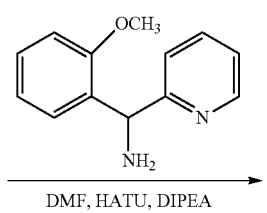

154

Example-37: N-(cyclohexyl(pyridin-2-yl)methyl)-1-(2-phenoxyethyl)piperidine-4-carboxamide (37)

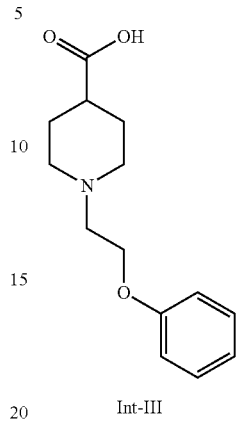 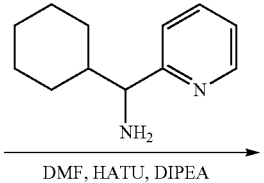

Int-III

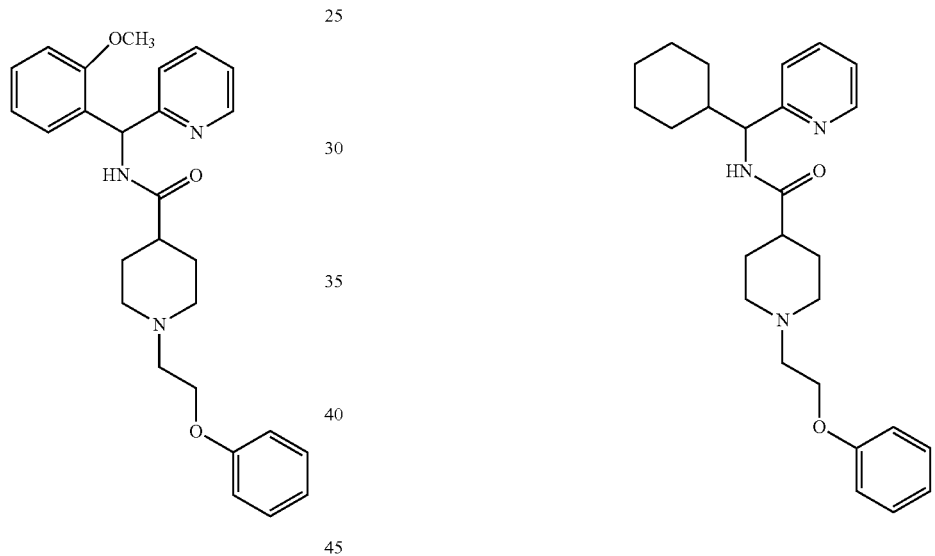

Title compound was prepared from coupling of 1-(2-phenoxyethyl)piperidine-4-carboxylic acid III (0.251 g, 1.008 mmol, 1.2 equiv) and (2-methoxyphenyl)(pyridin-2-yl)methanamine (0.180 g, 0.840 mmol, 1 equiv) using the conditions in step 5 in the general methodology of key Intermediate-I. The crude residue was purified by column chromatography (2% MeOH in DCM as eluent) afforded 0.050 g N-((2-methoxyphenyl)(pyridin-2-yl)methyl)-1-(2-phenoxyethyl) piperidine-4-carboxamide (Yield=13%). $^{1}$H NMR (500 MHz, DMSO-$d_6$): δ 8.51 (d, 1H, J=8.0 Hz), 8.44 (d, 1H, J=5.0 Hz), 7.73-7.69 (m, 1H), 7.28-7.19 (m, 6H), 6.95-6.87 (m, 5H), 6.40 (d, 1H, J=8.0 Hz), 4.03-4.00 (m, 2H), 3.73 (s, 3H), 2.95-2.91 (m, 2H), 2.69-2.63 (m, 2H), 2.35-2.31 (m, 1H), 1.99-1.95 (m, 2H), 1.64-1.62 (m, 2H), 1.56-1.52 (m, 2H); ESI+MS: m/z: 446.5 ([M+H]$^{+}$).

Title compound was prepared from coupling of 1-(2-phenoxyethyl)piperidine-4-carboxylic acid III (0.283 g, 1.13 mmol, 1.2 equiv) and cyclohexyl(pyridin-2-yl)methanamine (0.180 g, 0.946 mmol, 1 equiv) using the conditions in step 5 in the general methodology of key Intermediate-I. The crude residue was purified by column chromatography (2% MeOH in DCM as eluent) and afforded 0.030 g of N-(cyclohexyl(pyridin-2-yl)methyl)-1-(2-phenoxyethyl)piperidine-4-carboxamide (Yield=7%). $^{1}$H NMR (500 MHz, DMSO-$d_6$): δ 8.51 (d, 1H, J=8.0 Hz), 8.44 (d, 1H, J=5.0 Hz), 7.73-7.69 (m, 1H), 7.28-7.19 (m, 4H), 6.95-6.87 (m, 3H), 4.69 (t, 1H, J=17.0 Hz), 4.04 (t, 2H, J=12.0 Hz), 2.96-2.90 (m, 2H), 2.67-2.50 (m, 2H), 2.30-2.22 (m, 1H), 2.04-1.97 (m, 2H), 1.78-1.76 (m, 1H), 1.66 (bs, 3H), 1.60-1.48 (m, 4H), 1.23-1.09 (m, 2H), 1.09 (bs, 3H), 1.00-0.89 (m, 2H); ESI+MS: m/z: 446.5 ([M+H]$^{+}$).

155

Example-38: N-(2-methyl-1-(pyridin-2-yl)propyl)-1-(2-phenoxyethyl)piperidine-4-carboxamide (38)

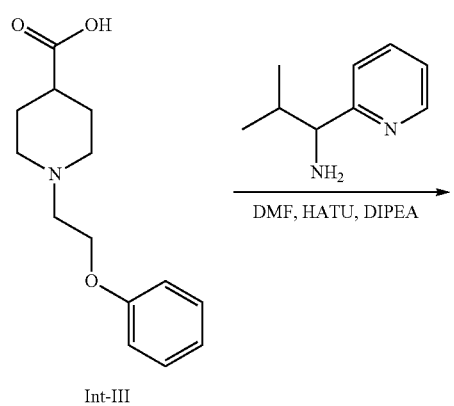

156

Example-39: N-((4(4-chlorophenyl)(phenyl)methyl)-1-(2-phenoxyethyl)piperidine-4-carboxamide (39)

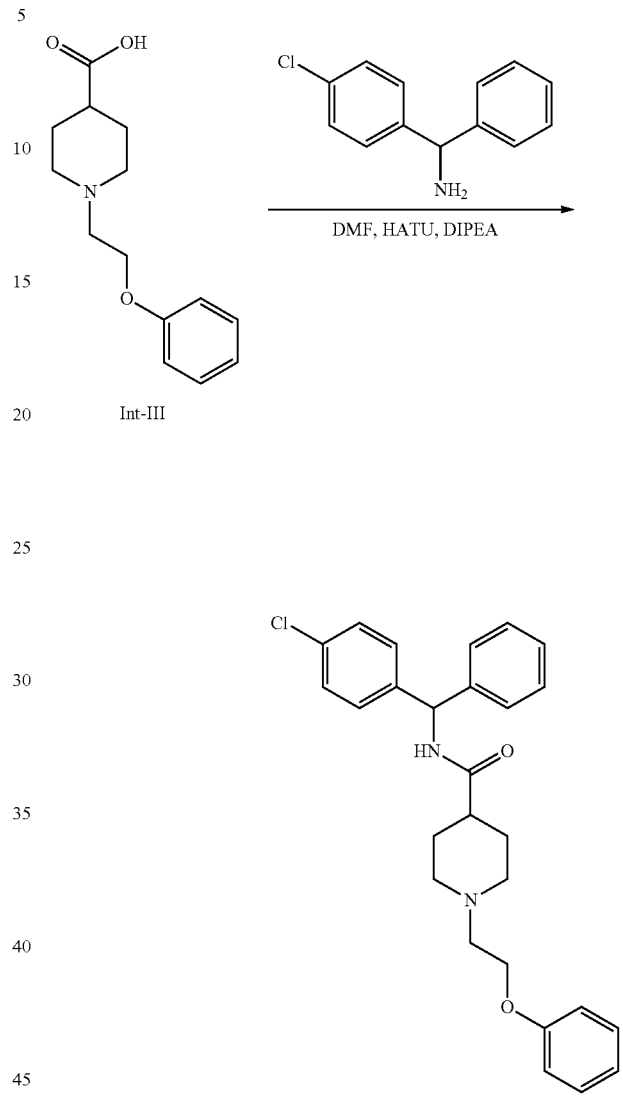

Title compound was prepared from coupling of 1-(2-phenoxyethyl)piperidine-4-carboxylic acid III (0.199 g, 0.799 mmol, 1.2 equiv) and 2-methyl-1-(pyridin-2-yl)propan-1-amine (0.100 g, 0.666 mmol, 1 equiv) using the conditions in step 5 in the general methodology of key Intermediate-I. The crude compound was purified by column chromatography (2% MeOH in DCM as elutant) afforded 0.050 g of N-(2-methyl-1-(pyridin-2-yl)propyl)-1-(2-phenoxyethyl) piperidine-4-carboxamide (Yield=20%). $^1$H NMR (500 MHz, DMSO-$d_6$): δ 8.50 (d, 1H, J=4.0 Hz), 8.02 (d, 1H, J=9.0 Hz), 7.74-7.71 (m, 1H), 7.30-7.22 (m, 4H), 6.93-6.90 (m, 3H), 4.69 (t, 1H, J=8.0 Hz), 4.04 (t, 2H, J=6.0 Hz), 2.96 2.91 (m, 2H), 2.67-2.65 (m, 2H), 2.29-2.25 (m, 1H), 2.15-2.10 (m, 1H), 2.05-1.98 (m, 2H), 1.70-1.67 (m, 1H), 1.62-1.50 (m, 3H), 0.83 (d, 3H, J=6.0 Hz), 0.72 (d, 3H, J=7.0 Hz). Ion trap: m/z: 382.4 ([M+H]$^+$).

Title compound was prepared from coupling of 1-(2-phenoxyethyl)piperidine-4-carboxylic acid III (0.275 g, 1.10 mmol, 1.2 equiv) and (4-chlorophenyl)(phenyl)methanamine (0.200 g, 0.919 mmol, 1 equiv) using the conditions in step 5 in the general methodology of key Intermediate-I. The crude residue was purified by column chromatography (2% MeOH in DCM as eluent) furnished 0.060 g of N-((4-chlorophenyl)(phenyl)methyl)-1-(2-phenoxyethyl)piperidine-4-carboxamide (Yield=14%). $^1$H NMR (500 MHz, DMSO-$d_6$): δ 8.67 (d, 1H, J=8.5 Hz), 7.37 (d, 2H, J=8.5 Hz), 7.33-7.22 (m, 9H), 6.92-6.89 (m, 3H), 6.09 (d, 1H, J=8.0 Hz), 4.10-4.04 (m, 2H), 2.96-2.95 (m, 2H), 2.67-2.63 (m, 2H), 2.28-2.26 (m, 1H), 2.04-2.01 (m, 2H), 1.66-1.58 (m, 4H); ESI+MS: m/z: 449.5 ([M+H]$^+$).

Example-40: N((4-chlorophenyl)(2-fluorophenyl)methyl)-1-(2-phenoxyethyl) piperidine-4-carboxamide (40)

Example-41: N-((4(4-chlorophenyl)(3-fluorophenyl)methyl)-1-(2-phenoxyethyl)piperidine-4-carboxamide (41)

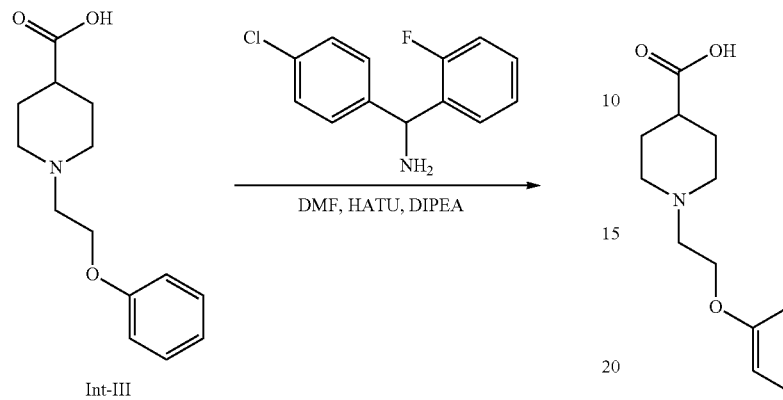

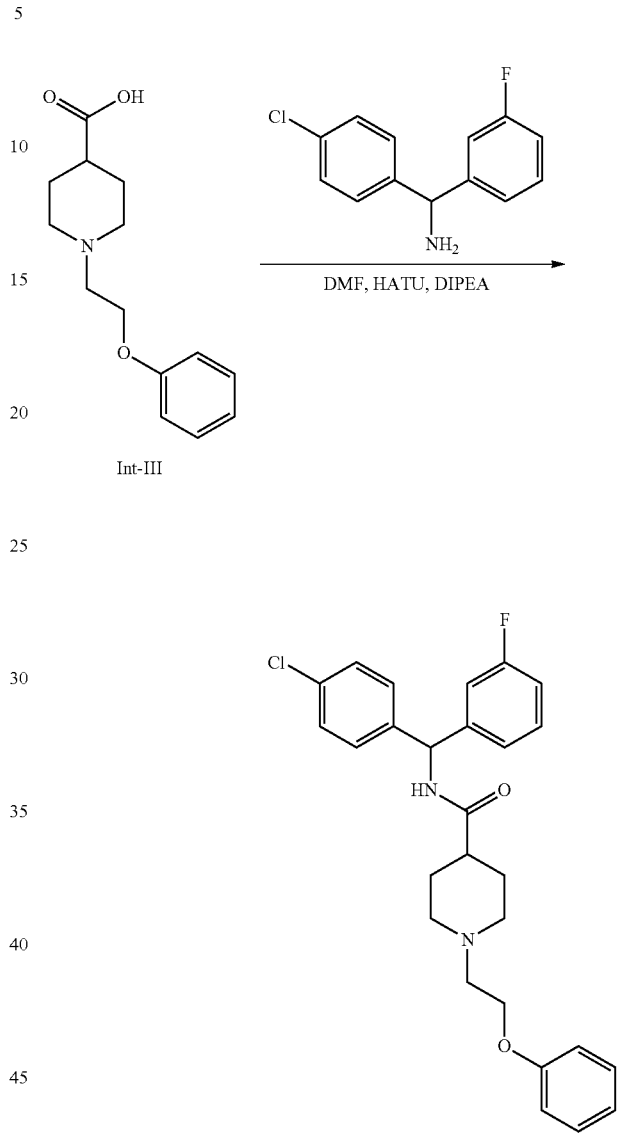

Title compound was prepared from coupling of 1-(2-phenoxyethyl)piperidine-4-carboxylic acid III (0.076 g, 0.305 mmol, 1.2 equiv) and (4-chlorophenyl)(2-fluorophenyl)methanamine (0.060 g, 0.255 mmol, 1 equiv) using the conditions in step 5 in the general methodology of key Intermediate-I. The crude residue was purified by prep HPLC afforded 0.030 g of N-((4-chlorophenyl)(2-fluorophenyl)methyl)-1-(2-phenoxyethyl)piperidine-4-carboxamide (Yield=24%). $^1$H NMR (500 MHz, DMSO-$d_6$): δ 8.72 (d, 1H, J=8.5 Hz), 7.41-7.32 (m, 4H), 7.29-7.16 (m, 6H), 6.93-6.90 (m, 3H), 6.33 (d, 1H, J=8.0 Hz), 4.06 (t, 2H, J=5.5 Hz), 2.97-2.95 (m, 2H), 2.68-2.64 (m, 2H), 2.29-2.27 (m, 1H), 2.05-2.02 (m, 2H), 1.68-1.57 (m, 4H); ESI+MS: m/z: 467.5 ([M+H]$^+$). Enantiomers of 40 were separated using chiral HPLC (method K) and afforded pure enantiomers 40a and 40b.

Title compound was prepared from coupling of 1-(2-phenoxyethyl)piperidine-4-carboxylic acid III (0.178 g, 0.713 mmol, 1.2 equiv) and (4-chlorophenyl)(3-fluorophenyl)methanamine (0.140 g, 0.594 mmol, 1 equiv) using the conditions in step 5 in the general methodology of key Intermediate-I. The crude residue was purified by prep HPLC furnished 0.030 g of N-((4-chlorophenyl)(3-fluorophenyl)methyl)-1-(2-phenoxyethyl)piperidine-4-carboxamide (Yield=11%). $^1$H NMR (400 MHz, CD$_3$OD): δ 7.35-7.33 (m, 3H), 7.29-7.21 (m, 4H), 7.05 (d, 1H, J=6.4 Hz), 7.02-6.93 (m, 5H), 6.17 (s, 1H), 4.19 (t, 2H, J=4.8 Hz), 3.31-3.34 (m, 2H), 3.08-3.05 (m, 2H), 2.53-2.46 (m, 3H), 1.92-1.90 (m, 4H); ESI+MS: m/z: 467.3 ([M+H]$^+$).

159

Example-42: N-((4(4-chlorophenyl)(4-fluorophenyl)methyl)-1-(2-phenoxyethyl)piperidine-4-carboxamide (42)

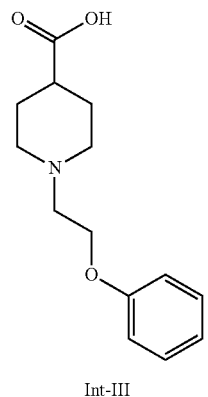
Int-III

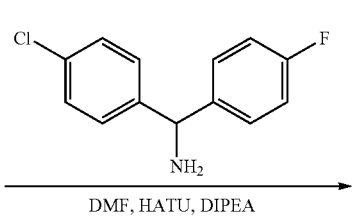
DMF, HATU, DIPEA

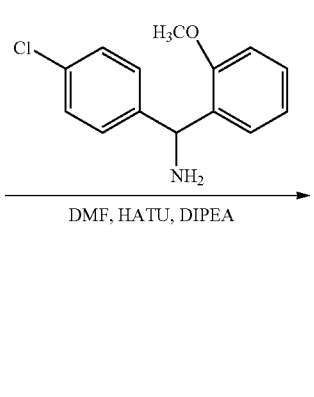

Title compound was prepared from coupling of 1-(2-phenoxyethyl)piperidine-4-carboxylic acid III (0.152 g, 0.611 mmol, 1.2 equiv) and (4-chlorophenyl)(4-fluorophenyl)methanamine (0.120 g, 0.509 mmol, 1 equiv) using the conditions in step 5 in the general methodology of key Intermediate-I. The crude residue was purified by column chromatography eluting with 2% MeOH in DCM as elutant affording 0.035 g N-((4-chlorophenyl) (4-fluorophenyl)methyl)-1-(2-phenoxyethyl)piperidine-4-carboxamide (Yield=15%). $^1$H NMR (400 MHz, CD$_3$OD): δ 7.36-7.32 (m, 2H), 7.28-7.21 (m, 6H), 7.09-7.05 (m, 2H), 6.94-6.90 (m, 3H), 6.16 (s, 1H), 4.13 (t, 2H, J=5.6 Hz), 3.12 (d, 2H, J=11.6 Hz), 2.83 (t, 2H, J=5.6 Hz), 2.38-2.36 (m, 1H), 2.28-2.21 (m, 2H), 1.92-1.82 (m, 4H). ESI+MS: m/z: 467.2 ([M+H]$^+$). Enantiomers of 42 were separated using chiral HPLC (method K) and afforded pure enantiomers 42a and 42b.

160

Example-43: N-((4(4-chlorophenyl)(2-methoxyphenyl)methyl)-1-(2-phenoxyethyl)piperidine-4-carboxamide (43)

Title compound was prepared from coupling of 1-(2-phenoxyethyl)piperidine-4-carboxylic acid III (0.145 g, 0.581 mmol, 1.2 equiv) and (4-chlorophenyl)(2-methoxyphenyl) methanamine (0.120 g, 0.484 mmol, 1 equiv) using the conditions in step 5 in the general methodology of key Intermediate-I. The crude residue was purified by column chromatography (2% MeOH in DCM as eluent) furnished 0.080 g of N-((4-chlorophenyl)(2-methoxyphenyl)methyl)-1-(2-phenoxyethyl)piperidine-4-carboxamide (Yield=34%). $^1$H NMR (500 MHz, CD$_3$OD): δ 7.33-7.29 (m, 5H), 7.18 (d, 3H, J=8.0 Hz), 7.01-6.93 (m, 5H), 6.43 (s, 1H), 4.32 (t, 2H, J=5.0 Hz), 3.78 (s, 3H), 3.62-3.58 (m, 2H), 3.46-3.44 (m, 2H), 3.02-3.00 (m, 2H), 2.68-2.64 (m, 1H), 2.03 (d, 4H, J=16.5 Hz). ESI+MS: m/z: 479.2 ([M+H]$^+$).

Example-44: N-((4(4-chlorophenyl)(4-methoxyphenyl)methyl)-1-(2-phenoxyethyl)piperidine-4-carboxamide (44)

Example-45: N-((4(4-fluorophenyl)(phenyl)methyl)-1-(2-phenoxyethyl)piperidine-4-carboxamide (45)

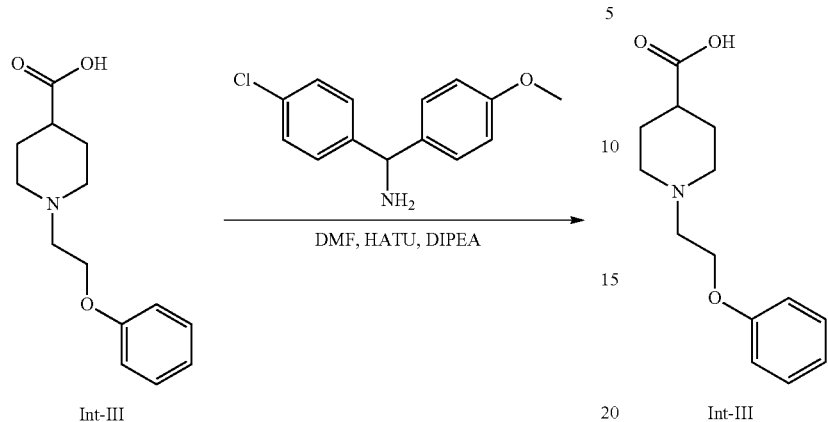
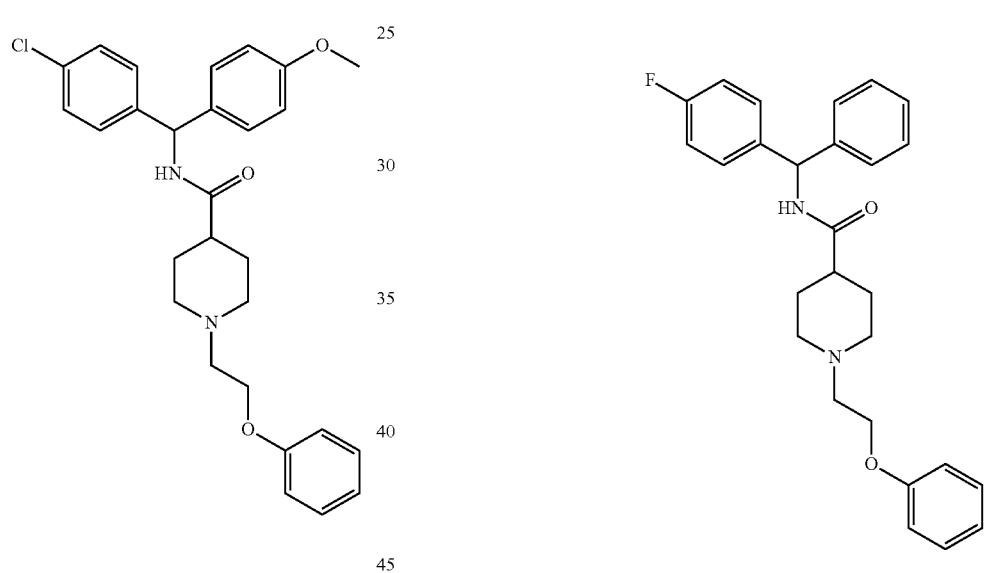

Title compound was prepared from coupling of 1-(2-phenoxyethyl)piperidine-4-carboxylic acid III (0.121 g, 0.484 mmol, 1.2 equiv) and (4-chlorophenyl)(4-methoxyphenyl)methanamine (0.100 g, 0.404 mmol, 1 equiv) using the conditions in step 5 in the general methodology of key Intermediate-I. The crude residue was purified by column chromatography eluting with (2% MeOH in DCM as eluent) afforded 0.056 g of N-((4-chlorophenyl)(4-methoxyphenyl)methyl)-1-(2-phenoxyethyl)piperidine-4-carboxamide (Yield=29%). $^1$H NMR (400 MHz, CD$_3$OD): δ 7.33-7.26 (m, 4H), 7.21 (d, 2H, J=8.4 Hz), 7.13 (d, 2H, J=8.8 Hz), 6.96-6.93 (m, 3H), 6.88 (d, 2H, J=8.4 Hz), 6.09 (s, 1H), 4.21 (t, 2H, J=5.6 Hz), 3.80 (s, 3H), 3.35-3.34 (m, 2H), 3.12-3.11 (m, 2H), 2.60-2.59 (m, 2H), 2.50-2.46 (m, 1H), 1.93-1.91 (m, 4H); ESI+MS: m/z: 479.3 ([M+H]$^+$).

Title compound was prepared from coupling of 1-(2-phenoxyethyl)piperidine-4-carboxylic acid III (0.223 g, 0.894 mmol, 1.2 equiv) and (4-fluorophenyl)(phenyl)methanamine (0.150 g, 0.745 mmol, 1 equiv) using the conditions in step 5 in the general methodology of key Intermediate-I. The crude compound was purified by prep. HPLC column chromatography to furnish 0.060 g of N-((4-fluorophenyl)(phenyl)methyl)-1-(2-phenoxyethyl)piperidine-4-carboxamide (Yield=19%). $^1$H NMR (400 MHz, CD$_3$OD): δ 7.34-7.31 (m, 2H), 7.28-7.22 (m, 7H), 7.04 (t, 2H, J=10.0 Hz), 6.93-6.91 (m, 3H), 6.16 (s, 1H), 4.15 (t, 2H, J=5.6 Hz), 3.17 (d, 2H, J=11.6 Hz), 2.93-2.91 (m, 2H), 2.41-2.35 (m, 3H), 1.89-1.83 (m, 4H); ESI+MS: m/z: 433.2 ([M+H]$^+$). Enantiomers of 45 were separated using chiral HPLC (method H) and afforded pure enantiomers 45a and 45b.

Example-46: N-((4(3-methoxyphenyl)(phenyl)methyl)-1-(2-phenoxyethyl)piperidine-4-carboxamide (46)

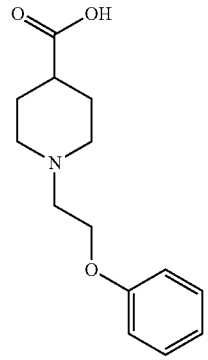
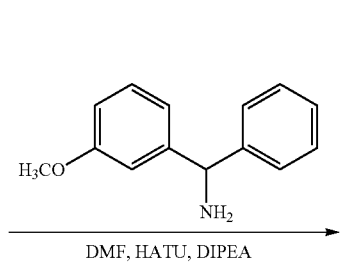

Int-III

Example-47: N-(bis(4-fluorophenyl)methyl)-1-(2-phenoxyethyl)piperidine-4-carboxamide (47)

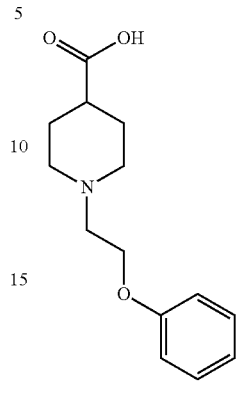
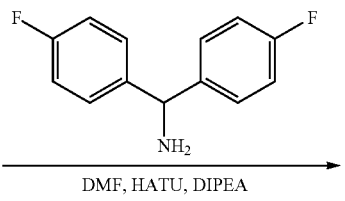

Int-III

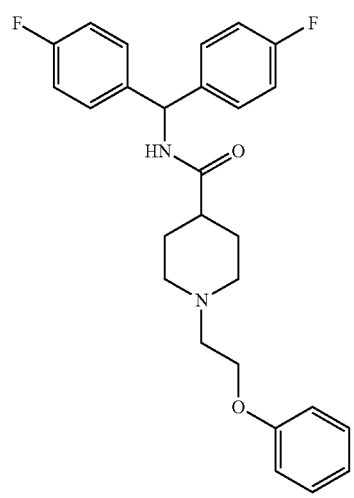

Title compound was prepared from coupling of 1-(2-phenoxyethyl)piperidine-4-carboxylic acid III (0.210 g, 0.844 mmol, 1.2 equiv) and (4-fluorophenyl)(phenyl)methanamine (0.150 g, 0.703 mmol, 1 equiv) using the conditions in step 5 in the general methodology of key Intermediate-I. The crude residue was purified by silica gel column chromatography (2% MeOH in DCM as elutant) afforded 0.035 g of N-((3-methoxyphenyl)(phenyl)methyl)-1-(2-phenoxyethyl) piperidine-4-carboxamide. (Yield=11%). $^1$H NMR (400 MHz, CD$_3$OD): δ 7.33-7.30 (m, 2H), 7.28-7.21 (m, 6H), 6.93-6.90 (m, 3H), 6.83-6.80 (m, 3H), 6.13 (s, 1H), 4.14 (t, 2H, J=5.6 Hz), 3.74 (s, 3H), 3.15 (d, 2H, J=12.0 Hz), 2.88 (t, 2H, J=5.2 Hz), 2.45-2.37 (m, 1H), 2.34-2.28 (m, 2H), 1.92-1.84 (m, 4H); ESI+MS: m/z: 445.3 ([M+H]$^+$).

Title compound was prepared from coupling of 1-(2-phenoxyethyl)piperidine-4-carboxylic acid III (0.205 g, 0.821 mmol, 1.2 equiv) and bis(4-fluorophenyl)methanamine (0.150 g, 0.684 mmol, 1 equiv) using the conditions in step 5 in the general methodology of key Intermediate-I. The crude compound was purified by prep HPLC purification to furnish 0.010 g of N-(bis(4-fluorophenyl)methyl)-1-(2-phenoxyethyl)piperidine-4-carboxamide (Yield=4%). $^1$H NMR (400 MHz, CD$_3$OD): δ 7.30-7.24 (m, 6H), 7.10-7.06 (m, 4H), 6.95-6.92 (m, 3H), 6.19 (s, 1H), 4.14 (t, 2H, J=5.6 Hz), 3.13 (d, 2H, J=11.6 Hz), 2.85 (t, 2H, J=5.2 Hz), 2.41-2.35 (m, 1H), 2.25 (dt, 2H, J$_{1,2}$=4.4 Hz, J$_{1,4}$=14.8 Hz), 1.92-1.82 (m, 4H); Ion trap: m/z: 451.4 ([M+H]$^+$).

Example-48: N-(bis(2-fluorophenyl)methyl)-1-(2-phenoxyethyl)piperidine-4-carboxamide (48)

Example-49: N-((2-fluorophenyl)(4-fluorophenyl)methyl)-1-(2-phenoxyethyl)piperidine-4-carboxamide (49)

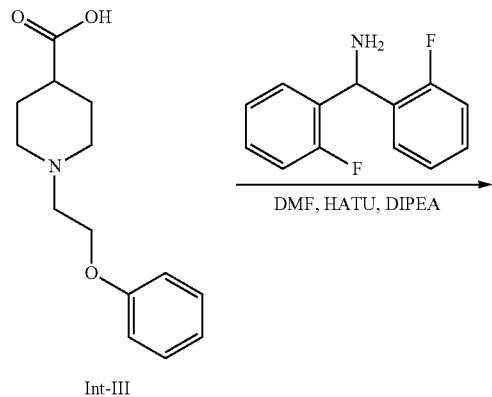
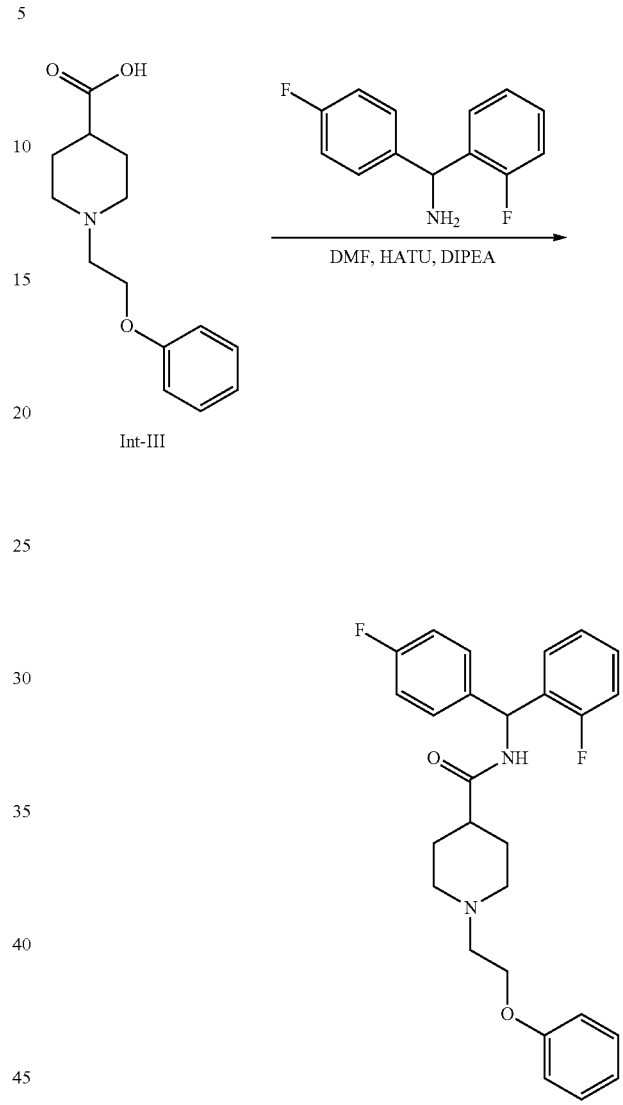

Title compound was prepared from coupling of 1-(2-phenoxyethyl)piperidine-4-carboxylic acid III (0.171 g, 0.684 mmol, 1.2 equiv) and bis(2-fluorophenyl)methanamine (0.125 g, 0.570 mmol, 1 equiv) using the conditions in step 5 in the general methodology of key Intermediate-I. The crude residue was purified by column chromatography (5% MeOH in DCM as eluent) furnished N-(bis(2-fluorophenyl)methyl)-1-(2-phenoxyethyl)piperidine-4-carboxamide 0.025 g (Yield=9%). $^1$H NMR (400 MHz, CD$_3$OD): δ 7.35-7.28 (m, 4H), 7.24-7.09 (m, 6H), 6.99-6.96 (m, 3H), 6.67 (s, 1H), 4.26 (t, 2H, J=5.2 Hz), 3.44 (d, 2H, J=12.0 Hz), 3.26-3.25 (m, 2H), 2.82-2.77 (m, 2H), 2.60-2.52 (m, 1H), 1.99-1.93 (m, 4H); ESI+MS: m/z: m/z: 451.5 ([M+H]$^+$).

Title compound was prepared from coupling of 1-(2-phenoxyethyl)piperidine-4-carboxylic acid III (0.205 g, 0.821 mmol, 1.2 equiv) and (2-fluorophenyl)(4-fluorophenyl)methanamine 4 (0.150 g, 0.684 mmol, 1 equiv) using the conditions in step 5 in the general methodology of key Intermediate-I. The crude residue was purified by column chromatography (2% MeOH in DCM as eluent) afforded 0.040 g N-((2-fluorophenyl)(4-fluorophenyl)methyl)-1-(2-phenoxyethyl)piperidine-4-carboxamide (Yield=13%). $^1$H NMR (400 MHz, CD$_3$OD): δ 7.35-7.16 (m, 6H), 7.13-6.99 (m, 7H), 6.41 (s, 1H), 4.35 (t, 2H, J=4.8 Hz), 3.68-3.66 (m, 2H), 3.57 (t, 2H, J=4.8 Hz), 3.13-3.11 (m, 2H), 2.69-2.67 (m, 1H), 2.09-2.03 (m, 4H); ESI+MS: m/z 451.5 ([M+H]$^+$).

Example-50: N-((4(2-fluorophenyl)(3-methoxyphenyl)methyl)-1-(2-phenoxyethyl)piperidine-4-carboxamide (50)

Example-51: N((4-chlorophenyl)(pyridin-2-yl)methyl)-N-methyl-1-(2-phenoxyethyl) piperidine-4-carboxamide (51)

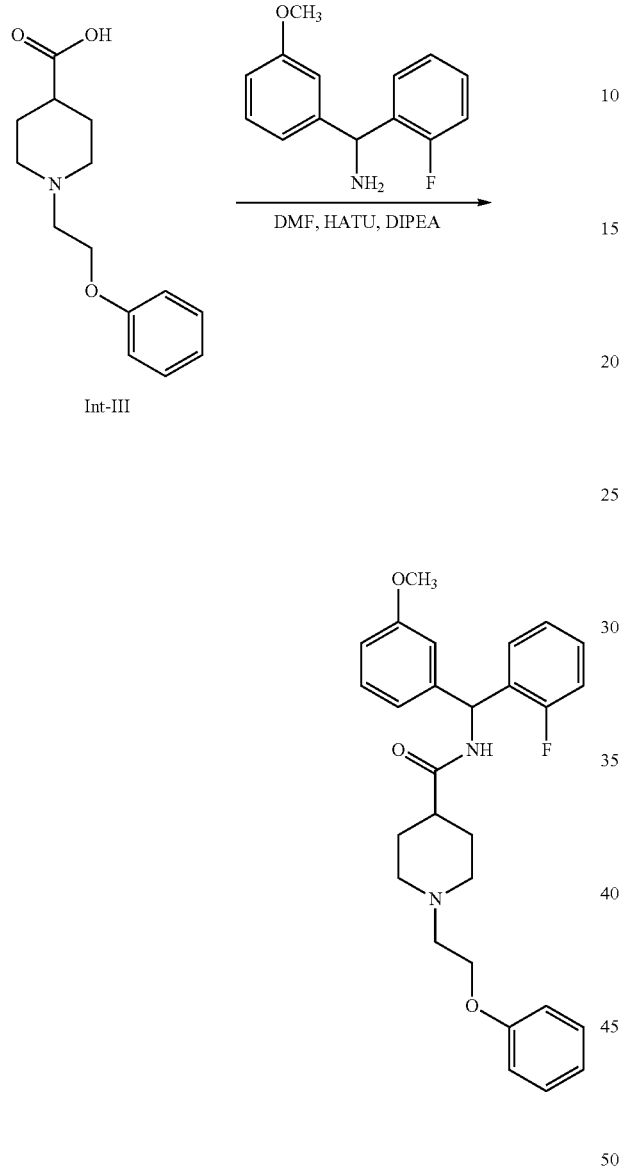

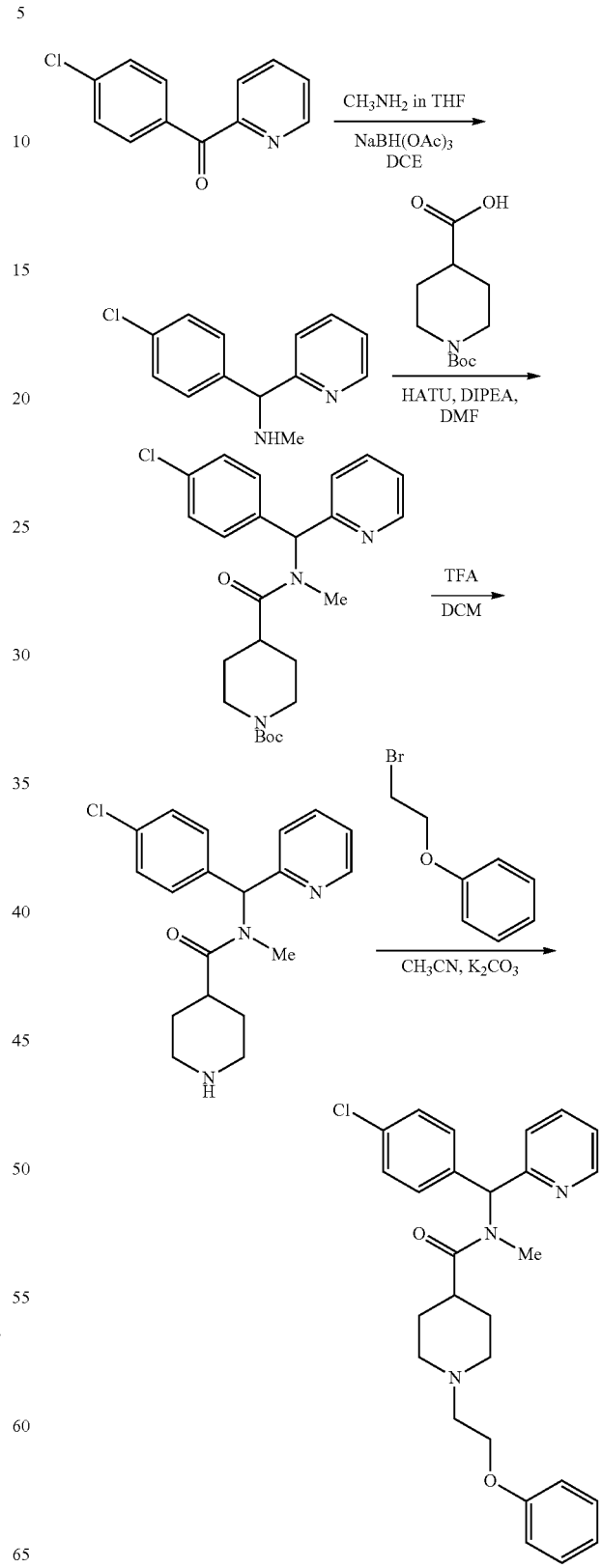

Title compound was prepared from coupling of 1-(2-phenoxyethyl)piperidine-4-carboxylic acid III (0.194 g, 0.778 mmol, 1.2 equiv) and (2-fluorophenyl)(3-methoxyphenyl) methanamine 4 (0.150 g, 0.649 mmol, 1 equiv) using the conditions in step 5 in the general methodology of key Intermediate-I. The crude compound was purified by column chromatography (2% MeOH in DCM as eluent) afforded 0.080 g of N-((2-fluorophenyl)(3-methoxy phenyl) methyl)-1-(2-phenoxyethyl)piperidine-4-carboxamide (Yield=26%). $^1$H NMR (400 MHz, CD$_3$OD): δ 7.34-7.21 (m, 5H), 7.17-7.06 (m, 2H), 6.92-6.89 (m, 3H), 6.84-6.81 (m, 1H), 6.81-6.77 (m, 2H), 6.40 (s, 1H), 4.11 (t, 2H, J=5.6 Hz), 3.74 (s, 3H), 3.13-3.07 (m, 2H), 2.81 (t, 2H, J=5.6 Hz), 2.42-2.34 (m, 1H), 2.26-2.19 (m, 2H), 1.90-1.78 (m, 4H); ESI+MS: m/z: 463.6 ([M+H]$^+$).

169
1-(4-chlorophenyl)-N-methyl-1-(pyridin-2-yl)methanamine

170
N-((4-chlorophenyl)(pyridin-2-yl)methyl)-N-methyl-piperidine-4-carboxamide

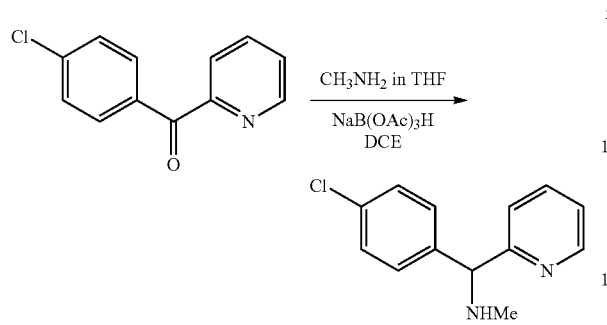

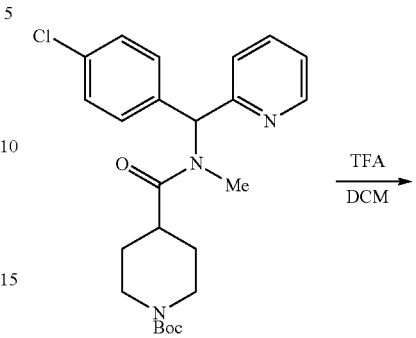

Title compound was prepared by reductive amination of (4-chlorophenyl)(pyridin-2-yl)methanone (1 g, 4.59 mmol) using the general methodology of Example-59 and afforded 0.5 g of 1-(4-chlorophenyl)-N-methyl-1-(pyridin-2-yl)methanamine (Yield=47%). tert-butyl-4-(((4-chlorophenyl)(pyridin-2-yl)methyl)(methyl)carbamoyl)piperidine-1-carboxylate:

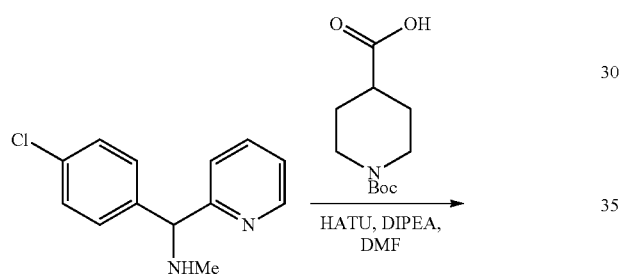

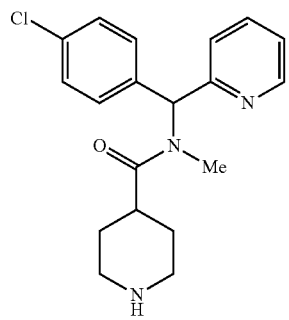

Title compound was prepared from deprotection of (tert-butyl 4-(((4-chlorophenyl)(pyridin-2-yl)methyl)(methyl)carbamoyl)piperidine-1-carboxylate (0.180 g, 0.405 mmol) using the conditions described in step 6 in the general methodology of key Intermediate-I and afforded 0.1 g of N-((4-chlorophenyl)(pyridin-2-yl)methyl)-N-methylpiperidine-4-carboxamide (Yield=72%).

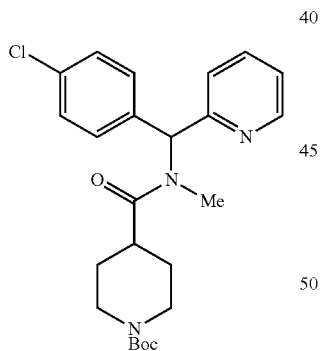

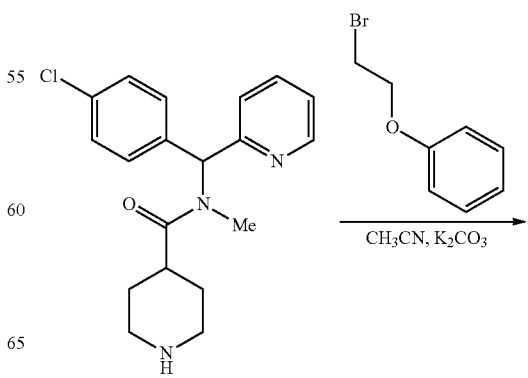

Title compound was prepared from coupling of 1 1-(tert-butoxycarbonyl)piperidine-4-carboxylic acid (0.049 g, 0.215 mmol, 1 equiv) and 1-(4-chlorophenyl)-N-methyl-1-(pyridin-2-yl)methanamine (0.050 g, 0.215 mmol, 1 equiv) using the conditions in step 5 in the general methodology of key Intermediate-I and afforded 0.060 g of tert-butyl 4-(((4-chlorophenyl)(pyridin-2-yl)methyl)(methyl)carbamoyl)piperidine-1-carboxylate. Crude material was used in the next step without further purification.

171

-continued

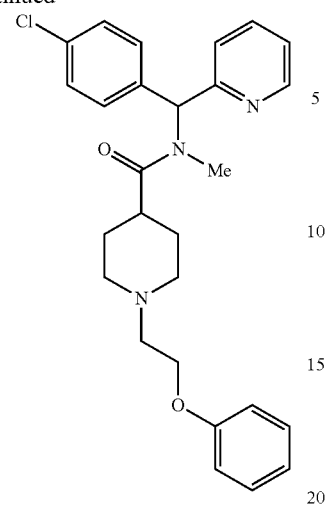

Title compound was prepared from N-((4-chlorophenyl)(pyridin-2-yl)methyl)-N-methyl piperidine-4-carboxamide (0.1 g, 0.29 mmol) using the general methodology of Example-1. The crude residue was purified by prep HPLC purification to afford 0.039 g of N-((4-chlorophenyl)(pyridin-2-yl)methyl)-N-methyl-1-(2-phenoxyethyl)piperidine-4-carboxamide (Yield=21%). ¹H NMR (400 MHz, CD₃OD): δ 8.57-8.56 (m, 1H), 7.81 (t, 1H, J=7.6 Hz), 7.40-7.33 (m, 3H), 7.29-7.23 (m, 3H), 7.14 (d, 2H, J=6.8 Hz), 7.06 (d, 1H, J=8.4 Hz), 6.97-6.89 (m, 4H), 4.13 (t, 2H, J=5.6 Hz), 3.14-3.12 (m, 2H), 2.97 (s, 3H), 2.67-2.63 (m, 2H), 2.13-2.07 (m, 2H), 1.72-1.57 (m, 4H); ESI+MS: m/z: 464.4 ([M+H]⁺).

Synthesis of Intermediate IV

172

-continued

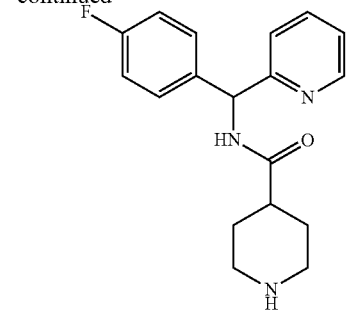

Int-IV tert-butyl 4-(((4-fluorophenyl)(pyridin-2-yl)methyl)carbamoyl)piperidine-1-carboxylate

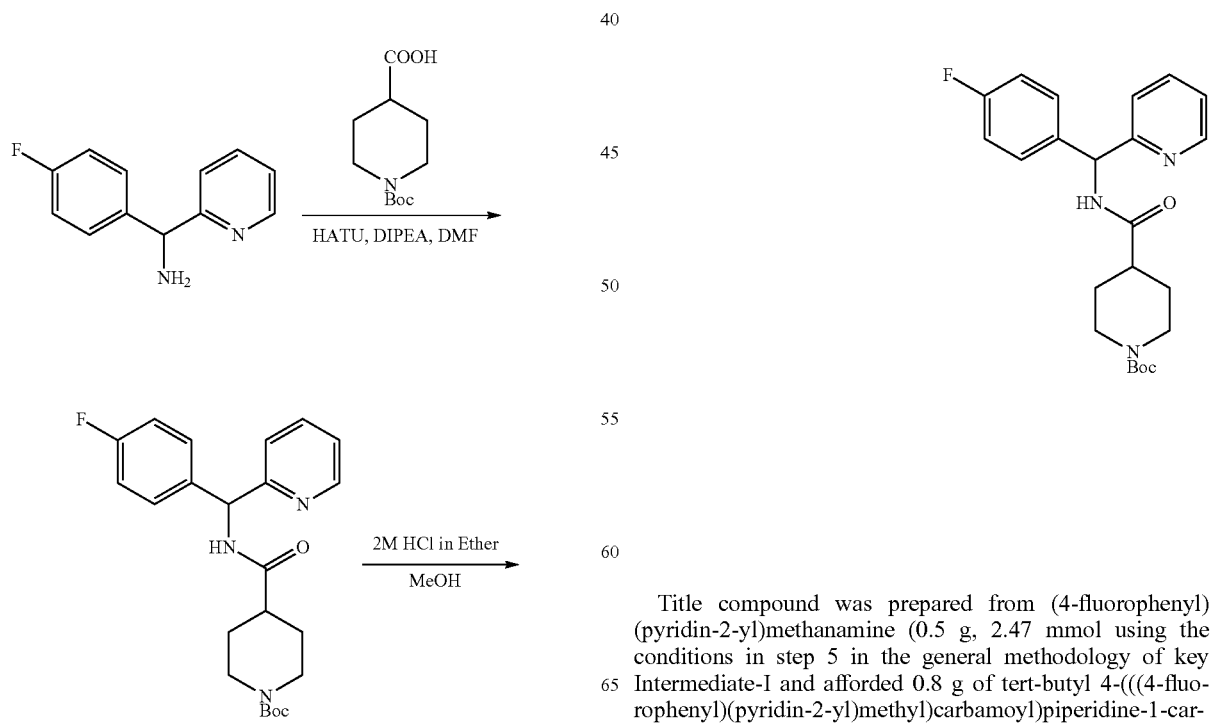

Title compound was prepared from (4-fluorophenyl)(pyridin-2-yl)methanamine (0.5 g, 2.47 mmol using the conditions in step 5 in the general methodology of key Intermediate-I and afforded 0.8 g of tert-butyl 4-(((4-fluorophenyl)(pyridin-2-yl)methyl)carbamoyl)piperidine-1-carboxylate (Yield=78%).

173

N-((4-fluorophenyl)(pyridin-2-yl)methyl)piperidine-4-carboxamide

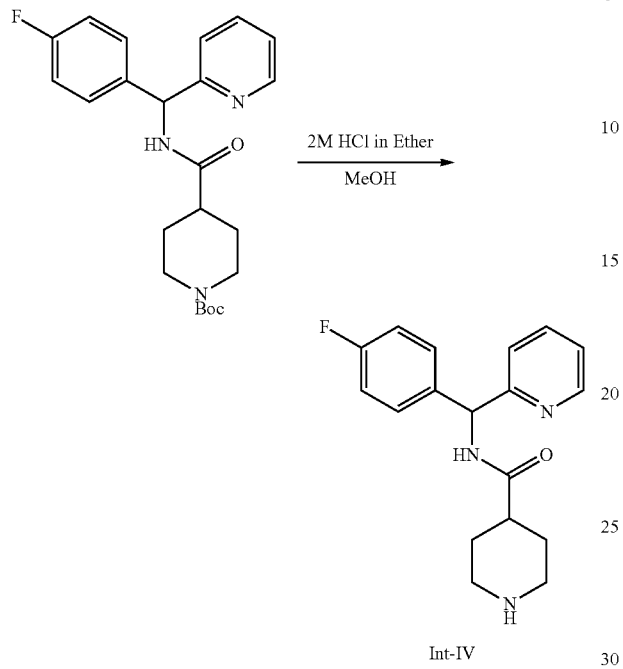

To a stirred solution of tert-butyl 4-(((4-fluorophenyl)(pyridin-2-yl)methyl)carbamoyl) piperidine-1-carboxylate (0.8 g, 1.93 mmol) in MeOH (5 mL) was added 2M HCl in ether (0.47 mL, 9.67 mmol, 5 equiv) at 0° C. The reaction mixture was warmed to room temperature and stirred for 3 h. After completion of the reaction, the volatiles were removed under reduced pressure. The pH was adjusted to 7 with saturated NaHCO₃ solution and extracted with EtOAc (3×50 mL). The combined organic extract was dried over sodium sulphate, filtered and concentrated under reduced pressure to afford 0.5 g of N-((4-fluorophenyl)(pyridin-2-yl)methyl)piperidine-4-carboxamide (Yield=82%).

Example-52: N-((4(4-fluorophenyl)(pyridin-2-yl)methyl)-1-(2-(2-(trifluoromethyl)phenoxy)ethyl)piperidine-4-carboxamide (52)

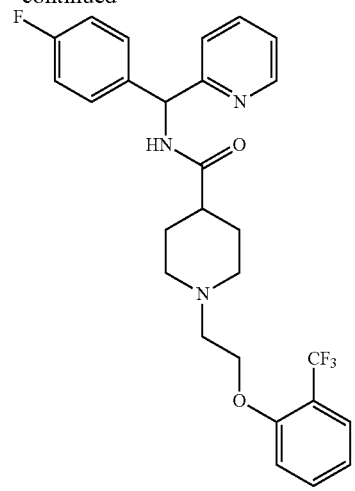

Title compound was prepared from N-((4-fluorophenyl)(pyridin-2-yl)methyl)piperidine-4-carboxamide key Intermediate-IV (0.150 g, 0.47 mmol) using the general methodology of Example-1. Purification using preparative HPLC afforded 0.005 g of N-((4-fluorophenyl)(pyridin-2-yl)methyl)-1-(2-(2-(trifluoromethyl)phenoxy)ethyl)piperidine-4-carboxamide (Yield=2%). ¹H NMR (400 MHz, CD₃OD): δ 8.52 (d, 1H, J=4.8 Hz), 7.81-7.71 (m, 1H), 7.55 (t, 2H, J=7.6 Hz), 7.37 (d, 1H, J=7.6 Hz), 7.31-7.27 (m, 3H), 7.16 (d, 1H, J=8.4 Hz), 7.06-7.01 (m, 3H), 6.16 (s, 1H), 4.23 (t, 2H, J=5.6 Hz), 3.01 (d, 2H, J=12.2 Hz), 2.85 (t, 2H, J=5.2 Hz), 2.44-2.36 (m, 1H), 2.30-2.23 (m, 2H), 1.83-1.74 (m, 4H). ESI+MS: m/z: 502 ([M+H]⁺). Enantiomers of 52 were separated using chiral HPLC (method A) and afforded pure enantiomers 52a and 52b.

Example-53: 1-(2-(2-chlorophenoxy)ethyl)-N-((4-fluorophenyl)(pyridin-2-yl)methyl) piperidine-4-carboxamide (53)

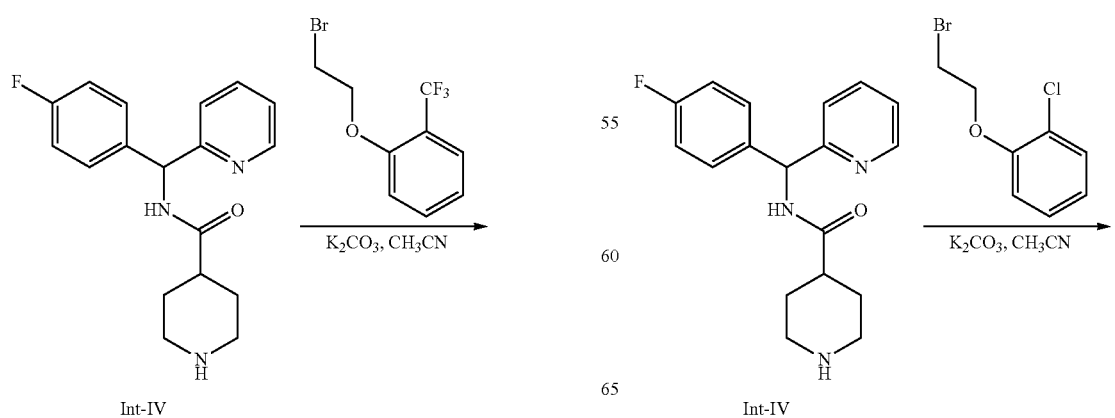

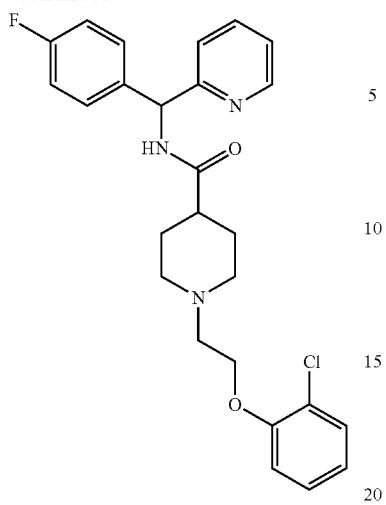
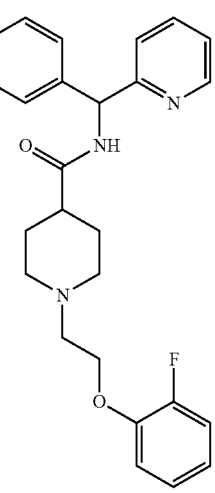

Title compound was prepared from N-((4-fluorophenyl)(pyridin-2-yl)methyl)piperidine-4-carboxamide key Intermediate-IV (0.150 g, 0.47 mmol) using the general methodology of Example-1. The product was purified by using silica gel column chromatography (3% MeOH/DCM as eluent) afforded 0.040 g of 1-(2-(2-chlorophenoxy)ethyl)-N-((4-fluorophenyl)(pyridin-2-yl)methyl)piperidine-4-carboxamide (Yield=17%). $^1$H NMR (400 MHz, CD$_3$OD): δ 8.52-8.51 (m, 1H), 7.79 (dt, 1H, J$_{1,2}$=1.6 Hz, J$_{1,4}$=9.6 Hz), 7.39 (d, 1H, J=8.0 Hz), 7.34 (dd, 1H, J$_{1,2}$=1.6 Hz, J$_{1,3}$=7.6 Hz), 7.32-7.26 (m, 3H), 7.25-7.22 (m, 1H), 7.07-7.06 (m, 1H), 7.05-7.01 (m, 2H), 6.91 (dt, 1H, J$_{1,2}$=1.6 Hz, J$_{1,4}$=9.2 Hz), 6.16 (s, 1H), 4.20 (t, 2H, J=5.6 Hz), 3.17 (t, 2H, J=11.6 Hz), 2.90 (t, 2H, J=5.2 Hz), 2.46-2.38 (m, 1H), 2.37-2.30 (m, 2H), 1.85-1.80 (m, 4H); ESI+MS: m/z: 468.2 ([M+H]$^+$). Enantiomers of 53 were separated using chiral HPLC (method A) and afforded pure enantiomers 53a and 53b.

Title compound was prepared from N-((4-fluorophenyl)(pyridin-2-yl)methyl)piperidine-4-carboxamide key intermediate IV (0.150 g, 0.47 mmol) using the general methodology of Example-1. The product was purified by using silica gel column chromatography (3% MeOH/DCM as eluent) afforded 0.040 g of 1-(2-(2-fluorophenoxy)ethyl)-N-((4-fluorophenyl)(pyridin-2-yl)methyl)piperidine-4-carboxamide (Yield=19%). $^1$H NMR (400 MHz, CD$_3$OD): δ 8.52 (d, 1H, J=4.4 Hz), 7.79 (dt, 1H, J$_{1,2}$=1.6 Hz, J$_{1,4}$=9.2 Hz), 7.39 (d, 1H, J=8.0 Hz), 7.32-7.27 (m, 3H), 7.11-7.01 (m, 5H), 6.94-6.88 (m, 1H), 6.16 (s, 1H), 4.19 (t, 2H, J=5.6 Hz), 3.11 (d, 2H, J=7.2 Hz), 2.85 (t, 2H, J=5.6 Hz), 2.45-2.37 (m, 1H), 2.30-2.24 (m, 2H), 1.85-1.79 (m, 4H); ESI+MS: m/z: 452.2 ([M+H]$^+$). Enantiomers of 54 were separated using chiral HPLC (method B) and afforded pure enantiomers 54a and 54b.

Example-54: 1-(2-(2-fluorophenoxy)ethyl)-N-((4-fluorophenyl)(pyridin-2-yl)methyl) piperidine-4-carboxamide (54)

Example-55: 1-(2-(benzo[d]thiazol-6-yloxy)ethyl)-N-((4-fluorophenyl)(pyridin-2-yl)methyl)piperidine-4-carboxamide (55)

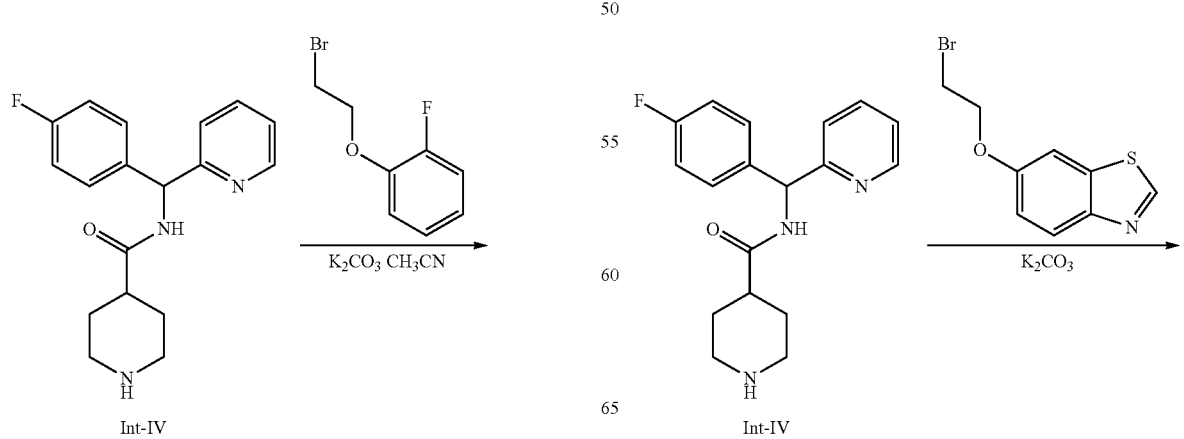

177
-continued

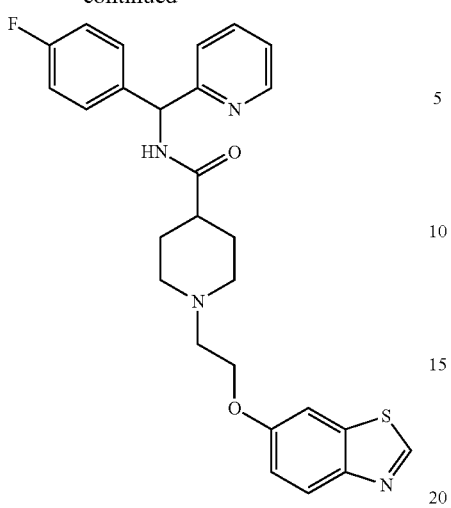

178
-continued

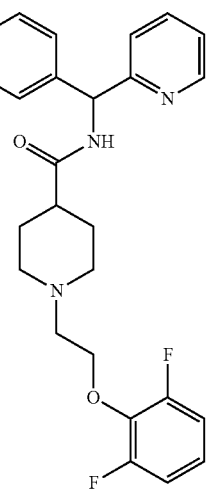

Title compound was prepared from N-((4-fluorophenyl)(pyridin-2-yl)methyl)piperidine-4-carboxamide key Intermediate-IV (0.1 g, 0.31 mmol) using the general methodology of Example-1. The crude residue was purified by column chromatography and further purified by Prep HPLC to afford 0.013 g of 1-(2-(benzo[d]thiazol-6-yloxy)ethyl)-N-((4-fluorophenyl) (pyridin-2-yl)methyl)piperidine-4-carboxamide Yield (8%). $^1$H NMR (400 MHz, CD$_3$OD): δ δ 9.03 (s, 1H), 8.52 (d, 1H, J=4.4 Hz), 7.92 (d, 1H, J=9.2 Hz), 7.78 (dt, 1H, J$_{1,2}$=2.0 Hz, J$_{1,4}$=9.6 Hz), 7.59 (d, 1H, J=2.0 Hz), 7.38 (d, 1H, J=8.0 Hz), 7.31-7.27 (m, 3H), 7.16 (dd, 1H, J$_{1,2}$=2.4 Hz, J$_{1,3}$=9.2 Hz), 7.06-7.01 (m, 2H), 6.16 (s, 1H), 4.20 (t, 2H, J=5.6 Hz), 3.09 (d, 2H, J=12.0 Hz), 2.84 (t, 2H, J=5.6 Hz), 2.45-2.37 (m, 1H), 2.26-2.19 (m, 2H), 1.85-1.80 (m, 4H); ESI+MS: m/z:491.4 ([M+H]$^+$).

Example-56: 1-(2-(2,6-difluorophenoxy)ethyl)-N-((4-fluorophenyl)(pyridin-2-yl)methyl) piperidine-4-carboxamide (56)

Title compound was prepared from N-((4-fluorophenyl)(pyridin-2-yl)methyl)piperidine-4-carboxamide key Intermediate-IV (0.120 g, 0.38 mmol) using the general methodology of Example-1. The product was purified by using silica gel column chromatography (3% MeOH/DCM as eluent) and further purified by prep HPLC purification to afford 0.030 g 1-(2-(2,6-difluorophenoxy)ethyl)-N-((4-fluorophenyl)(pyridin-2-yl)methyl)piperidine-4-carboxamide (Yield=17%). $^1$H NMR (500 MHz, DMSO-d$_6$): δ 8.68 (d, 1H, J=8.0 Hz), 8.51 (d, 1H, J=4.0 Hz), 7.78 (t, 1H, J=8.0 Hz), 7.44 (d, 1H, J=8.0 Hz), 7.35-7.28 (m, 2H), 7.28-7.26 (m, 1H), 7.15-7.09 (m, 5H), 6.13 (d, 1H, J=8.0 Hz), 4.17 (t, 2H, J=5.0 Hz), 2.89 (d, 2H, J=11.0 Hz), 2.65 (t, 2H, J=5.5 Hz), 2.33-2.29 (m, 1H), 2.00 (t, 2H, J=11.0 Hz), 1.65-1.63 (m, 2H), 1.52-1.45 (m, 2H); ESI+MS: m/z: 470.5 ([M+H]$^+$).

Example-57: 1-(2-(2,5-difluorophenoxy)ethyl)-N-((4-fluorophenyl)(pyridin-2-yl)methyl) piperidine-4-carboxamide (57)

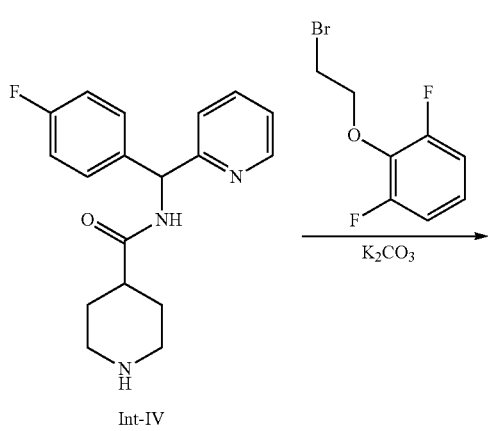

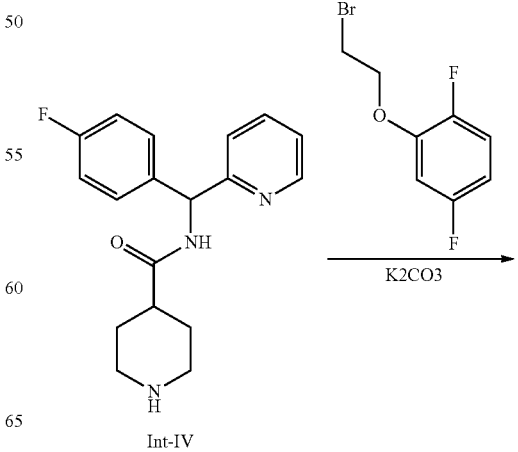

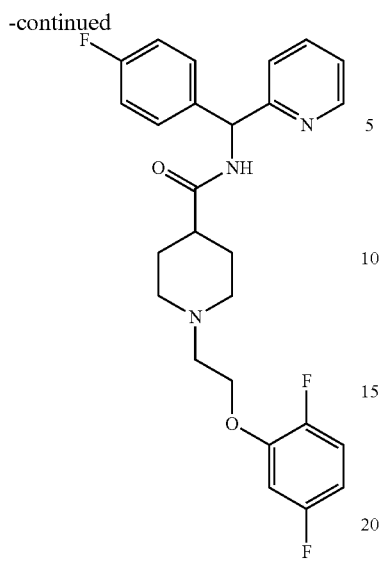

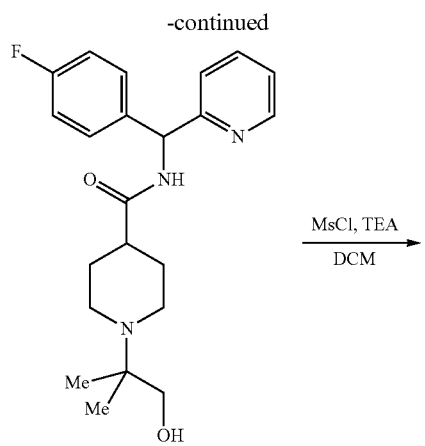

Title compound was prepared from N-((4-fluorophenyl)(pyridin-2-yl)methyl)piperidine-4-carboxamide key Intermediate-IV (0.1 g, 0.31 mmol) using the general methodology of Example-1. The product was purified by silica gel column chromatography (2% MeOH/DCM as eluent) to afford 0.060 g of 1-(2-(2,5-difluorophenoxy)ethyl)-N-((4-fluorophenyl)(pyridin-2-yl)methyl)piperidine-4-carboxamide (Yield=40%). ¹H NMR (500 MHz, DMSO-d₆): δ 8.69 (d, 1H, J=8.5 Hz), 8.51 (d, 1H, J=4.5 Hz), 7.85 (t, 1H, J=8.0 Hz), 7.45 (d, 1H, J=8.0 Hz), 7.35-7.22 (m, 4H), 7.16-7.13 (m, 3H), 6.76 (t, 1H, J=8.0 Hz), 6.14 (d, 1H, J=8.5 Hz), 4.15 (t, 2H, J=5.5 Hz), 2.96-2.94 (m, 2H), 2.69-2.67 (m, 2H), 2.36-2.31 (m, 1H), 2.05-2.01 (m, 2H), 1.67-1.65 (m, 2H), 1.66-1.54 (m, 2H); ESI+MS: m/z: 470.5 ([M+H]⁺).

Example-58: N-((4(4-fluorophenyl)(pyridin-2-yl)methyl)-1-(2-methyl-1-phenoxypropan-2-yl)piperidine-4-carboxamide (58)

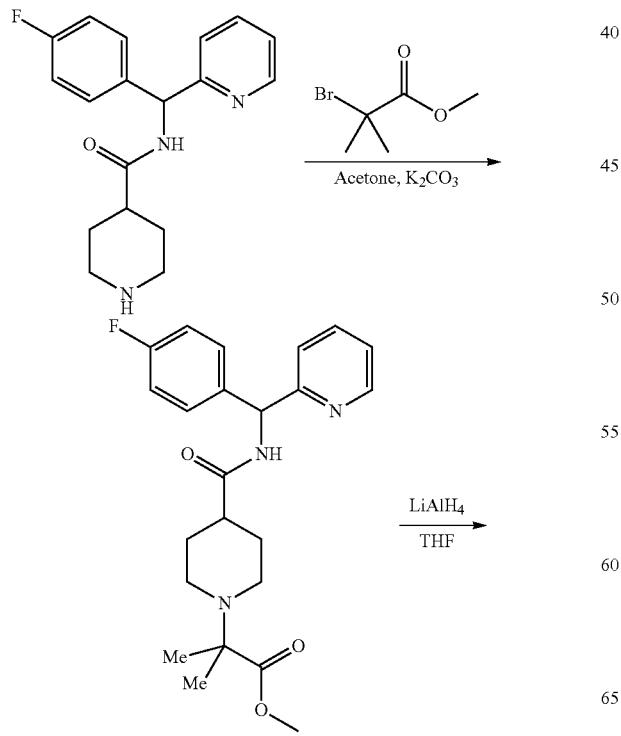

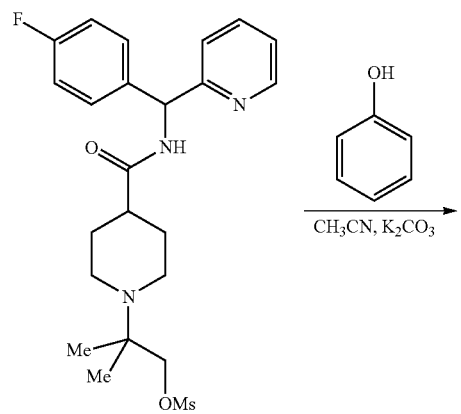

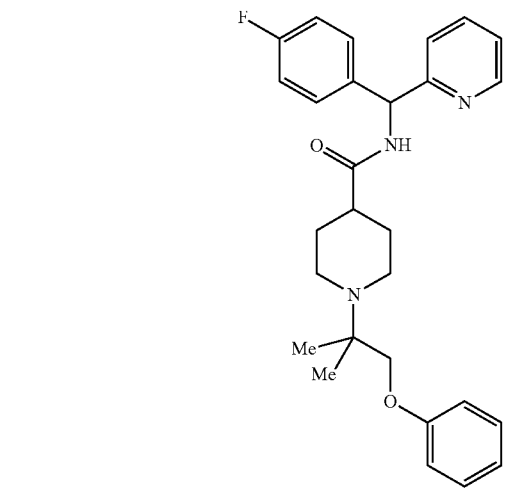 [SMILES: CC(C)(COc1ccccc1)N1CCC(C(=O)NC(c2ccc(F)cc2)c2ccccn2)CC1]

Methyl 2-(4-(((4-fluorophenyl)(pyridin-2-yl)methyl)carbamoyl)piperidin-1-yl)-2-methyl propanoate

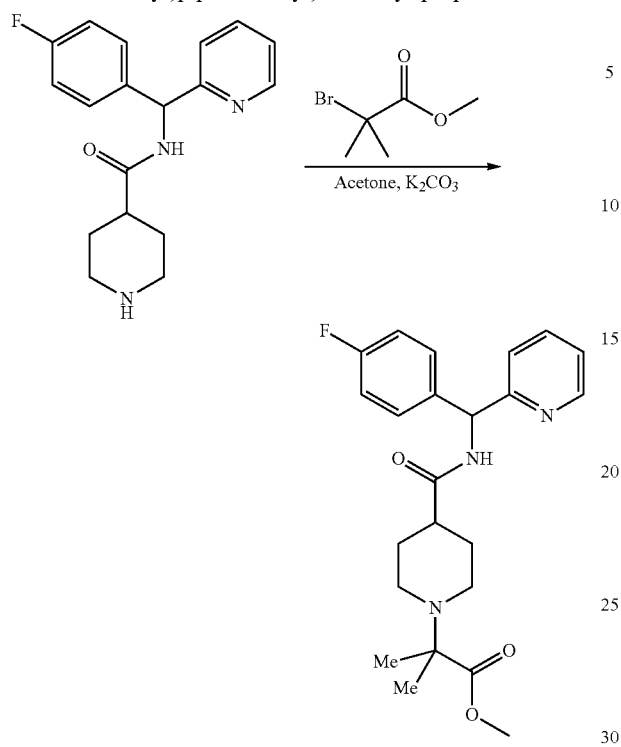

To a solution of N-((4-fluorophenyl)(pyridin-2-yl)methyl)piperidine-4-carboxamide (0.3 g, 0.957 mmol) and methyl 2-bromo-2-methylpropanoate (0.173 g, 0.957 mmol, 1.0 equiv) in acetone was added potassium carbonate. The reaction mixture was stirred at 70° C. for 16 hrs. Then it was quenched by addition of water and ethyl acetate and the aqueous phase was reextracted twice with ethyl acetate. The combined organic layers were then dried over Na$_2$SO$_4$, filtered and concentrated. Column chromatography on silica gel using 1% methanol in DCM afforded 0.22 g of methyl-2-(4-(((4-fluorophenyl)(pyridin-2-yl)methyl)carbamoyl)piperidin-1-yl)-2-methyl propanoate (Yield=56%); ESI+MS: m/z: 414.4 ([M+H]$^+$).

N-((4(4-fluorophenyl)(pyridin-2-yl)methyl)-1-(1-hydroxy-2-methylpropan-2-yl)piperidine-4-carboxamide

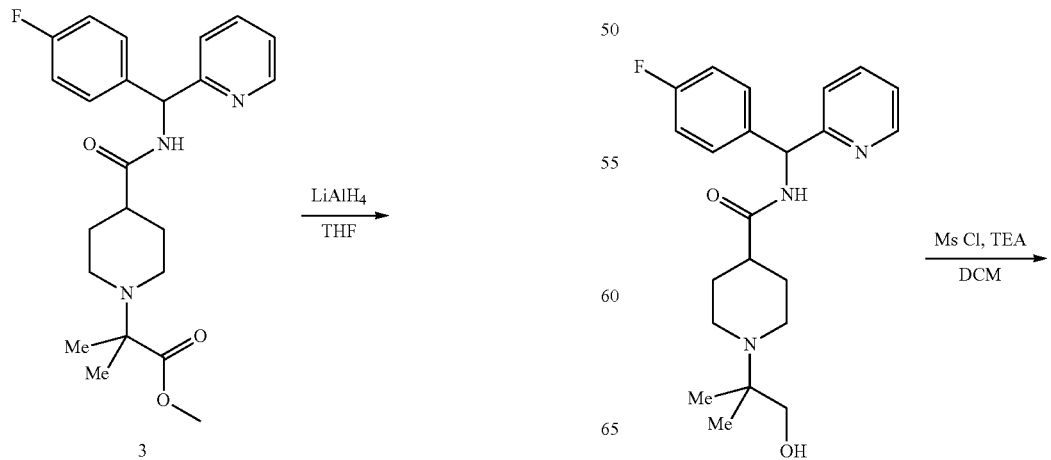

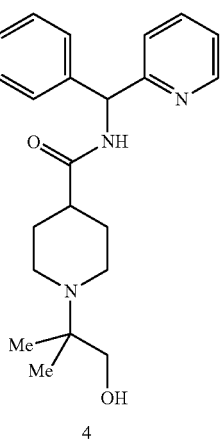

To a stirred solution of (4-(((4-fluorophenyl)(pyridin-2-yl)methyl)carbamoyl)piperidin-1-yl)-2-methylpropanoate (0.22 g, 0.53 mmol) in THF (3 mL) was added lithium aluminium hydride (0.0303 g, 0.798 mmol, 1.5 equiv) at 0° C. The reaction was stirred at room temperature for 2 h. After completion, the reaction mass was quenched with ethyl acetate, aq. Na$_2$SO$_4$ and extracted with EtOAc. The combined organic extract was washed with brine and dried under reduced pressure to afforded 0.150 g of N-((4-fluorophenyl)(pyridin-2-yl)methyl)-1-(1-hydroxy-2-methylpropan-2-yl)piperidine-4-carboxamide (Yield=73%); ESI+MS: m/z: 386.4 ([M+H]$^+$).

2-(4-(((4-fluorophenyl)(pyridin-2-yl)methyl)carbamoyl)piperidin-1-yl)-2-methylpropyl methanesulfonate 183
-continued

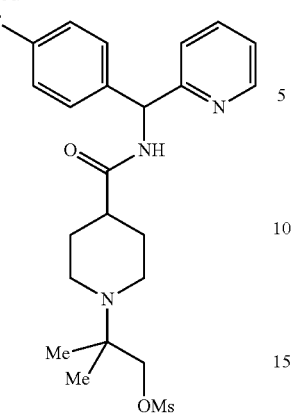

184
-continued

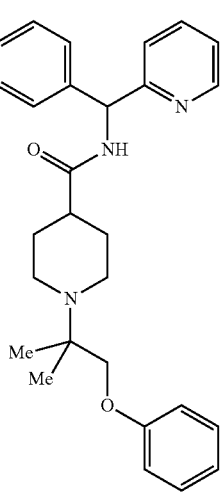

To a stirred solution of N-((4-fluorophenyl)(pyridin-2-yl) methyl)-1-(1-hydroxy-2-methyl propan-2-yl)piperidine-4-carboxamide (0.150 g, 0.389 mmol) in DCM (5 mL) were added triethylamine (0.079 g, 0.778 mmol, 2 equiv) and methane sulfonyl chloride (0.049 g, 0.428 mmol, 1.2 equiv) at 0° C. The reaction mixture was stirred at room temperature for 1 h. After completion, the reaction mass was quenched with water and extracted with EtOAc. The combined organic extracts were washed with brine, filtered and dried over sodium sulphate. The solvent was removed under reduced pressure to afford crude 0.150 g of 2-(4-(((4-fluorophenyl)(pyridin-2-yl)methyl)carbamoyl)piperidin-1-yl)-2-methylpropyl methanesulfonate (Yield=83%).

N-((4(4-fluorophenyl)(pyridin-2-yl)methyl)-1-(2-methyl-1-phenoxy propan-2-yl)piperidine-4-carboxamide To a solution of 2-(4-(((4-fluorophenyl)(pyridin-2-yl) methyl)carbamoyl)piperidin-1-yl)-2-methylpropylmethanesulfonate (0.150 g, 0.32 mmol) and phenol (0.0457 g, 0.48 mmol, 1.5 equiv) in acetonitrile was added potassium carbonate (134 mg, 0.97 mmol, 3.0 equiv.). The reaction mixture was stirred at 80° C. for 16 hrs. After completion of the reaction (monitored by TLC), diluted with water and extracted with ethyl acetate. The organic layer was dried over $Na_2SO_4$, filtered and concentrated under reduced pressure. The crude compound was purified by prep HPLC purification to afford 0.020 g of N-((4-fluorophenyl)(pyridin-2-yl)methyl)-1-(2-methyl-1-phenoxypropan-2-yl)piperidine-4-carboxamide (Yield=13%). $^1$H NMR (400 MHz, DMSO-$D_6$): δ 8.68 (d, 1H, J=8.4 Hz), 8.51-8.50 (m, 1H), 7.77 (dt, 1H, $J_{1,2}$=1.6 Hz, $J_{1,4}$=9.2 Hz), 7.44 (d, 1H, J=8.0 Hz), 7.35-7.31 (m, 2H), 7.28-7.24 (m, 3H), 7.14-7.09 (m, 2H), 7.05-7.01 (m, 1H), 6.96-6.94 (m, 2H), 6.13 (d, 1H, J=8.4 Hz), 2.96 (d, 2H, J=11.6 Hz), 2.50-2.49 (m, 2H), 2.30-2.27 (m, 1H), 2.17 (dt, 2H, $J_{1,2}$=4.4 Hz, $J_{1,4}$=14.8 Hz), 1.63-1.59 (m, 4H), 1.20 (s, 6H); ESI+MS: m/z: 462.6 ([M+H]$^+$).

Example-59: 1-(benzofuran-2-ylmethyl)-N-((4(4-fluorophenyl)(pyridin-2-yl)methyl)piperidine-4-carboxamide (59)

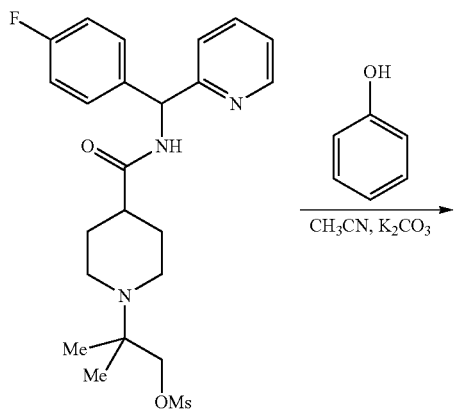

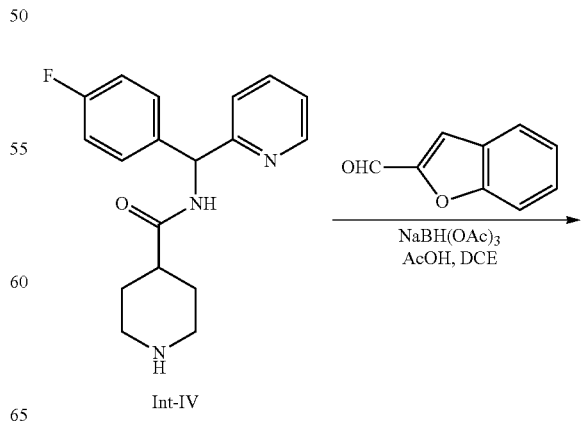

Int-IV

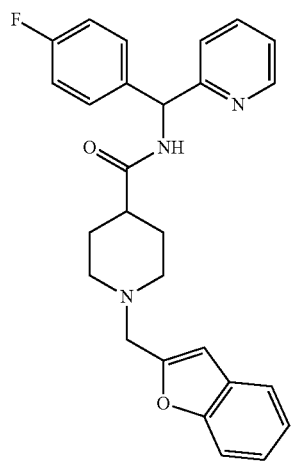

To a stirred solution of N-((4(4-fluorophenyl)(pyridin-2-yl)methyl)piperidine-4-carboxamide (key Intermediate-IV) (0.150 g, 0.479 mmol) in DCE (3 mL) were added benzofuran-2-carbaldehyde (0.07 g, 0.479 mmol, 1 equiv), and acetic acid (0.0287 g, 0.479 mmol, 1 equiv) at 0° C. and the reaction was stirred at room temperature for 1 h. Then sodium triacetoxy borohydride (0.281 g, 1.43 mmol, 3 equiv) was added. After completion, the reaction mass was quenched with water and pH was adjusted ~7 with saturated $NaHCO_3$ solution and extracted with $CH_2Cl_2$. The combined organic extract was dried over sodium sulphate, filtered and concentrated under reduced pressure. The crude compound was purified by prep HPLC to afford 0.040 g of 1-(benzofuran-2-ylmethyl)-N-((4(4-fluorophenyl)(pyridin-2-yl)methyl)piperidine-4-carboxamide (Yield=19%). $^1H$ NMR (400 MHz, DMSO-$D_6$): δ 8.66 (d, 1H, J=8.4 Hz), 8.50-8.49 (m, 1H), 7.76 (dt, $J_{1,2}$=2.0 Hz, 1H, $J_{1,4}$=9.6 Hz), 7.58-7.51 (m, 2H), 7.43 (d, 1H, J=8.0 Hz), 7.34-7.30 (m, 2H), 7.27-7.18 (m, 3H), 7.13-7.09 (m, 2H), 6.74 (s, 1H), 6.12 (d, 1H, J=8.4 Hz), 3.64 (s, 2H), 2.89 (d, 2H, J=10.8 Hz), 2.35-2.29 (m, 1H), 2.07-2.00 (m, 2H), 1.69-1.53 (m, 4H); ESI+MS: m/z: 444.5 ([M+H]$^+$).

Example-60: 1-(benzo[d]oxazol-2-ylmethyl)-N-((4-fluorophenyl)(pyridin-2-yl)methyl)piperidine-4-carboxamide (60)

Title compound was prepared from N-((4-fluorophenyl)(pyridin-2-yl)methyl)piperidine-4-carboxamide key Intermediate-IV (0.100 g, 0.319 mmol) using the general methodology of Example-1. The product was purified by prep HPLC purification to afford 0.040 g of 1-(2-(2,6-difluorophenoxy)ethyl)-N-((4(4-fluorophenyl)(pyridin-2-yl)methyl)piperidine-4-carboxamide (Yield=28%). $^1H$ NMR (400 MHz, DMSO-$d_6$): δ 8.67 (d, 1H, J=8.4 Hz), 8.49 (dd, 1H, $J_{1,2}$=0.8 Hz, $J_{1,3}$=4.8 Hz), 7.78-7.70 (m, 3H), 7.44-7.24 (m, 6H), 7.13-7.09 (m, 2H), 6.12 (d, 1H, J=8.0 Hz), 3.83 (s, 2H), 2.92 (d, 2H, J=11.2 Hz), 2.37-2.29 (m, 1H), 2.19-2.13 (m, 2H), 1.70-1.54 (m, 4H); ESI+MS: m/z:445.5 ([M+H]$^+$).

Example-61: 1-((2,3-dihydro-1H-inden-2-yl)methyl)-N-((4-fluorophenyl)(pyridin-2-yl)methyl)piperidine-4-carboxamide (61)

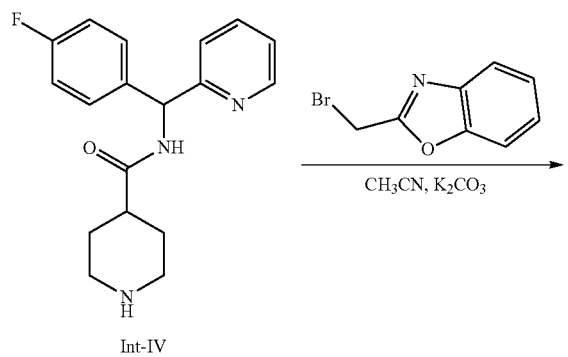

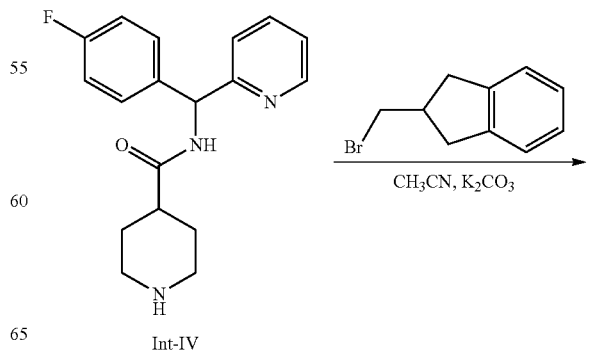

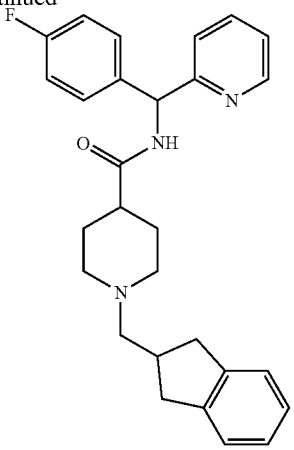

Title compound was prepared from N-((4-fluorophenyl)(pyridin-2-yl)methyl)piperidine-4-carboxamide key Intermediate-IV (0.100 g, 0.319 mmol) using the general methodology of Example-1. The product was purified by Prep HPLC purification to afford 0.030 g of 1-((2,3-dihydro-1H-inden-2-yl)methyl)-N-((4-fluorophenyl)(pyridin-2-yl)methyl)piperidine-4-carboxamide (Yield=20%). $^1$H NMR (400 MHz, CD$_3$OD): δ 8.52 (d, 1H, J=7.6 Hz), 7.80 (dt, 1H, J$_{1,3}$=7.6 Hz, J$_{1,4}$=6.0 Hz), 7.39 (d, 1H, J=8.0 Hz), 7.32-7.27 (m, 3H), 7.15-7.12 (m, 2H), 7.08-7.02 (m, 4H), 6.17 (s, 1H), 3.83 (s, 2H), 3.04-3.01 (m, 4H), 2.75-2.64 (m, 3H), 2.45-2.35 (m, 3H), 2.11-2.04 (m, 2H), 1.84-1.79 (m, 4H); ESI+ MS: m/z:444.6 ([M+H]$^+$).

Example-62: N-((4(4-chlorophenyl)(pyridin-2-yl)methyl)-1-(3-phenoxypropyl)piperidine-4-carboxamide (62)

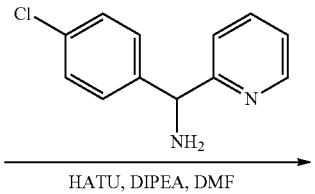

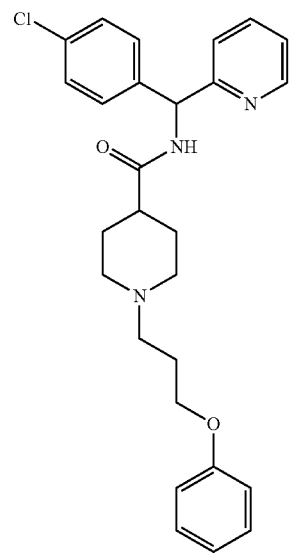

Methyl 1-(3-phenoxypropyl)piperidine-4-carboxylate

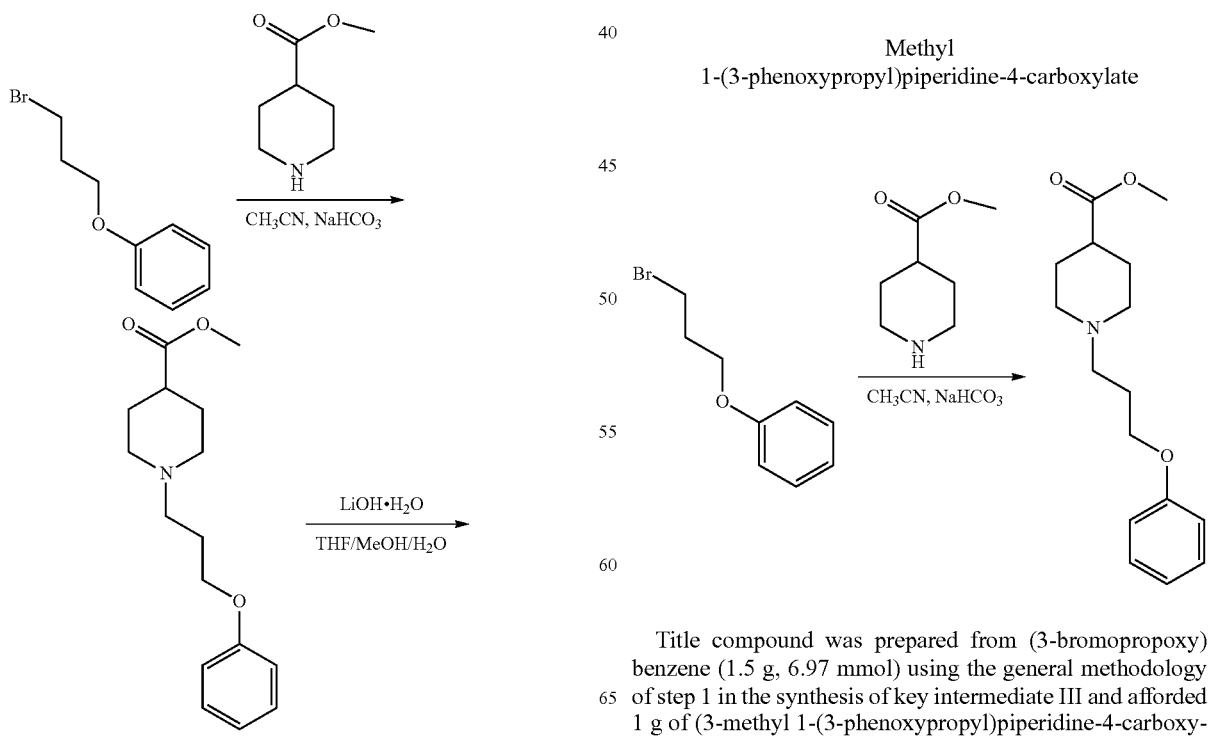

Title compound was prepared from (3-bromopropoxy)benzene (1.5 g, 6.97 mmol) using the general methodology of step 1 in the synthesis of key intermediate III and afforded 1 g of (3-methyl 1-(3-phenoxypropyl)piperidine-4-carboxylate (Yield=52%).

1-(3-phenoxypropyl)piperidine-4-carboxylic acid

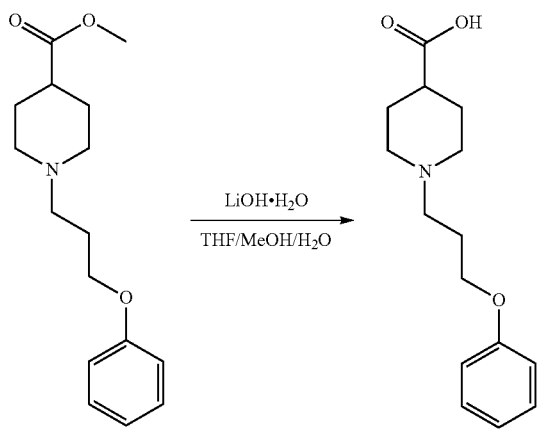 [SMILES: COC(=O)C1CCN(CCCOc2ccccc2)CC1 ; "LiOH·H2O" ; O=C(O)C1CCN(CCCOc2ccccc2)CC1]

Title compound was prepared from methyl 1-(3-phenoxypropyl)piperidine-4-carboxylate (1 g, 3.61 mmol) using the general methodology of step 2 in the synthesis of key intermediate III and afforded 0.8 g of 1-(3-phenoxypropyl)piperidine-4-carboxylic acid (Yield=84%).

N-((4-chlorophenyl)(pyridin-2-yl)methyl)-1-(3-phenoxypropyl)piperidine-4-carboxamide

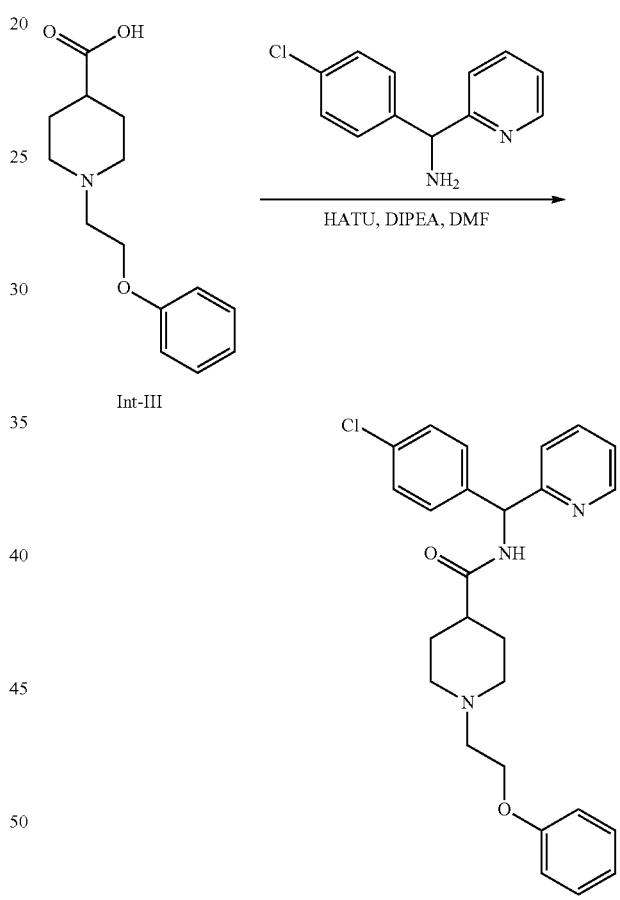

Title compound was prepared from 1-(3-phenoxypropyl)piperidine-4-carboxylic acid (0.1 g, 0.457 mmol) using the conditions in step 5 in the general methodology of key Intermediate-I. The product was purified by preparative HPLC to afford 0.04 g of N-((4-chlorophenyl)(pyridin-2-yl)methyl)-1-(3-phenoxypropyl)piperidine-4-carboxamide (Yield=19%). $^1$H NMR (400 MHz, DMSO-d6): δ 8.70 (d, J=8.4 Hz, 1H), 8.51 (d, J=4.0 Hz, 1H), 7.81 (dt, 1H, $J_{1,3}$=7.6 Hz, $J_{1,2}$=1.6 Hz), 7.44 (d, J=7.6 Hz, 1H), 7.45-7.24 (m, 7H), 6.92-6.88 (m, 3H), 6.13 (d, J=8.4 Hz, 1H), 3.97 (t, J=6.4 Hz, 2H), 2.88 (d, J=10.8 Hz, 2H), 2.41-2.30 (m, 3H), 1.90-1.82 (m, 4H), 1.65-1.53 (m, 4H); ESI+MS: m/z 465 ([M+H]$^+$).

Example-63: N-((4(4-chlorophenyl)(pyridin-2-yl)methyl)-1-(2-phenoxyethyl)piperidine-4-carboxamide (63)

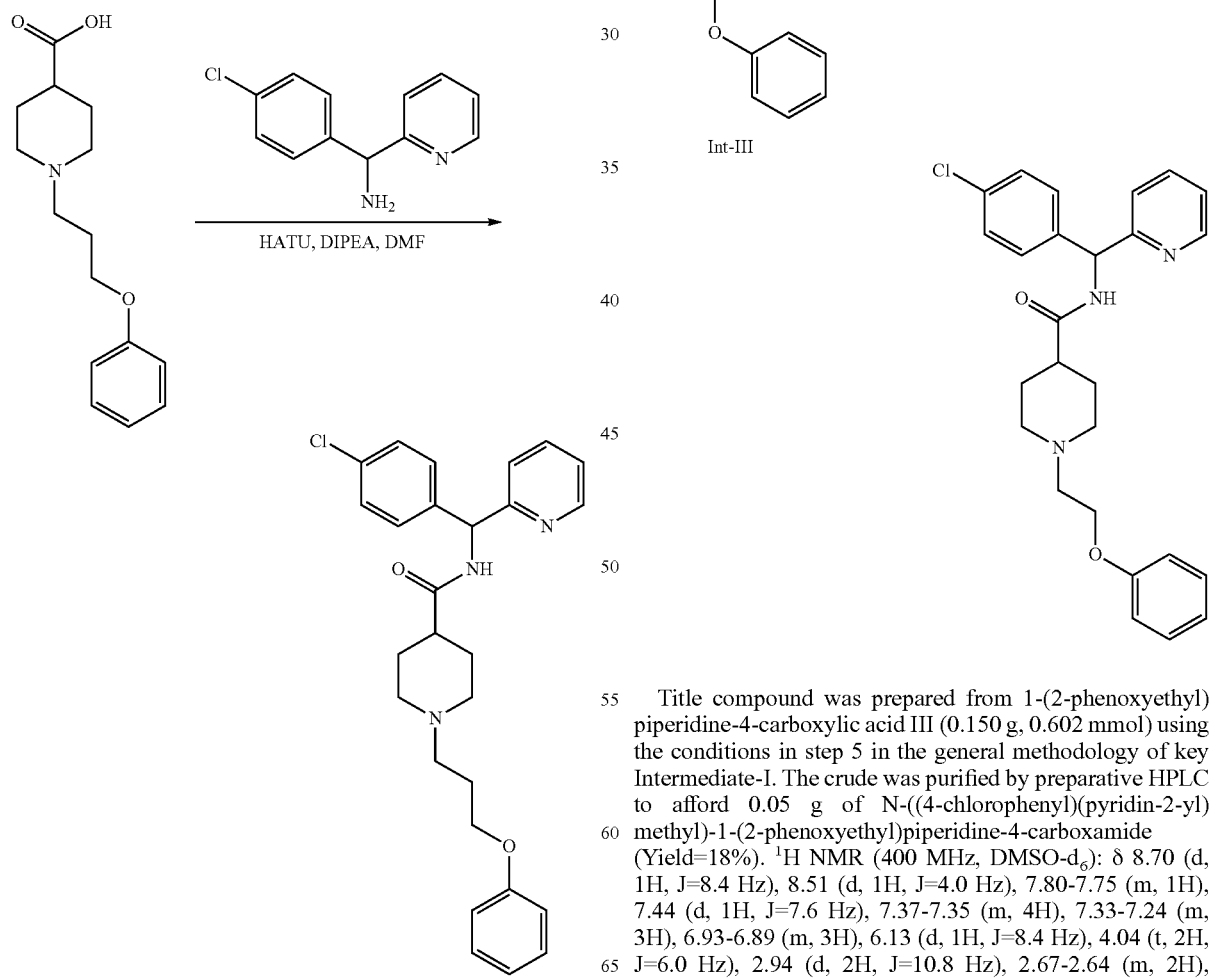

Title compound was prepared from 1-(2-phenoxyethyl)piperidine-4-carboxylic acid III (0.150 g, 0.602 mmol) using the conditions in step 5 in the general methodology of key Intermediate-I. The crude was purified by preparative HPLC to afford 0.05 g of N-((4-chlorophenyl)(pyridin-2-yl)methyl)-1-(2-phenoxyethyl)piperidine-4-carboxamide (Yield=18%). $^1$H NMR (400 MHz, DMSO-d$_6$): δ 8.70 (d, 1H, J=8.4 Hz), 8.51 (d, 1H, J=4.0 Hz), 7.80-7.75 (m, 1H), 7.44 (d, 1H, J=7.6 Hz), 7.37-7.35 (m, 4H), 7.33-7.24 (m, 3H), 6.93-6.89 (m, 3H), 6.13 (d, 1H, J=8.4 Hz), 4.04 (t, 2H, J=6.0 Hz), 2.94 (d, 2H, J=10.8 Hz), 2.67-2.64 (m, 2H), 2.36-2.32 (m, 1H), 2.31-2.30 (m, 2H), 2.04-1.93 (m, 2H), 1.65 (s, 2H), 1.61-1.513 (m, 2H); ESI+MS: m/z 450 ([M+

Example-64: N-((4(4-chlorophenyl)(pyridin-2-yl)methyl)-1-methylpiperidine-4-carboxamide (64)

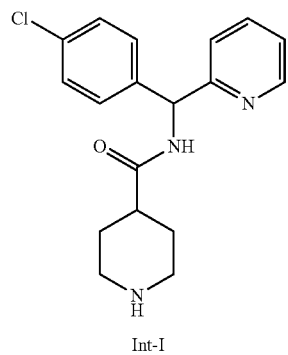

Int-I

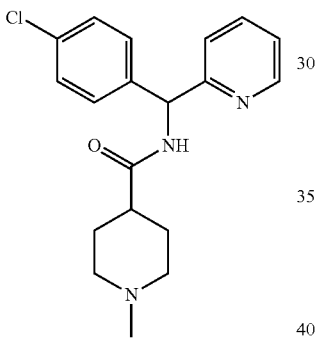

Example-65: N-((4(4-chlorophenyl)(pyridin-2-yl)methyl)-1-(2-methoxyethyl)piperidine-4-carboxamide (65)

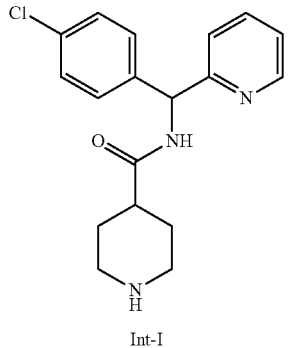

Int-I

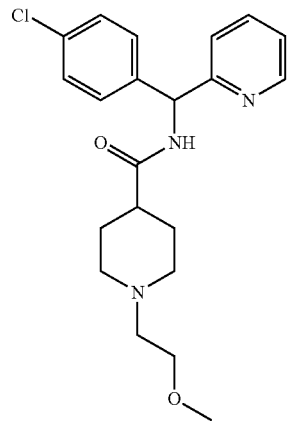

To a solution of N-((4-chlorophenyl)(pyridin-2-yl)methyl)piperidine-4-carboxamide (0.240 g, 0.728 mmol) in CH$_2$Cl$_2$ (3 mL) under argon atmosphere were added paraformaldehyde (0.03 g, 1.09 mmol), sodium triacetoxy borohydride (0.463 g, 2.18 mmol, 3 equiv) and acetic acid (0.04 mL) at 0° C. The reaction mixture was and stirred at room temperature for 16 h. After completion, the reaction was diluted with CH$_2$Cl$_2$ and washed with saturated NaHCO$_3$ solution and brine. The combined organic extract was dried over sodium sulfate, filtered and concentrated under reduced pressure. Purification using silica gel column chromatography (4% MeOH/CH$_2$Cl$_2$ as eluent) afforded 0.08 g of N-((4-chlorophenyl)(pyridin-2-yl)methyl)-1-methylpiperidine-4-carboxamide (Yield=31%). $^1$H NMR (400 MHz, DMSO-d$_6$): δ 8.70 (d, 1H, J=8.4 Hz), 8.50 (d, 1H, J=4.4 Hz), 7.80-7.76 (m, 1H), 7.44 (d, 1H, J=7.6 Hz), 7.37-7.25 (m, 5H), 6.12 (d, 1H, J=8.4 Hz), 2.75 (t, 2H, J=11.2 Hz), 2.32-2.25 (m, 1H), 2.12 (s, 3H), 1.80 (t, 2H, J=11.6 Hz), 1.62-1.49 (m, 4H); ESI+MS: m/z 344 ([M+H]$^+$).

To a solution of N-((4-chlorophenyl)(pyridin-2-yl)methyl)piperidine-4-carboxamide (0.130 g, 0.394 mmol) in 5 mL of DMF under argon atmosphere were added potassium carbonate (0.163 g, 1.18 mmol, 3 equiv), 1-chloro-2-methoxy ethane (0.056 g, 0.591 mmol, 1.5 eqiuv) at 0° C. and the reaction was heated to 80° C. and stirred for 16 h. After completion, the volatiles were removed under reduced pressure; water was added to the residue and extracted with EtOAc. The combined organic extract was dried over sodium sulfate, filtered and concentrated under reduced pressure. Purification using preparative HPLC afforded 0.035 g of N-((4-chlorophenyl)(pyridin-2-yl)methyl)-1-(2-methoxyethyl)piperidine-4-carboxamide (Yield=22%). $^1$H NMR (400 MHz, DMSO-d6): δ 8.69 (d, 1H, J=8.4 Hz), 8.50 (t, 1H, J=4.8 Hz), 7.80-7.75 (m, 1H), 7.44 (d, 1H, J=7.6 Hz), 7.37-7.25 (m, 5H), 6.12 (d, 1H, J=8.0 Hz), 3.40 (t, 2H, J=11.6 Hz), 3.21 (s, 3H), 2.87 (d, 2H, J=12.8 Hz), 2.44-2.43 (m, 2H), 2.33-2.28 (m, 1H), 1.95-1.90 (m, 2H), 1.62-1.49 (m, 4H); ESI+MS: m/z: 387 ([M+H]$^+$).

193

Example-66: 1-(2-(2-chlorophenoxy)ethyl)-N-((4-chlorophenyl)(pyridin-2-yl)methyl) piperidine-4-carboxamide (66)

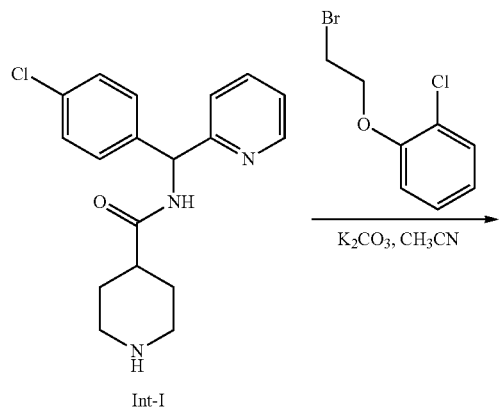

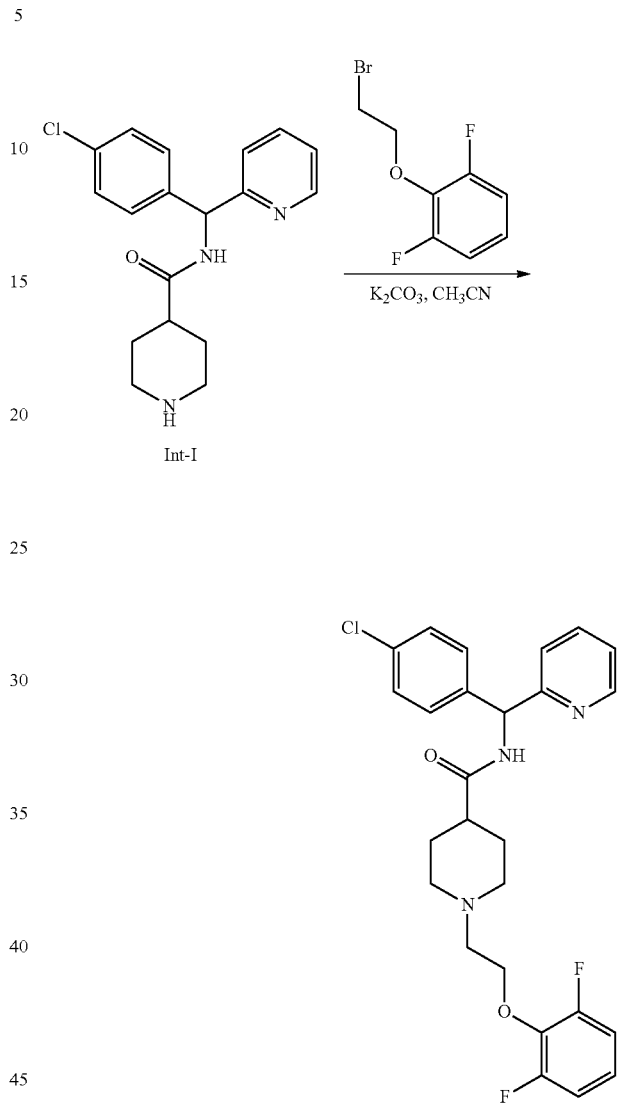

194

Example-67: N-((4(4-chlorophenyl)(pyridin-2-yl)methyl)-1-(2-(2,6-difluorophenoxy)ethyl) piperidine-4-carboxamide (67)

Title compound was prepared from N-((4-chlorophenyl)(pyridin-2-yl)methyl)piperidine-4-carboxamide (0.2 g, 0.606 mmol) using the general methodology of Example-1. The crude compound was purified using silica gel column chromatography (3% MeOH/CH$_2$Cl$_2$ as eluent) to afford 0.155 g of 1-(2-(2-chlorophenoxy)ethyl)-N-((4-chlorophenyl)(pyridin-2-yl)methyl)piperidine-4-carboxamide (Yield=51%). $^1$H NMR (500 MHz, DMSO-d$_6$): δ 8.70 (d, 1H, J=8.0 Hz), 8.50 (d, 1H, J=4.5 Hz), 7.79-7.75 (m, 1H), 7.44 (d, 2H, J=8.5 Hz), 7.40-7.25 (m, 6H), 7.15 (d, 1H, J=8.0 Hz), 6.93 (t, 1H, J=8.0 Hz), 6.12 (d, 1H, J=8.5 Hz), 4.19-4.10 (m, 2H), 2.97 (d, 2H, J=9.0 Hz), 2.75-2.70 (m, 2H), 2.34 (d, 1H, J=10.5 Hz), 2.10-2.04 (m, 2H), 1.65-1.54 (m, 4H); ESI+MS: m/z: 484 ([M+H]$^+$).

Title compound was prepared from N-((4-chlorophenyl)(pyridin-2-yl)methyl)piperidine-4-carboxamide (0.120 g, 0.364 mmol) using the general methodology of Example-1. The crude was washed with pentane to afford 0.1 g of N-((4-chlorophenyl)(pyridin-2-yl)methyl)-1-(2-(2,6-difluorophenoxy)ethyl)piperidine-4-carboxamide (Yield=57%). $^1$H NMR (400 MHz, DMSO-d$_6$): δ 8.69 (d, 1H, J=8.4 Hz), 8.50 (dd, 1H, J$_{1,2}$=0.8 Hz, J$_{1,3}$=4.8 Hz), 7.80-7.75 (m, 1H), 7.44 (d, 1H, J=8.0 Hz), 7.37-7.25 (m, 5H), 7.12-7.07 (m, 3H), 6.12 (d, 1H, J=8.4 Hz), 4.16 (t, 2H, J=5.6 Hz), 2.88 (d, 2H, J=11.2 Hz), 2.67-2.62 (m, 2H), 2.33-2.27 (m, 1H), 1.98 (t, 2H, J=9.6 Hz), 1.64-1.61 (m, 2H), 1.52-1.42 (m, 2H); ESI+MS: m/z 486 ([M+H]$^+$).

Example-68: N-((4-chlorophenyl)(pyridin-2-yl)methyl)-1-(2-(2-(trifluoromethoxy)phenoxy) ethyl) piperidine-4-carboxamide (68)

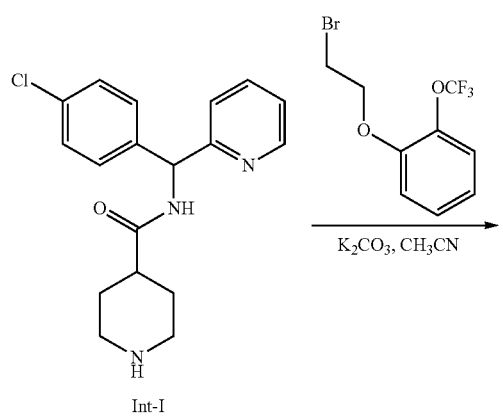

Int-I

Title compound was prepared from N-((4-chlorophenyl)(pyridin-2-yl)methyl)piperidine-4-carboxamide (0.120 g, 0.364 mmol) using the general methodology of Example-1. The crude was purified by silica gel column chromatography (2% MeOH/CH$_2$Cl$_2$ as eluent) to afford 0.1 g of N-((4-chlorophenyl)(pyridin-2-yl)methyl)-1-(2-(2-(trifluoromethoxy)phenoxy)ethyl) piperidine-4-carboxamide (52%). $^1$H NMR (500 MHz, DMSO-d$_6$): δ 8.71 (d, 1H, J=8.5 Hz), 8.52 (d, 1H, J=4.5 Hz), 7.79 (t, 1H, J=7.5 Hz,), 7.45 (d, 1H, J=8.0 Hz), 7.38-7.25 (m, 8H), 7.01 (t, 1H, J=7.5 Hz), 6.13 (t, 1H, J=8.0 Hz), 4.17-4.15 (m, 2H), 2.96 (d, 2H, J=9.5 Hz), 2.71-2.69 (m, 2H), 2.37-2.34 (m, 1H), 2.05 (t, 2H, J=11.0 Hz), 166-1.55 (m, 4H); ESI+MS: m/z 534 ([M+H]$^+$).

Synthesis of Intermediate V

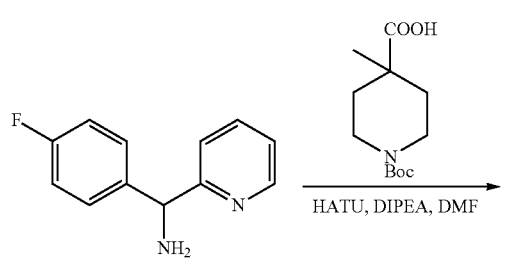

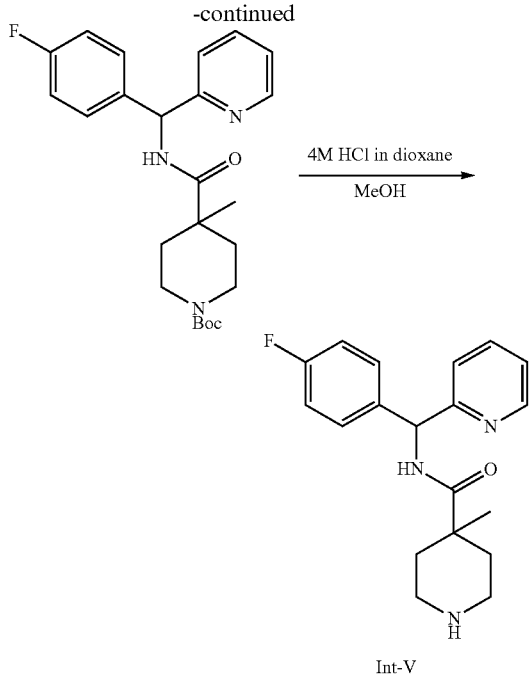

Int-V

Step 1: tert-butyl-4-(((4-fluorophenyl)(pyridin-2-yl)methyl)carbamoyl)-4-methylpiperidine-1-carboxylate

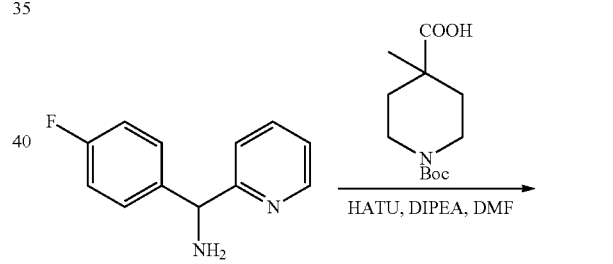

Title compound was prepared from (4-fluorophenyl)(pyridin-2-yl)methanamine (0.3 g, 1.48 mmol) using the conditions in step 5 in the general methodology of key Intermediate-I. The crude compound was purified by silica gel column chromatography to afford 0.5 g of tert-butyl 4-(((4-fluorophenyl)(pyridin-2-yl)methyl)carbamoyl)-4-methylpiperidine-1-carboxylate (Yield=79%).

Step 2: N-((4-fluorophenyl)(pyridin-2-yl)methyl)-4-methylpiperidine-4-carboxamide hydrochloride

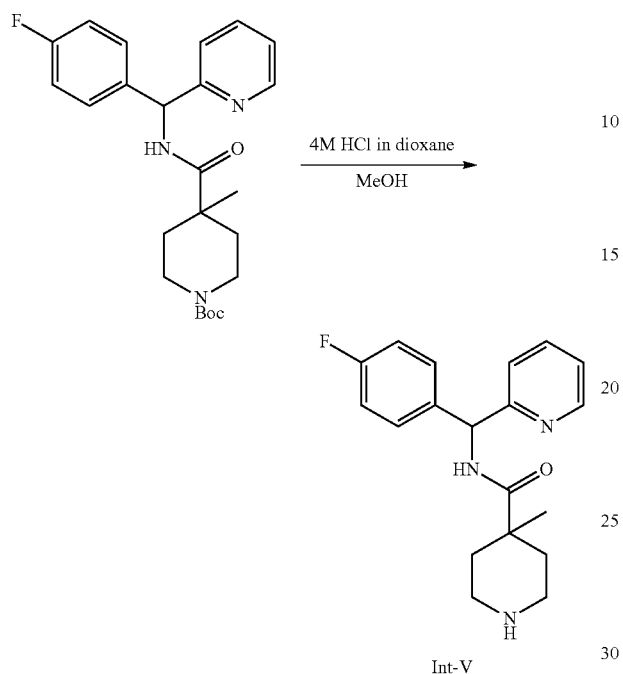

To a stirred solution of tert-butyl 4-(((4-fluorophenyl)(pyridin-2-yl)methyl)carbamoyl)-4-methylpiperidine-1-carboxylate (0.5 g, 1.17 mmol) in MeOH (2 mL) was added 4 N HCl in 1,4-dioxane (0.5 mL) at 0° C. The reaction was stirred at room temperature for 4 h. After completion, the volatiles were removed under reduced pressure. The crude was washed with ether to afford 0.2 g of N-((4-fluorophenyl)(pyridin-2-yl)methyl)-4-methylpiperidine-4-carboxamide hydrochloride (Yield=47%). ESI+MS: m/z 328.4 ([M+H]$^+$).

Example-69: N-((4(4-fluorophenyl)(pyridin-2-yl)methyl)-4-methyl-1-(2-phenoxyethyl)piperidine-4-carboxamide (69)

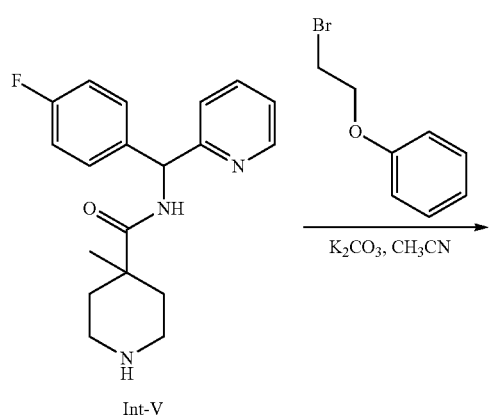

-continued

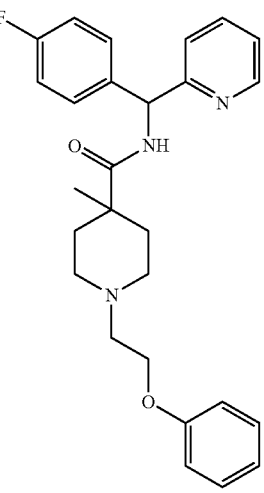

Title compound was prepared from N-((4-fluorophenyl)(pyridin-2-yl)methyl)-4-methyl piperidine-4-carboxamide hydrochloride (0.1 g, 0.305 mmol) using the general methodology of Example-1. The crude compound was purified by preparative HPLC to afford 0.090 g of N-((4-fluorophenyl)(pyridin-2-yl)methyl)-4-methyl-1-(2-phenoxyethyl)piperidine-4-carboxamide (Yield=64%). $^1$H NMR (500 MHz, CD$_3$OD): δ 8.56 (d, 1H, J=5.0 Hz), 7.80 (dt, 1H, J$_{1,2}$=2.0 Hz, J$_{1,4}$=9.0 Hz), 7.39 (d, 1H, J=8.5 Hz), 7.34-7.26 (m, 5H), 7.03 (t, 2H, J=8.0 Hz), 6.95-6.91 (m, 3H), 6.21 (s, 1H), 4.12 (t, 2H, J=5.5 Hz), 2.84-2.82 (m, 4H), 2.50-2.46 (m, 2H), 2.21-2.19 (m, 2H), 1.66-1.61 (m, 2H), 1.23 (s, 3H); ESI+MS: m/z 448 ([M+H]$^+$). Enantiomers of 69 were separated using chiral HPLC (method G) and afforded pure enantiomers 69a and 69b.

Example-70: N-((4(4-fluorophenyl)(pyridin-2-yl)methyl)-4-methyl-1-(2-(2-(trifluoromethyl) phenoxy)ethyl) piperidine-4-carboxamide (70)

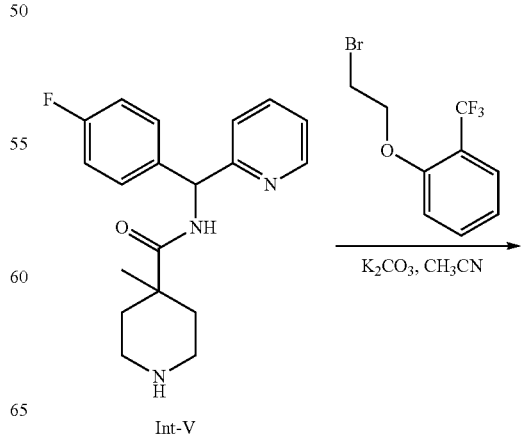

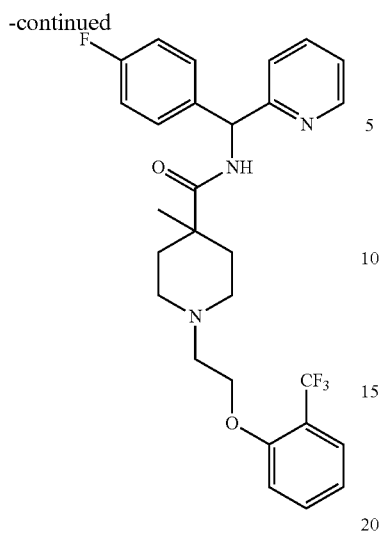

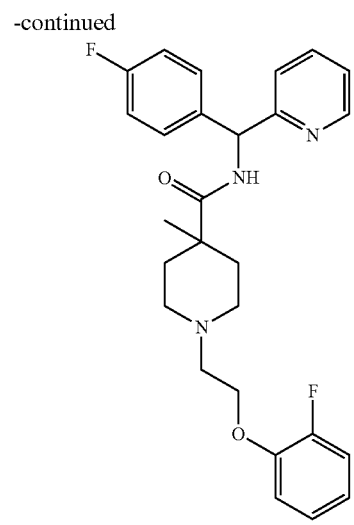

Title compound was prepared from N-((4-fluorophenyl)(pyridin-2-yl)methyl)-4-methyl piperidine-4-carboxamide hydrochloride (0.1 g, 0.305 mmol) using the general methodology of Example-1. The crude was purified by preparative HPLC to afford 0.1 g of N-((4-fluorophenyl)(pyridin-2-yl)methyl)-4-methyl-1-(2-(2-(trifluoromethyl)phenoxy)ethyl) piperidine-4-carboxamide (Yield=64%). $^1$H NMR (500 MHz, CD$_3$OD): δ 8.55 (d, 1H, J=4.5 Hz), 7.79 (dt, 1H, J$_{1,2}$=1.5 Hz, J$_{1,4}$=8.5 Hz), 7.59-7.56 (m, 2H), 7.39 (d, 1H, J=8.0 Hz), 7.33-7.27 (m, 3H), 7.17 (d, 1H, J=8.5 Hz), 7.09-7.02 (m, 3H), 6.21 (s, 1H), 4.21 (t, 2H, J=5.5 Hz), 2.89-2.85 (m, 4H), 2.51-2.49 (m, 2H), 2.21-2.18 (m, 2H), 1.64-1.59 (m, 2H), 1.22 (s, 3H); ESI+MS: m/z 516 ([M+H]$^+$). Enantiomers of 70 were separated using chiral HPLC (method B) and afforded pure enantiomers 70a and 70b.

Example-71: 1-(2-(2-fluorophenoxy)ethyl)-N-((4-fluorophenyl)(pyridin-2-yl)methyl)-4-methylpiperidine-4-carboxamide (71)

Title compound was prepared from N-((4-fluorophenyl)(pyridin-2-yl)methyl)-4-methyl piperidine-4-carboxamide hydrochloride (0.3 g, 0.825 mmol) using the general methodology of Example-1, and afforded 150 mg of 1-(2-(2-fluorophenoxy)ethyl)-N-((4-fluorophenyl)(pyridin-2-yl)methyl)-4-methylpiperidine-4-carboxamide (Yield=51%). $^1$H NMR (400 MHz, DMSO-d$_6$): δ 8.52 (d, 1H, J=4.0 Hz), 8.33 (d, 1H, J=6.8 Hz), 7.80-7.76 (m, 1H), 7.44 (d, 1H, J=8.0 Hz), 7.34-7.26 (m, 3H), 7.21-7.09 (m, 5H), 6.95-6.92 (m, 1H), 6.21 (d, 1H, J=7.6 Hz), 4.15-4.13 (m, 2H), 2.72-2.71 (m, 4H), 2.34-2.32 (m, 2H), 2.15-2.05 (m, 2H), 1.50-1.45 (m, 2H), 1.14 (s, 3H); ESI+MS: m/z: 466 ([M+H]$^+$).

Synthesis of Intermediate VI

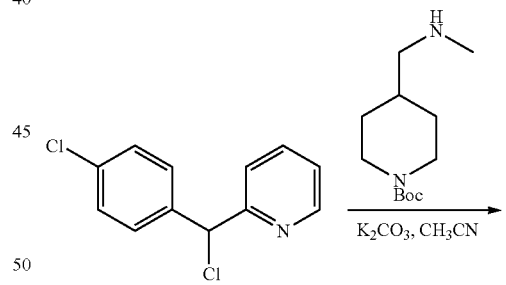

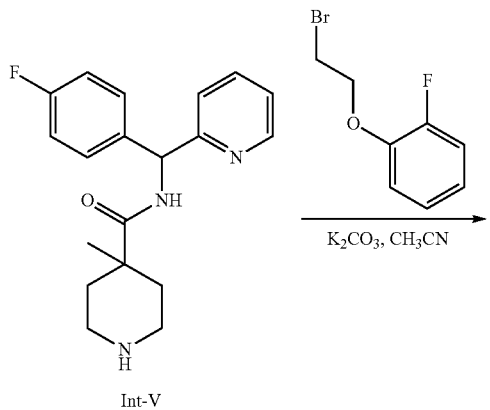

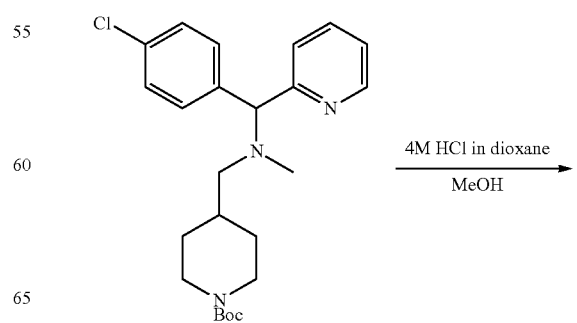

202

1-(4-chlorophenyl)-N-methyl-N-(piperidin-4-ylmethyl)-1-(pyridin-2-yl)methanamine hydrochloride

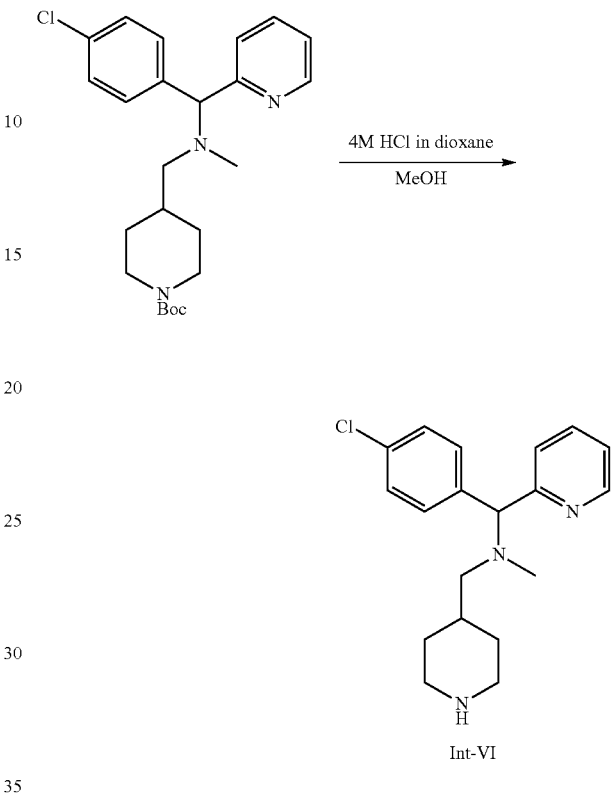

Title compound was prepared from tert-butyl 4-((((4-chlorophenyl)(pyridin-2-yl)methyl)(methyl)amino)methyl)piperidine-1-carboxylate (0.45 g, 1.04 mmol) using the general methodology of step 2 of the synthesis of intermediate-V to afford 0.3 g of 1-(4-chlorophenyl)-N-methyl-N-(piperidin-4-ylmethyl)-1-(pyridin-2-yl)methanamine hydrochloride (Yield=78%).

Example-72: 1-(4-chlorophenyl)-N-((4(1-(2-(2-fluorophenoxy)ethyl)piperidin-4-yl)methyl)-N-methyl-1-(pyridin-2-yl)methanamine (72)

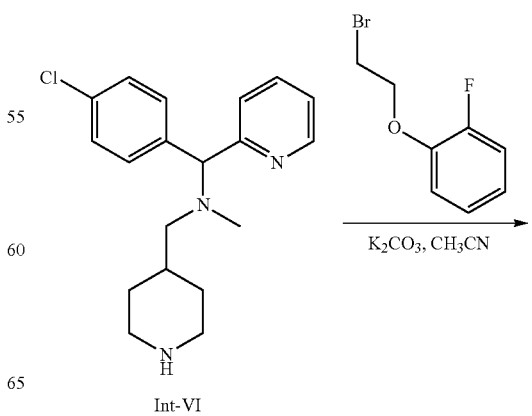

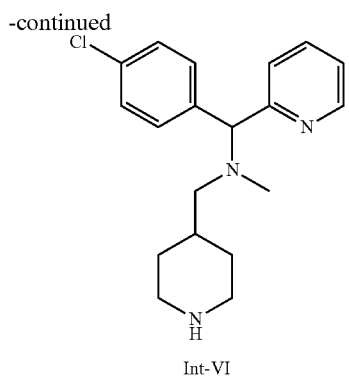

tert-butyl 4-((((4-chlorophenyl)(pyridin-2-yl)methyl)(methyl)amino)methyl)piperidine-1-carboxylate Title compound was prepared from 2-(chloro(4-chlorophenyl)methyl)pyridine (0.3 g, 1.26 mmol) and tert-butyl 4-((methylamino)methyl)piperidine-1-carboxylate (0.288 g, 1.26 mmol, 1 equiv) using the general methodology of Example-1. Purification using silica gel column chromatography (40% EtOAc/Hexanes as eluent) afforded 0.450 g of tert-butyl 4-((((4-chlorophenyl)(pyridin-2-yl)methyl)(methyl)amino)methyl)piperidine-1-carboxylate (Yield=83%).

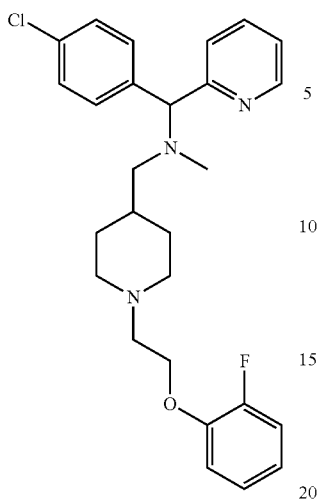

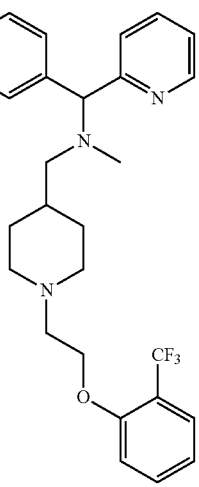

Title compound was prepared from 1-(4-chlorophenyl)-N-methyl-N-(piperidin-4-ylmethyl)-1-(pyridin-2-yl)methanamine hydrochloride (0.2 g, 0.546 mmol) using the general methodology of Example-1. The crude compound was purified by preparative HPLC to afford 0.050 g of 1-(4-chlorophenyl)-N-((1-(2-(2-fluorophenoxy)ethyl)piperidin-4-yl)methyl)-N-methyl-1-(pyridin-2-yl)methanamine (Yield=19%). $^1$H NMR (500 MHz, DMSO-d$_6$): δ 8.44 (d, 1H, J=4.0 Hz), 7.77-7.74 (m, 1H), 7.55 (d, 1H, J=7.5 Hz), 7.43 (d, 2H, J=8.0 Hz), 7.35 (d, 2H, J=8.5 Hz), 7.23-7.11 (m, 4H), 6.93-6.91 (m, 1H), 4.50 (s, 1H), 4.11 (t, 2H, J=6.0 Hz), 2.88 (d, 2H, J=11.5 Hz), 2.68-2.64 (m, 2H), 2.13-1.98 (m, 7H), 1.72 (d, 2H, J=11.50 Hz), 1.55-1.48 (m, 1H), 0.99-0.89 (m, 2H); ESI+MS: m/z: 468 ([M+H]$^+$). Enantiomers of 72 were separated using chiral HPLC (method K) and afforded pure enantiomers 72a and 72b.

Example-73: 1-(4-chlorophenyl)-N-methyl-1-(pyridin-2-yl)-N-((4(1-(2-(2-(trifluoromethyl) phenoxy) ethyl)piperidin-4-yl)methyl)methanamine (73)

Title compound was prepared from 1-(4-chlorophenyl)-N-methyl-N-(piperidin-4-ylmethyl)-1-(pyridin-2-yl)methanamine hydrochloride (0.15 g, 0.45 mmol) using the general methodology of Example-1 to afford 0.06 g (Yield=28%). $^1$H NMR (400 MHz, DMSO-d$_6$): δ 8.43 (d, 1H, J=5.2 Hz), 7.77-7.72 (m, 1H), 7.62-7.53 (m, 3H), 7.42 (d, 2H, J=8.4 Hz), 7.34-7.32 (m, 2H), 7.26-7.19 (m, 2H), 7.07 (t, 1H, J=7.6 Hz), 4.49 (s, 1H), 4.17 (t, 2H, J=6.0 Hz), 2.86 (d, 2H, J=11.2 Hz), 2.69-2.66 (m, 2H), 2.13-2.00 (m, 7H), 1.70 (d, 2H, J=12.0 Hz), 1.54-1.48 (m, 1H), 0.98-0.88 (m, 2H); ESI+MS: m/z: 518 ([M+H]$^+$).

Synthesis of Intermediate VII

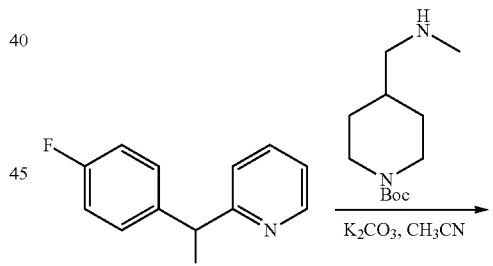

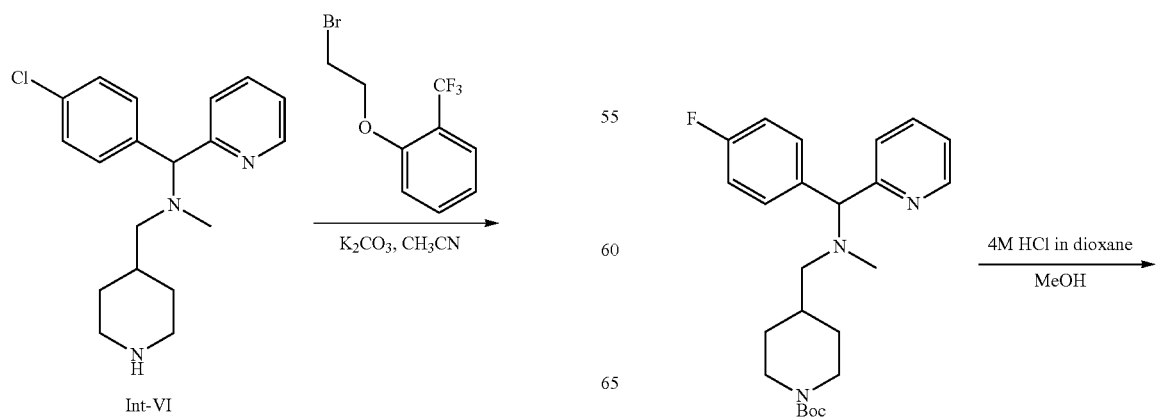

-continued

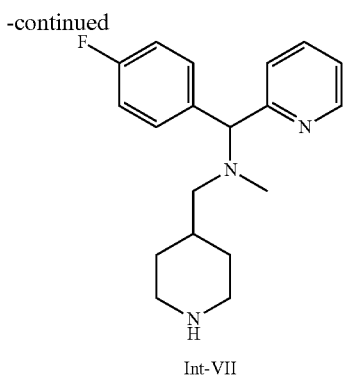
Int-VII 1-(4-fluorophenyl)-N-methyl-N-(piperidin-4-ylmethyl)-1-(p yridin-2-yl)methanamine hydrochloride (Int-VII)

1-(4-fluorophenyl)-N-methyl-N-(piperidin-4-ylmethyl)-1-(pyridin-2-yl)methanamine hydrochloride was synthesized in 2 steps using the same chemistry as described for key intermediate-VI by replacing 2-(chloro(4-chlorophenyl)methyl)pyridine by 2-(chloro(4-fluorophenyl)methyl)pyridine and afforded 450 mg of 1-(4-fluorophenyl)-N-methyl-N-(piperidin-4-ylmethyl)-1-(pyridin-2-yl)methanamine hydrochloride (Yield=89%). ESI+MS: m/z 314.4 ([M+H]$^+$).

Example-74: 1-(4-fluorophenyl)-N-methyl-N-((1-(2-phenoxyethyl)piperidin-4-yl)methyl)-1-(pyridin-2-yl)methanamine (74)

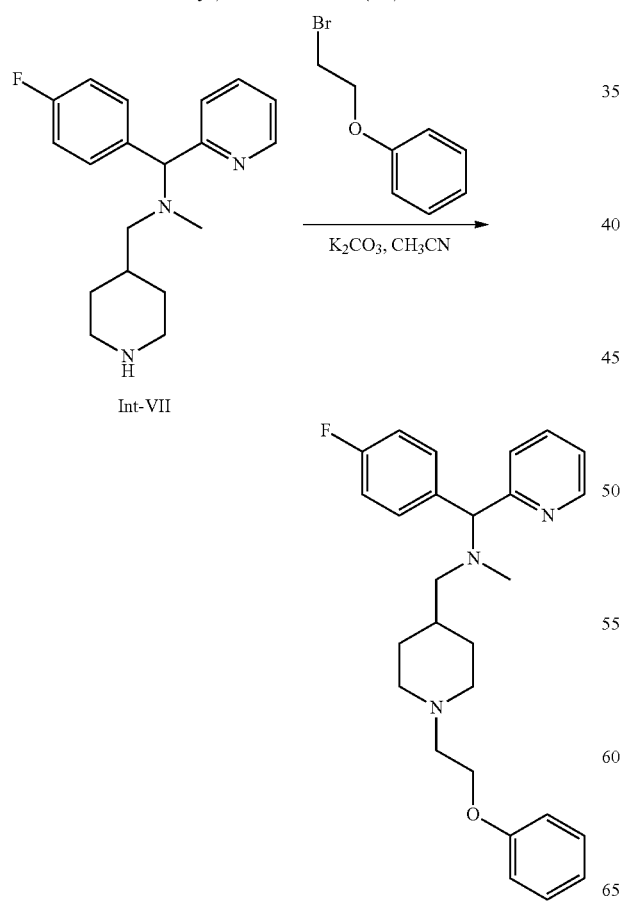

Title compound was prepared from 1-(4-fluorophenyl)-N-methyl-N-(piperidin-4-ylmethyl)-1-(pyridin-2-yl)methanamine hydrochloride (0.20 g, 0.57 mmol) using the general methodology of Example-1 to afford 0.15 g (Yield=60%). $^1$H NMR (500 MHz, DMSO-d$_6$): δ 8.44 (d, 1H, J=4.5 Hz), 7.73-7.70 (m, 1H), 7.56 (d, 1H, J=7.5 Hz), 7.43 (t, 2H, J=8.5 Hz), 7.29-7.20 (m, 3H), 7.11 (t, 2H, J=9.0 Hz), 6.92 (d, 3H, J=6.5 Hz), 4.49 (s, 1H), 4.10-4.03 (m, 2H), 2.87 (d, 2H, J=9.5 Hz), 2.65-2.63 (m, 2H), 2.14-2.11 (m, 1H), 2.06 (s, 3H), 2.03-1.99 (m, 3H), 1.73 (d, 2H, J=12.0 Hz), 1.55-1.52 (m, 1H), 0.99-0.96 (m, 2H). ESI+MS: m/z 434 ([M+H]$^+$). Enantiomers of 74 were separated using chiral HPLC (method D) and afforded pure enantiomers 74a and 74b.

Example-75: N-((4(1-(2-(2-fluorophenoxy)ethyl)piperidin-4-yl)methyl)-1-(4-fluorophenyl)-N-methyl-1-(pyridin-2-yl)methanamine (75)

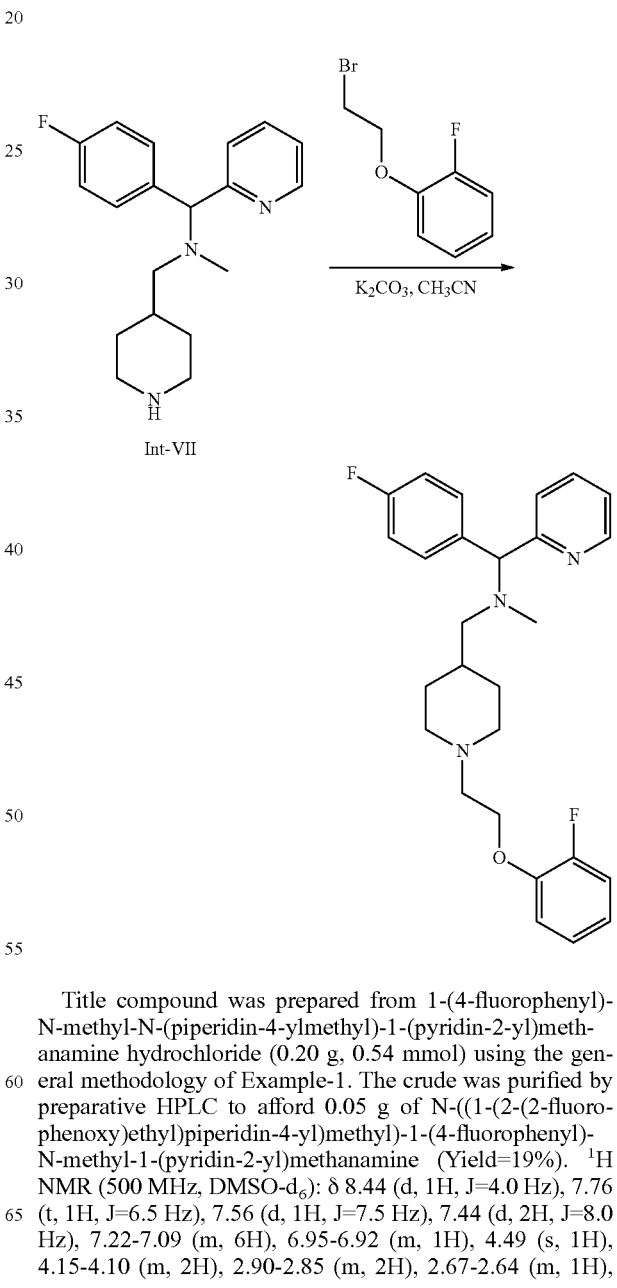

Title compound was prepared from 1-(4-fluorophenyl)-N-methyl-N-(piperidin-4-ylmethyl)-1-(pyridin-2-yl)methanamine hydrochloride (0.20 g, 0.54 mmol) using the general methodology of Example-1. The crude was purified by preparative HPLC to afford 0.05 g of N-((1-(2-(2-fluorophenoxy)ethyl)piperidin-4-yl)methyl)-1-(4-fluorophenyl)-N-methyl-1-(pyridin-2-yl)methanamine (Yield=19%). $^1$H NMR (500 MHz, DMSO-d$_6$): δ 8.44 (d, 1H, J=4.0 Hz), 7.76 (t, 1H, J=6.5 Hz), 7.56 (d, 1H, J=7.5 Hz), 7.44 (d, 2H, J=8.0 Hz), 7.22-7.09 (m, 6H), 6.95-6.92 (m, 1H), 4.49 (s, 1H), 4.15-4.10 (m, 2H), 2.90-2.85 (m, 2H), 2.67-2.64 (m, 1H), 2.14-2.01 (m, 7H), 1.72 (d, 2H, J=11.0 Hz), 1.53-1.51 (m, 1H), 0.97-0.94 (m, 2H); ESI+MS: m/z 452 ([M+H]$^+$).

Example-76: 1-(3-methoxyphenyl)-N-methyl-N-((1-(2-phenoxyethyl)piperidin-4-yl)methyl)-1-(pyridin-2-yl)methanamine (76)

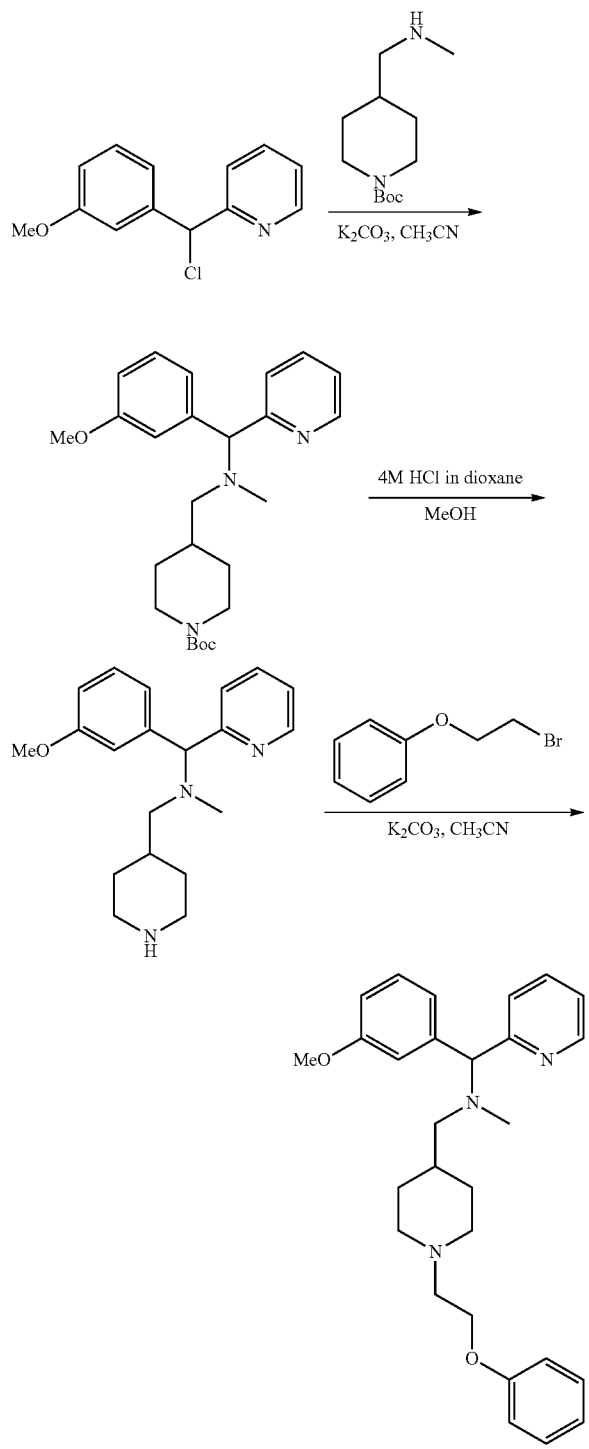

1-(3-methoxyphenyl)-N-methyl-N-(piperidin-4-ylmethyl)-1-(pyridin-2-yl)methanamine hydrochloride

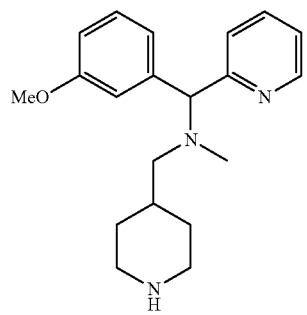 [SMILES: COc1cccc(C(c2ccccn2)N(C)CC2CCNCC2)c1]

Title compound was synthesized in 2 steps using the same chemistry as described for key intermediate-VI by replacing 2-(chloro(4-chlorophenyl)methyl)pyridine with 2-(chloro(3-methoxyphenyl)methyl)pyridine and afforded 0.8 g of 1-(4-fluorophenyl)-N-methyl-N-(piperidin-4-ylmethyl)-1-(pyridin-2-yl)methanamine hydrochloride (Yield=65%). ESI+ MS: m/z 414.5 ([M+H]$^+$).

1-(3-methoxyphenyl)-N-methyl-N-((1-(2-phenoxyethyl)piperidin-4-yl)methyl)-1-(pyridin-2-yl)methanamine

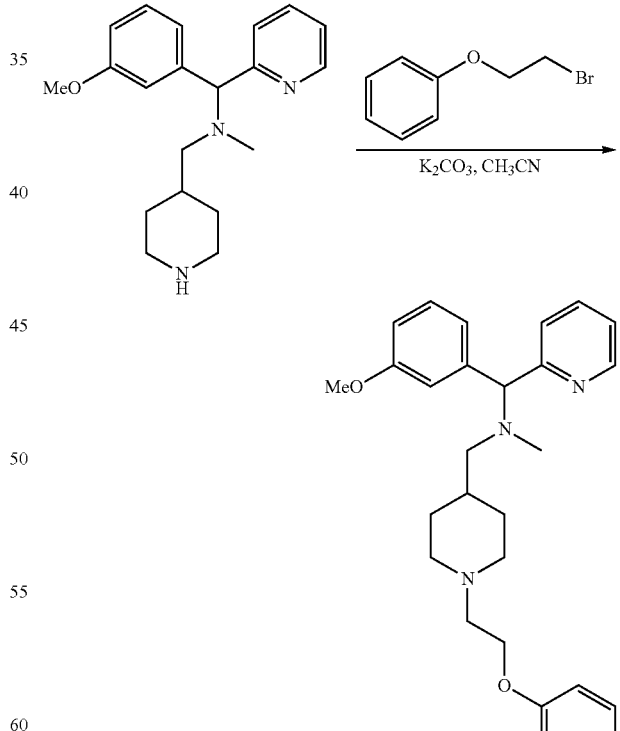

Title compound was prepared from 1-(3-methoxyphenyl)-N-methyl-N-(piperidin-4-ylmethyl)-1-(pyridin-2-yl)methanamine hydrochloride (0.150 g, 0.461 mmol) using the general methodology of Example-1 to afford 0.1 g of 1-(3- methoxyphenyl)-N-methyl-N-((1-(2-phenoxyethyl) piperidin-4-yl)methyl)-1-(pyridin-2-yl)methanamine (Yield=48%). ¹H NMR (400 MHz, CD₃OD): δ 8.38 (d, 1H, J=4.8 Hz), 7.80-7.71 (m, 2H), 7.28-7.22 (m, 3H), 7.17 (m, 1H, J=8.0 Hz), 7.03 (t, 2H, J=8.0 Hz), 6.93-6.91 (m, 3H), 6.74 (dd, 1H, J$_{1,2}$=2.4 Hz, J$_{1,3}$=8.4 Hz), 4.38 (s, 1H), 4.13 (t, 2H, J=5.6 Hz), 3.75 (s, 3H), 3.07 (d, 2H, J=8.8 Hz), 2.85 (t, 2H, J=5.2 Hz), 2.31-2.22 (m, 3H), 2.20 (s, 3H), 2.12-2.07 (m, 1H), 1.95 (d, 1H, J=13.6 Hz), 1.86 (d, 1H, J=14.0 Hz), 1.72-1.68 (m, 1H), 1.20-1.15 (m, 2H); ESI+MS: m/z 446 ([M+H]⁺). Enantiomers of 76 were separated using chiral HPLC (method D) and afforded pure enantiomers 76a and 76b.

Example-77: N-((4(1-(2-(2-fluorophenoxy)ethyl) piperidin-4-yl)methyl)-1-(3-methoxyphenyl)-N-methyl-1-(pyridin-2-yl)methanamine (77)

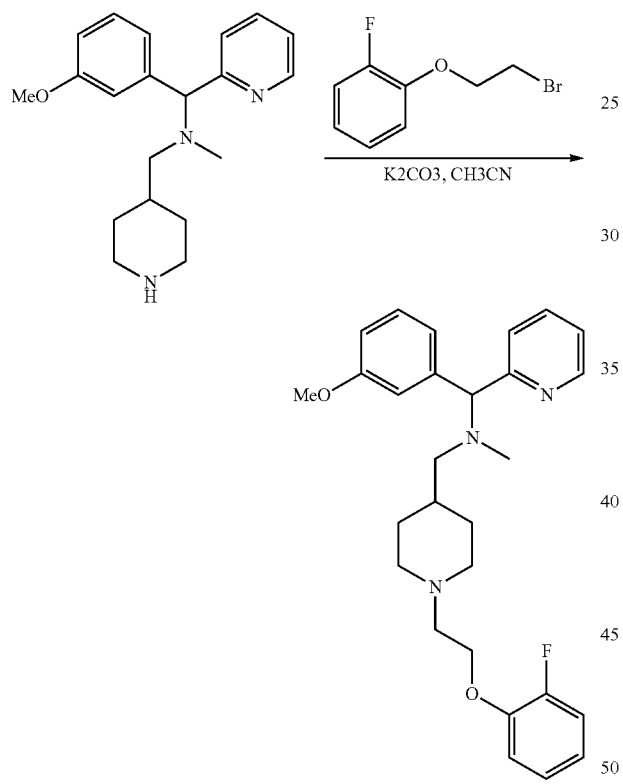

Title compound was prepared from 1-(3-methoxyphenyl)-N-methyl-N-(piperidin-4-ylmethyl)-1-(pyridin-2-yl)methanamine hydrochloride (0.150 g, 0.414 mmol) using the general methodology of Example-1. The crude compound was purified using silica gel column chromatography (2% MeOH/CH₂Cl₂ as eluent) to afford 0.120 g of N-((1-(2-(2-fluorophenoxy)ethyl)piperidin-4-yl)methyl)-1-(3-methoxyphenyl)-N-methyl-1-(pyridin-2-yl)methanamine (Yield=60%). ¹HNMR (400 MHz, DMSO-d₆): δ 8.41 (d, 1H, J=4.0 Hz), 7.73 (dt, 1H, J$_{1,2}$=2.0 Hz, J$_{1,4}$=9.6 Hz), 7.56 (d, 1H, J=8.0 Hz), 7.21-7.08 (m, 5H), 6.98-6.93 (m, 3H), 6.77-6.74 (m, 1H), 4.40 (s, 1H), 4.12-4.11 (m, 2H), 3.70 (s, 3H), 2.89-2.88 (m, 2H), 2.72-2.71 (m, 1H), 2.70-2.65 (m, 1H), 2.17-2.12 (m, 1H), 2.03-2.00 (m, 6H), 1.80-1.73 (m, 2H), 1.57-1.53 (m, 1H), 0 99-0.95 (m, 2H); ESI+MS: m/z 463 ([M+H]⁺). Enantiomers of 77 were separated using chiral HPLC (method K) and afforded pure enantiomers 77a and 77b.

Example-78: 1-(4-fluorophenyl)-N-((1-(2-phenoxyethyl)piperidin-4-yl)methyl)-1-(pyridin-2-yl) methanamine (78)

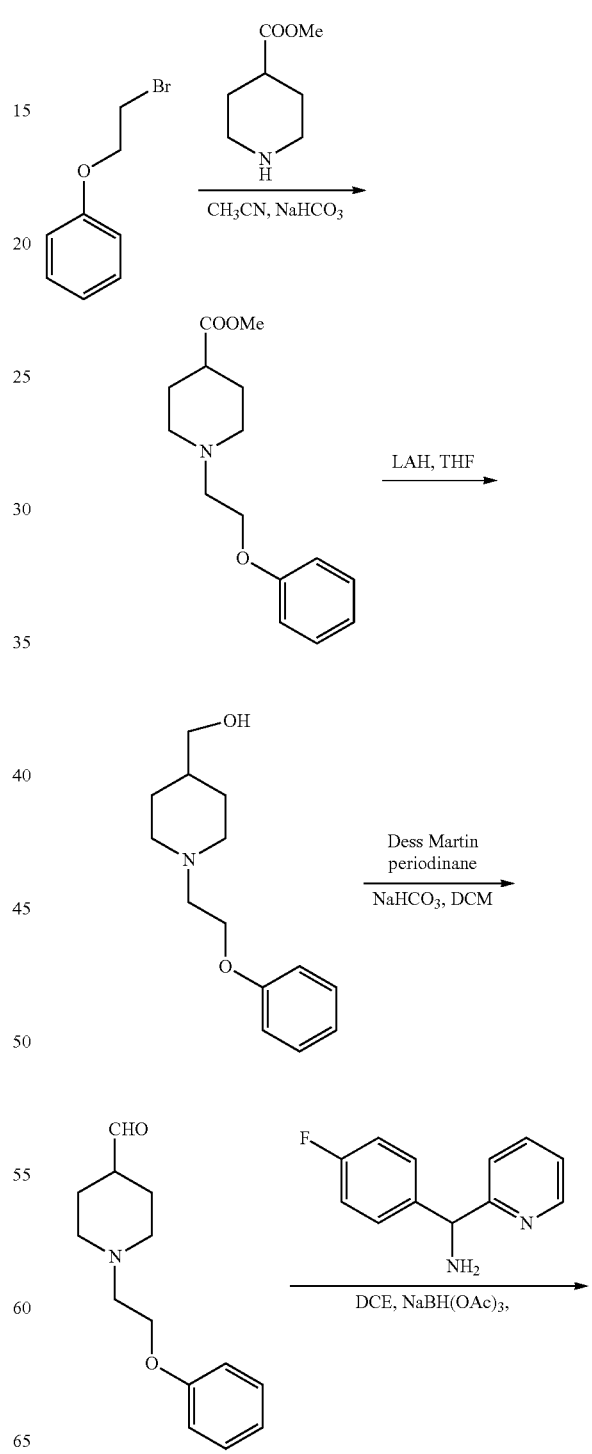

-continued

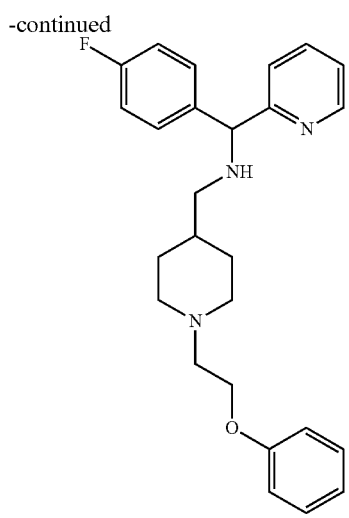

Step 1: Methyl 1-(2-phenoxyethyl)piperidine-4-carboxylate

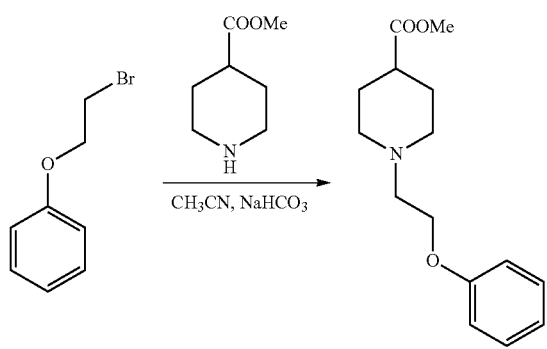 [SMILES: BrCCOc1ccccc1 ; COC(=O)C1CCNCC1 ; COC(=O)C1CCN(CCOc2ccccc2)CC1]

Title compound was prepared from (2-bromoethoxy)benzene (1.5 g, 7.46 mmol) using the general methodology of step 1 in the synthesis of key intermediate III and afforded 1 g of methyl 1-(2-phenoxyethyl)piperidine-4-carboxylate (Yield=51%).

Step 2: (1-(2-Phenoxyethyl)piperidin-4-yl)methanol

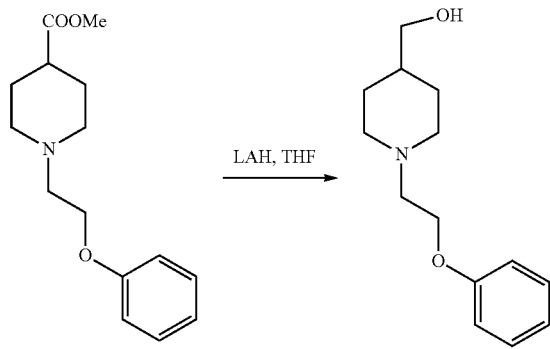 [SMILES: COC(=O)C1CCN(CCOc2ccccc2)CC1 ; OCC1CCN(CCOc2ccccc2)CC1]

To a solution of methyl 1-(2-phenoxyethyl) piperidine-4-carboxylate (1 g, 3.80 mmol) in THF at 0° C. was added lithium aluminium hydride (0.216 g, 5.7 mmol, 1.5 equiv.) portionwise over a period of 10 minutes and then the reaction was maintained at RT for 2 h. After completion, the reaction mixture was quenched with sat.Na$_2$SO$_4$ and extracted with ethyl acetate. The organic layer was dried over anhydrous Na$_2$SO$_4$, filtered and concentrated under reduced pressure to afford 0.8 g of (1-(2-phenoxyethyl) piperidin-4-yl)methanol (Yield=90%). ESI+MS: m/z: 236.2 ([M+H]$^+$).

Step 3: 1-(2-phenoxyethyl)piperidine-4-carbaldehyde

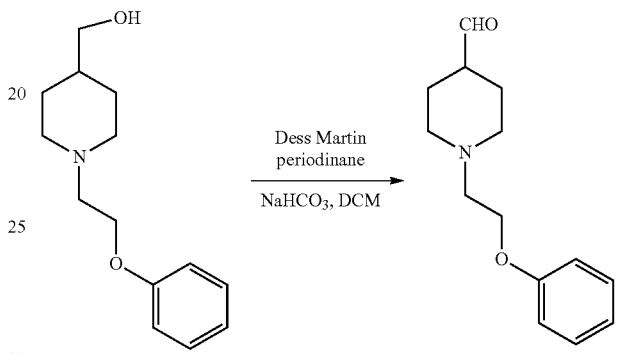

To a stirred solution of (1-(2-phenoxyethyl)piperidin-4-yl)methanol (0.6 g, 2.55 mmol) in DCM (5 mL) were added Dess-Martin periodinane (1.62 g, 3.82 mmol, 1.5 equiv) and sodium hydrogen carbonate (0.428 g, 5.10 mmol, 2 equiv) at 0° C. The reaction mixture was stirred at room temperature for 16 h. After completion, the reaction mass was quenched with sat. sodium thiosulphate and extracted with EtOAc. The combined organic extract was washed with brine, filtered and dried over sodium sulphate. The solvent was removed under reduced pressure. The crude residue was purified by column chromatography eluting with 10% EtOAc in hexane to afford 0.3 g of 1-(2-phenoxyethyl) piperidine-4-carbaldehyde (Yield=50%).

Step 4: 1-(4-fluorophenyl)-N-((1-(2-phenoxyethyl)piperidin-4-yl)methyl)-1-(pyridin-2-yl) methanamine

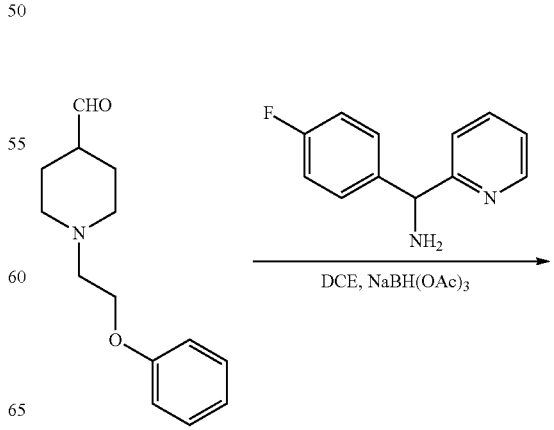

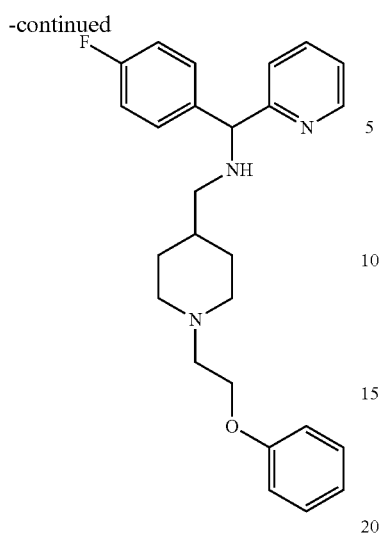

Title compound was prepared from reductive amination of 1-(2-phenoxyethyl)piperidine-4-carbaldehyde (0.150 g, 0.643 mmol) using the general methodology described in Example-59. The crude residue was purified by Prep HPLC purification to afford 0.025 g of 1-(4-fluorophenyl)-N-((1-(2-phenoxyethyl)piperidin-4-yl)methyl)-1-(pyridin-2-yl)methanamine (Yield=12%). $^1$H NMR (400 MHz, CD$_3$OD): δ 8.49 (d, 1H, J=4.4 Hz), 7.76 (dt, 1H, J$_{1,2}$=1.6 Hz, J$_{1,4}$=9.2 Hz), 7.48-7.42 (m, 3H), 7.28-7.23 (m, 3H), 7.01 (t, 2H, J=6.8 Hz), 6.93-6.90 (m, 3H), 4.91 (s, 1H), 4.13 (t, 2H, J=5.6 Hz), 3.08 (d, 2H, J=11.2 Hz), 2.85 (t, 2H, J=5.6 Hz), 2.47-2.38 (m, 2H), 2.23 (t, 2H, J=11.6 Hz), 1.84-1.80 (m, 2H), 1.61-1.55 (m, 1H), 1.34-1.24 (m, 2H); ESI+MS: m/z: 420.5 ([M+H]$^+$). Enantiomers of 78 were separated using chiral HPLC (method B) and afforded pure enantiomers 78a and 78b.

Example-79: 1-(4-chlorophenyl)-N-methyl-N-((1-(2-phenoxyethyl)piperidin-4-yl)methyl)-1-(pyridin-2-yl)methanamine (79)

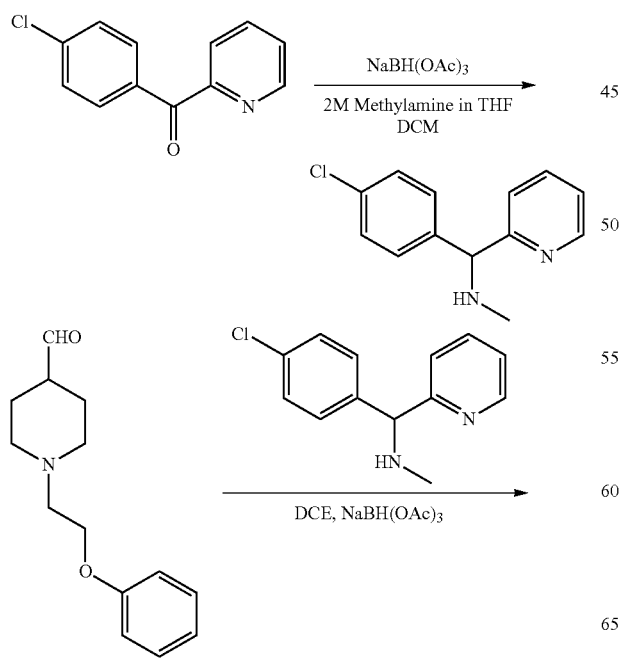

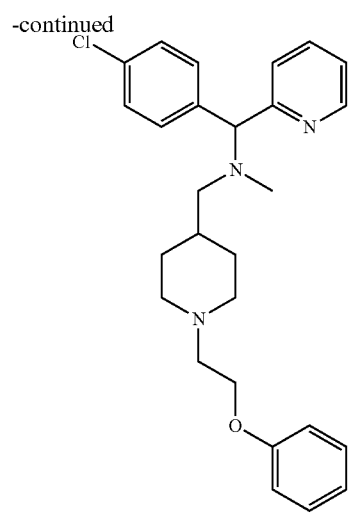

1-(4-chlorophenyl)-N-methyl-1-(pyridin-2-yl)methanamine (SBF-MA1304-025)

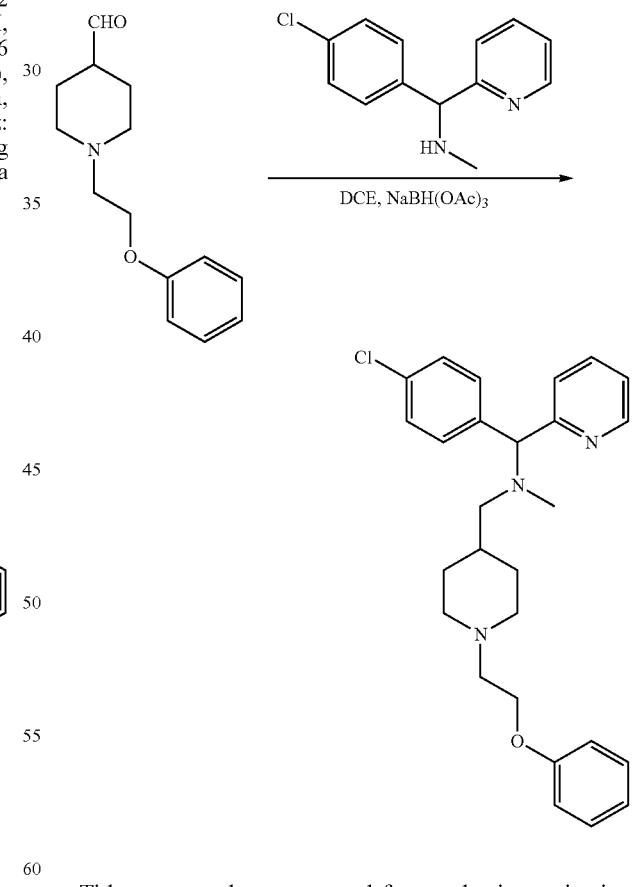

Title compound was prepared from reductive amination of (4-chlorophenyl)(pyridin-2-yl)methanone (1 g, 4.59 mmol) using the general methodology of Example-59. The crude compound was purified by column chromatography eluting with 5% Methanol in DCM to afforded 0.535 g of 1-(4-chlorophenyl)-N-methyl-1-(pyridin-2-yl)methanamine (Yield=50%).

1-(4-chlorophenyl)-N-methyl-N-((1-(2-phenoxyethyl)piperidin-4-yl) methyl)-1-(pyridin-2-yl)methanamine Title compound was prepared from reductive amination of 1-(2-phenoxyethyl)piperidine-4-carbaldehyde (0.130 g, 0.559 mmol) and 1-(4-chlorophenyl)-N-methyl-1-(pyridin-2-yl) methanamine (0.1 g, 0.430 mmol, 1 equiv) using the general methodology of Example-59. The crude residue was purified by prep HPLC purification to furnish 0.050 g of 1-(4-chlorophenyl)-N-methyl-N-((1-(2-phenoxyethyl)piperidin-4-yl)methyl)-1-(pyridin-2-yl)methanamine (Yield=26%). $^1$H NMR (400 MHz, CD$_3$OD): δ 8.39 (dd, 1H, $J_{1,2}$=0.8 Hz, $J_{1,3}$=4.8 Hz), 7.79 (dt, 1H, $J_{1,2}$=1.6 Hz, $J_{1,4}$=9.61 Hz), 7.70 (d, 1H, J=8.0 Hz), 7.45-7.43 (m, 2H), 7.30-7.23 (m, 5H), 6.93-6.90 (m, 3H), 4.44 (s, 1H), 4.12 (t, 2H, J=5.6 Hz), 3.05-3.02 (m, 2H), 2.82 (t, 2H, J=5.2 Hz), 2.25-2.09 (m, 7H), 1.92-1.84 (m, 2H), 1.70-1.64 (m, 1H), 1.19-1.01 (m, 2H); Ion trap: m/z: 450.8 ([M+H]$^+$). Enantiomers of 79 were separated using chiral HPLC (method H) and afforded pure enantiomers 79a and 79b.

Example-80: 1-(3-methoxyphenyl)-N-((1-(2-phenoxyethyl)piperidin-4-yl)methyl)-1-(pyridin-2-yl)methanamine (80)

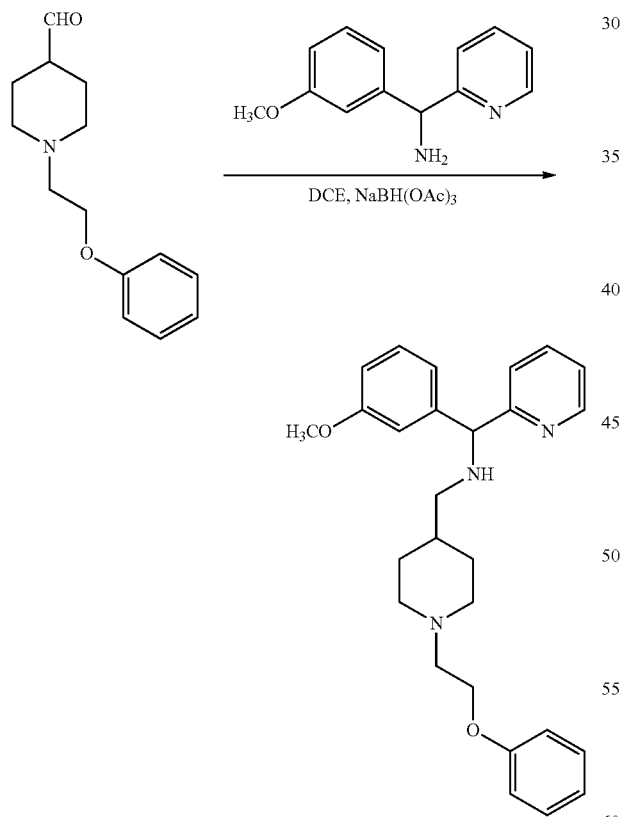

Title compound was prepared from reductive amination of 1-(2-phenoxyethyl)piperidine-4-carbaldehyde (0.142 g, 0.607 mmol) and (3-methoxyphenyl)(pyridin-2-yl)methanamine (0.1 g, 0.467 mmol, 1 equiv) using the general methodology of Example-59. The crude material was purified by prep HPLC purification to afford 0.080 g of 1-(3-methoxyphenyl)-N-((1-(2-phenoxyethyl)piperidin-4-yl)methyl)-1-(pyridin-2-yl)methanamine (Yield=40%).

$^1$H NMR (400 MHz, CD$_3$OD): δ 8.49-8.47 (m, 1H), 7.75 (dt, 1H, $J_{1,2}$=1.6 Hz, $J_{1,4}$=9.6 Hz), 7.47 (d, 1H, J=8.0 Hz), 7.28-7.18 (m, 4H), 7.01-7.0 (m, 1H), 6.99-6.97 (m, 1H), 6.92-6.89 (m, 3H), 6.80-6.77 (m, 1H), 4.85 (s, 1H), 4.11 (t, 2H, J=5.6 Hz), 3.76 (s, 3H), 3.04 (d, 2H, J=11.6 Hz), 2.80 (t, 2H, J=5.6 Hz), 2.48-2.38 (m, 2H), 2.17 (t, 2H, J=12.0 Hz), 1.82-1.79 (m, 2H), 1.61-1.53 (m, 1H), 1.34-1.31 (m, 1H), 1.29-1.23 (m, 1H); ESI+MS: m/z: 432.6 ([M+H]$^+$).

Example-81: 1-(4-chlorophenyl)-1-(2-fluorophenyl)-N-((1-(2-phenoxyethyl)piperidine-4-yl) methyl)methanamine (81)

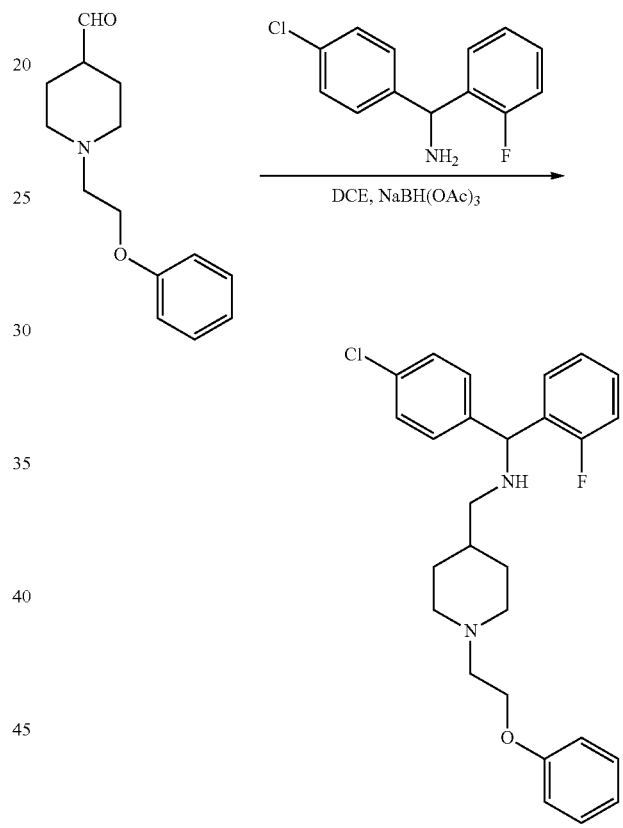

Title compound was prepared from reductive amination of 1-(2-phenoxyethyl)piperidine-4-carbaldehyde (0.129 g, 0.552 mmol) and (4-chlorophenyl)(2-fluorophenyl)methanamine (0.1 g, 0.424 mmol, 1 equiv) using the general methodology of Example-59. The crude residue was purified by prep HPLC purification to afford 0.1 g of 1-(4-chlorophenyl)-1-(2-fluorophenyl)-N-((1-(2-phenoxyethyl)piperidin-4-yl)methyl)methanamine (Yield=35%). $^1$H NMR (500 MHz, DMSO-D$_6$): δ 7.59 (t, 1H, J=6.4 Hz), 7.39-7.34 (m, 4H) 7.28-7.24 (m, 3H), 7.20-7.09 (m, 2H), 6.93-6.90 (m, 3H), 5.02 (s, 1H), 4.04 (t, 2H, J=6.0 Hz), 2.89 (d, 2H, J=11.0 Hz), 2.65 (t, 2H, J=5.5 Hz), 2.50-2.49 (m, 1H), 2.30-2.29 (m, 2H), 1.98 (t, 2H, J=11.0 Hz), 1.70 (d, 2H, J=12.0 Hz), 1.41-1.34 (m, 1H), 1.14-1.10 (m, 2H); ESI+MS: m/z: 453.5 ([M+H]$^+$). Enantiomers of 81 were separated using chiral HPLC (method C) and afforded pure enantiomers 81a and 81b.

217

Example-82: 1-(2-(benzo[d]thiazol-6-yloxy)ethyl)-N-((3-methoxyphenyl)(pyridin-2-yl)methyl) piperidine-4-carboxamide (82)

218

Example-83: N-(bis(4-fluorophenyl)methyl)-1-(2-(2-chlorophenoxy)ethyl)piperidine-4-carboxamide (83)

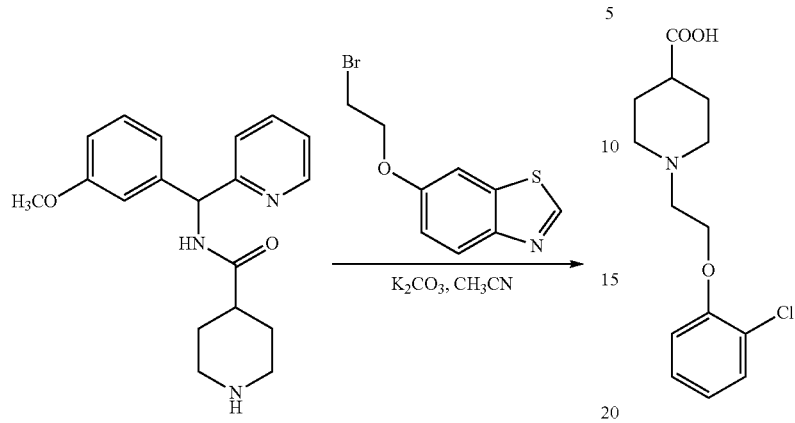

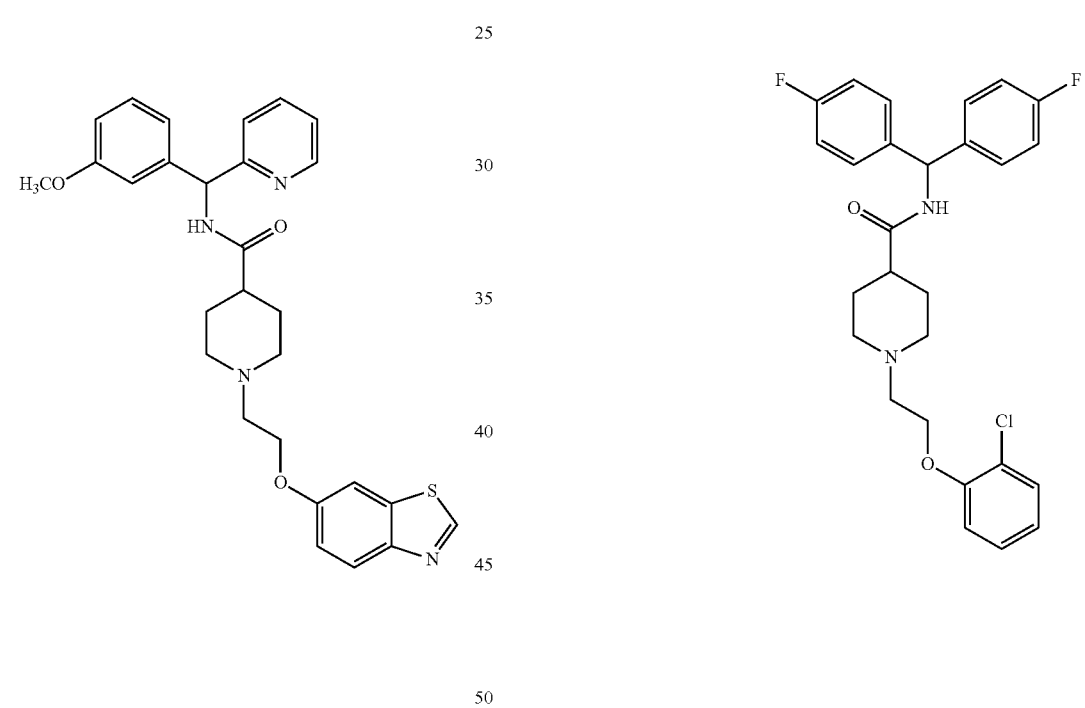

Title compound was prepared from N-((3-methoxyphenyl)(pyridin-2-yl)methyl)piperidine-4-carboxamide (100 mg, 0.307 mmol) using the general methodology of Example-1. The crude residue was purified by prep HPLC to afford 0.060 g of 1-(2-(benzo[d]thiazol-6-yloxy)ethyl)-N-((3-methoxyphenyl)(pyridin-2-yl)methyl)piperidine-4-carboxamide (Yield=38%). $^1$H NMR (400 MHz, CD$_3$OD): δ 9.04 (s, 1H), 8.52-8.50 (m, 1H), 7.93 (d, 1H, J=8.8 Hz), 7.78 (dt, 1H, $J_{1,2}$=2.0 Hz, $J_{1,4}$=9.6 Hz), 7.60 (d, 1H, J=2.4 Hz), 7.39 (d, 1H, J=8.0 Hz), 7.31-7.28 (m, 1H), 7.23-7.16 (m, 2H), 6.84-6.79 (m, 3H), 6.13 (s, 1H), 4.22 (t, 2H, J=5.6 Hz), 3.74 (s, 3H), 3.13-3.08 (m, 2H), 2.86 (t, 2H, J=5.2 Hz), 2.46-2.39 (m, 1H), 2.28-2.22 (m, 2H), 1.89-1.77 (m, 4H); Ion trap: m/z:503.7 ([M+H]$^+$).

Title compound was prepared from coupling of 1-(2-(2-chlorophenoxy)ethyl)piperidine-4-carboxylic acid (0.233 g, 0.821 mmol, 1.2 equiv) and bis(4-fluorophenyl)methanamine (0.150 g, 0.684 mmol, 1 equiv) using the conditions in step 5 in the general methodology of key Intermediate-I. The crude compound was purified by prep HPLC purification to furnish 0.012 g of N-(bis(4-fluorophenyl)methyl)-1-(2-(2-chlorophenoxy)ethyl)piperidine-4-carboxamide (Yield=4%). $^1$H NMR (400 MHz, CD$_3$OD): δ 7.34 (dd, 1H, $J_{1,2}$=1.6 Hz, $J_{1,3}$=8.0 Hz), 7.26-7.22 (m, 5H), 7.07-7.02 (m, 5H), 6.91 (dt, 1H, $J_{1,2}$=1.2 Hz, $J_{1,4}$=8.8 Hz), 6.16 (s, 1H), 4.02 (t, 2H, J=5.6 Hz), 3.18 (d, 2H, J=12.0 Hz), 2.91 (t, 2H, J=5.6 Hz), 2.41-2.31 (m, 3H), 1.89-1.80 (m, 4H); Ion trap: m/z: 485.5 ([M+H]$^+$).

Example-84: N-(bis(2-fluorophenyl)methyl)-1-(2-(2-chlorophenoxy)ethyl)piperidine-4-carboxamide (84)

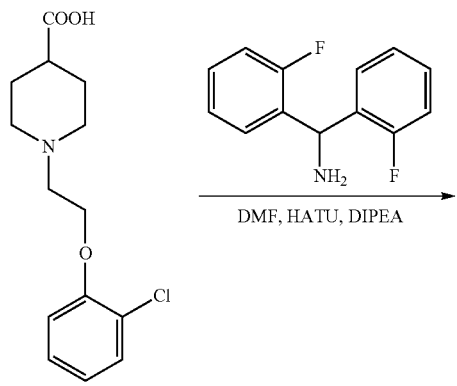

Example-85: 1-(2-(2-chlorophenoxy)ethyl)-N-((2-fluorophenyl)(4-fluorophenyl)methyl) piperidine-4-carboxamide (85)

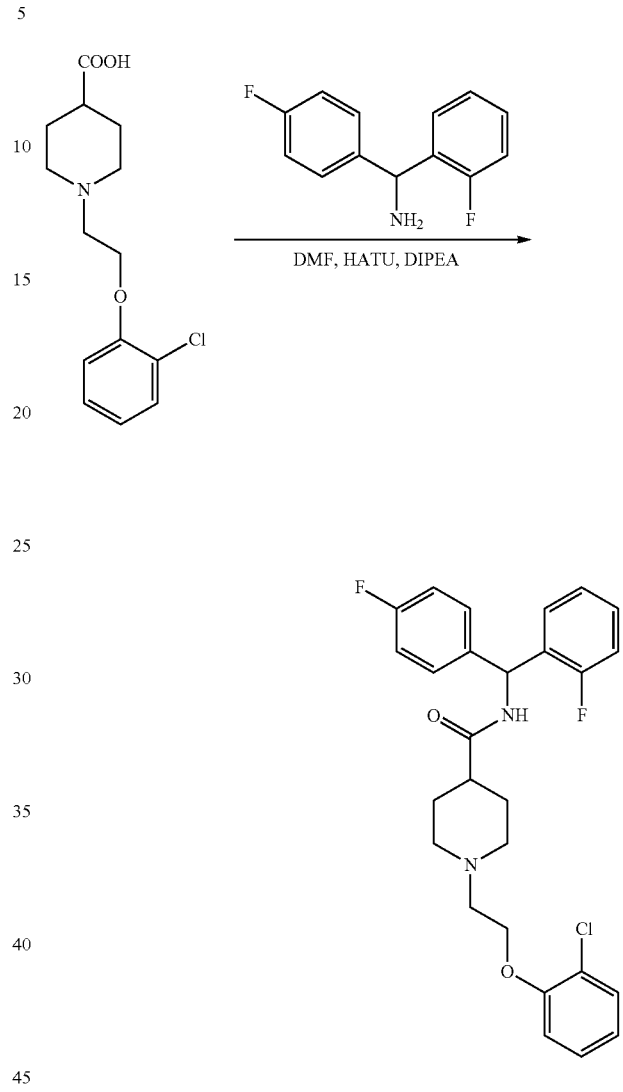

Title compound was prepared from coupling of 1-(2-(2-chlorophenoxy)ethyl)piperidine-4-carboxylic acid (0.194 g, 0.684 mmol, 1.2 equiv) and bis(2-fluorophenyl)methanamine (0.125 g, 0.570 mmol, 1 equiv) using the conditions in step 5 in the general methodology of key Intermediate-I. The crude compound was purified by silica gel column chromatography (2% MeOH/DCM as eluent) afforded 0.030 g of N-(bis(2-fluorophenyl)methyl)-1-(2-(2-chlorophenoxy)ethyl) piperidine-4-carboxamide (Yield=10%). $^1$H NMR (400 MHz, CD$_3$OD): δ 7.41 (dd, 1H, $J_{1,2}$=1.6 Hz, $J_{1,3}$=7.6 Hz), 7.36-7.29 (m, 3H), 7.22 (dt, 2H, $J_{1,2}$=1.2 Hz, $J_{1,4}$=9.2 Hz), 7.18-7.09 (m, 5H), 7.02 (dt, 1H, $J_{1,2}$=1.2 Hz, $J_{1,4}$=8.8 Hz), 6.66 (m, 1H), 4.44 (t, 2H, J=4.8 Hz), 3.81-3.80 (m, 2H), 3.64 (t, 2H, J=4.8 Hz), 3.31-3.30 (m, 2H), 2.70-2.69 (m, 1H), 2.10-2.09 (m, 4H); ESI+MS: m/z: 485.4 ([M+H]$^+$).

Title compound was prepared from coupling of 1-(2-(2-chlorophenoxy)ethyl)piperidine-4-carboxylic acid (0.233 g, 0.821 mmol, 1.2 equiv) and (2-fluorophenyl)(4-fluorophenyl)methanamine (0.150 g, 0.684 mmol, 1 equiv) using the conditions in step 5 in the general methodology of key Intermediate-I. The crude compound was purified by silica gel column chromatography (2% MeOH/DCM as eluent) afforded 0.050 g of 1-(2-(2-chlorophenoxy)ethyl)-N-((2-fluorophenyl)(4-fluorophenyl)methyl)piperidine-4-carboxamide (Yield=15%). $^1$H NMR (500 MHz, DMSO-d$_6$): δ 8.69 (d, 1H, J=8.0 Hz), 7.40-7.12 (m, 12H), 6.92 (t, 1H, J=7.5 Hz), 6.31 (d, 1H, J=8.5 Hz), 4.13 (t, 2H, J=6.0 Hz), 2.97-2.96 (m, 2H), 2.71-2.69 (m, 2H), 2.27-2.23 (m, 1H), 2.07-2.03 (m, 2H), 1.63-1.51 (m, 4H); ESI+MS: m/z: 485.5 ([M+H]$^+$).

Example-86: 1-(2-(2-chlorophenoxy)ethyl)-N-((2-fluorophenyl)(3-methoxyphenyl) methyl) piperidine-4-carboxamide (86)

Example-87: 1-(4-chlorophenyl)-N-((1-(2-(2-fluorophenoxy)ethyl)piperidin-4-yl)methyl)-1-(2-fluorophenyl)methanamine (87)

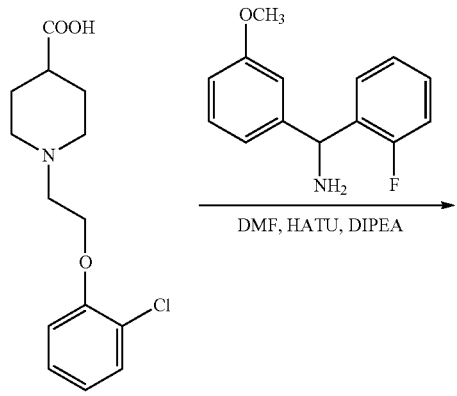

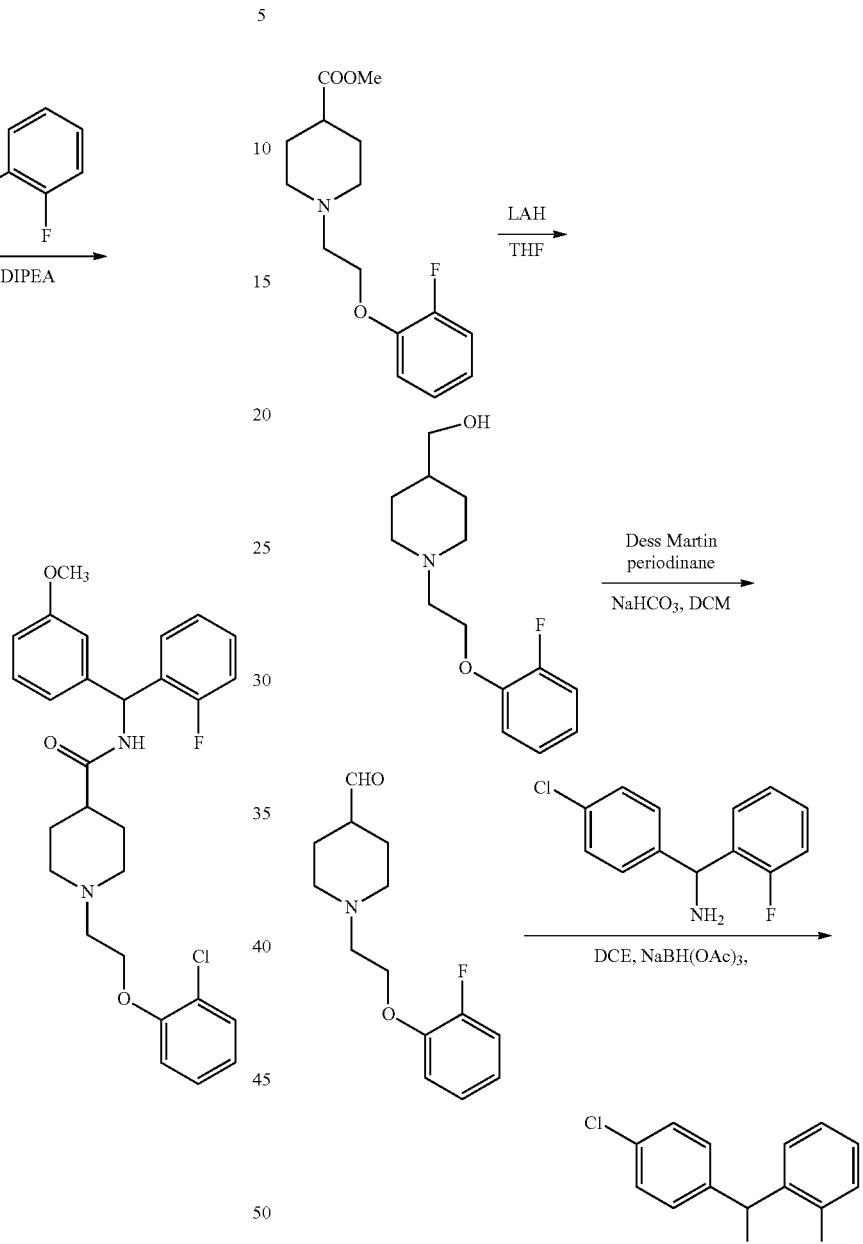

Title compound was prepared from coupling of 1-(2-(2-chlorophenoxy)ethyl)piperidine-4-carboxylic acid (0.147 g, 0.519 mmol, 1.2 equiv) and (2-fluorophenyl)(3-methoxyphenyl) methanamine (0.100 g, 0.432 mmol, 1 equiv) using the conditions in step 5 in the general methodology of key Intermediate-I. The crude compound was purified by prep HPLC purification to furnish 0.040 g of 1-(2-(2-chlorophenoxy)ethyl)-N-((2-fluorophenyl)(3-methoxyphenyl) methyl)piperidine-4-carboxamide (Yield=18%). $^1$H NMR (400 MHz, CD$_3$OD): δ 7.35-7.32 (m, 2H), 7.30-7.21 (m, 3H), 7.17-7.11 (m, 1H), 7.08-7.05 (m, 2H), 6.91 (dt, 1H, $J_{1,2}$=1.2 Hz, $J_{1,4}$=8.8 Hz), 6.84-6.77 (m, 3H), 6.40 (s, 1H), 4.20 (t, 2H, J=5.2 Hz), 3.74 (s, 3H), 3.18-3.15 (m, 2H), 2.89 (t, 2H, J=5.2 Hz), 2.41-2.29 (m, 3H), 1.88-1.79 (m, 4H); ESI+MS: m/z: 497.6 ([M+H]$^+$).

223

(1-(2-(2-fluorophenoxy)ethyl)piperidin-4-yl)methanol

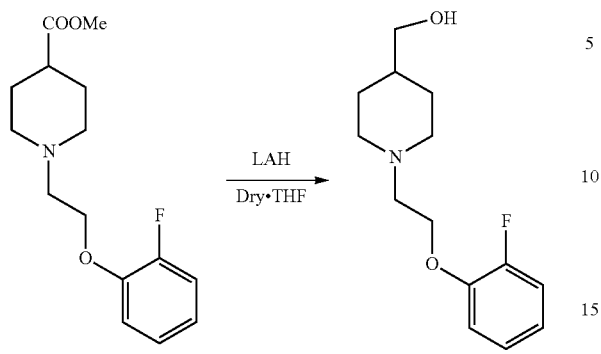

Title compound was prepared from methyl 1-(2-(2-fluorophenoxy)ethyl)piperidine-4-carboxylate (1.2 g, 4.27 mmol) using the conditions of step 2 in Example-78 to obtain 0.850 g (1-(2-(2-fluorophenoxy)ethyl)piperidin-4-yl)methanol (Yield=67%).

1-(2-(2-fluorophenoxy)ethyl)piperidine-4-carbaldehyde

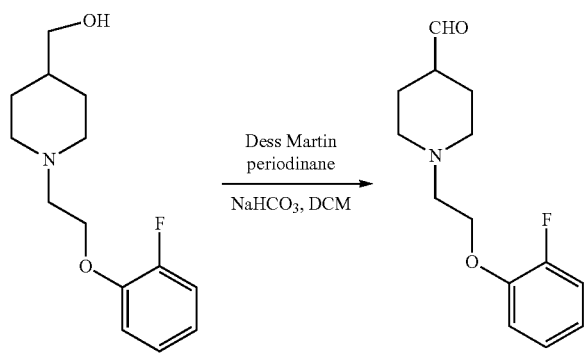 [SMILES: OCC1CCN(CCOc2ccccc2F)CC1 ; O=CC1CCN(CCOc2ccccc2F)CC1]

Title compound was prepared (1-(2-(2-fluorophenoxy)ethyl)piperidin-4-yl)methanol (0.850 g, 3.36 mmol) using the conditions of step 3 in Example-78 to obtain 0.5 g 1-(2-(2-fluorophenoxy)ethyl)piperidine-4-carbaldehyde (Yield=59%).

1-(4-chlorophenyl)-N-((1-(2-(2-fluorophenoxy)ethyl)piperidin-4-yl)methyl)-1-(2-fluorophenyl)methanamine

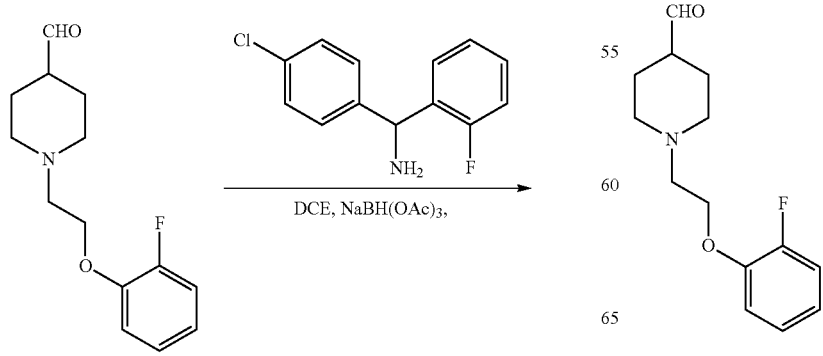

224

-continued

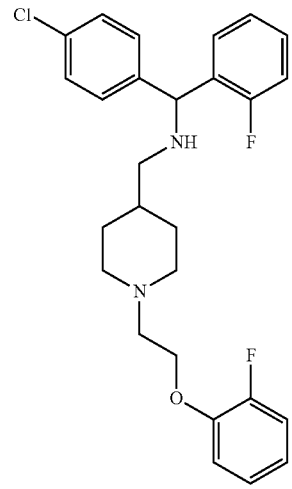

Title compound was prepared from of 1-(2-(2-fluorophenoxy) ethyl) piperidine-4-carbaldehyde (0.147 g, 0.583 mmol) using the general methodology of Example-59. The crude residue was purified by preparative HPLC purification to afford 0.040 g of 1-(4-chlorophenyl)-N-((1-(2-(2-fluorophenoxy)ethyl)piperidin-4-yl)methyl)-1-(2-fluorophenyl)methanamine (Yield=16%). $^1$H NMR (400 MHz, CD$_3$OD): δ 7.54 (dt, 1H, $J_{1,2}$=2.0 Hz, $J_{1,4}$=9.2 Hz), 7.39-7.37 (m, 2H), 7.30-7.21 (m, 3H), 7.17-7.13 (m, 1H), 7.10-7.00 (m, 4H), 6.94-6.90 (m, 1H), 5.11 (s, 1H), 4.20 (t, 2H, J=5.6 Hz), 3.10 (d, 2H, J=11.6 Hz), 2.89 (t, 2H, J=5.2 Hz), 2.43 (d, 2H, J=6.8 Hz), 2.29-2.23 (m, 2H), 1.84-1.81 (m, 2H), 1.58-1.54 (m, 1H), 1.30-1.29 (m, 2H); ESI+MS: m/z: 471.5 ([M+H]$^+$).

Example-88: N-((4(1-(2-(2-fluorophenoxy)ethyl)piperidin-4-yl)methyl)-1-(3-methoxyphenyl)-1-(pyridin-2-yl)methanamine (88)

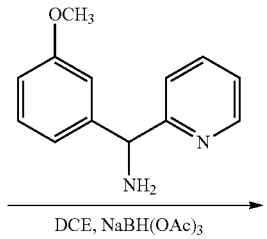

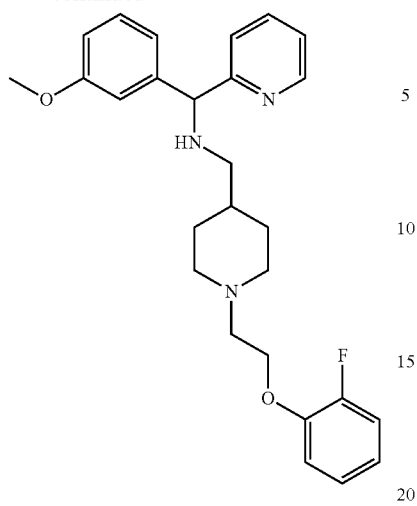

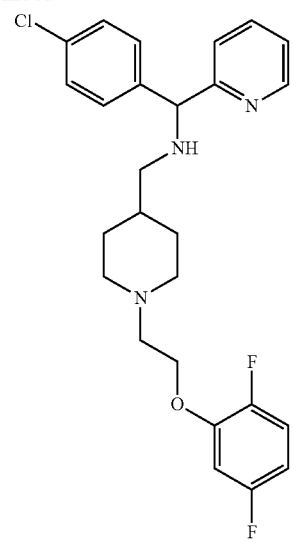

Title compound was prepared from reductive amination of 1-(2-phenoxyethyl)piperidine-4-carbaldehyde (0.117 g, 0.467 mmol) and (3-methoxyphenyl)(pyridin-2-yl)methanamine (0.1 g, 0.467 mmol, 1 equiv) using the general methodology of Example-59. The crude residue was purified by prep HPLC purification to afford 0.050 g of N-((1-(2-(2-fluorophenoxy)ethyl)piperidin-4-yl)methyl)-1-(3-methoxyphenyl)-1-(pyridin-2-yl)methanamine (Yield=26%). $^1$H NMR (400 MHz, CD$_3$OD): δ 8.48 (d, 1H, J=4.0 Hz), 7.75 (dt, 1H, J$_{1,2}$=1.6 Hz, J$_{1,4}$=9.6 Hz), 7.46 (d, 1H, J=8.0 Hz), 7.27-7.19 (m, 2H), 7.11-7.05 (m, 3H), 7.01-6.97 (m, 2H), 6.94-6.89 (m, 1H), 6.79 (dd, 1H, J$_{1,2}$=2.0 Hz, J$_{1,3}$=8.4 Hz), 4.83 (s, 1H), 4.20 (t, 2H, J=5.6 Hz), 3.76 (s, 3H), 3.13-3.08 (m, 2H), 2.87 (t, 2H, J=5.6 Hz), 2.50-2.40 (m, 2H), 2.25 (t, 2H, J=11.6 Hz), 1.82 (d, 2H, J=12.4 Hz), 1.60-1.59 (m, 1H), 1.34-1.26 (m, 2H); ESI+MS: m/z: 450.5 ([M+H]$^+$). Enantiomers of 88 were separated using chiral HPLC (method B) and afforded pure enantiomers 88a and 88b.

Example-89: 1-(4-chlorophenyl)-N-((1-(2-(2,5-difluorophenoxy)ethyl)piperidin-4-yl)methyl)-1-(pyridin-2-yl)methanamine (89)

Title compound was prepared from 1-(4-chlorophenyl)-N-(piperidin-4-ylmethyl)-1-(pyridin-2-yl)methanamine dihydrochloride 1 (100 mg, 0.257 mmol) using the general methodology of Example-1. The product was purified by using silica gel column chromatography (2% MeOH/CH$_2$Cl$_2$ as eluent) afforded 0.050 g of 1-(4-chlorophenyl)-N-((1-(2-(2,5-difluorophenoxy) ethyl)piperidin-4-yl) methyl)-1-(pyridin-2-yl)methanamine (Yield=41%).

$^1$H NMR (400 MHz, DMSO-D$_6$): δ 8.46 (d, 1H, J=4.0 Hz), 7.73 (dt, 1H, J$_{1,2}$=1.6 Hz, J$_{1,4}$=9.2 Hz), 7.45 (s, 1H), 7.41 (d, 2H, J=8.4 Hz), 7.33 (d, 2H, J=8.4 Hz), 7.25-7.19 (m, 2H), 7.15-7.10 (m, 2H), 6.76-6.70 (m, 1H), 4.83 (s, 1H), 4.13 (t, 2H, J=7.6 Hz), 2.89 (d, 2H, J=10.4 Hz), 2.67-2.66 (m, 2H), 2.33-2.29 (m, 2H), 2.10-1.98 (m, 2H), 1.68 (d, 2H, J=11.2 Hz), 1.48-1.40 (m, 1H), 1.13-1.05 (m, 2H); ESI+MS: m/z:472.5 ([M+H]$^+$). Enantiomers of 89 were separated using chiral HPLC (method L) and afforded pure enantiomers 89a and 89b.

Example-90: 1-(2-(2,5-difluorophenoxy)ethyl)-N-((3-methoxyphenyl)(pyridin-2-yl)methyl) piperidine-4-carboxamide (90)

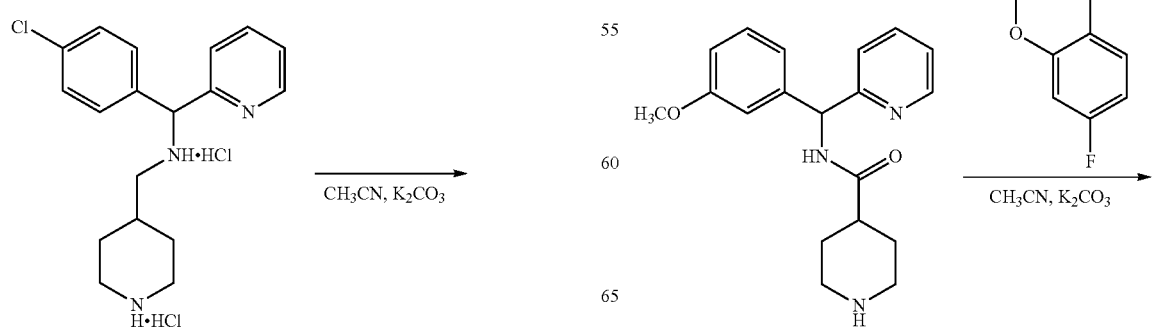

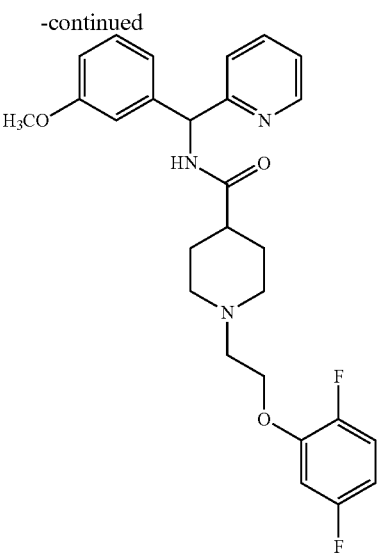

Title compound was prepared from N-((3-methoxyphenyl)(pyridin-2-yl)methyl)piperidine-4-carboxamide (100 mg, 0.461 mmol) using the general methodology of Example-1. The product was purified by using silica gel column chromatography (2% MeOH/DCM as eluent) afforded 0.070 g of 1-(2-(2,5-difluorophenoxy)ethyl)-N-((3-methoxyphenyl)(pyridin-2-yl)methyl) piperidine-4-carboxamide (Yield=31%). $^1$H NMR (400 MHz, CD$_3$OD): δ 8.51 (d, 1H, J=4.4 Hz), 7.79 (dt, 1H, J$_{12}$=1.6 Hz, J$_{1,4}$=9.2 Hz), 7.39 (d, 1H, J=8.0 Hz), 7.31-7.28 (m, 1H), 7.23-7.19 (m, 1H), 7.10-7.04 (m, 1H), 6.95-6.90 (m, 1H), 6.85-6.80 (m, 3H), 6.66-6.60 (m, 1H), 6.13 (s, 1H), 4.18 (t, 2H, J=5.6 Hz), 3.75 (s, 3H), 3.10 (d, 2H, J=12.0 Hz), 2.86 (t, 2H, J=5.2 Hz), 2.46-2.38 (m, 1H), 2.31-2.24 (m, 2H), 1.91-1.76 (m, 4H); ESI+MS: m/z 482.6 ([M+H]$^+$).

Example-91: N-((4(4-chlorophenyl)(3-fluoropyridin-4-yl)methyl)-1-(2-(2-fluorophenoxy)ethyl) piperidine-4-carboxamide (91)

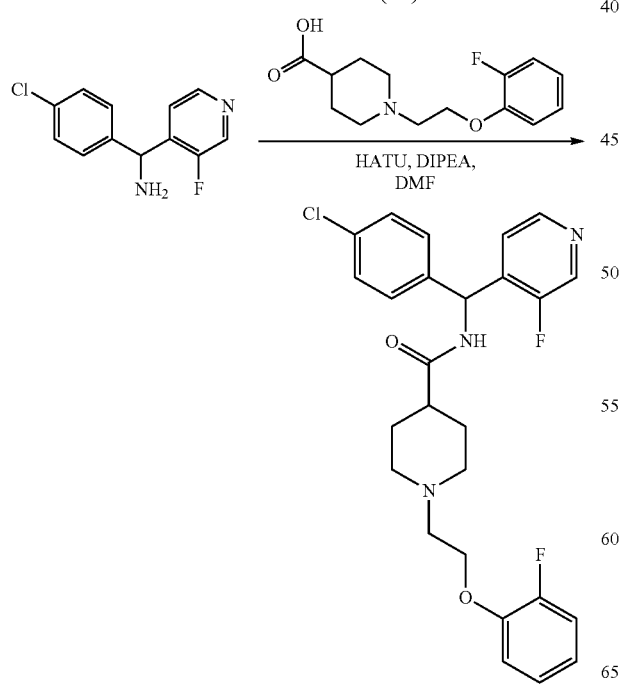

Title compound was prepared from coupling of 1-(2-(2-fluorophenoxy)ethyl)piperidine-4-carboxylic acid (0.271 g, 1.01 mmol, 1.2 equiv) and (4-chlorophenyl)(3-fluoropyridin-4-yl)methanamine 5 (0.2 g, 0.845 mmol, 1 equiv) using the conditions in step 5 in the general methodology of key Intermediate-I. The product was purified by using silica gel column chromatography (2% MeOH/DCM as eluent) to afford 0.1 g of N-((4-chlorophenyl)(3-fluoropyridin-4-yl)methyl)-1-(2-(2-fluorophenoxy)ethyl)piperidine-4-carboxamide (Yield=24%). $^1$H NMR (400 MHz, CD$_3$OD): δ 8.42 (d, 1H, J=2.0 Hz), 8.40 (d, 1H, J=5.2 Hz), 7.40-7.36 (m, 3H), 7.24 (d, 2H, J=8.4 Hz), 7.12-7.06 (m, 3H), 6.97-6.93 (m, 1H), 6.39 (s, 1H), 4.25 (t, 2H, J=5.2 Hz), 3.30-3.26 (m, 2H), 3.13-3.03 (m, 2H), 2.50-2.32 (m, 3H), 1.89-1.88 (m, 4H); ESI+MS: m/z: 486.4 ([M+H]$^+$). Enantiomers of 91 were separated using chiral HPLC (method C) and afforded pure enantiomers 91a and 91b.

Example-92: N-((4(4-chlorophenyl)(5-fluoropyridin-2-yl)methyl)-1-(2-(2-fluorophenoxy)ethyl) piperidine-4-carboxamide (92)

Title compound was prepared from coupling of 1-(2-(2-fluorophenoxy)ethyl)piperidine-4-carboxylic acid (0.271 g, 1.01 mmol, 1.2 equiv) and (4-chlorophenyl)(5-fluoropyridin-2-yl)methanamine (0.2 g, 0.845 mmol, 1 equiv) using the conditions in step 5 in the general methodology of key Intermediate-I. The product was purified by using silica gel column chromatography (2% MeOH/DCM as eluent) to afford 0.2 g of N-((4-chlorophenyl)(5-fluoropyridin-2-yl)methyl)-1-(2-(2-fluorophenoxy)ethyl)piperidine-4-carboxamide (Yield=47%). $^1$H NMR (500 MHz, CD$_3$OD): δ 8.45 (s, 1H), 7.61-7.58 (m, 1H), 7.44-7.29 (m, 1H), 7.29-7.10 (m, 4H), 7.14-7.08 (m, 3H), 6.95 (t, 1H, J=6.0 Hz), 6.19 (s, 1H), 4.25 (t, 2H, J=5.5 Hz), 3.23 (d, 2H, J=11.0 Hz), 3.12-2.99 (m, 2H), 2.48-2.45 (m, 3H), 1.89-1.88 (m, 4H); ESI+MS: m/z: 486 ([M]$^+$). Enantiomers of 92 were separated using chiral HPLC (method G) and afforded pure enantiomers 92a and 92b.

Example-93: 1-(2-(2-fluorophenoxy)ethyl)-N-(pyridin-2-yl(3-(trifluoromethoxy)phenyl) methyl)piperidine-4-carboxamide (93)

Example-94: N-((2,2-difluorobenzo[d][1,3]dioxol-5-yl)(pyridin-2-yl)methyl)-1-(2-(2-fluoro phenoxy)ethyl)piperidine-4-carboxamide (94)

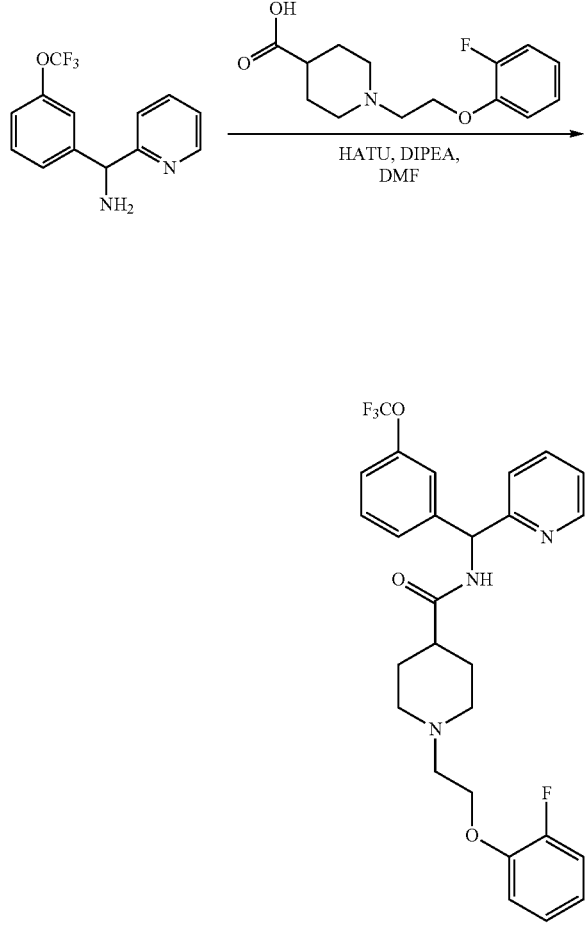

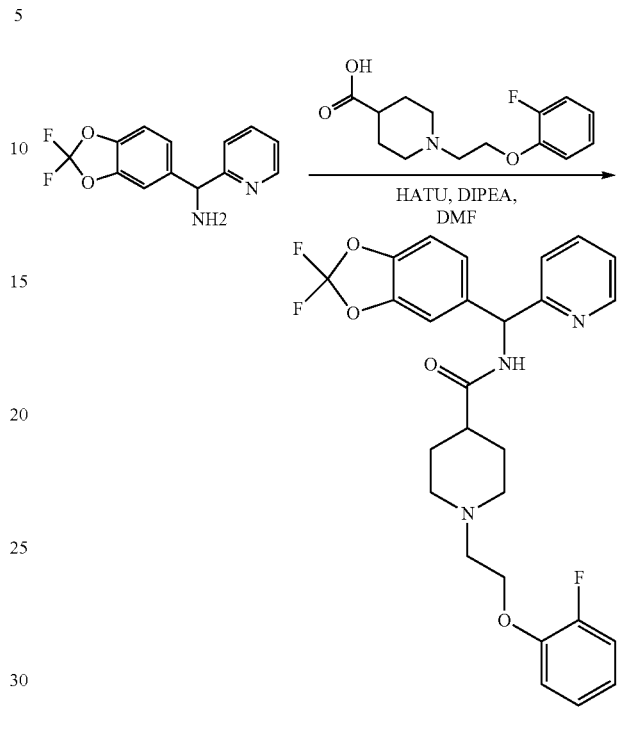

Title compound was prepared from coupling of 1-(2-(2-fluorophenoxy)ethyl)piperidine-4-carboxylic acid 6 (0.243 g, 0.908 mmol, 1.2 equiv) and (2,2-difluorobenzo[d][1,3]dioxol-5-yl)(pyridin-2-yl)methanamine 5 (0.2 g, 0.757 mmol, 1 equiv) using the conditions in step 5 in the general methodology of key Intermediate-I. The product was purified by using silica gel column chromatography (2% MeOH/DCM as eluent) to afford 0.2 g of N-((2,2-difluoro benzo [d][1,3]dioxol-5-yl)(pyridin-2-yl)methyl)-1-(2-(2-fluorophenoxy)ethyl)piperidine-4-carboxamide (Yield=50%). $^1$H NMR (500 MHz, DMSO-$d_6$): δ 8.70 (d, 1H, J=8.5 Hz), 8.51 (d, 1H, J=4.5 Hz), 7.77 (t, 1H, J=8.0 Hz), 7.46 (d, 1H, J=7.5 Hz), 7.39 (s, 1H), 7.33-7.26 (m, 2H), 7.19-7.09 (m, 4H), 6.92-6.91 (m, 1H), 6.16 (d, 1H, J=8.0 Hz), 4.12 (t, 2H, J=5.5 Hz), 2.95 (d, 2H, J=11.0 Hz), 2.69 (t, 2H, J=5.5 Hz), 2.33-2.31 (m, 1H), 2.03 (t, 2H, J=11.5 Hz), 1.68-1.54 (m, 4H); ESI+MS: m/z: 514.6 ([M+H]$^+$). Enantiomers of 94 were separated using chiral HPLC (method A) and afforded pure enantiomers 94a and 94b.

Title compound was prepared from coupling of 1-(2-(2-fluorophenoxy)ethyl)piperidine-4-carboxylic acid 6 (0.179 g, 0.671 mmol, 1.2 equiv) and pyridin-2-yl(3-(trifluoromethoxy)phenyl)methanamine 5 (0.15 g, 0.559 mmol, 1 equiv) using the conditions in step 5 in the general methodology of key Intermediate-I. The product was purified by using silica gel column chromatography (2% MeOH/DCM as eluent) to afford 0.1 g of 1-(2-(2-fluorophenoxy)ethyl)-N-(pyridin-2-yl(3-(trifluoromethoxy)phenyl)methyl)piperidine-4-carboxamide (Yield=32%). $^1$H NMR (400 MHz, DMSO-$d_6$): δ 8.77 (d, 1H, J=8.5 Hz), 8.52 (d, 1H, J=4.5 Hz), 7.79 (t, 1H, J=7.0 Hz), 7.49 (d, 1H, J=7.5 Hz), 7.43 (t, 1H, J=8.0 Hz), 7.30-7.27 (m, 3H), 7.22-7.16 (m, 3H), 7.10 (t, 1H, J=7.5 Hz), 6.94-6.90 (m, 1H), 6.20 (d, 1H, J=8.0 Hz), 4.12 (t, 2H, J=5.5 Hz), 2.95 (d, 2H, J=8.5 Hz), 2.69 (t, 2H, J=5.5 Hz), 2.37-2.33 (m, 1H), 2.03 (t, 2H, J=11.0 Hz), 1.69-1.52 (m, 4H); ESI+MS: m/z: 518.6 ([M+H]$^+$). Enantiomers of 93 were separated using chiral HPLC (method M) and afforded pure enantiomers 93a and 93b.

Example-95: N-(benzo[d][1,3]dioxol-5-yl(pyridin-2-yl)methyl)-1-(2-(2-fluorophenoxy) ethyl) piperidine-4-carboxamide (95)

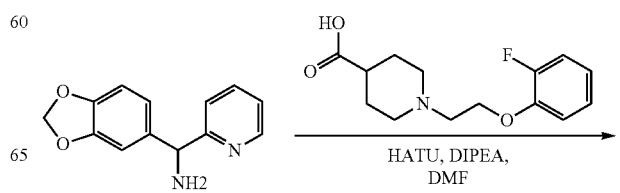

231
-continued

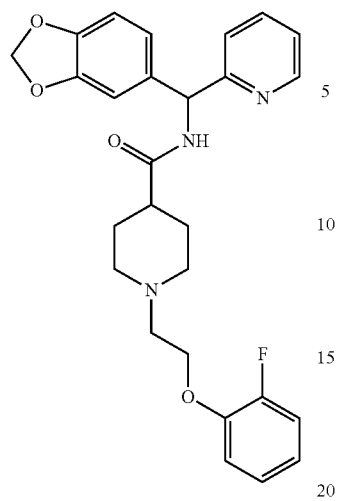

232
-continued

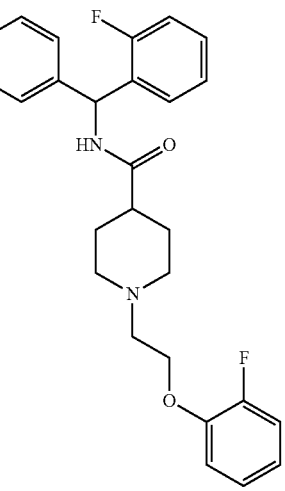

Title compound was prepared from coupling of 1-(2-(2-fluorophenoxy)ethyl)piperidine-4-carboxylic acid 6 (0.281 g, 1.05 mmol, 1.2 equiv) and benzo[d][1,3]dioxol-5-yl(pyridin-2-yl)methanamine 5 (0.2 g, 0.876 mmol, 1 equiv) using the conditions in step 5 in the general methodology of key Intermediate-I. The product was purified by using silica gel column chromatography (2% MeOH/DCM as eluent) and further purified by prep HPLC purification to furnish 0.1 g of N-(benzo[d][1,3]dioxol-5-yl(pyridin-2-yl)methyl)-1-(2-(2-fluorophenoxy) ethyl) piperidine-4-carboxamide (Yield=24%). $^1$H NMR (400 MHz, CD$_3$OD): δ 8.51 (d, 1H, J=4.4 Hz), 7.80-7.76 (m, 1H), 7.37 (d, 1H, J=8.0 Hz), 7.31-7.28 (m, 1H), 7.15-7.08 (m, 3H), 6.98-6.93 (m, 1H), 6.77-6.74 (m, 3H), 6.07 (s, 1H), 5.90 (d, 2H, J=2.4 Hz), 4.29 (t, 2H, J=4.8 Hz), 3.38 (d, 2H, J=11.2 Hz), 3.20-3.17 (m, 2H), 2.71-2.51 (m, 3H), 2.03-1.85 (m, 4H); ESI+MS: m/z: 478.5 ([M+H]$^+$). Enantiomers of 95 were separated using chiral HPLC (method G) and afforded pure enantiomers 95a and 95b.

Example-96: N-((4-chlorophenyl)(2-fluorophenyl)methyl)-1-(2-(2-fluorophenoxy)ethyl) piperidine-4-carboxamide (96)

Title compound was prepared from coupling of 1-(2-(2-fluorophenoxy)ethyl)piperidine-4-carboxylic acid 2 (0.204 g, 0.764 mmol, 1.2 equiv) (4-chlorophenyl)(2-fluorophenyl)methanamine 1 (0.150 g, 0.636 mmol, 1 equiv) using the conditions in step 5 in the general methodology of key Intermediate-I. The product was purified by prep HPLC purification to furnish 0.015 g of N-((4-chlorophenyl)(2-fluorophenyl)methyl)-1-(2-(2-fluorophenoxy)ethyl) piperidine-4-carboxamide (Yield=5%). $^1$H NMR (400 MHz, CD$_3$OD): δ 7.36-7.30 (m, 3H), 7.26 (dt, 1H, J$_{1,2}$=2.0 Hz, J$_{1,4}$=9.211Z), 7.21-7.15 (m, 3H), 7.12-7.04 (m, 4H), 6.94-6.88 (m, 1H), 6.41 (s, 1H), 4.18 (t, 2H, J=5.6 Hz), 3.12-3.08 (m, 2H), 2.83 (t, 2H, J=5.6 Hz), 2.41-2.33 (m, 1H), 2.27-2.21 (m, 2H), 1.89-1.77 (m, 4H); ESI+MS: m/z: 485.6 ([M+H]$^+$). Enantiomers of 96 were separated using chiral HPLC (method N) and afforded pure enantiomers 96a and 96b.

Example-97: N((4-chlorophenyl)(pyridin-2-yl)methyl)-N-methyl-1-(1-(2-phenoxy ethyl) piperidin-4-yl)ethan-1-amine (97)

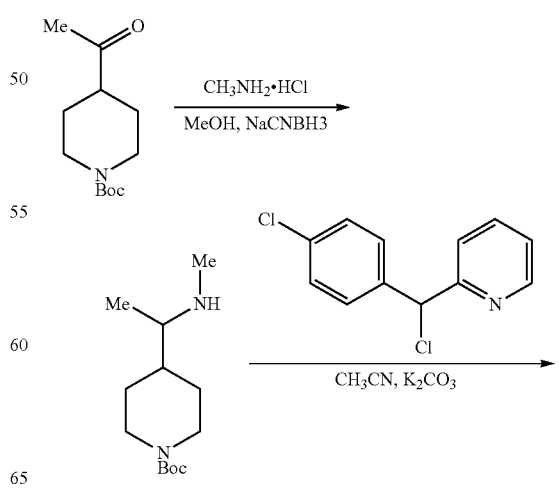

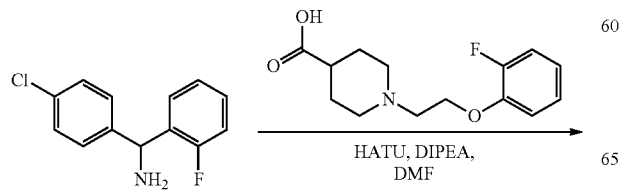

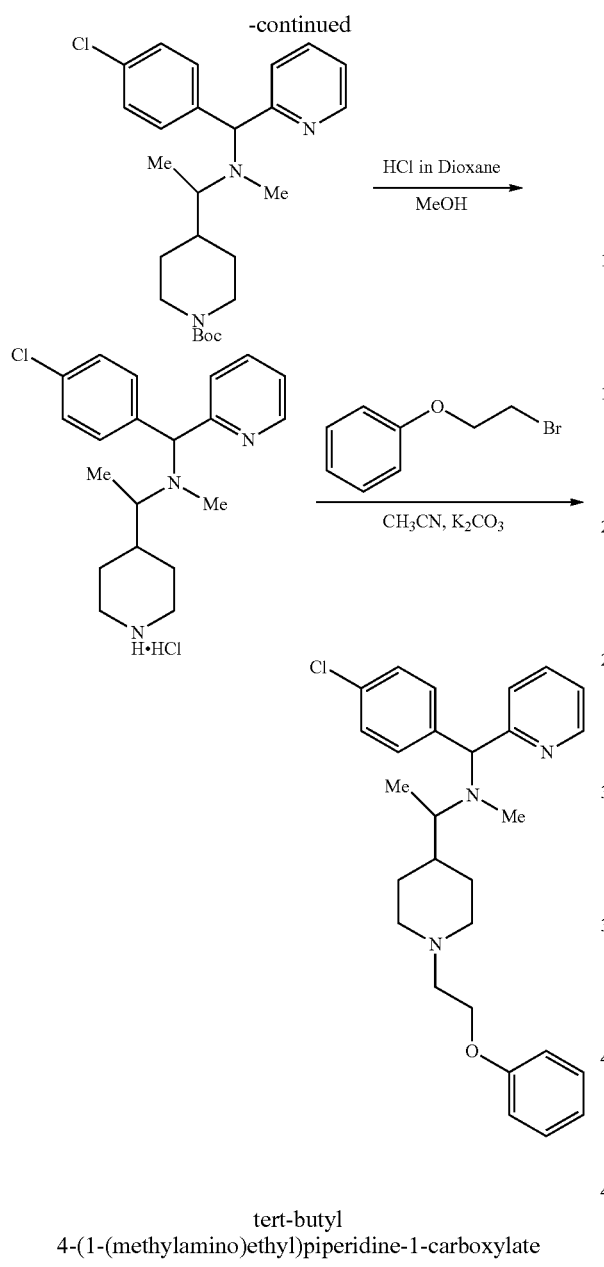

tert-butyl
4-(1-(methylamino)ethyl)piperidine-1-carboxylate

To a stirred solution of tert-butyl 4-acetylpiperidine-1-carboxylate (1 g, 4.40 mmol) in MeOH (10 mL) under argon atmosphere were added methanamine hydrochloride (0.594 g, 8.80 mmol, 2 equiv) and sodium cyanoborohydride (0.829 g, 13.20 mmol, 3 equiv) at 0° C. The reaction mixture was warmed to room temperature and stirred for 16 h. After completion of the reaction, the volatiles were removed and the solvent was removed under reduced pressure. The pH was adjusted to 7 with saturated NaHCO$_3$ solution and extracted with CH$_2$Cl$_2$. The combined organic extract was dried over sodium sulfate, filtered and concentrated under reduced pressure to afford crude residue which was purified by column chromatography eluting with 50% ethyl acetate in Hexane to afford 0.5 g of tert-butyl 4-(1-(methylamino)ethyl) piperidine-1-carboxylate (Yield=47%). ESI+MS: m/z 243.3 ([M+H]$^+$).

N-((4-chlorophenyl)(pyridin-2-yl)methyl)-1-(2-(4-fluorophenoxy)ethyl)piperidine-4-carboxamide

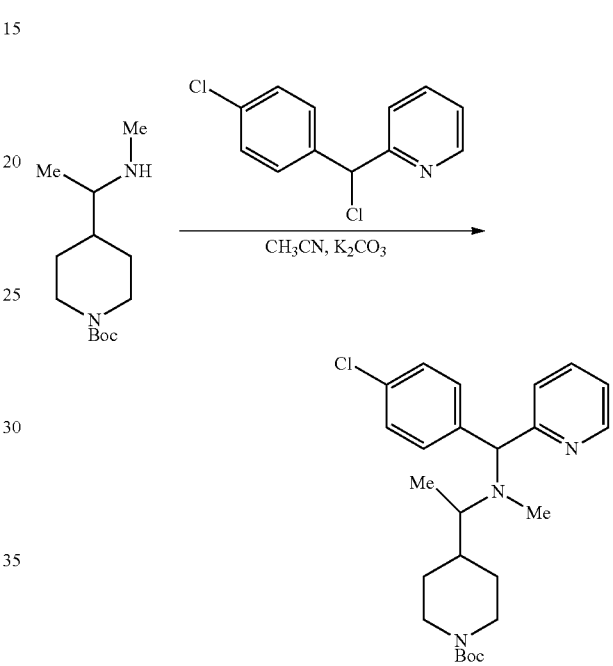

Title compound was prepared from tert-butyl 4-(1-(methylamino)ethyl)piperidine-1-carboxylate (0.5 g, 2.06 mmol) using the general methodology of Example-1. The crude residue was purified by column chromatography eluting with (3% MeOH in DCM as eluent) to afford 0.4 g of N-((4-chlorophenyl)(pyridin-2-yl)methyl)-1-(2-(4-fluorophenoxy)ethyl)piperidine-4-carboxamide (Yield=44%).

N-((4-chlorophenyl)(pyridin-2-yl)methyl)-N-methyl-1-(piperidin-4-yl)ethan-1-amine hydrochloride

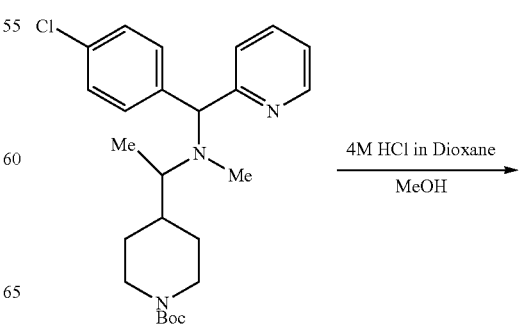

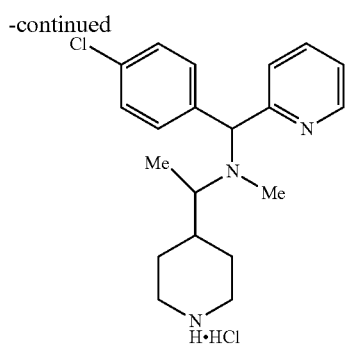

Title compound was prepared from N-((4(4-chlorophenyl)(pyridin-2-yl)methyl)-1-(2-(4-fluorophenoxy)ethyl)piperidine-4-carboxamide (0.4 g, 0.901 mmol) using the general methodology of step 2 in the synthesis of intermediate-V. The crude HCl salt 0.3 g of N-((4-chlorophenyl)(pyridin-2-yl)methyl)-N-methyl-1-(piperidin-4-yl)ethan-1-amine hydrochloride was used in the next step as such (Yield=88%).

N-((4-chlorophenyl)(pyridin-2-yl)methyl)-N-methyl-1-(1-(2-phenoxyethyl)piperidin-4-yl)ethan-1-amine Title compound was prepared from N-((4-chlorophenyl)(pyridin-2-yl)methyl)-N-methyl-1-(piperidin-4-yl)ethan-1-amine hydrochloride (0.3 g, 0.789 mmol) using the general methodology of Example-1. The crude residue was purified by column chromatography eluting with (3% MeOH in DCM as eluent) to afford 0.14 g of N-((4-chlorophenyl)(pyridin-2-yl)methyl)-N-methyl-1-(1-(2-phenoxyethyl)piperidin-4-yl)ethan-1-amine (Yield=38%).

$^1$H NMR (400 MHz, DMSO-d$_6$): δ 8.41 (t, 1H, J=4.8 Hz), 7.75-7.72 (m, 1H), 7.63-7.7.44 (m, 3H), 7.34-7.26 (m, 4H), 7.19-7.17 (m, 1H), 6.93 (d, 3H, J=7.6 Hz), 4.76 (d, 1H, J=13.6 Hz), 4.05 (bs, 2H), 3.05-2.85 (m, 2H), 2.65-2.63 (m, 1H), 2.32-2.16 (m, 2H), 2.01-1.94 (m, 5H), 1.56-1.54 (m, 1H), 1.25-1.20 (m, 4H), 1.17-1.14 (m, 1H), 0.85-0.80 (m, 2H); ESI+MS: m/z: 344.4 ([M+H]$^+$). All stereoisomers of 97 were separated using chiral HPLC (method H) and afforded 97a, 97b, 97c and 97d.

Example-98: 2-((4-chlorophenyl)(pyridin-2-yl)methyl)-5-(2-phenoxyethyl)octahydro-1H-pyrrolo[3,4-c]pyridine (98)

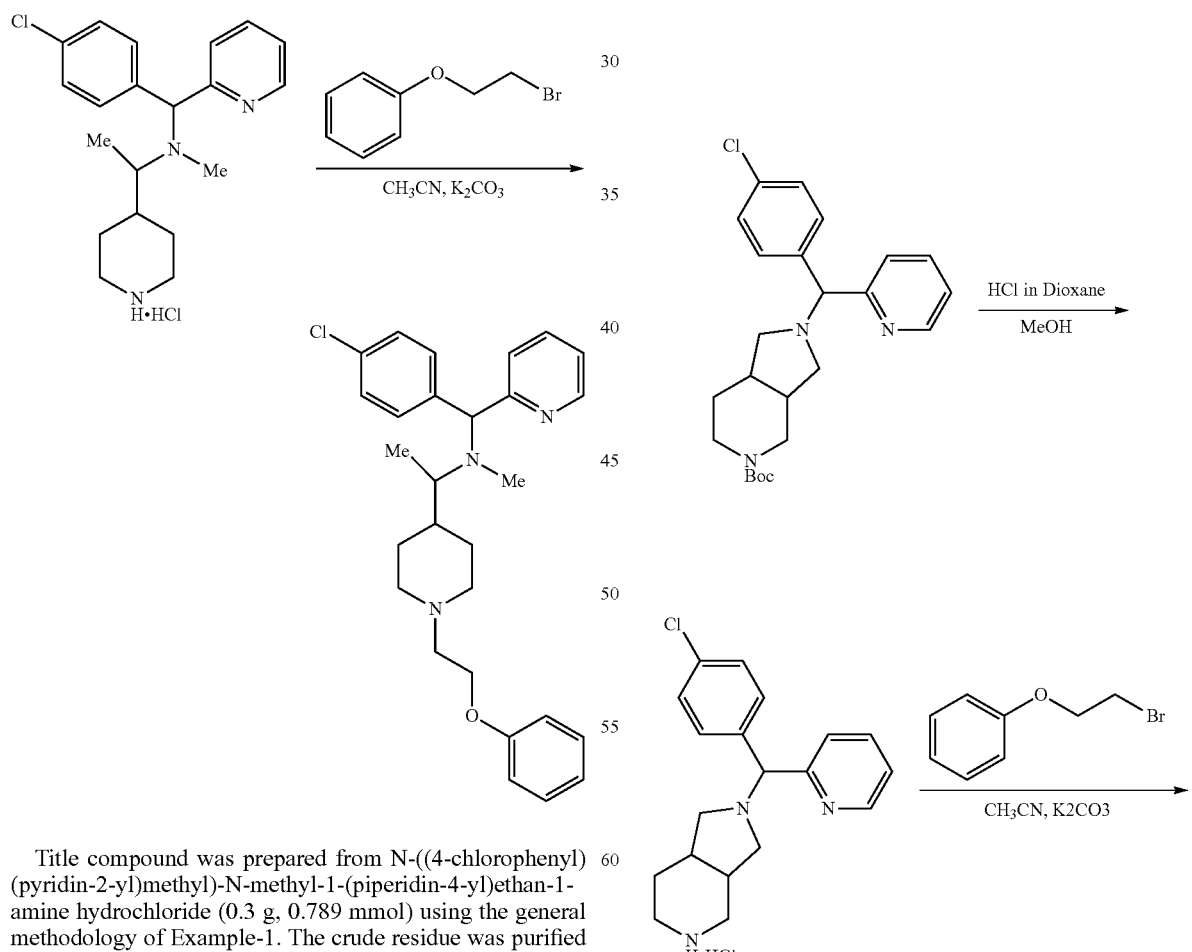

237

-continued

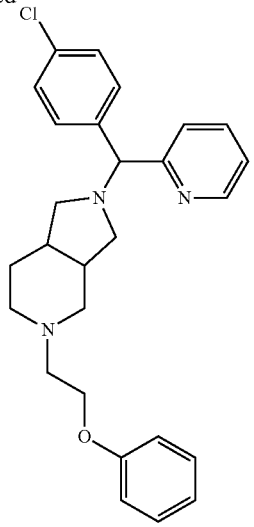

238

2-((4-chlorophenyl)(pyridin-2-yl)methyl)octahydro-1H-pyrrolo[3,4-c]pyridine hydrochloride

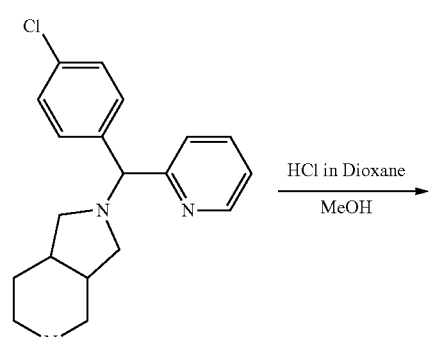

tert-butyl 2-((4-chlorophenyl)(pyridin-2-yl)methyl)octahydro-5H-pyrrolo[3,4-c]pyridine-5-carboxylate

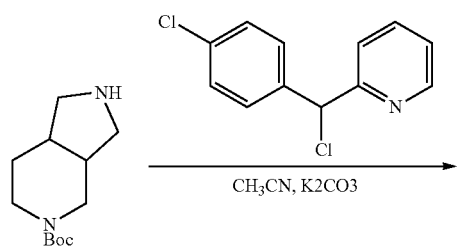

Title compound was prepared from 2-(2-phenoxyethyl)octahydro-5H-pyrrolo[3,4-c]pyridine-5-carboxylate (0.3 g, 0.701 mmol) using the general methodology of step 2 in the synthesis of intermediate-V. The crude HCl salt 0.220 g of 2-((4-chlorophenyl)(pyridin-2-yl)methyl) octahydro-1H-pyrrolo[3,4-c]pyridine hydrochloride was used in the next step as such (Yield=86%).

2-((4-chlorophenyl)(pyridin-2-yl)methyl)-5-(2-phenoxyethyl)octahydro-1H-pyrrolo[3,4-c]pyridine

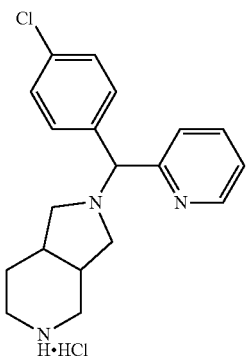

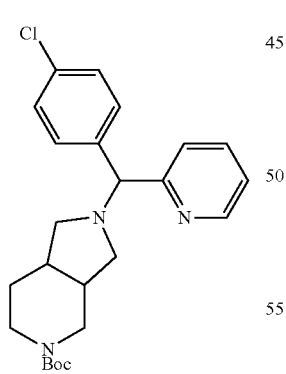

Title compound was prepared from tert-butyl 4-(1-(methylamino)ethyl)piperidine-1-carboxylate (0.190 g, 0.840 mmol) using the general methodology of Example-1. The crude residue was purified by column chromatography eluting with (50% EtOAc in Hexane as eluent) to afford 0.3 g of tert-butyl 2-((4-chlorophenyl)(pyridin-2-yl)methyl)octahydro-5H-pyrrolo[3,4-c]pyridine-5-carboxylate (Yield=83%).

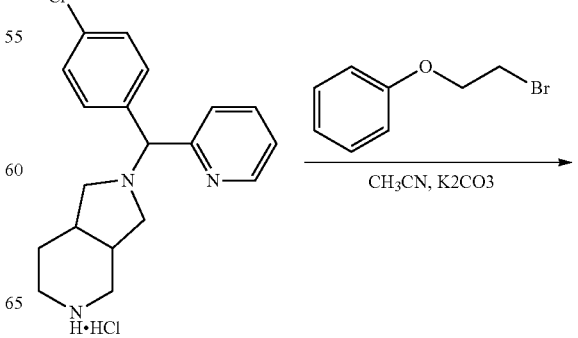

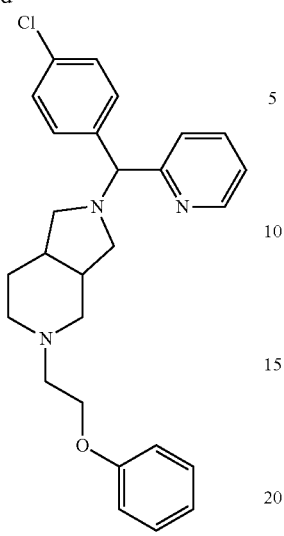

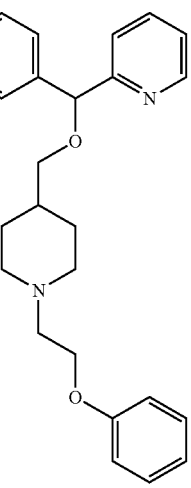

Title compound was prepared from 2-((4-chlorophenyl)(pyridin-2-yl)methyl)octahydro-1H-pyrrolo[3,4-c]pyridine hydrochloride (0.220 g, 0.604 mmol) using the general methodology of Example-1. The crude residue was purified by column chromatography eluting with (4% MeOH in DCM as eluent) to afford 0.150 g diastereomeric mixture of 2-((4-chlorophenyl)(pyridin-2-yl)methyl)-5-(2-phenoxyethyl)octahydro-1H-pyrrolo[3,4-c]pyridine (Yield=54%). $^1$H NMR (400 MHz, DMSO-$d_6$): δ 8.40 (d, 1H, J=4.0 Hz), 7.74 (t, 1H, J=7.6 Hz), 7.56 (d, 1H, J=7.6 Hz), 7.47 (d, 2H, J=8.4 Hz), 7.32 (d, 2H, J=8.0 Hz), 7.26 (t, 2H, J=15.6 Hz), 7.18 (t, 1H, J=12.0 Hz), 6.90 (t, 3H, J=7.2 Hz), 4.65 (s, 1H), 4.03 (t, 2H, J=6.0 Hz), 2.67-2.66 (m, 2H), 2.58-2.53 (m, 2H), 2.44-2.40 (m, 3H), 2.25-2.08 (m, 3H), 1.64-1.61 (m, 2H), 1.25-1.22 (m, 2H); ESI+MS: m/z: 448.5 ([M+H]$^+$).

Example-99: 2-((4-chlorophenyl)((1-(2-phenoxyethyl)piperidin-4-yl)methoxy) methyl) pyridine (99)

To a stirred solution of (1-(2-phenoxyethyl)piperidin-4-yl)methanol (0.3 g, 1.27 mmol) in THF (5 mL) was added sodium hydride (0.046 g, 1.9 mmol, 1.5 equiv) and 10 minutes later, 2-(chloro(4-chlorophenyl)methyl)pyridine (0.304 g, 1.27 mmol, 1.0 equiv) at room temperature. The reaction mixture was heated at 80° C. and stirred for 16 h. After completion, water was added to the reaction mixture and extracted with EtOAc. The combined organic extract was washed with brine, dried over sodium sulphate, filtered and concentrated under reduced pressure. Purification using prep HPLC purification to furnish 0.012 g of 2-((4-chlorophenyl)((1-(2-phenoxyethyl)piperidin-4-yl)methoxy)methyl)pyridine (Yield=2%). $^1$H NMR (400 MHz, CD$_3$OD-$d_4$): δ 8.45-8.43 (m, 1H), 7.86-7.82 (m, 1H), 7.62-7.60 (m, 1H), 7.39-7.36 (m, 2H), 7.32-7.23 (m, 5H), 6.93-6.89 (m, 3H), 5.42 (s, 1H), 4.12 (t, 2H, J=5.6 Hz), 3.36 (d, 2H, J=6.0 Hz), 3.07 (d, 2H, J=11.6 Hz), 2.82 (t, 2H, J=5.6 Hz), 2.22-2.16 (m, 2H), 1.89-1.69 (m, 3H), 1.46-1.36 (m, 2H); ESI+MS: m/z: 437 ([M+H]$^+$).

Example-100: 2-((4-chlorophenyl)(pyridin-2-yl)methyl)-5-(2-(2-(trifluoromethyl)phenoxy) ethyl) octahydro-1H-pyrrolo[3,4-c]pyridine (100)

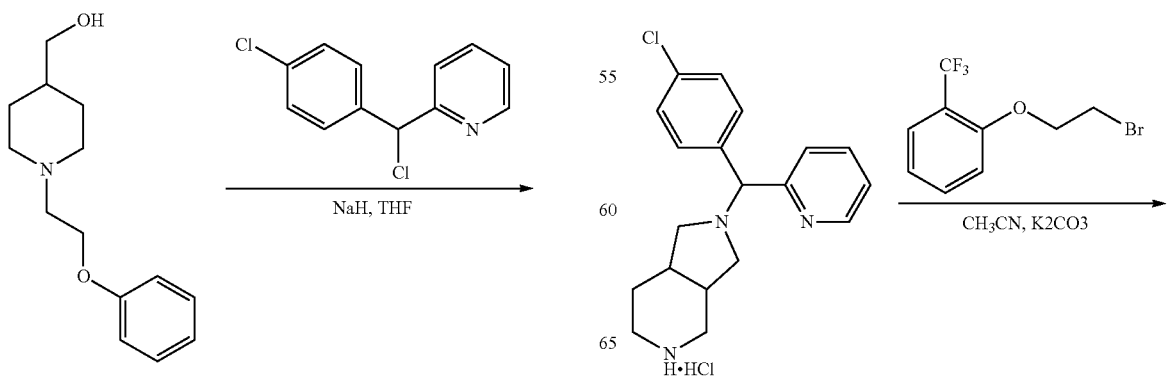

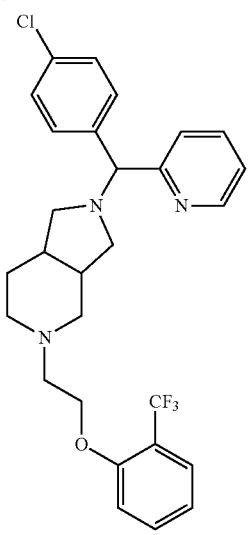

Title compound was prepared from 24(4-chlorophenyl)(pyridin-2-yl)methyl)octahydro-1H-pyrrolo[3,4-c]pyridine hydrochloride (0.200 g, 0.529 mmol) using the general methodology of Example-1. The crude residue was purified by prep HPLC purification to furnish 0.130 g 2-((4-chlorophenyl)(pyridin-2-yl)methyl)-5-(2-(2-(trifluoromethyl) phenoxy) ethyl) octahydro-1H-pyrrolo[3,4-c]pyridine (Yield=46%). $^1$H NMR (400 MHz, CD$_3$OD): δ 8.41 (d, 1H, J=5.2 Hz), 7.82-7.78 (m, 1H), 7.69 (d, 1H, J=7.6 Hz), 7.58-7.48 (m, 4H), 7.30-7.24 (m, 3H), 7.16 (d, 1H, J=8.0 Hz), 7.06 (t, 1H, J=7.6 Hz), 4.37 (s, 1H), 4.23 (t, 2H, J=5.6 Hz), 2.85 (t, 2H, J=5.6 Hz), 2.60-2.50 (m, 6H), 2.35 (s, 2H), 1.70-1.67 (m, 6H); ESI+MS: m/z: 530.6 ([M+H]$^+$).

Example-101: 1-(4-fluorophenyl)-N-((4-methyl-1-(2-(2-(trifluoromethyl)phenoxy)ethyl) piperidin-4-yl)methyl)-1-(pyridin-2-yl)methanamine (101)

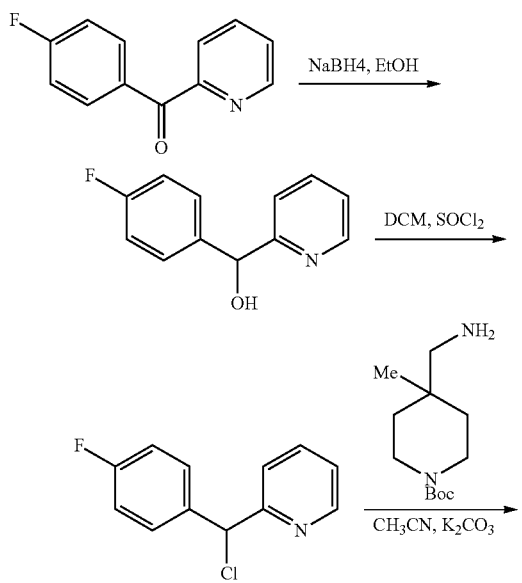

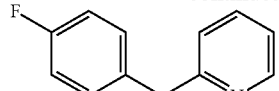

(4-fluorophenyl)(pyridin-2-yl)methanol

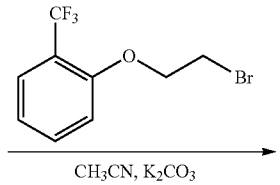

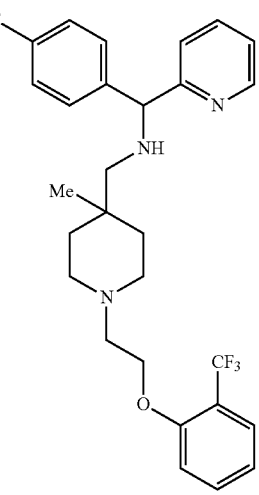

To a stirred solution of (4-fluorophenyl)(pyridin-2-yl)methanone (1) (0.5 g, 2.48 mmol) in MeOH (5 mL) was added sodium borohydride (0.282 g, 7.46 mmol, 3 equiv) at 0° C. The reaction mixture was warmed to room temperature and stirred for 4 h. After completion, the reaction mixture was filtered through celite, washed with CH₂Cl₂ and the filtrate was concentrated under reduced pressure to afford 0.450 g of (4-fluorophenyl)(pyridin-2-yl)methanol (Yield=89%).

2-(chloro(4-fluorophenyl)methyl)pyridine

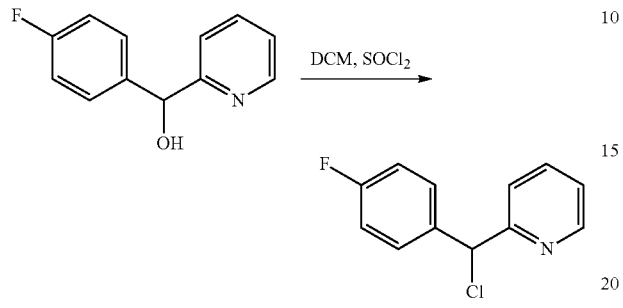

(4-fluorophenyl)(pyridin-2-yl)methanol (0.450 g, 2.21 mmol) was diluted in DCM (5 mL) and thionyl chloride (0.395 g, 3.32 mmol) was added at 0° C. The reaction mixture was stirred at room temperature for 6 hrs. The solvents were then evaporated and the mixture was dissolved in DCM and washed with a saturated solution of sodium bicarbonate. The combined organic layers were dried over Na₂SO₄, filtered and concentrated. Flash chromatography on silica gel using 10% ethyl acetate in hexanes afforded 0.450 g of 2-(chloro(4-fluorophenyl)methyl)pyridine (Yield=92%).

tert-butyl 4-((((4-fluorophenyl)(pyridin-2-yl)methyl)amino)methyl)-4-methylpiperidine-1-carboxylate

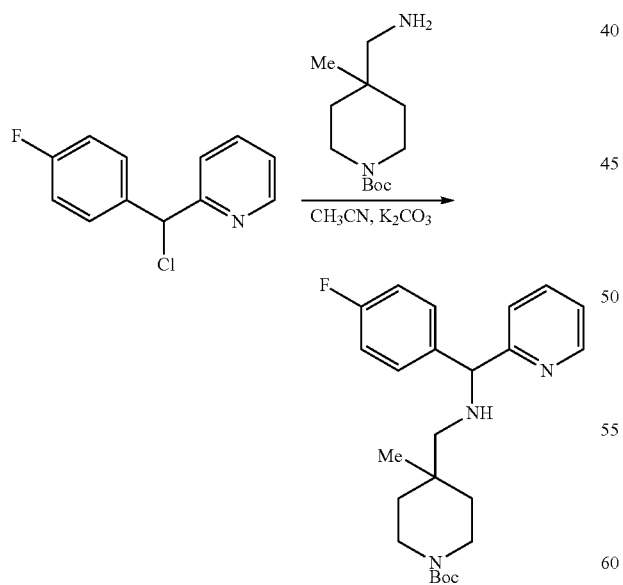

Title compound was prepared from 2-(chloro(4-fluorophenyl)methyl)pyridine (0.4 g, 1.80 mmol) using the general methodology of Example-1. The crude residue was purified by column chromatography eluting with (40% EtOAc in Hexane as eluent) to afford 0.6 g of tert-butyl 4-((((4-fluorophenyl)(pyridin-2-yl)methyl)amino)methyl)-4-methylpiperidine-1-carboxylate (Yield=80%).

1-(4-fluorophenyl)-N-((4-methylpiperidin-4-yl)methyl)-1-(pyridin-2-yl)methanamine hydrochloride

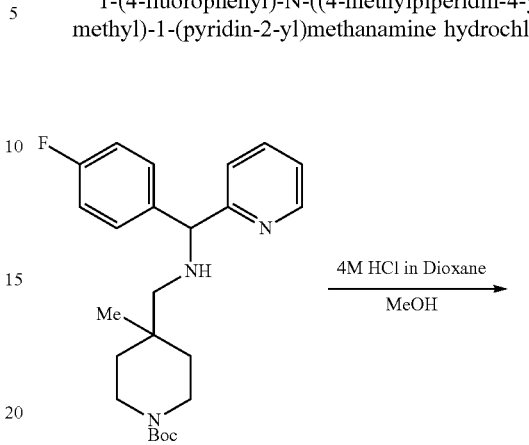

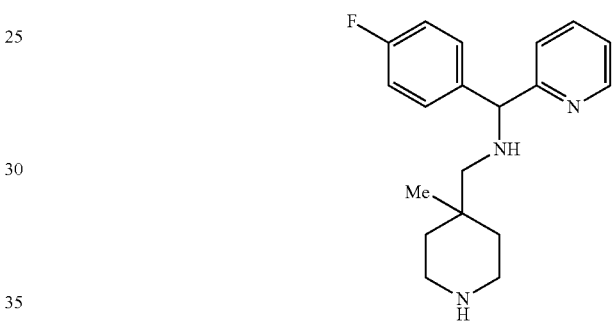

Title compound was prepared from tert-butyl 4-((((4-fluorophenyl)(pyridin-2-yl)methyl) amino) methyl)-4-methylpiperidine-1-carboxylate (0.6 g, 1.45 mmol) using conditions described in step 2 of the synthesis of key intermediate-V. The crude HCl salt 0.450 g of 1-(4-fluorophenyl)-N-((4-methylpiperidin-4-yl)methyl)-1-(pyridin-2-yl)methanamine hydrochloride was used in the next step as such (Yield=80%).

1-(4-fluorophenyl)-N-((4-methyl-1-(2-(2-(trifluoromethyl)phenoxy) ethyl) piperidin-4-yl)methyl)-1-(pyridin-2-yl)methanamine

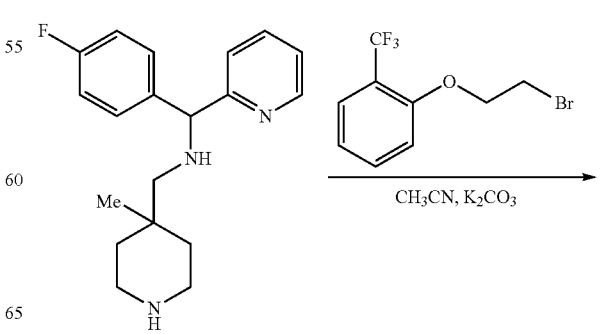

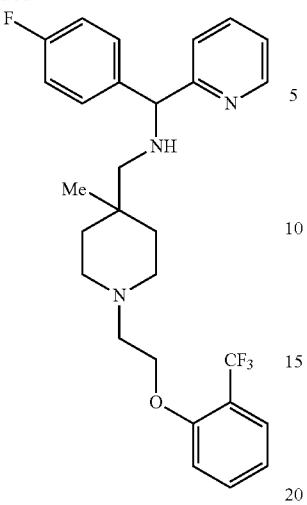

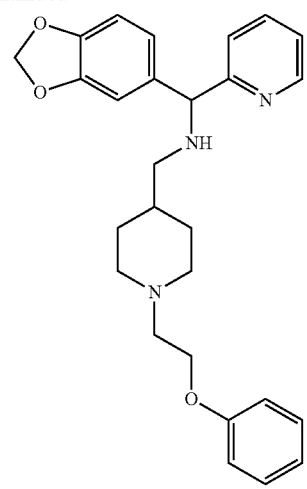

Title compound was prepared from 1-(4-fluorophenyl)-N-((4-methylpiperidin-4-yl)methyl)-1-(pyridin-2-yl)methanamine hydrochloride (0.450 g, 1.16 mmol) using the general methodology of Example-1. The crude residue was purified by column chromatography (3% MeOH in DCM) afforded 0.3 g 1-(4-fluorophenyl)-N-((4-methyl-1-(2-(2-(trifluoromethyl) phenoxy) ethyl) piperidin-4-yl)methyl)-1-(pyridin-2-yl)methanamine (Yield=51%). $^1$H NMR (400 MHz, DSMO-d$_6$): δ 8.47 (d, 1H, J=4.8 Hz), 7.74-7.70 (m, 1H), 7.63-7.58 (m, 2H), 7.44-7.40 (m, 3H), 7.27-7.19 (m, 2H), 7.10 (t, 3H, J=8.4 Hz), 4.82 (s, 1H), 4.18-4.17 (m, 2H), 2.67-2.66 (m, 2H), 2.56-2.54 (m, 1H), 2.46-2.45 (m, 2H), 2.35-2.32 (m, 2H), 2.26-2.25 (m, 2H), 1.46-1.45 (m, 2H), 1.36-1.23 (m, 2H), 0.91 (s, 3H); ESI+MS: m/z: 502.6 ([M+H]$^+$). Enantiomers of 101 were separated using chiral HPLC (method P) and afforded pure enantiomers 101a and 101b.

Example-102: 1-(benzo[d][1,3]dioxol-5-yl)-N-((1-(2-phenoxyethyl)piperidin-4-yl)methyl)-1-(pyridin-2-yl)methanamine (102)

Title compound was prepared from benzo[d][1,3]dioxol-5-yl(pyridin-2-yl)methanamine (0.098 g, 0.429 mmol) and 1-(2-phenoxyethyl)piperidine-4-carbaldehyde (0.1 g, 0.429 mmol, 1 equiv) using the conditions described in Example 68 to afford 0.015 g (Yield=8%). $^1$H NMR (400 MHz, CD$_3$OD): δ 8.46 (dd, 1H, J$_{1,2}$=0.8 Hz, J$_{1,3}$=4.8 Hz), 7.74 (dt, 1H, J$_{1,2}$=2.0 Hz, J$_{1,4}$=15.6 Hz), 7.45 (d, 1H, J=8.0 Hz), 7.27-7.22 (m, 3H), 6.92-8.87 (m, 5H), 6.73 (d, 1H, J=7.6 Hz), 5.87 (dd, 2H, J$_{1,2}$=1.2 Hz, J$_{1,3}$=5.2 Hz), 4.84-4.80 (m, 1H), 4.10 (t, 2H, J=5.6 Hz), 3.02 (d, 2H, J=11.2 Hz), 2.78 (t, 2H, J=5.6 Hz), 2.46-2.36 (m, 2H), 2.17 (t, 2H, J=11.6 Hz), 1.79 (d, 2H, J=11.6 Hz), 1.59-1.50 (m, 1H), 1.32-1.28 (m, 1H), 1.26-1.21 (m, 1H); ESI+MS: m/z 446 ([M+H]$^+$). Enantiomers of 102 were separated using chiral HPLC (method D) and afforded pure enantiomers 102a and 102b.

Example-103: N-((4-chlorophenyl)(pyridin-2-yl)methyl)-N-((1-(2-phenoxyethyl)piperidin-4-yl)methyl) propan-2-amine (103)

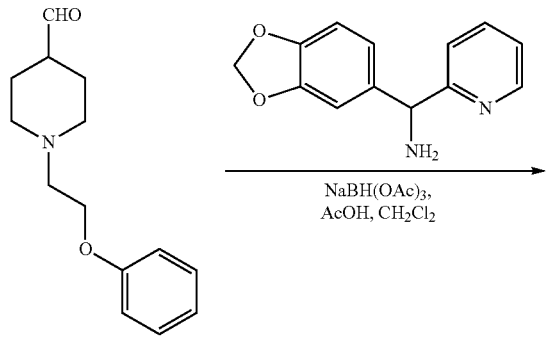

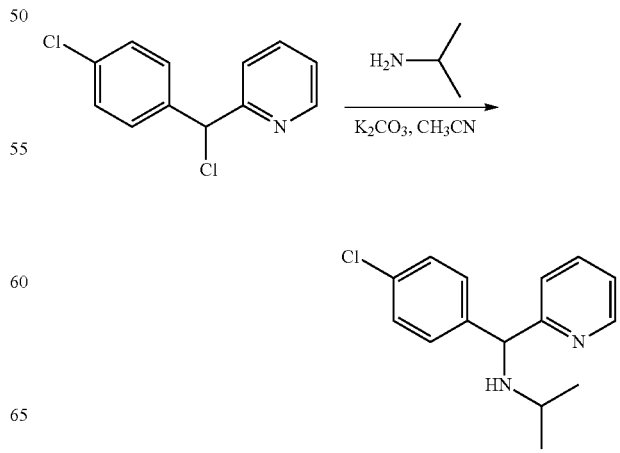

247

-continued

248

N-((4(4-chlorophenyl)(pyridin-2-yl)methyl)-N-((1-(2-phenoxyethyl)piperidin-4-yl)methyl)propan-2-amine

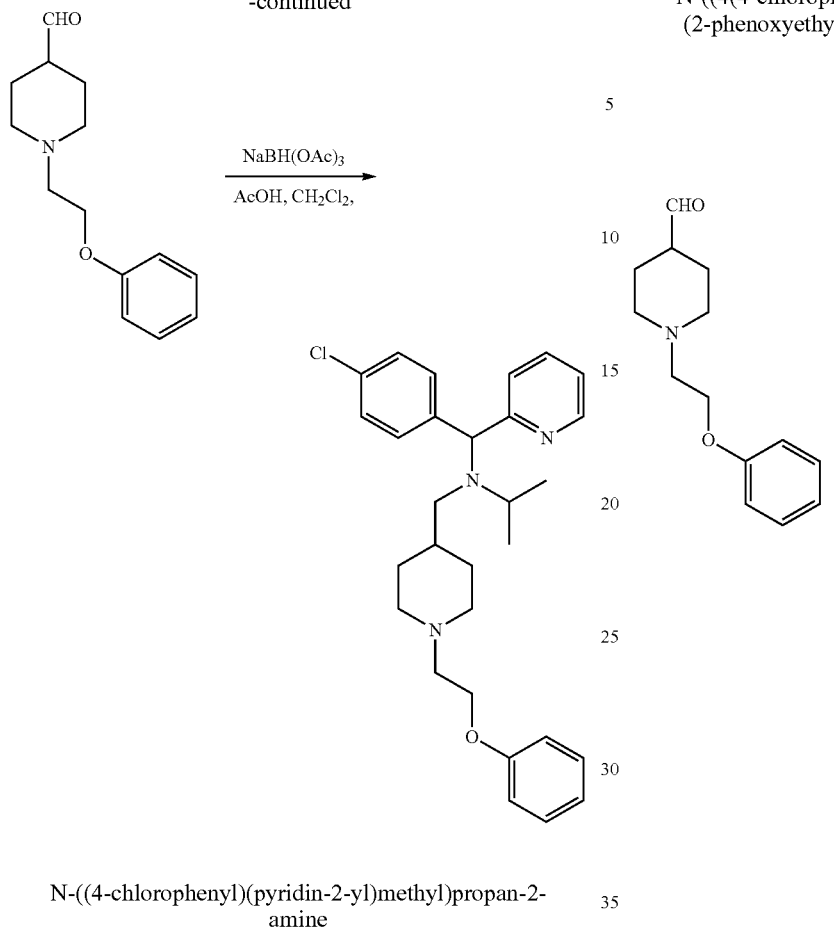

N-((4-chlorophenyl)(pyridin-2-yl)methyl)propan-2-amine

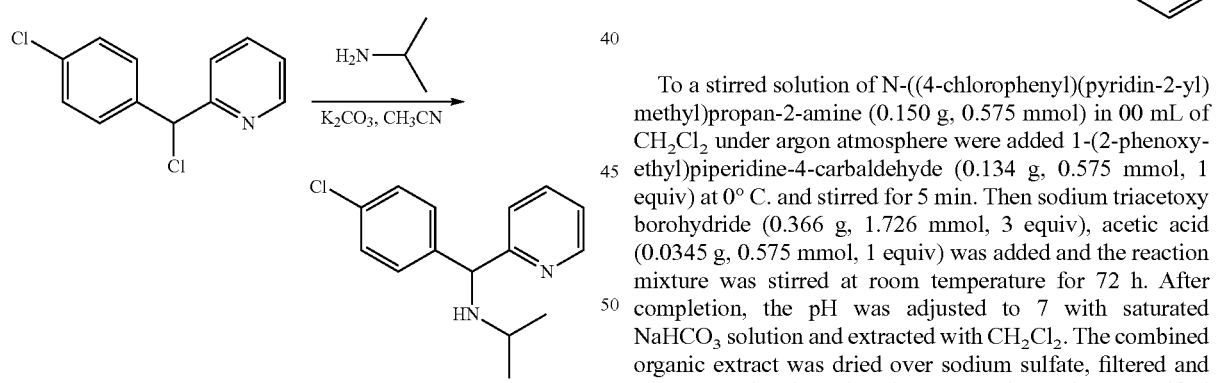

To a solution of 2-(chloro(4-chlorophenyl)methyl)pyridine (1 g, 4.20 mmol) in CH$_3$CN (25 mL) under argon atmosphere were added isopropyl amine (5 mL, 61.1 mmol, 14.54 equiv) and potassium carbonate (1.71 g, 12.64 mmol, 3 equiv) in a sealed tube and the reaction was heated at 80° C. for 16 h. After completion, the reaction was diluted with water and extracted with EtOAc. The combined organic extract was dried over sodium sulfate, filtered and concentrated under reduced pressure. Purification using silica gel column chromatography (40% EtOAc/Hexanes as eluent) afforded 0.360 g of N-((4-chlorophenyl)(pyridin-2-yl)methyl)propan-2-amine (Yield=33%). ESI+MS: m/z 261.2 ([M+H]$^+$).

To a stirred solution of N-((4-chlorophenyl)(pyridin-2-yl)methyl)propan-2-amine (0.150 g, 0.575 mmol) in 00 mL of CH$_2$Cl$_2$ under argon atmosphere were added 1-(2-phenoxyethyl)piperidine-4-carbaldehyde (0.134 g, 0.575 mmol, 1 equiv) at 0° C. and stirred for 5 min. Then sodium triacetoxy borohydride (0.366 g, 1.726 mmol, 3 equiv), acetic acid (0.0345 g, 0.575 mmol, 1 equiv) was added and the reaction mixture was stirred at room temperature for 72 h. After completion, the pH was adjusted to 7 with saturated NaHCO$_3$ solution and extracted with CH$_2$Cl$_2$. The combined organic extract was dried over sodium sulfate, filtered and concentrated under reduced pressure. The crude was purified by preparative HPLC to afford 0.013 g of N-((4-chlorophenyl)(pyridin-2-yl)methyl)-N-((1-(2-phenoxyethyl)piperidin-4-yl)methyl)propan-2-amine (Yield=5%). $^1$H NMR (400 MHz, CD$_3$OD): δ 8.42 (dd, 1H, J$_{1,2}$=1.2 Hz, J$_{1,3}$=5.2 Hz), 7.82-7.77 (m, 1H), 7.66 (d, 1H, J=8.0 Hz), 7.38-7.36 (m, 2H), 7.29-7.23 (m, 5H), 6.92-6.89 (m, 3H), 5.03 (s, 1H), 4.08 (t, 2H, J=5.6 Hz), 3.12-3.05 (m, 1H), 2.96 (d, 2H, J=11.6 Hz), 2.73 (t, 2H, J=5.6 Hz), 2.47-2.36 (m, 2H), 1.94-1.87 (m, 2H), 1.70-1.63 (m, 2H), 1.12-1.00 (m, 2H), 0.97 (d, 3H, J=6.4 Hz), 0.89-0.86 (m, 4H); ESI+MS: m/z 478 ([M+H]$^+$). Enantiomers of 103 were separated using chiral HPLC (method C) and afforded pure enantiomers 103a and 103b.

249

Example-104: 2((4-chlorophenyl)(pyridin-2-yl)methyl)-7-(2-phenoxyethyl)-2,7-diaza spiro[3.5] nonane (104)

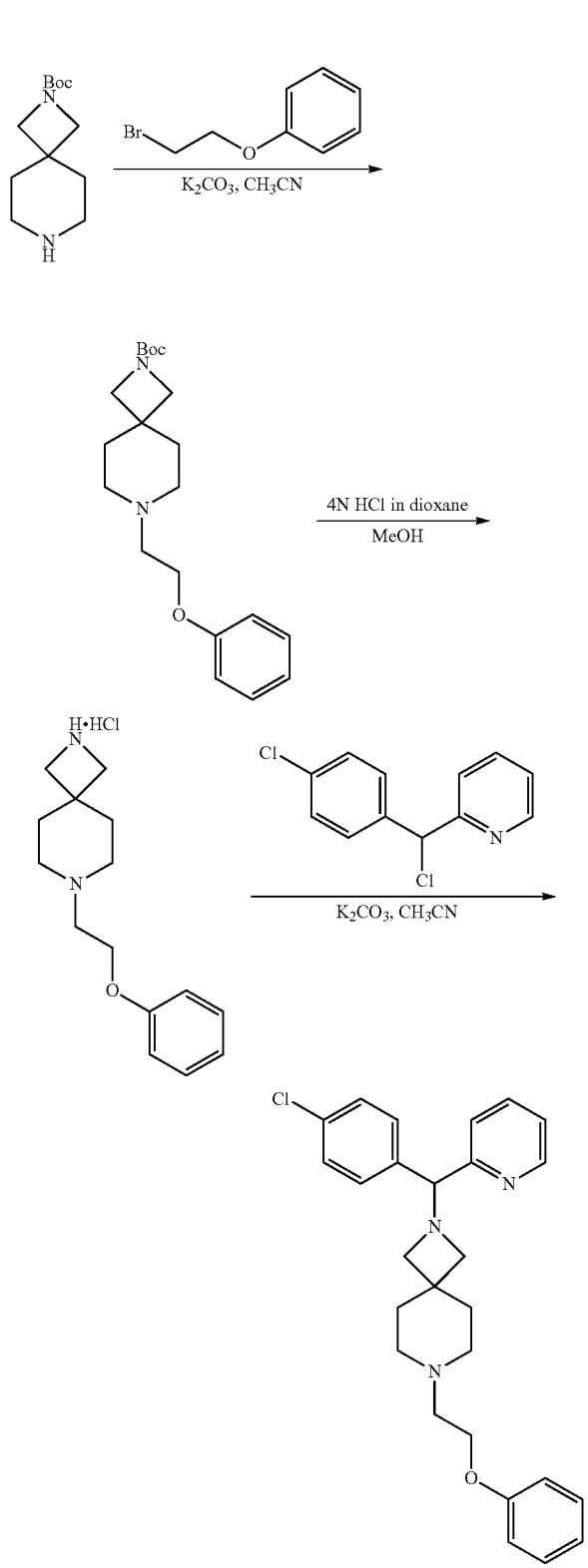

250 tert-butyl 7-(2-phenoxyethyl)-2,7-diazaspiro[3.5]nonane-2-carboxylate

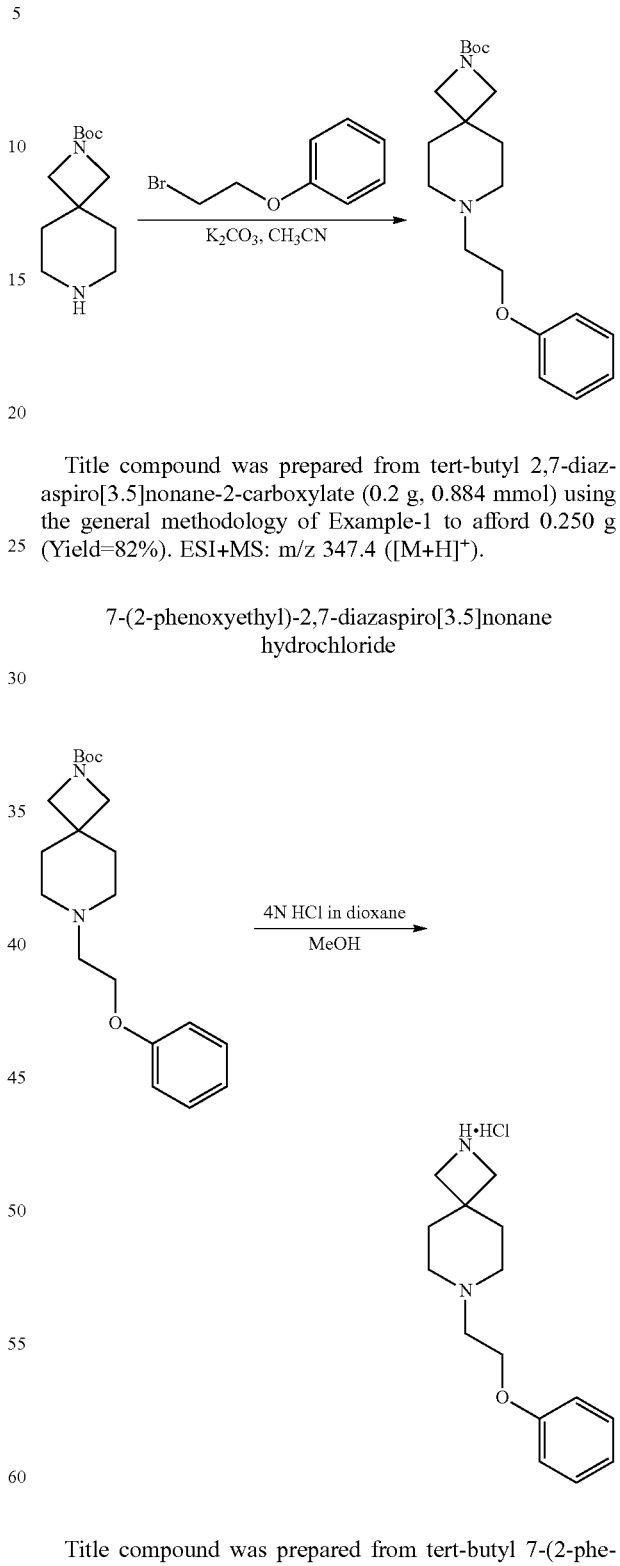

Title compound was prepared from tert-butyl 2,7-diazaspiro[3.5]nonane-2-carboxylate (0.2 g, 0.884 mmol) using the general methodology of Example-1 to afford 0.250 g (Yield=82%). ESI+MS: m/z 347.4 ([M+H]$^+$).

7-(2-phenoxyethyl)-2,7-diazaspiro[3.5]nonane hydrochloride

Title compound was prepared from tert-butyl 7-(2-phenoxyethyl)-2,7-diazaspiro[3.5]nonane-2-carboxylate (0.250 g, 0.722 mmol) using the conditions described in step 2 for the synthesis of key Intermediate-V to afford 0.170 g (Yield=83%). ESI+MS: m/z 247.3 ([M+H]$^+$).

2-((4-chlorophenyl)(pyridin-2-yl)methyl)-7-(2-phenoxyethyl)-2,7-diazaspiro[3.5]nonane Example-105: 2-((4-chlorophenyl)(pyridin-2-yl)methyl)-8-(2-phenoxyethyl)-2,8-diazaspiro[4.5]decane (105)

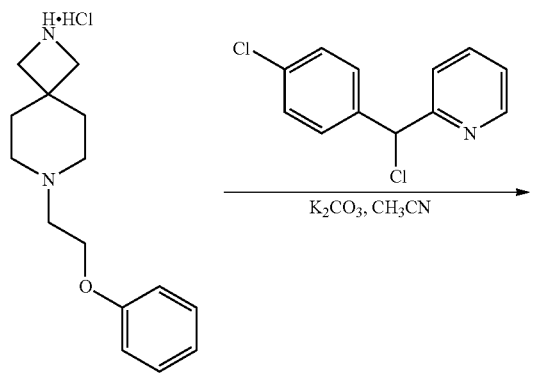

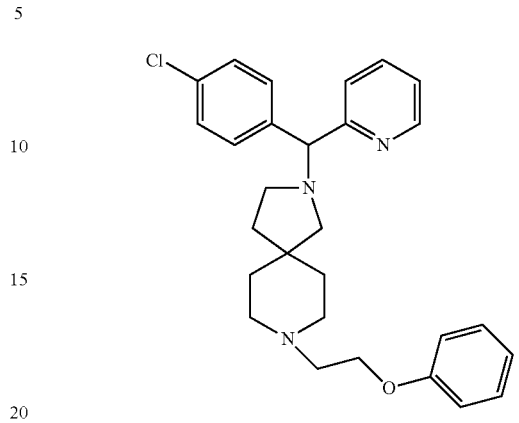

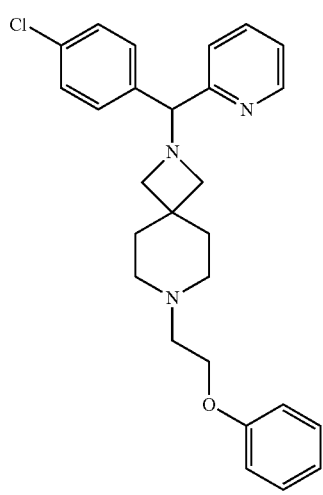

2-((4-chlorophenyl)(pyridin-2-yl)methyl)-8-(2-phenoxyethyl)-2,8-diazaspiro[4.5]decane was synthesized in 3 steps using the same chemistry as Example-104 and replacing tert-butyl 2,7-diazaspiro[3.5]nonane-2-carboxylate with tert-butyl 2,8-diazaspiro[4.5]decane-8-carboxylate to afford 0.060 g of 2-((4-chlorophenyl)(pyridin-2-yl)methyl)-8-(2-phenoxyethyl)-2,8-diaza spiro[4.5]decane (Yield=41%). $^1$H NMR (500 MHz, DMSO-$d_6$): δ 8.42 (d, 1H, J=4.5 Hz), 7.77-7.74 (m, 1H), 7.58 (d, 1H, J=8.0 Hz), 7.47 (d, 2H, J=8.5 Hz), 7.34 (d, 2H, J=8.5 Hz), 7.28-7.19 (m, 3H), 6.91-6.90 (m, 3H), 4.36 (s, 1H), 4.02 (t, 2H, J=6.0 Hz), 3.10-2.90 (m, 2H), 2.63-2.60 (m, 3H), 2.41-2.36 (m, 5H), 2.25-2.21 (m, 2H), 1.56-1.51 (m, 4H); ESI+MS: m/z 462 ([M+H]$^+$). Enantiomers of 105 were separated using chiral HPLC (method B) and afforded pure enantiomers 105a and 105b.

Example-106: 2-((4-chlorophenyl)(pyridin-2-yl)methyl)-8-(2-(2-(trifluoromethyl)phenoxy) ethyl)-2,8-diazaspiro[4.5]decane (106)

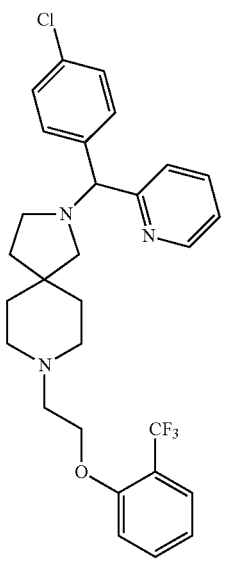 [SMILES: FC(F)(F)c1ccccc1OCCN1CCC2(CC1)CCN(C(c1ccc(Cl)cc1)c1ccccn1)C2]

Title compound was prepared from 2-(chloro(4-chlorophenyl)methyl)pyridine (0.126 g, 0.530 mmol) and 7-(2-phenoxyethyl)-2,7-diazaspiro[3.5]nonane hydrochloride (0.150 g, 0.530 mmol, 1 equiv) using the general methodology of Example-1. The crude was purified by preparative HPLC purification to afford 0.010 g 2-((4-chlorophenyl)(pyridin-2-yl)methyl)-7-(2-phenoxy ethyl)-2,7-diazaspiro[3.5]nonane (Yield=4%). $^1$H NMR (400 MHz, CD$_3$OD): δ 8.43 (m, 1H), 7.80-7.76 (m, 1H), 7.58 (d, 1H, J=8.0 Hz), 7.44-7.42 (m, 2H), 7.29-7.22 (m, 5H), 6.92-6.88 (m, 3H), 4.58 (s, 1H), 4.09 (t, 2H, J=5.6 Hz), 3.01-2.94 (m, 4H), 2.74 (t, 2H, J=5.6 Hz), 2.50 (br s, 4H), 1.84 (t, 4H, J=5.2 Hz); ESI+MS: m/z 448 ([M+H]$^+$).

Title compound was synthesized in 3 steps using the same chemistry as Example-104 and replacing tert-butyl 2,7- diazaspiro[3.5]nonane-2-carboxylate with tert-butyl 2,8-diaza spiro[4.5]decane-8-carboxylate and (2-bromoethoxy)-benzene with 1-(2-bromoethoxy)-2-(trifluoromethyl)benzene to afford 0.130 g of product (Yield=46%). $^1$H NMR (400 MHz, CD$_3$OD): δ 8.41 (d, 1H, J=5.2 Hz), 7.82-7.78 (m, 1H), 7.69 (d, 1H, J=7.6 Hz), 7.58-7.48 (m, 4H), 7.30-7.24 (m, 3H), 7.16 (d, 1H, J=8.0 Hz), 7.06 (t, 1H, J=7.6 Hz), 4.37 (s, 1H), 4.23 (t, 2H, J=5.6 Hz), 2.85 (t, 2H, J=5.6 Hz), 2.60-2.50 (m, 6H), 2.35 (s, 2H), 1.70-1.67 (m, 6H); ESI+ MS: m/z: 530.6 ([M+H]$^+$).

Example-107: N-((4-chlorophenyl)(pyridin-2-yl)methyl)-N-((1-(2-phenoxyethyl)piperidin-4-yl)methyl) acetamide (107)

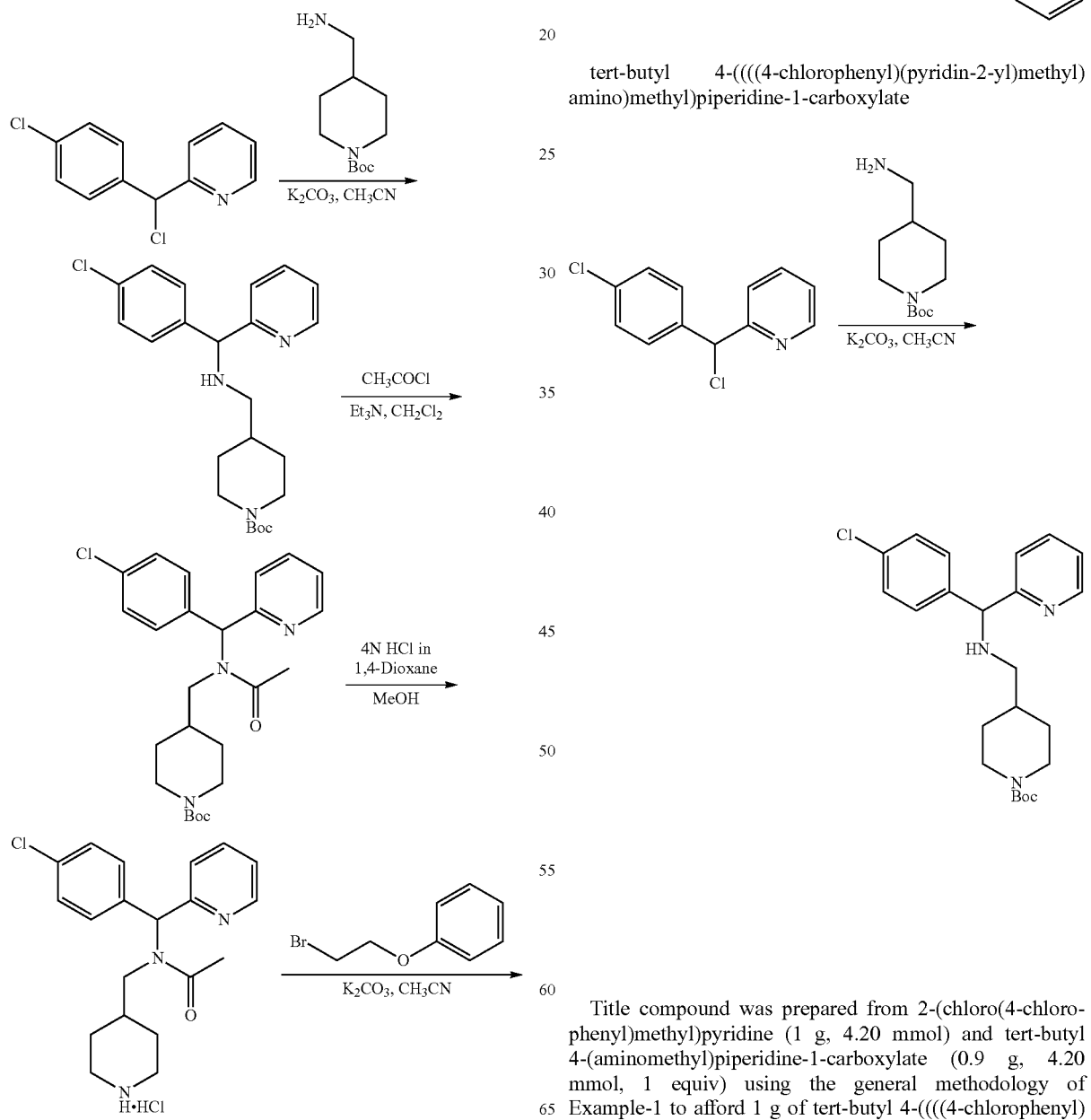

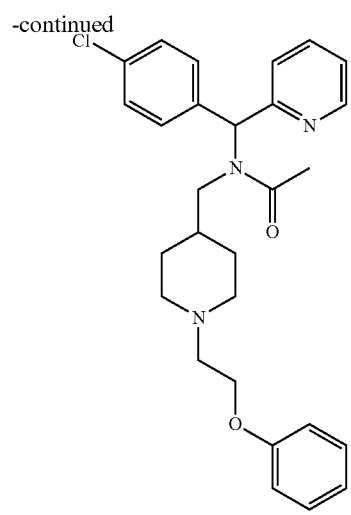

tert-butyl 4-((((4-chlorophenyl)(pyridin-2-yl)methyl)amino)methyl)piperidine-1-carboxylate Title compound was prepared from 2-(chloro(4-chlorophenyl)methyl)pyridine (1 g, 4.20 mmol) and tert-butyl 4-(aminomethyl)piperidine-1-carboxylate (0.9 g, 4.20 mmol, 1 equiv) using the general methodology of Example-1 to afford 1 g of tert-butyl 4-((((4-chlorophenyl)(pyridin-2-yl)methyl)amino)methyl)piperidine-1-carboxylate (Yield=57%).

255 tert-butyl 4-((((4-chlorophenyl)(pyridin-2-yl)methyl) acetamido)methyl)piperidine-1-carboxylate

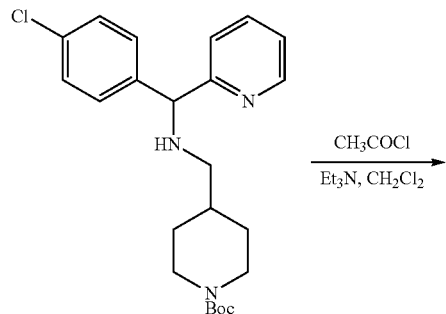

To a solution of tert-butyl 4-((((4-chlorophenyl)(pyridin-2-yl)methyl)amino)methyl) piperidine-1-carboxylate (0.3 g, 0.721 mmol) in $CH_2Cl_2$ (5 mL) under argon atmosphere were added triethyl amine (0.3 mL, 2.16 mmol, 3 equiv) and acetyl chloride (0.07 mL, 1.082 mmol, 1.5 equiv) at 0° C. The reaction was stirred at room temperature for 16 h. After completion, the reaction was diluted with water and extracted with $CH_2Cl_2$ (2×25 mL). The combined organic extract was dried over sodium sulfate, filtered and concentrated under reduced pressure. Purification using column chromatography (30% EtOAc/Hexanes as eluent) afforded 0.250 g of tert-butyl 4-((N-((4-chlorophenyl)(pyridin-2-yl) methyl) acetamido)methyl)piperidine-1-carboxylate (Yield=76%). ESI+MS: m/z 458.5 ([M+H]$^+$).

N-((4-chlorophenyl)(pyridin-2-yl)methyl)-N-(piperidin-4-ylmethyl)acetamide hydrochloride

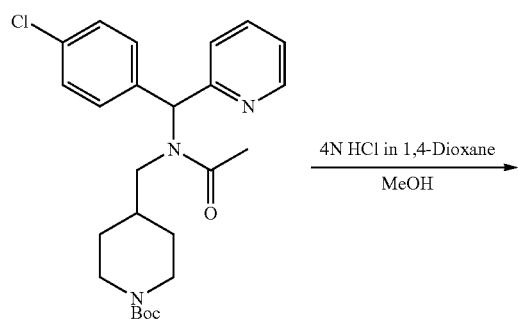

256

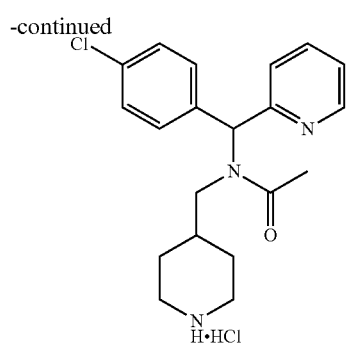

Title compound was prepared from tert-butyl 4-((N-((4-chlorophenyl)(pyridin-2-yl)methyl)acetamido)methyl)piperidine-1-carboxylate (0.250 g, 0.546 mmol) using the conditions described in step 2 for the synthesis of key intermediate-V and afforded 0.2 g of N-((4-chlorophenyl)(pyridin-2-yl)methyl)-N-(piperidin-4-ylmethyl)acetamide hydrochloride (Yield=93%). ESI+MS: m/z 358.4 ([M+H]$^+$).

N-((4(4-chlorophenyl)(pyridin-2-yl)methyl)-N-((1-(2-phenoxyethyl)piperidin-4-yl) methyl) acetamide

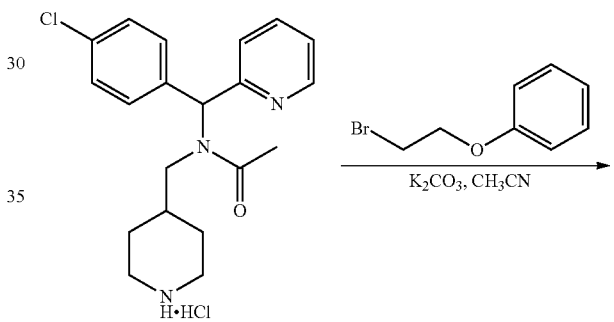

Title compound was prepared from N-((4-chlorophenyl)(pyridin-2-yl)methyl)-N-(piperidin-4-ylmethyl)acetamide hydrochloride (0.2 g, 0.507 mmol) and (2-bromoethoxy)benzene (0.102 g, 0.507 mmol, 1 equiv) using general methodology of Example-1. The crude was purified by preparative HPLC to afford 0.060 g of N-((4-chlorophenyl)(pyridin-2-yl)methyl)-N-((1-(2-phenoxyethyl)piperidin-4-yl) methyl) acetamide (Yield=24%). $^1$H NMR (500 MHz, DMSO-d$_6$): δ 8.55 (br s, 1H), 7.78 (brs, 1H), 7.40 (d, 2H, J=7.5 Hz), 7.31-7.21 (m, 5H), 6.93-6.89 (m, 3H), 6.43 (br s, 1H), 4.00 (t, 2H, J=6.0 Hz), 3.37-3.35 (m, 2H), 2.76 (br s, 2H), 2.64-2.57 (m, 2H), 2.08 (s, 3H), 1.71-1.69 (m, 2H), 1.30-1.25 (m, 4H), 0.88-0.86 (m, 2H); ESI+MS: m/z 478 ([M+H]$^+$).

Example-108: N-(isoquinolin-1-ylmethyl)-1-(2-(2-methoxyphenoxy)ethyl)piperidine-4-carboxamide (108)

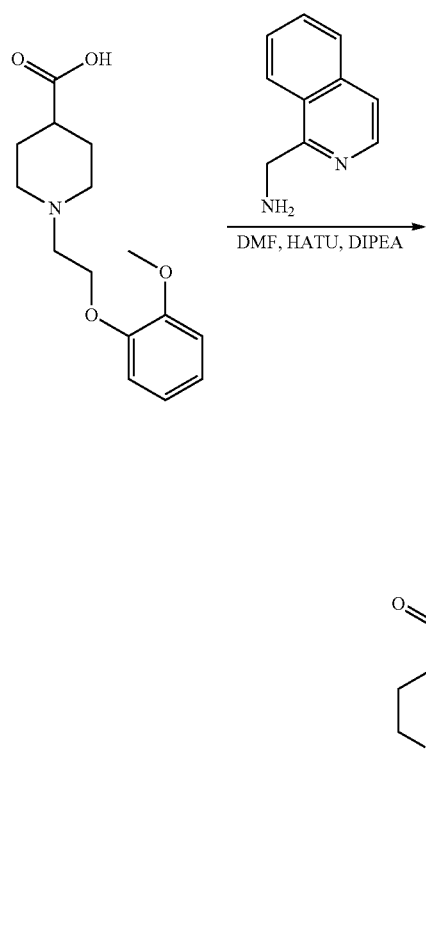

Title compound was prepared from coupling of 1-(2-(2-methoxyphenoxy)ethyl)piperidine-4-carboxylic acid (0.05 g, 0.179 mmol, 1.1 equiv) and isoquinolin-1-ylmethanamine (0.026 g, 0.163 mmol, 1 equiv) using the conditions in step 5 in the general methodology of key Intermediate-I. The crude compound was purified by column chromatography (2% MeOH in DCM as elutant) afforded 0.026 g of N-(isoquinolin-1-ylmethyl)-1-(2-phenoxyethyl)piperidine-4-carboxamide (Yield=38%). $^1$H NMR (300 MHz, CD$_3$OD): δ 8.69 (s, 1H), 8.39 (d, 1H, J=7.0 Hz), 8.26 (d, 1H, J=7.0 Hz), 7.98 (d, 1H, J=7.0 Hz), 7.85-7.65 (m, 3H), 7.10-7.00 (m, 3H), 6.95-6.85 (m, 1H), 5.06 (s, 2H), 4.33 (s, 2H), 3.87 (s, 3H), 3.85-3.70 (m, 2H), 3.58 (bs, 2H), 3.25-3.05 (m, 2H), 2.80-2.60 (m, 2H), 2.25-2.00 (m, 4H). ESI+MS: m/z 420.4 ([M+H]$^+$).

Example-109: N-((4(4-chlorophenyl)(pyridin-2-yl)methyl)-1-(2-(2-methoxyphenoxy) ethyl)piperidine-4-carboxamide (109)

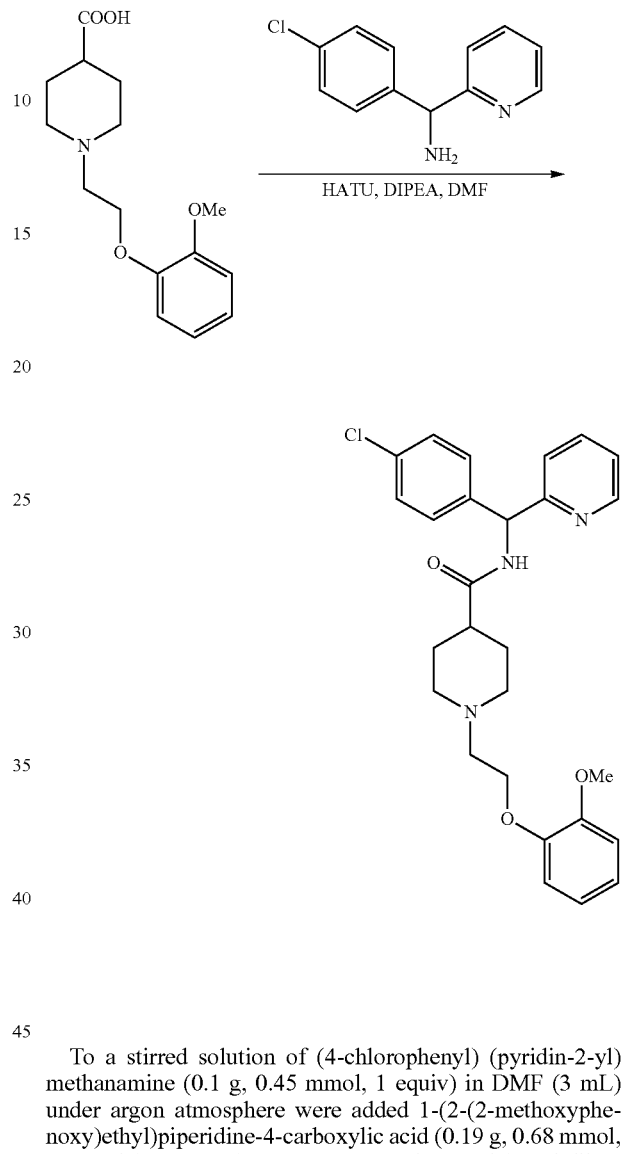

To a stirred solution of (4-chlorophenyl) (pyridin-2-yl) methanamine (0.1 g, 0.45 mmol, 1 equiv) in DMF (3 mL) under argon atmosphere were added 1-(2-(2-methoxyphenoxy)ethyl)piperidine-4-carboxylic acid (0.19 g, 0.68 mmol, 1.5 equiv), HATU (0.34 g, 0.91 mmol, 2 equiv) and diisopropyl ethyl amine (0.2 mL, 1.14 mmol, 2.5 equiv) at 0° C. The reaction mixture was warmed to room temperature and stirred for 16 h. After completion, the reaction mixture was quenched with cold water and extracted with EtOAc. The combined organic extract was dried over sodium sulfate, filtered and concentrated under reduced pressure. Purification using silica gel column chromatography (6% MeOH/CH$_2$Cl$_2$ as eluent) afforded 0.08 g of N-((4-chlorophenyl)(pyridin-2-yl)methyl)-1-(2-(2-methoxyphenoxy)ethyl)piperidine-4-carboxamide (Yield=36%). $^1$H NMR (DMSO-d$_6$, 400 MHz): δ 8.71 (d, J=8.4 Hz, 1H), 8.51 (d, J=4.0 Hz, 1H), 7.80-7.76 (m, 1H), 7.45 (d, J=8.0 Hz, 1H), 7.37-7.31 (m, 4H), 7.29-7.26 (m, 1H), 6.98-6.90 (m, 2H), 6.89-6.84 (m, 2H), 6.13 (d, J=8.4 Hz, 1H), 4.06-4.02 (m, 2H), 3.74 (s, 3H), 3.01-2.97 (m, 2H), 2.69-2.64 (m, 1H), 2.35-2.33 (m, 1H), 2.08-2.01 (m, 2H), 1.67-1.56 (m, 5H); ESI+MS: m/z 480 ([M+H]$^+$).

259

Example-110: N-((4(4-chlorophenyl)(pyridin-2-yl)methyl)-1-(4-henoxybutyl)piperidine-4-carboxamide (110)

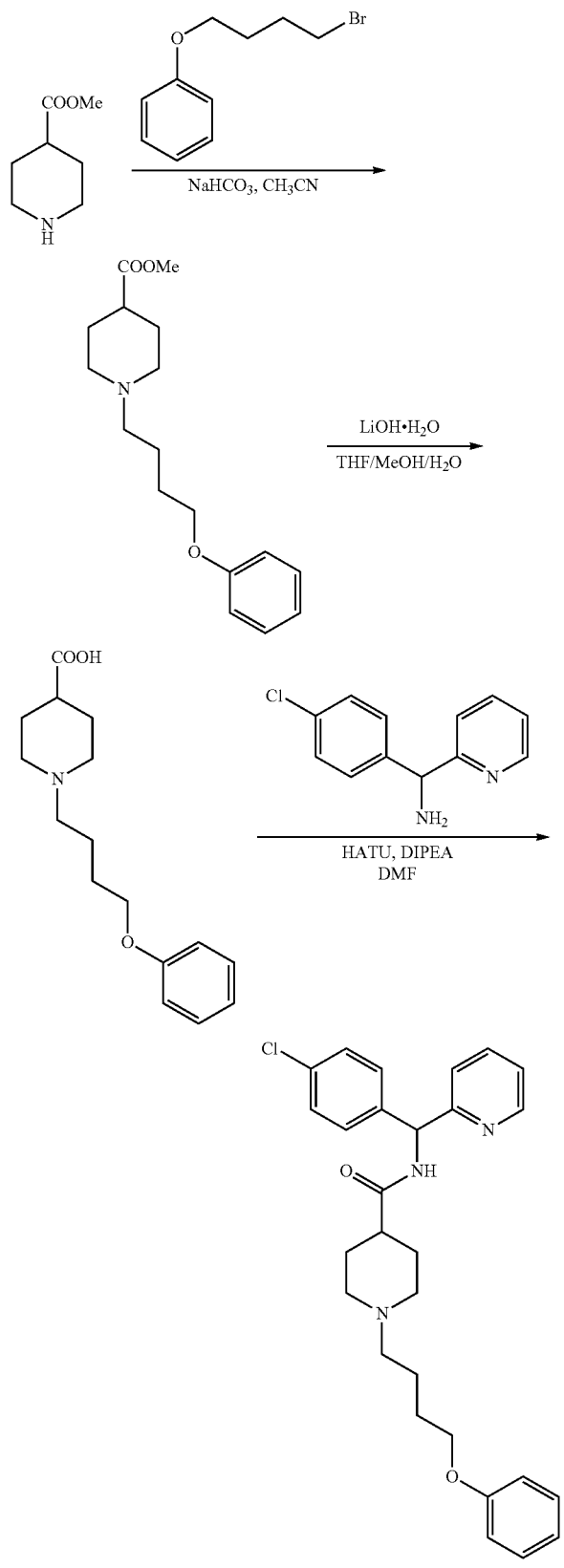

260

Methyl 1-(4-phenoxybutyl)piperidine-4-carboxylate

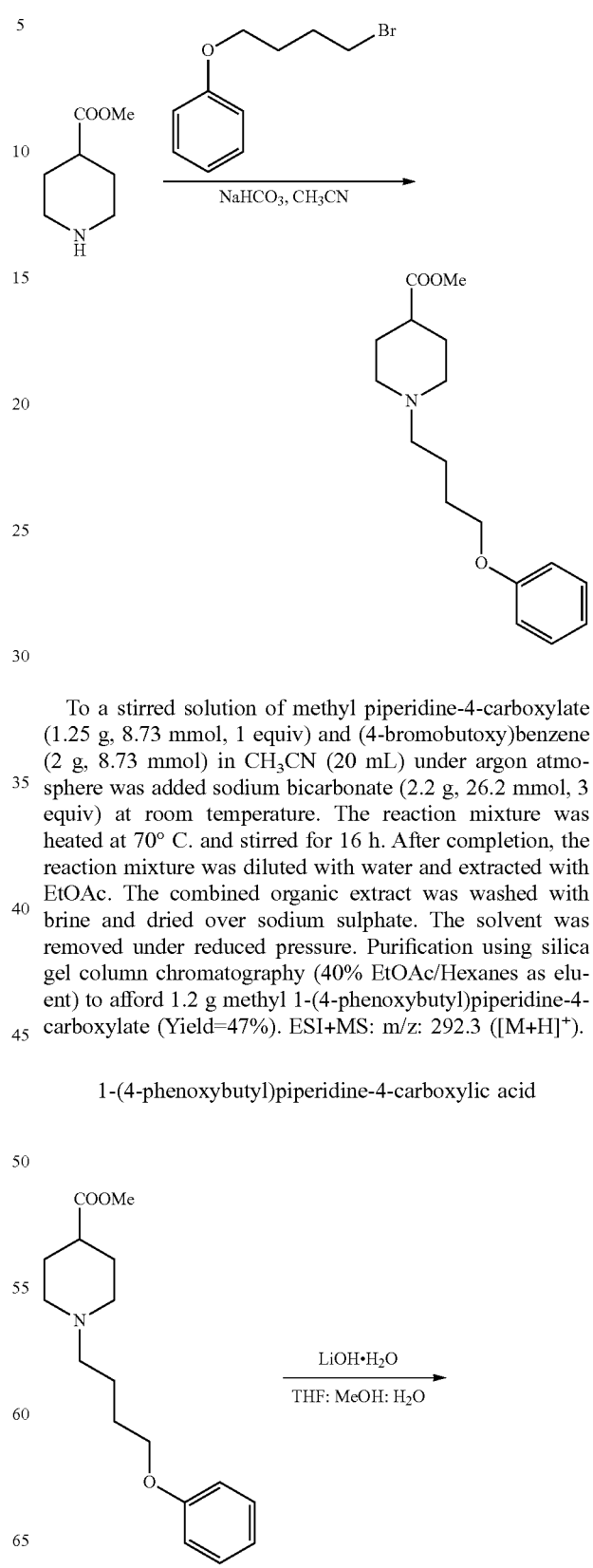

To a stirred solution of methyl piperidine-4-carboxylate (1.25 g, 8.73 mmol, 1 equiv) and (4-bromobutoxy)benzene (2 g, 8.73 mmol) in $CH_3CN$ (20 mL) under argon atmosphere was added sodium bicarbonate (2.2 g, 26.2 mmol, 3 equiv) at room temperature. The reaction mixture was heated at 70° C. and stirred for 16 h. After completion, the reaction mixture was diluted with water and extracted with EtOAc. The combined organic extract was washed with brine and dried over sodium sulphate. The solvent was removed under reduced pressure. Purification using silica gel column chromatography (40% EtOAc/Hexanes as eluent) to afford 1.2 g methyl 1-(4-phenoxybutyl)piperidine-4-carboxylate (Yield=47%). ESI+MS: m/z: 292.3 ([M+H]$^+$).

1-(4-phenoxybutyl)piperidine-4-carboxylic acid

-continued

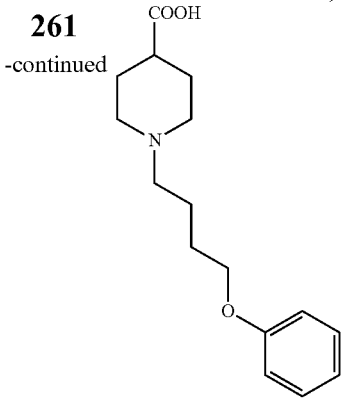

To a stirred solution of methyl 1-(4-phenoxybutyl)piperidine-4-carboxylate (1.0 g, 3.43 mmol, 1 equiv) in 25 mL of 2:2:1 mixture of THF:MeOH:H₂O was added lithium hydroxide (0.43 g, 10.30 mmol, 3 equiv) at 0° C. and the reaction mixture was stirred at room temperature for 3 h. After completion, volatiles were removed under reduced pressure; pH was adjusted to 7 with 1N HCl (aq), the obtained solid was filtered and dried under reduced pressure to afford 0.9 g of 1-(4-phenoxybutyl)piperidine-4-carboxylic acid (Yield=95%). ESI+MS: m/z: 278.0 ([M+H]⁺).

N-((4(4-chlorophenyl)(pyridin-2-yl)methyl)-1-(4-henoxybutyl)piperidine-4-carboxamide

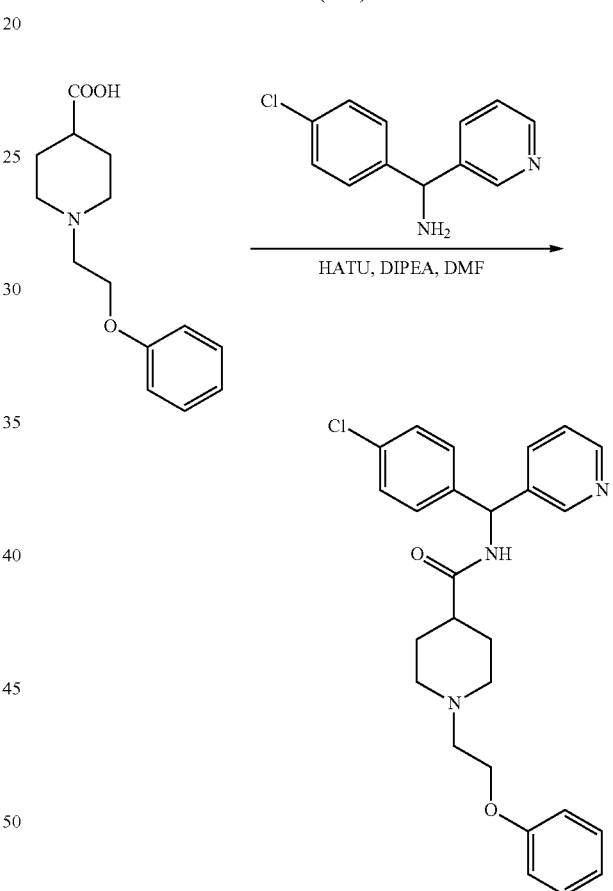

Title compound was prepared from coupling of (4-chlorophenyl) (pyridin-2-yl) methanamine (0.1 g, 0.45 mmol, 1 equiv) and 1-(4-phenoxybutyl)piperidine-4-carboxylic acid (0.19 g, 0.68 mmol, 1.5 equiv) using the conditions in step 5 in the general methodology of key Intermediate-I. Purification using silica gel column chromatography (4% MeOH/CH₂Cl₂ as eluent) afforded 0.07 g of N-((4-chlorophenyl)(pyridin-2-yl)methyl)-1-(4-benoxybutyl)piperidine-4-carboxamide (Yield=31%). ¹H NMR (DMSO-d₆, 400 MHz): δ 8.72 (br s, 1H), 8.51 (d, J=3.6 Hz, 1H), 7.78 (dt, J=9.2, 1.6 Hz, 1H), 7.44 (d, J=8.0 Hz, 1H), 7.37-7.24 (m, 7H), 6.92-6.88 (m, 3H), 6.13 (d, J=8.4 Hz, 1H), 3.96 (t, J=6.4 Hz, 2H), 3.31-3.29 (m, 1H), 2.94-2.89 (m, 2H), 2.38-2.35 (m, 2H), 1.92-1.84 (m, 2H), 1.72-1.54 (m, 8H); ESI+MS: m/z 479 ([M+H]⁺).

Example-111: N((4-chlorophenyl)(pyridin-3-yl)methyl)-1-(2-phenoxyethyl) piperidine-4-carboxamide (111)

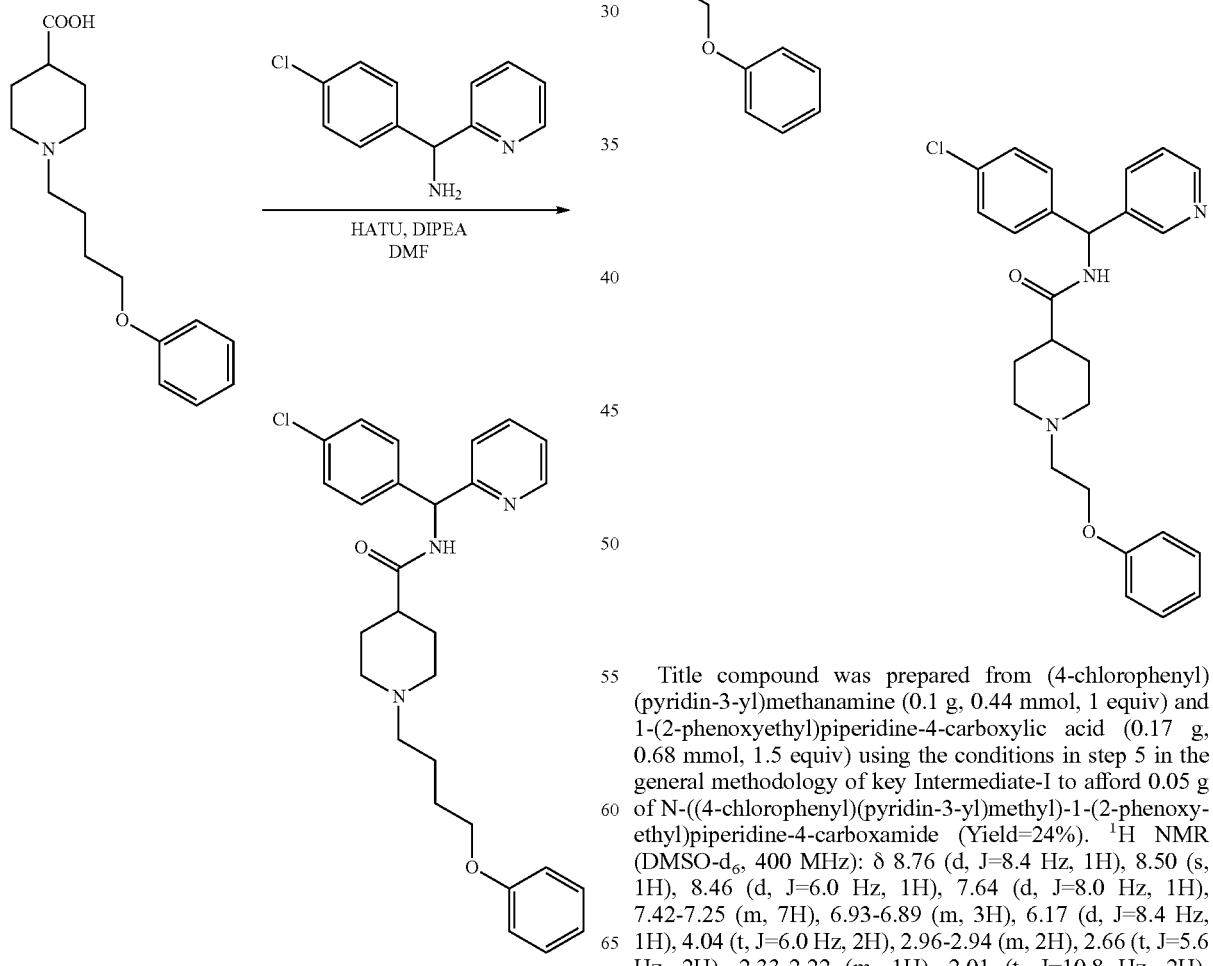

Title compound was prepared from (4-chlorophenyl)(pyridin-3-yl)methanamine (0.1 g, 0.44 mmol, 1 equiv) and 1-(2-phenoxyethyl)piperidine-4-carboxylic acid (0.17 g, 0.68 mmol, 1.5 equiv) using the conditions in step 5 in the general methodology of key Intermediate-I to afford 0.05 g of N-((4-chlorophenyl)(pyridin-3-yl)methyl)-1-(2-phenoxyethyl)piperidine-4-carboxamide (Yield=24%). ¹H NMR (DMSO-d₆, 400 MHz): δ 8.76 (d, J=8.4 Hz, 1H), 8.50 (s, 1H), 8.46 (d, J=6.0 Hz, 1H), 7.64 (d, J=8.0 Hz, 1H), 7.42-7.25 (m, 7H), 6.93-6.89 (m, 3H), 6.17 (d, J=8.4 Hz, 1H), 4.04 (t, J=6.0 Hz, 2H), 2.96-2.94 (m, 2H), 2.66 (t, J=5.6 Hz, 2H), 2.33-2.22 (m, 1H), 2.01 (t, J=10.8 Hz, 2H), 1.69-1.54 (m, 4H); ESI+MS: m/z 450.5 ([M+H]⁺).

Example-112: N((4-chlorophenyl)(pyridin-4-yl)methyl)-1-(2-phenoxyethyl) piperidine-4-carboxamide (112)

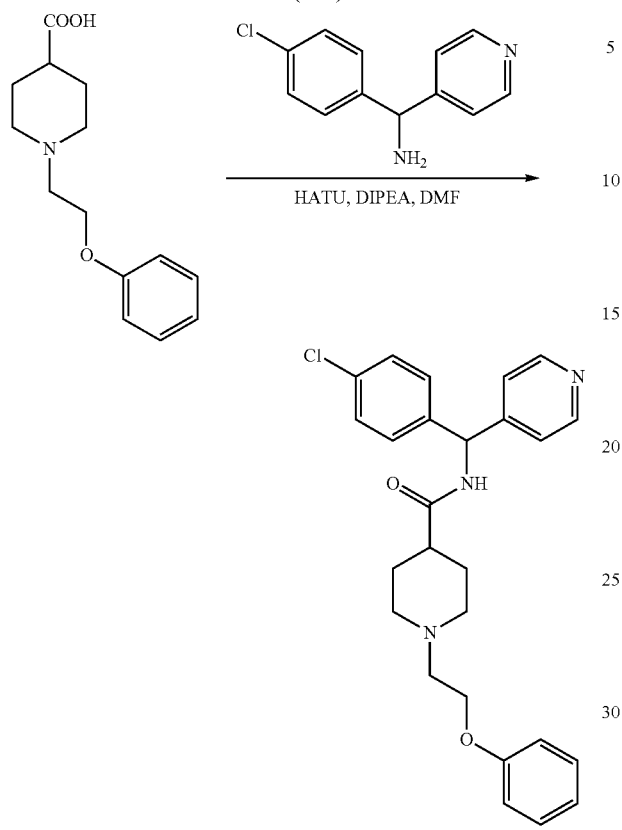

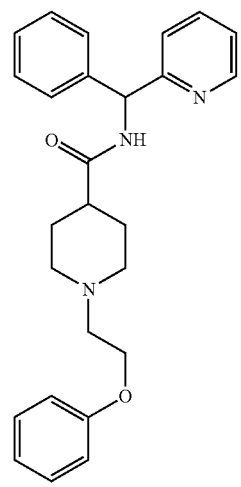

Title compound was prepared from (4-chlorophenyl)(pyridin-4-yl)methanamine (0.1 g, 0.44 mmol, 1 equiv) and 1-(2-phenoxyethyl)piperidine-4-carboxylic acid (0.17 g, 0.68 mmol, 1.5 equiv) using the conditions in step 5 in the general methodology of key Intermediate-I to afford 0.07 g of N-((4-chlorophenyl)(pyridin-4-yl)methyl)-1-(2-phenoxyethyl)piperidine-4-carboxamide (Yield=34%). $^1$H NMR (CDCl$_3$, 400 MHz): δ 8.56 (d, J=6.0 Hz, 2H), 7.32 (d, J=8.8 Hz, 2H), 7.29-7.27 (m, 1H), 7.12-7.10 (m, 4H), 6.95 (t, J=7.2 Hz, 1H), 6.89 (d, J=7.6 Hz, 2H), 6.17 (d, J=7.6 Hz, 1H), 6.07-6.05 (m, 1H), 4.11 (t, J=5.6 Hz, 2H), 3.12-3.09 (m, 2H), 2.85 (t, J=5.6 Hz, 2H), 2.26-2.23 (m, 3H), 1.91-1.80 (m, 4H); Ion trap: m/z 450.5 ([M+H]$^+$).

Example-113: 1-(2-phenoxyethyl)-N-(phenyl(pyridin-2-yl)methyl)piperidine-4-carboxamide (113)

Title compound was prepared from phenyl(pyridin-2-yl)methanamine (0.1 g, 0.54 mmol, 1 equiv) and 1-(2-phenoxyethyl)piperidine-4-carboxylic acid (0.20 g, 0.81 mmol, 1.5 equiv) using the conditions in step 5 in the general methodology of key Intermediate-I to afford 0.12 g of 1-(2-phenoxyethyl)-N-(phenyl(pyridin-2-yl)methyl)piperidine-4-carboxamide (Yield=53%). $^1$H NMR (DMSO-d$_6$, 400 MHz): δ 8.69 (d, J=8.4 Hz, 1H), 8.50 (d, J=4.4 Hz, 1H), 7.76 (dt, J=9.2, 1.6 Hz, 1H), 7.44 (d, J=8.0 Hz, 1H), 7.30-7.19 (m, 8H), 6.94-6.90 (m, 3H), 6.13 (d, J=8.4 Hz, 1H), 4.06 (t, J=5.6 Hz, 2H), 2.99-2.97 (m, 2H), 2.74-2.69 (m, 2H), 2.40-2.33 (m, 1H), 2.09-2.04 (m, 2H), 1.67-1.57 (m, 4H); ESI+MS: m/z 416 ([M+H]$^+$).

Example-114: 1-(4-chlorophenyl)-N-((1-(2-phenoxyethyl)piperidin-4-yl)methyl)-1-(pyridin-2-yl)methanamine (114)

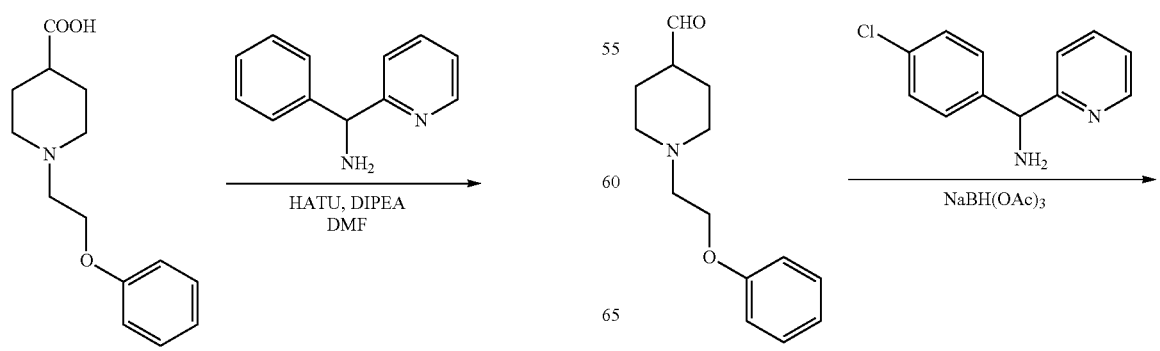

265

-continued

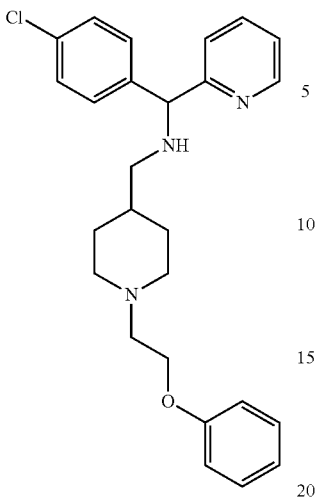

266

-continued

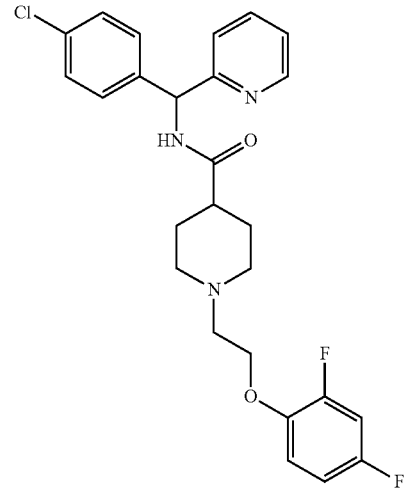

Title compound was prepared from 1-(2-phenoxyethyl) piperidine-4-carbaldehyde (0.1 g, 0.42 mmol, 1 equiv) and (4-chlorophenyl)(pyridin-2-yl)methanamine (0.14 g, 0.64 mmol, 1.5 equiv) using the general methodology described in Example-59. Purification using preparative HPLC afforded 0.03 g of 1-(4-chlorophenyl)-N-((1-(2-phenoxyethyl)piperidin-4-yl)methyl)-1-(pyridin-2-1)methanamine (Yield=16%). $^1$H NMR (DMSO-d$_6$, 400 MHz): δ 8.46 (d, J=4.0 Hz, 1H), 7.72 (dt, J=9.6, 1.6 Hz, 1H), 7.44-7.40 (m, 3H), 7.33 (d, J=8.4 Hz, 2H), 7.28-7.19 (m, 4H), 6.92-6.89 (m, 4H), 4.03 (t, J=5.2 Hz, 2H), 2.90-2.88 (m, 2H), 2.67-2.63 (m, 2H), 2.30-2.29 (m, 2H), 1.99-1.95 (m, 2H), 1.70-1.67 (m, 2H), 1.33-1.28 (m, 1H); 1.12-1.09 (m, 2H); ESI+ MS: m/z 436.4 ([M+H]$^+$). Enantiomers of 114 were separated using chiral HPLC (method H) and afforded pure enantiomers 114a and 114b.

Example-115: N-((4(4-chlorophenyl)(pyridin-2-yl)methyl)-1-(2-(2,4-difluorophenoxy) ethyl)piperidine-4-carboxamide (115)

Title compound was prepared from N-((4-chlorophenyl)(pyridin-2-yl)methyl)piperidine-4-carboxamide (0.1 g, 0.30 mmol, 1 equiv) and 1-(2-bromoethoxy)-2,4-difluorobenzene (0.07 g, 0.3 mmol, 1 equiv) using the general methodology of Example-1 to afford 0.098 g of N-((4-chlorophenyl)(pyridin-2-yl)methyl)-1-(2-(2,4-difluorophenoxy)ethyl)piperidine-4-carboxamide (Yield=78%). $^1$H NMR (DMSO-d$_6$, 400 MHz): δ 8.72 (d, J=8.0 Hz, 1H), 8.51 (d, J=4.0 Hz, 1H), 7.78 (dt, J=9.6, 2.0 Hz, 1H), 7.44 (d, J=8.0 Hz, 1H), 7.37-7.31 (m, 4H), 7.28-7.01 (m, 3H), 6.98 (t, J=6.4 Hz, 1H), 6.13 (d, J=8.4 Hz, 1H), 4.14-4.12 (m, 2H), 3.01-2.94 (m, 2H), 2.75-2.71 (m, 2H), 2.36-2.32 (m, 1H), 2.08-2.07 (m, 2H), 1.67-1.56 (m, 4H); ESI+MS: m/z 486.0 ([M+H]$^+$). Enantiomers of 115 were separated using chiral HPLC (method E) and afforded pure enantiomers 115a and 115b.

Example-116: N((4-chlorophenyl)(5-fluoropyridin-2-yl)methyl)-1-(2-phenoxyethyl) piperidine-4-carboxamide (116)

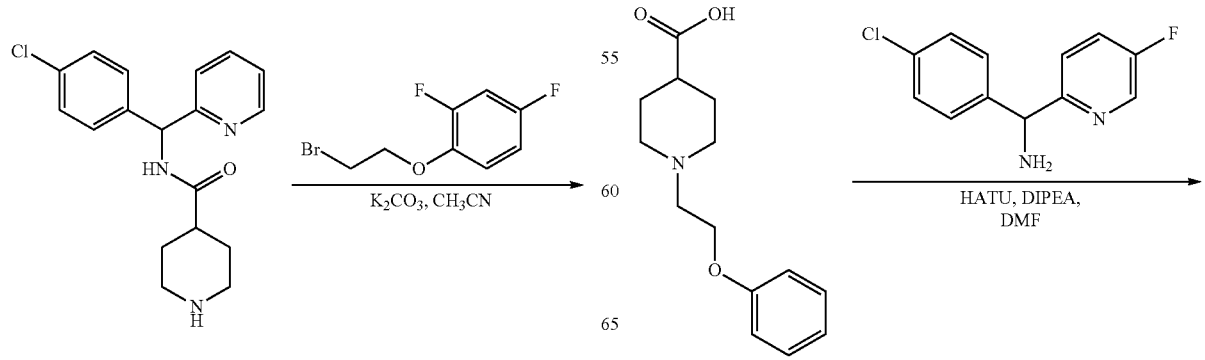

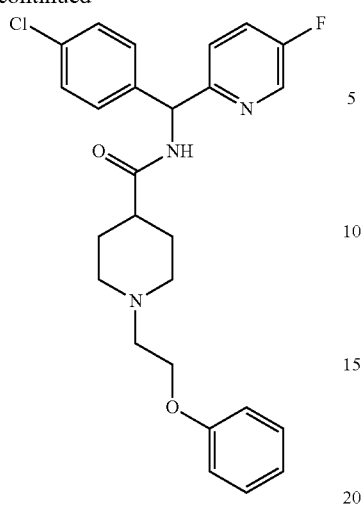

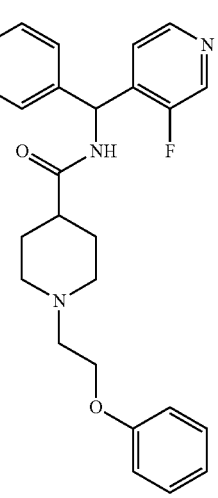

Title compound was prepared from (4-chlorophenyl)(5-fluoropyridin-2-yl)methanamine (0.2 g, 0.84 mmol, 1 equiv) and 1-(2-phenoxyethyl)piperidine-4-carboxylic acid (0.25 g, 1.01 mmol, 1.2 equiv) using the conditions in step 5 in the general methodology of key Intermediate-I to afford 0.08 g of N-((4-chlorophenyl)(5-fluoropyridin-2-yl)methyl)-1-(2-phenoxyethyl)piperidine-4-carboxamide (Yield=20%). $^1$H NMR (DMSO-$d_6$, 500 MHz): δ 8.72 (d, J=8.0 Hz, 1H), 8.51 (s, 1H), 7.73 (dt, J=12.0, 3.0 Hz, 1H), 7.54-7.51 (m, 1H), 7.38-7.26 (m, 6H), 6.93-6.90 (m, 3H), 6.17 (d, J=8.5 Hz, 1H), 4.05 (t, J=6.0 Hz, 2H), 2.96-2.94 (m, 2H), 2.67-2.64 (m, 2H), 2.36-2.33 (m, 1H), 2.02 (t, J=10.5 Hz, 2H), 1.69-1.65 (m, 2H), 1.60-1.56 (m, 2H); ESI+MS: m/z 468.4 ([M+H]$^+$).

Title compound was prepared from (4-chlorophenyl)(3-fluoropyridin-4-yl)methanamine (0.2 g, 0.84 mmol, 1 equiv) and 1-(2-phenoxyethyl)piperidine-4-carboxylic acid (0.25 g, 1.01 mmol, 1.2 equiv) using the conditions in step 5 in the general methodology of key Intermediate-I to afford 0.06 g of N-((4-chlorophenyl)(3-fluoropyridin-4-yl)methyl)-1-(2-phenoxyethyl) piperidine-4-carboxamide (Yield=15%). $^1$H NMR (DMSO-$d_6$, 400 MHz): δ 8.81 (d, J=8.0 Hz, 1H), 8.51 (s, 1H), 8.44 (d, J=4.8 Hz, 1H), 7.43-7.38 (m, 3H), 7.28-7.25 (m, 4H), 6.93-6.89 (m, 3H), 6.30 (d, J=8.0 Hz, 1H), 4.04 (t, J=6.0 Hz, 2H), 2.96-2.93 (m, 2H), 2.67-2.65 (m, 2H), 2.27-2.24 (m, 1H), 2.01 (t, J=12.0 Hz, 2H), 1.70-1.54 (m, 4H); Ion trap: m/z 468.7 ([M+H]$^+$).

Example-117: N-((4(4-chlorophenyl)(3-fluoropyridin-4-yl)methyl)-1-(2-phenoxyethyl)piperidine-4-carboxamide (117)

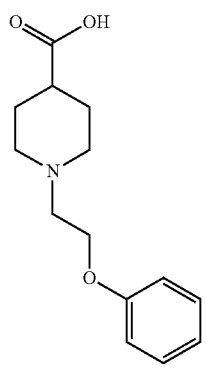 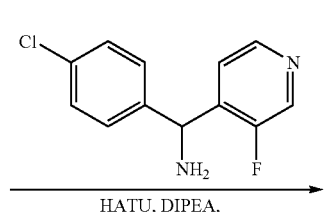

Example-118: 1-(2-phenoxyethyl)-N-(pyridin-2-yl (3-(trifluoromethoxy)phenyl)methyl) piperidine-4-carboxamide (118)

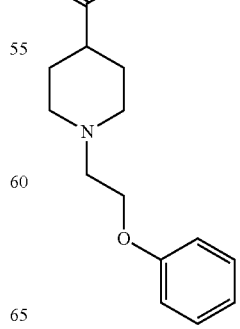 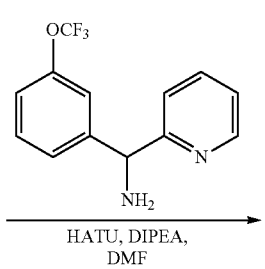

-continued

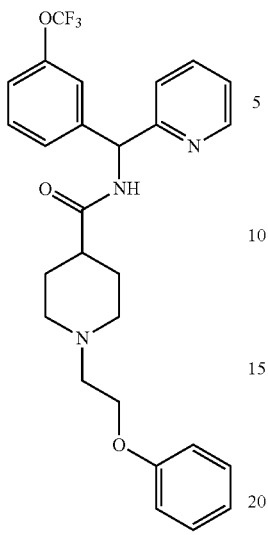

Title compound was prepared from pyridin-2-yl(3-(trifluoromethoxy)phenyl)methanamine (0.1 g, 0.55 mmol, 1 equiv) and 1-(2-phenoxyethyl)piperidine-4-carboxylic acid (0.16 g, 0.67 mmol, 1.2 equiv) using the conditions in step 5 in the general methodology of key Intermediate-I. Purification using preparative HPLC afforded 0.1 g of 1-(2-phenoxyethyl)-N-(pyridin-2-yl(3-(trifluoromethoxy)phenyl) methyl)piperidine-4-carboxamide (Yield=36%). $^1$H NMR (DMSO-$d_6$, 400 MHz): δ 8.78 (d, J=8.4 Hz, 1H), 8.52 (d, J=4.0 Hz, 1H), 7.79 (dt, J=9.6, 2.0 Hz, 1H), 7.49-7.41 (m, 2H), 7.36-7.34 (m, 1H) 7.30-7.20 (m, 5H), 6.93-6.89 (m, 3H), 6.20 (d, J=8.4 Hz, 1H), 4.05 (t, J=5.6 Hz, 2H), 2.96-2.94 (m, 2H), 2.68-2.64 (m, 2H), 2.39-2.32 (m, 1H), 2.02 (t, J=11.6 Hz, 2H), 1.70-1.52 (m, 4H); ESI+MS: m/z 500.6 ([M+H]$^+$). Enantiomers of 118 were separated using chiral HPLC (method M) and afforded pure enantiomers 118a and 118b.

Example-119: N-((4(2,2-difluorobenzo[d][1,3]dioxol-5-yl)(pyridin-2-yl)methyl)-1-(2-phenoxy ethyl) piperidine-4-carboxamide (119)

-continued

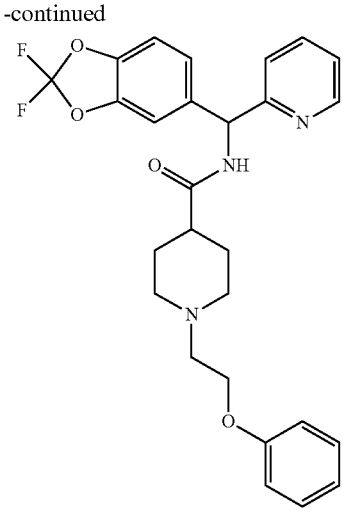

Title compound was prepared from (2,2-difluorobenzo[d][1,3]dioxol-5-yl)(pyridin-2-yl)methanamine (0.2 g, 0.75 mmol, 1 equiv) and 1-(2-phenoxyethyl)piperidine-4-carboxylic acid (0.22 g, 0.90 mmol, 1.2 equiv) using the conditions in step 5 in the general methodology of key Intermediate-I to afford 0.11 g of N-((4(2,2-difluorobenzo[d][1,3]dioxol-5-yl)(pyridin-2-yl)methyl)-1-(2-phenoxyethyl)piperidine-4-carboxamide (Yield=29%). $^1$H NMR (DMSO-$d_6$, 400 MHz): δ 8.70 (d, J=8.4 Hz, 1H), 8.51 (d, J=5.6 Hz, 1H), 7.77 (dt, J=9.6, 1.6 Hz, 1H), 7.46 (d, J=8.0 Hz, 1H), 7.39-7.37 (m, 1H), 7.33-7.31 (m, 1H), 7.28-7.24 (m, 3H), 7.18 (d, J=8.4 Hz, 1H), 6.93-6.89 (m, 3H), 6.15 (d, J=8.0 Hz, 1H), 4.04 (t, J=6.0 Hz, 2H), 2.96-2.93 (m, 2H), 2.67-2.64 (m, 2H), 2.36-2.29 (m, 1H), 2.01 (t, J=11.2 Hz, 2H), 1.68-1.52 (m, 4H); ESI+MS: m/z 496.5 ([M+H]$^+$. Enantiomers of 119 were separated using chiral HPLC (method D) and afforded pure enantiomers 119a and 119b.

Example-120: 1-(4-chlorophenyl)-1-(pyridin-2-yl)-N-((1-(2-(2-(trifluoromethyl) phenoxy)ethyl) piperidin-4-yl)methyl)methanamine (120)

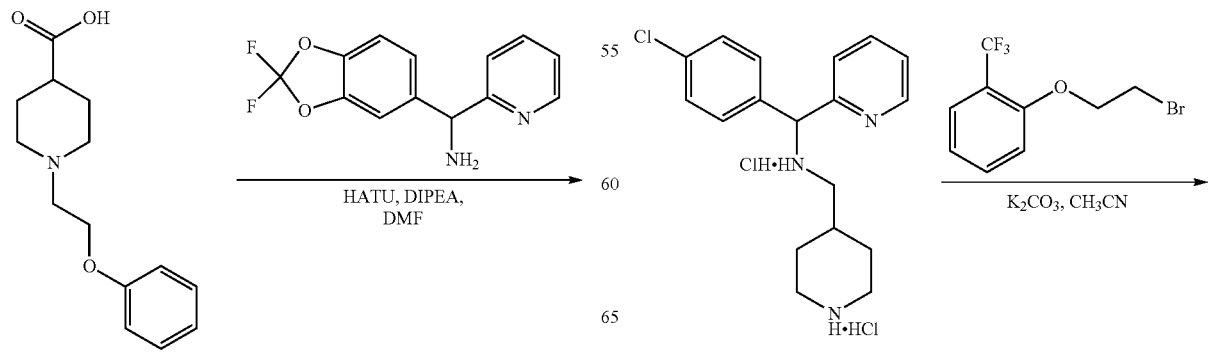

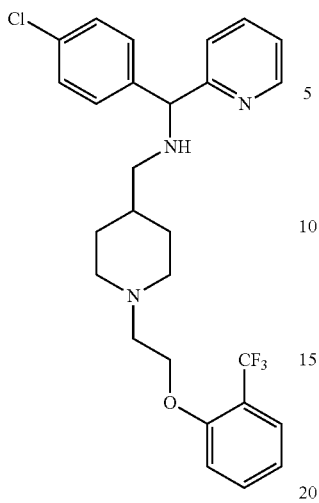

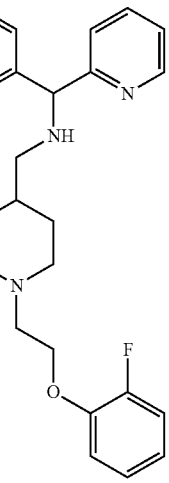

Title compound was prepared from 1-(4-chlorophenyl)-N-(piperidin-4-ylmethyl)-1-(pyridin-2-yl)methanamine dihydrochloride (0.2 g, 0.514 mmol, 1 equiv) and 1-(2-bromoethoxy)-2-(trifluoromethyl)benzene (0.138 g, 0.514 mmol, 1 equiv) using the general methodology of Example-1 to afford 0.1 g of N-((4-chlorophenyl)(pyridin-2-yl)methyl)-1-(2-(2,4-difluorophenoxy)ethyl)piperidine-4-carboxamide (Yield=38%). $^1$H NMR (DMSO-$d_6$, 500 MHz): δ 8.47 (d, J=4.0 Hz, 1H), 7.73 (dt, J=8.5, 1.5 Hz, 1H), 7.62-7.59 (m, 2H), 7.45-7.33 (m, 5H), 7.27-7.20 (m, 2H), 7.07 (t, J=7.5 Hz, 1H), 4.83 (d, J=5.0 Hz, 1H), 4.18 (t, J=6.0 Hz, 2H), 2.90-2.88 (m, 2H), 2.69-2.64 (m, 2H), 2.29 (t, J=6.0 Hz, 2H), 2.01 (t, J=11.0 Hz, 2H), 1.69-1.66 (m, 2H), 1.41-1.39 (m, 1H), 1.12-1.07 (m, 2H). ESI+MS: m/z 504 ([M+H]$^+$).

Example 121: 1-(4-chlorophenyl)-N-((1-(2-(2-fluorophenoxy) ethyl) piperidin-4-yl) methyl)-1-(pyridin-2-yl) methanamine (121)

To a stirred solution of (4-chlorophenyl)(pyridin-2-yl)methanamine (0.10 g, 0.43 mmol) in CH$_2$Cl$_2$ (5 mL) under argon atmosphere was added 1-(2-(2-fluorophenoxy) ethyl) piperidine-4-carbaldehyde (0.108 g, 0.43 mmol, 1 equiv) at 0° C. and stirred for 5 min. Then sodium triacetoxy borohydride (0.27 g, 1.28 mmol, 3 equiv) and acetic acid (0.024 mL, 0.43 mmol, 1 equiv) were added. The reaction mixture was warmed to room temperature and stirred for 16 h. After completion, the pH of the reaction mixture was adjusted to ~7 using saturated NaHCO$_3$ solution (5 mL) and extracted with CH$_2$Cl$_2$ (2×20 mL). The combined organic extract was dried over sodium sulfate, filtered and concentrated under reduced pressure. The crude was purified by preparative HPLC to afford 0.03 g of 1-(4-chlorophenyl)-N-((1-(2-(2-fluorophenoxy) ethyl) piperidin-4-yl) methyl)-1-(pyridin-2-yl) methanamine (Yield=15%).

$^1$HNMR (400 MHz, CD$_3$OD): δ 8.49-8.47 (m, 1H), 7.77 (dt, 1H, J$_{1,2}$=2.0 Hz, J$_{1,4}$=9.6 Hz), 7.48 (d, 1H, J=8.0 Hz,), 7.42-7.40 (m, 2H), 7.31-7.24 (m, 3H), 7.09-7.04 (m, 3H), 6.94-6.90 (m, 1H), 4.91 (s, 1H), 4.19 (t, 2H, J=5.6 Hz), 3.06 (d, 2H, J=11.2 Hz), 2.84 (t, 2H, J=5.6 Hz), 2.46-2.37 (m, 2H), 2.21 (t, 2H, J=11.6 Hz), 1.80 (d, 2H, J=11.6 Hz), 1.59-1.53 (m, 1H), 1.32-1.26 (m, 1H), 1.25-1.22 (m, 1H); ESI+MS: m/z 454 ([M+H]$^+$).

Example-122: N-((1-(2-(2-fluorophenoxy) ethyl) piperidin-4-yl) methyl)-1-(4-fluorophenyl)-1-(pyridin-2-yl) methanamine (122)

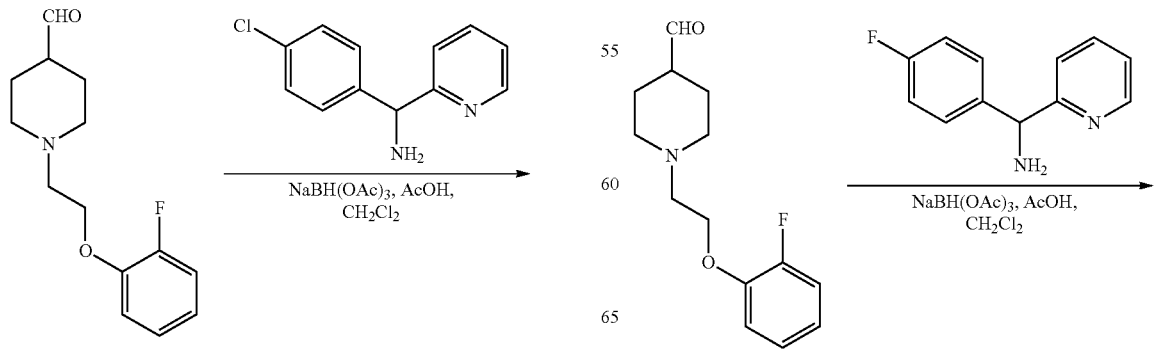

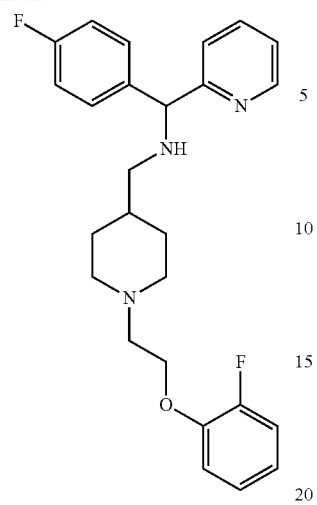

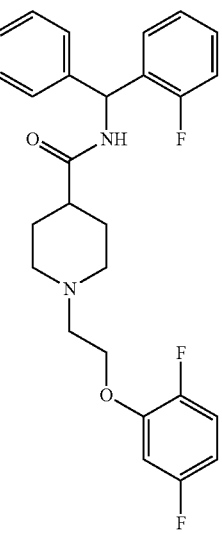

Title compound was prepared from (4-fluorophenyl)(pyridin-2-yl) methanamine (0.10 g, 0.27 mmol) using the methodology of Example-121 and afforded 0.03 g of N-((1-(2-(2-fluorophenoxy) ethyl) piperidin-4-yl) methyl)-1-(4-fluorophenyl)-1-(pyridin-2-yl) methanamine (Yield=14%). ¹HNMR (400 MHz, CD₃OD): δ 8.50 (d, 1H, J=4.0 Hz), 7.77 (dt, 1H, J$_{1,2}$=2.0 Hz, J$_{1,4}$=9.6 Hz), 7.47-7.43 (m, 3H), 7.29-7.26 (m, 1H), 7.13-7.02 (m, 5H), 6.96-6.91 (m, 1H), 4.98 (s, 1H), 4.25 (t, 2H, J=5.2 Hz), 3.22 (d, 2H, J=11.6 Hz) 3.03 (t, 2H, J=5.2 Hz), 2.49-2.41 (m, 4H), 1.89-1.86 (m, 2H), 1.67-1.63 (m, 1H), 1.39-1.26 (m, 2H); ESI+MS: m/z 438 ([M+H]⁺).

Example-123: N-((4-chlorophenyl)(2-fluorophenyl) methyl)-1-(2-(2,5-difluorophenoxy) ethyl) piperidine-4-carboxamide (123)

Title compound was prepared from (4-chlorophenyl)(2-fluorophenyl) methanamine (0.15 g, 0.63 mmol) and 1-(2-(2,5-difluorophenoxy)ethyl)piperidine-4-carboxylic acid (0.18 g, 0.63 mmol) using the conditions in step 5 in the general methodology of key Intermediate-I and afforded 0.20 g of N((4-chlorophenyl)(2-fluorophenyl)methyl)-1-(2-(2,5-difluorophenoxy) ethyl) piperidine-4-carboxamide (Yield=62%). ¹HNMR (400 MHz, CD₃OD): δ 7.38-7.36 (m, 3H), 7.29-7.02 (m, 7H), 6.78-6.75 (m, 1H), 6.42 (s, 1H), 4.43 (t, J=4.5 Hz, 2H), 3.70-3.46 (m, 4H), 3.18-3.12 (m, 2H), 2.69-2.67 (m, 1H), 2.10-2.07 (m, 4H); ESI+MS: m/z 503 ([M+H]⁺).

Example-125: N-((4(4-chlorophenyl)(pyridin-2-yl) methyl)-2,2,2-trifluoro-N-((1-(2-phenoxyethyl)piperidin-4-yl)methyl)ethanamine (125)

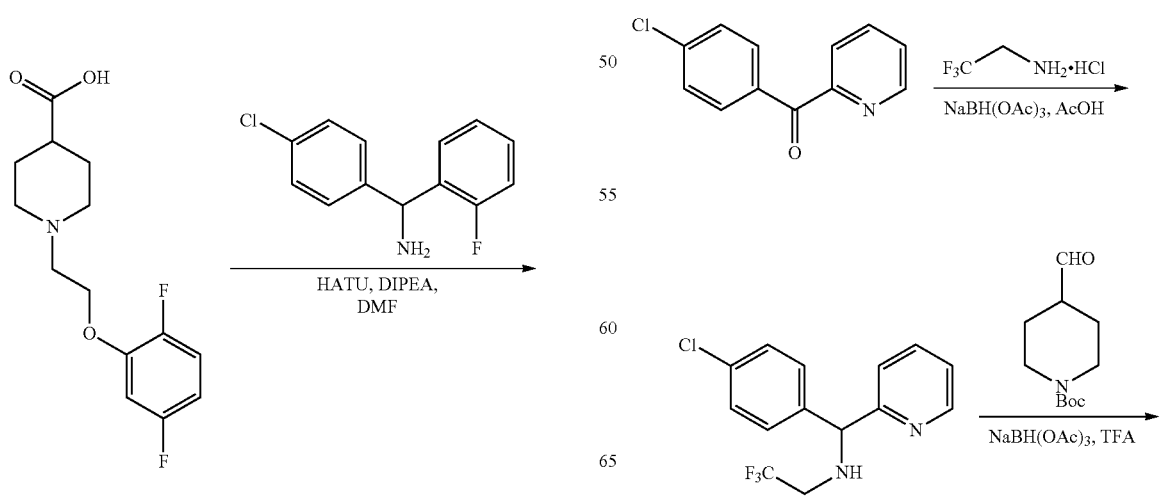

275

-continued

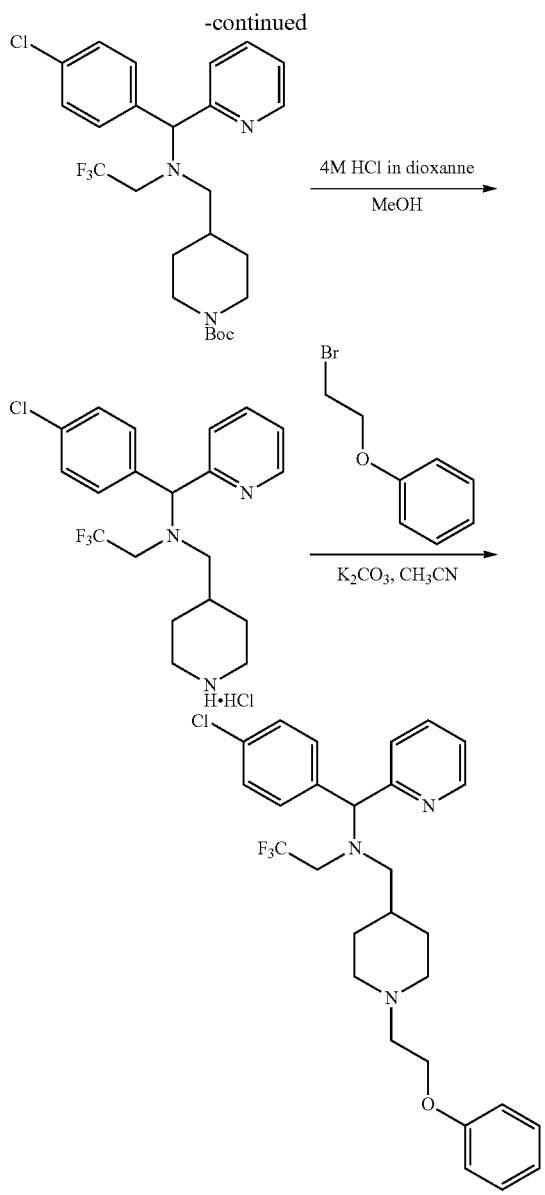

N-((4(4-chlorophenyl)(pyridin-2-yl)methyl)-2,2,2-trifluoroethanamine

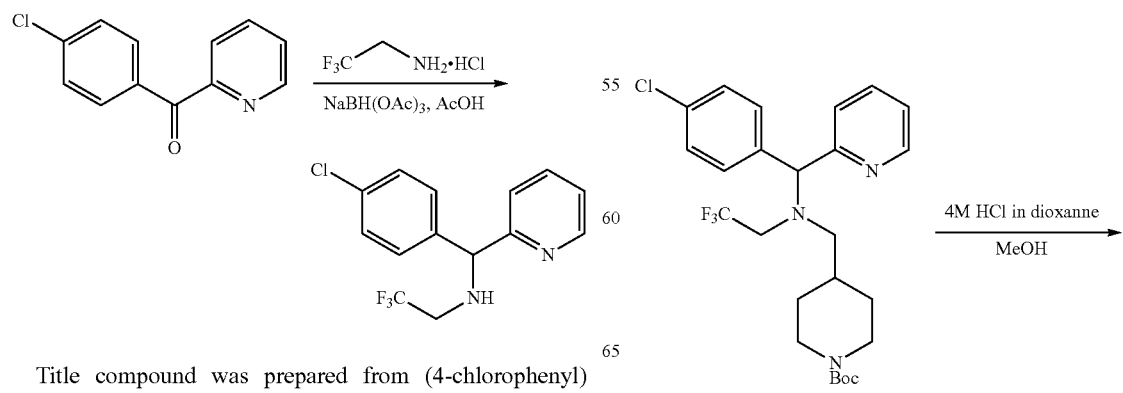

Title compound was prepared from (4-chlorophenyl)(pyridin-2-yl)methanone (1.2 g, 5.5 mmol) using the meth-

276 odology of Example-121 and afforded 0.5 g of N-((4-chlorophenyl)(pyridin-2-yl)methyl)-2,2,2-trifluoroethanamine (Yield=31%). ESI+MS: m/z 301.2 ([M+H]$^+$).

tert-butyl 4-((((4-chlorophenyl)(pyridin-2-yl)methyl)(2,2,2-trifluoroethyl)amino)methyl) piperidine-1-carboxylate

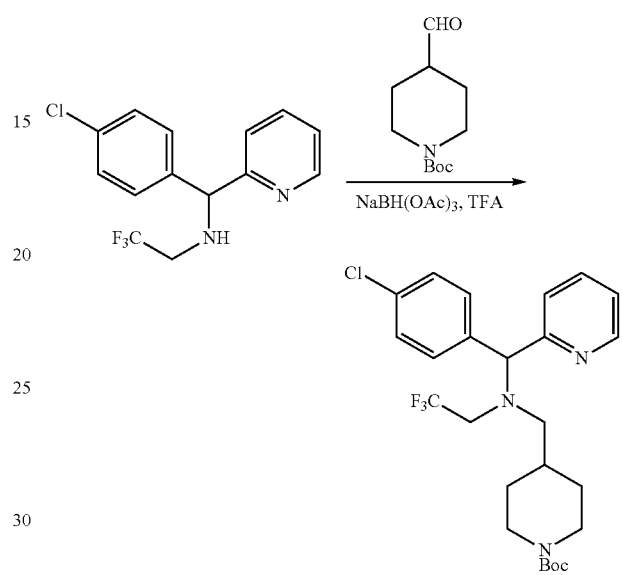

To a stirred solution of N-((4-chlorophenyl)(pyridin-2-yl)methyl)-2,2,2-trifluoroethanamine (0.3 g, 1.0 mmol) and tert-butyl 4-formylpiperidine-1-carboxylate (0.21 g, 1.0 mmol) in DCM (5 ml) was added TFA (0.077 ml, 1.0 mmol) followed by NaBH(OAc)$_3$ (0.63 g, 3.0 mmol) at 0° C. The reaction mixture was brought to RT and continued for 16 h. After completion of the reaction (monitored by TLC), the mixture was diluted with sat.NaHCO$_3$ and extracted with DCM. The organic layer was dried over anhydrous Na$_2$SO$_4$ and concentrated under reduced pressure. The crude compound was purified by column chromatography (20% ethyl acetate in hexane) to afford tert-butyl 4-((((4-chlorophenyl)(pyridin-2-yl)methyl)(2,2,2-trifluoroethyl)amino)methyl)piperidine-1-carboxylate as thick syrup. ESI+MS: m/z 498.6 ([M+H]$^+$).

N-((4-chlorophenyl)(pyridin-2-yl)methyl)-2,2,2-trifluoro-N-(piperidin-4-ylmethyl)ethanamine hydrochloride

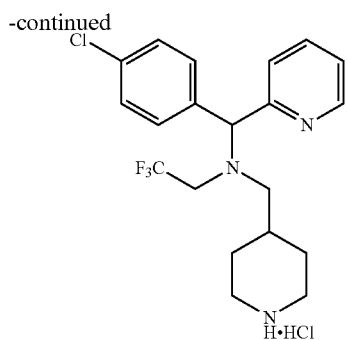

Title compound was prepared from tert-butyl 4-((((4-chlorophenyl)(pyridin-2-yl)methyl)(2,2,2-trifluoroethyl)amino)methyl)piperidine-1-carboxylate (0.20 g, 0.40 mmol) using the conditions described in step 2 for the synthesis of key intermediate-V and afforded 0.15 g of N-((4-chlorophenyl)(pyridin-2-yl)methyl)-2,2,2-trifluoro-N-(piperidin-4-yl-methyl)ethanamine hydrochloride (Yield=86%). ESI+MS: m/z 398.4 ([M+H]+).

N-((4-chlorophenyl)(pyridin-2-yl)methyl)-2,2,2-trifluoro-N-((1-(2-phenoxyethyl)piperidin-4-yl)methyl)ethanamine (125)

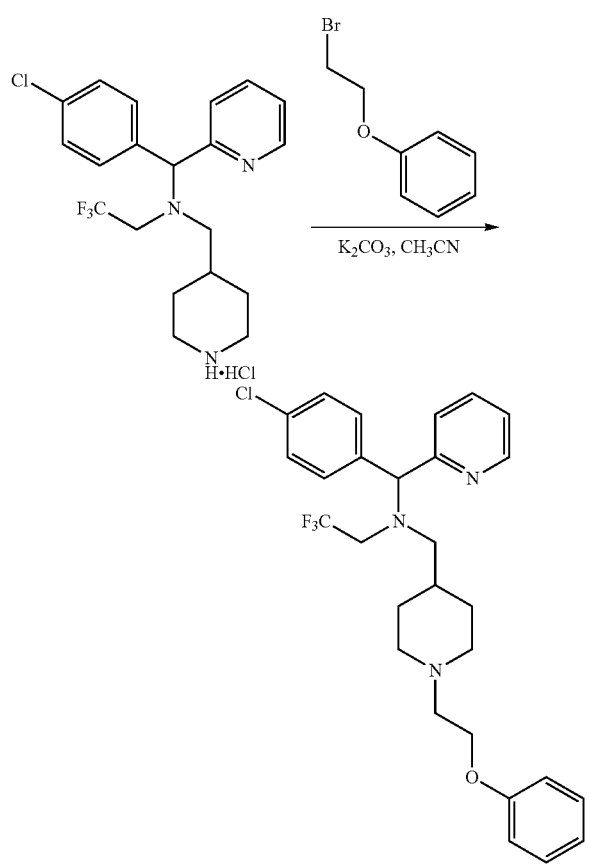

Title compound was prepared from N-((4-chlorophenyl)(pyridin-2-yl)methyl)-2,2,2-trifluoro-N-(piperidin-4-yl-methyl)ethanamine hydrochloride (0.15 g, 0.35 mmol) using the general methodology of Example-1. The crude compound was purified by silica gel column chromatography to afford 0.10 g of N-((4-chlorophenyl)(pyridin-2-yl)methyl)-2,2,2-trifluoro-N-((1-(2-phenoxyethyl)piperidin-4-yl)methyl)ethanamine (Yield=56%). $^1$H NMR (400 MHz, CD$_3$OD): δ 8.56-8.54 (m, 1H), 7.85-7.80 (m, 1H), 7.51-7.49 (m, 1H), 7.34-7.23 (m, 7H), 6.93-6.89 (m, 3H), 5.27 (s, 1H), 4.11 (t, J=5.6 Hz, 2H), 3.48-3.33 (m, 2H), 3.04-2.99 (m, 2H), 2.79 (t, J=5.6 Hz, 2H), 2.66-2.53 (m, 2H), 2.18-2.11 (m, 2H), 1.95-1.91 (m, 1H), 1.72-1.67 (m, 1H), 1.62-1.60 (m, 1H), 1.19-1.09 (m, 2H); ESI+MS: m/z: 518.6 ([M+H]+).

Enantiomers of 125 were separated using chiral HPLC (method R) and afforded pure enantiomers 125a and 125b.

Example-126: 2-(4-chlorophenyl)-N-(1-(2-phenoxyethyl)piperidin-4-yl)-2-(pyridin-2-yl)acetamide (126)

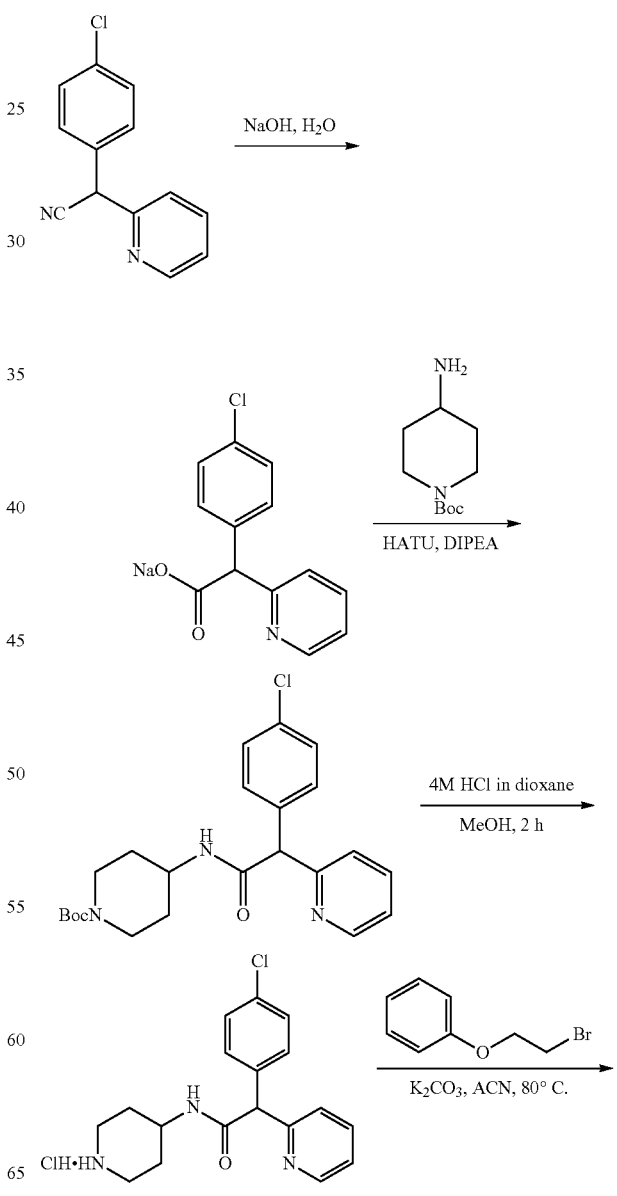

279
-continued

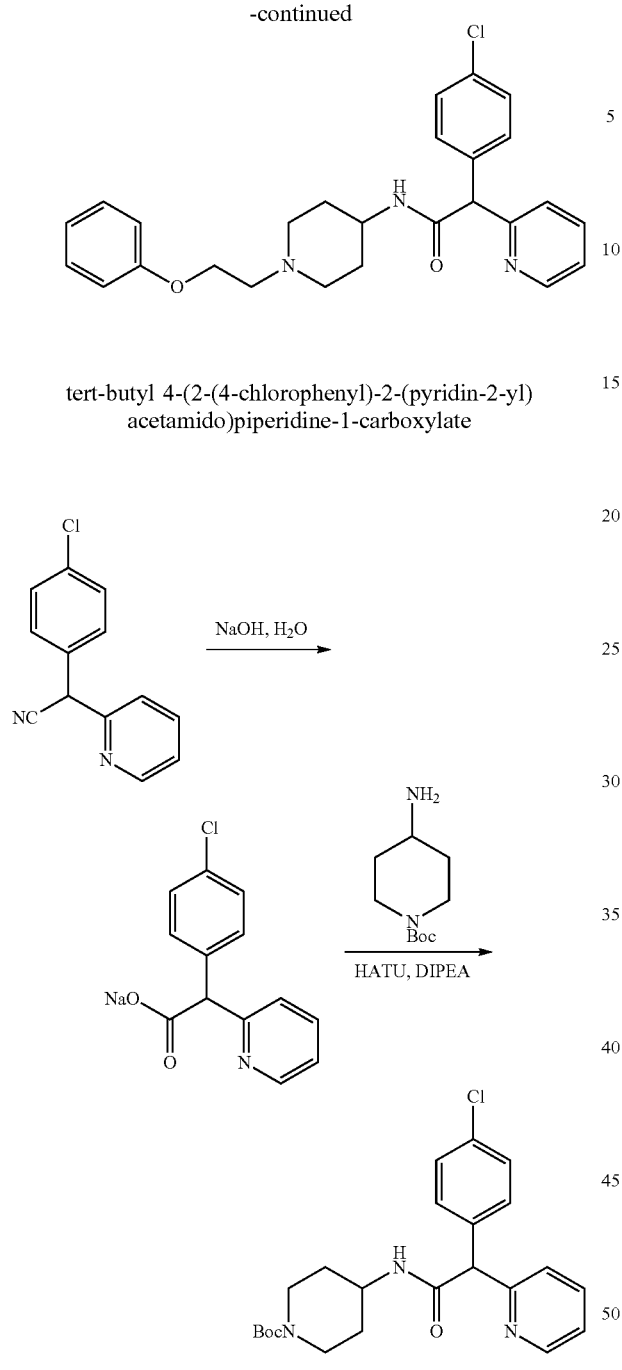

tert-butyl 4-(2-(4-chlorophenyl)-2-(pyridin-2-yl)acetamido)piperidine-1-carboxylate To a solution of 2-(4-chlorophenyl)-2-(pyridin-2-yl)acetonitrile (0.5 g, 2.19 mmol) in H₂O (5 mL) was added NaOH (87 mg, 2.19 mmol) at RT. The reaction mixture was stirred at 100° C. for 12 h. After completion of the reaction, aq. layer was lyophilized and afforded the crude of sodium salt (750 mg) as a white solid with 93% LCMS purity. This material was used in the next step without further purification. To a stirred solution of the crude sodium salt (0.40 g) in DMF (10 mL) were added HATU (0.85 g, 2.23 mmol), DIPEA (0.38 g, 2.97 mmol) and tert-butyl 4-aminopiperidine-1-carboxylate (0.30 g, 1.48 mmol) at 0° C. The reaction mixture was stirred at RT for 12 h. After completion, the reaction mass was diluted with ice-cold water. The obtained solid was filtered and dried under vaccum. The crude solid

280 was purified by triturating with EtOAc/Pentane to afford pure compound as off white solid (0.23 g, 35% yield).

2-(4-chlorophenyl)-N-(piperidin-4-yl)-2-(pyridin-2-yl)acetamide hydrochloride

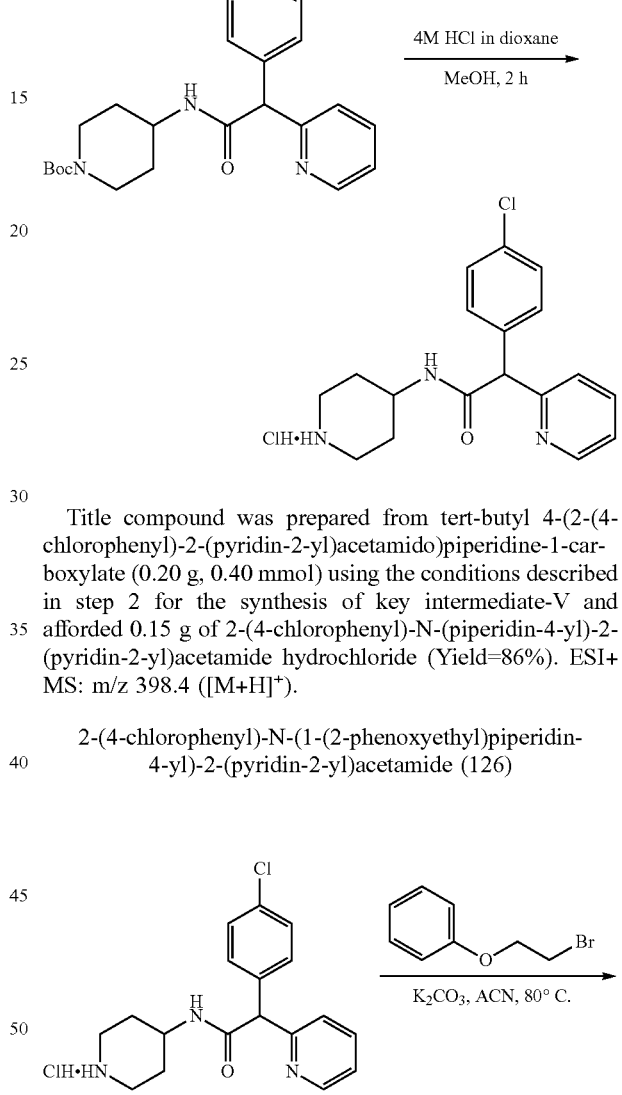

Title compound was prepared from tert-butyl 4-(2-(4-chlorophenyl)-2-(pyridin-2-yl)acetamido)piperidine-1-carboxylate (0.20 g, 0.40 mmol) using the conditions described in step 2 for the synthesis of key intermediate-V and afforded 0.15 g of 2-(4-chlorophenyl)-N-(piperidin-4-yl)-2-(pyridin-2-yl)acetamide hydrochloride (Yield=86%). ESI+ MS: m/z 398.4 ([M+H]⁺).

2-(4-chlorophenyl)-N-(1-(2-phenoxyethyl)piperidin-4-yl)-2-(pyridin-2-yl)acetamide (126)

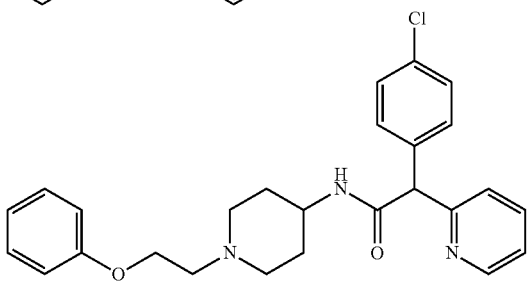

Title compound was prepared from 2-(4-chlorophenyl)-N-(piperidin-4-yl)-2-(pyridin-2-yl)acetamide hydrochloride (0.19 g, 0.58 mmol) using the general methodology of Example-1. The crude compound was purified by silica gel column chromatography to afford 0.08 g of 2-(4-chlorophenyl)-N-(1-(2-phenoxyethyl)piperidin-4-yl)-2-(pyridin-2-yl) acetamide (Yield=29%). $^1$H NMR (400 MHz, DMSO-d$_6$): δ 8.47 (d, J=7.2 Hz, 1H), 8.33 (d, J=7.6 Hz, 1H), 7.71 (dt, J=9.6, 2.0 Hz, 1H), 7.38-7.36 (m, 5H), 7.28-7.23 (m, 3H), 6.92 (d, J=7.6 Hz, 3H), 5.09 (s, 1H), 4.05-4.02 (m, 2H), 3.61-3.52 (m, 1H), 2.89-2.79 (m, 2H), 2.69-2.62 (m, 2H), 2.13-2.08 (m, 2H), 1.73-1.67 (m, 2H), 1.44-1.33 (m, 2H); ESI+MS: m/z: 450.5 ([M+H]$^+$).

Example-127: 2-((4-chlorophenyl)((1-(2-(2-(trifluoromethyl)phenoxy)ethyl)piperidin-4-yl)methoxy)methyl)pyridine (127)

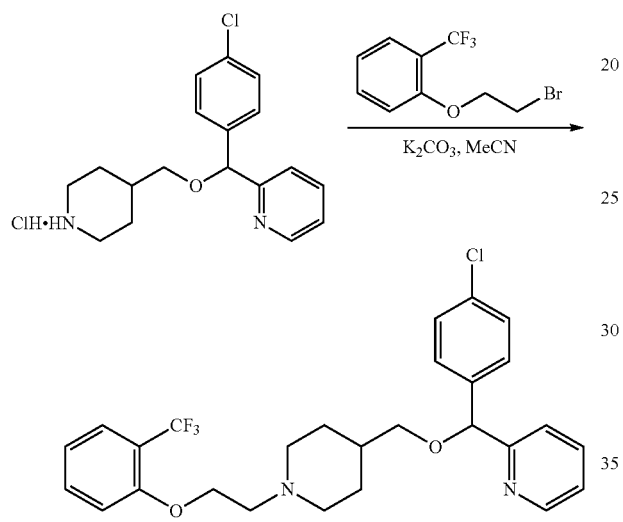

The title compound was prepared from 2-((4-chlorophenyl)(piperidin-4-ylmethoxy)methyl)pyridine hydrochloride (0.42 g, 1.19 mmol) using the general methodology of Example-1. The crude compound was purified by silica gel column chromatography to afford 0.15 g of 2-((4-chlorophenyl)((1-(2-(2-(trifluoromethyl)phenoxy)ethyl)piperidin-4-yl)methoxy)methyl)pyridine (Yield=25%). $^1$H NMR (500 MHz, CD$_3$OD): δ 8.45 (d, 1H, J=4.5 Hz), 7.79 (t, 1H, J=7.0 Hz), 7.58 (d, 2H, J=8.0 Hz), 7.50 (d, 1H, J=8.0 Hz), 7.38-7.35 (m, 4H), 7.26-7.23 (m, 2H), 7.07 (t, 1H, J=7.0 Hz), 5.42 (s, 1H), 4.19 (bs, 2H), 3.30-3.26 (m, 2H), 2.91 (bs, 2H), 2.69 (bs, 2H), 2.04 (bs, 2H), 1.70-1.50 (m, 3H), 1.25-1.15 (m, 2H); ESI+MS: m/z: 505.5 ([M+H]$^+$).

Example-129: N-((4(3-methoxyphenyl)(oxazol-4-yl)methyl)-1-(2-phenoxyethyl)piperidine-4-carboxamide (129)

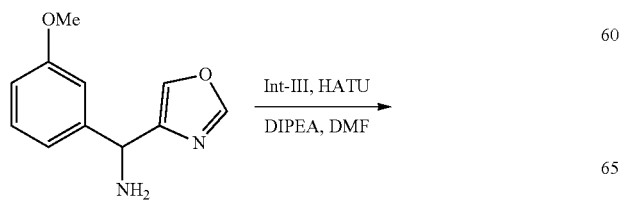

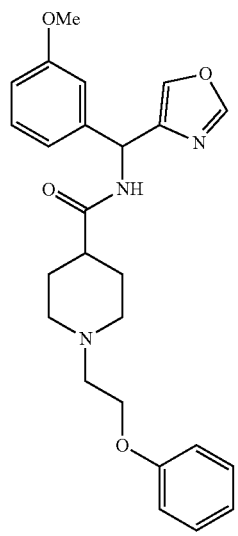

Title compound was prepared from coupling of (3-methoxyphenyl)(oxazol-4-yl)methanamine (0.2 g, 0.98 mmol, 1 equiv) and 1-(2-phenoxyethyl) piperidine-4-carboxylic acid (Int-III) (0.366 g, 1.47 mmol, 1.5 equiv) using the amide bond coupling step conditions used in general methodology for key Intermediate-I and afforded 0.018 g of N-((3-methoxyphenyl)(oxazol-4-yl)methyl)-1-(2-phenoxyethyl)piperidine-4-carboxamide (Yield=4%). $^1$H NMR (400 MHz, CD$_3$OD): δ 8.16 (s, 1H), 7.61 (t, J=1.0 Hz, 1H), 7.27-7.23 (m, 3H), 6.94-6.89 (m, 5H), 6.88-6.83 (m, 1H), 6.09 (s, 1H), 4.12 (t, J=5.6 Hz, 2H), 3.77 (s, 3H), 3.12-3.06 (m, 2H), 2.81 (t, J=5.6 Hz, 2H), 2.39-2.30 (m, 1H), 2.26-2.18 (m, 2H), 1.87-1.77 (m, 4H); ESI+MS: m/z: 436.2 ([M+H]$^+$).

Example-130: N-((4(2,2-difluorobenzo[d][1,3]dioxol-5-yl)(pyridin-2-yl)methyl)-1-(2-(2,4-difluorophenoxy)ethyl)piperidine-4-carboxamide (130)

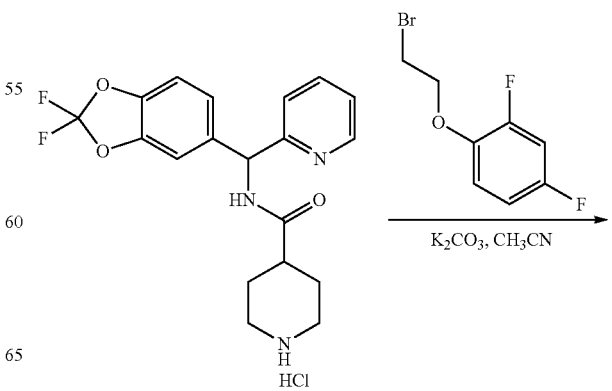

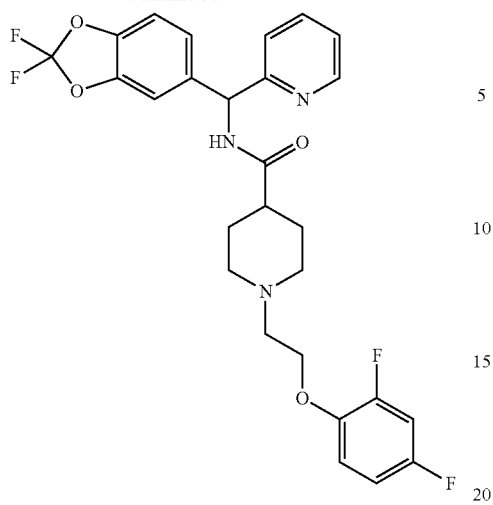

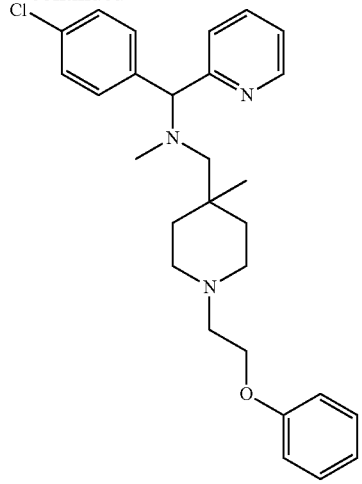

Title compound was prepared from N-((2,2-difluorobenzo[d][1,3]dioxol-5-yl)(pyridin-2-yl)methyl)piperidine-4-carboxamide hydrochloride (0.2 g, 0.49 mmol) using the general methodology of Example-1. The crude compound was purified by silica gel column chromatography to afford 0.20 g of N-((2,2-difluorobenzo[d][1,3]dioxol-5-yl)(pyridin-2-yl)methyl)-1-(2-(2,4-difluorophenoxy)ethyl)piperidine-4-carboxamide (Yield=77%). $^1$H NMR (400 MHz, DMSO-d6): δ 8.70 (d, 1H, J=8.0 Hz), 8.52-8.50 (m, 1H), 7.78 (dt, 1H, J=9.6 Hz, 1.6 Hz), 7.46 (d, 1H, J=8.0 Hz), 7.39-7.38 (m, 1H), 7.28 (d, 1H, J=8.4 Hz), 7.30-7.17 (m, 4H), 7.01-6.97 (m, 1H), 6.15 (d, 1H, J=8.0 Hz), 4.11 (t, 2H, J=5.6 Hz), 2.93 (d, 2H, J=10.8 Hz), 2.68-2.65 (m, 2H), 2.35-2.30 (m, 1H), 2.02 (t, 2H, J=10.8 Hz), 1.68-1.52 (m, 4H); ESI+MS: m/z: 532.4 ([M+H]$^+$). Enantiomers of 130 were separated using chiral HPLC (method F) and afforded pure enantiomers 130a and 130b.

Example-131: 1-(4-chlorophenyl)-N-methyl-N-((4 (4-methyl-1-(2-phenoxyethyl)piperidin-4-yl) methyl)-1-(pyridin-2-yl)methanamine (131)

Title compound was prepared from 1-(4-chlorophenyl)-N-methyl-N-((4-methylpiperidin-4-yl)methyl)-1-(pyridin-2-yl)methanamine hydrochloride (0.09 g, 0.24 mmol) using the general methodology of Example-1. The crude compound was purified by silica gel column chromatography to afford 0.012 g of 1-(4-chlorophenyl)-N-methyl-N-((4-methyl-1-(2-phenoxyethyl)piperidin-4-yl)methyl)-1-(pyridin-2-yl)methanamine (Yield=11%). $^1$H NMR (400 MHz, DMSO-d6): δ 8.74 (d, J=4.4 Hz, 1H), 7.95-7.91 (m, 1H), 7.60 (d, J=8.4 Hz, 2H), 7.52-7.46 (m, 4H), 7.30 (t, J=8.4 Hz, 2H), 7.01-6.97 (m, 3H), 5.70 (s, 1H), 4.35 (bs, 2H), 3.58 (bs, 4H), 3.31-3.24 (m, 3H), 3.03-2.99 (m, 1H), 2.79 (s, 3H), 2.00-1.69 (m, 4H), 1.28 (s, 3H); ESI+MS: m/z: 464.5 ([M+H]$^+$).

Example-132: 1-(4-chlorophenyl)-N-((1-(2-(4-fluorophenoxy)ethyl)piperidin-4-yl)methyl)-1-(pyridin-2-yl)methanamine (132)

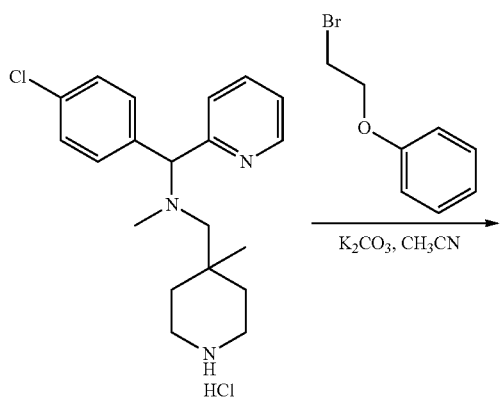

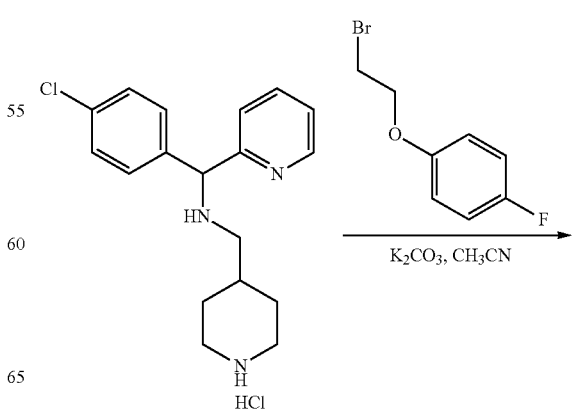

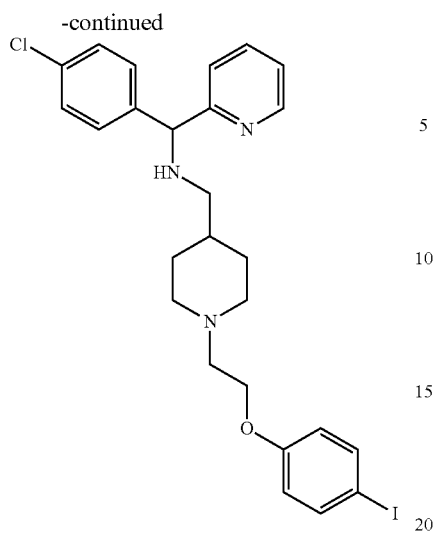

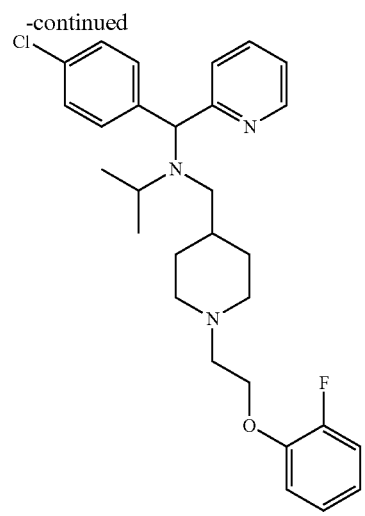

Title compound was prepared from 1-(4-chlorophenyl)-N-(piperidin-4-ylmethyl)-1-(pyridin-2-yl)methanamine hydrochloride (0.2 g, 0.57 mmol) using the general methodology of Example-1. The crude compound was purified by silica gel column chromatography to afford 0.12 g of 1-(4-chlorophenyl)-N-((1-(2-(4-fluorophenoxy)ethyl)piperidin-4-yl)methyl)-1-(pyridin-2-yl)methanamine (Yield=47%). $^1$H NMR (400 MHz, DMSO-d6): δ 8.47-8.46 (m, 1H), 7.74-7.70 (m, 1H), 7.44-7.40 (m, 3H), 7.34-7.32 (m, 2H), 7.22-7.19 (m, 1H), 7.11-7.06 (m, 2H), 6.94-6.91 (m, 2H), 4.82 (s, 1H), 4.01 (t, J=6.0 Hz, 2H), 2.87 (d, J=11.2 Hz, 2H), 2.64-2.61 (m, 2H), 2.33-2.28 (m, 2H), 1.96 (t, J=9.6 Hz, 2H), 1.68 (d, J=11.2 Hz, 2H), 1.43-1.37 (m, 1H), 1.13-1.05 (m, 2H); ESI+MS: m/z: 454.5 ([M+H]$^+$).

Title compound was prepared from N-((4-chlorophenyl)(pyridin-2-yl)methyl)-N-(piperidin-4-ylmethyl)propan-2-amine hydrochloride (0.15 g, 0.38 mmol) using the general methodology of Example-1. The crude compound was purified by silica gel column chromatography to afford 0.07 g of N-((4-chlorophenyl)(pyridin-2-yl)methyl)-N-((1-(2-(2-fluorophenoxy)ethyl)piperidin-4-yl)methyl)propan-2-amine (Yield=37%). $^1$H NMR (400 MHz, DMSO-d6): δ 8.47 (d, J=4.0 Hz, 1H), 7.77-7.71 (m, 1H), 7.48 (d, J=7.6 Hz, 1H), 7.39-7.32 (m, 4H), 7.25-7.07 (m, 4H), 6.93-6.88 (m, 1H), 5.00 (s, 1H), 4.08 (t, J=6.0 Hz, 2H), 3.05-2.99 (m, 1H), 2.84-2.83 (m, 2H), 2.62-2.59 (m, 2H), 2.35-2.32 (m, 2H), 1.81-1.79 (m, 2H), 1.60-1.52 (m, 2H), 0.92-0.84 (m, 6H), 0.73 (d, J=6.4 Hz, 3H); ESI+MS: m/z: 496.2 ([M+H]$^+$). Enantiomers of 133 were separated using chiral HPLC (method C) and afforded pure enantiomers 133a and 133b.

Example-133: N-((4(4-chlorophenyl)(pyridin-2-yl)methyl)-N-((1-(2-(2-fluorophenoxy)ethyl)piperidin-4-yl)methyl)propan-2-amine (133)

Example-134: N-((4(1-(2-(2-fluorophenoxy)ethyl)piperidin-4-yl)methyl)-N-((3-methoxyphenyl)(pyridin-2-yl)methyl)propan-2-amine (134)

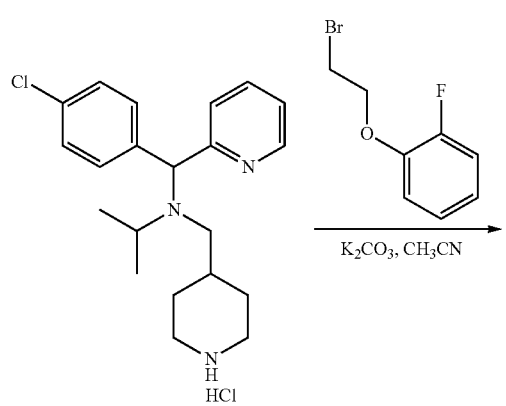

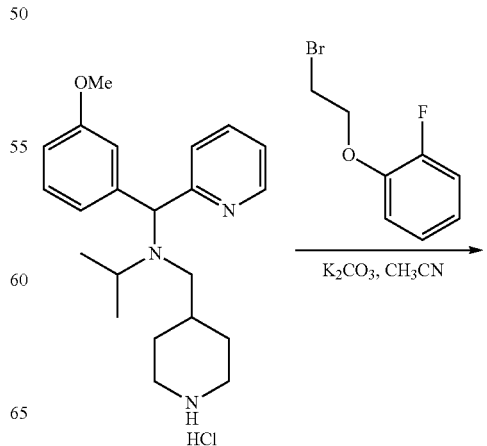

287

-continued

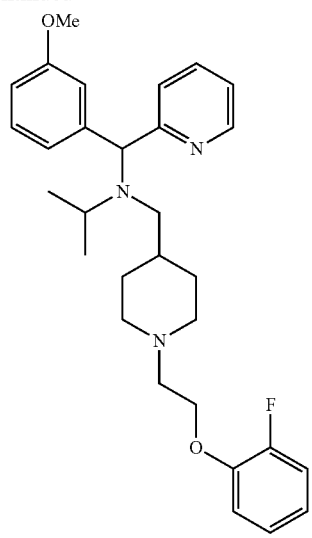

Title compound was prepared from N-((3-methoxyphenyl)(pyridin-2-yl)methyl)-N-(piperidin-4-ylmethyl)propan-2-amine hydrochloride (0.2 g, 0.51 mmol) using the general methodology of Example-1. The crude compound was purified by silica gel column chromatography to afford 0.07 g of N-((1-(2-(2-fluorophenoxy)ethyl)piperidin-4-yl)methyl)-N-((3-methoxyphenyl)(pyridin-2-yl)methyl)propan-2-amine (Yield=28%). $^1$H NMR (400 MHz, DMSO-d6): δ 8.46 (d, J=3.6 Hz, 1H), 7.75-7.71 (m, 1H), 7.48 (d, J=8.0 Hz, 1H), 7.24-7.09 (m, 5H), 6.96-6.88 (m, 3H), 6.78-6.76 (m, 1H), 4.94 (s, 1H), 4.08 (t, J=5.6 Hz, 2H), 3.70 (s, 3H), 3.08-3.01 (m, 1H), 2.84-2.82 (m, 2H), 2.61-2.59 (m, 2H), 2.50-2.49 (m, 2H), 2.36-2.25 (m, 2H), 1.77-1.74 (m, 2H), 1.58-1.55 (m, 2H), 0.91-0.85 (m, 4H), 0.73 (d, J=6.4 Hz, 3H); ESI+ MS: m/z: 492.3 ([M+H]$^+$).

Example-135: N-((4(4-chlorophenyl)(pyridin-2-yl)methyl)-N-((1-(2-(4-fluorophenoxy)ethyl)piperidin-4-yl)methyl)propan-2-amine (135)

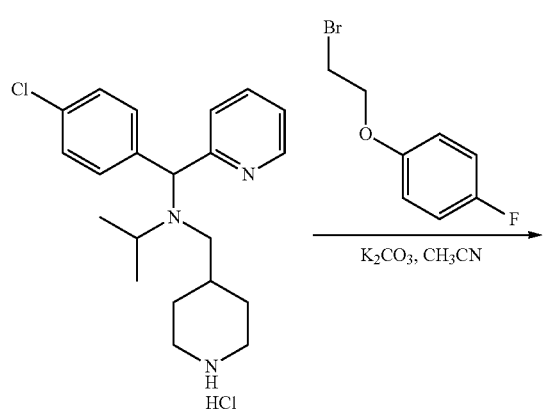

288

-continued

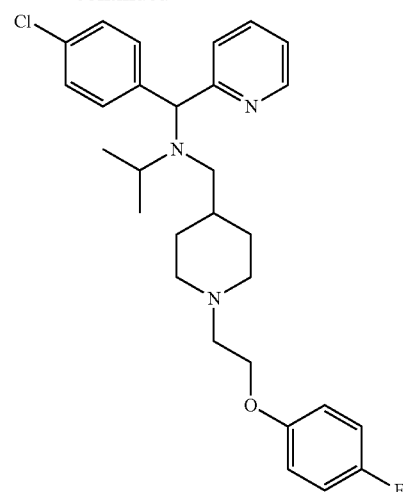

Title compound was prepared from N-((4-chlorophenyl)(pyridin-2-yl)methyl)-N-(piperidin-4-ylmethyl)propan-2-amine hydrochloride (0.15 g, 0.38 mmol) using the general methodology of Example-1. The crude compound was purified by silica gel column chromatography to afford 0.025 g of N-((4-chlorophenyl)(pyridin-2-yl)methyl)-N-((1-(2-(4-fluorophenoxy)ethyl)piperidin-4-yl)methyl)propan-2-amine (Yield=14%). $^1$H NMR (400 MHz, CD$_3$OD): δ 8.43-8.41 (m, 1H), 7.82-7.78 (m, 1H), 7.66 (d, J=8.0 Hz, 1H), 7.37 (d, J=8.4 Hz, 2H), 7.30-7.27 (m, 3H), 7.01-6.88 (m, 4H), 5.03 (s, 1H), 4.05 (t, J=5.6 Hz, 2H), 3.13-3.05 (m, 1H), 2.98-2.95 (m, 2H), 2.73 (t, J=11.2 Hz, 2H), 2.45-2.37 (m, 2H), 1.92 (t, J=12.0 Hz, 2H), 1.74-1.65 (m, 2H), 1.16-1.1.04 (m, 2H), 0.98 (d, J=6.8 Hz, 3H), 0.87-0.86 (m, 1H), 0.85 (d, J=6.8 Hz, 3H); ESI+MS: m/z: 496.6 ([M+H]$^+$).

Example-136: N-((4(4-chlorophenyl)(pyridin-2-yl)methyl)-2,2,2-trifluoro-N-((1-(2-(2-fluorophenoxy)ethyl)piperidin-4-yl)methyl)ethan-1-amine (136)

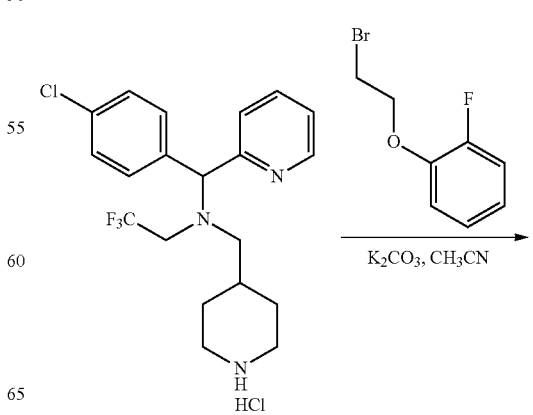

289

-continued

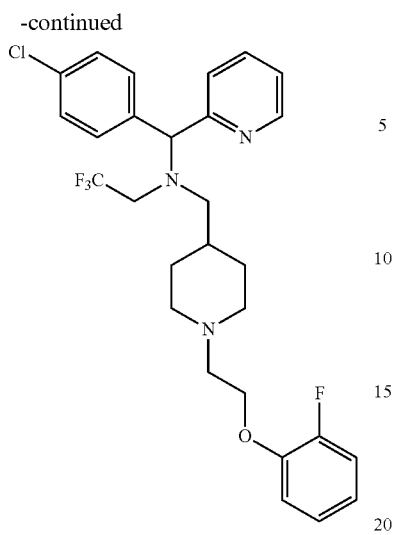

290

-continued

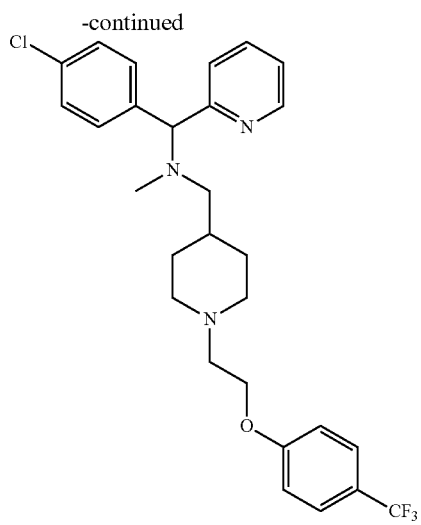

Title compound was prepared from N-((4-chlorophenyl)(pyridin-2-yl)methyl)-2,2,2-trifluoro-N-(piperidin-4-ylmethyl)ethan-1-amine hydrochloride (0.2 g, 0.46 mmol) using the general methodology of Example-1. The crude compound was purified by silica gel column chromatography to afford 0.10 g of N-((4-chlorophenyl)(pyridin-2-yl)methyl)-2,2,2-trifluoro-N-((1-(2-(2-fluorophenoxy)ethyl)piperidin-4-yl)methyl)ethan-1-amine (Yield=41%). $^1$H NMR (400 MHz, DMSO-d6): δ 8.61-8.60 (m, 1H), 7.83-7.79 (m, 1H), 7.44 (d, J=7.6 Hz, 1H), 7.39-7.35 (m, 2H), 7.34-7.31 (m, 1H), 7.26 (d, J=8.4 Hz, 2H), 7.20-7.14 (m, 2H), 7.12-7.08 (m, 1H), 6.94-6.89 (m, 1H), 5.25 (s, 1H), 4.12 (t, J=6.0 Hz, 2H), 3.53-3.46 (m, 1H), 3.40-3.31 (m, 1H), 2.90-2.85 (m, 2H), 2.66 (t, J=5.6 Hz, 2H), 2.53-2.50 (m, 1H), 2.49-2.44 (m, 1H), 1.99 (t, J=11.6 Hz, 2H), 1.82-1.77 (m, 1H), 1.57-1.53 (m, 2H), 0.97-0.91 (m, 2H); ESI+MS: m/z: 536.6 ([M+H]$^+$). Enantiomers of 136 were separated using chiral HPLC (method R) and afforded pure enantiomers 136a and 136b.

Example-137: 1-(4-chlorophenyl)-N-methyl-1-(pyridin-2-yl)-N-((1-(2-(4-(trifluoromethyl)phenoxy)ethyl)piperidin-4-yl)methyl)methanamine (137)

Title compound was prepared from 1-(4-chlorophenyl)-N-methyl-N-(piperidin-4-ylmethyl)-1-(pyridin-2-yl)methanamine hydrochloride (0.10 g, 0.27 mmol) using the general methodology of Example-1. The crude compound was purified by silica gel column chromatography to afford 0.05 g of 1-(4-chlorophenyl)-N-methyl-1-(pyridin-2-yl)-N-((1-(2-(4-(trifluoromethyl)phenoxy)ethyl)piperidin-4-yl)methyl)methanamine (Yield=35%). $^1$H NMR (400 MHz, CD$_3$OD): δ 8.41-8.39 (m, 1H), 7.81-7.77 (m, 1H), 7.69 (d, J=8.0 Hz, 1H), 7.56 (d, J=8.4 Hz, 2H), 7.45-7.43 (m, 2H), 7.30-7.23 (m, 3H), 7.07 (d, J=8.8 Hz, 2H), 4.45 (s, 1H), 4.19 (t, J=5.6 Hz, 2H), 3.04-3.01 (m, 2H), 2.84 (t, J=5.2 Hz, 2H), 2.26-2.19 (m, 3H), 2.15 (s, 3H), 2.12-2.09 (m, 1H), 1.92-1.84 (m, 2H), 1.70-1.64 (m, 1H), 1.20-1.09 (m, 2H); ESI+MS: m/z: 518.6 ([M+H]$^+$).

Example-138: 1-(benzo[d][1,3]dioxol-5-yl)-N-((1-(2-(2-fluorophenoxy)ethyl)piperidin-4-yl)methyl)-N-methyl-1-(pyridin-2-yl)methanamine (138)

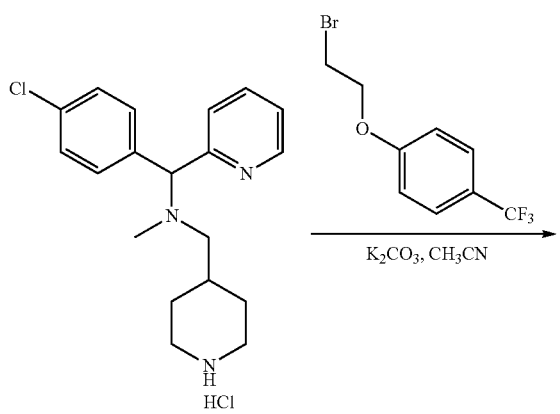

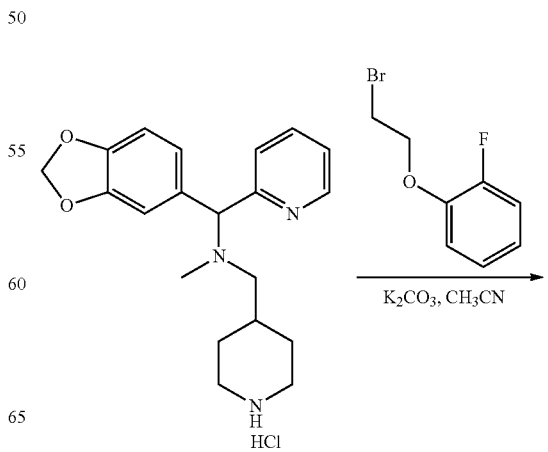

291

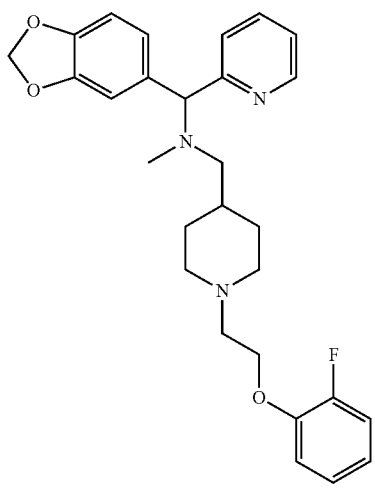

Title compound was prepared from 1-(benzo[d][1,3]dioxol-5-yl)-N-methyl-N-(piperidin-4-ylmethyl)-1-(pyridin-2-yl)methanamine hydrochloride (0.20 g, 0.53 mmol) using the general methodology of Example-1. The crude compound was purified by silica gel column chromatography to afford 0.08 g of 1-(benzo[d][1,3]dioxol-5-yl)-N-((1-(2-(2-fluorophenoxy)ethyl)piperidin-4-yl)methyl)-N-methyl-1-(pyridin-2-yl)methanamine (Yield=32%). $^1$H NMR (400 MHz, CD$_3$OD): δ 8.38-8.37 (m, 1H), 7.80-7.76 (m, 1H), 7.71-7.69 (m, 1H), 7.25-7.21 (m, 1H), 7.11-7.03 (m, 3H), 6.97 (s, 1H), 6.94-6.85 (m, 2H), 6.70 (d, J=8.0 Hz, 1H), 5.87 (dd, J=1.2 Hz, J=7.2 Hz, 2H), 4.32 (s, 1H), 4.18 (t, J=5.6 Hz, 2H), 3.02 (d, J=11.6 Hz, 2H), 2.82 (t, J=5.6 Hz, 2H), 2.28-2.16 (m, 3H), 2.14 (s, 3H) 2.10-2.05 (m, 1H), 1.91-1.82 (m, 2H), 1.68-1.61 (m, 1H), 1.19-1.08 (m, 2H); ESI+MS: m/z: 478.6 ([M+H]$^+$). Enantiomers of 138 were separated using chiral HPLC (method F) and afforded pure enantiomers 138a and 138b.

Example-139: 1-(benzo[d][1,3]dioxol-5-yl)-N-((1-(2-(2-fluorophenoxy)ethyl)piperidin-4-yl)methyl)-1-(pyridin-2-yl)methanamine (139)

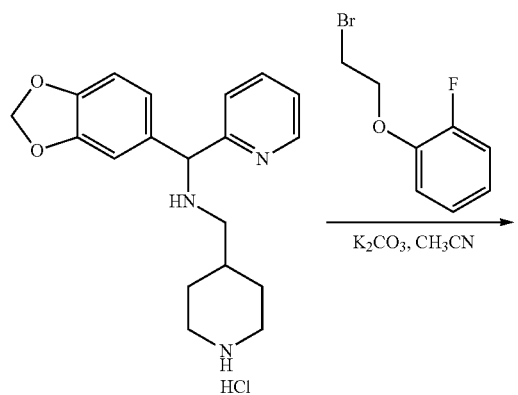

292

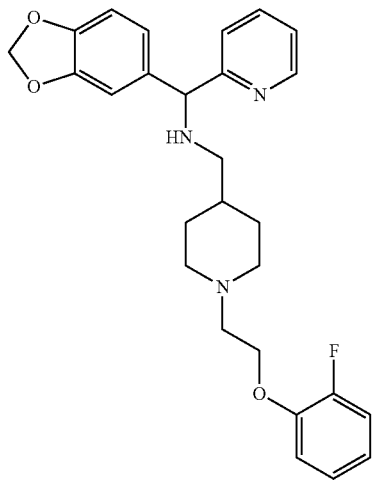

Title compound was prepared from 1-(benzo[d][1,3]dioxol-5-yl)-N-(piperidin-4-ylmethyl)-1-(pyridin-2-yl)methanamine hydrochloride (0.125 g, 0.35 mmol) using the general methodology of Example-1. The crude compound was purified by silica gel column chromatography to afford 0.07 g of 1-(benzo[d][1,3]dioxol-5-yl)-N-((1-(2-(2-fluorophenoxy)ethyl)piperidin-4-yl)methyl)-1-(pyridin-2-yl)methanamine (Yield=44%). $^1$H NMR (400 MHz, CD$_3$OD): δ 8.49-8.48 (m, 1H), 7.77-7.73 (m, 1H), 7.44 (d, J=8 Hz, 1H), 7.27-7.24 (m, 1H), 7.10-7.05 (m, 3H), 6.94-6.88 (m, 3H), 6.74 (d, J=7.6 Hz, 1H), 5.89 (dd, J=1.2 Hz, J=5.2 Hz, 2H), 4.90 (s, 1H), 4.20 (t, J=5.6 Hz, 2H), 3.09 (d, J=11.6 Hz, 2H), 2.87 (t, J=5.6 Hz, 2H), 2.49-2.39 (m, 2H), 2.27-2.22 (m, 2H), 1.85-1.77 (m, 2H), 1.61-1.55 (m, 1H), 1.40-1.20 (m, 2H); ESI+MS: m/z: 464.5 ([M+H]$^+$). Enantiomers of 139 were separated using chiral HPLC (method D) and afforded pure enantiomers 139a and 139b.

Example-140: N-((4-chlorophenyl)(pyridin-2-yl)methyl)-1-((2,3-dihydrobenzo[b][1,4]dioxin-2-yl)methyl)piperidine-4-carboxamide (140)

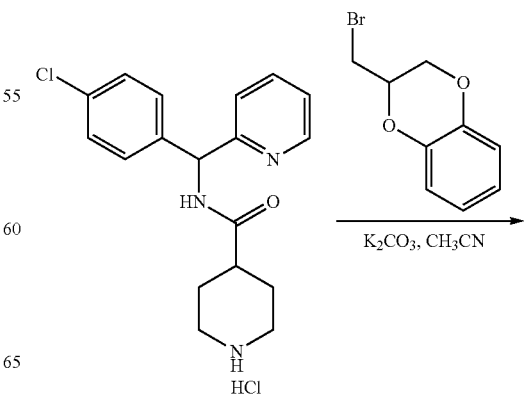

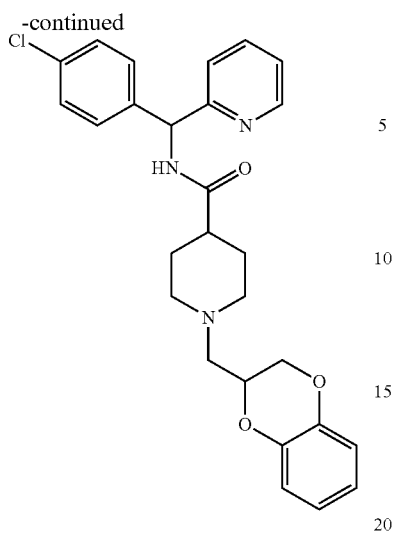

Title compound was prepared from N-((4-chlorophenyl)(pyridin-2-yl)methyl)piperidine-4-carboxamide hydrochloride (0.2 g, 0.55 mmol) using the general methodology of Example-1. The crude compound was purified by silica gel column chromatography to afford 0.08 g of N-((4-chlorophenyl)(pyridin-2-yl)methyl)-1-((2,3-dihydrobenzo[b][1,4]dioxin-2-yl)methyl)piperidine-4-carboxamide (Yield=31%). $^1$H NMR (400 MHz, CD$_3$OD): δ 8.53-8.51 (m, 1H), 7.81-7.77 (m, 1H), 7.39 (d, J=8.0 Hz, 1H), 7.32-7.25 (m, 5H), 6.84-6.77 (m, 4H), 6.16 (s, 1H), 4.33-4.25 (m, 2H), 3.95-3.90 (m, 1H), 3.12-3.09 (m, 1H), 3.02-2.98 (m, 1H), 2.68-2.57 (m, 2H), 2.43-2.35 (m, 1H), 2.27-2.15 (m, 2H), 1.85-1.78 (m, 4H); ESI+MS: m/z: 478.5 ([M+H]$^+$).

Example-141: N-((4(4-chlorophenyl)(pyridin-2-yl)methyl)-1-(2-(pyridin-2-yloxy)ethyl)piperidine-4-carboxamide (141)

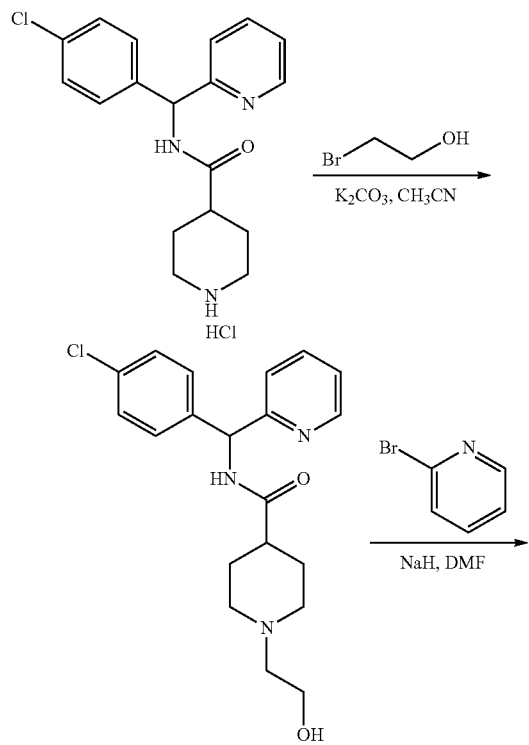

N-((4-chlorophenyl)(pyridin-2-yl)methyl)-1-(2-hydroxyethyl)piperidine-4-carboxamide

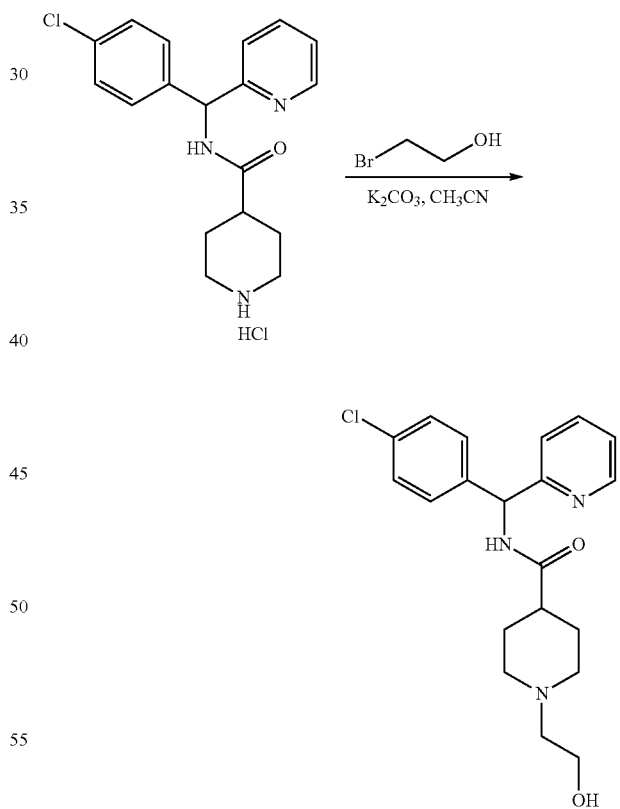

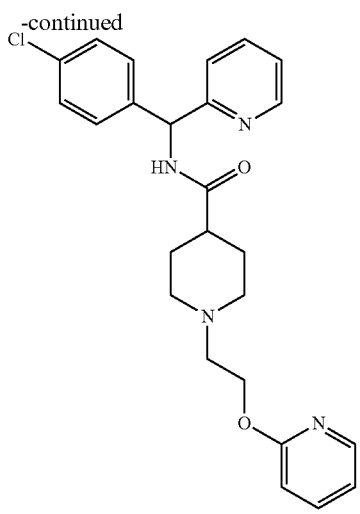

Title compound was prepared from N-((4-chlorophenyl)(pyridin-2-yl)methyl)piperidine-4-carboxamide hydrochloride (0.15 g, 0.41 mmol) using the general methodology of Example-1. The crude compound was purified by silica gel column chromatography to afford 0.13 g of N-((4-chlorophenyl)(pyridin-2-yl)methyl)-1-(2-hydroxyethyl)piperidine-4-carboxamide (Yield=85%). ESI+MS: m/z: 374.4 ([M+H]$^+$).

N-((4(4-chlorophenyl)(pyridin-2-yl)methyl)-1-(2-(pyridin-2-yloxy)ethyl)piperidine-4-carboxamide

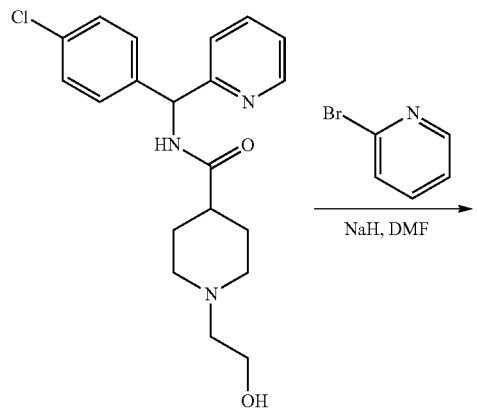

Example-142: N-((4(4-chlorophenyl)(pyridin-2-yl)methyl)-1-(2-(pyridin-4-yloxy)ethyl)piperidine-4-carboxamide (142)

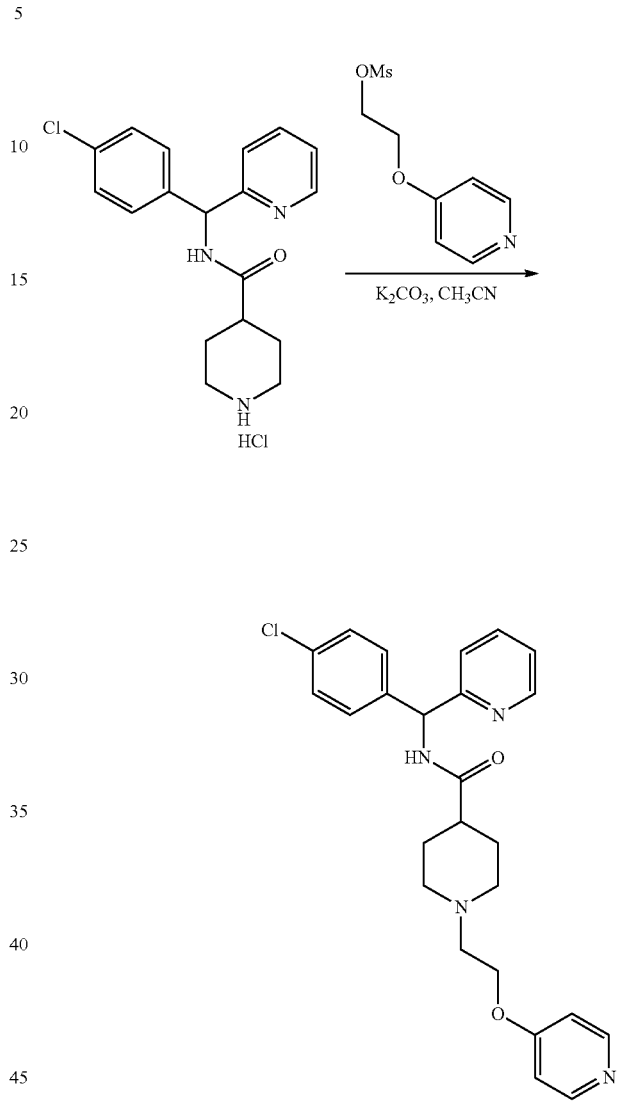

To a solution of N-((4-chlorophenyl)(pyridin-2-yl)methyl)-1-(2-hydroxyethyl)piperidine-4-carboxamide (0.13 g, 0.35 mmol) in DMF (2 mL) at 0° C. under nitrogen was added NaH (0.033 g, 1.39 mmol) and the reaction mixture was stirred for 10 minutes. 2-bromopyridine (0.22 g, 1.39 mmol) was then added dropwise and the reaction mixture was stirred at 100° C. for 16 hours. The reaction mixture was then diluted in water and extracted with DCM, dried over Na2SO4, filtered and concentrated. Purification by flash chromatography on silica gel afforded N-((4-chlorophenyl)(pyridin-2-yl)methyl)-1-(2-(pyridin-2-yloxy)ethyl)piperidine-4-carboxamide (0.01 g, Yield 7%) as a thick sirup. $^1$H NMR (400 MHz, CD$_3$OD): δ 8.53-8.51 (m, 1H), 8.11-8.09 (m, 1H), 7.81-7.77 (m, 1H), 7.68-7.64 (m, 1H), 7.38 (d, J=8.0 Hz, 1H), 7.33-7.24 (m, 5H), 6.95-6.91 (m, 1H), 6.80-6.78 (m, 1H), 6.16 (s, 1H), 4.42 (t, J=5.6 Hz, 2H), 3.12-3.07 (m, 2H), 2.82 (t, J=6.0 Hz, 2H), 2.45-2.37 (m, 1H), 2.27-2.20 (m, 2H), 1.84-1.78 (m, 4H); ESI+MS: m/z: 451.5 ([M+H]$^+$).

Title compound was prepared from N-((4-chlorophenyl)(pyridin-2-yl)methyl)piperidine-4-carboxamide hydrochloride (0.3 g, 0.82 mmol) using the general methodology of Example-1. The crude compound was purified by silica gel column chromatography to afford 0.03 g of N-((4-chlorophenyl)(pyridin-2-yl)methyl)-1-(2-(pyridin-4-yloxy)ethyl)piperidine-4-carboxamide (Yield=8%). $^1$H NMR (400 MHz, CD$_3$OD): δ 8.55-8.50 (m, 1H), 8.36-8.34 (m, 1H), 7.83-7.78 (m, 1H), 7.40 (d, J=8.0 Hz, 1H), 7.36-7.25 (m, 5H), 7.03-7.00 (m, 2H), 6.17 (s, 1H), 4.25 (t, J=5.6 Hz, 2H), 3.12-3.06 (m, 2H), 2.86 (t, J=5.2 Hz, 2H), 2.46-2.38 (m, 1H), 2.30-2.20 (m, 2H), 1.85-1.75 (m, 4H); ESI+MS: m/z: 451.5 ([M+H]$^+$).

Example-143: N-((4(3-methoxyphenyl)(pyridin-2-yl)methyl)-4-methyl-1-(2-phenoxyethyl)piperidine-4-carboxamide (143)

Example-144: N-((4(4-chlorophenyl)(pyridin-2-yl)methyl)-4-methyl-1-(2-phenoxyethyl)piperidine-4-carboxamide (144)

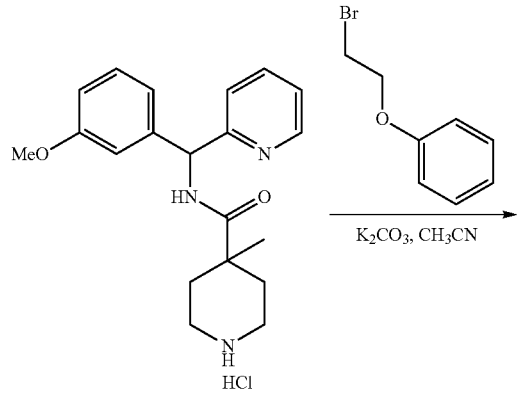

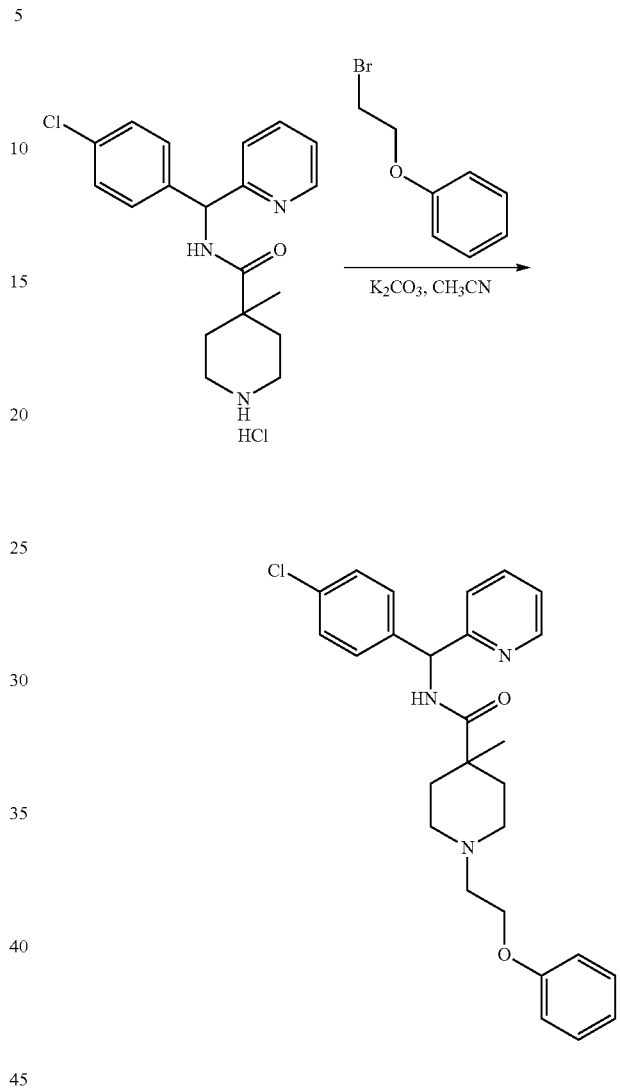

Title compound was prepared from N-((3-methoxyphenyl)(pyridin-2-yl)methyl)-4-methylpiperidine-4-carboxamide hydrochloride (0.15 g, 0.40 mmol) using the general methodology of Example-1. The crude compound was purified by silica gel column chromatography to afford 0.06 g of N-((3-methoxyphenyl)(pyridin-2-yl)methyl)-4-methyl-1-(2-phenoxyethyl)piperidine-4-carboxamide (Yield=33%). $^1$H NMR (400 MHz, DMSO-d6): δ 8.48-8.47 (m, 1H), 8.08 (d, J=8.0 Hz, 1H), 7.75-7.70 (m, 1H), 7.30-7.20 (m, 5H), 7.16-7.14 (m, 1H), 6.98 (d, J=7.6 Hz, 1H), 6.92-6.85 (m, 4H), 6.44 (d, J=7.6 Hz, 1H), 4.02 (t, J=5.6 Hz, 2H), 3.77 (s, 3H), 2.65-2.50 (m, 4H), 2.30-2.20 (m, 2H), 2.08-2.02 (m, 2H), 1.44-1.35 (m, 2H), 1.11 (s, 3H); ESI+MS: m/z: 460.5 ([M+H]$^+$).

Title compound was prepared from N-((4-chlorophenyl)(pyridin-2-yl)methyl)-4-methylpiperidine-4-carboxamide hydrochloride (0.2 g, 0.53 mmol) using the general methodology of Example-1. The crude compound was purified by silica gel column chromatography to afford 0.1 g of N-((4-chlorophenyl)(pyridin-2-yl)methyl)-4-methyl-1-(2-phenoxyethyl)piperidine-4-carboxamide (Yield=41%). $^1$H NMR (400 MHz, DMSO-d6): δ 8.53-8.51 (m, 1H), 8.29 (d, J=8.0 Hz, 1H), 7.81-7.76 (m, 1H), 7.45 (d, J=8.0 Hz, 1H), 7.37-7.23 (m, 7H), 6.93-6.88 (m, 3H), 6.19 (d, J=8.0 Hz, 1H), 4.02 (t, J=5.6 Hz, 2H), 2.65-2.55 (m, 4H), 2.26-2.20 (m, 2H), 2.09-2.04 (m, 2H), 1.45-1.40 (m, 2H), 1.12 (s, 3H); ESI+MS: m/z: 464.7 ([M+H]$^+$). Enantiomers of 144 were separated using chiral HPLC (method E) and afforded pure enantiomers 144a and 144b.

Example-145: 1-(2-(2,4-difluorophenoxy)ethyl)-N-((3-methoxyphenyl)(pyridin-2-yl)methyl)piperidine-4-carboxamide (145)

Example-146: N-((4(3-methoxyphenyl)(phenyl)methyl)-1-(2-phenoxyethyl)piperidine-4-carboxamide (146)

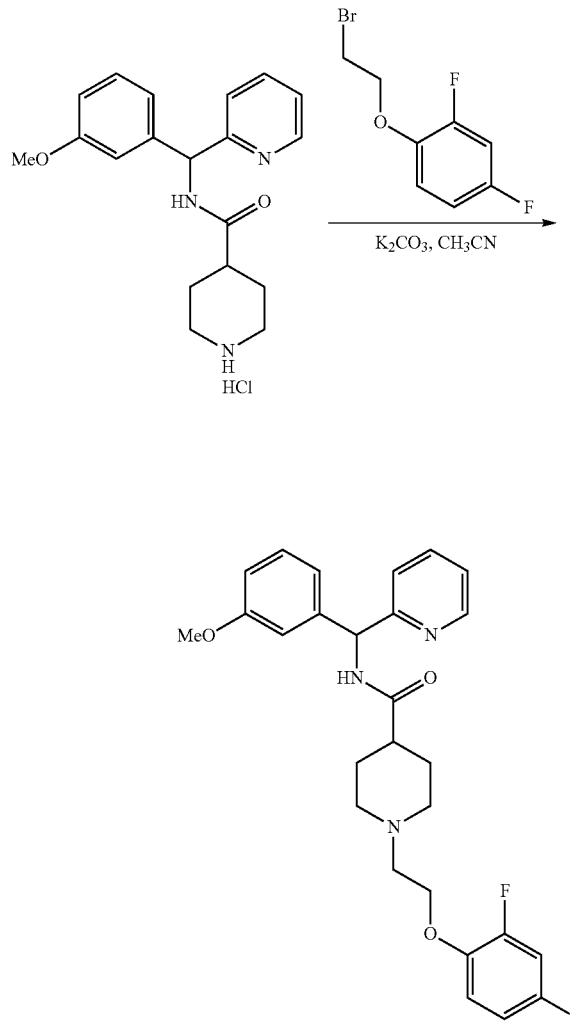

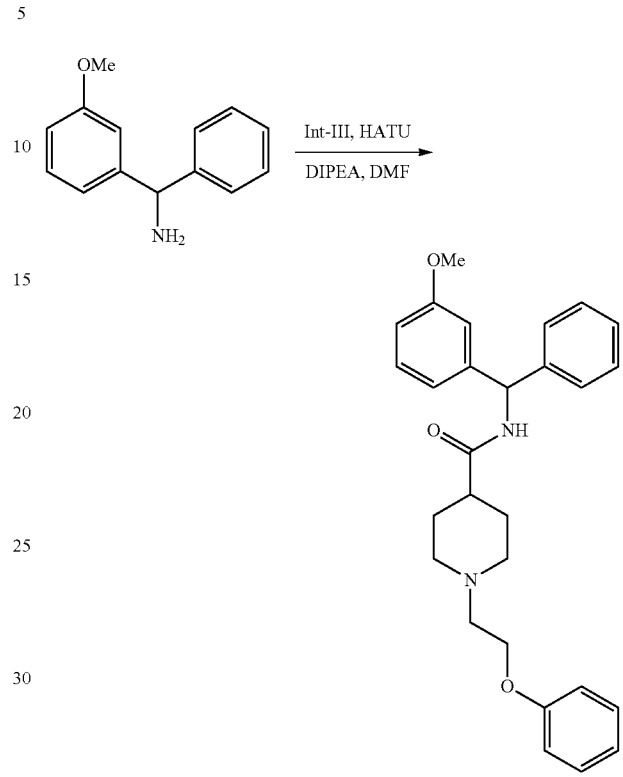

Title compound was prepared from coupling of (3-methoxyphenyl)(phenyl)methanamine (0.15 g, 0.70 mmol, 1 equiv) and 1-(2-phenoxyethyl) piperidine-4-carboxylic acid (Int-III) (0.21 g, 0.84 mmol, 1.2 equiv) using the amide bond coupling step conditions used in general methodology for key Intermediate-I and afforded 0.035 g of N-((3-methoxyphenyl)(phenyl)methyl)-1-(2-phenoxyethyl) piperidine-4-carboxamide (Yield=11%). $^1$H NMR (400 MHz, CD$_3$OD): δ 7.33-7.30 (m, 2H), 7.28-7.21 (m, 6H), 6.93-6.90 (m, 3H), 6.83-6.80 (m, 3H), 6.13 (s, 1H), 4.14 (t, J=5.6 Hz, 2H), 3.75 (s, 3H), 3.15 (d, J=12.0 Hz, 2H), 2.88 (t, J=5.2 Hz, 2H), 2.45-2.37 (m, 1H), 2.34-2.28 (m, 2H), 1.92-1.82 (m, 4H); ESI+MS: m/z: 445.3 ([M+H]$^+$).

One of skill in the art would understand the present invention to encompass subgenera that may be derived from the foregoing genera, subgenera and list of exemplary compounds, as herein disclosed or herein listed. Further, from the foregoing and the disclosure herein, the skilled person can readily select suitable moieties for any of the variable substituents identified in the formulae herein described.

Example 147: Chiral Separation Using HPLC

Mixtures of stereoisomers (e.g., enantiomers or diastereomers) described herein were separated with any one of Method A to Method R of chiral HPLC. The earlier-eluted stereoisomer was designated with "a", and the later-eluted stereoisomer was designated with "b". For example, enantiomers of 1 were separated using chiral HPLC, Method D, and afforded the pure enantiomers 1a and 1b, wherein 1a was the earlier-eluted stereoisomer, and 1b was the later-eluted stereoisomer.

Title compound was prepared from N-((3-methoxyphenyl)(pyridin-2-yl)methyl)piperidine-4-carboxamide hydrochloride (0.2 g, 0.55 mmol) using the general methodology of Example-1. The crude compound was purified by silica gel column chromatography to afford 0.12 g of 1-(2-(2,4-difluorophenoxy)ethyl)-N-((3-methoxyphenyl)(pyridin-2-yl)methyl)piperidine-4-carboxamide (Yield=45%). $^1$H NMR (400 MHz, DMSO-d6): δ 8.66 (d, J=8.0 Hz, 1H), 8.50 (d, J=4.0 Hz, 1H), 7.78-7.74 (m, 1H), 7.44 (d, J=8.0 Hz, 1H), 7.28-7.15 (m, 4H), 7.01-6.97 (m, 1H), 6.89-6.85 (m, 2H), 6.80-6.75 (m, 1H), 6.09 (d, J=8.4 Hz, 1H), 4.15-4.05 (m, 2H), 3.71 (s, 3H), 2.98-2.90 (m, 2H), 2.68-2.66 (m, 2H), 2.34-2.32 (m, 1H), 2.08-1.98 (m, 2H), 1.70-1.50 (m, 4H); ESI+MS: m/z: 482.5 ([M+H]$^+$). Enantiomers of 145 were separated using chiral HPLC (method G) and afforded pure enantiomers 145a and 145b.

Method A:
Column: Chiralpak ADH (250×4.6 mm, 5 μm)
Eluent A: n-Hexanes
Eluent B: Ethanol
Elution using A:B 75:25 at 1 ml/min
Method B:
Column: Chiralpak ADH (250×4.6 mm, 5 μm)
Eluent A: 0.1% DEA in n-Hexanes
Eluent B: Ethanol
Elution using A:B 80:20 at 1 ml/min
Method C:
Column: Chiralpak IA (250×4.6 mm, 5 μm)
Eluent A: 0.1% DEA in n-Hexanes
Eluent B: DCM/Methanol 80:20
Elution using A:B 98:2 at 1 ml/min
Method D:
Column: Chiralpak ADH (250×4.6 mm, 5 μm)
Eluent A: 0.1% DEA in n-Hexanes
Eluent B: Ethanol/Methanol 50:50
Elution using A:B 75:25 at 1 ml/min
Method E:
Column: Chiralpak IC (250×4.6 mm, 5 μm)
Eluent A: 0.1% DEA in n-Hexanes
Eluent B: DCM/Methanol 50:50
Elution using A:B 90:10 at 1 ml/min
Method F:
Column: Chiralpak IC (250×4.6 mm, 5 μm)
Eluent A: 0.1% DEA in n-Hexanes
Eluent B: Ethanol
Elution using A:B 95:5 at 1 ml/min
Method G:
Column: Chiralpak IA (250×4.6 mm, 5 μm)
Eluent A: 0.1% DEA in n-Hexanes
Eluent B: DCM/Methanol 50:50
Elution using A:B 90:10 at 1 ml/min
Method H:
Column: Chiralpak IB (250×4.6 mm, 5 μm)
Eluent A: 0.1% DEA in n-Hexanes
Eluent B: DCM/Methanol 50:50
Elution using A:B 90:10 at 1 ml/min
Method I:
Column: Chiralpak IA (250×4.6 mm, 5 μm)
Eluent A: n-Hexanes
Eluent B: DCM/Methanol 50:50
Elution using A:B 80:20 at 1 ml/min
Method J:
Column: Chiralpak IA (250×4.6 mm, 5 μm)
Eluent A: n-Hexanes
Eluent B: Ethanol
Elution using A:B 70:30 at 1 ml/min
Method K:
Column: Chiralpak ADH (250×4.6 mm, 5 μm)
Eluent A: 0.1% DEA in n-Hexanes
Eluent B: Ethanol
Elution using A:B 85:15 at 1 ml/min
Method L:
Column: Chiralpak IA (250×4.6 mm, 5 μm)
Eluent A: 0.1% DEA in n-Hexanes
Eluent B: Isopropanol
Elution using A:B 90:10 at 1 ml/min
Method M:
Column: Chiralpak IA (250×4.6 mm, 5 μm)
Eluent A: 0.1% DEA in n-Hexanes
Eluent B: Ethanol
Elution using A:B 85:15 at 1 ml/min
Method N:
Column: Chiralcel ODH (250×4.6 mm, 5 μm)
Eluent A: 0.1% TFA in n-Hexanes
Eluent B: Ethanol/Methanol 50:50
Elution using A:B 90:10 at 1 ml/min
Method P:
Column: Chiralpak ADH (250×4.6 mm, 5 μm)
Eluent A: 0.1% DEA in n-Hexanes
Eluent B: Isopropanol
Elution using A:B 90:10 at 1 ml/min
Method R:
Column: Chiralpak IB (250×4.6 mm, 5 μm)
Eluent A: 0.1% DEA in n-Hexanes
Eluent B: Isopropanol
Elution using A:B 95:5 at 1 ml/min Example-148: Biological Activity Suitable cell lines for use in the below assays, e.g., Gi/cAMP and β-arrestin assays include CHO-K1 cell expressing human D2R/β-arrestin (purchased from DiscoveR$_x$). The cell lines were grown or maintained in growth media comprising Ham's F-12 (Cellgro 10-080-CV), 10% HI FBS (Gibco 16140), 1× Penn/Strep/Glutamine (Gibco #10378), 600 ug/ml Geneticin (Gibco #10131) and 300 ug/ml Hygromycin (Invitrogen 10687-010).

Cells were prepared for assays by growing cultures for up to 2 weeks (from about 6-20 passages). A vial of frozen cells was thawed in a water bath held at 37° C. The cells were then transferred into a 50 ml tube with 10 ml growth media. The vial was rinsed with growth media and the contents transferred to the 50 ml tube. The 50 ml tube was centrifuged at 1200 rpm for 5 minutes at room temperature. The supernatant was decanted and the pellet of cells were re-suspended in growth media and grown at 37° C., 95% humidity, 5% $CO_2$. When the cells reached about 90% confluence (approximately 3 days between passages), the cells were passaged and used for either the agonist or antagonist assays as described below.

β-Arrestin Agonist Assay

The cells were prepared for β-arrestin assays as described above. The assays were performed using a PathHunter® β-Arrestin Detecting Kit (DiscoveR$_x$). The cells were grown on 225 mm dishes, then washed once with 1×PBS (Cellgro), followed by digestion with 2.5 ml 1× Detachment reagent (DRX 92-0009) for approximately 2 minutes. Plating 2 reagent ((DRX 93-0563R2B, 10 ml) was added to the plate, and the cells were transferred into a 50 ml centrifuge tube and centrifuged at room temperature using BD Dynac III at 1200 rpm for 5 minutes. The supernatant was decanted and the pellet was re-suspended in Plating 2 reagent at an optimized density of 2.5×10$^5$ cells/ml. The cells were then plated onto white 384 well plates, to a final cell density of 5000 cells/20 μl/well. The plates were then transferred to a humidified incubator maintained at 37° C., 5% $CO_2$, and incubated for 24 hours prior to testing. The compounds were then pin-transferred (100 nL) to the cells, and was incubated for 90 minutes at 37° C. The detection reagent (9.6 μL, Buffer:Emerald II:Galactor-Star in a 19:5:1 ratio, i.e., 14.06 mL:3.7 mL:0.74 mL=18.5 mL) was then added to the agonist plates. The plates were then incubated for 60 minutes at room temperature in the dark, before reading the assay results using the protocol Luminescence (Aperture luminescence 384-well) on an EnVision® detection instrument (Perkin Elmer).

β-Arrestin Antagonist Assay

The cells were prepared for β-arrestin assays as described above. The assays were performed using a PathHunter® β-Arrestin Detecting Kit (DiscoveR$_x$). The cells were grown on 225 mm dishes, then washed once with 1×PBS (Cellgro), followed by digestion with 2.5 ml 1× Detachment reagent (DRX 92-0009) for approximately 2 minutes. Plating 2 reagent ((DRX 93-0563R2B, 10 ml) was added to the plate, and the cells were transferred into a 50 ml centrifuge tube and centrifuged at room temperature using BD Dynac III at 1200 rpm for 5 minutes. The supernatant was decanted and the pellet was re-suspended in Plating 2 reagent at an optimized density of $2.5 \times 10^5$ cells/ml. The cells were then plated onto white 384 well plates, to an optimized final cell density of 5000 cells/20 µl/well. The plates were then transferred to a humidified incubator maintained at 37° C., 5% $CO_2$, and incubated for 24 hours prior to testing. The compounds were then pin-transferred (100 nL) to the cells, and incubated for 10 minutes at 37° C., before addition of Quinpirole (5 uL of a 650 nM solution, 78.50 of quinpirole (100 µM in DMSO) into 12 mL Plating 2 reagent) to each well, to final concentration of 130 nM. The plates were then incubated for 90 minutes at 37° C. before addition of the detection reagents (12 µL, Buffer:Emerald II:Galactor-Star=19:5:1 ratio 14.06 mL:3.7 mL:0.74 mL=18.5 mL) to the plates. The plates were then incubated for 60 minutes at room temperature in the dark before reading the assay results using the protocol Luminescence (Aperture luminescence 384-well) on an EnVision® detection instrument (Perkin Elmer).

Gi/cAMP Agonist Assay

The cells were prepared for Gi/cAMP assays as described above. The assays were performed using a PE Lance Ultra cAMP kit (TRF0263). The cells were grown on 225 mm dishes, then washed once with 1×PBS (Cellgro) before digestion with 2.5 ml 1× Detachment reagent (DRX 92-0009) for about 2 minutes. PBS (20 ml) was then added to the plate, and the cells were transferred to a 50 ml centrifuge tube, and centrifuged at room temperature using BD Dynac III, at 1200 rpm for 5 minutes. The supernatant was decanted and the pellet was re-suspended in stimulation buffer at an optimal density of $6.67 \times 10e5$ cells/ml, before plating onto white 384 well plates (150/well) to a final concentration of 10,000 cells/ISO/well. Compounds were pin-transferred (100 nL) to the cells, and incubated for 10 min. at 37° C. Forskolin (50 of a 10 µM solution, 12 µL Forskolin (10 mM in DMSO) into 12 mL Stimulation buffer) was then added to each well to final concentration to 2.504 Forskolin, and the plates were then incubated at room temperature for 30 minutes. Eu-cAMP tracer solution (100, PerkinElmer, 3600 of Tracer in 17.64 ml kit buffer) and ULight-anti-cAMP solution (100, 120 µL antibody in 17.88 ml kit buffer) was then added to each well. The plates were then incubated at room temperature for about 1 hr in the dark before reading the assay results using protocol Lance (Excitation 320 nm, Emission filter 665 nm, second emission filter 615 nm, Top mirror Lance Delfia) on an EnVision® detection instrument (Perkin Elmer).

Gi/cAMP Antagonist Assay

The cells were prepared for Gi/cAMP assays as described above. The assays were performed using a PE Lance Ultra cAMP kit (TRF0263). The cells were grown on 225 mm dishes, then washed once with 1×PBS (Cellgro) before digestion with 2.5 ml 1× Detachment reagent (DRX 92-0009) for about 2 minutes. PBS (20 ml) was then added to the plate, and the cells were transferred to a 50 ml centrifuge tube, and centrifuged at room temperature using BD Dynac III at 1200 rpm for 5 minutes. The supernatant was decanted and the pellet was re-suspended in stimulation buffer at an optimized density of $6.67 \times 10e5$ cells/ml, before plating onto white 384 well plates (150/well) to a final concentration of about 10,000 cells/ISO/well. Chemical plate was pin-transferred (100 nL) to the cells, and incubated for 10 min. at 37° C. A 5 µl mixture containing Forskolin (10 µM, 12 µL Forskolin (10 mM in DMSO) into 12 mL stimulation buffer) and Quinpirole (10.8 nM, 131 µL Quinpirole (1 µM in DMSO) into 12 mL Forskolin buffer) were added to each well to a final concentration of 2.504 Forskolin and 2.7 nM Quinpirole. The plates were then incubated at room temperature for about 30 minutes before addition of Eu-cAMP tracer solution (100, PerkinElmer) and then ULight-anti-cAMP solution (100) to each well. Following incubation at room temperature for 1 hr in the dark, the assay results were read using protocol Lance (Excitation 320 nm, Emission filter 665 nm, second emission filter 615 nm, Top mirror Lance Delfia) on an EnVision® detection instrument (Perkin Elmer).

Pharmacokinetic Studies on Mice Brains

Twelve male C57BL/6 mice were weighed and administered intraperitoneally with a dose of test compound (of Example 35) solution formulation. The dosing volume administered for the intraperitoneal route was at 10 mL/kg. Blood samples (approximately 60 µL) were collected from retro-orbital plexus of each mouse under light isoflurane anesthesia at 0.08, 0.5, 1, 2, 4, and 8 hr. Following the collection of blood, plasma was also harvested by centrifugation and stored at −70° C. until analysis. After collection of plasma, the animals were euthanized and brain samples were isolated at 0.08, 0.5, 1, 2, 4, and 8 hr. Tissue samples (brain) were homogenized using ice-cold phosphate buffer saline (pH 7.4) and homogenates were stored below −70° C. until analysis. Total homogenate volume was three times the tissue weight. Concentrations of test compound in mouse plasma and brain samples were determined by LC-MS/MS method.

Identical extraction procedures were used for the plasma/brain homogenate study samples and the spiked plasma calibration standards: A 25 µL sample of either study sample (plasma/brain) or spiked calibration standard was added to individual pre-labeled micro-centrifuge tubes. A volume of 100 µL of IS (antipyrine, 500 ng/mL) prepared in acetonitrile was then added to the micro-centrifuge tubes, except in a sample used as a negative control where only acetonitrile was added and vortexed for 5 minutes. Samples were centrifuged for 20 minutes at the speed of 4000 rpm at 4° C. Following centrifugation, 100 µL of the supernatant was sampled from each centrifuge tube and transferred into insert vials. These vials remained within the auto-sampler for the LC/MS/MS analysis. Standards used for calibration were prepared by spiking 10 µL of the test compound in 190 µL of control (used as a negative control) mouse plasma/brain homogenate.

The plasma and brain concentration-time data of test compound was provided for data analysis. The plasma and brain concentration-time data was then used for the pharmacokinetic analysis. Non-Compartmental-Analysis module in Phoenix® WinNonlin® (Version 6.3) was used to assess the pharmacokinetic parameters. Peak plasma concentrations ($C_{max}$) and time for the peak plasma concentrations ($T_{max}$) were the observed values. The areas under the concentration time curve ($AUC_{last}$ and $AUC_{inf}$) were calculated by linear trapezoidal rule. The terminal elimination rate constant, ke was determined by regression analysis of the linear terminal portion of the log plasma concentration-time curve.

Figure 2:
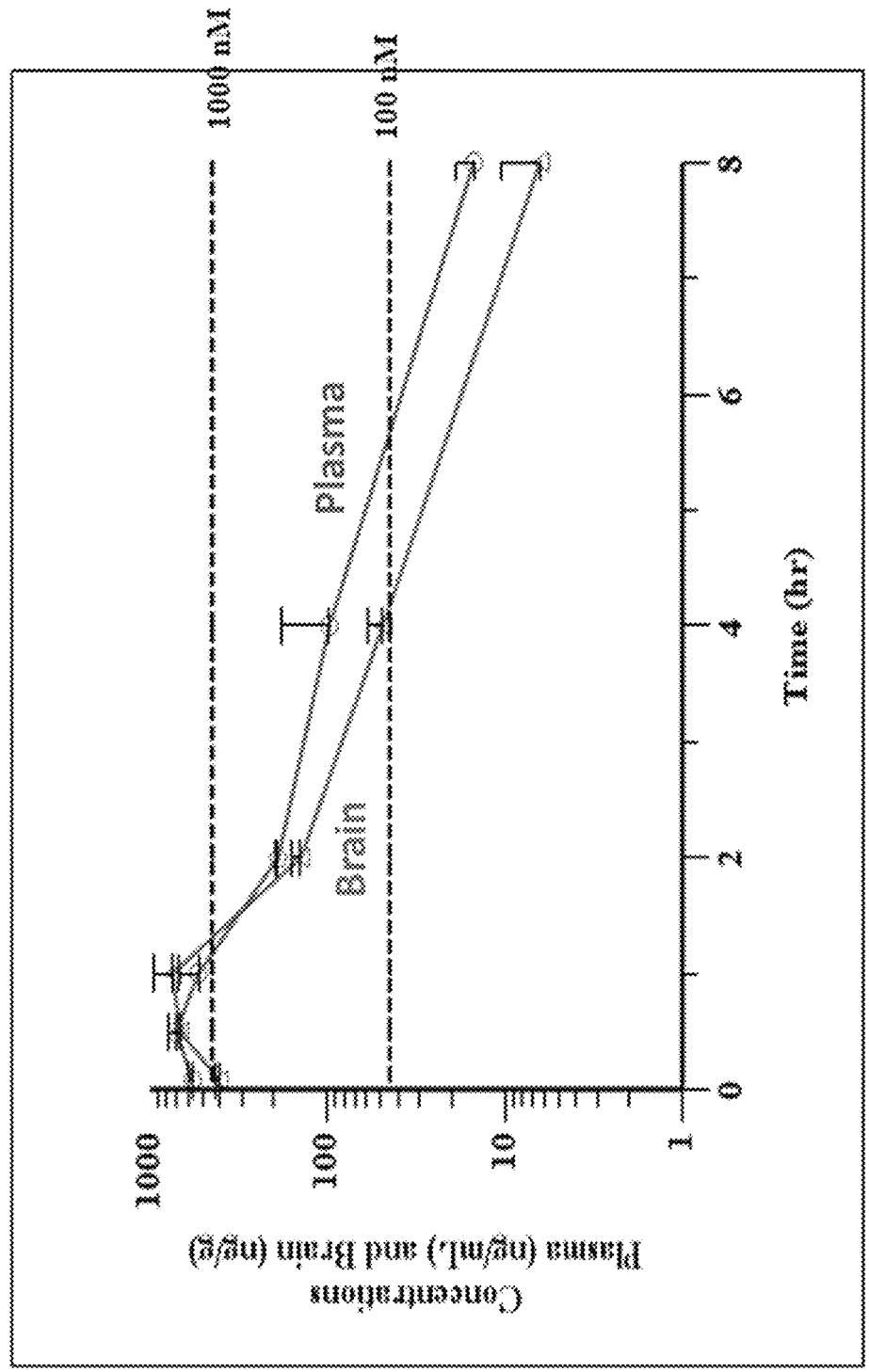
FIG. 2 shows pharmacokinetic and brain distribution of Compound 35b following a single intraperitoneal dose administration of 10 mg/kg in male C57BL/6 mice.

Illustrative results are presented in FIG. 2, the pharmacokinetic parameters are as follow:

| Compound | Matrix | Route | $T_{max}$ (hr) | $C_{max}$ (µg/L) | $AUC_{last}$ (µg/L*hr) | $AUC_{INF}$ (µg/L*hr) | $T_{1/2}$ (hr) | CL (L/hr/kg) | Vss (L/kg) |
|---|---|---|---|---|---|---|---|---|---|
| | Plasma | i.p. | 0.50 | 709.91 | 1470.78 | 1507.16 | 1.62 | 6.64 | 15.48 |
| | Brain | i.p. | 1.00 | 740.63 | 1335.28 | 1347.55 | 1.35 | 7.42 | 14.41 |

| | | | $T_{max}$ (hr) | $C_{max}$ (µmol/L) | $AUC_{last}$ (hr*µmol/L) | $AUC_{INF}$ (hr*µmol/L) | $T_{1/2}$ (hr) | CL mg/(hr* µmol/L)/kg | Vss mg/(µmol/L)/ kg |
|---|---|---|---|---|---|---|---|---|---|
| Example 35b | | | | | | | | | |
| | Plasma | i.p. | 0.50 | 1.59 | 3.31 | 3.39 | 1.62 | 2.96 | 6.89 |
| | Brain | i.p. | 1.00 | 1.66 | 3.00 | 3.03 | 1.35 | 3.30 | 6.41 |

Positron Emission Tomography Studies on Rodents

All animal procedures were performed in accordance with the National Institutes of Health Guide for the Care and Use of Laboratory Animals and were approved by the Massachusetts General Hospital Institutional Animal Care and Use Facility. Male Sprague-Dawley rats (8-14 weeks old, Charles River Labs) were used for the study with animals pair-housed on a diurnal 12:12 light/dark cycle with free access to food and water. The rats were stabilized under anesthesia (2% isoflurane in 1.5 L/min oxygen) before an intravenous (i.v.) catheter was placed in the lateral tail vein (BD Angiocath #381112, 24G) and non-radiolabeled test compounds were administered 5-180 minutes prior to radiotracer administration. All test compounds (vehicle, compound of Example 35, Clozapine) were solubilized in a solution of (10% DMSO, 10% Tween-80, 80% saline) and injected at a volume ≤2 mL/kg. Baseline control scans were obtained from pretreatment time-matched control animals administered an equivalent volume of vehicle alone. Respiration of each animal was monitored for the duration of the procedure.

Carbon 11-labeled raclopride ([$^{11}$C]RAC) was synthesized from the O-desmethyl RAC precursor and [11C] methyl iodide and subsequently purified by high-performance liquid chromatography as previously described (Farde L, et al. (1985) PNAS, USA 82(11):3863-3867). For each scan, 1.0±0.15 mCi [$^{11}$C]RAC radiotracer was administered via i.v. catheter in a volume ≤1.5 mL in a vehicle containing (10% ethanol, 90% saline). Positron emission tomography (PET) and skeletal computed tomography (CT) data were collected using a GammaMedica Triumph trimodal PET/SPECT/CT scanner (Quebec, Canada) or PET data alone using a Concorde Microsystems R4 microPET scanner (Knoxville, Tenn., USA). Each [$^{11}$C]RAC scan included subtraction of random coincidences collected in a delayed time window. Scatter-corrected sinograms were reconstructed using a 3-dimensional iterative maximum likelihood expectation maximization (3D-MLEM) algorithm with 16 iterations yielding an image resolution of ~1.5 mm FWHM (Full Width at Half Maximum). Pixel size in reconstructed images was 0.26 mm transaxially, 0.6 mm slice thickness. Regions of Interest (ROIs) were drawn on reconstructed images estimating peak [$^{11}$C]RAC uptake in striata (averaged between left and right hemispheres) and cerebellum as reference region for non-displaceable (ND) tracer uptake. ROI dimensions, placement and striatal D2/D3 binding potential ($BP_{ND}$) were evaluated by graphical analysis using Logan distribution volume ratio (DVR) linearization as previously described ($BP_{ND}$=DVR-1; Alexoff D, et al. (2002) JNucMed 44(5): 815-822; Logan J, et al. (1996) JCerebral Blood Flow and Metabolism 16(5):843-840).

Figure 3:
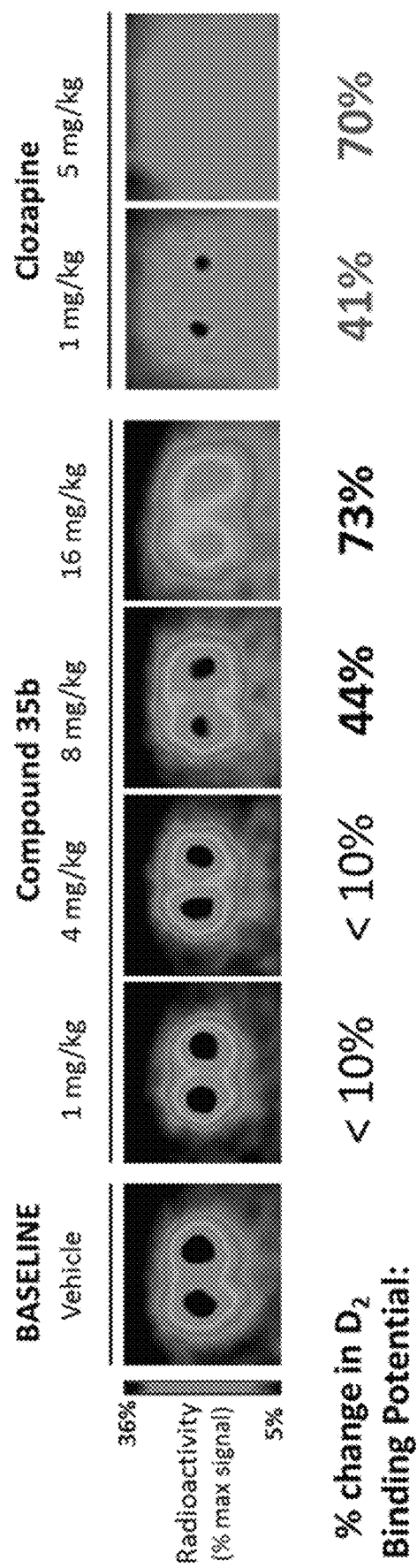
FIG. 3 shows positron emission tomography at different doses of Compound 35b in comparison with Clozapine. The compounds compete with [$^{11}$C]Raclopride.

Illustrative results are presented in FIG. 3.

Amphetamine Induced Hyperactivity Studies

Amphetamine-induced hyperactivity (AIH) was examined in eight identical open-field chambers (16.5"×16"×12"; AccuScan Instruments, Columbus, Ohio). Activity was detected by infrared beam breaks and recorded automatically by VersaMax software (AccuScan). Daily sessions were automatically binned in 5 minute intervals (VersaDat; AccuSacn) for statistical analysis. AIH was run over three consecutive days as follows:

Day 1: Mice were acclimated to the injection procedure by injecting 30 minutes prior to being placed in the chambers (to match the timing of day 3 compound administration). Mice were then placed into the open-field for 20 minutes and then removed for a saline injection (to match the timing of amphetamine administration on day 3). Mice were placed back into the open-field for an additional 30 minutes, at which point the mice were returned to their home cage.

Day 2 was run identically to Day 1, with the exception that the second day lasted for one hour (20 minutes→injection→40 minutes).

Day 3 was the amphetamine challenge day. Mice were pre-treated with D2 antagonist compounds (compound of Example 35) 30 minutes prior to being placed in the open field. After 20 minutes, mice were removed and challenged with amphetamine, following protocols known to one skilled in the art, for example Jones C. A, et. al. Br J Pharmacol. 2011, 164(4):1162-1194; Pan J Q, et. al. Neuropsychopharmacology. 2011, 36(7):1397-1411.

Figure 4:
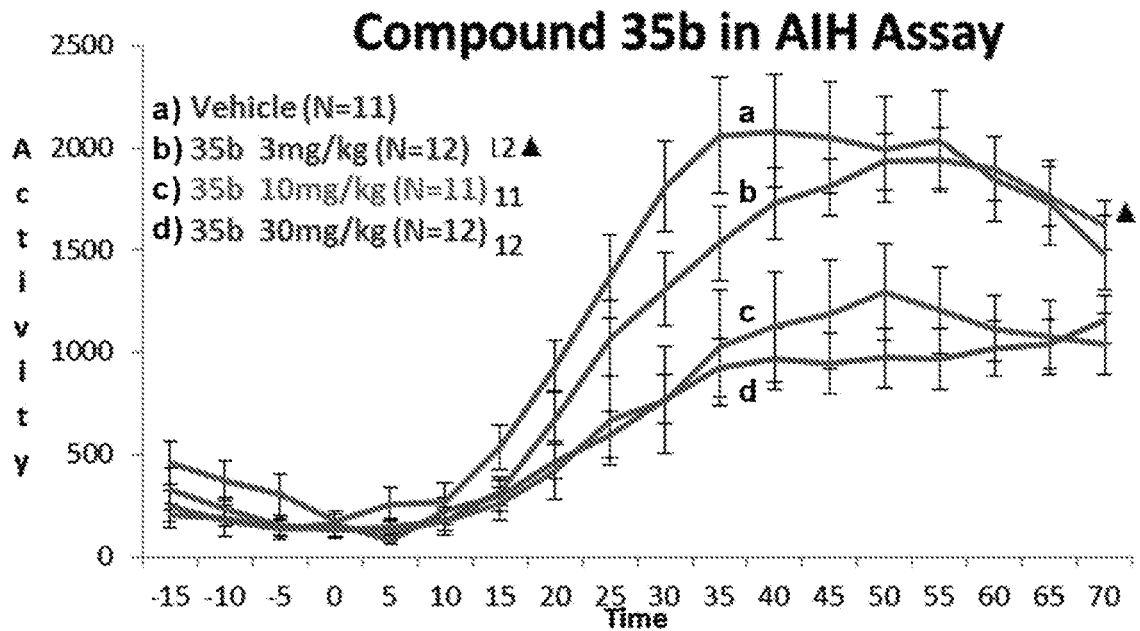
FIG. 4 shows the effect of Compound 35b in comparison with vehicle to attenuate amphetamine induced hyperactivity (AIH) over time. Compound 35b dose-dependently attenuates AIH in mice and shows efficacy at 10 and 30 mg/kg. The x-axis shows the time in minutes.

Illustrative results are presented in FIG. 4.

Rotarod Performance

Figure 5:
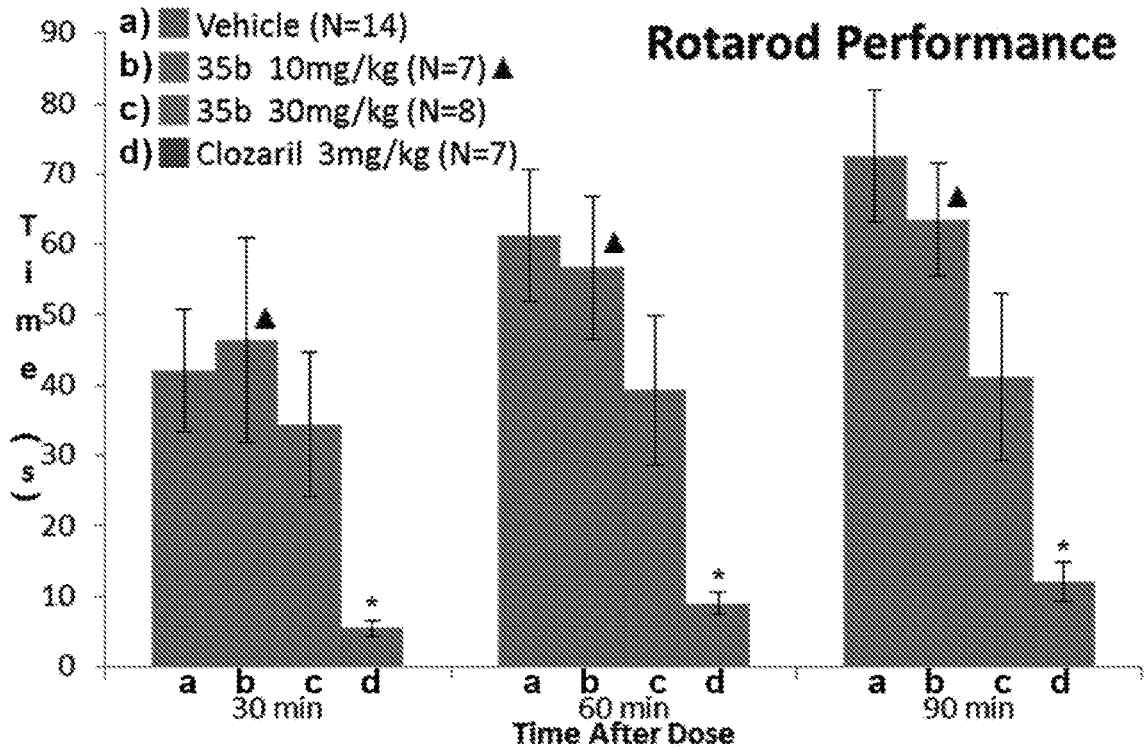
FIG. 5 shows the effect of Compound 35b in comparison with vehicle and Clozapine in the rotarod assay: Compound 35b promotes significantly less motor impairment than Clozapine at efficacious doses.

In the test, mice were placed on a horizontally oriented, rotating cylinder (rod) suspended above a cage floor, which was low enough not to injure the animal, but high enough to induce avoidance of fall. The mice naturally try to stay on the rotating cylinder, or rotarod, and avoid falling to the ground. Mice were administered clozaril at 3 mg/kg (test group was 7); or the compound of Example 35 (either 10 mg/kg (test group was 7) or 30 mg/kg (test group was 8) or vehicle (test group was 14). The mice had an average weight of 20 grams (as do the mice in all examples herein). The length of time that a given animal stays on this rotating rod is a measure of the animal's balance, coordination, physical condition, and motor-planning. The speed of the rotarod is mechanically driven, and was held constant. The results are illustrated in FIG. 5. The compound of Example 35 promotes far less catalepsy than the known antipsychotic Clozapine at efficacious doses.

Heatmap

Figure 6:
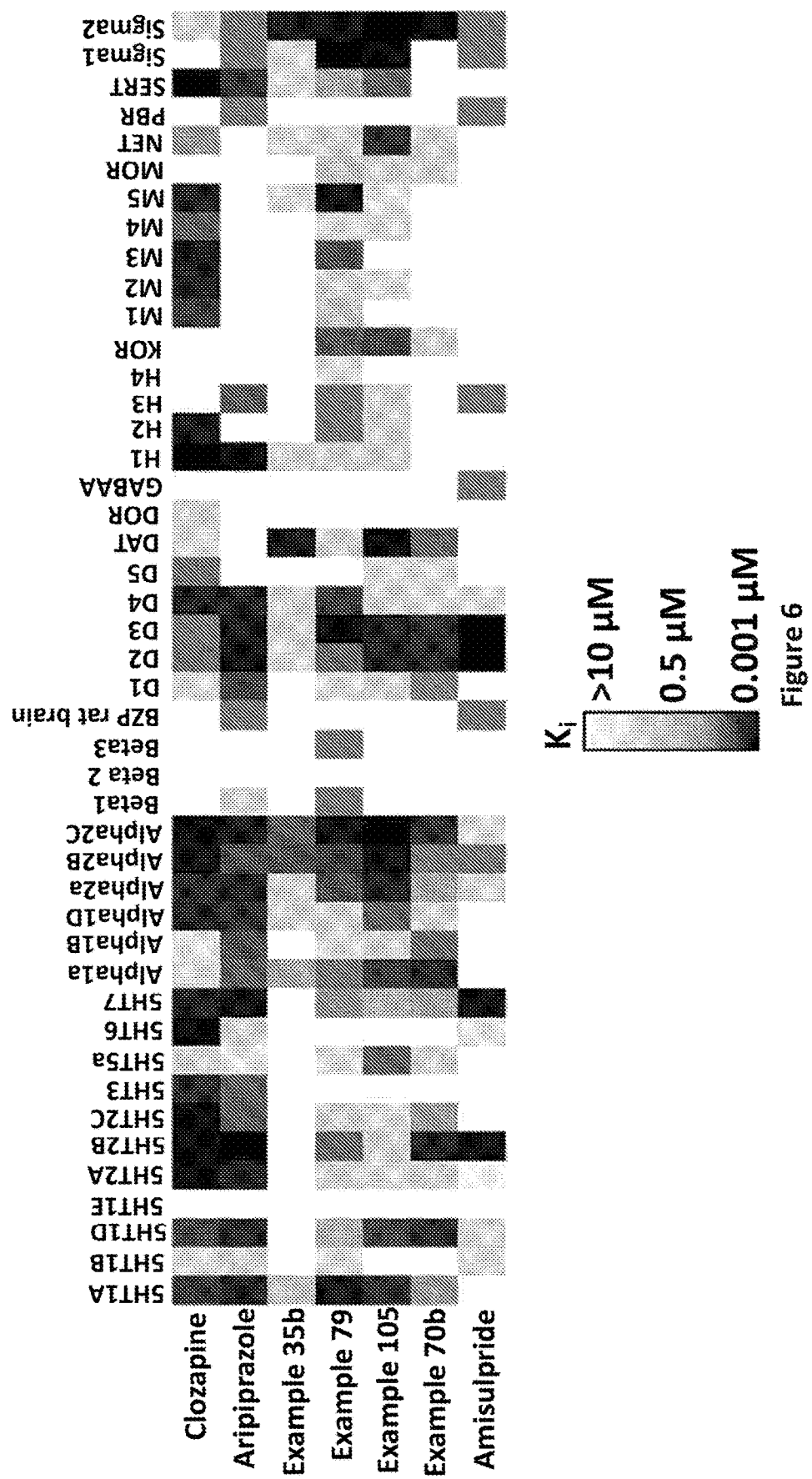
FIG. 6 shows a heat map representation of binding across various GPCR receptors for compounds of the invention and control compounds.

The heatmap of FIG. 6 represents binding across various relevant CNS biological targets including GPCRs, transporters, etc. for clozapine, aripiprazole and amisulpride, alongside exemplary compounds of the invention--compounds 35b, 79, 105, and 70b.

Results of Gi/cAMP and β-Arrestin Antagonist and Agonist Aassays using CHO-K1 Cell Line Expressing Human D2R/β-Arrestin Herein exemplified compounds were analyzed by way of the foregoing Gi/cAMP and β-arrestin antagonist and agonist assays using CHO-K1 cell line expressing human D2R/β-arrestin and thus both the Gi/cAMP and β-arrestin pathways were monitored in both agonist and antagonist (Quinpirole was used as agonist) modes. FIG. 1 shows representative curves obtained for selected D2 ligands: Clozapine, Aripiprazole, and compounds of the invention 35b, 63, 79, 16a and 52. Compounds 35b, 63 and 79 are representative β-arrestin biased D2R antagonists. Compound 16 is a representative cAMP-biased agonist, and Compound 52 is a representative dual antagonist. Table 3 tabulates the results as to the various exemplified compounds, in dopamine β-arrestin and cAMP assays in agonist and antagonist modes. In table 3, Emax is higher than 20%.

MDR1-MDCKII Permeability Assay

This is a standard permeability assay that predicts brain penetration. It was ran by the CRO Absorption Systems (www.absorption.com/drug-discovery/permeability/cell-based/).

TABLE 3

Biological data from testing compounds in the foregoing Gi/cAMP and β-arrestin antagonist and agonist assays using CHO-K1 cell line expressing human D2R/β-arrestin. Both the Gi/cAMP and β-arrestin pathways were monitored in both agonist and antagonist (quinpirole used as agonist) modes. The D2 binding $K_i$ values were determined using a radioligand binding assay. $EC_{50}$ or $IC_{50}$ values were categorized as follows. Emax values for a given pathway ranged from 10-100%.

| Compound # | D2 binding $K_i$ | β-arrestin Antagonist | cAMP Antagonist | β-arrestin Agonist | cAMP Agonist |
|---|---|---|---|---|---|
| Aripiprazole | A | A | E | A | A |
| Clozapine | B | B | B | E | E |
| UNC9994 |  | B | E | B | A |
| UNC9975 |  | B | B | E | A |
| Quinpirole |  | E | E | A | A |
| Dopamine |  | E | E | B | A |
| MLS1547 |  | C | E | E | A |
| 63 | B | B | E | E | B |
| 63a |  | C | E | E | B |
| 63b |  | B | B | E | E |
| 113 |  | C | E | E | A |
| 24 |  | C | E | E | C |
| 23 |  | B | B | E | E |
| 33 |  | D | E | E | C |
| 32 |  | B | B | E | D |
| 31 |  | C | E | E | B |
| 30 |  | D | E | E | C |
| 29 |  | C | E | E | B |
| 28 |  | C | E | E | B |
| 27 |  | C | E | E | B |
| 26 |  | C | B | E | E |
| 25 | C | C | D | E | D |
| 25a |  | C | E | E | B |
| 25b |  | C | C | E | E |
| 78 |  | C | C | E | B |
| 78a |  | C | C | E | B |
| 78b |  | C | C | E | E |
| 122 |  | B | B | E | C |
| 74 |  | B | B | E | A |
| 74a |  | C | E | E | C |
| 74b |  | B | B | E | B |
| 75 |  | B | B | E | A |
| 36 |  | D | E | E | E |
| 35 |  | C | C | E | C |
| 35a |  | D | D | E | D |
| 35b | C | C | C | E | C |
| 118 |  | C | E | E | A |
| 118a |  | D | E | E | D |
| 118b |  | C | E | E | C |
| 93 |  | B | E | E | A |
| 93a |  | C | B | E | D |
| 93b |  | C | E | E | B |
| 34 |  | C | E | E | B |
| 95 | B | B | B | E | B |
| 95a |  | B | B | E | E |
| 95b |  | B | B | E | C |
| 119 |  | B | E | E | A |
| 119a |  | C | C | E | E |
| 119b |  | C | E | B | A |
| 94 |  | B | E | B | A |
| 94a | B | B | A | E | E |
| 94b | B | E | E | B | A |
| 46 |  | C | C | E | E |
| 37 |  | B | C | E | E |
| 38 |  | C | E | E | C |
| 39 |  | B | B | E | E |
| 111 |  | B | E | E | B |
| 112 |  | C | E | E | A |
| 40 | C | B | B | E | E |
| 40a |  | B | B | E | E |
| 40b |  | C | E | E | C |
| 96 |  | B | B | E | B |
| 96a |  | C | E | E | C |
| 96b |  | B | B | E | E |
| 123 |  | B | E | E | A |
| 41 |  | C | B | E | E |
| 42 | B | B | B | E | B |
| 42a |  | B | B | E | B |
| 42b |  | C | C | E | D |
| 43 |  | C | E | E | C |
| 44 |  | C | D | E | E |
| 51 |  | C | E | E | B |
| 79 | B | B | E | E | A |
| 79a |  | C | C | E | E |
| 79b | B | C | E | E | B |
| 114 | B | B | A | E | E |
| 114a | B | A | A | E | B |
| 114b |  | B | E | E | B |
| 107 |  | B | E | E | B |
| 103 |  | A | E | E | A |
| 103a |  | B | A | E | B |
| 103b |  | B | E | B | A |
| 105 | A | B | E | C | B |
| 105a |  | B | E | B | A |
| 105b |  | C | E | C | B |
| 104 | D | E | E | E | C |
| 97 |  | A | A | E | E |
| 97a |  | C | B | E | B |
| 97b |  | B | B | E | B |
| 97c |  | A | A | E | E |
| 97d |  | B | B | E | E |
| 98 |  | E | E | B | A |
| 121 |  | B | B | E | E |
| 89 |  | B | B | E | E |
| 89a |  | B | B | E | E |
| 89b |  | C | D | E | B |
| 120 |  | A | A | E | E |
| 72 | A | A | C | E | A |
| 72a | B | B | E | C | B |
| 72b |  | A | A | E | E |
| 73 |  | A | A | E | E |
| 80 |  | C | C | E | B |
| 102 |  | B | B | E | B |
| 102a |  | C | C | E | E |
| 102b |  | C | C | E | C |
| 88 |  | B | B | E | A |

TABLE 3-continued

Biological data from testing compounds in the foregoing Gi/cAMP and β-arrestin antagonist and agonist assays using CHO-K1 cell line expressing human D2R/β-arrestin. Both the Gi/cAMP and β-arrestin pathways were monitored in both agonist and antagonist (quinpirole used as agonist) modes. The D2 binding Ki values were determined using a radioligand binding assay. $EC_{50}$ or $IC_{50}$ values were categorized as follows. Emax values for a given pathway ranged from 10-100%.

| Compound # | D2 binding $K_i$ | β-arrestin Antagonist | cAMP Antagonist | β-arrestin Agonist | cAMP Agonist |
|---|---|---|---|---|---|
| 88a | | C | B | E | E |
| 88b | | C | C | E | B |
| 76 | | C | D | E | A |
| 76a | | C | B | E | B |
| 76b | | C | C | E | C |
| 77 | | B | C | E | A |
| 77a | B | B | B | E | B |
| 77b | | C | B | E | E |
| 81 | | B | B | E | E |
| 81a | | B | B | E | E |
| 81b | | C | B | E | E |
| 87 | | B | B | E | E |
| 62 | | C | B | E | E |
| 110 | | C | B | E | E |
| 65 | | D | C | E | E |
| 64 | | D | C | E | E |
| 18 | | C | E | E | B |
| 61 | | D | D | E | E |
| 109 | | A | A | E | E |
| 12 | | C | B | E | D |
| 13 | | C | E | E | C |
| 68 | | A | A | E | E |
| 66 | B | A | A | E | D |
| 1 | | B | E | E | A |
| 1a | | C | B | E | E |
| 1b | | C | E | C | A |
| 2 | | C | E | E | B |
| 3 | | B | E | E | A |
| 3a | | B | B | E | E |
| 3b | | B | E | E | A |
| 4 | | B | E | E | A |
| 4a | | C | E | C | B |
| 4b | | C | B | E | E |
| 5 | | C | C | E | D |
| 115 | | C | E | E | B |
| 115a | | C | E | E | B |
| 115b | | B | B | E | E |
| 14 | | B | E | E | A |
| 14a | | C | E | B | A |
| 14b | | B | C | E | E |
| 67 | | B | A | E | E |
| 9 | | C | C | E | E |
| 10 | | D | E | E | B |
| 11 | D | E | D | E | E |
| 11a | | B | C | E | E |
| 11b | | E | E | E | E |
| 6 | B | A | A | E | E |
| 6a | | A | A | E | E |
| 6b | | A | A | E | E |
| 7 | | B | B | E | B |
| 8 | | D | E | E | D |
| 17 | | C | B | E | E |
| 19 | | C | E | E | B |
| 15 | | D | E | E | E |
| 16 | D | E | E | C | A |
| 16a | | E | E | C | A |
| 16b | | E | E | E | C |
| 116 | | C | E | E | B |
| 92 | B | B | B | E | B |
| 92a | | B | B | E | B |
| 92b | | C | C | E | D |
| 117 | | C | E | E | B |
| 91 | | B | B | E | B |
| 91a | | C | E | E | B |
| 91b | | B | B | E | E |
| 45 | | A | A | E | E |
| 45a | | B | B | E | E |
| 45b | | B | B | E | B |
| 54 | | B | B | E | E |
| 54a | | A | A | E | E |
| 54b | | C | E | E | B |
| 56 | | B | B | E | E |
| 57 | | B | E | E | B |
| 53 | B | A | A | E | E |
| 53a | | B | B | E | E |
| 53b | | B | B | E | E |
| 52 | | A | A | E | E |
| 52a | | B | A | E | E |
| 52b | | B | B | E | E |
| 70 | | B | B | E | B |
| 70a | | A | A | E | E |
| 70b | | C | E | E | A |
| 69 | | B | E | B | A |
| 69a | | C | E | B | B |
| 69b | B | B | E | B | A |
| 55 | | C | C | E | E |
| 59 | | E | D | E | E |
| 60 | | E | E | E | E |
| 47 | | C | B | E | E |
| 83 | | A | A | E | E |
| 49 | | B | C | E | C |
| 85 | | A | A | E | E |
| 48 | | C | E | E | C |
| 84 | | B | B | E | E |
| 50 | | C | E | E | B |
| 86 | | A | A | E | E |
| 22 | | B | B | E | E |
| 22a | | B | B | E | D |
| 22b | | B | B | E | E |
| 90 | | C | C | E | C |
| 21 | | B | B | E | E |
| 20 | | B | A | E | E |
| 82 | | D | C | E | E |
| 108 | | C | E | E | A |
| 58 | | D | D | E | E |
| 71 | | B | E | A | A |
| 99 | | C | E | E | B |
| 101 | | B | A | E | E |
| 101a | | B | B | E | E |
| 101b | | B | B | E | E |
| 106 | | B | C | E | C |
| 124 | | A | A | E | E |
| 125 | B | B | B | E | B |
| 125a | | C | E | E | B |
| 125b | | B | C | E | E |
| 126 | | C | E | E | A |
| 127 | | A | A | E | E |
| 128 | | B | B | E | A |
| 128a | | D | B | E | E |
| 128b | C | B | B | E | A |
| 129 | | E | E | E | C |
| 130 | | C | E | B | A |
| 130a | | C | B | E | E |
| 130b | | C | E | B | A |
| 146 | | C | C | E | E |
| 131 | | C | E | C | A |
| 132 | | C | C | E | E |
| 133 | | A | A | E | A |
| 133a | | A | A | E | E |
| 133b | | B | E | A | A |
| 134 | | B | B | E | A |
| 135 | | C | B | E | E |
| 136 | | A | A | E | C |
| 136a | | B | E | B | C |
| 136b | | A | A | E | E |
| 137 | | C | C | E | E |

TABLE 3-continued

Biological data from testing compounds in the foregoing Gi/cAMP and β-arrestin antagonist and agonist assays using CHO-K1 cell line expressing human D2R/β-arrestin. Both the Gi/cAMP and β-arrestin pathways were monitored in both agonist and antagonist (quinpirole used as agonist) modes. The D2 binding Ki values were determined using a radioligand binding assay. $EC_{50}$ or $IC_{50}$ values were categorized as follows. Emax values for a given pathway ranged from 10-100%.

| Compound # | D2 binding $K_i$ | β-arrestin Antagonist | cAMP Antagonist | β-arrestin Agonist | cAMP Agonist |
|---|---|---|---|---|---|
| 138 | | B | E | E | B |
| 138a | | B | E | B | A |
| 138b | | B | A | E | A |
| 139 | | C | B | E | C |
| 139a | | B | B | E | A |
| 139b | | C | B | E | B |
| 140 | | C | C | E | C |
| 141 | | C | C | E | E |
| 142 | | D | D | E | E |
| 143 | | C | E | C | B |
| 144 | | A | E | A | A |
| 144a | A | A | E | A | A |
| 144b | | B | E | B | A |
| 145 | | C | C | E | D |
| 145a | | D | C | E | E |
| 145b | | C | B | E | E |

(A = <0.1 μM, B = 0.1-1.0 μM, C = 1.0-10.0 μM, D = 10.0-30.0 μM, E = >30 μM)

UNC9994 is of the formula:

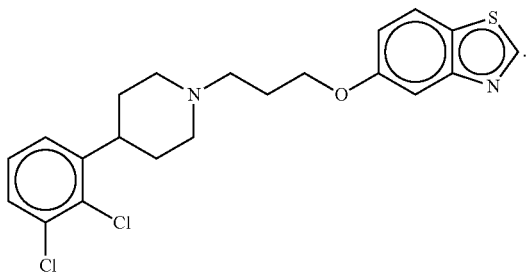

UNC9975 is of the formula:

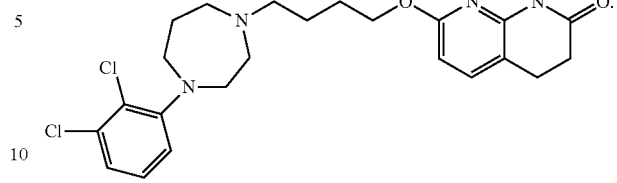

Quinpirole is of the formula

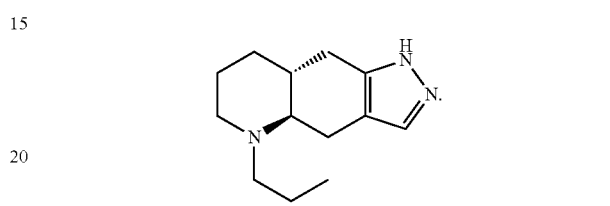

Dopamine is of the formula:

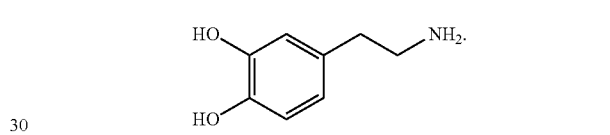

MLS1547 is of the formula:

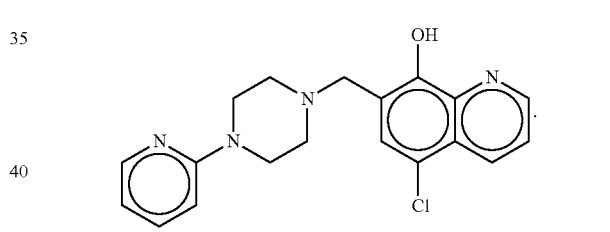

TABLE 4

Additional exemplary results of the biological assays of select compounds of the invention, and exemplary analytical data of select compounds of the invention

| Compound Number | MDR1-MDCKII A-B/B-A | Caco2 A-B/B-A | Solubility in PBS (μM) | Protein Binding % bound | Analytical (h: human; m: mouse; r: rat) Plasma Stability: % remaining after 5 hours | Microsomal Stability: % remaining after 60 minutes |
|---|---|---|---|---|---|---|
| 63 | | 25.1/19.9 | 476 | h96.3, m97.4 | h94.5, m93.4 | h58, m37, r55 |
| 23 | | | 225 | h97.7, m97.0, r96.7 | h100, m100, r96 | h76, m41, r77 |
| 32 | | | 151 | h97.0, m96.9, r97.7 | h91, m74, r98 | h61, m37, r46 |
| 31 | | | 27 | h97.7, m97.4, r98.6 | h94.2, m84.5, r100 | h53, m57, r55 |
| 28 | | | 434 | h75.3, m72.2, r76.7 | h100, m95, r99 | h87, m52, r78 |
| 26 | | | 460 | h93.8, m94.3, r95.4 | h100, m92, r99 | h84, m66, r96 |
| 25 | | 33.7/50.5 | 452 | h92, m95.3, r97 | h100, m97, r94.5 | h93, m76, r100 |
| 35 | | 26.7/46.7 | 441 | h91.4, m92.6, r95.8 | h100, m98, r99.6 | h83, m74, r80 |
| 35b | 0.97/53.1 | | 472 | h91.9, m91.3, r93.3 | h98, m100, r87 | h75, m62, r96 |
| 118b | | | | | | m35 |
| 93 | | | | | | m12 |
| 93b | | | | | | m19 |
| 95 | | | | | | m33 |

TABLE 4-continued

Additional exemplary results of the biological assays of select compounds of the invention, and exemplary analytical data of select compounds of the invention

| Compound Number | MDR1-MDCKII A-B/B-A | Caco2 A-B/B-A | Solubility in PBS (µM) | Protein Binding % bound | Analytical (h: human; m: mouse; r: rat) Plasma Stability: % remaining after 5 hours | Microsomal Stability: % remaining after 60 minutes |
|---|---|---|---|---|---|---|
| 95b | | | | | | m12 |
| 119b | | | | m97.4 | m100 | m51 |
| 94a | | | | | | m2 |
| 94b | | | | | | m26 |
| 146 | | | | h97.8, m96.0, r97.9 | h98, m96, r88 | h56, m36, r27 |
| 37 | | | 197 | h95.3, m94.9, r97.6 | h100, m98, r100 | h71, m31, r28 |
| 39 | | | 3.3 | h97.9, m98.0, r95.4 | h100, m93, r86 | h49, m65, r55 |
| 111 | | | 496/217 | h94.7, m97.3, r97.8 | h100, m100, r98 | h60, m39, r51 |
| 112 | | | 19 | h93.6, m95, r98 | h100, m95, r95 | h52, m29, r53 |
| 40 | | 4.4/1.9 | 0.4 | h98.9, m99.0, r97.7 | h100, m100, r90 | h45, m50, r57 |
| 96 | | | | | | m26 |
| 41 | | | <0.1 | h99.3, m99.4, r98.6 | h100, m100, r96 | h45, m64, r78 |
| 42 | | | <0.1 | h99.3, m99.3, r98.6 | h98, m100, r93 | h40, m59, r70 |
| 51 | | | | | | m0 |
| 79 | 6.17/22.1 | | | | | m0 |
| 79b | | | 8 | m100 | m100 | m0 |
| 114 | | | >500/159 | h98.6, m97.7, r99.5 | h100, m100, r100 | h63, m6, r20 |
| 99 | | | | | | m7 |
| 103 | | | | m100 | m97 | m1 |
| 135 | | | | | | m2 |
| 125 | | | | | | m12 |
| 105 | | | | | | m18 |
| 105a | | | | | | m1 |
| 104 | | | | | | m45 |
| 97b | | | | | | m3 |
| 72a | | | 1.4 | m100 | m100 | m0 |
| 137 | | | | | | m1 |
| 88 | | | 461 | | | m1 |
| 77a | | | | | | m1 |
| 18 | | | 352 | h95.4, m94.4, r97.3 | h94.9, m90.5, r93.2 | h78, m43, r55 |
| 109 | | | >500 | | | h59, m40, r57 |
| 66 | | 15.1/2.4 | 10.5 | h99.3, m99.2, r99.4 | h99.7, m100, r88.1 | h46, m7, r35 |
| 3 | | | 43 | h75.4, m98.5, r68.5 | h92, m100, r86 | h64, m22, r44 |
| 5 | | | 311 | h80.5, m97.9, r85.8 | h91.2, m90.5, r95.2 | h71, m42, r84 |
| 115 | | 30.4/11.5 | 220 | h99.2, m98.5, r99.5 | h91.2, m86.2, r98.0 | h63, m26, r77 |
| 14 | | | 36.1 | h99.1, m98.5, r99.4 | h96.7, m100, r78.2 | h49, m11, r44 |
| 10 | | | >500 | | | h75, m44, r57 |
| 11 | | | >500 | h51.5, m60.9, r78.9 | h98.2, m89.5, r100 | h95, m100, r100 |
| 6 | | | 0.7 | h99.3, m99.2, r100 | h99, m98.8, r69.3 | h52, m22, r32 |
| 6a | | | | | | m31 |
| 6b | | | | | | m2 |
| 7 | | | 0.7 | h100, m99.6, r100 | h91.5, m100, r93.5 | h87, m44, r76 |
| 8 | | | 1.1 | h100, m100, r100 | h100, m100, r98.1 | h82, m53, r100 |
| 15 | | | 4.1 | h97.7, m97.4, r99.0 | h96, m100, r91 | h56, m44, r68 |
| 16 | | | 14 | h99, m97.7, r97.9 | h98, m94, r97 | h34, m45, r75 |
| 92 | | | | | | m22 |
| 91b | | | | | | m1 |
| 45 | | | 6.5 | h98.3, m98.5, r98.8 | h95, m91, r85 | h56, m62, r59 |
| 54 | | 28.4/39.3 | >500 | h95.8, m96.1, r97.3 | h96, m100, r78 | h70, m29, r66 |
| 53 | | 27.4/23.9 | 149 | h79.0, m97.9, r91.4 | h100, m96, r78 | h42, m3, r16 |
| 52 | | 12.5/9.0 | 27 | h99.1, m99.1, r97.9 | h84, m89, r55 | h46, m7, r7 |
| 70b | | | | | | m0 |
| 144a | | | | | | m1 |
| 22b | | | | | | m12 |

The foregoing examples are presented for the purpose of illustrating the invention and should not be construed as imposing any limitation on the scope of the invention. It will be readily apparent that numerous modifications and alterations may be made to the specific embodiments of the invention described above and illustrated in the examples without departing from the principles underlying the invention. All such modifications and alterations not departing from the spirit or scope of the present invention are intended to be embraced by this application.

What is claimed is:

1. A compound of Formula I:

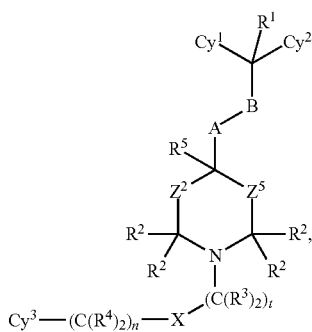

(I)

or a stereoisomer, racemate, tautomer, polymorph, hydrate, or solvate thereof, or a pharmaceutically acceptable salt thereof, wherein:

A-B is $C(O)-NR^{13}$, $C(O)-CR^{11}R^{12}$, $C(O)-O$, $CR^{11}R^{12}-NR^{13}$, $CR^{11}R^{12}-O$, $CR^{11}R^{12}-C(O)$, $NR^{13}-C(O)$, $NR^{13}-CR^{11}R^{12}$, $O-CR^{11}R^{12}$, or $O-C(O)$;

$R^{11}$ and $R^{12}$ are each independently H, halogen, or $C_1$-$C_6$ alkyl;

$R^{13}$ is H, $C_1$-$C_6$ alkyl, $C_1$-$C_6$ haloalkyl, $C_3$-$C_6$ cycloalkyl, $C_3$-$C_6$ heterocycle, $C_6$-$C_{10}$ aryl, heteroaryl comprising one or two 5- or 6-membered rings and one to four heteroatoms selected from N, O, and S, $C(O)-C_1$-$C_6$ alkyl, $C(O)$-phenyl, $C(O)O-C_1$-$C_6$ alkyl, $C(O)NR^{17}R^{18}$, $S(O)_2-C_1$-$C_6$ alkyl, or $S(O)_2NR^{17}R^{18}$;

$R^{17}$ and $R^{18}$ are each independently H, $C_1$-$C_6$ alkyl, or $C_6$-$C_{10}$ aryl;

$R^5$ is H, halogen, OH, $C_1$-$C_6$ alkyl, $O-C_1$-$C_6$ alkyl, $OCF_3$, $OCHF_2$, $OCH_2F$, $NR^{17}R^{18}$, $NR^{17}C(O)-C_1$-$C_6$ alkyl, $C(O)NR^{17}R^{18}$, $S-C_1$-$C_6$ alkyl, $S(O)-C_1$-$C_6$ alkyl, $S(O)_2-C_1$-$C_6$ alkyl, $S(O)_2NR^{17}R^{18}$, $NR^{17}S(O)_2-C_1$-$C_6$ alkyl, $C_6$-$C_{10}$ aryl, phenyl, benzyl, heteroaryl comprising one 5- or 6-membered ring and one to four heteroatoms selected from N, O, and S, $C_3$-$C_6$ cycloalkyl, or heterocyclyl comprising one 4- to 6-membered ring and one to four heteroatoms selected from N, O, and S;

provided that when A-B is $NR^{13}-C(O)$, $NR^{13}-CR^{11}R^{12}$, $O-CR^{11}R^{12}$, or $O-C(O)$, then $R^5$ is not OH, $O-C_1$-$C_6$ alkyl, $S-C_1$-$C_6$ alkyl, $NR^{17}R^{18}$, $NR^{17}C(O)-C_1$-$C_6$ alkyl, or $NR^{17}S(O)_2-C_1$-$C_6$ alkyl;

$Z^2$ is $C(R^2)_2$ or $C(O)$;

$Z^5$ is $C(R^2)_2$ or $C(O)$;

each $R^2$ is independently H, halogen, OH, $C_1$-$C_6$ alkyl, $CF_3$, $O-C_1$-$C_6$ alkyl, $OCF_3$, $OCHF_2$, $OCH_2F$, $C_3$-$C_8$ cycloalkyl, $C_3$-$C_8$ heterocycle, $C_6$-$C_{10}$ aryl, $O-C_6$-$C_{10}$ aryl, $C(O)-C_1$-$C_6$ alkyl, $C(O)NR^{17}R^{18}$, $NR^{17}R^{18}$, $NR^{17}C(O)-C_1$-$C_6$ alkyl, $S(O)_2NR^{17}R^{18}$, or $NR^{17}S(O)_2-C_1$-$C_6$ alkyl;

provided that when $R^2$ is bonded to a carbon atom adjacent to the nitrogen atom in

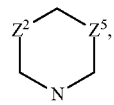

then $R^2$ is H, halogen, $C_1$-$C_6$ alkyl, $CF_3$, $C_3$-$C_8$ cycloalkyl, $C_3$-$C_8$ heterocycloalkyl, $C_6$-$C_{10}$ aryl, $C(O)-C_1$-$C_6$ alkyl, $C(O)NR^{17}R^{18}$, or $S(O)_2NR^{17}R^{18}$;

$R^1$ is H or $C_1$-$C_6$ alkyl;

$Cy^1$ and $Cy^2$ are each independently $C_6$-$C_{10}$ aryl, heteroaryl comprising one or two 5- or 6-membered rings and one to four heteroatoms selected from N, O, and S, $C_3$-$C_{10}$ cycloalkyl, $C_5$-$C_{13}$ bicyclic group, or heterocyclyl comprising one or two 3- to 6-membered rings and one to four heteroatoms selected from N, O, and S, wherein the aryl, heteroaryl, cycloalkyl, bicyclic group, and heterocycyl are each independently optionally substituted with one or more substituents independently selected from:

halogen, $CH_2F$, $CHF_2$, $CF_3$, $C_1$-$C_6$ alkyl, $C_3$-$C_8$ cycloalkyl, OH, $O-C_1$-$C_6$ alkyl, $OCF_3$, $OCHF_2$, $OCH_2F$, $C_6$-$C_{10}$ aryl, heteroaryl comprising one 5- or 6-membered ring and one to four heteroatoms selected from N, O, and S, and $NR^{17}R^{18}$;

t is 2, 3, or 4;

each $R^3$ is independently H, halogen, $C_1$-$C_6$ alkyl, $C_3$-$C_8$ cycloalkyl, $C_3$-$C_8$ heterocycle, OH, $O-C_1$-$C_6$ alkyl, $S-C_1$-$C_6$ alkyl, $NR^{17}R^{18}$, $C(O)NR^{17}R^{18}$, $NR^{17}C(O)-C_1$-$C_6$ alkyl, $NR^{17}S(O)_2-C_1$-$C_6$ alkyl, or $S(O)_2NR^{17}R^{18}$, or any two $R^3$ bonded to the same carbon atom, together with the carbon atom to which the two $R^3$ are bonded, form C=O, provided that the C=O is not directly bonded to the nitrogen atom in

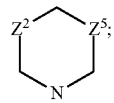

provided that when X is O, S, or $NR^{16}$, then the $R^3$ in the $C(R^3)_2$ directly bonded to X is not OH, $O-C_1$-$C_6$ alkyl, $S-C_1$-$C_6$ alkyl, $NR^{17}R^{18}$, $NR^{17}C(O)-C_1$-$C_6$ alkyl, $NR^{17}S(O)_2-C_1$-$C_6$ alkyl, or $S(O)_2NR^{17}R^{18}$;

X is a O, $CR^{14}R^{15}$, S, S(O), $S(O)_2$, C=O, or $NR^{16}$;

$R^{16}$ is H, $C_1$-$C_6$ alkyl, phenyl, heteroaryl comprising one 5- or 6-membered ring and one to four heteroatoms selected from N, O, and S, $C(O)-C_1$-$C_6$ alkyl, $C(O)$-phenyl, $C(O)O-C_1$-$C_6$ alkyl, $C(O)NR^{17}R^{18}$, $S(O)_2-C_1$-$C_6$ alkyl, or $S(O)_2NR^{17}R^{18}$;

n is 0, 1, or 2;

each $R^4$ is independently H, halogen, $C_1$-$C_6$ alkyl, $C_3$-$C_8$ cycloalkyl, $C_3$-$C_8$ heterocycle, OH, $O-C_1$-$C_6$ alkyl, $S-C_1$-$C_6$ alkyl, $NR^{17}R^{18}$, $C(O)NR^{17}R^{18}$, $NR^{17}C(O)-C_1$-$C_6$ alkyl, $NR^{17}S(O)_2-C_1$-$C_6$ alkyl, or $S(O)_2NR^{17}R^{18}$, or any two $R^4$ bonded to the same carbon atom, together with the carbon atom to which the two $R^4$ are bonded, form C=O;

provided that when X is O, S, or $NR^{16}$, then the $R^4$ in the $C(R^4)_u$ directly bonded to X is not OH, O—$C_1$-$C_6$ alkyl, S—$C_1$-$C_6$ alkyl, or $NR^{17}R^{18}$; and $Cy^3$ is $C_6$-$C_{10}$ aryl, heteroaryl comprising one or two 5- or 6-membered rings and one to four heteroatoms selected from N, O, and S, $C_3$-$C_{10}$ cycloalkyl, $C_5$-$C_{13}$ bicyclic group, or heterocyclyl comprising one or two 3- to 6-membered rings and one to four heteroatoms selected from N, O, and S, wherein the aryl, heteroaryl, cycloalkyl, bicyclic group, and heterocycyl are each independently optionally substituted with one or more substituents independently selected from:

halogen, $CH_2F$, $CHF_2$, $CF_3$, $C_1$-$C_6$ alkyl, $C_3$-$C_8$ cycloalkyl, OH, O—$C_1$-$C_6$ alkyl, $OCF_3$, $OCHF_2$, $OCH_2F$, $C_6$-$C_{10}$ aryl, heteroaryl comprising one 5- or 6-membered ring and one to four heteroatoms selected from N, O, and S, and $NR^{17}R^{18}$ provided that when $(C(R^4)_2)_n$—X—$(C(R^3)_2)_t$ is $(CH_2)_{3-6}$, then $Cy^3$ is not phenyl, which is optionally substituted, methylenedioxyphenyl, isoindoline-1,3,-dione, or dihydrobenzofuranyl.

2. The compound of claim 1, having Formula II:

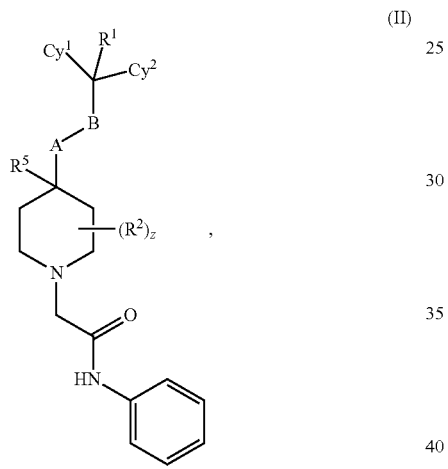

(II)

or a stereoisomer, racemate, tautomer, polymorph, hydrate, or solvate thereof, or a pharmaceutically acceptable salt thereof, wherein z is 1, 2, 3, 4, 5, 6, 7, or 8.

3. The compound of claim 1, having Formula IV:

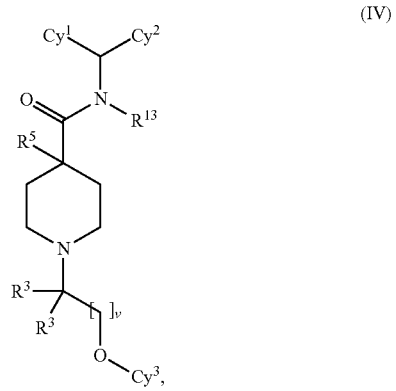

(IV)

or a stereoisomer, racemate, tautomer, polymorph, hydrate, or solvate thereof, or a pharmaceutically acceptable salt thereof, wherein:

$Cy^1$, $Cy^2$, and $Cy^3$ are each independently phenyl, heteroaryl comprising one or two 5- or 6-membered rings and one to four heteroatoms selected from N, O, and S, $C_5$-$C_6$ cycloalkyl, $C_5$-$C_{13}$ bicyclic group, or heterocyclyl comprising one or two 3- to 6-membered rings and one to four heteroatoms selected from N, O, and S, wherein $Cy^1$, $Cy^2$, and $Cy^3$ are each independently optionally substituted with one or more substituents independently selected from halogen, $CH_2F$, $CHF_2$, $CF_3$, $C_1$-$C_6$ alkyl, OH, O—$C_1$-$C_6$ alkyl, $OCF_3$, $OCHF_2$, $OCH_2F$, and $NR^{17}R^{18}$;

each $R^3$ is the same and is selected from H and $C_1$-$C_3$ alkyl;

$R^5$ is H or $C_1$-$C_3$ alkyl;

$R^{13}$ is H or $C_1$-$C_3$ alkyl;

$R^{17}$ and $R^{18}$ are each independently H or $C_1$-$C_3$ alkyl; and v is 1, 2, or 3.

4. The compound of claim 1, having Formula V:

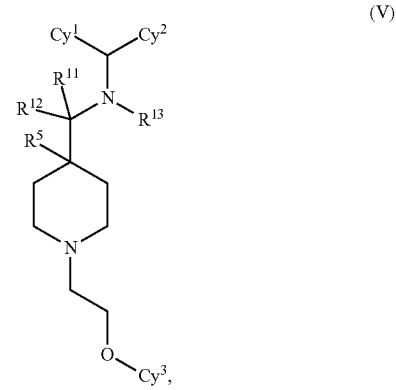

(V)

or a stereoisomer, racemate, tautomer, polymorph, hydrate, or solvate thereof, or a pharmaceutically acceptable salt thereof, wherein:

$Cy^1$, $Cy^2$ and $Cy^3$ are each independently phenyl, heteroaryl comprising one or two 5- or 6-membered rings and one to four heteroatoms selected from N, O, and S, or $C_5$-$C_{13}$ bicyclic group, wherein $Cy^1$, $Cy^2$, and $Cy^3$ are each independently optionally substituted with one or more substituents independently selected from halogen, $CH_2F$, $CHF_2$, $CF_3$, $C_1$-$C_6$ alkyl, OH, O—$C_1$-$C_6$ alkyl, $OCF_3$, $OCHF_2$, $OCH_2F$, and $NR^{17}R^{18}$;

$R^5$ is H or $C_1$-$C_3$ alkyl;

$R^{11}$ and $R^{12}$ are each independently H or $C_1$-$C_3$ alkyl;

$R^{13}$ is H, $C_1$-$C_3$ alkyl, $C_1$-$C_3$ haloalkyl, or C(O)—$C_1$-$C_3$ alkyl; and $R^{17}$ and $R^{18}$ are each independently H or $C_1$-$C_3$ alkyl.

5. The compound of claim 1, having Formula VII:

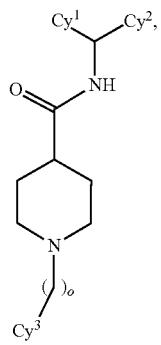

(VII)

or a stereoisomer, racemate, tautomer, polymorph, hydrate, or solvate thereof, or a pharmaceutically acceptable salt thereof, wherein:
  $Cy^1$, $Cy^2$ and $Cy^3$ are each independently phenyl, heteroaryl comprising one or two 5- or 6-membered rings and one to four heteroatoms selected from N, O, and S, or $C_5$-$C_{13}$ bicyclic group, wherein $Cy^1$, $Cy^2$, and $Cy^3$ are each independently optionally substituted with one or more substituents independently selected from halogen, $CH_2F$, $CHF_2$, $CF_3$, $C_1$-$C_6$ alkyl, OH, O—$C_1$-$C_6$ alkyl, $OCF_3$, $OCHF_2$, $OCH_2F$, and $NR^{17}R^{18}$;
  $R^{17}$ and $R^{18}$ are each independently H or $C_1$-$C_3$ alkyl; and
  o is 1, 2, or 3.

6. The compound of claim 1, or a stereoisomer, tautomer, polymorph, hydrate, or solvate thereof, or a pharmaceutically acceptable salt thereof, wherein $Cy^1$, $Cy^2$ or $Cy^3$ is independently $C_6$-$C_{10}$ aryl, heteroaryl comprising one or two 5- or 6-membered rings and one to four heteroatoms selected from N, O, and S, $C_3$-$C_{10}$ cycloalkyl, or $C_5$-$C_{13}$ bicyclic group, wherein the aryl, heteroaryl, cycloalkyl, and bicyclic group are each independently optionally substituted with one or more substituents independently selected from halogen, $CH_2F$, $CHF_2$, $CF_3$, $C_1$-$C_6$ alkyl, OH, O—$C_1$-$C_6$ alkyl, $OCF_3$, $OCHF_2$, $OCH_2F$, and $NR^{17}R^{18}$.

7. The compound of claim 1, or a stereoisomer, racemate, tautomer, polymorph, hydrate, or solvate thereof, or a pharmaceutically acceptable salt thereof, wherein $R^1$ is H.

8. The compound of claim 1, or a stereoisomer, racemate, tautomer, polymorph, hydrate, or solvate thereof, or a pharmaceutically acceptable salt thereof, wherein A-B is C(O)—$NR^{13}$.

9. The compound of claim 1, or a stereoisomer, racemate, tautomer, polymorph, hydrate, or solvate thereof, or a pharmaceutically acceptable salt thereof, wherein X is O.

10. The compound of claim 1, or a stereoisomer, racemate, tautomer, polymorph, hydrate, or solvate thereof, or a pharmaceutically acceptable salt thereof, wherein n is 0.

11. A compound of the formula:

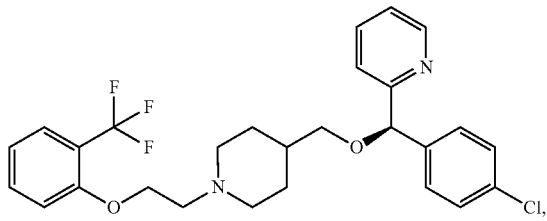

-continued

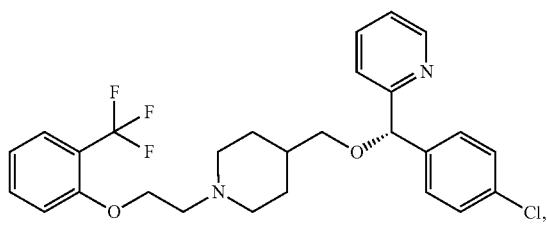

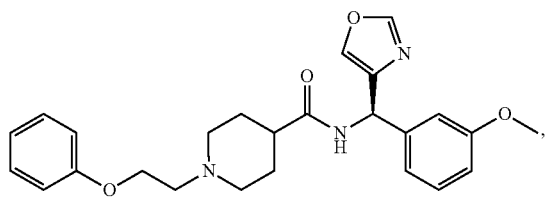

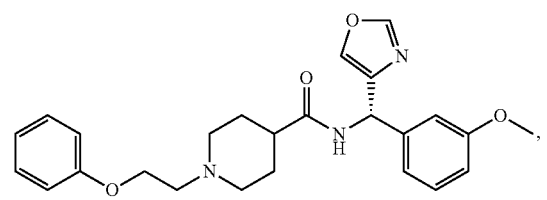

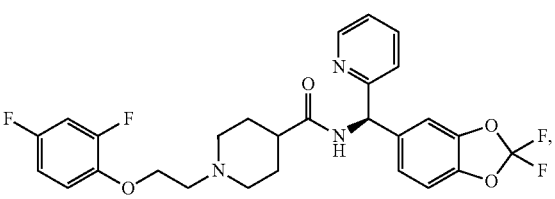

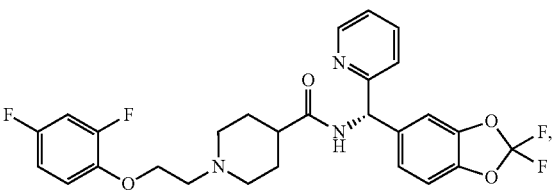

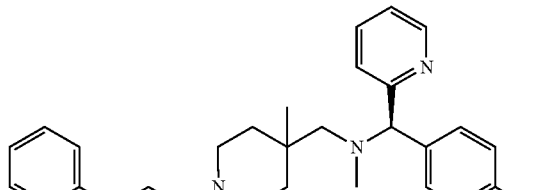

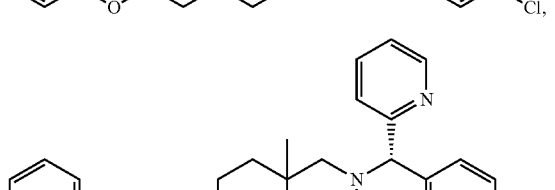

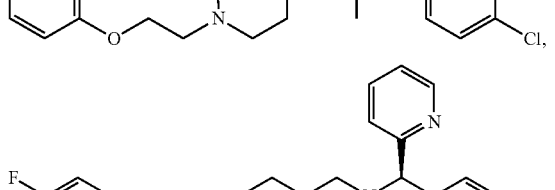

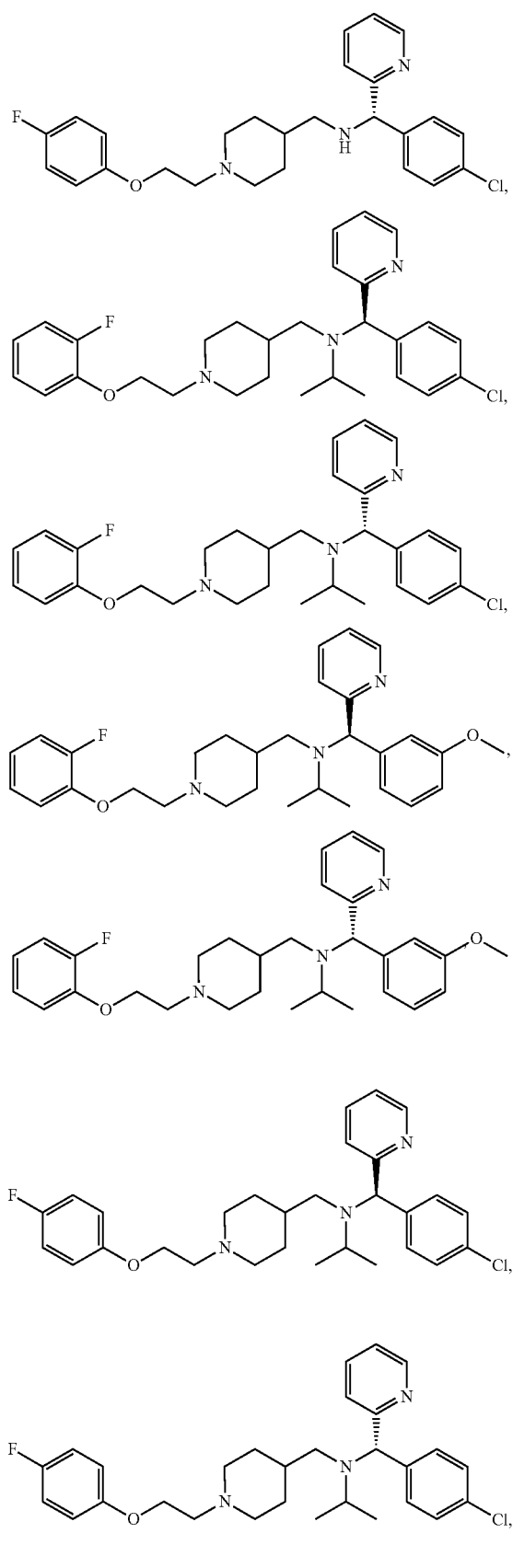
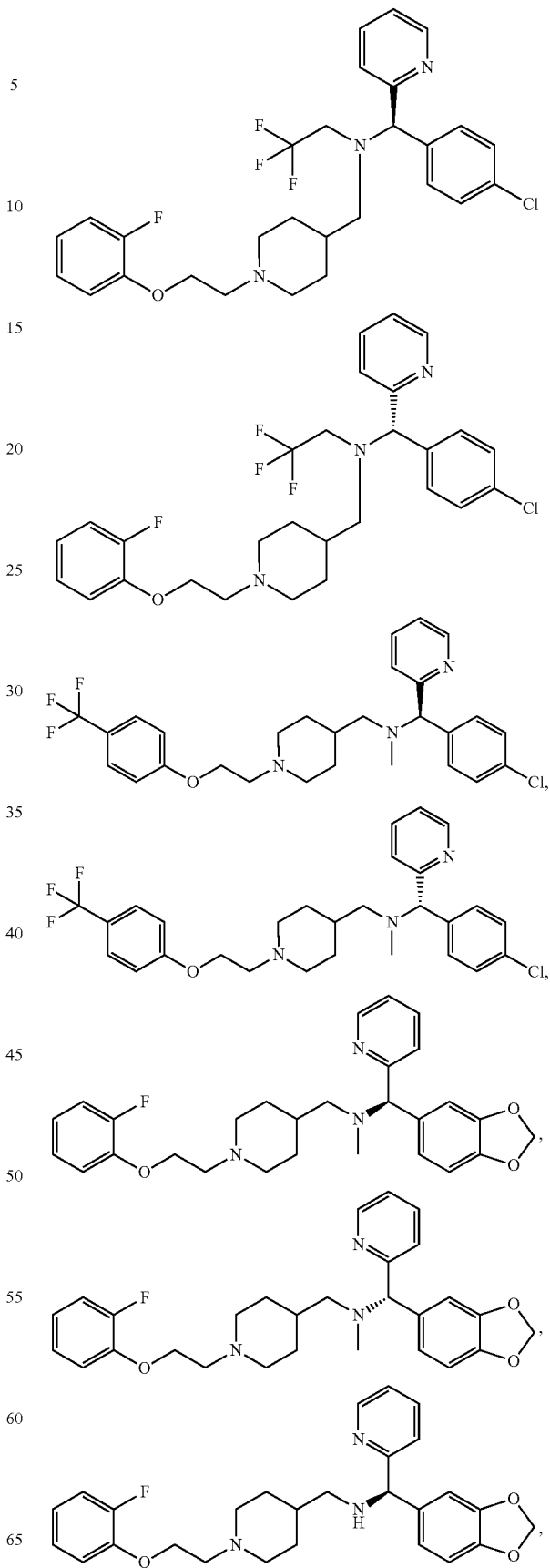

-continued

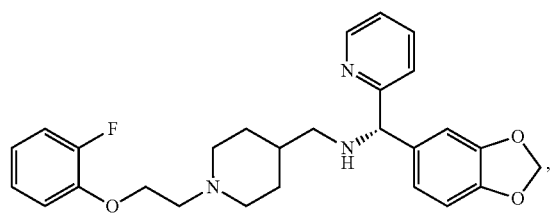

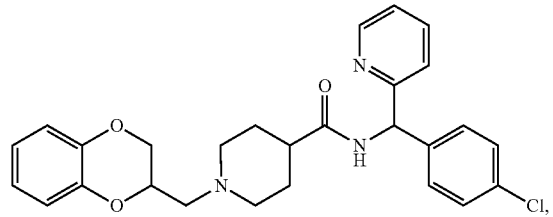

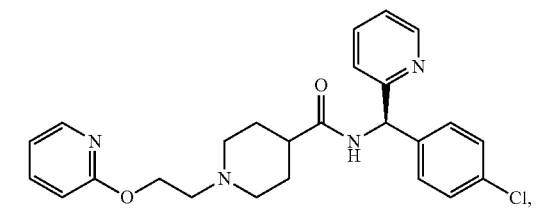

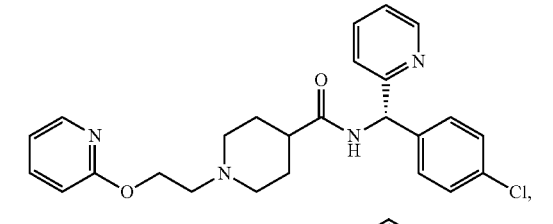

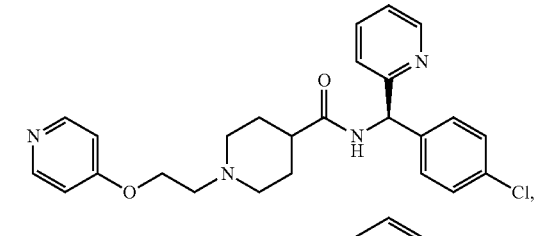

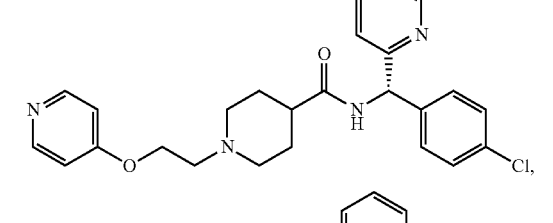

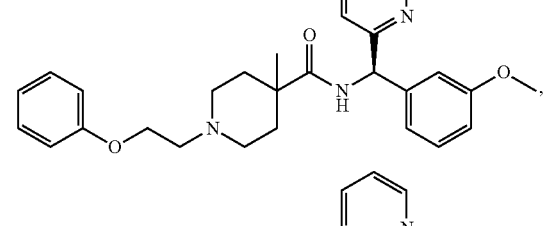

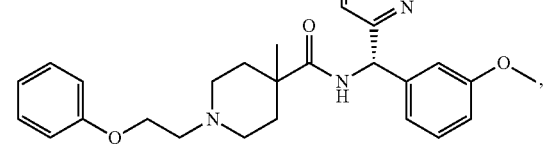

-continued

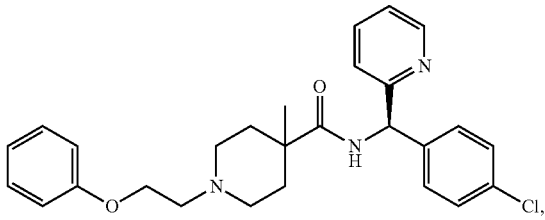

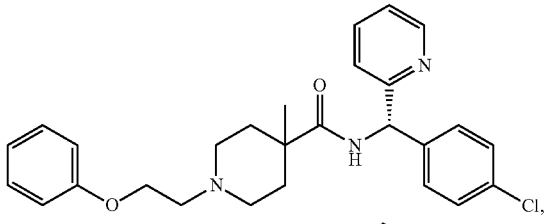

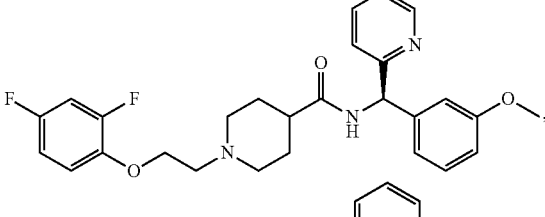

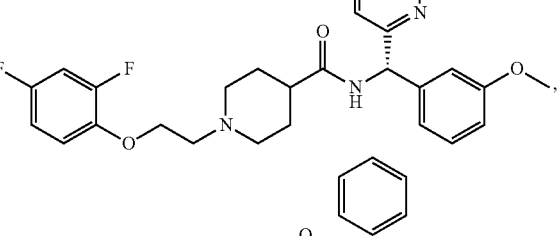

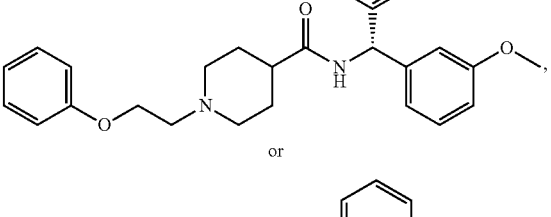

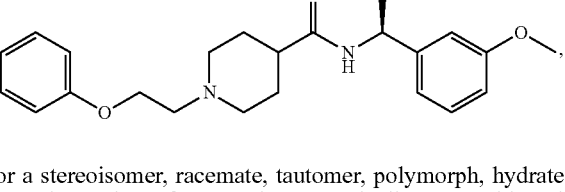

or

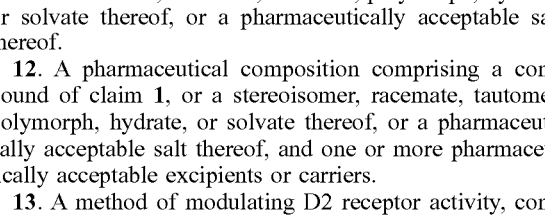

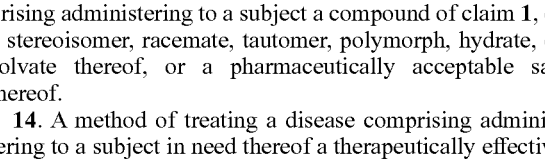

or a stereoisomer, racemate, tautomer, polymorph, hydrate, or solvate thereof, or a pharmaceutically acceptable salt thereof.

12. A pharmaceutical composition comprising a compound of claim 1, or a stereoisomer, racemate, tautomer, polymorph, hydrate, or solvate thereof, or a pharmaceutically acceptable salt thereof, and one or more pharmaceutically acceptable excipients or carriers.

13. A method of modulating D2 receptor activity, comprising administering to a subject a compound of claim 1, or a stereoisomer, racemate, tautomer, polymorph, hydrate, or solvate thereof, or a pharmaceutically acceptable salt thereof.

14. A method of treating a disease comprising administering to a subject in need thereof a therapeutically effective amount of a compound of claim 1, or a stereoisomer, racemate, tautomer, polymorph, hydrate, or solvate thereof, or a pharmaceutically acceptable salt thereof, in combination with a pharmaceutically acceptable excipient or carrier, wherein the disease is:
an anxiety disorder;
a dissociative disorder;
a mood disorder;
an eating disorder;
a sleep disorder;
a developmental disorder;
a somatoform disorder;
a personality disorder;
a psychiatric syndrome;
a psychotic disorder;
substance abuse;
Parkinson's disease;
Huntington's disease;
Alzheimer's disease;
dementia;
Niemann-Pick disorder;
a pituitary disorder;
Tourette's syndrome;
Tourette-like disorder; or
restless leg syndrome.

15. The compound of claim 1, or a stereoisomer, racemate, tautomer, polymorph, hydrate, or solvate thereof, or a pharmaceutically acceptable salt thereof, wherein $Cy^3$ is phenyl, optionally substituted with one or more substituents independently selected from halogen, $CH_2F$, $CHF_2$, $CF_3$, $C_1$-$C_6$ alkyl, OH, O—$C_1$-$C_6$ alkyl, $OCF_3$, $OCHF_2$, $OCH_2F$, and $NR^{17}R^{18}$, wherein $R^{17}$ and $R^{18}$ are each independently H or $C_1$-$C_3$ alkyl.

16. The compound of claim 1, or a stereoisomer, racemate, tautomer, polymorph, hydrate, or solvate thereof, or a pharmaceutically acceptable salt thereof, wherein —$(C(R^4)_2)_n$—X—$(C(R^3)_2)_t$— is —O—$(CH_2)_2$—.

17. The compound of claim 1, or a stereoisomer, racemate, tautomer, polymorph, hydrate, or solvate thereof, or a pharmaceutically acceptable salt thereof, wherein $R^5$ is H or —$CH_3$.

18. The compound of claim 1, or a stereoisomer, racemate, tautomer, polymorph, hydrate, or solvate thereof, or a pharmaceutically acceptable salt thereof, wherein A-B is $CR^{11}R^{12}$—$NR^{13}$.

19. The compound of claim 1, or a stereoisomer, racemate, tautomer, polymorph, hydrate, or solvate thereof, or a pharmaceutically acceptable salt thereof, wherein A-B is $CR^{11}R^{12}$—O.

20. The compound of claim 1, or a stereoisomer, racemate, tautomer, polymorph, hydrate, or solvate thereof, or a pharmaceutically acceptable salt thereof, wherein $Cy^1$ is phenyl, and $Cy^2$ is pyridyl, wherein the phenyl and the pyridyl are each independently optionally substituted with one or more substituents independently selected from halogen, $CH_2F$, $CHF_2$, $CF_3$, $C_1$-$C_6$ alkyl, OH, O—$C_1$-$C_6$ alkyl, $OCF_3$, $OCHF_2$, $OCH_2F$, and $NR^{17}R^{18}$, wherein $R^{17}$ and $R^{18}$ are each independently H or $C_1$-$C_3$ alkyl.

21. The compound of claim 1, wherein the compound is of the formula:

| Compound No. | Compound Formula |
|---|---|
| 99 | 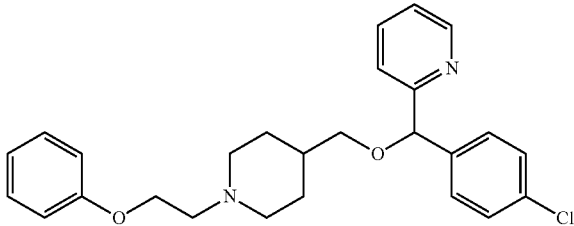 [SMILES: Clc1ccc(C(OCC2CCN(CCOc3ccccc3)CC2)c2ccccn2)cc1] |
| 126 | 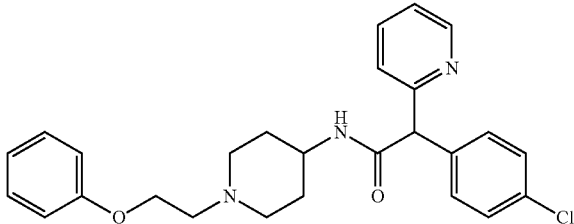 [SMILES: O=C(NC1CCN(CCOc2ccccc2)CC1)C(c1ccc(Cl)cc1)c1ccccn1] |
| 127 | 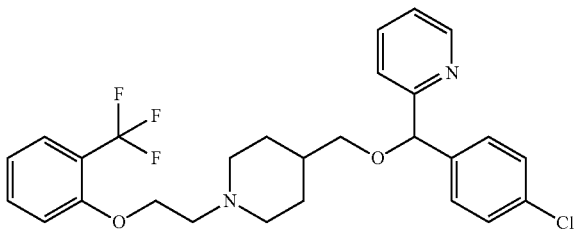 [SMILES: FC(F)(F)c1ccccc1OCCN1CCC(COC(c2ccc(Cl)cc2)c2ccccn2)CC1] |

-continued
| Compound No. | Compound Formula |
|---|---|
| 1 | 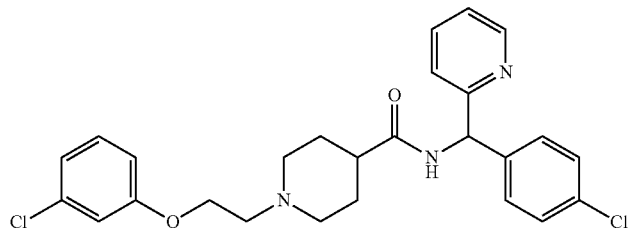 [SMILES: O=C(NC(c1ccc(Cl)cc1)c1ccccn1)C1CCN(CCOc2cccc(Cl)c2)CC1] |
| 2 | 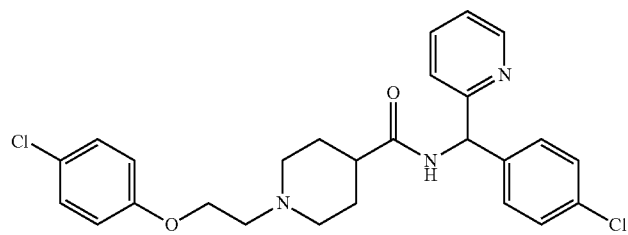 [SMILES: O=C(NC(c1ccc(Cl)cc1)c1ccccn1)C1CCN(CCOc2ccc(Cl)cc2)CC1] |
| 3 | 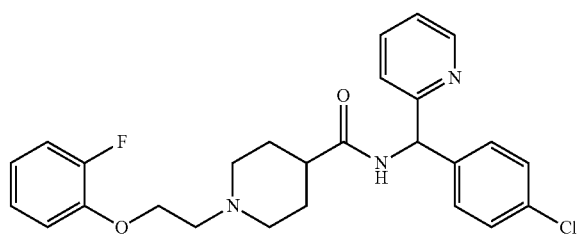 [SMILES: O=C(NC(c1ccc(Cl)cc1)c1ccccn1)C1CCN(CCOc2ccccc2F)CC1] |
| 4 | 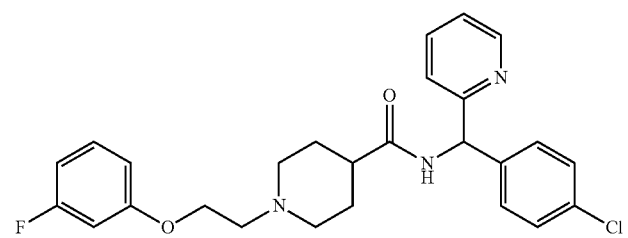 [SMILES: O=C(NC(c1ccc(Cl)cc1)c1ccccn1)C1CCN(CCOc2cccc(F)c2)CC1] |
| 5 | 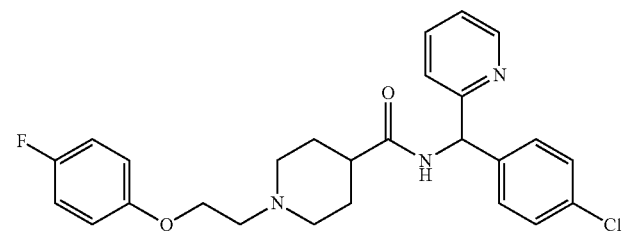 [SMILES: O=C(NC(c1ccc(Cl)cc1)c1ccccn1)C1CCN(CCOc2ccc(F)cc2)CC1] |
| 6 | 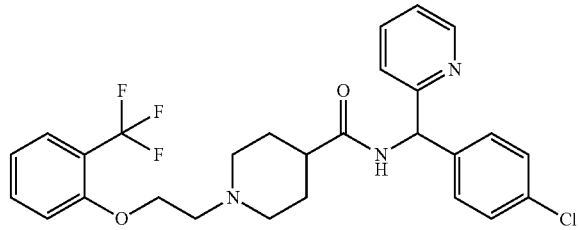 [SMILES: O=C(NC(c1ccc(Cl)cc1)c1ccccn1)C1CCN(CCOc2ccccc2C(F)(F)F)CC1] |

-continued
| Compound No. | Compound Formula |
|---|---|
| 7 | 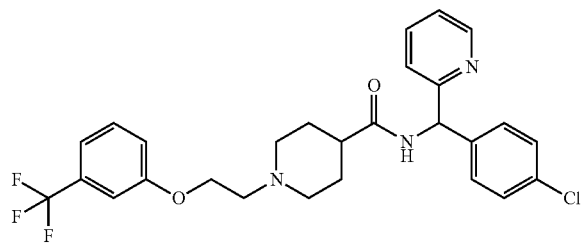 [SMILES: O=C(NC(c1ccc(Cl)cc1)c1ccccn1)C1CCN(CCOc2cccc(C(F)(F)F)c2)CC1] |
| 8 | 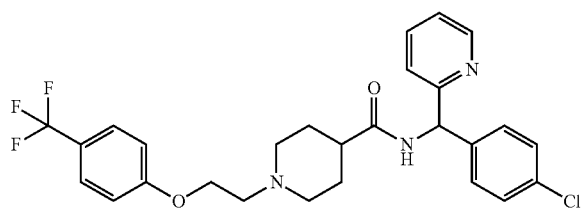 [SMILES: O=C(NC(c1ccc(Cl)cc1)c1ccccn1)C1CCN(CCOc2ccc(C(F)(F)F)cc2)CC1] |
| 10 | 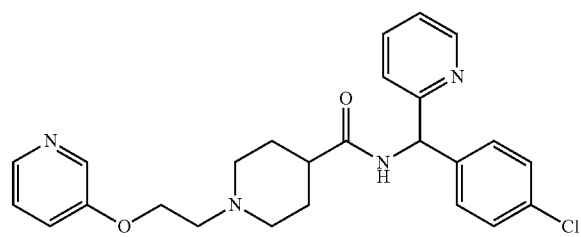 [SMILES: O=C(NC(c1ccc(Cl)cc1)c1ccccn1)C1CCN(CCOc2cccnc2)CC1] |
| 12 | 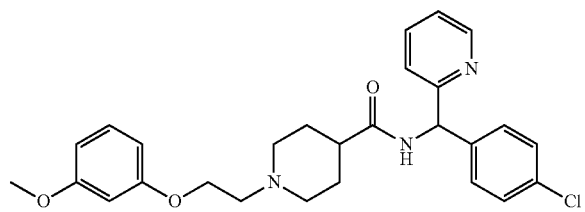 [SMILES: COc1cccc(OCCN2CCC(C(=O)NC(c3ccc(Cl)cc3)c3ccccn3)CC2)c1] |
| 13 | 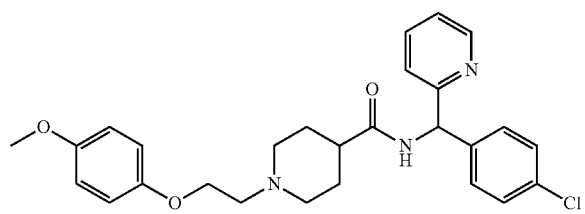 [SMILES: COc1ccc(OCCN2CCC(C(=O)NC(c3ccc(Cl)cc3)c3ccccn3)CC2)cc1] |
| 14 | 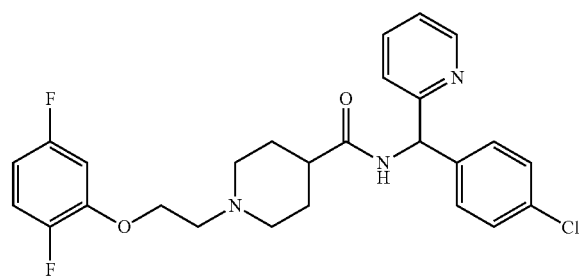 [SMILES: O=C(NC(c1ccc(Cl)cc1)c1ccccn1)C1CCN(CCOc2cc(F)ccc2F)CC1] |

-continued
| Compound No. | Compound Formula |
|---|---|
| 15 | 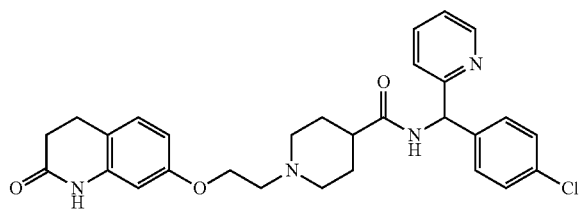 [SMILES: O=C1CCc2ccc(OCCN3CCC(C(=O)NC(c4ccc(Cl)cc4)c4ccccn4)CC3)cc2N1] |
| 16 | 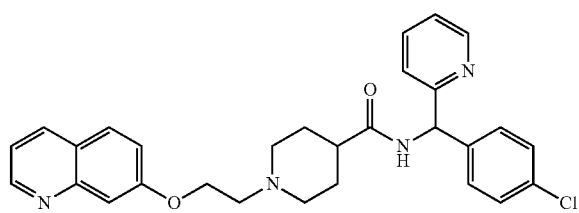 [SMILES: O=C(NC(c1ccc(Cl)cc1)c1ccccn1)C1CCN(CCOc2ccc3cccnc3c2)CC1] |
| 17 | 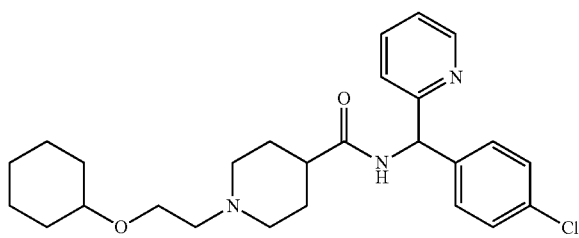 [SMILES: O=C(NC(c1ccc(Cl)cc1)c1ccccn1)C1CCN(CCOC2CCCCC2)CC1] |
| 19 | 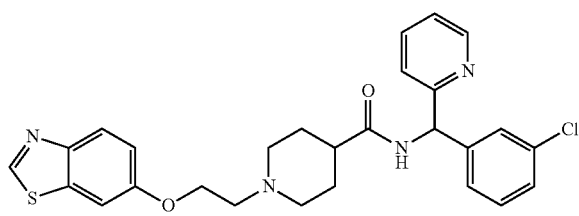 [SMILES: O=C(NC(c1cccc(Cl)c1)c1ccccn1)C1CCN(CCOc2ccc3ncsc3c2)CC1] |
| 20 | 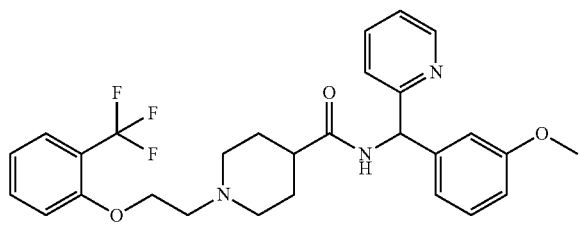 [SMILES: COc1cccc(C(NC(=O)C2CCN(CCOc3ccccc3C(F)(F)F)CC2)c2ccccn2)c1] |
| 21 | 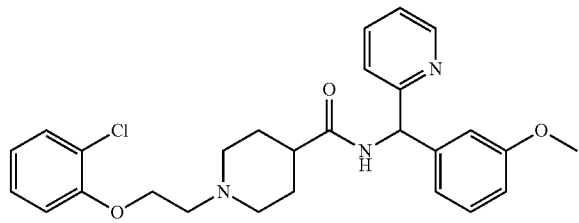 [SMILES: COc1cccc(C(NC(=O)C2CCN(CCOc3ccccc3Cl)CC2)c2ccccn2)c1] |
| 22 | 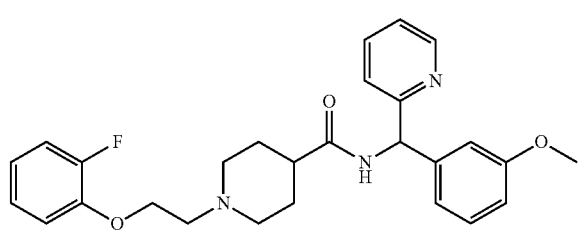 [SMILES: COc1cccc(C(NC(=O)C2CCN(CCOc3ccccc3F)CC2)c2ccccn2)c1] |

-continued
| Compound No. | Compound Formula |
|---|---|
| 23 | 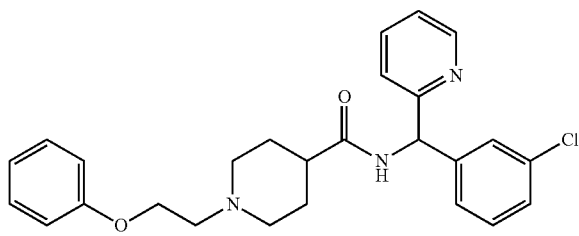 [SMILES: O=C(NC(c1cccc(Cl)c1)c1ccccn1)C1CCN(CCOc2ccccc2)CC1] |
| 24 | 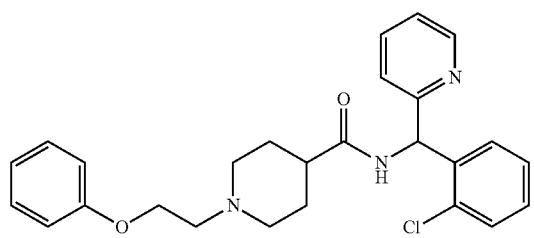 |
| 25 | 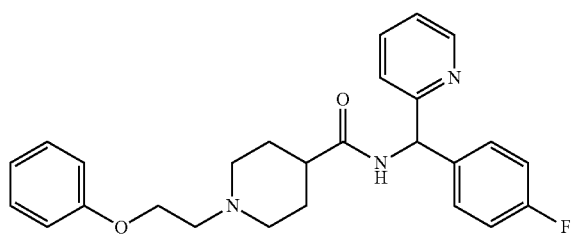 |
| 26 | 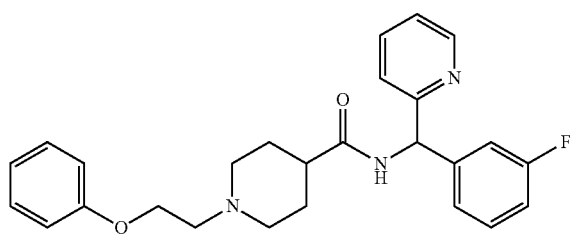 [SMILES: O=C(NC(c1cccc(F)c1)c1ccccn1)C1CCN(CCOc2ccccc2)CC1] |
| 27 | 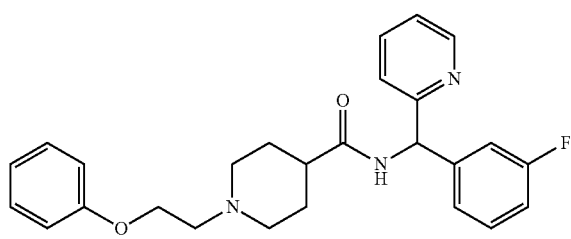 [SMILES: O=C(NC(c1cccc(F)c1)c1ccccn1)C1CCN(CCOc2ccccc2)CC1] |
| 28 | 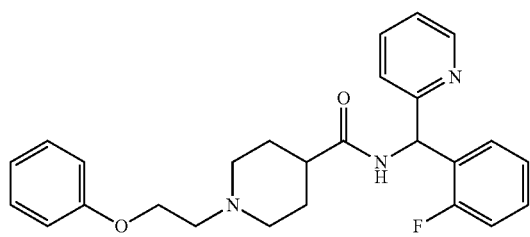 [SMILES: O=C(NC(c1ccccn1)c1ccccc1F)C1CCN(CCOc2ccccc2)CC1] |

-continued
| Compound No. | Compound Formula |
|---|---|
| 29 | 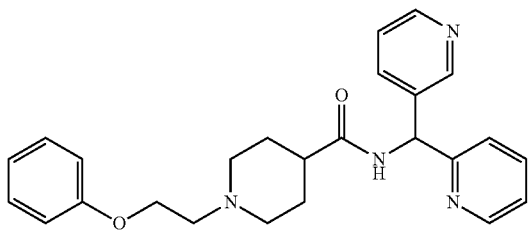 [SMILES: O=C(NC(c1cccnc1)c1ccccn1)C1CCN(CCOc2ccccc2)CC1] |
| 30 | 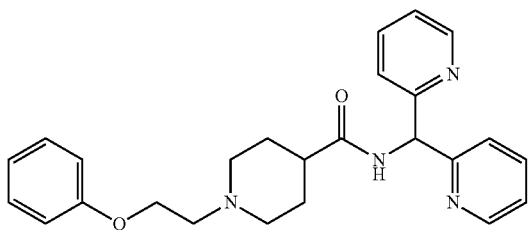 [SMILES: O=C(NC(c1ccccn1)c1ccccn1)C1CCN(CCOc2ccccc2)CC1] |
| 31 | 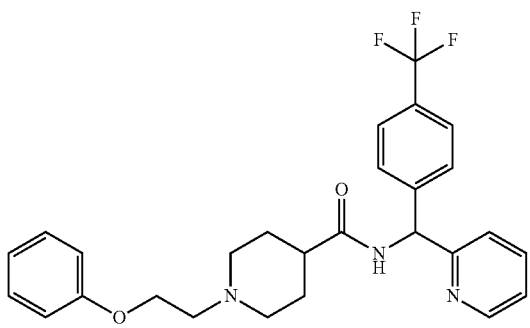 [SMILES: O=C(NC(c1ccc(C(F)(F)F)cc1)c1ccccn1)C1CCN(CCOc2ccccc2)CC1] |
| 32 | 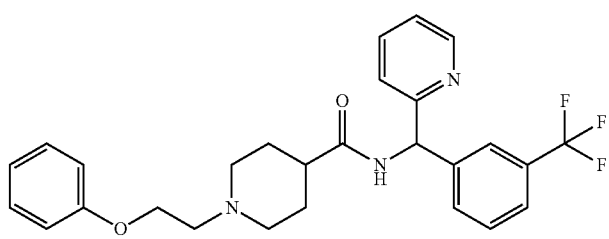 [SMILES: O=C(NC(c1cccc(C(F)(F)F)c1)c1ccccn1)C1CCN(CCOc2ccccc2)CC1] |
| 33 | 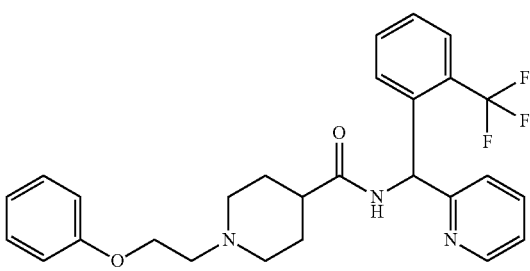 [SMILES: O=C(NC(c1ccccn1)c1ccccc1C(F)(F)F)C1CCN(CCOc2ccccc2)CC1] |
| 34 | 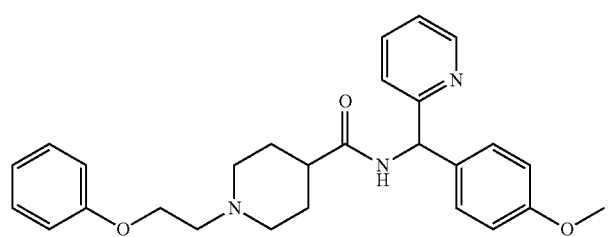 [SMILES: COc1ccc(C(NC(=O)C2CCN(CCOc3ccccc3)CC2)c2ccccn2)cc1] |

-continued
| Compound No. | Compound Formula |
|---|---|
| 35 | 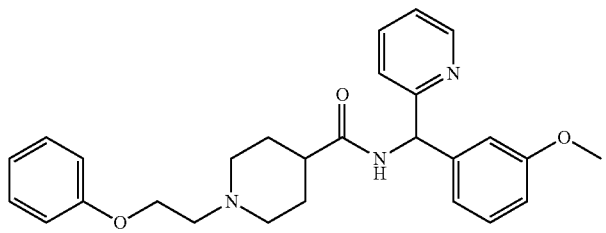 [SMILES: COc1cccc(C(NC(=O)C2CCN(CCOc3ccccc3)CC2)c2ccccn2)c1] |
| 36 | 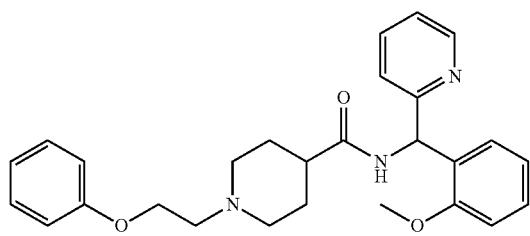 [SMILES: COc1ccccc1C(NC(=O)C1CCN(CCOc2ccccc2)CC1)c1ccccn1] |
| 37 | 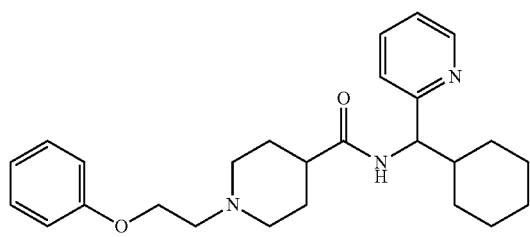 [SMILES: O=C(NC(c1ccccn1)C1CCCCC1)C1CCN(CCOc2ccccc2)CC1] |
| 39 | 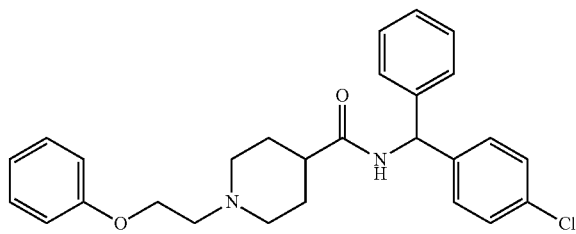 [SMILES: O=C(NC(c1ccccc1)c1ccc(Cl)cc1)C1CCN(CCOc2ccccc2)CC1] |
| 40 | 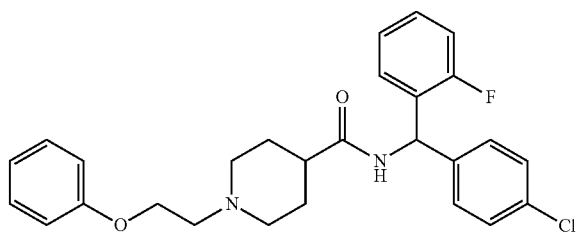 [SMILES: O=C(NC(c1ccc(Cl)cc1)c1ccccc1F)C1CCN(CCOc2ccccc2)CC1] |
| 41 | 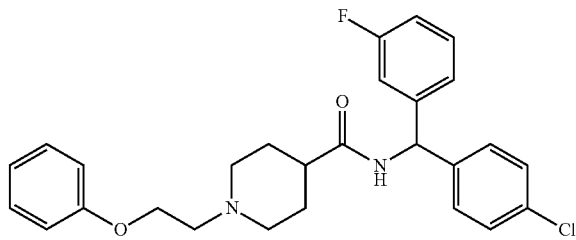 [SMILES: O=C(NC(c1ccc(Cl)cc1)c1cccc(F)c1)C1CCN(CCOc2ccccc2)CC1] |

| Compound No. | Compound Formula |
|---|---|
| 42 | 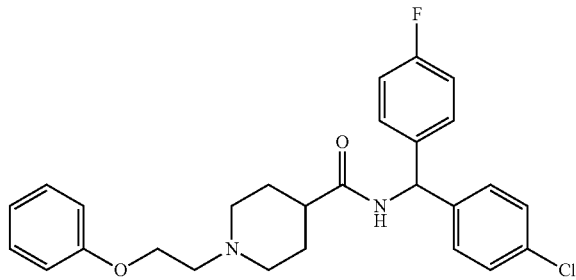 [SMILES: O=C(NC(c1ccc(F)cc1)c1ccc(Cl)cc1)C1CCN(CCOc2ccccc2)CC1] |
| 43 | 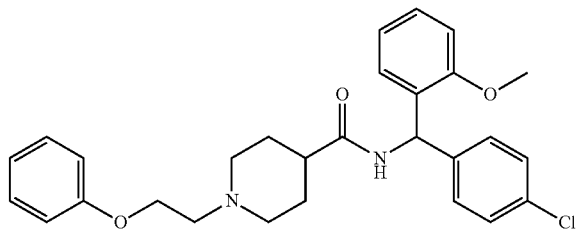 [SMILES: COc1ccccc1C(NC(=O)C1CCN(CCOc2ccccc2)CC1)c1ccc(Cl)cc1] |
| 44 | 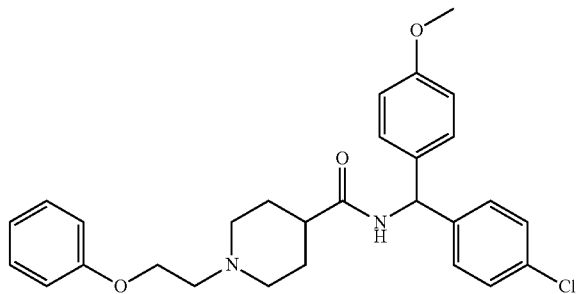 [SMILES: COc1ccc(C(NC(=O)C2CCN(CCOc3ccccc3)CC2)c2ccc(Cl)cc2)cc1] |
| 45 | 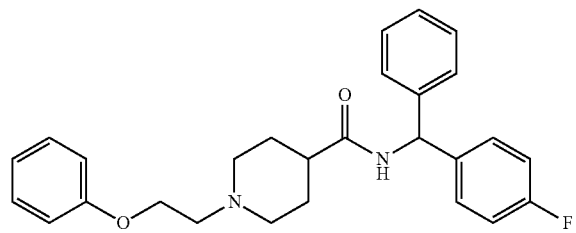 [SMILES: O=C(NC(c1ccccc1)c1ccc(F)cc1)C1CCN(CCOc2ccccc2)CC1] |
| 46 | 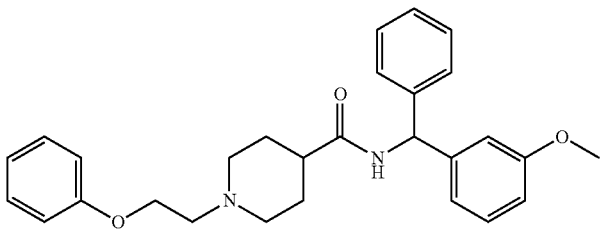 |
| 47 | 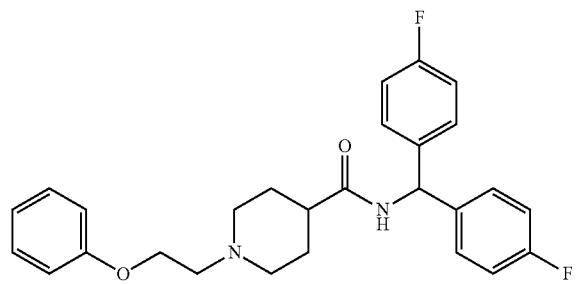 [SMILES: O=C(NC(c1ccc(F)cc1)c1ccc(F)cc1)C1CCN(CCOc2ccccc2)CC1] |

| Compound No. | Compound Formula |
|---|---|
| 48 | 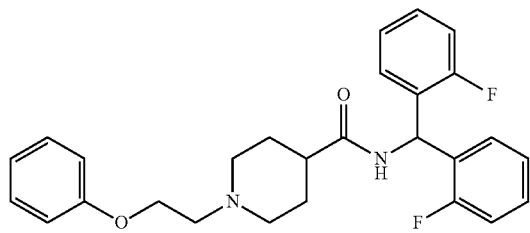 [SMILES: O=C(NC(c1ccccc1F)c1ccccc1F)C1CCN(CCOc2ccccc2)CC1] |
| 49 | 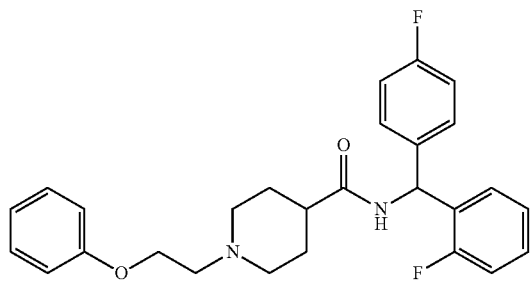 [SMILES: O=C(NC(c1ccc(F)cc1)c1ccccc1F)C1CCN(CCOc2ccccc2)CC1] |
| 50 | 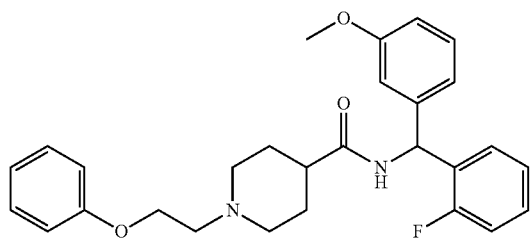 [SMILES: COc1cccc(C(NC(=O)C2CCN(CCOc3ccccc3)CC2)c2ccccc2F)c1] |
| 51 | 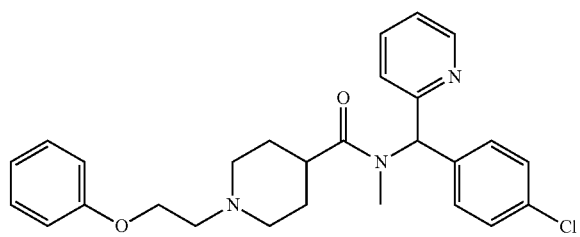 |
| 52 | 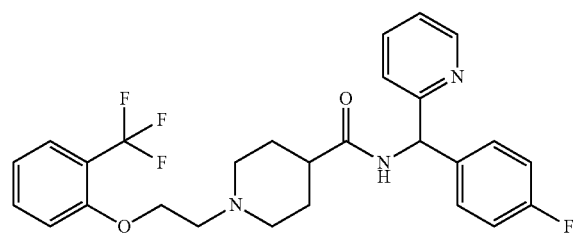 |
| 53 | 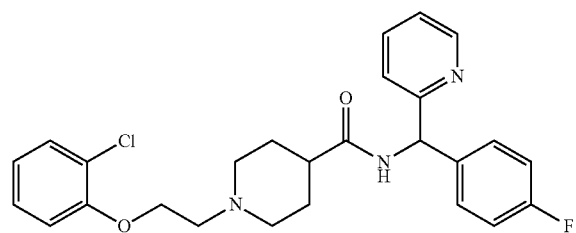 [SMILES: O=C(NC(c1ccc(F)cc1)c1ccccn1)C1CCN(CCOc2ccccc2Cl)CC1] |

-continued
| Compound No. | Compound Formula |
|---|---|
| 54 | 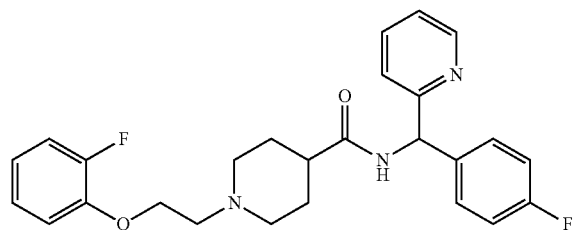 [SMILES: O=C(NC(c1ccc(F)cc1)c1ccccn1)C1CCN(CCOc2ccccc2F)CC1] |
| 55 | 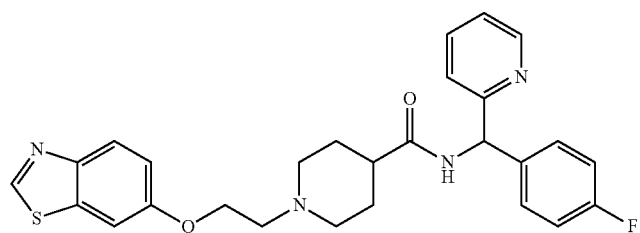 [SMILES: O=C(NC(c1ccc(F)cc1)c1ccccn1)C1CCN(CCOc2ccc3ncsc3c2)CC1] |
| 56 | 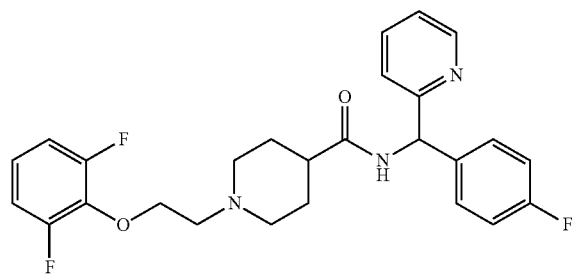 [SMILES: O=C(NC(c1ccc(F)cc1)c1ccccn1)C1CCN(CCOc2c(F)cccc2F)CC1] |
| 57 | 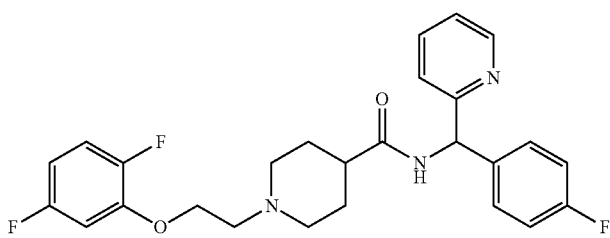 [SMILES: O=C(NC(c1ccc(F)cc1)c1ccccn1)C1CCN(CCOc2cc(F)ccc2F)CC1] |
| 58 | 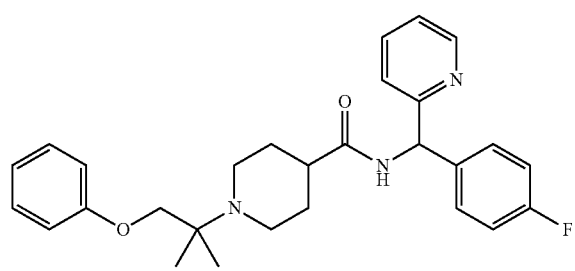 [SMILES: CC(C)(COc1ccccc1)N1CCC(C(=O)NC(c2ccc(F)cc2)c2ccccn2)CC1] |
| 62 | 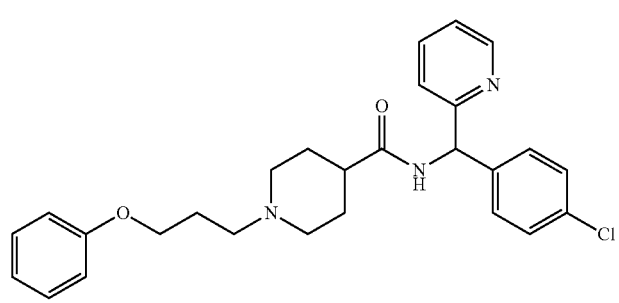 [SMILES: O=C(NC(c1ccc(Cl)cc1)c1ccccn1)C1CCN(CCCOc2ccccc2)CC1] |

-continued
| Compound No. | Compound Formula |
|---|---|
| 63 | 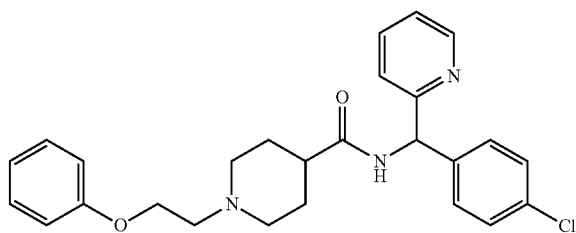 [SMILES: O=C(NC(c1ccc(Cl)cc1)c1ccccn1)C1CCN(CCOc2ccccc2)CC1] |
| 66 | 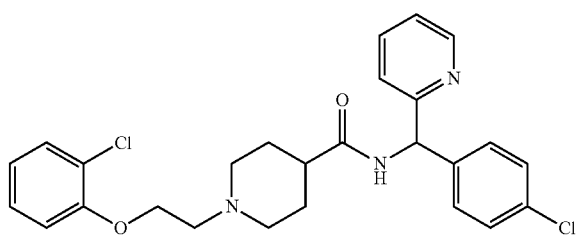 [SMILES: O=C(NC(c1ccc(Cl)cc1)c1ccccn1)C1CCN(CCOc2ccccc2Cl)CC1] |
| 67 | 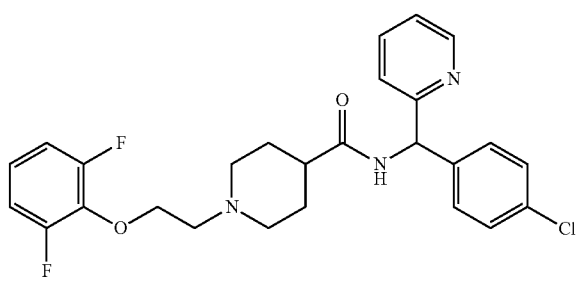 [SMILES: O=C(NC(c1ccc(Cl)cc1)c1ccccn1)C1CCN(CCOc2c(F)cccc2F)CC1] |
| 68 | 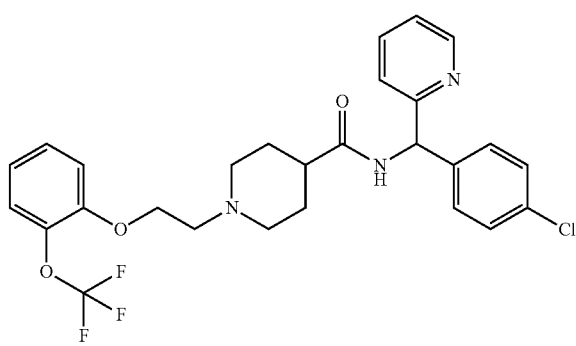 [SMILES: O=C(NC(c1ccc(Cl)cc1)c1ccccn1)C1CCN(CCOc2ccccc2OC(F)(F)F)CC1] |
| 69 | 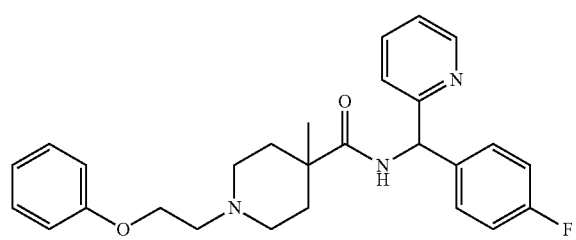 [SMILES: CC1(C(=O)NC(c2ccc(F)cc2)c2ccccn2)CCN(CCOc2ccccc2)CC1] |
| 70 | 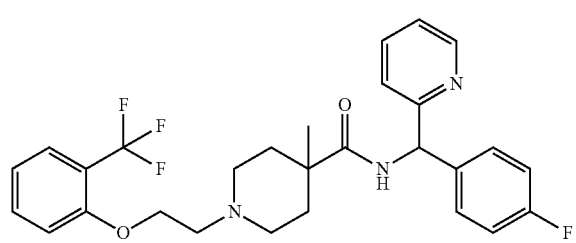 [SMILES: CC1(C(=O)NC(c2ccc(F)cc2)c2ccccn2)CCN(CCOc2ccccc2C(F)(F)F)CC1] |

-continued

| Compound No. | Compound Formula |
|---|---|
| 71 | |
| 82 | |
| 83 | |
| 84 | |
| 85 | |
| 86 | |

-continued

| Compound No. | Compound Formula |
|---|---|
| 90 | |
| 91 | |
| 92 | |
| 93 | |
| 94 | |

| Compound No. | Compound Formula |
|---|---|
| 95 | 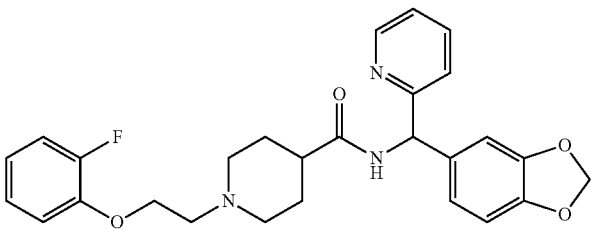 [SMILES: O=C(NC(c1ccc2c(c1)OCO2)c1ccccn1)C1CCN(CCOc2ccccc2F)CC1] |
| 96 | 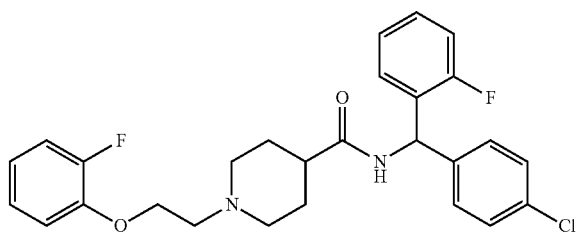 [SMILES: O=C(NC(c1ccc(Cl)cc1)c1ccccc1F)C1CCN(CCOc2ccccc2F)CC1] |
| 109 | 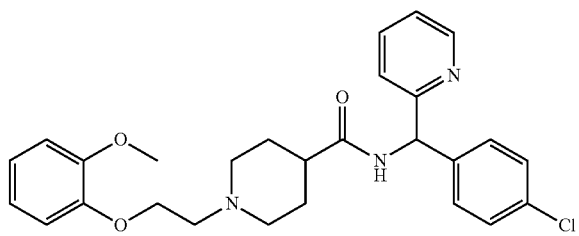 [SMILES: COc1ccccc1OCCN1CCC(C(=O)NC(c2ccc(Cl)cc2)c2ccccn2)CC1] |
| 110 | 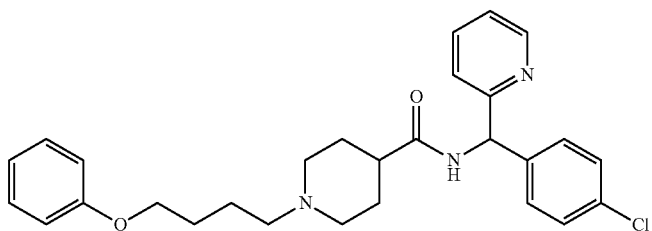 [SMILES: O=C(NC(c1ccc(Cl)cc1)c1ccccn1)C1CCN(CCCCOc2ccccc2)CC1] |
| 111 | 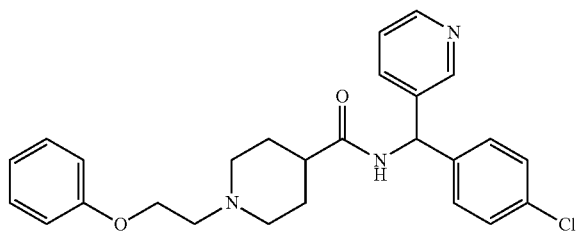 [SMILES: O=C(NC(c1ccc(Cl)cc1)c1cccnc1)C1CCN(CCOc2ccccc2)CC1] |
| 112 | 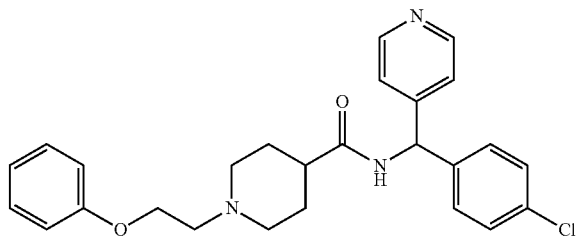 [SMILES: O=C(NC(c1ccncc1)c1ccc(Cl)cc1)C1CCN(CCOc2ccccc2)CC1] |

-continued
| Compound No. | Compound Formula |
|---|---|
| 113 | 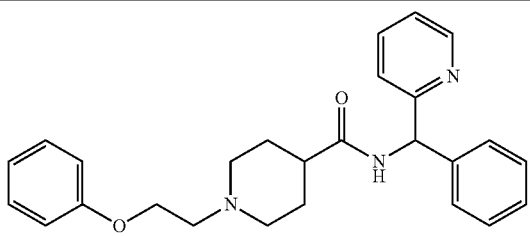 |
| 115 | 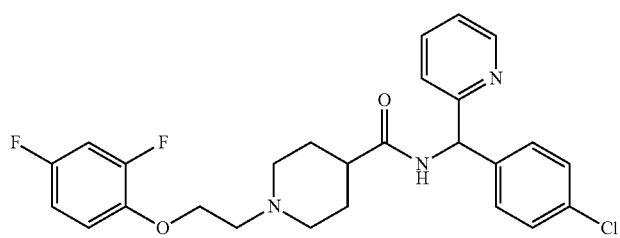 [SMILES: O=C(NC(c1ccc(Cl)cc1)c1ccccn1)C1CCN(CCOc2ccc(F)cc2F)CC1] |
| 116 | 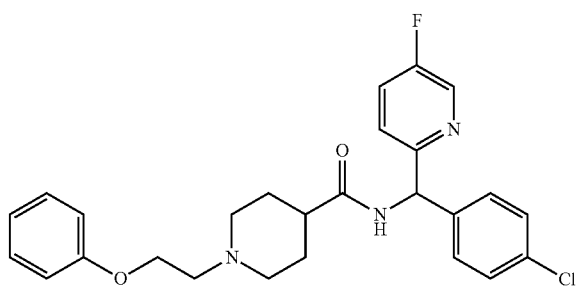 [SMILES: O=C(NC(c1ccc(Cl)cc1)c1ccc(F)cn1)C1CCN(CCOc2ccccc2)CC1] |
| 117 | 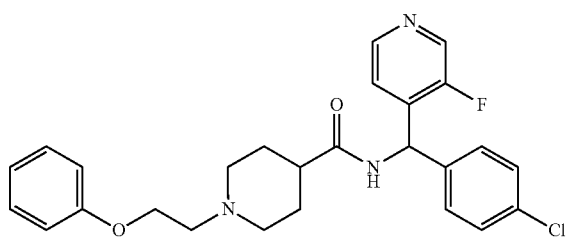 [SMILES: O=C(NC(c1ccc(Cl)cc1)c1ccncc1F)C1CCN(CCOc2ccccc2)CC1] |
| 118 | 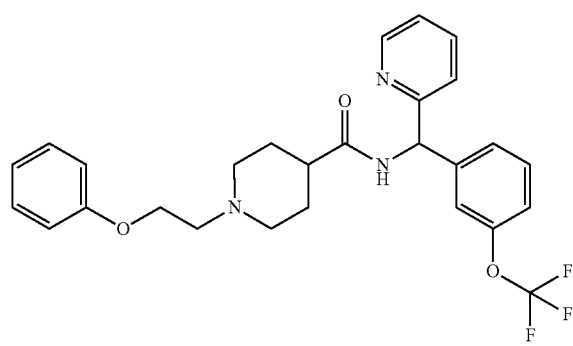 [SMILES: O=C(NC(c1cccc(OC(F)(F)F)c1)c1ccccn1)C1CCN(CCOc2ccccc2)CC1] |
| 119 | 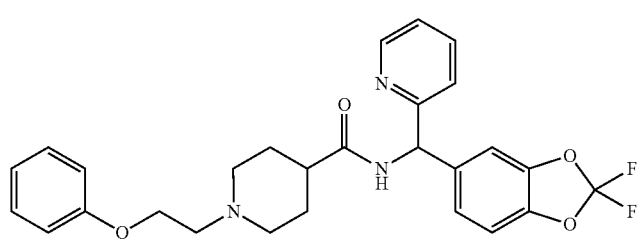 [SMILES: O=C(NC(c1ccc2c(c1)OC(F)(F)O2)c1ccccn1)C1CCN(CCOc2ccccc2)CC1] |

-continued
| Compound No. | Compound Formula |
|---|---|
| 123 | 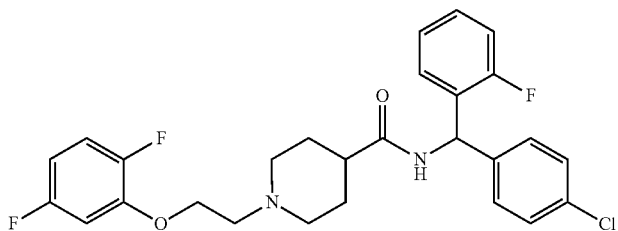 [SMILES: O=C(NC(c1ccc(Cl)cc1)c1ccccc1F)C1CCN(CCOc2cc(F)ccc2F)CC1] |
| 129 | 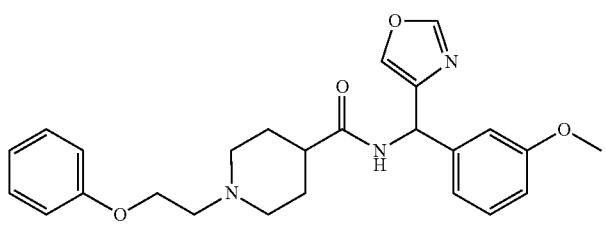 [SMILES: COc1cccc(C(NC(=O)C2CCN(CCOc3ccccc3)CC2)c2cocn2)c1] |
| 130 | 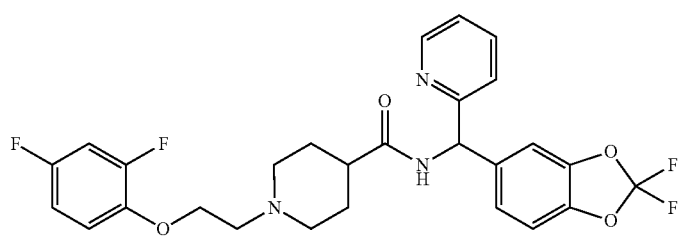 [SMILES: O=C(NC(c1ccc2c(c1)OC(F)(F)O2)c1ccccn1)C1CCN(CCOc2ccc(F)cc2F)CC1] |
| 141 | 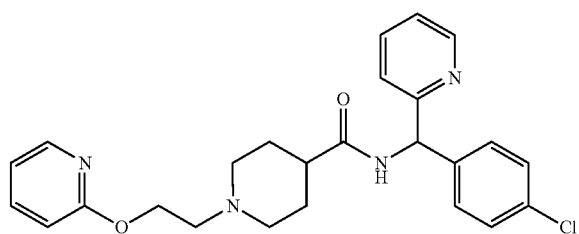 |
| 142 | 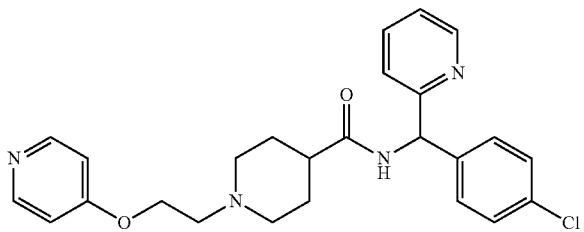 [SMILES: O=C(NC(c1ccc(Cl)cc1)c1ccccn1)C1CCN(CCOc2ccncc2)CC1] |
| 143 | 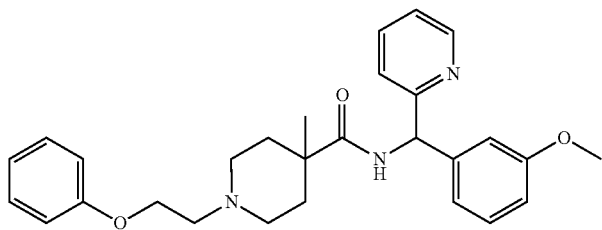 [SMILES: COc1cccc(C(NC(=O)C2(C)CCN(CCOc3ccccc3)CC2)c2ccccn2)c1] |

-continued
| Compound No. | Compound Formula |
|---|---|
| 144 | 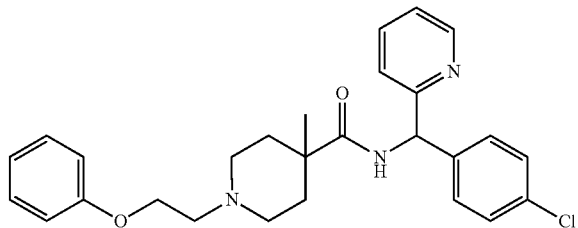 [SMILES: CC1(C(=O)NC(c2ccc(Cl)cc2)c2ccccn2)CCN(CCOc2ccccc2)CC1] |
| 145 | 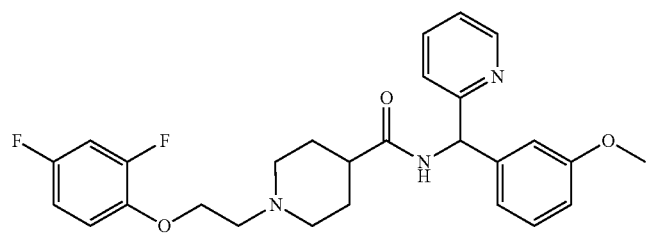 [SMILES: COc1cccc(C(NC(=O)C2CCN(CCOc3ccc(F)cc3F)CC2)c2ccccn2)c1] |
| 146 | 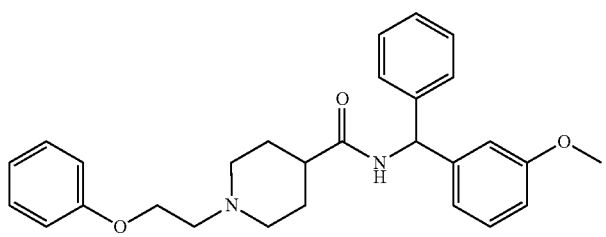 |
| 72 | 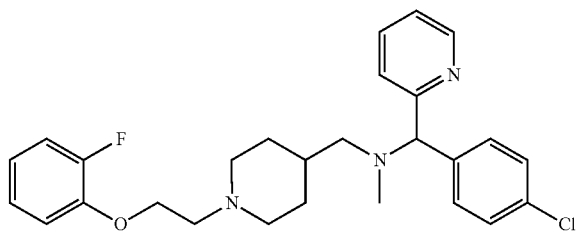 [SMILES: CN(CC1CCN(CCOc2ccccc2F)CC1)C(c1ccc(Cl)cc1)c1ccccn1] |
| 73 | 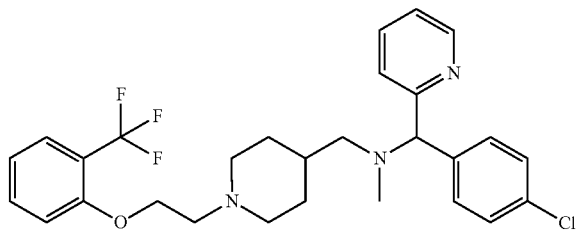 [SMILES: CN(CC1CCN(CCOc2ccccc2C(F)(F)F)CC1)C(c1ccc(Cl)cc1)c1ccccn1] |
| 74 | 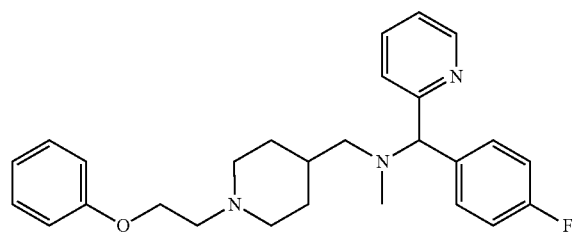 [SMILES: CN(CC1CCN(CCOc2ccccc2)CC1)C(c1ccc(F)cc1)c1ccccn1] |

| Compound No. | Compound Formula |
|---|---|
| 75 | 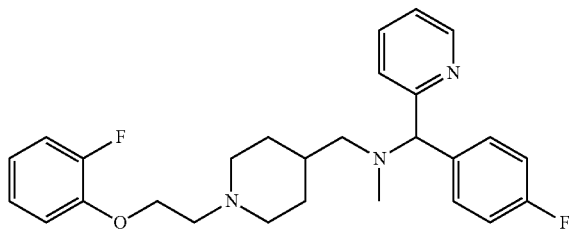 [SMILES: CN(CC1CCN(CCOc2ccccc2F)CC1)C(c1ccc(F)cc1)c1ccccn1] |
| 76 | 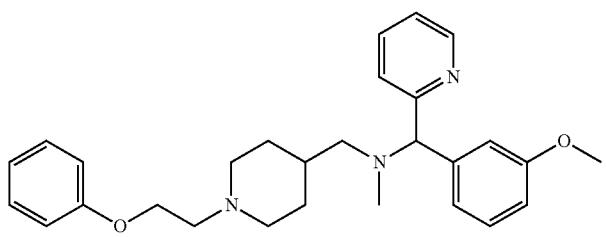 [SMILES: COc1cccc(C(c2ccccn2)N(C)CC2CCN(CCOc3ccccc3)CC2)c1] |
| 77 | 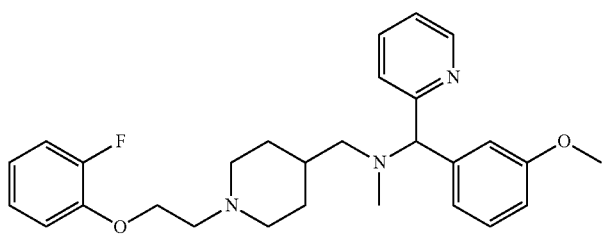 |
| 78 | 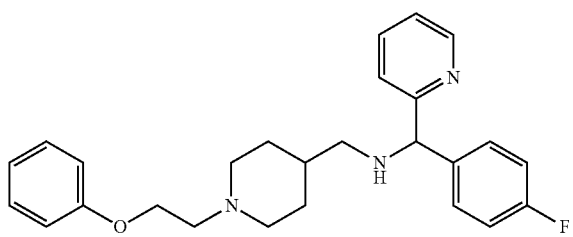 [SMILES: Fc1ccc(C(NCC2CCN(CCOc3ccccc3)CC2)c2ccccn2)cc1] |
| 79 | 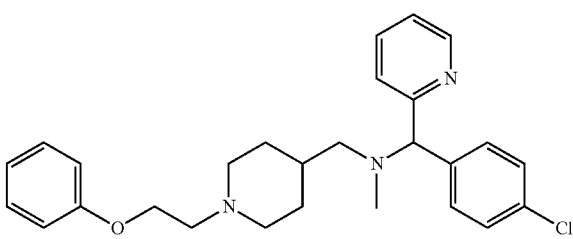 [SMILES: CN(CC1CCN(CCOc2ccccc2)CC1)C(c1ccc(Cl)cc1)c1ccccn1] |
| 80 | 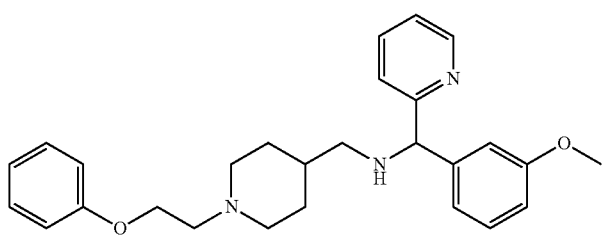 [SMILES: COc1cccc(C(NCC2CCN(CCOc3ccccc3)CC2)c2ccccn2)c1] |

-continued
| Compound No. | Compound Formula |
|---|---|
| 81 | 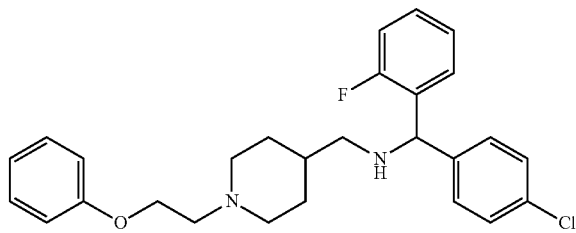 [SMILES: Fc1ccccc1C(NCC1CCN(CCOc2ccccc2)CC1)c1ccc(Cl)cc1] |
| 87 | 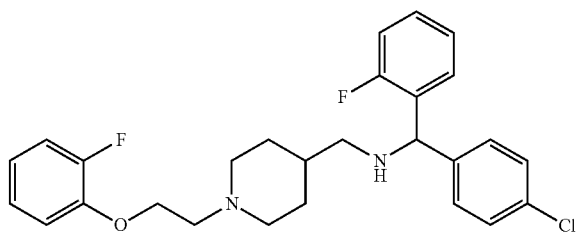 [SMILES: Fc1ccccc1OCCN1CCC(CNC(c2ccc(Cl)cc2)c2ccccc2F)CC1] |
| 88 | 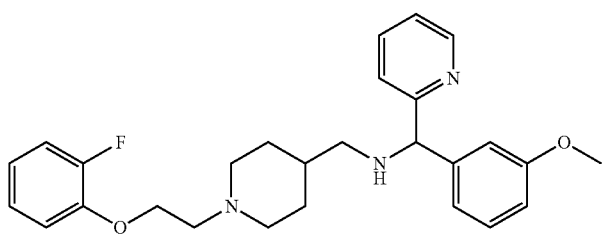 [SMILES: COc1cccc(C(NCC2CCN(CCOc3ccccc3F)CC2)c2ccccn2)c1] |
| 89 | 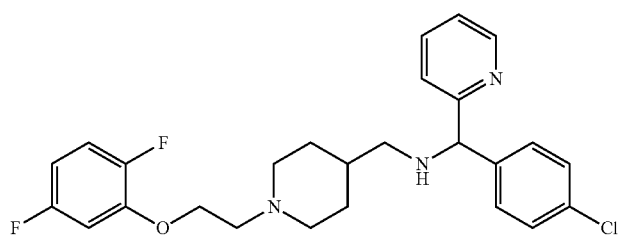 [SMILES: Fc1ccc(F)c(OCCN2CCC(CNC(c3ccc(Cl)cc3)c3ccccn3)CC2)c1] |
| 97 | 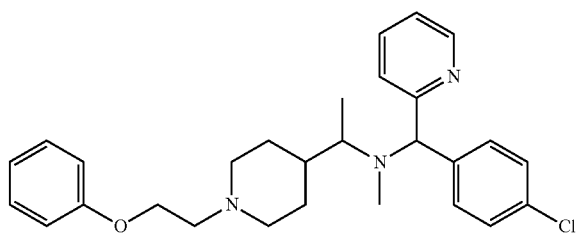 [SMILES: CC(C1CCN(CCOc2ccccc2)CC1)N(C)C(c1ccc(Cl)cc1)c1ccccn1] |
| 101 | 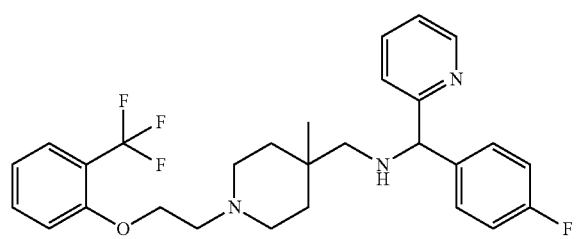 [SMILES: CC1(CNC(c2ccc(F)cc2)c2ccccn2)CCN(CCOc2ccccc2C(F)(F)F)CC1] |

-continued
| Compound No. | Compound Formula |
|---|---|
| 102 | 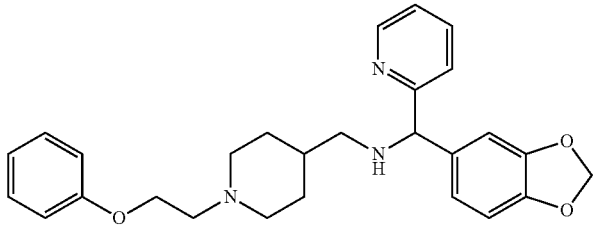 [SMILES: c1ccc(OCCN2CCC(CNC(c3ccc4c(c3)OCO4)c3ccccn3)CC2)cc1] |
| 103 | 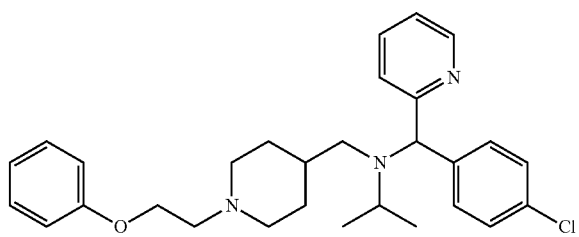 [SMILES: CC(C)N(CC1CCN(CCOc2ccccc2)CC1)C(c1ccc(Cl)cc1)c1ccccn1] |
| 107 | 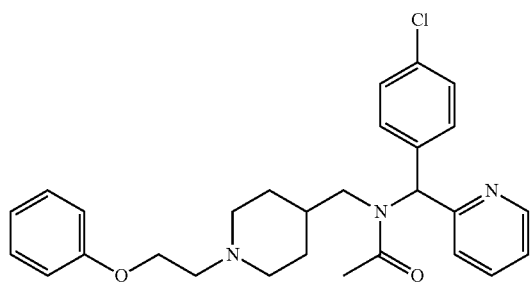 [SMILES: CC(=O)N(CC1CCN(CCOc2ccccc2)CC1)C(c1ccc(Cl)cc1)c1ccccn1] |
| 114 | 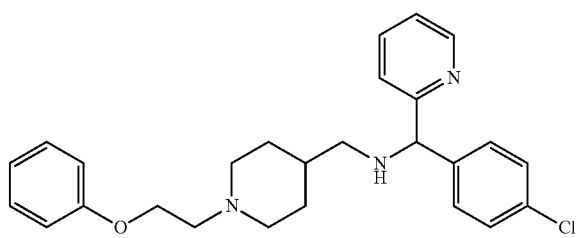 |
| 120 | 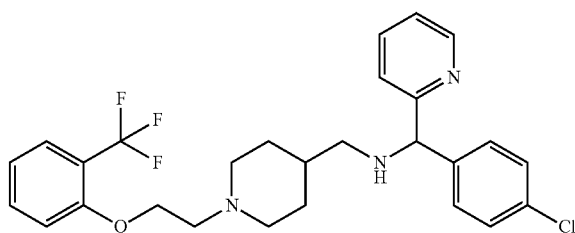 [SMILES: FC(F)(F)c1ccccc1OCCN1CCC(CNC(c2ccc(Cl)cc2)c2ccccn2)CC1] |
| 121 | 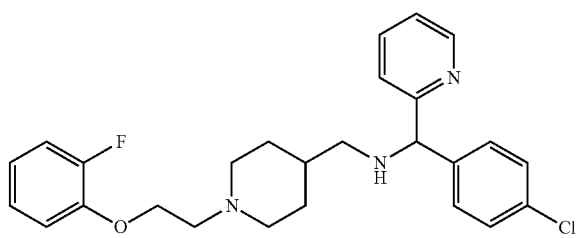 [SMILES: Fc1ccccc1OCCN1CCC(CNC(c2ccc(Cl)cc2)c2ccccn2)CC1] |

-continued

| Compound No. | Compound Formula |
|---|---|
| 122 | (structure) |
| 125 | (structure) |
| 131 | (structure) |
| 132 | (structure) |
| 133 | (structure) |
| 134 | (structure) |

| Compound No. | Compound Formula |
|---|---|
| 135 | 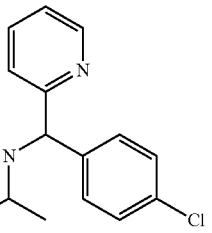 |
| 136 | 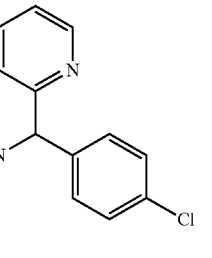 |
| 137 | 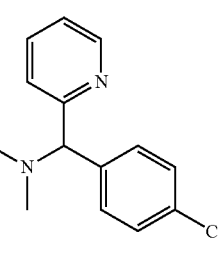 |
| 138 | 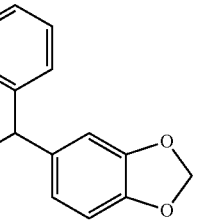 |
| 139 | 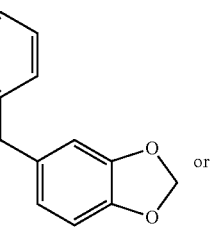 |
| 18 | 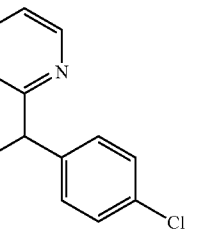 |
or a stereoisomer, racemate, tautomer, polymorph, hydrate, or solvate thereof, or a pharmaceutically acceptable salt thereof.

22. The compound of claim 1, wherein the compound is of the formula:

| Compound No. | Compound Formula |
|---|---|
| 99 | 4-chlorophenyl-(pyridin-2-yl)methyl ether linked via -OCH2- to 1-(2-phenoxyethyl)piperidin-4-yl |
| 3 | N-[(4-chlorophenyl)(pyridin-2-yl)methyl]-1-[2-(2-fluorophenoxy)ethyl]piperidine-4-carboxamide |
| 25 | N-[(4-fluorophenyl)(pyridin-2-yl)methyl]-1-(2-phenoxyethyl)piperidine-4-carboxamide |
| 35 | N-[(3-methoxyphenyl)(pyridin-2-yl)methyl]-1-(2-phenoxyethyl)piperidine-4-carboxamide |
| 63 | N-[(4-chlorophenyl)(pyridin-2-yl)methyl]-1-(2-phenoxyethyl)piperidine-4-carboxamide |
| 69 | N-[(4-fluorophenyl)(pyridin-2-yl)methyl]-4-methyl-1-(2-phenoxyethyl)piperidine-4-carboxamide |

-continued
| Compound No. | Compound Formula |
|---|---|
| 70 | 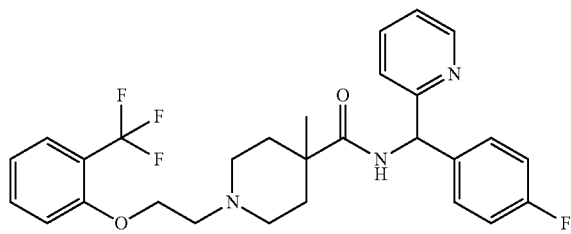 [SMILES: CC1(C(=O)NC(c2ccc(F)cc2)c2ccccn2)CCN(CCOc2ccccc2C(F)(F)F)CC1] |
| 144 | 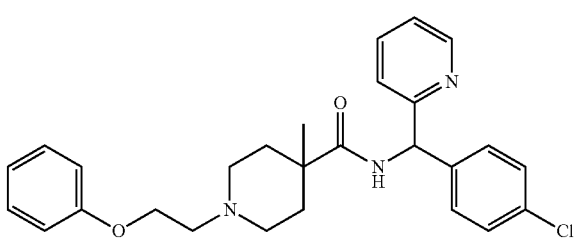 [SMILES: CC1(C(=O)NC(c2ccc(Cl)cc2)c2ccccn2)CCN(CCOc2ccccc2)CC1] |
| 72 | 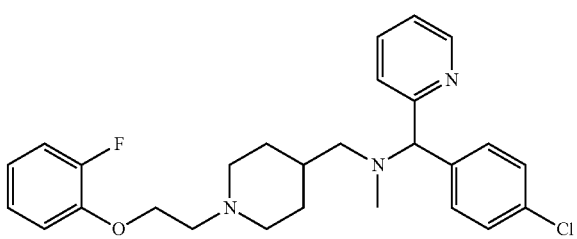 [SMILES: CN(CC1CCN(CCOc2ccccc2F)CC1)C(c1ccc(Cl)cc1)c1ccccn1] |
| 79 | 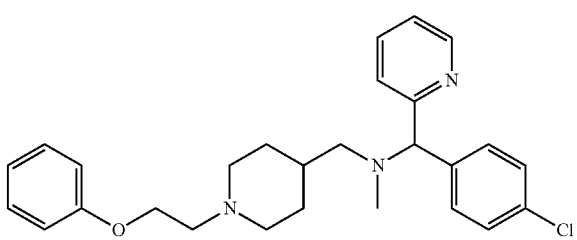 [SMILES: CN(CC1CCN(CCOc2ccccc2)CC1)C(c1ccc(Cl)cc1)c1ccccn1] |
| 103 | 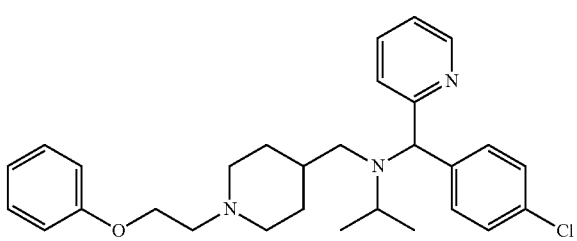 [SMILES: CC(C)N(CC1CCN(CCOc2ccccc2)CC1)C(c1ccc(Cl)cc1)c1ccccn1] |
| 125 | 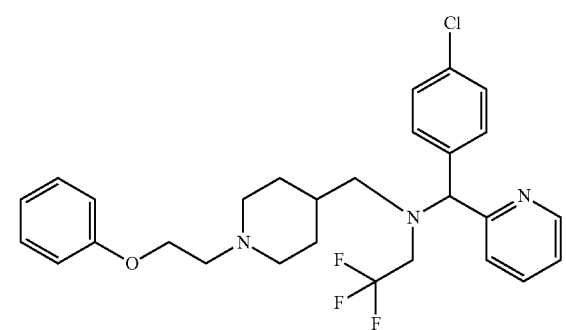 [SMILES: FC(F)(F)CN(CC1CCN(CCOc2ccccc2)CC1)C(c1ccc(Cl)cc1)c1ccccn1] |

| Compound No. | Compound Formula |
|---|---|
| 133 | *(structure shown)* |
| 136 | *(structure shown)* | or a pharmaceutically acceptable salt thereof.

23. A pharmaceutical composition comprising a compound of claim 11, or a stereoisomer, racemate, tautomer, polymorph, hydrate, or solvate thereof, or a pharmaceutically acceptable salt thereof, and one or more pharmaceutically acceptable excipients or carriers.

24. The method of claim 14, wherein the disease is:
an anxiety disorder selected from phobias, generalized anxiety disorder, social anxiety disorder, panic disorder, agoraphobia, obsessive-compulsive disorder, and post-traumatic stress disorder;
a dissociative disorder selected from dissociative amnesia, dissociative fugue, dissociative identity disorder, and depersonalization disorder;
a mood disorder selected from depression, dysthymia, bipolar disorder, mania, hypomania, and cyclothymic disorder;
an eating disorder selected from anorexia nervosa, bulimia nervosa, exercise bulimia, and binge eating disorder;
a sleep disorder selected from insomnia, hypersomnia, narcolepsy, nightmare disorder, sleep terror disorder, and sleepwalking;
a developmental disorder selected from autism spectrum disorder, oppositional defiant disorder, conduct disorder, and attention deficit hyperactivity disorder;
a somatoform disorder selected from body dysmorphic disorder, conversion disorder, hypochondriasis disorder, pain disorder, and somatization disorder;
a personality disorder selected from antisocial personality disorder, borderline personality disorder, and narcissistic personality disorder;
a psychiatric syndrome selected from Capgras syndrome, De Clerambault syndrome, Othello syndrome, Ganser syndrome, Cotard delusion, Ekbom syndrome, Couvade syndrome, and Geschwind syndrome;
a psychotic disorder selected from brief psychotic disorder, delusional disorder, Schizoaffective disorder, Schizophrenia, Schizophreniform, and shared psychotic disorder;
substance abuse;
Parkinson's disease;
Huntington's disease;
Alzheimer's disease;
dementia;
Niemann-Pick disorder;
a pituitary disorder selected from pituitary adenoma and pituitary tumor;
Tourette's syndrome;
Tourette-like disorder; or
restless leg syndrome.

25. A method of treating a disease comprising administering to a subject in need thereof a therapeutically effective amount of a compound of claim 11, or a stereoisomer, racemate, tautomer, polymorph, hydrate, or solvate thereof, or a pharmaceutically acceptable salt thereof, in combination with a pharmaceutically acceptable excipient or carrier, wherein the disease is:
an anxiety disorder;
a dissociative disorder;
a mood disorder;
an eating disorder;
a sleep disorder;
a developmental disorder;
a somatoform disorder;
a personality disorder;
a psychiatric syndrome;
a psychotic disorder;
substance abuse;
Parkinson's disease;
Huntington's disease;
Alzheimer's disease;
dementia;
Niemann-Pick disorder;
a pituitary disorder;
Tourette's syndrome;
Tourette-like disorder; or
restless leg syndrome.

26. A method of treating a disease comprising administering to a subject in need thereof a therapeutically effective amount of a compound of claim 21, or a stereoisomer, racemate, tautomer, polymorph, hydrate, or solvate thereof, or a pharmaceutically acceptable salt thereof, in combination with a pharmaceutically acceptable excipient or carrier, wherein the disease is:
- an anxiety disorder;
- a dissociative disorder;
- a mood disorder;
- an eating disorder;
- a sleep disorder;
- a developmental disorder;
- a somatoform disorder;
- a personality disorder;
- a psychiatric syndrome;
- a psychotic disorder;
- substance abuse;
- Parkinson's disease;
- Huntington's disease;
- Alzheimer's disease;
- dementia;
- Niemann-Pick disorder;
- a pituitary disorder;
- Tourette's syndrome;
- Tourette-like disorder; or
- restless leg syndrome.

27. A method of treating a disease comprising administering to a subject in need thereof a therapeutically effective amount of a compound of claim 22, or a stereoisomer, racemate, tautomer, polymorph, hydrate, or solvate thereof, or a pharmaceutically acceptable salt thereof, in combination with a pharmaceutically acceptable excipient or carrier, wherein the disease is:
- an anxiety disorder;
- a dissociative disorder;
- a mood disorder;
- an eating disorder;
- a sleep disorder;
- a developmental disorder;
- a somatoform disorder;
- a personality disorder;
- a psychiatric syndrome;
- a psychotic disorder;
- substance abuse;
- Parkinson's disease;
- Huntington's disease;
- Alzheimer's disease;
- dementia;
- Niemann-Pick disorder;
- a pituitary disorder;
- Tourette's syndrome;
- Tourette-like disorder; or
- restless leg syndrome.

28. A method of modulating D2 receptor activity comprising administering to a subject a compound of claim 11, or a stereoisomer, racemate, tautomer, polymorph, hydrate, or solvate thereof, or a pharmaceutically acceptable salt thereof.

* * * * *